US012502368B2

(12) United States Patent
Tavazoie et al.

(10) Patent No.: US 12,502,368 B2
(45) **Date of Patent: *Dec. 23, 2025**

(54) TREATMENT AND DIAGNOSIS OF MELANOMA

(71) Applicant: The Rockefeller University, New York, NY (US)

(72) Inventors: Sohail F. Tavazoie, New York, NY (US); Nora Pencheva, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/403,027

(22) Filed: Jan. 3, 2024

(65) Prior Publication Data

US 2024/0252458 A1 Aug. 1, 2024

Related U.S. Application Data

(60) Division of application No. 17/201,493, filed on Mar. 15, 2021, now Pat. No. 11,865,094, which is a division of application No. 16/725,493, filed on Dec. 23, 2019, now Pat. No. 10,945,978, which is a continuation of application No. 15/881,231, filed on Jan. 26, 2018, now Pat. No. 10,543,183, which is a continuation of application No. 15/650,480, filed on Jul. 14, 2017, now Pat. No. 9,962,348, which is a continuation of application No. 15/228,643, filed on Aug. 4, 2016, now Pat. No. 9,707,195, which is a continuation of application No. 14/486,477, filed on Sep. 15, 2014, now Pat. No. 9,526,710, which is a continuation of application No. PCT/US2013/054690, filed on Aug. 13, 2013.

(60) Provisional application No. 61/784,057, filed on Mar. 14, 2013, provisional application No. 61/682,339, filed on Aug. 13, 2012.

(51) Int. Cl.

| | |
|---|---|
| ***A61K 31/195*** | (2006.01) |
| ***A61K 31/136*** | (2006.01) |
| ***A61K 31/18*** | (2006.01) |
| ***A61K 31/265*** | (2006.01) |
| ***A61K 31/415*** | (2006.01) |
| ***A61K 31/4155*** | (2006.01) |
| ***A61K 31/416*** | (2006.01) |
| ***A61K 31/4164*** | (2006.01) |
| ***A61K 31/4174*** | (2006.01) |
| ***A61K 31/47*** | (2006.01) |
| ***A61K 31/5377*** | (2006.01) |
| ***A61K 31/675*** | (2006.01) |
| ***A61K 38/17*** | (2006.01) |
| ***A61K 45/06*** | (2006.01) |
| ***C07C 217/54*** | (2006.01) |
| ***C07D 233/64*** | (2006.01) |
| ***C07F 9/6506*** | (2006.01) |
| ***C12Q 1/6886*** | (2018.01) |
| ***G01N 33/574*** | (2006.01) |

(52) U.S. Cl.

CPC .......... *A61K 31/195* (2013.01); *A61K 31/136* (2013.01); *A61K 31/18* (2013.01); *A61K 31/265* (2013.01); *A61K 31/415* (2013.01); *A61K 31/4155* (2013.01); *A61K 31/416* (2013.01); *A61K 31/4164* (2013.01); *A61K 31/4174* (2013.01); *A61K 31/47* (2013.01); *A61K 31/5377* (2013.01); *A61K 31/675* (2013.01); *A61K 38/1709* (2013.01); *A61K 38/177* (2013.01); *A61K 45/06* (2013.01); *C07C 217/54* (2013.01); *C07D 233/64* (2013.01); *C07F 9/6506* (2013.01); *C12Q 1/6886* (2013.01); *G01N 33/5743* (2013.01); *C12Q 2600/118* (2013.01); *C12Q 2600/136* (2013.01); *C12Q 2600/158* (2013.01); *C12Q 2600/178* (2013.01); *G01N 2500/10* (2013.01)

(58) Field of Classification Search

CPC .................................................... A61K 31/195

See application file for complete search history.

(56) References Cited

U.S. PATENT DOCUMENTS

| | | | |
|---|---|---|---|
| 5,324,731 | A | 6/1994 | Kaddurah-Daouk et al. |
| 5,676,978 | A | 10/1997 | Teicher et al. |
| 6,316,503 | B1 | 11/2001 | Li et al. |
| 7,247,748 | B2 | 7/2007 | Thompson et al. |
| 7,365,085 | B2 | 4/2008 | Bhat et al. |
| 7,560,586 | B2 | 7/2009 | Thompson et al. |
| 7,576,215 | B2 | 8/2009 | Collini et al. |
| 7,799,782 | B2 | 9/2010 | Munson et al. |
| 7,998,995 | B2 | 8/2011 | Boren et al. |

(Continued)

FOREIGN PATENT DOCUMENTS

| | | |
|---|---|---|
| JP | H11507371 A | 6/1999 |
| JP | 2008-509948 A | 4/2008 |

(Continued)

OTHER PUBLICATIONS

Bergenfelz et al., "Systemic Monocytic-MDSCs are Generated from Monocytes and Correlate with Disease Progression in Breast Cancer Patients," PLoS One (2015); 10(5):e0127028 (pp. 1-15).

(Continued)

*Primary Examiner* — Rei Tsang Shiao

(74) *Attorney, Agent, or Firm* — FOX ROTHSCHILD LLP

(57) ABSTRACT

The present invention discloses novel agents and methods for diagnosis and treatment of melanoma. Also disclosed are related arrays, kits, and screening methods.

21 Claims, 59 Drawing Sheets

Specification includes a Sequence Listing.

(56) References Cited

U.S. PATENT DOCUMENTS

| | | | | |
|---|---|---|---|---|
| 9,399,028 | B2 * | 7/2016 | Tavazoie | A61P 9/00 |
| 9,526,710 | B2 * | 12/2016 | Tavazoie | A61P 35/02 |
| 9,707,195 | B2 * | 7/2017 | Tavazoie | A61K 31/416 |
| 9,962,348 | B2 * | 5/2018 | Tavazoie | A61K 31/4155 |
| 10,543,183 | B2 * | 1/2020 | Tavazoie | A61K 31/136 |
| 2004/0072868 | A1 | 4/2004 | Collins et al. | |
| 2005/0107444 | A1 | 5/2005 | Thompsom et al. | |
| 2005/0113580 | A1 | 5/2005 | Thompson et al. | |
| 2005/0131014 | A1 | 6/2005 | Collini et al. | |
| 2005/0282908 | A1 | 12/2005 | Collins et al. | |
| 2009/0286780 | A1 | 11/2009 | Okuda et al. | |
| 2010/0048944 | A1 | 2/2010 | Parhami | |
| 2010/0069367 | A1 | 3/2010 | Boren et al. | |
| 2010/0249096 | A1 | 9/2010 | Aay et al. | |
| 2010/0298410 | A1 | 11/2010 | Obad et al. | |
| 2011/0028384 | A1 | 2/2011 | Blacklow et al. | |
| 2011/0166079 | A1 | 7/2011 | Vitek et al. | |
| 2012/0156216 | A1 | 6/2012 | Oh | |
| 2013/0071403 | A1 | 3/2013 | Rolland et al. | |
| 2015/0023955 | A1 | 1/2015 | Tavazoie et al. | |

FOREIGN PATENT DOCUMENTS

| | | | |
|---|---|---|---|
| JP | 2011525616 | A | 9/2011 |
| JP | 2012-503984 | A | 2/2012 |
| JP | 2012-528180 | A | 11/2012 |
| WO | 03082802 | A1 | 10/2003 |
| WO | 2004043939 | A1 | 5/2004 |
| WO | 2006/004030 | A1 | 1/2006 |
| WO | 2006018182 | A1 | 2/2006 |
| WO | 2007/002563 | A1 | 1/2007 |
| WO | 2008011071 | A2 | 1/2008 |
| WO | 2010036959 | A2 | 4/2010 |
| WO | 2010138598 | A2 | 12/2010 |
| WO | 2011115892 | A1 | 9/2011 |
| WO | 2011130426 | A2 | 10/2011 |
| WO | 2011158667 | A1 | 12/2011 |
| WO | 2012095505 | A1 | 7/2012 |
| WO | 2012096573 | A1 | 7/2012 |
| WO | 2012135082 | A1 | 10/2012 |

OTHER PUBLICATIONS

Chuu et al., "Modulation of Liver X Receptor Signaling as Novel Therapy for Prostate Cancer," Journal of Biomedical Science (Mar. 20, 2007): 14:543-553.

Gielen et al., "Increase in Both CD14-Positive and CD15-Positive Myeloid-Derived Suppressor Cell Subpopulations in the Blood of Patients with Glioma But Predominance of CD15-Positive Myeloid-Derived Suppressor Cells in Glioma Tissue," J NeuropatholExp Neurol (May 2015); 74(5):390-400.

Gros et al., "Myeloid Cells Obtained form the Blood but not from the Tumor Can Suppress T-cell Proliferation in Patients with Melanoma," Clin Cancer Res. (Oct. 1, 2012); 18(19):5212-5223.

Haas, M.J., "Melanoma: three ways around BRAF inhibition," SciBX 3(47); doi: 10.1038/scibx.2010.1400 published online Dec. 9, 2010.

Li et al., "miR-495 and miR-551a inhibit the migration and invasion of human gastric cancer cells by directly interacting with PRL-3," Cancer Lett (Mar. 30, 2012); 323(1):41-47.

Obermajer et al., "PGE2-Induced CXCL12 Production and CXCR4 Expression Controls the Accumulation of Human MDSCs in Ovarian Cancer Environment," Cancer Res. (2011); 71(24):7463-7470.

Pencheva et al., "Broad-Spectrum Therapeutic Suppression of Metastatic melanoma thorugh Nuclear Hormone Receptor Activation," Cell (Feb. 27, 2014); 156(5):986-1001.

Pencheva et al., "Control of metastatic progression by microRNA regulatory networks," Nature Cell Biology (Jun. 3, 2013); 15(6):546-554.

Rudolph et al., "Increased frequencies of CD11b+CD33+CD14+ HLA-DRlow myeloid-derived suppressor cells are an early eent in melanoma patients," Experimental Dermatology (2014); 23:199-218.

Scoles et al., "LiverX receptor agonist inhibits proliferation of ovarian carcinoma cells stimulated by oxidized low density lipoprotein," Gynecology Oncology (2010): 116:109-116.

Talmadge et al., "History of myeloid derived suppressor cells (MDSCs) in the macro-and micro-environment of tumour-bearing hosts," Nat Rev Cancer (2013); 13(10):739-752.

Weber et al., "Phase I/II Study of Metastatic Melanoma Patients Treated with Nivolumab Who Had Progressed after Ipilimumab," Cancer Immunol Res (Apr. 2016); 4(4):345-353.

Zhang et al., "Liver X receptor activation induces apoptosis of melanoma cell through caspase pathway," Cancer Cell International (Feb. 25, 2014); 14(1):16 (1-6).

Zhang et al., A novel subset of B7—H3+CD14+HLA-DR-/low myeloid-derived suppressor cells are associated with progression of human NSCLC, Oncolmmunology (Feb. 2015): 4(2): e977164-1-e977164-12.

Zigler et al., "Tumor Immunotherapy in Melanoma—Strategies for Overcoming Mechanisms of Resistance and Escape," Am J Clin Dermatol (2008); 9(50):307-311.

Marino Jr., J. P. "The Discovery of Tertiary-Amine LXR Agonists with Potent Cholesteroal Efflux Activity in in Macrophages", Bioorganic & Medicinal Chemistry Letters (2009), vol. 19, pp. 5617-5621.

Rough, J. J.et al., "Anti-Proliferative Effect of LXR Agonist T0901317 in Ovarian Carcinoma Cells", J. of Ovarian Research (2010), vol. 3:13, 10 pgs.

Extended European Search Report issued Jun. 28, 2023 in related European Patent Application No. 23155232.4, 10 pgs.

* cited by examiner

Table S1 List of the 50 most upregulated genes in MeWo human melanoma cells in response to GW3965 treatment

| Gene ID | Fold-change* | q-value | Rank | Gene ID | Fold-change* | q-value | Rank |
|---|---|---|---|---|---|---|---|
| *ABCA1* | 19.34 | 1.98E-11 | 1 | *CEACAM1* | 1.83 | 5.58E-06 | 26 |
| *SREBF1* | 8.08 | 9.12E-15 | 2 | *LDLR* | 1.79 | 1.29E-05 | 27 |
| *FABP7* | 7.43 | 1.85E-11 | 3 | *IL1RAPL1* | 1.78 | 1.58E-09 | 28 |
| *LOC645313* | 4.34 | 2.25E-10 | 4 | *PPP1R3C* | 1.78 | 1.64E-07 | 29 |
| ***APOE*** | **4.11** | **1.04E-07** | 5 | *ABCD1* | 1.76 | 4.24E-07 | 30 |
| *KRT34* | 4.09 | 5.99E-18 | 6 | *C10ORF75* | 1.67 | 2.91E-06 | 31 |
| *FASN* | 3.72 | 2.48E-07 | 7 | *LSS* | 1.66 | 1.86E-05 | 32 |
| *IGFBP5* | 2.91 | 1.15E-13 | 8 | *DHCR7* | 1.64 | 2.58E-06 | 33 |
| *TF* | 2.88 | 2.37E-12 | 9 | *CAPS* | 1.63 | 8.35E-06 | 34 |
| *INSIG1* | 2.62 | 3.15E-16 | 10 | *PCYT2* | 1.63 | 3.08E-06 | 35 |
| *MYLIP* | 2.56 | 9.21E-07 | 11 | *C5ORF28* | 1.62 | 3.71E-02 | 36 |
| *LPCAT3* | 2.54 | 2.80E-15 | 12 | *TMEM119* | 1.60 | 1.15E-04 | 37 |
| *ACACA* | 2.43 | 1.56E-12 | 13 | *LPXN* | 1.60 | 1.15E-07 | 38 |
| *SCD* | 2.42 | 3.56E-08 | 14 | *SMPDL3A* | 1.59 | 2.39E-04 | 39 |
| *FCRLA* | 2.19 | 9.13E-09 | 15 | *SPOCD1* | 1.58 | 7.18E-07 | 40 |
| *FADS1* | 2.12 | 2.01E-09 | 16 | *ACLY* | 1.58 | 6.56E-11 | 41 |
| *ACSS2* | 2.02 | 1.88E-08 | 17 | *VGLL3* | 1.57 | 1.32E-04 | 42 |
| *SLC2A6* | 2.02 | 5.99E-18 | 18 | *MVD* | 1.57 | 1.13E-03 | 43 |
| *ACSL3* | 1.94 | 5.35E-10 | 19 | *NAV3* | 1.55 | 2.32E-04 | 44 |
| *TMEM135* | 1.91 | 9.06E-07 | 20 | *HS.538962* | 1.55 | 1.40E-07 | 45 |
| *ADM* | 1.88 | 3.78E-05 | 21 | *TUBB2B* | 1.53 | 3.46E-08 | 46 |
| *LPIN1* | 1.88 | 5.94E-08 | 22 | *LOC728285* | 1.53 | 2.19E-06 | 47 |
| *MID1IP1* | 1.85 | 7.48E-09 | 23 | *PHLDA2* | 1.52 | 2.77E-07 | 48 |
| *FDPS* | 1.84 | 5.49E-05 | 24 | *APOLD1* | 1.51 | 9.50E-05 | 49 |
| *CCL2* | 1.83 | 1.00E-08 | 25 | *BEX1* | 1.51 | 1.08E-09 | 50 |

* Fold-upregulation in array-based gene expression for GW3965 treatment (1 μM, 48 hrs) versus DMSO control treatment

FIG. 26

SEQUENCE LISTING

```
Sequence total quantity: 141
SEQ ID NO: 1            moltype = DNA  length = 1223
FEATURE                 Location/Qualifiers
source                  1..1223
                        mol_type = unassigned DNA
                        organism = Homo sapiens
SEQUENCE: 1
gggatccttg agtcctactc agccccagcg gaggtgaagg acgtccttcc ccaggagccg  60
actggccaat cacaggcagg aagatgaagg ttctgtgggc tgcgttgctg gtcacattcc  120
tggcaggatg ccaggccaag gtggagcaag cggtggagac agagccggag cccgagctgc  180
gccagcagac cgagtggcag agcggccagc gctgggaact ggcactgggt cgcttttggg  240
attacctgcg ctgggtgcag acactgtctg agcaggtgca ggaggagctg ctcagctccc  300
aggtcaccca ggaactgagg gcgctgatgg acgagaccat gaaggagttg aaggcctaca  360
aatcggaact ggaggaacaa ctgaccccgg tggcggagga gacgcgggca cggctgtcca  420
aggagctgca ggcggcgcag gcccggctgg gcgcggacat ggaggacgtg tgcggccgcc  480
tggtgcagta ccgcggcgag gtgcaggcca tgctcggcca gagcaccgag gagctgcggg  540
tgcgcctcgc ctcccacctg cgcaagctgc gtaagcggct cctccgcgat gccgatgacc  600
tgcagaagcg cctggcagtg taccaggccg gggcccgcga gggcgccgag cgcggcctca  660
gcgccatccg cgagcgcctg gggcccctgg tggaacaggg ccgcgtgcgg gccgccactg  720
tgggctccct ggccggccag ccgctacagg agcgggccca ggcctggggc gagcggctgc  780
gcgcgcggat ggaggagatg ggcagccgga cccgcgaccg cctggacgag gtgaaggagc  840
aggtggcgga ggtgcgcgcc aagctggagg agcaggccca gcagatacgc ctgcaggccg  900
aggccttcca ggcccgcctc aagagctggt tcgagcccct ggtggaagac atgcagcgcc  960
agtgggccgg gctggtggag aaggtgcagg ctgccgtggg caccagcgcc gcccctgtgc  1020
ccagcgacaa tcactgaacg ccgaagcctg cagccatgcg accccacgcc accccgtgcc  1080
tcctgcctcc gcgcagcctg cagcgggaga ccctgtcccc gccccagccg tcctcctggg  1140
gtggacccta gtttaataaa gattcaccaa gtttcacgca aaaaaaaaaa aaaaaaaaaa  1200
aaaaaaaaaa aaaaaaaaaa aaa                                          1223

SEQ ID NO: 2            moltype = AA  length = 317
FEATURE                 Location/Qualifiers
source                  1..317
                        mol_type = protein
                        organism = Homo sapiens
SEQUENCE: 2
MKVLWAALLV TFLAGCQAKV EQAVETEPEP ELRQQTEWQS GQRWELALGR FWDYLRWVQT  60
LSEQVQEELL SSQVTQELRA LMDETMKELK AYKSELEEQL TPVAEETRAR LSKELQAAQA  120
RLGADMEDVC GRLVQYRGEV QAMLGQSTEE LRVRLASHLR KLRKRLLRDA DDLQKRLAVY  180
QAGAREGAER GLSAIRERLG PLVEQGRVRA ATVGSLAGQP LQERAQAWGE RLRARMEEMG  240
SRTRDRLDEV KEQVAEVRAK LEEQAQQIRL QAEAFQARLK SWFEPLVEDM QRQWAGLVEK  300
VQAAVGTSAA PVPSDNH                                                 317

SEQ ID NO: 3            moltype = RNA  length = 3203
FEATURE                 Location/Qualifiers
source                  1..3203
                        mol_type = unassigned RNA
                        organism = Homo sapiens
SEQUENCE: 3
agtcccaccc ttcggcgcag ggctccggcc aacacagccc tccaggccgc ctactctcca  60
gccagccggc tccacggacc cacggaaggg caagggggcg gcctcggggc ggcgggacag  120
ttgtcggagg gcgccctcca ggcccaagcc gccttctccg gcccccgcca tggcccgggg  180
cggcagtcag agctggagct ccggggaatc agacgggcag ccaaaggagc agacgcccga  240
gaagcccaga cacaagatgg tgaaggagac ccagtactat gacatcctgg gcgtgaagcc  300
cagcgcgtcc ccggaggaga tcaagaaggc ctatcggaag ctggcgctca agtaccaccc  360
ggacaagaac ccggatgagg gcgagaagtt taaactcata tcccaggcat atgaagtgct  420
ttcagatcca aagaaaaggg atgtttatga ccaaggcgga gagcaggcaa ttaaagaagg  480
aggctcaggc agccccagct tctcttcacc catggacatc tttgacatgt tctttggtgg  540
tggtggacgg atggctagag agagaagagg caagaatgtt gtacaccagt tatctgtaac  600
tcttgaagat ctatataatg gagtcacgaa gaaattggcc ctccagaaaa atgtaatttg  660
tgagaaatgt gaaggtgttg gtgggaagaa gggatcggtg gagaagtgcc cgctgtgcaa  720
ggggcggggg atgcagatcc acatccagca gatcgggccg ggcatggtac agcagatcca  780
gaccgtgtgc atcgagtgca agggccaggg tgagcgcatc aaccccaagg accgctgcga  840
gagctgcagc ggggccaagg tgatccgtga gaagaagatt atcgaggtac atgttgaaaa  900
aggtatgaaa gatgggcaaa agatactatt tcatggagaa ggagatcagg agcctgagct  960
ggagcctggt gatgtcataa ttgtgcttga tcagaaggat catagtgtct ttcagagacg  1020
aggccatgac ttgatcatga aaatgaaaat tcagctttct gaagctcttt gtggcttcaa  1080
gaagacgata aaaacattgg acaatcgaat tcttgttatt acatccaaag caggtgaggt  1140
gataaagcac ggggacctga gatgcgtgcg cgatgaagga atgcccatct acaaagcacc  1200
cctggaaaaa gggattctga tcatacagtt tttagtaatc tttcctgaaa aacactggct  1260
ttctctggaa aagcttcctc agctggaagc tttactccct cctcgacaga aagtgaggat  1320
tacagatgac atggatcagg tggagctgaa ggagttttgt cccaatgagc agaactggcg  1380
tcagcacagg gaggcctacg aggaggacga agacgggccc caggctggag tgcagtgcca  1440
gacggcatga cgtggtgcgg ggcagcgtgg ccccaccgga ctagcacatg atgaatgtaa  1500
```

-continued

```
agttggcaca atgaaaatga catcgcttta atggccttgt gtttgggatg tcctgtgtat  1560
gtgttcagca ttcttaattg ctgagtgtct ttttggcttt tcttttggtt gtaacttaag  1620
ttatagctta atttatattt aaatgtttta agtataaatc acctctagtc tgcatatgga  1680
atctgttcat ttctatttc aggatatact tttgagatgt cagtgattgc accaatactt   1740
tgtgcttcta gtggctttgc cataattcag tgtcaccaat aaggcacagc ccagttagca  1800
gcttagcccc cctagcaaac cccaaggcac aaagtgggca tcctgactca tctctaggtc  1860
tgtggtttct cccctcttcc cttggcagag ttattgaggg catgatctca gggctgctaa  1920
gataacattt ctgaggattc tagatgatcc tcttaaagaa taaaagcaca tccgtggatc  1980
ggacatggct gcatgtgcct gcttaacagg gccaacttag ttcctactgt tctgtgccct  2040
tcagtggatg gaacgtgagt gtctgatcat ctctcttgga agttttctga accttccaag  2100
ctctgtggtg aggacaaacc agtgtttgaa tcatatgctg ataactgttt gcctgtgacc  2160
ctcacacctt gttcttcagg gttttaatga ttttctgttg acaacttttg caatgctttc  2220
ccaccaaagt gcttacttgt aaagaaaact aaatccttct gtgtccccgg cagcctcagt  2280
gcagcaacag aagccaaggg agaatgctgc tggtttggcc catggcacag ccagcttctc  2340
tgaccagtaa tccggggtga cttgagggtc tgcaaaggca tagaactccc cagtgttttc  2400
cacctcattc tcccagattg agctcccttc caaaggatcg ttcctctcat tgcacagcca  2460
tattacaaag ggtttcctgc tcaagtgatg ttttggtaag aacttcgctg agttccactg  2520
tggattacag tttgtatgga ctactactgt aaattatagc ttgtttggag ggatattagt  2580
cattatttta ttcatgacag gtagactaca attcgaactt agggttacct cagtctttag  2640
ccattactgc ttatttcttt tccccaagtc acaaaaaact tgtaagctgc tgggttaaag  2700
cagaggccac ctgtcagatc taccctaccc ttatttggtt acatggcacc tgagagtttc  2760
actcagacca gggatcttcc ttaggagggt caaagtgcag atcagaccat gcaggtaagg  2820
tgaaccagct gcacggacca ggttcccgca aaacattgcc agctagtgag gcataatttg  2880
ctcaaagtat agaaacagcc cacctgtgcc cactttgacc attggtgagg atagatataa  2940
aatcacttct tccaacgaag cctaggtgaa aatctattta taaatggacc acaactctgg  3000
ggtgtcgttt ttgtgctgtg acttcctaat tattgctaaa gaactactgt ttagttggta  3060
atggtgtaaa attacattca gctccttctt gtcatataaa aggaatttgg agggtgtcgc  3120
ttaaaatttt attccacctg tacatttgtc actttaaaat taaaattgag ctggtatgag  3180
agataaaaaa aaaaaaaaaa aaa                                           3203

SEQ ID NO: 4            moltype = AA  length = 426
FEATURE                 Location/Qualifiers
source                  1..426
                        mol_type = protein
                        organism = Homo sapiens
SEQUENCE: 4
MARGGSQSWS SGESDGQPKE QTPEKPRHKM VKETQYYDIL GVKPSASPEE IKKAYRKLAL  60
KYHPDKNPDE GEKFKLISQA YEVLSDPKKR DVYDQGGEQA IKEGGSGSPS FSSPMDIFDM  120
FFGGGGRMAR ERRGKNVVHQ LSVTLEDLYN GVTKKLALQK NVICEKCEGV GGKKGSVEKC  180
PLCKGRGMQI HIQQIGPGMV QQIQTVCIEC KGQGERINPK DRCESCSGAK VIREKKIIEV  240
HVEKGMKDGQ KILFHGEGDQ EPELEPGDVI IVLDQKDHSV FQRRGHDLIM KMKIQLSEAL  300
CGFKKTIKTL DNRILVITSK AGEVIKHGDL RCVRDEGMPI YKAPLEKGIL IIQFLVIFPE  360
KHWLSLEKLP QLEALLPPRQ KVRITDDMDQ VELKEFCPNE QNWRQHREAY EEDEDGPQAG  420
VQCQTA                                                              426

SEQ ID NO: 5            moltype = RNA  length = 3064
FEATURE                 Location/Qualifiers
source                  1..3064
                        mol_type = unassigned RNA
                        organism = Homo sapiens
SEQUENCE: 5
gtgaccgtga cgcgcgagcg ggcggcgggg gcgcgggcca ggggcgcggg ccagggtgcc  60
ggcaggggcg tccggggcgc tctgaccggc ctcgcccgcc ccccccgcag acacaagatg  120
gtgaaggaga cccagtacta tgacatcctg ggcgtgaagc ccagcgcgtc cccggaggag  180
atcaagaagg cctatcggaa gctggcgctc aagtaccacc cggacaagaa cccggatgag  240
ggcgagaagt ttaaactcat atcccaggca tatgaagtgc tttcagatcc aaagaaaagg  300
gatgtttatg accaaggcgg agagcaggca attaaagaag gaggctcagg cagccccagc  360
ttctcttcac ccatggacat ctttgacatg ttctttggtg gtggtggacg gatggctaga  420
gagagaagag gcaagaatgt tgtacaccag ttatctgtaa ctcttgaaga tctatataat  480
ggagtcacga agaaattggc cctccagaaa aatgtaattt gtgagaaatg tgaaggtgtt  540
ggtgggaaga agggatcggt ggagaagtgc ccgctgtgca agggcgcggg gatgcagatc  600
cacatccagc agatcgggcc gggcatggta cagcagatcc agaccgtgtg catcgagtgc  660
aagggccagg gtgagcgcat caaccccaag gaccgctgcg agagctgcag cggggccaag  720
gtgatccgtg agaagaagat tatcgaggta catgttgaaa aaggtatgaa agatgggcaa  780
aagatactat ttcatggaga aggagatcag gagcctgagc tggagcctgg tgatgtcata  840
attgtgcttg atcagaagga tcatagtgtc tttcagagac gaggccatga cttgatcatg  900
aaaatgaaaa ttcagctttc tgaagctctt tgtggcttca agaagacgat aaaaacattg  960
gacaatcgaa ttcttgttat tacatccaaa gcaggtgagg tgataaagca cggggacctg  1020
agatgcgtgc gcgatgaagg aatgcccatc tacaaagcac ccctggaaaa agggattctg  1080
atcatacagt ttttagtaat ctttcctgaa aaacactggc tttctctgga aaagcttcct  1140
cagctggaag ctttactccc tcctcgacag aaagtgagga ttacagatga catggatcag  1200
gtggagctga aggagttttg tcccaatgag cagaactggc gtcagcacag ggaggcctac  1260
gaggaggacg aagacgggcc ccaggctgga gtgcagtgcc agacggcatg acgtggtgcg  1320
gggcagcgtg gccccaccgg actagcacat gatgaatgta aagttggcac aatgaaaatg  1380
acatcgcttt aatggccttg tgtttgggat gtcctgtgta tgtgttcagc attcttaatt  1440
gctgagtgtc tttttggctt ttcttttggt tgtaacttaa gttatagctt aatttatatt  1500
taaatgtttt aagtataaat cacctctagt ctgcatatgg aatctgttca tttctatttt  1560
caggatatac ttttgagatg tcagtgattg caccaatact ttgtgcttct agtggctttg  1620
ccataattca gtgtcaccaa taaggcacag cccagttagc agcttagccc ccctagcaaa  1680
```

```
ccccaaggca caaagtgggc atcctgactc atctctaggt ctgtggtttc tcccctcttc  1740
ccttggcaga gttattgagg gcatgatctc agggctgcta agataacatt tctgaggatt  1800
ctagatgatc ctcttaaaga ataaaagcac atccgtggat cggacatggc tgcatgtgcc  1860
tgcttaacag ggccaactta gttcctactg ttctgtgccc ttcagtggat ggaacgtgag  1920
tgtctgatca tctctcttgg aagttttctg aaccttccaa gctctgtggt gaggacaaac  1980
cagtgtttga atcatatgct gataactgtt tgcctgtgac cctcacacct tgttcttcag  2040
ggttttaatg attttctgtt gacaactttt gcaatgcttt cccaccaaag tgcttacttg  2100
taaagaaaac taaatccttc tgtgtccccg gcagcctcag tgcagcaaca gaagccaagg  2160
gagaatgctg ctggtttggc ccatggcaca gccagcttct ctgaccagta atccggggtg  2220
acttgagggt ctgcaaaggc atagaactcc ccagtgtttt ccacctcatt ctcccagatt  2280
gagctccctt ccaaaggatc gttcctctca ttgcacagcc atattacaaa gggtttcctg  2340
ctcaagtgat gttttggtaa gaacttcgct gagttccact gtggattaca gtttgtatgg  2400
actactactg taaattatag cttgtttgga gggatattag tcattatttt attcatgaca  2460
ggtagactac aattcgaact tagggttacc tcagtcttta gccattactg cttatttctt  2520
ttccccaagt cacaaaaaac ttgtaagctg ctgggttaaa gcagaggcca cctgtcagat  2580
ctaccctacc cttatttggt tacatggcac ctgagagttt cactcagacc agggatcttc  2640
cttaggaggg tcaaagtgca gatcagacca tgcaggtaag gtgaaccagc tgcacggacc  2700
aggttcccgc aaaacattgc cagctagtga ggcataattt gctcaaagta tagaaacagc  2760
ccacctgtgc ccactttgac cattggtgag gatagatata aaatcacttc ttccaacgaa  2820
gcctaggtga aaatctattt ataaatggac cacaactctg ggtgtcgtt tttgtgctgt  2880
gacttcctaa ttattgctaa agaactactg tttagttggt aatggtgtaa aattacattc  2940
agctccttct tgtcatataa aaggaatttg gagggtgtcg cttaaaattt tattccacct  3000
gtacatttgt cactttaaaa ttaaaattga gctggtatga gagataaaaa aaaaaaaaaa  3060
aaaa                                                                3064

SEQ ID NO: 6           moltype = AA  length = 397
FEATURE                Location/Qualifiers
source                 1..397
                       mol_type = protein
                       organism = Homo sapiens
SEQUENCE: 6
MVKETQYYDI LGVKPSASPE EIKKAYRKLA LKYHPDKNPD EGEKFKLISQ AYEVLSDPKK  60
RDVYDQGGEQ AIKEGGSGSP SFSSPMDIFD MFFGGGGRMA RERRGKNVVH QLSVTLEDLY  120
NGVTKKLALQ KNVICEKCEG VGGKKGSVEK CPLCKGRGMQ IHIQQIGPGM VQQIQTVCIE  180
CKGQGERINP KDRCESCSGA KVIREKKIIE VHVEKGMKDG QKILFHGEGD QEPELEPGDV  240
IIVLDQKDHS VFQRRGHDLI MKMKIQLSEA LCGFKKTIKT LDNRILVITS KAGEVIKHGD  300
LRCVRDEGMP IYKAPLEKGI LIIQFLVIFP EKHWLSLEKL PQLEALLPPR QKVRITDDMD  360
QVELKEFCPN EQNWRQHREA YEEDEDGPQA GVQCQTA                            397

SEQ ID NO: 7           moltype = RNA  length = 2891
FEATURE                Location/Qualifiers
source                 1..2891
                       mol_type = unassigned RNA
                       organism = Homo sapiens
SEQUENCE: 7
acatttcagc aagctggcta aagacatgtg ggaaagcctg accctggatt caggtcaaat  60
ctcagcactc acaagattta aactcatatc ccaggcatat gaagtgcttt cagatccaaa  120
gaaaagggat gtttatgacc aaggcggaga gcaggcaatt aaagaaggag gctcaggcag  180
ccccagcttc tcttcaccca tggacatctt tgacatgttc tttggtggtg gtggacggat  240
ggctagagag agaagaggca agaatgttgt acaccagtta tctgtaactc ttgaagatct  300
atataatgga gtcacgaaga aattggccct ccagaaaaat gtaatttgtg agaaatgtga  360
aggtgttggt gggaagaagg gatcggtgga gaagtgcccg ctgtgcaagg ggcgggggat  420
gcagatccac atccagcaga tcgggccggg catggtacag cagatccaga ccgtgtgcat  480
cgagtgcaag ggccagggtg agcgcatcaa ccccaaggac cgctgcgaga gctgcagcgg  540
ggccaaggtg atccgtgaga agaagattat cgaggtacat gttgaaaaag gtatgaaaga  600
tgggcaaaag atactatttc atggagaagg agatcaggag cctgagctgg agcctggtga  660
tgtcataatt gtgcttgatc agaaggatca tagtgtcttt cagagacgag gccatgactt  720
gatcatgaaa atgaaaattc agctttctga agctctttgt ggcttcaaga agacgataaa  780
aacattggac aatcgaattc ttgttattac atccaaagca ggtgaggtga taaagcacgg  840
ggacctgaga tgcgtgcgcg atgaaggaat gcccatctac aaagcacccc tggaaaaagg  900
gattctgatc atacagtttt tagtaatctt tcctgaaaaa cactggcttt ctctggaaaa  960
gcttcctcag ctggaagctt tactccctcc tcgacagaaa gtgaggatta cagatgacat  1020
ggatcaggtg gagctgaagg agttttgtcc caatgagcag aactggcgtc agcacaggga  1080
ggcctacgag gaggacgaag acgggcccca ggctggagtg cagtgccaga cggcatgacg  1140
tggtgcgggg cagcgtggcc ccaccggact agcacatgat gaatgtaaag ttggcacaat  1200
gaaaatgaca tcgctttaat ggccttgtgt ttgggatgtc ctgtgtatgt gttcagcatt  1260
cttaattgct gagtgtcttt ttggcttttc ttttggttgt aacttaagtt atagcttaat  1320
ttatatttaa atgttttaag tataaatcac ctctagtctg catatggaat ctgttcattt  1380
ctattttcag gatatacttt tgagatgtca gtgattgcac caatactttg tgcttctagt  1440
ggctttgcca taattcagtg tcaccaataa ggcacagccc agttagcagc ttagcccccc  1500
tagcaaaccc caaggcacaa agtgggcatc ctgactcatc tctaggtctg tggtttctcc  1560
cctcttccct tggcagagtt attgagggca tgatctcagg gctgctaaga taacatttct  1620
gaggattcta gatgatcctc ttaaagaata aaagcacatc cgtggatcgg acatggctgc  1680
atgtgcctgc ttaacagggc caacttagtt cctactgttc tgtgcccttc agtggatgga  1740
acgtgagtgt ctgatcatct ctcttggaag ttttctgaac cttccaagct ctgtggtgag  1800
gacaaaccag tgtttgaatc atatgctgat aactgtttgc ctgtgaccct cacaccttgt  1860
tcttcagggt tttaatgatt ttctgttgac aacttttgca atgctttccc accaaagtgc  1920
ttacttgtaa agaaaactaa atccttctgt gtccccggca gcctcagtgc agcaacagaa  1980
gccaagggag aatgctgctg gtttggccca tggcacagcc agcttctctg accagtaatc  2040
```

-continued

```
cggggtgact tgagggtctg caaaggcata gaactcccca gtgttttcca cctcattctc  2100
ccagattgag ctcccttcca aaggatcgtt cctctcattg cacagccata ttacaaaggg  2160
tttcctgctc aagtgatgtt ttggtaagaa cttcgctgag ttccactgtg gattacagtt  2220
tgtatggact actactgtaa attatagctt gtttggaggg atattagtca ttattttatt  2280
catgacaggt agactacaat tcgaacttag ggttacctca gtctttagcc attactgctt  2340
atttcttttc cccaagtcac aaaaaacttg taagctgctg ggttaaagca gaggccacct  2400
gtcagatcta ccctaccctt atttggttac atggcacctg agagtttcac tcagaccagg  2460
gatcttcctt aggagggtca aagtgcagat cagaccatgc aggtaaggtg aaccagctgc  2520
acggaccagg ttcccgcaaa acattgccag ctagtgaggc ataatttgct caaagtatag  2580
aaacagccca cctgtgccca ctttgaccat tggtgaggat agatataaaa tcacttcttc  2640
caacgaagcc taggtgaaaa tctatttata aatggaccac aactctgggg tgtcgttttt  2700
gtgctgtgac ttcctaatta ttgctaaaga actactgttt agttggtaat ggtgtaaaat  2760
tacattcagc tccttcttgt catataaaag gaatttggag ggtgtcgctt aaaattttat  2820
tccacctgta catttgtcac tttaaaatta aaattgagct ggtatgagag ataaaaaaaa  2880
aaaaaaaaaa a                                                       2891

SEQ ID NO: 8           moltype = AA  length = 370
FEATURE                Location/Qualifiers
source                 1..370
                       mol_type = protein
                       organism = Homo sapiens
SEQUENCE: 8
MWESLTLDSG QISALTRFKL ISQAYEVLSD PKKRDVYDQG GEQAIKEGGS GSPSFSSPMD  60
IFDMFFGGGG RMARERRGKN VVHQLSVTLE DLYNGVTKKL ALQKNVICEK CEGVGGKKGS  120
VEKCPLCKGR GMQIHIQQIG PGMVQQIQTV CIECKGQGER INPKDRCESC SGAKVIREKK  180
IIEVHVEKGM KDGQKILFHG EGDQEPELEP GDVIIVLDQK DHSVFQRRGH DLIMKMKIQL  240
SEALCGFKKT IKTLDNRILV ITSKAGEVIK HGDLRCVRDE GMPIYKAPLE KGILIIQFLV  300
IFPEKHWLSL EKLPQLEALL PPRQKVRITD DMDQVELKEF CPNEQNWRQH REAYEEDEDG  360
PQAGVQCQTA                                                         370

SEQ ID NO: 9           moltype = RNA  length = 14905
FEATURE                Location/Qualifiers
source                 1..14905
                       mol_type = unassigned RNA
                       organism = Homo sapiens
SEQUENCE: 9
cagcggtgcg agctccaggc ccatgcactg aggaggcgga aacaagggga gcccccagag  60
ctccatcaag ccccctccaa aggctcccct acccggtcca cgccccccac ccccctccc   120
cgcctcctcc caattgtgca tttttgcagc cggaggcggc tccgagatgg ggctgtgagc  180
ttcgcccggg gagggggaaa gagcagcgag gagtgaagcg ggggggtggg gtgaagggtt  240
tggatttcgg ggcagggggc gcacccccgt cagcaggccc tccccaaggg gctcggaact  300
ctacctcttc acccacgccc ctggtgcgct ttgccgaagg aaagaataag aacagagaag  360
gaggaggggg aaaggaggaa aagggggacc ccccaactgg ggggggtgaa ggagagaagt  420
agcaggacca gaggggaagg ggctgctgct tgcatcagcc cacaccatgc tgaccccgcc  480
gttgctcctg ctgctgcccc tgctctcagc tctggtcgcg gcggctatcg acgcccctaa  540
gacttgcagc cccaagcagt ttgcctgcag agatcaaata acctgtatct caaagggctg  600
gcggtgcgac ggtgagaggg actgcccaga cggatctgac gaggcccctg agatttgtcc  660
acagagtaag gcccagcgat gccagccaaa cgagcataac tgcctgggta ctgagctgtg  720
tgttcccatg tcccgcctct gcaatggggt ccaggactgc atggacggct cagatgaggg  780
gccccactgc cgagagctcc aaggcaactg ctctcgcctg ggctgccagc accattgtgt  840
ccccacactc gatgggccca cctgctactg caacagcagc tttcagcttc aggcagatgg  900
caagacctgc aaagattttg atgagtgctc agtgtacggc acctgcagcc agctatgcac  960
caacacagac ggctccttca tatgtggctg tgttgaagga tacctcctgc agccggataa  1020
ccgctcctgc aaggccaaga acgagccagt agaccggccc cctgtgctgt tgatagccaa  1080
ctcccagaac atcttggcca cgtacctgag tggggcccag gtgtctacca tcacacctac  1140
gagcacgcgg cagaccacag ccatggactt cagctatgcc aacgagaccg tatgctgggt  1200
gcatgttggg gacagtgctg ctcagacgca gctcaagtgt gcccgcatgc ctggcctaaa  1260
gggcttcgtg gatgagcaca ccatcaacat ctccctcagt ctgcaccacg tggaacagat  1320
ggccatcgac tggctgacag gcaacttcta ctttgtggat gacatcgatg ataggatctt  1380
tgtctgcaac agaaatgggg acacatgtgt cacattgcta gacctggaac tctacaaccc  1440
caagggcatt gccctggacc ctgccatggg gaaggtgttt ttcactgact atgggcagat  1500
cccaaaggtg gaacgctgtg acatggatgg gcagaaccgc accaagctcg tcgacagcaa  1560
gattgtgttt cctcatggca tcacgctgga cctggtcagc cgccttgtct actgggcaga  1620
tgcctatctg gactatattg aagtggtgga ctatgagggc aagggccgcc agaccatcat  1680
ccagggcatc ctgattgagc acctgtacgg cctgactgtg tttgagaatt atctctatgc  1740
caccaactcg gacaatgcca atgcccagca gaagacgagt gtgatccgtg tgaaccgctt  1800
taacagcacc gagtaccagg ttgtcacccg ggtggacaag ggtggtgccc tccacatcta  1860
ccaccagagg cgtcagcccc gagtgaggag ccatgcctgt gaaaacgacc agtatgggaa  1920
gccgggtggc tgctctgaca tctgcctgct ggccaacagc cacaaggcgc ggacctgccg  1980
ctgccgttcc ggcttcagcc tgggcagtga cgggaagtca tgcaagaagc cggagcatga  2040
gctgttcctc gtgtatggca agggccggcc aggcatcatc cggggcatgg atatgggggc  2100
caaggtcccg gatgagcaca tgatccccat tgaaaacctc atgaaccccc gagccctgga  2160
cttccacgct gagaccggct tcatctactt tgccgacacc accagctacc tcattggccg  2220
ccagaagatt gatggcactg agcgggagac catcctgaag gacggcatcc acaatgtgga  2280
gggtgtggcc gtggactgga tgggagacaa tctgtactgg acggacgatg ggcccaaaaa  2340
gacaatcagc gtggccaggc tggagaaagc tgctcagacc cgcaagactt taatcgaggg  2400
caaaatgaca caccccaggg ctattgtggt ggatccactc aatgggtgga tgtactggac  2460
agactgggag gaggacccca aggacagtcg gcgtgggcgg ctggagaggg cgtggatgga  2520
tggctcacac cgagacatct ttgtcacctc caagacagtg ctttggccca atgggctaag  2580
```

-continued

```
cctggacatc ccggctgggc gcctctactg ggtggatgcc ttctacgacc gcatcgagac  2640
gatactgctc aatggcacag accggaagat tgtgtatgaa ggtcctgagc tgaaccacgc  2700
ctttggcctg tgtcaccatg gcaactacct cttctggact gagtatcgga gtggcagtgt  2760
ctaccgcttg gaacggggtg taggaggcgc accccccact gtgacccttc tgcgcagtga  2820
gcggcccccc atctttgaga tccgaatgta tgatgcccag cagcagcaag ttggcaccaa  2880
caaatgccgg gtgaacaatg gcggctgcag cagcctgtgc ttggccaccc ctgggagccg  2940
ccagtgcgcc tgtgctgagg accaggtgtt ggacgcagac ggcgtcactt gcttggcgaa  3000
cccatcctac gtgcctccac cccagtgcca gccaggcgag tttgcctgtg ccaacagccg  3060
ctgcatccag gagcgctgga agtgtgacgg agacaacgat tgcctggaca acagtgatga  3120
ggccccagcc ctctgccatc agcacacctg cccctcggac cgattcaagt gcgagaacaa  3180
ccggtgcatc cccaaccgct ggctctgcga cggggacaat gactgtggga acagtgaaga  3240
tgagtccaat gccacttgtt cagcccgcac ctgccccccc aaccagttct cctgtgccag  3300
tggccgctgc atccccatct cctggacgtg tgatctggat gacgactgtg gggaccgctc  3360
tgatgagtct gcttcgtgtg cctatcccac ctgcttcccc ctgactcagt ttacctgcaa  3420
caatggcaga tgtatcaaca tcaactggag atgcgacaat gacaatgact gtggggacaa  3480
cagtgacgaa gccggctgca gccactcctg ttctagcacc cagttcaagt gcaacagcgg  3540
gcgttgcatc cccgagcact ggacctgcga tggggacaat gactgcggag actacagtga  3600
tgagacacac gccaactgca ccaaccaggc cacgaggccc cctggtggct gccacactga  3660
tgagttccag tgccggctgg atggactatg catccccctg cggtggcgct gcgatgggga  3720
cactgactgc atggactcca gcgatgagaa gagctgtgag ggagtgaccc acgtctgcga  3780
tcccagtgtc aagtttggct gcaaggactc agctcggtgc atcagcaaag cgtgggtgtg  3840
tgatggcgac aatgactgtg aggataactc ggacgaggag aactgcgagt ccctggcctg  3900
caggccaccc tcgcaccctt gtgccaacaa cacctcagtc tgcctgcccc ctgacaagct  3960
gtgtgatggc aacgacgact gtggcgacgg ctcagatgag ggcgagctct gcgaccagtg  4020
ctctctgaat aacggtggct gcagccacaa ctgctcagtg gcacctggcg aaggcattgt  4080
gtgttcctgc cctctgggca tggagctggg gcccgacaac cacacctgcc agatccagag  4140
ctactgtgcc aagcatctca aatgcagcca aaagtgcgac cagaacaagt tcagcgtgaa  4200
gtgctcctgc tacgagggct gggtcctgga acctgacggc gagagctgcc gcagcctgga  4260
ccccttcaag ccgttcatca ttttctccaa ccgccatgaa atccggcgca tcgatcttca  4320
caaaggagac tacagcgtcc tggtgcccgg cctgcgcaac accatcgccc tggacttcca  4380
cctcagccag agcgccctct actggaccga cgtggtggag gacaagatct accgcgggaa  4440
gctgctggac aacggagccc tgactagttt cgaggtggtg attcagtatg gcctggccac  4500
acccgagggc ctggctgtag actggattgc aggcaacatc tactgggtgg agagtaacct  4560
ggatcagatc gaggtggcca agctggatgg gaccctccgg accaccctgc tggccggtga  4620
cattgagcac ccaagggcaa tcgcactgga tccccgggat gggatcctgt tttggacaga  4680
ctgggatgcc agcctgcccc gcattgaggc agcctccatg agtggggctg ggcgccgcac  4740
cgtgcaccgg gagaccggct ctgggggctg gcccaacggg ctcaccgtgg actacctgga  4800
gaagcgcatc ctttggattg acgccaggtc agatgccatt tactcagccc gttacgacgg  4860
ctctggccac atggaggtgc ttcggggaca cgagttcctg tcgcacccgt ttgcagtgac  4920
gctgtacggg ggggaggtct actggactga ctggcgaaca aacacactgg ctaaggccaa  4980
caagtggacc ggccacaatg tcaccgtggt acagaggacc aacacccagc cctttgacct  5040
gcaggtgtac caccctcccc gccagcccat ggctcccaat ccctgtgagg ccaatggggg  5100
ccagggcccc tgctcccacc tgtgtctcat caactacaac cggaccgtgt cctgcgcctg  5160
cccccacctc atgaagctcc acaaggacaa caccacctgc tatgagttta agaagttcct  5220
gctgtacgca cgtcagatgg agatccgagg tgtggacctg gatgctccct actacaacta  5280
catcatctcc ttcacggtgc ccgacatcga caacgtcaca gtgctagact acgatgcccg  5340
cgagcagcgt gtgtactggt ctgacgtgcg gacacaggcc atcaagcggg ccttcatcaa  5400
cggcacaggc gtggagacag tcgtctctgc agacttgcca aatgcccacg ggctggctgt  5460
ggactgggtc tcccgaaacc tgttctggac aagctatgac accaataaga agcagatcaa  5520
tgtggcccgg ctggatggct ccttcaagaa cgcagtggtg cagggcctgg agcagcccca  5580
tggccttgtc gtccaccctc tgcgtgggaa gctctactgg accgatggtg acaacatcag  5640
catggccaac atggatggca gcaatcgcac cctgctcttc agtggccaga agggccccgt  5700
gggcctggct attgacttcc ctgaaagcaa actctactgg atcagctccg ggaaccatac  5760
catcaaccgc tgcaacctgg atgggagtgg gctggaggtc atcgatgcca tgcggagcca  5820
gctgggcaag gccaccgccc tggccatcat gggggacaag ctgtggtggg ctgatcaggt  5880
gtcggaaaag atgggcacat gcagcaaggc tgacggctcg ggctccgtgg tccttcggaa  5940
cagcaccacc ctggtgatgc acatgaaggt ctatgacgag agcatccagc tggaccataa  6000
gggcaccaac ccctgcagtg tcaacaacgg tgactgctcc cagctctgcc tgcccacgtc  6060
agagacgacc cgctcctgca tgtgcacagc cggctatagc ctccggagtg gccagcaggc  6120
ctgcgagggc gtaggttcct ttctcctgta ctctgtgcat gagggaatca ggggaattcc  6180
cctggatccc aatgacaagt cagatgccct ggtcccagtg tccgggacct cgctggctgt  6240
cggcatcgac ttccacgctg aaaatgacac catctactgg gtggacatgg gcctgagcac  6300
gatcagccgg gccaagcggg accagacgtg gcgtgaagac gtggtgacca atggcattgg  6360
ccgtgtggag ggcattgcag tggactggat cgcaggcaac atctactgga cagaccaggg  6420
ctttgatgtc atcgaggtcg cccggctcaa tggctccttc cgctacgtgg tgatctccca  6480
gggtctagac aagccccggg ccatcaccgt ccacccggag aaagggtact tgttctggac  6540
tgagtggggt cagtatccgc gtattgagcg gtctcggcta gatggcacgg agcgtgtggt  6600
gctggtcaac gtcagcatca gctggcccaa cggcatctca gtggactacc aggatgggaa  6660
gctgtactgg tgcgatgcac ggacagacaa gattgaacgg atcgacctgg agacaggtga  6720
gaaccgcgag gtggttctgt ccagcaacaa catggacatg ttttcagtgt ctgtgtttga  6780
ggatttcatc tactggagtg acaggactca tgccaacggc tctatcaagc gcgggagcaa  6840
agacaatgcc acagactccg tgcccctgcg aaccggcatc ggcgtccagc ttaaagacat  6900
caaagtcttc aaccgggacc ggcagaaagg caccaacgtg tgcgcggtgg ccaatggcgg  6960
gtgccagcag ctgtgcctgt accggggccg tgggcagcgg gcctgcgcct gtgcccacgg  7020
gatgctggct gaagacggag catcgtgccg cgagtatgcc ggctacctgc tctactcaga  7080
gcgcaccatt ctcaagagta tccacctgtc ggatgagcgc aacctcaatg cgcccgtgca  7140
gcccttcgag gaccctgagc acatgaagaa cgtcatcgcc ctggcctttg actaccgggc  7200
aggcacctct ccgggcaccc ccaatcgcat cttcttcagc gacatccact ttgggaacat  7260
ccaacagatc aacgacgatg gctccaggag gatcaccatt gtggaaaacg tgggctccgt  7320
```

-continued ggaaggcctg gcctatcacc gtggctggga cactctctat tggacaagct acacgacatc 7380
caccatcacg cgccacacag tggaccagac ccgcccaggg gccttcgagc gtgagaccgt 7440
catcactatg tctggagatg accacccacg ggccttcgtt ttggacgagt gccagaacct 7500
catgttctgg accaactgga atgagcagca tcccagcatc atgcgggcgg cgctctcggg 7560
agccaatgtc ctgaccctta tcgagaagga catccgtacc cccaatggcc tggccatcga 7620
ccaccgtgcc gagaagctct acttctctga cgccaccctg gacaagatcg agcggtgcga 7680
gtatgacggc tcccaccgct atgtgatcct aaagtcagag cctgtccacc ccttcgggct 7740
ggccgtgtat ggggagcaca ttttctggac tgactgggtg cggcgggcag tgcagcgggc 7800
caacaagcac gtgggcagca acatgaagct gctgcgcgtg gacatccccc agcagcccat 7860
gggcatcatc gccgtggcca acgacaccaa cagctgtgaa ctctctccat gccgaatcaa 7920
caacggtggc tgccaggacc tgtgtctgct cactcaccag ggccatgtca actgctcatg 7980
ccgagggggc cgaatcctcc aggatgacct cacctgccga gcggtgaatt cctcttgccg 8040
agcacaagat gagtttgagt gtgccaatgg cgagtgcatc aacttcagcc tgacctgcga 8100
cggcgtcccc cactgcaagg acaagtccga tgagaagcca tcctactgca actcccgccg 8160
ctgcaagaag actttccggc agtgcagcaa tgggcgctgt gtgtccaaca tgctgtggtg 8220
caacggggcc gacgactgtg gggatggctc tgacgagatc ccttgcaaca agacagcctg 8280
tggtgtgggc gagttccgct gccgggacgg gacctgcatc gggaactcca gccgctgcaa 8340
ccagtttgtg gattgtgagg acgcctcaga tgagatgaac tgcagtgcca ccgactgcag 8400
cagctacttc cgcctgggcg tgaagggcgt gctcttccag ccctgcgagc ggacctcact 8460
ctgctacgca cccagctggg tgtgtgatgg cgccaatgac tgtggggact acagtgatga 8520
gcgcgactgc ccaggtgtga aacgccccag atgccctctg aattacttcg cctgccctag 8580
tgggcgctgc atccccatga gctggacgtg tgacaaagag gatgactgtg aacatggcga 8640
ggacgagacc cactgcaaca agttctgctc agaggcccag tttgagtgcc agaaccatcg 8700
ctgcatctcc aagcagtggc tgtgtgacgg cagcgatgac tgtggggatg gctcagacga 8760
ggctgctcac tgtgaaggca agacgtgcgg cccctcctcc ttctcctgcc ctggcaccca 8820
cgtgtgcgtc cccgagcgct ggctctgtga cggtgacaaa gactgtgctg atggtgcaga 8880
cgagagcatc gcagctggtt gcttgtacaa cagcacttgt gacgaccgtg agttcatgtg 8940
ccagaaccgc cagtgcatcc ccaagcactt cgtgtgtgac cacgaccgtg actgtgcaga 9000
tggctctgat gagtcccccg agtgtgagta cccgacctgc ggccccagtg agttccgctg 9060
tgccaatggg cgctgtctga gctcccgcca gtgggagtgt gatggcgaga atgactgcca 9120
cgaccagagt gacgaggctc ccaagaaccc acactgcacc agccaagagc acaagtgcaa 9180
tgcctcgtca cagttcctgt gcagcagtgg gcgctgtgtg gctgaggcac tgctctgcaa 9240
cggccaggat gactgtggcg acagctcgga cgagcgtggc tgccacatca atgagtgtct 9300
cagccgcaag ctcagtggct gcagccagga ctgtgaggac ctcaagatcg gcttcaagtg 9360
ccgctgtcgc cctggcttcc ggctgaagga cgacggccgg acgtgtgctg atgtggacga 9420
gtgcagcacc accttcccct gcagccagcg ctgcatcaac actcatggca gctataagtg 9480
tctgtgtgtg gagggctatg caccccgcgg cggcgacccc cacagctgca aggctgtgac 9540
tgacgaggaa ccgtttctga tcttcgccaa ccggtactac ctgcgcaagc tcaacctgga 9600
cgggtccaac tacacgttac ttaagcaggg cctgaacaac gccgttgcct tggattttga 9660
ctaccgagag cagatgatct actggacaga tgtgaccacc cagggcagca tgatccgaag 9720
gatgcacctt aacgggagca atgtgcaggt cctacaccgt acaggcctca gcaaccccga 9780
tgggctggct gtggactggg tgggtggcaa cctgtactgg tgcgacaaag gccgggacac 9840
catcgaggtg tccaagctca atggggccta tcggacggtg ctggtcagct ctggcctccg 9900
tgagcccagg gctctggtgg tggatgtgca gaatgggtac ctgtactgga cagactgggg 9960
tgaccattca ctgatcggcc gcatcggcat ggatgggtcc agccgcagcg tcatcgtgga 10020
caccaagatc acatggccca atggcctgac gctggactat gtcactgagc gcatctactg 10080
ggccgacgcc cgcgaggact acattgaatt tgccagcctg gatggctcca atcgccacgt 10140
tgtgctgagc caggacatcc cgcacatctt tgcactgacc ctgtttgagg actacgtcta 10200
ctggaccgac tgggaaacaa agtccattaa ccgagcccac aagaccacgg gcaccaacaa 10260
aacgctcctc atcagcacgc tgcaccggcc catggacctg catgtcttcc atgccctgcg 10320
ccagccagac gtgcccaatc accccctgcaa ggtcaacaat ggtggctgca gcaacctgtg 10380
cctgctgtcc cccgggggag ggcacaaatg tgcctgcccc accaacttct acctgggcag 10440
cgatgggcgc acctgtgtgt ccaactgcac ggctagccag tttgtatgca agaacgacaa 10500
gtgcatcccc ttctggtgga agtgtgacac cgaggacgac tgcggggacc actcagacga 10560
gcccccggac tgccctgagt tcaagtgccg gcccggacag ttccagtgct ccacaggtat 10620
ctgcacaaac cctgccttca tctgcgatgg cgacaatgac tgccaggaca acagtgacga 10680
ggccaactgt gacatccacg tctgcttgcc cagtcagttc aaatgcacca acaccaaccg 10740
ctgtattccc ggcatcttcc gctgcaatgg gcaggacaac tgcggagatg gggaggatga 10800
gagggactgc cccgaggtga cctgcgcccc caaccagttc cagtgctcca ttaccaaacg 10860
gtgcatcccc cgggtctggg tctgcgaccg ggacaatgac tgtgtggatg gcagtgatga 10920
gcccgccaac tgcacccaga tgacctgtgg tgtggacgag ttccgctgca aggattcggg 10980
ccgctgcatc ccagcgcgtt ggaagtgtga cggagaggat gactgtgggg atggctcgga 11040
tgagcccaag gaagagtgtg atgaacgcac ctgtgagcca taccagttcc gctgcaagaa 11100
caaccgctgc gtgcccggcc gctggcagtg cgactacgac aacgattgcg gtgacaactc 11160
cgatgaagag agctgcaccc ctcggccctg ctccgagagt gagttctcct gtgccaacgg 11220
ccgctgcatc gcggggcgct ggaaatgcga tggagaccac gactgcgcgg acggctcgga 11280
cgagaaagac tgcacccccc gctgtgacat ggaccagttc cagtgcaaga gcggccactg 11340
catccccctg cgctggcgct gtgacgcaga cgccgactgc atggacggca gcgacgagga 11400
ggcctgcggc actggcgtgc ggacctgccc cctggacgag ttccagtgca acaacacctt 11460
gtgcaagccg ctggcctgga agtgcgatgg cgaggatgac tgtggggaca actcagatga 11520
gaaccccgag gagtgtgccc ggttcgtgtg ccctcccaac cggcccttcc gttgcaagaa 11580
tgaccgcgtc tgtctgtgga tcgggcgcca atgcgatggc acggacaact gtggggatgg 11640
gactgatgaa gaggactgtg agcccccccac agcccacacc acccactgca aagacaagaa 11700
ggagtttctg tgccggaacc agcgctgcct ctcctcctcc ctgcgctgca acatgttcga 11760
tgactgcggg gacggctctg acgaggagga ctgcagcatc gaccccaagc tgaccagctg 11820
cgccaccaat gccagcatct gtggggacga ggcacgctgc gtgcgcaccg agaaagcggc 11880
ctactgtgcc tgccgctcgg gcttccacac cgtgcccggc cagcccggat gccaagacat 11940
caacgagtgc ctgcgcttcg gcacctgctc ccagctctgc aacaacacca agggcggcca 12000
cctctgcagc tgcgctcgga acttcatgaa gacgcacaac acctgcaagg ccgaaggctc 12060

-continued

```
tgagtaccag gtcctgtaca tcgctgatga caatgagatc cgcagcctgt tccccggcca  12120
cccccattcg gcttacgagc aggcattcca gggtgacgag agtgtccgca ttgatgctat  12180
ggatgtccat gtcaaggctg gccgtgtcta ttggaccaac tggcacacgg gcaccatctc  12240
ctaccgcagc ctgccacctg ctgcgcctcc taccacttcc aaccgccacc ggcgacagat  12300
tgaccggggt gtcacccacc tcaacatttc agggctgaag atgcccagag gcatcgccat  12360
cgactgggtg gccggaaacg tgtactggac cgactcgggc cgagatgtga ttgaggtggc  12420
gcagatgaag ggcgagaacc gcaagacgct catctcgggc atgattgacg agccccacgc  12480
cattgtggtg gacccactga gggggaccat gtactggtca gactggggca accaccccaa  12540
gattgagacg gcagcgatgg atgggacgct tcgggagaca ctggtgcagg acaacattca  12600
gtggcccaca ggcctggccg tggattatca caatgagcgg ctgtactggg cagacgccaa  12660
gctttcagtc atcggcagca tccggctcaa tggcacggac cccattgtgg ctgctgacag  12720
caaacgaggc ctaagtcacc ccttcagcat cgacgtcttt gaggattaca tctatggtgt  12780
cacctacatc aataatcgtg tcttcaagat ccataagttt ggccacagcc ccttggtcaa  12840
cctgacaggg ggcctgagcc acgcctctga cgtggtcctt taccatcagc acaagcagcc  12900
cgaagtgacc aacccatgtg accgcaagaa atgcgagtgg ctctgcctgc tgagccccag  12960
tgggcctgtc tgcacctgtc ccaatgggaa gcggctggac aacggcacat gcgtgcctgt  13020
gccctctcca acgccccccc cagatgctcc ccggcctgga acctgtaacc tgcagtgctt  13080
caacggtggc agctgtttcc tcaatgcacg gaggcagccc aagtgccgct gccaaccccg  13140
ctacacgggt gacaagtgtg aactggacca gtgctgggag cactgtcgca atgggggcac  13200
ctgtgctgcc tccccctctg gcatgcccac gtgccggtgc cccacgggct tcacgggccc  13260
caaatgcacc cagcaggtgt gtgcgggcta ctgtgccaac aacagcacct gcactgtcaa  13320
ccagggcaac cagccccagt gccgatgcct acccggcttc ctgggcgacc gctgccagta  13380
ccggcagtgc tctggctact gtgagaactt tggcacatgc cagatggctg ctgatggctc  13440
ccgacaatgc cgctgcactg cctactttga gggatcgagg tgtgaggtga acaagtgcag  13500
ccgctgtctc gaaggggcct gtgtggtcaa caagcagagt ggggatgtca cctgcaactg  13560
cacggatggc cgggtggccc ccagctgtct gacctgcgtc ggccactgca gcaatggcgg  13620
ctcctgtacc atgaacagca aaatgatgcc tgagtgccag tgcccacccc acatgacagg  13680
gccccggtgt gaggagcacg tcttcagcca gcagcagcca ggacatatag cctccatcct  13740
aatccctctg ctgttgctgc tgctgctggt tctggtggcc ggagtggtat tctggtataa  13800
gcggcgagtc caaggggcta agggcttcca gcaccaacgg atgaccaacg gggccatgaa  13860
cgtggagatt ggaaacccca cctacaagat gtacgaaggc ggagagcctg atgatgtggg  13920
aggcctactg gacgctgact ttgccctgga ccctgacaag cccaccaact tcaccaaccc  13980
cgtgtatgcc acactctaca tgggggggcca tggcagtcgc cactccctgg ccagcacgga  14040
cgagaagcga gaactcctgg gccggggccc tgaggacgag ataggggacc ccttggcata  14100
gggccctgcc ccgtcggact gcccccagaa agcctcctgc cccctgccgg tgaagtcctt  14160
cagtgagccc ctccccagcc agcccttccc tggccccgcc ggatgtataa atgtaaaaat  14220
gaaggaatta cattttatat gtgagcgagc aagccggcaa gcgagcacag tattatttct  14280
ccatcccctc cctgcctgct ccttggcacc cccatgctgc cttcagggag acaggcaggg  14340
agggcttggg gctgcacctc ctaccctccc accagaacgc accccactgg gagagctggt  14400
ggtgcagcct tcccctccct gtataagaca ctttgccaag gctctcccct ctcgccccat  14460
ccctgcttgc ccgctcccac agcttcctga gggctaattc tgggaaggga gagttctttg  14520
ctgcccctgt ctggaagacg tggctctggg tgaggtaggc gggaaaggat ggagtgtttt  14580
agttcttggg ggaggccacc ccaaacccca gccccaactc caggggcacc tatgagatgg  14640
ccatgctcaa cccccctccc agacaggccc tccctgtctc cagggccccc accgaggttc  14700
ccagggctgg agacttcctc tggtaaacat tcctccagcc tcccctcccc tggggacgcc  14760
aaggaggtgg gccacaccca ggaagggaaa gcgggcagcc ccgttttggg gacgtgaacg  14820
ttttaataat ttttgctgaa ttcctttaca actaaataac acagatattg ttataaataa  14880
aattgtaaaa aaaaaaaaaa aaaaa                                       14905

SEQ ID NO: 10          moltype = AA  length = 4544
FEATURE                Location/Qualifiers
source                 1..4544
                       mol_type = protein
                       organism = Homo sapiens
SEQUENCE: 10
MLTPPLLLLL PLLSALVAAA IDAPKTCSPK QFACRDQITC ISKGWRCDGE RDCPDGSDEA  60
PEICPQSKAQ RCQPNEHNCL GTELCVPMSR LCNGVQDCMD GSDEGPHCRE LQGNCSRLGC  120
QHHCVPTLDG PTCYCNSSFQ LQADGKTCKD FDECSVYGTC SQLCTNTDGS FICGCVEGYL  180
LQPDNRSCKA KNEPVDRPPV LLIANSQNIL ATYLSGAQVS TITPTSTRQT TAMDFSYANE  240
TVCWVHVGDS AAQTQLKCAR MPGLKGFVDE HTINISLSLH HVEQMAIDWL TGNFYFVDDI  300
DDRIFVCNRN GDTCVTLLDL ELYNPKGIAL DPAMGKVFFT DYGQIPKVER CDMDGQNRTK  360
LVDSKIVFPH GITLDLVSRL VYWADAYLDY IEVVDYEGKG RQTIIQGILI EHLYGLTVFE  420
NYLYATNSDN ANAQQKTSVI RVNRFNSTEY QVVTRVDKGG ALHIYHQRRQ PRVRSHACEN  480
DQYGKPGGCS DICLLANSHK ARTCRCRSGF SLGSDGKSCK KPEHELFLVY GKGRPGIIRG  540
MDMGAKVPDE HMIPIENLMN PRALDFHAET GFIYFADTTS YLIGRQKIDG TERETILKDG  600
IHNVEGVAVD WMGDNLYWTD DGPKKTISVA RLEKAAQTRK TLIEGKMTHP RAIVVDPLNG  660
WMYWTDWEED PKDSRRGRLE RAWMDGSHRD IFVTSKTVLW PNGLSLDIPA GRLYWVDAFY  720
DRIETILLNG TDRKIVYEGP ELNHAFGLCH HGNYLFWTEY RSGSVYRLER GVGGAPPTVT  780
LLRSERPPIF EIRMYDAQQQ QVGTNKCRVN NGGCSSLCLA TPGSRQCACA EDQVLDADGV  840
TCLANPSYVP PPQCQPGEFA CANSRCIQER WKCDGDNDCL DNSDEAPALC HQHTCPSDRF  900
KCENNRCIPN RWLCDGDNDC GNSEDESNAT CSARTCPPNQ FSCASGRCIP ISWTCDLDDD  960
CGDRSDESAS CAYPTCFPLT QFTCNNGRCI NINWRCDNDN DCGDNSDEAG CSHSCSSTQF  1020
KCNSGRCIPE HWTCDGDNDC GDYSDETHAN CTNQATRPPG GCHTDEFQCR LDGLCIPLRW  1080
RCDGDTDCMD SSDEKSCEGV THVCDPSVKF GCKDSARCIS KAWVCDGDND CEDNSDEENC  1140
ESLACRPPSH PCANNTSVCL PPDKLCDGND DCGDGSDEGE LCDQCSLNNG GCSHNCSVAP  1200
GEGIVCSCPL GMELGPDNHT CQIQSYCAKH LKCSQKCDQN KFSVKCSCYE GWVLEPDGES  1260
CRSLDPFKPF IIFSNRHEIR RIDLHKGDYS VLVPGLRNTI ALDFHLSQSA LYWTDVVEDK  1320
IYRGKLLDNG ALTSFEVVIQ YGLATPEGLA VDWIAGNIYW VESNLDQIEV AKLDGTLRTT  1380
LLAGDIEHPR AIALDPRDGI LFWTDWDASL PRIEAASMSG AGRRTVHRET GSGGWPNGLT  1440
```

-continued

```
VDYLEKRILW IDARSDAIYS ARYDGSGHME VLRGHEFLSH PFAVTLYGGE VYWTDWRTNT  1500
LAKANKWTGH NVTVVQRTNT QPFDLQVYHP SRQPMAPNPC EANGGQGPCS HLCLINYNRT  1560
VSCACPHLMK LHKDNTTCYE FKKFLLYARQ MEIRGVDLDA PYYNYIISFT VPDIDNVTVL  1620
DYDAREQRVY WSDVRTQAIK RAFINGTGVE TVVSADLPNA HGLAVDWVSR NLFWTSYDTN  1680
KKQINVARLD GSFKNAVVQG LEQPHGLVVH PLRGKLYWTD GDNISMANMD GSNRTLLFSG  1740
QKGPVGLAID FPESKLYWIS SGNHTINRCN LDGSGLEVID AMRSQLGKAT ALAIMGDKLW  1800
WADQVSEKMG TCSKADGSGS VVLRNSTTLV MHMKVYDESI QLDHKGTNPC SVNNGDCSQL  1860
CLPTSETTRS CMCTAGYSLR SGQQACEGVG SFLLYSVHEG IRGIPLDPND KSDALVPVSG  1920
TSLAVGIDFH AENDTIYWVD MGLSTISRAK RDQTWREDVV TNGIGRVEGI AVDWIAGNIY  1980
WTDQGFDVIE VARLNGSFRY VVISQGLDKP RAITVHPEKG YLFWTEWGQY PRIERSRLDG  2040
TERVVLVNVS ISWPNGISVD YQDGKLYWCD ARTDKIERID LETGENREVV LSSNNMDMFS  2100
VSVFEDFIYW SDRTHANGSI KRGSKDNATD SVPLRTGIGV QLKDIKVFNR DRQKGTNVCA  2160
VANGGCQQLC LYRGRGQRAC ACAHGMLAED GASCREYAGY LLYSERTILK SIHLSDERNL  2220
NAPVQPFEDP EHMKNVIALA FDYRAGTSPG TPNRIFFSDI HFGNIQQIND DGSRRITIVE  2280
NVGSVEGLAY HRGWDTLYWT SYTTSTITRH TVDQTRPGAF ERETVITMSG DDHPRAFVLD  2340
ECQNLMFWTN WNEQHPSIMR AALSGANVLT LIEKDIRTPN GLAIDHRAEK LYFSDATLDK  2400
IERCEYDGSH RYVILKSEPV HPFGLAVYGE HIFWTDWVRR AVQRANKHVG SNMKLLRVDI  2460
PQQPMGIIAV ANDTNSCELS PCRINNGGCQ DLCLLTHQGH VNCSCRGGRI LQDDLTCRAV  2520
NSSCRAQDEF ECANGECINF SLTCDGVPHC KDKSDEKPSY CNSRRCKKTF RQCSNGRCVS  2580
NMLWCNGADD CGDGSDEIPC NKTACGVGEF RCRDGTCIGN SSRCNQFVDC EDASDEMNCS  2640
ATDCSSYFRL GVKGVLFQPC ERTSLCYAPS WVCDGANDCG DYSDERDCPG VKRPRCPLNY  2700
FACPSGRCIP MSWTCDKEDD CEHGEDETHC NKFCSEAQFE CQNHRCISKQ WLCDGSDDCG  2760
DGSDEAAHCE GKTCGPSSFS CPGTHVCVPE RWLCDGDKDC ADGADESIAA GCLYNSTCDD  2820
REFMCQNRQC IPKHFVCDHD RDCADGSDES PECEYPTCGP SEFRCANGRC LSSRQWECDG  2880
ENDCHDQSDE APKNPHCTSQ EHKCNASSQF LCSSGRCVAE ALLCNGQDDC GDSSDERGCH  2940
INECLSRKLS GCSQDCEDLK IGFKCRCRPG FRLKDDGRTC ADVDECSTTF PCSQRCINTH  3000
GSYKCLCVEG YAPRGGDPHS CKAVTDEEPF LIFANRYYLR KLNLDGSNYT LLKQGLNNAV  3060
ALDFDYREQM IYWTDVTTQG SMIRRMHLNG SNVQVLHRTG LSNPDGLAVD WVGGNLYWCD  3120
KGRDTIEVSK LNGAYRTVLV SSGLREPRAL VVDVQNGYLY WTDWGDHSLI GRIGMDGSSR  3180
SVIVDTKITW PNGLTLDYVT ERIYWADARE DYIEFASLDG SNRHVVLSQD IPHIFALTLF  3240
EDYVYWTDWE TKSINRAHKT TGTNKTLLIS TLHRPMDLHV FHALRQPDVP NHPCKVNNGG  3300
CSNLCLLSPG GGHKCACPTN FYLGSDGRTC VSNCTASQFV CKNDKCIPFW WKCDTEDDCG  3360
DHSDEPPDCP EFKCRPGQFQ CSTGICTNPA FICDGDNDCQ DNSDEANCDI HVCLPSQFKC  3420
TNTNRCIPGI FRCNGQDNCG DGEDERDCPE VTCAPNQFQC SITKRCIPRV WVCDRDNDCV  3480
DGSDEPANCT QMTCGVDEFR CKDSGRCIPA RWKCDGEDDC GDGSDEPKEE CDERTCEPYQ  3540
FRCKNNRCVP GRWQCDYDND CGDNSDEESC TPRPCSESEF SCANGRCIAG RWKCDGDHDC  3600
ADGSDEKDCT PRCDMDQFQC KSGHCIPLRW RCDADADCMD GSDEEACGTG VRTCPLDEFQ  3660
CNNTLCKPLA WKCDGEDDCG DNSDENPEEC ARFVCPPNRP FRCKNDRVCL WIGRQCDGTD  3720
NCGDGTDEED CEPPTAHTTH CKDKKEFLCR NQRCLSSSLR CNMFDDCGDG SDEEDCSIDP  3780
KLTSCATNAS ICGDEARCVR TEKAAYCACR SGFHTVPGQP GCQDINECLR FGTCSQLCNN  3840
TKGGHLCSCA RNFMKTHNTC KAEGSEYQVL YIADDNEIRS LFPGHPHSAY EQAFQGDESV  3900
RIDAMDVHVK AGRVYWTNWH TGTISYRSLP PAAPPTTSNR HRRQIDRGVT HLNISGLKMP  3960
RGIAIDWVAG NVYWTDSGRD VIEVAQMKGE NRKTLISGMI DEPHAIVVDP LRGTMYWSDW  4020
GNHPKIETAA MDGTLRETLV QDNIQWPTGL AVDYHNERLY WADAKLSVIG SIRLNGTDPI  4080
VAADSKRGLS HPFSIDVFED YIYGVTYINN RVFKIHKFGH SPLVNLTGGL SHASDVVLYH  4140
QHKQPEVTNP CDRKKCEWLC LLSPSGPVCT CPNGKRLDNG TCVPVPSPTP PPDAPRPGTC  4200
NLQCFNGGSC FLNARRQPKC RCQPRYTGDK CELDQCWEHC RNGGTCAASP SGMPTCRCPT  4260
GFTGPKCTQQ VCAGYCANNS TCTVNQGNQP QCRCLPGFLG DRCQYRQCSG YCENFGTCQM  4320
AADGSRQCRC TAYFEGSRCE VNKCSRCLEG ACVVNKQSGD VTCNCTDGRV APSCLTCVGH  4380
CSNGGSCTMN SKMMPECQCP PHMTGPRCEE HVFSQQQPGH IASILIPLLL LLLLVLVAGV  4440
VFWYKRRVQG AKGFQHQRMT NGAMNVEIGN PTYKMYEGGE PDDVGGLLDA DFALDPDKPT  4500
NFTNPVYATL YMGGHGSRHS LASTDEKREL LGRGPEDEIG DPLA                  4544

SEQ ID NO: 11           moltype = RNA  length = 7783
FEATURE                 Location/Qualifiers
source                  1..7783
                        mol_type = unassigned RNA
                        organism = Homo sapiens
SEQUENCE: 11
gctggcggcg gccgcccagg gccggggccg cgcgcccagc ctgagcccgc cccgccgccg  60
agcgtcaccg aacctgcttg aaatgcagcc gaggagccgg ggcgggcggc agcggcggcg  120
gcggcggcgg cgggggcagc ggcaaccccg gcgccgcggc aaggactcgg agggctgaga  180
cgcggcggcg gcggcgcggg gagcgcgggg cgcggcggcc ggagccccgg gcccgccatg  240
ggcctccccg agccgggccc tctccggctt ctggcgctgc tgctgctgct gctgctgctg  300
ctgctgctgc agctccagca tcttgcggcg gcagcggctg atccgctgct cggcggccaa  360
gggccggcca aggattgcga aaaggaccaa ttccagtgcc ggaacgagcg ctgcatcccc  420
tctgtgtgga gatgcgacga ggacgatgac tgcttagacc acagcgacga ggacgactgc  480
cccaagaaga cctgtgcaga cagtgacttc acctgtgaca acggccactg catccacgaa  540
cggtggaagt gtgacggcga ggaggagtgt cctgatggct ccgatgagtc cgaggccact  600
tgcaccaagc aggtgtgtcc tgcagagaag ctgagctgtg gacccaccag ccacaagtgt  660
gtacctgcct cgtggcgctg cgacggggag aaggactgcg agggtggagc ggatgaggcc  720
ggctgtgcta ccttgtgcgc cccgcacgag ttccagtgcg gcaaccgctc gtgcctggcc  780
gccgtgttcg tgtgcgacgg cgacgacgac tgtggtgacg gcagcgatga gcgcggctgt  840
gcagacccgg cctgcgggcc ccgcgagttc cgctgcggcg gcgatggcgg cggcgcctgc  900
atcccggagc gctgggtctg cgaccgccag tttgactgcg aggaccgctc ggacgaggca  960
gccgagctct gcggccgtcc gggccccggg gccacgtccg cgcccgccgc ctgcgccacc  1020
gcctcccagt tcgcctgccg cagcggcgag tgcgtgcacc tgggctggcg ctgcgacggc  1080
gaccgcgact gcaaagacaa atcggacgag gccgactgcc cactgggcac ctgccgtggg  1140
gacgagttcc agtgtgggga tgggacatgt gtccttgcaa tcaagcactg caaccaggag  1200
```

-continued

```
caggactgtc cagatgggag tgatgaagct ggctgcctac aggggctgaa cgagtgtctg  1260
cacaacaatg gcggctgctc acacatctgc actgacctca agattggctt tgaatgcacg  1320
tgcccagcag gcttccagct cctggaccag aagacctgtg gcgacattga tgagtgcaag  1380
gacccagatg cctgcagcca gatctgtgtc aattacaagg gctattttaa gtgtgagtgc  1440
taccctggct acgagatgga cctactgacc aagaactgca aggctgctgc tggcaagagc  1500
ccatccctaa tcttcaccaa ccggcacgag gtgcggagga tcgacctggt gaagcggaac  1560
tattcacgcc tcatccccat gctcaagaat gtcgtggcac tagatgtgga agttgccacc  1620
aatcgcatct actggtgtga cctctcctac cgtaagatct atagcgccta catggacaag  1680
gccagtgacc cgaaagagca ggaggtcctc attgacgagc agttgcactc tccagagggc  1740
ctggcagtgg actgggtcca caagcacatc tactggactg actcgggcaa taagaccatc  1800
tcagtggcca cagttgatgg tggccgccga cgcactctct tcagccgtaa cctcagtgaa  1860
ccccgggcca tcgctgttga cccccctgcga gggttcatgt attggtctga ctgggggggac  1920
caggccaaga ttgagaaatc tgggctcaac ggtgtggacc ggcaaacact ggtgtcagac  1980
aatattgaat ggcccaacgg aatcaccctg gatctgctga gccagcgctt gtactgggta  2040
gactccaagc tacaccaact gtccagcatt gacttcagtg gaggcaacag aaagacgctg  2100
atctcctcca ctgacttcct gagccaccct tttgggatag ctgtgtttga ggacaaggtg  2160
ttctggacag acctggagaa cgaggccatt ttcagtgcaa atcggctcaa tggcctggaa  2220
atctccatcc tggctgagaa cctcaacaac ccacatgaca ttgtcatctt ccatgagctg  2280
aagcagccaa gagctccaga tgcctgtgag ctgagtgtcc agcctaatgg aggctgtgaa  2340
tacctgtgcc ttcctgctcc tcagatctcc agccactctc ccaagtacac atgtgcctgt  2400
cctgacacaa tgtggctggg tccagacatg aagaggtgct accgagcacc tcaatctacc  2460
tcaactacga cgttagcttc taccatgacg aggacagtac ctgccaccac aagagccccc  2520
gggaccaccg tccacagatc cacctaccag aaccacagca cagagacacc aagcctgaca  2580
gctgcagtcc caagctcagt tagtgtcccc agggctccca gcatcagccc gtctacccta  2640
agccctgcaa ccagcaacca ctcccagcac tatgcaaatg aagacagtaa gatgggctca  2700
acagtcactg ccgctgttat cgggatcatc gtgcccatag tggtgatagc cctcctgtgc  2760
atgagtggat acctgatctg gagaaactgg aagcggaaga acaccaaaag catgaatttt  2820
gacaacccag tctacaggaa aacaacagaa gaagaagacg aagatgagct ccatataggg  2880
agaactgctc agattggcca tgtctatcct gcagcaatca gcagctttga tcgcccactg  2940
tgggcagagc cctgtcttgg ggagaccaga gaaccggaag acccagcccc tgccctcaag  3000
gagcttttttg tcttgccggg ggaaccaagg tcacagctgc accaactccc gaagaaccct  3060
ctttccgagc tgcctgtcgt caaatccaag cgagtggcat taagccttga agatgatgga  3120
ctaccctgag gatgggatca ccccccttcgt gcctcatgga attcagtccc atgcactaca  3180
ctctggatgg tgtatgactg gatgaatggg tttctatata tgggtctgtg tgagtgtatg  3240
tgtgtgtgtg atttttttt taaatttatg ttgcggaaag gtaaccacaa agttatgatg  3300
aactgcaaac atccaaagga tgtgagagtt tttctatgta taatgtttta tacacttttt  3360
aactggttgc actacccatg aggaattcgt ggaatggcta ctgctgacta acatgatgca  3420
cataaccaaa tgggggccaa tggcacagta ccttactcat catttaaaaa ctatatttac  3480
agaagatgtt tggttgctgg gggggctttt ttaggttttg gggcatttgt tttttgtaaa  3540
taagatgatt atgctttgtg gctatccatc aacataagta aaaaaaaaaa aaaaacactt  3600
caactcccctc ccccatttag attatttatt aacatatttt aaaaatcaga tgagttctat  3660
aaataattta gagaagtgag agtatttatt tttggcatgt ttggcccacc acacagactc  3720
tgtgtgtgta tgtgtgtgtt tatatgtgta tgtgtgtgac agaaaaaatct gtagagaaga  3780
ggcacatcta tggctactgt tcaaatacat aaagataaat ttattttcac acagtccaca  3840
aggggtatat cttgtagttt tcagaaaagc ctttggaaat ctggatcaga aaatagatac  3900
catggtttgt gcaattatgt agtaaaaaag gcaaatcttt tcacctctgg ctattcctga  3960
gaccccagga agtcaggaaa agcctttcag ctcacccatg gctgctgtga ctcctaccag  4020
ggctttcttg gctttggcga aggtcagtgt acagacattc catggtacca gagtgctcag  4080
aaactcaaga taggatatgc ctcaccctca gctactcctt gttttaaagt tcagctcttt  4140
gagtaacttc ttcaatttct ttcaggacac ttgggttgaa ttcagtaagt ttcctctgaa  4200
gcaccctgaa gggtgccatc cttacagagc taagtggaga cgtttccaga tcagcccaag  4260
tttactatag agactggccc aggcactgaa tgtctaggac atgctgtgga tgaagataaa  4320
gatggtggaa taggttttat cacatctctt atttctcttt tcccccttact ctctaccatt  4380
tcctttatgt ggggaaacat tttaaggtaa taaataggtt acttaccatc atatgttcat  4440
atagatgaaa ctaatttttg gcttaagtca gaacaactgg ccaaaattga agtcatattt  4500
gaggggggaa atggcatacg caatattata ttatattgga tatttatgtt cacacaggaa  4560
tttggtttac tgctttgtaa ataaaaggaa aaactccggg tatatgtata gatgttcttc  4620
attatagaca tcttctttgc ttttcttggc cttgggggag gaagggagaa gtgctctttt  4680
ctacttgtgg ggtctcccat tggaaacata atcctatagt cccagaagga ttcagtcccc  4740
agtggctttc ccatccaaag agaaagagtt tgagtttctt aactctgctg ttctgccact  4800
tactcccact agacaaccag ggacaaggtg caacatggaa gtgtttgact taagtaggag  4860
cagaggagct gcatctaatc tcatcatacc tggaacttga cacacttaag caaatgcctt  4920
cccatcccta cctgccagat gcccccaact caatgaagtt ggatgtctca ccagcttgat  4980
accctttgaa ttttcagtca gacattctgg agttctagca tcctgtacct aggaccttcc  5040
tctgtgtcac tcttggcctc ctaaactcta agaaaataac tatattctgg agcttgggca  5100
gtgtgttttg cataatccag caatctcctc atgacatgca tgtgttgata gtcctgaaac  5160
attcattgag agggtaaatg cagttgacct agaatgacca ataccaaaca gaattttaag  5220
aacaggtggc caactcctat ggagcttact cacatattac tattctttta agaacggaaa  5280
gtaaaaattat ttttgactga agaaaaatga tgacagtgaa aaacatggaa atgtactcaa  5340
aacaagtgac tttttctgta accttccaaa gaaactgaat tttccaagga attaaatgat  5400
aacagtggct aaggcatagt ttctaaactt tcagtaagat cctggcattc acagaaaaaa  5460
atgatgaatg gggtctggac atacagcctg agatctcaaa atgacaatga aattcacaac  5520
tttttctcag agacattcat gtttcctgca tatgctacaa ctgcagtttg aaagaggcag  5580
caatgggagc aacccttttac aagaaacaaa ttgtgatata ttcatgtgtt ggacggcagt  5640
aaataagatg aaacctgagg agtcagatcc accttcccccc attcatagag gcttttcagc  5700
ctcattttga ggtacagtta catatctttt gccttttgcc cccgtgcata gctatctaca  5760
gccaatcaca gatcacagag tcactggact atagagctgg aaggaagctc agagacaatg  5820
ccaagggggc agaaaattta tcagaagcca gtcccagtgc gtttcctcca tttccttctg  5880
caggaagact attttgggct gcctgaacat tgtatcaaac ctgctaccta tactatggtc  5940
```

```
taccttteet ccagtggaat tacaaaggca ctaactgaaa tgccttctag aaacagagaa  6000
aacgaaactg tacttattta ctcttgatac acagattatt tataaaacag attgaagtaa  6060
cctgttaact ggcaaaaaga gaatgagatc ggatttaaat gtatggcagt aagtcctatt  6120
gatccctcca gttatctcag tatgactgca gtatattcat tcactaaaac cactcactag  6180
ataccaacta cacacctggc actgcagatg taaaggtcag tcacacatgt tctgacttta  6240
cagagttcac agtagcagtg gaggatgata tatgtggaaa caaaaaaggc attgattcta  6300
ttcagagcac tgttagggct caaaggagag aggggtcttt ccacctaaga aatgaggaat  6360
agggtcatca tagaagtgac cttaagtctt aaaaattaag aaggggattc caagctgctt  6420
cagacagaga cacatcgagc taaaacacag aggtatgaaa gagcacaggg actttaggaa  6480
ttgcacagtt cattctaaca ggaacaaaag gctcaagggg ggcaagaaat gaggctgtat  6540
ggaaagagat tcaatgtaag cactttataa aatagattaa tttctgattc aatgaagcat  6600
ttcttgatca ttgtgtacaa ggcactacat gcatcatgga aaattcatta ggatgcattg  6660
ccagcacttt gcagaactga tattattcag cctcaagctt tccagtggcc aaagggaaat  6720
gctgactgct tttcatatat ttgagtcaaa gattttttat atggtcaatg aagactaata  6780
taagggcagt gggattttca cagatgcatg ccatgttgtc gagagcctct tagatttttct  6840
caactgtgag aaagaaaaac gaaaatgttg aagacgttga gtctggagag gggatactaa  6900
tcactgtcca gttgggcact ggtgggaatg gggaaatggc acaggaatgc aagcctctcc  6960
accctacccc ccgaactcca gccatacact catcgtttca caaaatataa atgagttagc  7020
attaaatgtt tcagagtaaa taattccttt tcccgaaatg catgaagata gagtaacaga  7080
cttctcacac tgtattttta gggtatggag aatttagaag gttaaagaat tactgcttca  7140
atttttcagt taaaaaaaaa tcaggaagct ctgttcattc aggctatgca ccatgtgcac  7200
agtcaagaat tagcagaaac cctctgcatt tacaaacact ttgtgctata aaaaagtaat  7260
ttttaaaaag ccacgtgtgt gtgtgtgtat atatatatat atatatatat ttaaagccaa  7320
ggttttgata ctttttttaca aaaactacaa gagaaaacaa atatacctgt ccaaaccata  7380
tacttttaaa agagcatttt tttttccata caagctgttg ttaatttggg ggtaaagtgc  7440
tgatttgcaa acttcatcaa attgttccca agtggattct ccttgtttgt ctccccctac  7500
caaccccaaa gttaccatat ttgatgtaag aatcaggcat gttagaatgt tgtgtcacac  7560
taactgattc tgctcttttt gtcttgtcat tcaagttccg ttagcttctg tacgcggtgc  7620
cctttgcagt ctggtgtctc ttccagaggc gagggggctg aggatggggt gctgcatctc  7680
actagctata ctggcatcat cttggtaaac tgaaaaccaa atgtggacat ttgtaaaatc  7740
agtgcactgt ttctagagag agattaaatt catttaaaaa aaa                    7783

SEQ ID NO: 12          moltype = AA  length = 963
FEATURE                Location/Qualifiers
source                 1..963
                       mol_type = protein
                       organism = Homo sapiens
SEQUENCE: 12
MGLPEPGPLR LLALLLLLLL LLLLQLQHLA AAAADPLLGG QGPAKDCEKD QFQCRNERCI  60
PSVWRCDEDD DCLDHSDEDD CPKKTCADSD FTCDNGHCIH ERWKCDGEEE CPDGSDESEA  120
TCTKQVCPAE KLSCGPTSHK CVPASWRCDG EKDCEGGADE AGCATLCAPH EFQCGNRSCL  180
AAVFVCDGDD DCGDGSDERG CADPACGPRE FRCGGDGGGA CIPERWVCDR QFDCEDRSDE  240
AAELCGRPGP GATSAPAACA TASQFACRSG ECVHLGWRCD GDRDCKDKSD EADCPLGTCR  300
GDEFQCGDGT CVLAIKHCNQ EQDCPDGSDE AGCLQGLNEC LHNNGGCSHI CTDLKIGFEC  360
TCPAGFQLLD QKTCGDIDEC KDPDACSQIC VNYKGYFKCE CYPGYEMDLL TKNCKAAAGK  420
SPSLIFTNRH EVRRIDLVKR NYSRLIPMLK NVVALDVEVA TNRIYWCDLS YRKIYSAYMD  480
KASDPKEQEV LIDEQLHSPE GLAVDWVHKH IYWTDSGNKT ISVATVDGGR RRTLFSRNLS  540
EPRAIAVDPL RGFMYWSDWG DQAKIEKSGL NGVDRQTLVS DNIEWPNGIT LDLLSQRLYW  600
VDSKLHQLSS IDFSGGNRKT LISSTDFLSH PFGIAVFEDK VFWTDLENEA IFSANRLNGL  660
EISILAENLN NPHDIVIFHE LKQPRAPDAC ELSVQPNGGC EYLCLPAPQI SSHSPKYTCA  720
CPDTMWLGPD MKRCYRAPQS TSTTTLASTM TRTVPATTRA PGTTVHRSTY QNHSTETPSL  780
TAAVPSSVSV PRAPSISPST LSPATSNHSQ HYANEDSKMG STVTAAVIGI IVPIVVIALL  840
CMSGYLIWRN WKRKNTKSMN FDNPVYRKTT EEEDEDELHI GRTAQIGHVY PAAISSFDRP  900
LWAEPCLGET REPEDPAPAL KELFVLPGEP RSQLHQLPKN PLSELPVVKS KRVALSLEDD  960
GLP                                                               963

SEQ ID NO: 13          moltype = RNA  length = 7273
FEATURE                Location/Qualifiers
source                 1..7273
                       mol_type = unassigned RNA
                       organism = Homo sapiens
SEQUENCE: 13
gctggcggcg gccgcccagg gccggggccg cgcgcccagc ctgagcccgc cccgccgccg  60
agcgtcaccg aacctgcttg aaatgcagcc gaggagccgg ggcgggcggc agcggcggcg  120
gcggcggcgg cgggggcagc ggcaaccccg gcgccgcggc aaggactcgg agggctgaga  180
cgcggcggcg gcggcgcggg gagcgcgggg cgcggcggcc ggagccccgg gcccgccatg  240
ggcctccccg agccgggccc tctccggctt ctggcgctgc tgctgctgct gctgctgctg  300
ctgctgctgc agctccagca tcttgcggcg gcagcggctg atccgctgct cggcggccaa  360
gggccggcca aggattgcga aaaggaccaa ttccagtgcc ggaacgagcg ctgcatcccc  420
tctgtgtgga gatgcgacga ggacgatgac tgcttagacc acagcgacga ggacgactgc  480
cccaagaaga cctgtgcaga cagtgacttc acctgtgaca acggccactg catccacgaa  540
cggtggaagt gtgacggcga ggaggagtgt cctgatggct ccgatgagtc cgaggccact  600
tgcaccaagc aggtgtgtcc tgcagagaag ctgagctgtg gacccaccag ccacaagtgt  660
gtacctgcct cgtggcgctg cgacggggag aaggactgcg agggtggagc ggatgaggcc  720
ggctgtgcta cctggctgaa cgagtgtctg cacaacaatg gcggctgctc acacatctgc  780
actgacctca agattggctt tgaatgcacg tgcccagcag gcttccagct cctggaccag  840
aagacctgtg gcgacattga tgagtgcaag gacccagatg cctgcagcca gatctgtgtc  900
aattacaagg gctattttaa gtgtgagtgc taccctggct acgagatgga cctactgacc  960
aagaactgca aggctgctgc tggcaagagc ccatccctaa tcttcaccaa ccggcacgag  1020
```

-continued

```
gtgcggagga tcgacctggt gaagcggaac tattcacgcc tcatccccat gctcaagaat  1080
gtcgtggcac tagatgtgga agttgccacc aatcgcatct actggtgtga cctctcctac  1140
cgtaagatct atagcgccta catggacaag gccagtgacc cgaaagagca ggaggtcctc  1200
attgacgagc agttgcactc tccagagggc ctggcagtgg actgggtcca caagcacatc  1260
tactggactg actcgggcaa taagaccatc tcagtggcca cagttgatgg tggccgccga  1320
cgcactctct tcagccgtaa cctcagtgaa ccccgggcca tcgctgttga ccccctgcga  1380
gggttcatgt attggtctga ctggggggac caggccaaga ttgagaaatc tgggctcaac  1440
ggtgtggacc ggcaaacact ggtgtcagac aatattgaat ggcccaacgg aatcaccctg  1500
gatctgctga gccagcgctt gtactgggta gactccaagc tacaccaact gtccagcatt  1560
gacttcagtg gaggcaacag aaagacgctg atctcctcca ctgacttcct gagccaccct  1620
tttgggatag ctgtgtttga ggacaaggtg ttctggacag acctggagaa cgaggccatt  1680
ttcagtgcaa atcggctcaa tggcctggaa atctccatcc tggctgagaa cctcaacaac  1740
ccacatgaca ttgtcatctt ccatgagctg aagcagccaa gagctccaga tgcctgtgag  1800
ctgagtgtcc agcctaatgg aggctgtgaa tacctgtgcc ttcctgctcc tcagatctcc  1860
agccactctc ccaagtacac atgtgcctgt cctgacacaa tgtggctggg tccagacatg  1920
aagaggtgct accgagcacc tcaatctacc tcaactacga cgttagcttc taccatgacg  1980
aggacagtac ctgccaccac aagagccccc gggaccaccg tccacagatc cacctaccag  2040
aaccacagca cagagacacc aagcctgaca gctgcagtcc caagctcagt tagtgtcccc  2100
agggctccca gcatcagccc gtctacccta agccctgcaa ccagcaacca ctcccagcac  2160
tatgcaaatg aagacagtaa gatgggctca acagtcactg ccgctgttat cgggatcatc  2220
gtgcccatag tggtgatagc cctcctgtgc atgagtggat acctgatctg gagaaactgg  2280
aagcggaaga acaccaaaag catgaatttt gacaacccag tctacaggaa aacaacagaa  2340
gaagaagacg aagatgagct ccatataggg agaactgctc agattggcca tgtctatcct  2400
gcagcaatca gcagctttga tcgcccactg tgggcagagc cctgtcttgg ggagaccaga  2460
gaaccggaag acccagcccc tgccctcaag gagcttttttg tcttgccggg ggaaccaagg  2520
tcacagctgc accaactccc gaagaaccct ctttccgagc tgcctgtcgt caaatccaag  2580
cgagtggcat taagccttga agatgatgga ctaccctgag gatgggatca ccccccttcgt  2640
gcctcatgga attcagtccc atgcactaca ctctggatgg tgtatgactg gatgaatggg  2700
tttctatata tgggtctgtg tgagtgtatg tgtgtgtgtg atttttttttt taaatttatg  2760
ttgcggaaag gtaaccacaa agttatgatg aactgcaaac atccaaagga tgtgagagtt  2820
tttctatgta taatgtttta tacacttttt aactggttgc actacccatg aggaattcgt  2880
ggaatggcta ctgctgacta acatgatgca cataaccaaa tgggggccaa tggcacagta  2940
ccttactcat catttaaaaa ctatatttac agaagatgtt tggttgctgg gggggctttt  3000
ttaggttttg gggcatttgt tttttgtaaa taagatgatt atgctttgtg gctatccatc  3060
aacataagta aaaaaaaaaa aaaaacactt caactccctc ccccatttag attatttatt  3120
aacatatttt aaaaatcaga tgagttctat aaataattta gagaagtgag agtatttatt  3180
tttggcatgt ttggcccacc acacagactc tgtgtgtgta tgtgtgtgtt tatatgtgta  3240
tgtgtgtgac agaaaaatct gtagagaaga ggcacatcta tggctactgt tcaaatacat  3300
aaagataaat ttattttcac acagtccaca aggggtatat cttgtagttt tcagaaaagc  3360
ctttggaaat ctggatcaga aaatagatac catggtttgt gcaattatgt agtaaaaaag  3420
gcaaatcttt tcacctctgg ctattcctga gaccccagga agtcaggaaa agcctttcag  3480
ctcacccatg gctgctgtga ctcctaccag ggctttcttg gctttggcga aggtcagtgt  3540
acagacattc catggtacca gagtgctcag aaactcaaga taggatatgc ctcaccctca  3600
gctactcctt gttttaaagt tcagctcttt gagtaacttc ttcaatttct ttcaggacac  3660
ttgggttgaa ttcagtaagt ttcctctgaa gcaccctgaa gggtgccatc cttacagagc  3720
taagtggaga cgtttccaga tcagcccaag tttactatag agactggccc aggcactgaa  3780
tgtctaggac atgctgtgga tgaagataaa gatggtggaa taggttttat cacatctctt  3840
atttctcttt tccccttact ctctaccatt tcctttatgt ggggaaacat tttaaggtaa  3900
taaataggtt acttaccatc atatgttcat atagatgaaa ctaatttttg gcttaagtca  3960
gaacaactgg ccaaaattga agtcatattt gagggggggaa atggcatacg caatattata  4020
ttatattgga tatttatgtt cacacaggaa tttggtttac tgctttgtaa ataaaaggaa  4080
aaactccggg tatatgtata gatgttcttc attatagaca tcttctttgc ttttcttggc  4140
cttgggggag gaagggagaa gtgctctttt ctacttgtgg ggtctcccat tggaaacata  4200
atcctatagt cccagaagga ttcagtcccc agtggctttc ccatccaaag agaaagagtt  4260
tgagtttctt aactctgctg ttctgccact tactcccact agacaaccag ggacaaggtg  4320
caacatggaa gtgtttgact taagtaggag cagaggagct gcatctaatc tcatcatacc  4380
tggaacttga cacacttaag caaatgcctt cccatcccta cctgccagat gcccccaact  4440
caatgaagtt ggatgtctca ccagcttgat accctttgaa ttttcagtca gacattctgg  4500
agttctagca tcctgtacct aggaccttcc tctgtgtcac tcttggcctc ctaaactcta  4560
agaaaataac tatattctgg agcttgggca gtgtgttttg cataatccag caatctcctc  4620
atgacatgca tgtgttgata gtcctgaaac attcattgag agggtaaatg cagttgacct  4680
agaatgacca ataccaaaca gaattttaag aacaggtggc caactcctat ggagcttact  4740
cacatattac tattctttta agaacggaaa gtaaaattat ttttgactga agaaaaatga  4800
tgacagtgaa aaacatggaa atgtactcaa aacaagtgac tttttctgta accttccaaa  4860
gaaactgaat tttccaagga attaaatgat aacagtggct aaggcatagt ttctaaactt  4920
tcagtaagat cctggcattc acagaaaaaa atgatgaatg gggtctggac atacagcctg  4980
agatctcaaa atgacaatga aattcacaac tttttctcag agacattcat gtttcctgca  5040
tatgctacaa ctgcagtttg aaagaggcag caatgggagc aaccctttac aagaaacaaa  5100
ttgtgatata ttcatgtgtt ggacggcagt aaataagatg aaacctgagg agtcagatcc  5160
accttccccc attcatagag gcttttcagc ctcattttga ggtacagtta catatctttt  5220
gccttttgcc cccgtgcata gctatctaca gccaatcaca gatcacagag tcactggact  5280
atagagctgg aaggaagctc agagacaatg ccaagggggc agaaaattta tcagaagcca  5340
gtcccagtgc gtttcctcca tttccttctg caggaagact attttgggct gcctgaacat  5400
tgtatcaaac ctgctaccta tactatggtc tacctttcct ccagtggaat tacaaaggca  5460
ctaactgaaa tgccttctag aaacagagaa aacgaaactg tacttattta ctcttgatac  5520
acagattatt tataaaacag attgaagtaa cctgttaact ggcaaaaaga gaatgagatc  5580
ggatttaaat gtatggcagt aagtcctatt gatccctcca gttatctcag tatgactgca  5640
gtatattcat tcactaaaac cactcactag ataccaacta cacacctggc actgcagatg  5700
taaaggtcag tcacacatgt tctgacttta cagagttcac agtagcagtg gaggatgata  5760
```

tatgtggaaa caaaaaaggc attgattcta ttcagagcac tgttagggct caaaggagag 5820
aggggtcttt ccacctaaga aatgaggaat agggtcatca tagaagtgac cttaagtctt 5880
aaaaattaag aaggggattc caagctgctt cagacagaga cacatcgagc taaaacacag 5940
aggtatgaaa gagcacaggg actttaggaa ttgcacagtt cattctaaca ggaacaaaag 6000
gctcaagggg ggcaagaaat gaggctgtat ggaaagagat tcaatgtaag cactttataa 6060
aatagattaa tttctgattc aatgaagcat ttcttgatca ttgtgtacaa ggcactacat 6120
gcatcatgga aaattcatta ggatgcattg ccagcacttt gcagaactga tattattcag 6180
cctcaagctt tccagtggcc aaagggaaat gctgactgct tttcatatat ttgagtcaaa 6240
gattttttat atggtcaatg aagactaata taagggcagt gggattttca cagatgcatg 6300
ccatgttgtc gagagcctct tagattttct caactgtgag aaagaaaaac gaaaatgttg 6360
aagacgttga gtctggagag gggatactaa tcactgtcca gttgggcact ggtgggaatg 6420
gggaaatggc acaggaatgc aagcctctcc accctacccc ccgaactcca gccatacact 6480
catcgtttca caaaatataa atgagttagc attaaatgtt tcagagtaaa taattccttt 6540
tcccgaaatg catgaagata gagtaacaga cttctcacac tgtattttta gggtatggag 6600
aatttagaag gttaaagaat tactgcttca atttttcagt taaaaaaaaa tcaggaagct 6660
ctgttcattc aggctatgca ccatgtgcac agtcaagaat tagcagaaac cctctgcatt 6720
tacaaacact ttgtgctata aaaaagtaat ttttaaaaag ccacgtgtgt gtgtgtgtat 6780
atatatatat atatatatat ttaaagccaa ggttttgata ctttttttaca aaaactacaa 6840
gagaaaacaa atatacctgt ccaaaccata tacttttaaa agagcatttt tttttccata 6900
caagctgttg ttaatttggg ggtaaagtgc tgatttgcaa acttcatcaa attgttccca 6960
agtggattct ccttgtttgt ctccccctac caaccccaaa gttaccatat ttgatgtaag 7020
aatcaggcat gttagaatgt tgtgtcacac taactgattc tgctcttttt gtcttgtcat 7080
tcaagttccg ttagcttctg tacgcggtgc cctttgcagt ctggtgtctc ttccagaggc 7140
gagggggctg aggatggggt gctgcatctc actagctata ctggcatcat cttggtaaac 7200
tgaaaaccaa atgtggacat ttgtaaaatc agtgcactgt ttctagagag agattaaatt 7260
catttaaaaa aaa 7273

SEQ ID NO: 14 moltype = AA length = 793
FEATURE Location/Qualifiers
source 1..793
mol_type = protein
organism = Homo sapiens
SEQUENCE: 14
MGLPEPGPLR LLALLLLLLL LLLLQLQHLA AAAADPLLGG QGPAKDCEKD QFQCRNERCI 60
PSVWRCDEDD DCLDHSDEDD CPKKTCADSD FTCDNGHCIH ERWKCDGEEE CPDGSDESEA 120
TCTKQVCPAE KLSCGPTSHK CVPASWRCDG EKDCEGGADE AGCATWLNEC LHNNGGCSHI 180
CTDLKIGFEC TCPAGFQLLD QKTCGDIDEC KDPDACSQIC VNYKGYFKCE CYPGYEMDLL 240
TKNCKAAAGK SPSLIFTNRH EVRRIDLVKR NYSRLIPMLK NVVALDVEVA TNRIYWCDLS 300
YRKIYSAYMD KASDPKEQEV LIDEQLHSPE GLAVDWVHKH IYWTDSGNKT ISVATVDGGR 360
RRTLFSRNLS EPRAIAVDPL RGFMYWSDWG DQAKIEKSGL NGVDRQTLVS DNIEWPNGIT 420
LDLLSQRLYW VDSKLHQLSS IDFSGGNRKT LISSTDFLSH PFGIAVFEDK VFWTDLENEA 480
IFSANRLNGL EISILAENLN NPHDIVIFHE LKQPRAPDAC ELSVQPNGGC EYLCLPAPQI 540
SSHSPKYTCA CPDTMWLGPD MKRCYRAPQS TSTTTLASTM TRTVPATTRA PGTTVHRSTY 600
QNHSTETPSL TAAVPSSVSV PRAPSISPST LSPATSNHSQ HYANEDSKMG STVTAAVIGI 660
IVPIVVIALL CMSGYLIWRN WKRKNTKSMN FDNPVYRKTT EEEDEDELHI GRTAQIGHVY 720
PAAISSFDRP LWAEPCLGET REPEDPAPAL KELFVLPGEP RSQLHQLPKN PLSELPVVKS 780
KRVALSLEDD GLP 793

SEQ ID NO: 15 moltype = RNA length = 6994
FEATURE Location/Qualifiers
source 1..6994
mol_type = unassigned RNA
organism = Homo sapiens
SEQUENCE: 15
gctggcggcg gccgcccagg gccggggccg cgcgcccagc ctgagcccgc cccgccgccg 60
agcgtcaccg aacctgcttg aaatgcagcc gaggagccgg ggcgggcggc agcggcggcg 120
gcggcggcgg cgggggcagc ggcaaccccg gcgccgcggc aaggactcgg agggctgaga 180
cgcggcggcg gcggcgcggg gagcgcgggg cgcggcggcc ggagccccgg gcccgccatg 240
ggcctccccg agccgggccc tctccggctt ctggcgctgc tgctgctgct gctgctgctg 300
ctgctgctgc agctccagca tcttgcggcg gcagcggctg atccgctgct cggcggccaa 360
gggccggcca aggattgcga aaaggaccaa ttccagtgcc ggaacgagcg ctgcatcccc 420
tctgtgtgga gatgcgacga ggacgatgac tgcttagacc acagcgacga ggacgactgc 480
cccaagaaga cctgtgcaga cagtgacttc acctgtgaca acggccactg catccacgaa 540
cggtggaagt gtgacggcga ggaggagtgt cctgatggct ccgatgagtc cgaggccact 600
tgcaccaagc aggtgtgtcc tgcagagaag ctgagctgtg gacccaccag ccacaagtgt 660
gtacctgcct cgtggcgctg cgacggggag aaggactgcg agggtggagc ggatgaggcc 720
ggctgtgcta cctcactggg cacctgccgt ggggacgagt tccagtgtgg ggatgggaca 780
tgtgtccttg caatcaagca ctgcaaccag gagcaggact gtccagatgg gagtgatgaa 840
gctggctgcc tacaggggct gaacgagtgt ctgcacaaca atggcggctg ctcacacatc 900
tgcactgacc tcaagattgg ctttgaatgc acgtgcccag caggcttcca gctcctggac 960
cagaagacct gtggcgacat tgatgagtgc aaggacccag atgcctgcag ccagatctgt 1020
gtcaattaca agggctattt taagtgtgag tgctaccctg gctacgagat ggacctactg 1080
accaagaact gcaaggctgc tgctggcaag agcccatccc taatcttcac caaccggcac 1140
gaggtgcgga ggatcgacct ggtgaagcgg aactattcac gcctcatccc catgctcaag 1200
aatgtcgtgg cactagatgt ggaagttgcc accaatcgca tctactggtg tgacctctcc 1260
taccgtaaga tctatagcgc ctacatggac aaggccagtg acccgaaaga gcaggaggtc 1320
ctcattgacg agcagttgca ctctccagag ggcctggcag tggactgggt ccacaagcac 1380
atctactgga ctgactcggg caataagacc atctcagtgg ccacagttga tggtggccgc 1440
cgacgcactc tcttcagccg taacctcagt gaaccccggg ccatcgctgt tgaccccctg 1500

-continued

```
cgagggttca tgtattggtc tgactggggg gaccaggcca agattgagaa atctgggctc  1560
aacggtgtgg accggcaaac actggtgtca gacaatattg aatggcccaa cggaatcacc  1620
ctggatctgc tgagccagcg cttgtactgg gtagactcca agctacacca actgtccagc  1680
attgacttca gtggaggcaa cagaaagacg ctgatctcct ccactgactt cctgagccac  1740
ccttttggga tagctgtgtt tgaggacaag gtgttctgga cagacctgga gaacgaggcc  1800
attttcagtg caaatcggct caatggcctg gaaatctcca tcctggctga gaacctcaac  1860
aacccacatg acattgtcat cttccatgag ctgaagcagc caagagctcc agatgcctgt  1920
gagctgagtg tccagcctaa tggaggctgt gaatacctgt gccttcctgc tcctcagatc  1980
tccagccact ctcccaagta cacatgtgcc tgtcctgaca caatgtggct gggtccagac  2040
atgaagaggt gctaccgaga tgcaaatgaa gacagtaaga tgggctcaac agtcactgcc  2100
gctgttatcg ggatcatcgt gcccatagtg gtgatagccc tcctgtgcat gagtggatac  2160
ctgatctgga gaaactggaa gcggaagaac accaaaagca tgaattttga caacccagtc  2220
tacaggaaaa caacagaaga agaagacgaa gatgagctcc atatagggag aactgctcag  2280
attggccatg tctatcctgc acgagtggca ttaagccttg aagatgatgg actaccctga  2340
ggatgggatc accccccttcg tgcctcatgg aattcagtcc catgcactac actctggatg  2400
gtgtatgact ggatgaatgg gtttctatat atgggtctgt gtgagtgtat gtgtgtgtgt  2460
gatttttttt ttaaatttat gttgcggaaa ggtaaccaca aagttatgat gaactgcaaa  2520
catccaaagg atgtgagagt tttctatgt ataatgtttt atacactttt taactggttg  2580
cactacccat gaggaattcg tggaatggct actgctgact aacatgatgc acataaccaa  2640
atgggggcca atggcacagt accttactca tcatttaaaa actatattta cagaagatgt  2700
ttggttgctg ggggggcttt tttaggtttt ggggcatttg ttttttgtaa ataagatgat  2760
tatgctttgt ggctatccat caacataagt aaaaaaaaaa aaaaaacact tcaactccct  2820
cccccattta gattatttat taacatattt taaaaatcag atgagttcta taaataattt  2880
agagaagtga gagtatttat ttttggcatg tttggcccac cacacagact ctgtgtgtgt  2940
atgtgtgtgt ttatatgtgt atgtgtgtga cagaaaaatc tgtagagaag aggcacatct  3000
atggctactg ttcaaataca taaagataaa tttattttca cacagtccac aaggggtata  3060
tcttgtagtt ttcagaaaag cctttggaaa tctggatcag aaaatagata ccatggtttg  3120
tgcaattatg tagtaaaaaa ggcaaatctt ttcacctctg gctattcctg agaccccagg  3180
aagtcaggaa aagcctttca gctcacccat ggctgctgtg actcctacca gggctttctt  3240
ggctttggcg aaggtcagtg tacagacatt ccatggtacc agagtgctca gaaactcaag  3300
ataggatatg cctcaccctc agctactcct tgttttaaag ttcagctctt tgagtaactt  3360
cttcaatttc tttcaggaca cttgggttga attcagtaag tttcctctga agcaccctga  3420
agggtgccat ccttacagag ctaagtggag acgtttccag atcagcccaa gtttactata  3480
gagactggcc caggcactga atgtctagga catgctgtgg atgaagataa agatggtgga  3540
ataggtttta tcacatctct tatttctctt ttccccttac tctctaccat ttcctttatg  3600
tggggaaaca ttttaaggta ataaataggt tacttaccat catatgttca tatagatgaa  3660
actaattttt ggcttaagtc agaacaactg gccaaaattg aagtcatatt tgagggggga  3720
aatggcatac gcaatattat attatattgg atatttatgt tcacacagga atttggttta  3780
ctgctttgta aataaaagga aaaactccgg gtatatgtat agatgttctt cattatagac  3840
atcttctttg cttttcttgg ccttggggga ggaagggaga agtgctcttt tctacttgtg  3900
gggtctccca ttggaaacat aatcctatag tcccagaagg attcagtccc cagtggcttt  3960
cccatccaaa gagaaagagt ttgagtttct taactctgct gttctgccac ttactcccac  4020
tagacaacca gggacaaggt gcaacatgga agtgtttgac ttaagtagga gcagaggagc  4080
tgcatctaat ctcatcatac ctggaacttg acacacttaa gcaaatgcct tcccatccct  4140
acctgccaga tgcccccaac tcaatgaagt tggatgtctc accagcttga taccctttga  4200
attttcagtc agacattctg gagttctagc atcctgtacc taggaccttc ctctgtgtca  4260
ctcttggcct cctaaactct aagaaaataa ctatattctg gagcttgggc agtgtgtttt  4320
gcataatcca gcaatctcct catgacatgc atgtgttgat agtcctgaaa cattcattga  4380
gagggtaaat gcagttgacc tagaatgacc aataccaaac agaattttaa gaacaggtgg  4440
ccaactccta tggagcttac tcacatatta ctattctttt aagaacggaa agtaaaatta  4500
tttttgactg aagaaaaatg atgacagtga aaaacatgga aatgtactca aaacaagtga  4560
ctttttctgt aaccttccaa agaaactgaa ttttccaagg aattaaatga taacagtggc  4620
taaggcatag tttctaaact ttcagtaaga tcctggcatt cacagaaaaa aatgatgaat  4680
ggggtctgga catacagcct gagatctcaa aatgacaatg aaattcacaa ctttttctca  4740
gagacattca tgtttcctgc atatgctaca actgcagttt gaaagaggca gcaatgggag  4800
caaccctttta caagaaacaa attgtgatat attcatgtgt tggacggcag taaataagat  4860
gaaacctgag gagtcagatc caccttcccc cattcataga ggcttttcag cctcattttg  4920
aggtacagtt acatatcttt tgccttttgc ccccgtgcat agctatctac agccaatcac  4980
agatcacaga gtcactggac tatagagctg gaaggaagct cagagacaat gccaaggggg  5040
cagaaaattt atcagaagcc agtcccagtg cgtttcctcc atttccttct gcaggaagac  5100
tattttgggc tgcctgaaca ttgtatcaaa cctgctacct atactatggt ctacctttcc  5160
tccagtggaa ttacaaaggc actaactgaa atgccttcta gaaacagaga aaacgaaact  5220
gtacttattt actcttgata cacagattat ttataaaaca gattgaagta acctgttaac  5280
tggcaaaaag agaatgagat cggatttaaa tgtatggcag taagtcctat tgatccctcc  5340
agttatctca gtatgactgc agtatattca ttcactaaaa ccactcacta gataccaact  5400
acacacctgg cactgcagat gtaaaggtca gtcacacatg ttctgacttt acagagttca  5460
cagtagcagt ggaggatgat atatgtggaa acaaaaaagg cattgattct attcagagca  5520
ctgttagggc tcaaaggaga gaggggtctt tccacctaag aaatgaggaa tagggtcatc  5580
atagaagtga ccttaagtct taaaaattaa gaaggggatt ccaagctgct tcagacagag  5640
acacatcgag ctaaaacaca gaggtatgaa agagcacagg gactttagga attgcacagt  5700
tcattctaac aggaacaaaa ggctcaaggg gggcaagaaa tgaggctgta tggaaagaga  5760
ttcaatgtaa gcactttata aaatagatta atttctgatt caatgaagca tttcttgatc  5820
attgtgtaca aggcactaca tgcatcatgg aaaattcatt aggatgcatt gccagcactt  5880
tgcagaactg atattattca gcctcaagct ttccagtggc caaagggaaa tgctgactgc  5940
ttttcatata tttgagtcaa agatttttta tatggtcaat gaagactaat ataagggcag  6000
tgggattttc acagatgcat gccatgttgt cgagagcctc ttagattttc tcaactgtga  6060
gaaagaaaaa cgaaaatgtt gaagacgttg agtctggaga ggggatacta atcactgtcc  6120
agttgggcac tggtgggaat ggggaaatgg cacaggaatg caagcctctc caccctaccc  6180
cccgaactcc agccatacac tcatcgtttc acaaaatata aatgagttag cattaaatgt  6240
```

-continued

```
ttcagagtaa ataattcctt ttcccgaaat gcatgaagat agagtaacag acttctcaca  6300
ctgtattttt agggtatgga gaatttagaa ggttaaagaa ttactgcttc aatttttcag  6360
ttaaaaaaaa atcaggaagc tctgttcatt caggctatgc accatgtgca cagtcaagaa  6420
ttagcagaaa ccctctgcat ttacaaacac tttgtgctat aaaaaagtaa tttttaaaaa  6480
gccacgtgtg tgtgtgtgta tatatatata tatatatata tttaaagcca aggttttgat  6540
actttttac aaaaactaca agagaaaaca aatatacctg tccaaaccat atacttttaa  6600
aagagcattt ttttttccat acaagctgtt gttaatttgg gggtaaagtg ctgatttgca  6660
aacttcatca aattgttccc aagtggattc tccttgtttg tctcccccta ccaaccccaa  6720
agttaccata tttgatgtaa gaatcaggca tgttagaatg ttgtgtcaca ctaactgatt  6780
ctgctctttt tgtcttgtca ttcaagttcc gttagcttct gtacgcggtg ccctttgcag  6840
tctggtgtct cttccagagg cgagggggct gaggatgggg tgctgcatct cactagctat  6900
actggcatca tcttggtaaa ctgaaaacca aatgtggaca tttgtaaaat cagtgcactg  6960
tttctagaga gagattaaat tcatttaaaa aaaa                              6994

SEQ ID NO: 16          moltype = AA  length = 700
FEATURE                Location/Qualifiers
source                 1..700
                       mol_type = protein
                       organism = Homo sapiens
SEQUENCE: 16
MGLPEPGPLR LLALLLLLLL LLLLQLQHLA AAAADPLLGG QGPAKDCEKD QFQCRNERCI  60
PSVWRCDEDD DCLDHSDEDD CPKKTCADSD FTCDNGHCIH ERWKCDGEEE CPDGSDESEA  120
TCTKQVCPAE KLSCGPTSHK CVPASWRCDG EKDCEGGADE AGCATSLGTC RGDEFQCGDG  180
TCVLAIKHCN QEQDCPDGSD EAGCLQGLNE CLHNNGGCSH ICTDLKIGFE CTCPAGFQLL  240
DQKTCGDIDE CKDPDACSQI CVNYKGYFKC ECYPGYEMDL LTKNCKAAAG KSPSLIFTNR  300
HEVRRIDLVK RNYSRLIPML KNVVALDVEV ATNRIYWCDL SYRKIYSAYM DKASDPKEQE  360
VLIDEQLHSP EGLAVDWVHK HIYWTDSGNK TISVATVDGG RRRTLFSRNL SEPRAIAVDP  420
LRGFMYWSDW GDQAKIEKSG LNGVDRQTLV SDNIEWPNGI TLDLLSQRLY WVDSKLHQLS  480
SIDFSGGNRK TLISSTDFLS HPFGIAVFED KVFWTDLENE AIFSANRLNG LEISILAENL  540
NNPHDIVIFH ELKQPRAPDA CELSVQPNGG CEYLCLPAPQ ISSHSPKYTC ACPDTMWLGP  600
DMKRCYRDAN EDSKMGSTVT AAVIGIIVPI VVIALLCMSG YLIWRNWKRK NTKSMNFDNP  660
VYRKTTEEED EDELHIGRTA QIGHVYPARV ALSLEDDGLP                        700

SEQ ID NO: 17          moltype = RNA  length = 7606
FEATURE                Location/Qualifiers
source                 1..7606
                       mol_type = unassigned RNA
                       organism = Homo sapiens
SEQUENCE: 17
gctggcggcg gccgcccagg gccggggccg cgcgcccagc ctgagcccgc cccgccgccg  60
agcgtcaccg aacctgcttg aaatgcagcc gaggagccgg ggcgggcggc agcggcggcg  120
gcggcggcgg cgggggcagc ggcaaccccg gcgccgcggc aaggactcgg agggctgaga  180
cgcggcggcg gcggcgcggg gagcgcgggg cgcggcggcc ggagccccgg gcccgccatg  240
ggcctccccg agccgggccc tctccggctt ctggcgctgc tgctgctgct gctgctgctg  300
ctgctgctgc agctccagca tcttgcggcg gcagcggctg atccgctgct cggcggccaa  360
gggccggcca aggattgcga aaaggaccaa ttccagtgcc ggaacgagcg ctgcatcccc  420
tctgtgtgga gatgcgacga ggacgatgac tgcttagacc acagcgacga ggacgactgc  480
cccaagaaga cctgtgcaga cagtgacttc acctgtgaca acggccactg catccacgaa  540
cggtggaagt gtgacggcga ggaggagtgt cctgatggct ccgatgagtc cgaggccact  600
tgcaccaagc aggtgtgtcc tgcagagaag ctgagctgtg gacccaccag ccacaagtgt  660
gtacctgcct cgtggcgctg cgacggggag aaggactgcg agggtggagc ggatgaggcc  720
ggctgtgcta ccttgtgcgc cccgcacgag ttccagtgcg gcaaccgctc gtgcctggcc  780
gccgtgttcg tgtgcgacgg cgacgacgac tgtggtgacg gcagcgatga gcgcggctgt  840
gcagacccgg cctgcgggcc ccgcgagttc cgctgcggcg gcgatggcgg cggcgcctgc  900
atcccggagc gctgggtctg cgaccgccag tttgactgcg aggaccgctc ggacgaggca  960
gccgagctct gcggccgtcc gggcccccggg gccacgtccg cgcccgccgc ctgcgccacc  1020
gcctcccagt tcgcctgccg cagcggcgag tgcgtgcacc tgggctggcg ctgcgacggc  1080
gaccgcgact gcaaagacaa atcggacgag gccgactgcc cactgggcac ctgccgtggg  1140
gacgagttcc agtgtgggga tgggacatgt gtccttgcaa tcaagcactg caaccaggag  1200
caggactgtc cagatgggag tgatgaagct ggctgcctac aggggctgaa cgagtgtctg  1260
cacaacaatg gcggctgctc acacatctgc actgacctca agattggctt tgaatgcacg  1320
tgcccagcag gcttccagct cctggaccag aagacctgtg gcgacattga tgagtgcaag  1380
gacccagatg cctgcagcca gatctgtgtc aattacaagg gctattttaa gtgtgagtgc  1440
taccctggct acgagatgga cctactgaca aagaactgca aggctgctgc tggcaagagc  1500
ccatccctaa tcttcaccaa ccggcacgag gtgcggagga tcgacctggt gaagcggaac  1560
tattcacgcc tcatccccat gctcaagaat gtcgtggcac tagatgtgga agttgccacc  1620
aatcgcatct actggtgtga cctctcctac cgtaagatct atagcgccta catggacaag  1680
gccagtgacc cgaaagagca ggaggtcctc attgacgagc agttgcactc tccagagggc  1740
ctggcagtgg actgggtcca caagcacatc tactggactg actcgggcaa taagaccatc  1800
tcagtggcca cagttgatgg tggccgccga cgcactctct tcagccgtaa cctcagtgaa  1860
ccccgggcca tcgctgttga ccccctgcga gggttcatgt attggtctga ctggggggac  1920
caggccaaga ttgagaaatc tgggctcaac ggtgtggacc ggcaaacact ggtgtcagac  1980
aatattgaat ggcccaacgg aatcaccctg gatctgctga gccagcgctt gtactgggta  2040
gactccaagc tacaccaact gtccagcatt gacttcagtg gaggcaacag aaagacgctg  2100
atctcctcca ctgacttcct gagccaccct tttgggatag ctgtgtttga ggacaaggtg  2160
ttctggacag acctggagaa cgaggccatt ttcagtgcaa atcggctcaa tggcctggaa  2220
atctccatcc tggctgagaa cctcaacaac ccacatgaca ttgtcatctt ccatgagctg  2280
aagcagccaa gagctccaga tgcctgtgag ctgagtgtcc agcctaatgg aggctgtgaa  2340
tacctgtgcc ttcctgctcc tcagatctcc agccactctc ccaagtacac atgtgcctgt  2400
```

-continued

```
cctgacacaa tgtggctggg tccagacatg aagaggtgct accgagcacc tcaatctacc  2460
tcaactacga cgttagcttc taccatgacg aggacagtac ctgccaccac aagagccccc  2520
gggaccaccg tccacagatc cacctaccag aaccacagca cagagacacc aagcctgaca  2580
gctgcagtcc caagctcagt tagtgtcccc agggctccca gcatcagccc gtctacccta  2640
agccctgcaa ccagcaacca ctcccagcac tatgcaaatg aagacagtaa gatgggctca  2700
acagtcactg ccgctgttat cgggatcatc gtgcccatag tggtgatagc cctcctgtgc  2760
atgagtggat acctgatctg gagaaactgg aagcggaaga acaccaaaag catgaatttt  2820
gacaacccag tctacaggaa aacaacagaa gaagaagacg aagatgagct ccatataggg  2880
agaactgctc agattggcca tgtctatcct gcacgagtgg cattaagcct tgaagatgat  2940
ggactaccct gaggatggga tcaccccctt cgtgcctcat ggaattcagt cccatgcact  3000
acactctgga tggtgtatga ctggatgaat gggtttctat atatgggtct gtgtgagtgt  3060
atgtgtgtgt gtgatttttt ttttaaattt atgttgcgga aaggtaacca caaagttatg  3120
atgaactgca aacatccaaa ggatgtgaga gtttttctat gtataatgtt ttatacactt  3180
tttaactggt tgcactaccc atgaggaatt cgtggaatgg ctactgctga ctaacatgat  3240
gcacataacc aaatgggggc caatggcaca gtaccttact catcatttaa aaactatatt  3300
tacagaagat gtttggttgc tgggggggct tttttaggtt ttgggcatt tgttttttgt  3360
aaataagatg attatgcttt gtggctatcc atcaacataa gtaaaaaaaa aaaaaaaaca  3420
cttcaactcc ctcccccatt tagattattt attaacatat tttaaaaatc agatgagttc  3480
tataaataat ttagagaagt gagagtattt atttttggca tgtttggccc accacacaga  3540
ctctgtgtgt gtatgtgtgt gtttatatgt gtatgtgtgt gacagaaaaa tctgtagaga  3600
agaggcacat ctatggctac tgttcaaata cataaagata aatttatttt cacacagtcc  3660
acaaggggta tatcttgtag ttttcagaaa agcctttgga aatctggatc agaaaataga  3720
taccatggtt tgtgcaatta tgtagtaaaa aaggcaaatc ttttcacctc tggctattcc  3780
tgagacccca ggaagtcagg aaaagccttt cagctcaccc atggctgctg tgactcctac  3840
cagggctttc ttggctttgg cgaaggtcag tgtacagaca ttccatggta ccagagtgct  3900
cagaaactca agataggata tgcctcaccc tcagctactc cttgttttaa agttcagctc  3960
tttgagtaac ttcttcaatt tctttcagga cacttgggtt gaattcagta agtttcctct  4020
gaagcaccct gaagggtgcc atccttacag agctaagtgg agacgtttcc agatcagccc  4080
aagtttacta tagagactgg cccaggcact gaatgtctag gacatgctgt ggatgaagat  4140
aaagatggtg gaataggttt tatcacatct cttatttctc ttttcccctt actctctacc  4200
atttccttta tgtggggaaa cattttaagg taataaatag gttacttacc atcatatgtt  4260
catatagatg aaactaattt ttggcttaag tcagaacaac tggccaaaat tgaagtcata  4320
tttgaggggg gaaatggcat acgcaatatt atattatatt ggatatttat gttcacacag  4380
gaatttggtt tactgctttg taaataaaag gaaaaactcc gggtatatgt atagatgttc  4440
ttcattatag acatcttctt tgcttttctt ggccttgggg gaggaaggga gaagtgctct  4500
tttctacttg tggggtctcc cattggaaac ataatcctat agtcccagaa ggattcagtc  4560
cccagtggct ttcccatcca aagagaaaga gtttgagttt cttaactctg ctgttctgcc  4620
acttactccc actagacaac cagggacaag gtgcaacatg gaagtgtttg acttaagtag  4680
gagcagagga gctgcatcta atctcatcat acctggaact tgacacactt aagcaaatgc  4740
cttcccatcc ctacctgcca gatgccccca actcaatgaa gttggatgtc tcaccagctt  4800
gatacccttt gaattttcag tcagacattc tggagttcta gcatcctgta cctaggacct  4860
tcctctgtgt cactcttggc ctcctaaact ctaagaaaat aactatattc tggagcttgg  4920
gcagtgtgtt ttgcataatc cagcaatctc ctcatgacat gcatgtgttg atagtcctga  4980
aacattcatt gagagggtaa atgcagttga cctagaatga ccaataccaa acagaatttt  5040
aagaacaggt ggccaactcc tatggagctt actcacatat tactattctt ttaagaacgg  5100
aaagtaaaat tatttttgac tgaagaaaaa tgatgacagt gaaaaacatg gaaatgtact  5160
caaaacaagt gacttttttct gtaaccttcc aaagaaactg aattttccaa ggaattaaat  5220
gataacagtg gctaaggcat agtttctaaa ctttcagtaa gatcctggca ttcacagaaa  5280
aaaatgatga atggggtctg gacatacagc ctgagatctc aaaatgacaa tgaaattcac  5340
aacttttttct cagagacatt catgtttcct gcatatgcta caactgcagt ttgaaagagg  5400
cagcaatggg agcaaccctt tacaagaaac aaattgtgat atattcatgt gttggacggc  5460
agtaaataag atgaaacctg aggagtcaga tccaccttcc cccattcata gaggcttttc  5520
agcctcattt tgaggtacag ttacatatct tttgcctttt gcccccgtgc atagctatct  5580
acagccaatc acagatcaca gagtcactgg actatagagc tggaaggaag ctcagagaca  5640
atgccaaggg ggcagaaaat ttatcagaag ccagtcccag tgcgtttcct ccatttcctt  5700
ctgcaggaag actattttgg gctgcctgaa cattgtatca aacctgctac ctatactatg  5760
gtctaccttt cctccagtgg aattacaaag gcactaactg aaatgccttc tagaaacaga  5820
gaaaacgaaa ctgtacttat ttactcttga tacacagatt atttataaaa cagattgaag  5880
taacctgtta actggcaaaa agagaatgag atcggattta aatgtatggc agtaagtcct  5940
attgatccct ccagttatct cagtatgact gcagtatatt cattcactaa aaccactcac  6000
tagataccaa ctacacacct ggcactgcag atgtaaaggt cagtcacaca tgttctgact  6060
ttacagagtt cacagtagca gtggaggatg atatatgtgg aaacaaaaaa ggcattgatt  6120
ctattcagag cactgttagg gctcaaagga gagaggggtc tttccaccta agaaatgagg  6180
aatagggtca tcatagaagt gaccttaagt cttaaaaatt aagaagggga ttccaagctg  6240
cttcagacag agacacatcg agctaaaaca cagaggtatg aaagagcaca gggactttag  6300
gaattgcaca gttcattcta acaggaacaa aaggctcaag gggggcaaga aatgaggctg  6360
tatggaaaga gattcaatgt aagcacttta taaaatagat taatttctga ttcaatgaag  6420
catttcttga tcattgtgta caaggcacta catgcatcat ggaaaattca ttaggatgca  6480
ttgccagcac tttgcagaac tgatattatt cagcctcaag ctttccagtg gccaaaggga  6540
aatgctgact gcttttcata tatttgagtc aaagattttt tatatggtca atgaagacta  6600
atataagggc agtgggattt tcacagatgc atgccatgtt gtcgagagcc tcttagattt  6660
tctcaactgt gagaaagaaa aacgaaaatg ttgaagacgt tgagtctgga gaggggatac  6720
taatcactgt ccagttgggc actggtggga atggggaaat ggcacaggaa tgcaagcctc  6780
tccaccctac cccccgaact ccagccatac actcatcgtt tcacaaaata taaatgagtt  6840
agcattaaat gtttcagagt aaataattcc ttttcccgaa atgcatgaag atagagtaac  6900
agacttctca cactgtattt ttagggtatg gagaatttag aaggttaaag aattactgct  6960
tcaatttttc agttaaaaaa aaatcaggaa gctctgttca ttcaggctat gcaccatgtg  7020
cacagtcaag aattagcaga aaccctctgc atttacaaac actttgtgct ataaaaaagt  7080
aatttttaaa aagccacgtg tgtgtgtgtg tatatatata tatatatata tatttaaagc  7140
```

-continued

```
caaggttttg atactttttt acaaaaaacta caagagaaaa caaatatacc tgtccaaacc  7200
atatactttt aaaagagcat tttttttttcc atacaagctg ttgttaattt gggggtaaag  7260
tgctgatttg caaacttcat caaattgttc ccaagtggat tctccttgtt tgtctccccc  7320
taccaacccc aaagttacca tatttgatgt aagaatcagg catgttagaa tgttgtgtca  7380
cactaactga ttctgctctt tttgtcttgt cattcaagtt ccgttagctt ctgtacgcgg  7440
tgccctttgc agtctggtgt ctcttccaga ggcgaggggg ctgaggatgg ggtgctgcat  7500
ctcactagct atactggcat catcttggta aactgaaaac caaatgtgga catttgtaaa  7560
atcagtgcac tgtttctaga gagagattaa attcatttaa aaaaaa                 7606

SEQ ID NO: 18          moltype = AA  length = 904
FEATURE                Location/Qualifiers
source                 1..904
                       mol_type = protein
                       organism = Homo sapiens
SEQUENCE: 18
MGLPEPGPLR LLALLLLLLL LLLLQLQHLA AAAADPLLGG QGPAKDCEKD QFQCRNERCI  60
PSVWRCDEDD DCLDHSDEDD CPKKTCADSD FTCDNGHCIH ERWKCDGEEE CPDGSDESEA  120
TCTKQVCPAE KLSCGPTSHK CVPASWRCDG EKDCEGGADE AGCATLCAPH EFQCGNRSCL  180
AAVFVCDGDD DCGDGSDERG CADPACGPRE FRCGGDGGGA CIPERWVCDR QFDCEDRSDE  240
AAELCGRPGP GATSAPAACA TASQFACRSG ECVHLGWRCD GDRDCKDKSD EADCPLGTCR  300
GDEFQCGDGT CVLAIKHCNQ EQDCPDGSDE AGCLQGLNEC LHNNGGCSHI CTDLKIGFEC  360
TCPAGFQLLD QKTCGDIDEC KDPDACSQIC VNYKGYFKCE CYPGYEMDLL TKNCKAAAGK  420
SPSLIFTNRH EVRRIDLVKR NYSRLIPMLK NVVALDVEVA TNRIYWCDLS YRKIYSAYMD  480
KASDPKEQEV LIDEQLHSPE GLAVDWVHKH IYWTDSGNKT ISVATVDGGR RRTLFSRNLS  540
EPRAIAVDPL RGFMYWSDWG DQAKIEKSGL NGVDRQTLVS DNIEWPNGIT LDLLSQRLYW  600
VDSKLHQLSS IDFSGGNRKT LISSTDFLSH PFGIAVFEDK VFWTDLENEA IFSANRLNGL  660
EISILAENLN NPHDIVIFHE LKQPRAPDAC ELSVQPNGGC EYLCLPAPQI SSHSPKYTCA  720
CPDTMWLGPD MKRCYRAPQS TSTTTLASTM TRTVPATTRA PGTTVHRSTY QNHSTETPSL  780
TAAVPSSVSV PRAPSISPST LSPATSNHSQ HYANEDSKMG STVTAAVIGI IVPIVVIALL  840
CMSGYLIWRN WKRKNTKSMN FDNPVYRKTT EEEDEDELHI GRTAQIGHVY PARVALSLED  900
DGLP                                                            904

SEQ ID NO: 19          moltype = RNA  length = 2358
FEATURE                Location/Qualifiers
source                 1..2358
                       mol_type = unassigned RNA
                       organism = Homo sapiens
SEQUENCE: 19
aaactcacac aacaactctt ccccgctgag aggagacagc cagtgcgact ccaccctcca  60
gctcgacggc agccgccccg gccgacagcc ccgagacgac agcccggcgc gtcccggtcc  120
ccacctccga ccaccgccag cgctccaggc cccgccgctc cccgctcgcc gccaccgcgc  180
cctccgctcc gcccgcagtg ccaaccatga ccgccgccag tatgggcccc gtccgcgtcg  240
ccttcgtggt cctcctcgcc ctctgcagcc ggccggccgt cggccagaac tgcagcgggc  300
cgtgccggtg cccggacgag ccggcgccgc gctgcccggc gggcgtgagc ctcgtgctgg  360
acggctgcgg ctgctgccgc gtctgcgcca agcagctggg cgagctgtgc accgagcgcg  420
acccctgcga cccgcacaag ggcctcttct gtgacttcgg ctccccggcc aaccgcaaga  480
tcggcgtgtg caccgccaaa gatggtgctc cctgcatctt cggtggtacg gtgtaccgca  540
gcggagagtc cttccagagc agctgcaagt accagtgcac gtgcctggac ggggcggtgg  600
gctgcatgcc cctgtgcagc atggacgttc gtctgcccag ccctgactgc cccttcccga  660
ggagggtcaa gctgcccggg aaatgctgcg aggagtgggt gtgtgacgag cccaaggacc  720
aaaccgtggt tgggcctgcc ctcgcggctt accgactgga agacacgttt ggcccagacc  780
caactatgat tagagccaac tgcctggtcc agaccacaga gtggagcgcc tgttccaaga  840
cctgtgggat gggcatctcc acccgggtta ccaatgacaa cgcctcctgc aggctagaga  900
agcagagccg cctgtgcatg gtcaggcctt gcgaagctga cctggaagag aacattaaga  960
agggcaaaaa gtgcatccgt actcccaaaa tctccaagcc tatcaagttt gagctttctg  1020
gctgcaccag catgaagaca taccgagcta aattctgtgg agtatgtacc gacggccgat  1080
gctgcacccc ccacagaacc accaccctgc cggtggagtt caagtgccct gacggcgagg  1140
tcatgaagaa gaacatgatg ttcatcaaga cctgtgcctg ccattacaac tgtcccggag  1200
acaatgacat ctttgaatcg ctgtactaca ggaagatgta cggagacatg gcatgaagcc  1260
agagagtgag agacattaac tcattagact ggaacttgaa ctgattcaca tctcattttt  1320
ccgtaaaaat gatttcagta gcacaagtta tttaaatctg tttttctaac tgggggaaaa  1380
gattcccacc caattcaaaa cattgtgcca tgtcaaacaa atagtctatc aaccccagac  1440
actggtttga agaatgttaa gacttgacag tggaactaca ttagtacaca gcaccagaat  1500
gtatattaag gtgtggcttt aggagcagtg ggagggtacc agcagaaagg ttagtatcat  1560
cagatagcat cttatacgag taatatgcct gctatttgaa gtgtaattga gaaggaaaat  1620
tttagcgtgc tcactgacct gcctgtagcc ccagtgacag ctaggatgtg cattctccag  1680
ccatcaagag actgagtcaa gttgttcctt aagtcagaac agcagactca gctctgacat  1740
tctgattcga atgacactgt tcaggaatcg gaatcctgtc gattagactg gacagcttgt  1800
ggcaagtgaa tttgcctgta acaagccaga ttttttaaaa tttatattgt aaatattgtg  1860
tgtgtgtgtg tgtgtgtata tatatatata tgtacagtta tctaagttaa tttaaagttg  1920
tttgtgcctt tttatttttg tttttaatgc tttgatattt caatgttagc ctcaatttct  1980
gaacaccata ggtagaatgt aaagcttgtc tgatcgttca aagcatgaaa tggatactta  2040
tatggaaatt ctgctcagat agaatgacag tccgtcaaaa cagattgttt gcaaaggggga  2100
ggcatcagtg tccttggcag gctgatttct aggtaggaaa tgtggtagcc tcacttttaa  2160
tgaacaaatg gcctttatta aaaactgagt gactctatat agctgatcag ttttttcacc  2220
tggaagcatt tgtttctact ttgatatgac tgtttttcgg acagtttatt tgttgagagt  2280
gtgaccaaaa gttacatgtt tgcacctttc tagttgaaaa taaagtgtat atttttctta  2340
taaaaaaaaa aaaaaaaa                                             2358
```

-continued

```
SEQ ID NO: 20          moltype = AA  length = 349
FEATURE                Location/Qualifiers
source                 1..349
                       mol_type = protein
                       organism = Homo sapiens
SEQUENCE: 20
MTAASMGPVR VAFVVLLALC SRPAVGQNCS GPCRCPDEPA PRCPAGVSLV LDGCGCCRVC  60
AKQLGELCTE RDPCDPHKGL FCDFGSPANR KIGVCTAKDG APCIFGGTVY RSGESFQSSC  120
KYQCTCLDGA VGCMPLCSMD VRLPSPDCPF PRRVKLPGKC CEEWVCDEPK DQTVVGPALA  180
AYRLEDTFGP DPTMIRANCL VQTTEWSACS KTCGMGISTR VTNDNASCRL EKQSRLCMVR  240
PCEADLEENI KKGKKCIRTP KISKPIKFEL SGCTSMKTYR AKFCGVCTDG RCCTPHRTTT  300
LPVEFKCPDG EVMKKNMMFI KTCACHYNCP GDNDIFESLY YRKMYGDMA              349

SEQ ID NO: 21          moltype = RNA  length = 1939
FEATURE                Location/Qualifiers
source                 1..1939
                       mol_type = unassigned RNA
                       organism = Homo sapiens
SEQUENCE: 21
aggaaggagg ggtggcctga cccctcggca gtccctcccc tcagcctttc cccaaattgc  60
tacttctctg gggctccagg tcctgcttgt gctcagctcc agctcactgg ctggccaccg  120
agacttctgg acaggaaact gcaccatcct cttctcccag caagggggct ccagagactg  180
cccacccagg aagtctggtg gcctggggat ttggacagtg ccttggtaat gaccagggct  240
ccaggaagag atgtccttgt ggctgggggc ccctgtgcct gacattcctc ctgactctgc  300
ggtggagctg tggaagccag gcgcacagga tgcaagcagc caggcccagg gaggcagcag  360
ctgcatcctc agagaggaag ccaggatgcc ccactctgct gggggtactg caggggtggg  420
gctggaggct gcagagccca cagccctgct caccagggca gagccccctt cagaacccac  480
agagatccgt ccacaaaagc ggaaaaaggg gccagccccc aaaatgctgg ggaacgagct  540
atgcagcgtg tgtggggaca aggcctcggg cttccactac aatgttctga gctgcgaggg  600
ctgcaaggga ttcttccgcc gcagcgtcat caagggagcg cactacatct gccacagtgg  660
cggccactgc cccatggaca cctacatgcg tcgcaagtgc caggagtgtc ggcttcgcaa  720
atgccgtcag gctggcatgc gggaggagtg tgtcctgtca gaagaacaga tccgcctgaa  780
gaaactgaag cggcaagagg aggaacaggc tcatgccaca tccttgcccc ccagggcttc  840
ctcacccccc caaatcctgc cccagctcag cccggaacaa ctgggcatga tcgagaagct  900
cgtcgctgcc cagcaacagt gtaaccggcg ctccttttct gaccggcttc gagtcacgcc  960
ttggcccatg gcaccagatc cccatagccg ggaggcccgt cagcagcgct ttgcccactt  1020
cactgagctg gccatcgtct ctgtgcagga gatagttgac tttgctaaac agctacccgg  1080
cttcctgcag ctcagccggg aggaccagat tgccctgctg aagacctctg cgatcgaggt  1140
gatgcttctg gagacatctc ggaggtacaa ccctgggagt gagagtatca ccttcctcaa  1200
ggatttcagt tataaccggg aagactttgc caaagcaggg ctgcaagtgg aattcatcaa  1260
ccccatcttc gagttctcca gggccatgaa tgagctgcaa ctcaatgatg ccgagtttgc  1320
cttgctcatt gctatcagca tcttctctgc agaccggccc aacgtgcagg accagctcca  1380
ggtagagagg ctgcagcaca catatgtgga agccctgcat gcctacgtct ccatccacca  1440
tccccatgac cgactgatgt tcccacggat gctaatgaaa ctggtgagcc tccggaccct  1500
gagcagcgtc cactcagagc aagtgtttgc actgcgtctg caggacaaaa agctccccac  1560
gctgctctct gagatctggg atgtgcacga atgactgttc tgtccccata ttttctgttt  1620
tcttggccgg atggctgagg cctggtggct gcctcctaga agtggaacag actgagaagg  1680
gcaaacattc ctgggagctg ggcaaggaga tcctcccgtg gcattaaaag agagtcaaag  1740
ggttgcgagt tttgtggcta ctgagcagtg gagccctcgc taacactgtg ctgtgtctga  1800
agatcatgct gaccccacaa acggatgggc ctgggggcca ctttgcacag ggttctccag  1860
agccctgccc atcctgcctc caccacttcc tgtttttccc acagggcccc aagaaaaatt  1920
ctccactgtc aaaaaaaaa                                               1939

SEQ ID NO: 22          moltype = AA  length = 447
FEATURE                Location/Qualifiers
source                 1..447
                       mol_type = protein
                       organism = Homo sapiens
SEQUENCE: 22
MSLWLGAPVP DIPPDSAVEL WKPGAQDASS QAQGGSSCIL REEARMPHSA GGTAGVGLEA  60
AEPTALLTRA EPPSEPTEIR PQKRKKGPAP KMLGNELCSV CGDKASGFHY NVLSCEGCKG  120
FFRRSVIKGA HYICHSGGHC PMDTYMRRKC QECRLRKCRQ AGMREECVLS EEQIRLKKLK  180
RQEEEQAHAT SLPPRASSPP QILPQLSPEQ LGMIEKLVAA QQQCNRRSFS DRLRVTPWPM  240
APDPHSREAR QQRFAHFTEL AIVSVQEIVD FAKQLPGFLQ LSREDQIALL KTSAIEVMLL  300
ETSRRYNPGS ESITFLKDFS YNREDFAKAG LQVEFINPIF EFSRAMNELQ LNDAEFALLI  360
AISIFSADRP NVQDQLQVER LQHTYVEALH AYVSIHHPHD RLMFPRMLMK LVSLRTLSSV  420
HSEQVFALRL QDKKLPPLLS EIWDVHE                                      447

SEQ ID NO: 23          moltype = RNA  length = 1759
FEATURE                Location/Qualifiers
source                 1..1759
                       mol_type = unassigned RNA
                       organism = Homo sapiens
SEQUENCE: 23
aggaaggagg ggtggcctga cccctcggca gtccctcccc tcagcctttc cccaaattgc  60
tacttctctg gggctccagg tcctgcttgt gctcagctcc agctcactgg ctggccaccg  120
agacttctgg acaggaaact gcaccatcct cttctcccag caagggggct ccagagactg  180
cccacccagg aagtctggtg gcctggggat ttggacagtg ccttggtaat gaccagggct  240
ccaggaagag atgtccttgt ggctgggggc ccctgtgcct gacattcctc ctgactctgc  300
```

```
ggtggagctg tggaagccag gcgcacagga tgcaagcagc caggcccagg gaggcagcag  360
ctgcatcctc agagaggaag ccaggatgcc ccactctgct gggggtactg caggggtggg  420
gctggaggct gcagagccca cagccctgct caccagggca gagccccctt cagaacccac  480
agagatccgt ccacaaaagc ggaaaaaggg gccagccccc aaaatgctgg ggaacgagct  540
atgcagcgtg tgtggggaca aggcctcggg cttccactac aatgttctga gctgcgaggg  600
ctgcaaggga ttcttccgcc gcagcgtcat caagggagcg cactacatct gccacagtgg  660
cggccactgc cccatggaca cctacatgcg tcgcaagtgc caggagtgtc ggcttcgcaa  720
atgccgtcag gctggcatgc gggaggagtg tgtcctgtca gaagaacaga tccgcctgaa  780
gaaactgaag cggcaagagg aggaacaggc tcatgccaca tccttgcccc ccagggcttc  840
ctcacccccc caaatcctgc cccagctcag cccggaacaa ctgggcatga tcgagaagct  900
cgtcgctgcc cagcaacagt gtaaccggcg ctccttttct gaccggcttc gagtcacggt  960
gatgcttctg gagacatctc ggaggtacaa ccctgggagt gagagtatca ccttcctcaa  1020
ggatttcagt tataaccggg aagactttgc caaagcaggg ctgcaagtgg aattcatcaa  1080
ccccatcttc gagttctcca gggccatgaa tgagctgcaa ctcaatgatg ccgagtttgc  1140
cttgctcatt gctatcagca tcttctctgc agaccggccc aacgtgcagg accagctcca  1200
ggtagagagg ctgcagcaca catatgtgga agccctgcat gcctacgtct ccatccacca  1260
tccccatgac cgactgatgt tcccacggat gctaatgaaa ctggtgagcc tccggaccct  1320
gagcagcgtc cactcagagc aagtgtttgc actgcgtctg caggacaaaa agctccccacc  1380
gctgctctct gagatctggg atgtgcacga atgactgttc tgtccccata ttttctgttt  1440
tcttggccgg atggctgagg cctggtggct gcctcctaga agtggaacag actgagaagg  1500
gcaaacattc ctgggagctg ggcaaggaga tcctcccgtg gcattaaaag agagtcaaag  1560
ggttgcgagt tttgtggcta ctgagcagtg gagccctcgc taacactgtg ctgtgtctga  1620
agatcatgct gaccccacaa acggatgggc ctgggggcca ctttgcacag ggttctccag  1680
agccctgccc atcctgcctc caccacttcc tgtttttccc acagggcccc aagaaaaatt  1740
ctccactgtc aaaaaaaaa                                                1759
```

```
SEQ ID NO: 24          moltype = AA  length = 387
FEATURE                Location/Qualifiers
source                 1..387
                       mol_type = protein
                       organism = Homo sapiens
SEQUENCE: 24
MSLWLGAPVP DIPPDSAVEL WKPGAQDASS QAQGGSSCIL REEARMPHSA GGTAGVGLEA  60
AEPTALLTRA EPPSEPTEIR PQKRKKGPAP KMLGNELCSV CGDKASGFHY NVLSCEGCKG  120
FFRRSVIKGA HYICHSGGHC PMDTYMRRKC QECRLRKCRQ AGMREECVLS EEQIRLKKLK  180
RQEEEQAHAT SLPPRASSPP QILPQLSPEQ LGMIEKLVAA QQQCNRRSFS DRLRVTVMLL  240
ETSRRYNPGS ESITFLKDFS YNREDFAKAG LQVEFINPIF EFSRAMNELQ LNDAEFALLI  300
AISIFSADRP NVQDQLQVER LQHTYVEALH AYVSIHHPHD RLMFPRMLMK LVSLRTLSSV  360
HSEQVFALRL QDKKLPPLLS EIWDVHE                                      387
```

```
SEQ ID NO: 25          moltype = RNA  length = 1748
FEATURE                Location/Qualifiers
source                 1..1748
                       mol_type = unassigned RNA
                       organism = Homo sapiens
SEQUENCE: 25
atcttactta gggacctgct ggggtgcggg gaaaaggcgc agtctcggtg ggattgcgtg  60
caggagggtc gtggtctggc tgtggcggag gagcataaga agactctgcg gtggagctgt  120
ggaagccagg cgcacaggat gcaagcagcc aggcccaggg aggcagcagc tgcatcctca  180
gagaggaagc caggatgccc cactctgctg ggggtactgc aggggtgggg ctggaggctg  240
cagagcccac agccctgctc accagggcag agcccccttc agaacccaca gagatccgtc  300
cacaaaagcg gaaaaagggg ccagccccca aaatgctggg gaacgagcta tgcagcgtgt  360
gtggggacaa ggcctcgggc ttccactaca atgttctgag ctgcgagggc tgcaagggat  420
tcttccgccg cagcgtcatc aagggagcgc actacatctg ccacagtggc ggccactgcc  480
ccatggacac ctacatgcgt cgcaagtgcc aggagtgtcg gcttcgcaaa tgccgtcagg  540
ctggcatgcg ggaggagtgt gtcctgtcag aagaacagat ccgcctgaag aaactgaagc  600
ggcaagagga ggaacaggct catgccacat ccttgccccc cagggcttcc tcaccccccc  660
aaatcctgcc ccagctcagc ccggaacaac tgggcatgat cgagaagctc gtcgctgccc  720
agcaacagtg taaccggcgc tccttttctg accggcttcg agtcacggtg atgcttctgg  780
caccagatcc ccatagccgg gaggcccgtc agcagcgctt tgcccacttc actgagctgg  840
ccatcgtctc tgtgcaggag atagttgact ttgctaaaca gctacccggc ttcctgcagc  900
tcagccggga ggaccagatt gccctgctga agacctctgc gatcgaggtg atgcttctgg  960
agacatctcg gaggtacaac cctgggagtg agagtatcac cttcctcaag gatttcagtt  1020
ataaccggga agactttgcc aaagcagggc tgcaagtgga attcatcaac cccatcttcg  1080
agttctccag ggccatgaat gagctgcaac tcaatgatgc cgagtttgcc ttgctcattg  1140
ctatcagcat cttctctgca gaccggccca acgtgcagga ccagctccag gtagagaggc  1200
tgcagcacac atatgtggaa gccctgcatg cctacgtctc catccaccat ccccatgacc  1260
gactgatgtt cccacggatg ctaatgaaac tggtgagcct ccggaccctg agcagcgtcc  1320
actcagagca agtgtttgca ctgcgtctgc aggacaaaaa gctcccaccg ctgctctctg  1380
agatctggga tgtgcacgaa tgactgttct gtccccatat tttctgtttt cttggccgga  1440
tggctgaggc ctggtggctg cctcctagaa gtggaacaga ctgagaaggg caaacattcc  1500
tgggagctgg gcaaggagat cctcccgtgg cattaaaaga gagtcaaagg gttgcgagtt  1560
ttgtggctac tgagcagtgg agccctcgct aacactgtgc tgtgtctgaa gatcatgctg  1620
accccacaaa cggatgggcc tgggggccac tttgcacagg gttctccaga gccctgccca  1680
tcctgcctcc accacttcct gtttttccca cagggcccca agaaaaattc tccactgtca  1740
aaaaaaaa                                                            1748
```

```
SEQ ID NO: 26          moltype = AA  length = 402
FEATURE                Location/Qualifiers
```

```
source                  1..402
                        mol_type = protein
                        organism = Homo sapiens
SEQUENCE: 26
MPHSAGGTAG VGLEAAEPTA LLTRAEPPSE PTEIRPQKRK KGPAPKMLGN ELCSVCGDKA  60
SGFHYNVLSC EGCKGFFRRS VIKGAHYICH SGGHCPMDTY MRRKCQECRL RKCRQAGMRE  120
ECVLSEEQIR LKKLKRQEEE QAHATSLPPR ASSPPQILPQ LSPEQLGMIE KLVAAQQQCN  180
RRSFSDRLRV TPWPMAPDPH SREARQQRFA HFTELAIVSV QEIVDFAKQL PGFLQLSRED  240
QIALLKTSAI EVMLLETSRR YNPGSESITF LKDFSYNRED FAKAGLQVEF INPIFEFSRA  300
MNELQLNDAE FALLIAISIF SADRPNVQDQ LQVERLQHTY VEALHAYVSI HHPHDRLMFP  360
RMLMKLVSLR TLSSVHSEQV FALRLQDKKL PPLLSEIWDV HE                    402

SEQ ID NO: 27           moltype = RNA  length = 1928
FEATURE                 Location/Qualifiers
source                  1..1928
                        mol_type = unassigned RNA
                        organism = Homo sapiens
SEQUENCE: 27
gattctaact tagctaagca atgctactgg agaccatagg caaagccaag gtacagcttc  60
agggaagtct ttggtgagcc catctctcat taccaaggta acgaagcgca gactccgggc  120
ccgggtgggc ggcatcacca ccaggttcac gccgagaagg agctggagga gagccgcccg  180
gctccagccg gaccgcttgc ccgccatcac cgttgtaatc tatgcagcaa acaagctgga  240
acccgctggg tggcacctgc aagcagccgc ccggacgcac ccactctgcg gtggagctgt  300
ggaagccagg cgcacaggat gcaagcagcc aggcccaggg aggcagcagc tgcatcctca  360
gagaggaagc caggatgccc cactctgctg ggggtactgc aggggtgggg ctggaggctg  420
cagagcccac agccctgctc accagggcag agccccctc agaacccaca gagatccgtc  480
cacaaaagcg gaaaaagggg ccagcccccca aaatgctggg gaacgagcta tgcagcgtgt  540
gtggggacaa ggcctcgggc ttccactaca atgttctgag ctgcgagggc tgcaagggat  600
tcttccgccg cagcgtcatc aagggagcgc actacatctg ccacagtggc ggccactgcc  660
ccatggacac ctacatgcgt cgcaagtgcc aggagtgtcg gcttcgcaaa tgccgtcagg  720
ctggcatgcg ggaggagtgt gtcctgtcag aagaacagat ccgcctgaag aaactgaagc  780
ggcaagagga ggaacaggct catgccacat ccttgccccc cagggcttcc tcaccccccc  840
aaatcctgcc ccagctcagc ccggaacaac tgggcatgat cgagaagctc gtcgctgccc  900
agcaacagtg taaccggcgc tccttttctg accggcttcg agtcacgcct tggcccatgg  960
caccagatcc ccatagccgg gaggcccgtc agcagcgctt tgcccacttc actgagctgg  1020
ccatcgtctc tgtgcaggag atagttgact ttgctaaaca gctacccggc ttcctgcagc  1080
tcagccggga ggaccagatt gccctgctga agacctctgc gatcgaggtg atgcttctgg  1140
agacatctcg gaggtacaac cctgggagtg agagtatcac cttcctcaag gatttcagtt  1200
ataaccggga agactttgcc aaagcagggc tgcaagtgga attcatcaac cccatcttcg  1260
agttctccag ggccatgaat gagctgcaac tcaatgatgc cgagtttgcc ttgctcattg  1320
ctatcagcat cttctctgca gaccggccca acgtgcagga ccagctccag gtagagaggc  1380
tgcagcacac atatgtggaa gccctgcatg cctacgtctc catccaccat ccccatgacc  1440
gactgatgtt cccacggatg ctaatgaaac tggtgagcct ccggaccctg agcagcgtcc  1500
actcagagca agtgtttgca ctgcgtctgc aggacaaaaa gctcccaccg ctgctctctg  1560
agatctggga tgtgcacgaa tgactgttct gtccccatat tttctgtttt cttggccgga  1620
tggctgaggc ctggtggctg cctcctagaa gtggaacaga ctgagaaggg caaacattcc  1680
tgggagctgg gcaaggagat cctcccgtgg cattaaaaga gagtcaaagg gttgcgagtt  1740
ttgtggctac tgagcagtgg agccctcgct aacactgtgc tgtgtctgaa gatcatgctg  1800
accccacaaa cggatgggcc tgggggccac tttgcacagg gttctccaga gccctgccca  1860
tcctgcctcc accacttcct gtttttccca cagggcccca agaaaaattc tccactgtca  1920
aaaaaaaa                                                          1928

SEQ ID NO: 28           moltype = AA  length = 453
FEATURE                 Location/Qualifiers
source                  1..453
                        mol_type = protein
                        organism = Homo sapiens
SEQUENCE: 28
MQQTSWNPLG GTCKQPPGRT HSAVELWKPG AQDASSQAQG GSSCILREEA RMPHSAGGTA  60
GVGLEAAEPT ALLTRAEPPS EPTEIRPQKR KKGPAPKMLG NELCSVCGDK ASGFHYNVLS  120
CEGCKGFFRR SVIKGAHYIC HSGGHCPMDT YMRRKCQECR LRKCRQAGMR EECVLSEEQI  180
RLKKLKRQEE EQAHATSLPP RASSPPQILP QLSPEQLGMI EKLVAAQQQC NRRSFSDRLR  240
VTPWPMAPDP HSREARQQRF AHFTELAIVS VQEIVDFAKQ LPGFLQLSRE DQIALLKTSA  300
IEVMLLETSR RYNPGSESIT FLKDFSYNRE DFAKAGLQVE FINPIFEFSR AMNELQLNDA  360
EFALLIAISI FSADRPNVQD QLQVERLQHT YVEALHAYVS IHHPHDRLMF PRMLMKLVSL  420
RTLSSVHSEQ VFALRLQDKK LPPLLSEIWD VHE                              453

SEQ ID NO: 29           moltype = RNA  length = 2093
FEATURE                 Location/Qualifiers
source                  1..2093
                        mol_type = unassigned RNA
                        organism = Homo sapiens
SEQUENCE: 29
tcgtcaagtt tcacgctccg cccctcttcc ggacgtgacg caagggcggg gttgccggaa  60
gaagtggcga agttactttt gagggtattt gagtagcggc ggtgtgtcag gggctaaaga  120
ggaggacgaa gaaaagcaga gcaagggaac ccagggcaac aggagtagtt cactccgcga  180
gaggccgtcc acgagacccc cgcgcgcagc catgagcccc gcccccccgct gttgcttgga  240
gaggggcggg acctggagag aggctgctcc gtgaccccac catgtcctct cctaccacga  300
gttccctgga taccccccctg cctggaaatg gccccccctca gcctggcgcc ccttcttctt  360
```

-continued

```
cacccactgt aaaggaggag ggtccggagc cgtggcccgg gggtccggac cctgatgtcc  420
caggcactga tgaggccagc tcagcctgca gcacagactg ggtcatccca gatcccgaag  480
aggaaccaga gcgcaagcga aagaagggcc cagccccgaa gatgctgggc cacgagcttt  540
gccgtgtctg tggggacaag gcctccggct tccactacaa cgtgctcagc tgcgaaggct  600
gcaagggctt cttccggcgc agtgtggtcc gtggtggggc caggcgctat gcctgccggg  660
gtggcggaac ctgccagatg gacgctttca tgcggcgcaa gtgccagcag tgccggctgc  720
gcaagtgcaa ggaggcaggg atgagggagc agtgcgtcct ttctgaagaa cagatccgga  780
agaagaagat tcggaaacaa cagcagcagg agtcacagtc acagtcgcag tcacctgtgg  840
ggccgcaggg cagcagcagc tcagcctctg ggcctggggc ttcccctggt ggatctgagg  900
caggcagcca gggctccggg gaaggcgagg gtgtccagct aacagcggct caagaactaa  960
tgatccagca gttggtggcg gcccaactgc agtgcaacaa acgctccttc tccgaccagc  1020
ccaaagtcac gccctggccc ctgggcgcag acccccagtc ccgagatgcc cgccagcaac  1080
gctttgccca cttcacggag ctggccatca tctcagtcca ggagatcgtg gacttcgcta  1140
agcaagtgcc tggtttcctg cagctgggcc gggaggacca gatcgccctc ctgaaggcat  1200
ccactatcga gatcatgctg ctagagacag ccaggcgcta caaccacgag acagagtgta  1260
tcaccttctt gaaggacttc acctacagca aggacgactt ccaccgtgca ggcctgcagg  1320
tggagttcat caaccccatc ttcgagttct cgcgggccat gcggcggctg ggcctggacg  1380
acgctgagta cgccctgctc atcgccatca acatcttctc ggccgaccgg cccaacgtgc  1440
aggagccggg ccgcgtggag gcgttgcagc agccctacgt ggaggcgctg ctgtcctaca  1500
cgcgcatcaa gaggccgcag gaccagctgc gcttcccgcg catgctcatg aagctggtga  1560
gcctgcgcac gctgagctct gtgcactcgg agcaggtctt cgccttgcgg ctccaggaca  1620
agaagctgcc gcctctgctg tcggagatct gggacgtcca cgagtgaggg gctggccacc  1680
cagccccaca gccttgcctg accaccctcc agcagataga cgccggcacc ccttcctctt  1740
cctagggtgg aaggggccct gggccgagcc tgtagaccta tcggctctca tcccttggga  1800
taagccccag tccaggtcca ggaggctccc tccctgccca gcgagtcttc cagaaggggt  1860
gaaagggttg caggtcccga ccactgaccc ttcccggctg ccctccctcc ccagcttaca  1920
cctcaagccc agcacgcagt gcaccttgaa cagagggagg ggaggaccca tggctctccc  1980
ccctagcccg ggagaccagg gccttcctct tcctctgctt ttatttaata aaaactaaaa  2040
acagaaacag gaaaataaaa tatgaataca atccagcccg gagctggagt gca        2093

SEQ ID NO: 30          moltype = AA  length = 461
FEATURE                Location/Qualifiers
source                 1..461
                       mol_type = protein
                       organism = Homo sapiens
SEQUENCE: 30
MSSPTTSSLD TPLPGNGPPQ PGAPSSSPTV KEEGPEPWPG GPDPDVPGTD EASSACSTDW  60
VIPDPEEEPE RKRKKGPAPK MLGHELCRVC GDKASGFHYN VLSCEGCKGF FRRSVVRGGA  120
RRYACRGGGT CQMDAFMRRK CQQCRLRKCK EAGMREQCVL SEEQIRKKKI RKQQQQESQS  180
QSQSPVGPQG SSSSASGPGA SPGGSEAGSQ GSGEGEGVQL TAAQELMIQQ LVAAQLQCNK  240
RSFSDQPKVT PWPLGADPQS RDARQQRFAH FTELAIISVQ EIVDFAKQVP GFLQLGREDQ  300
IALLKASTIE IMLLETARRY NHETECITFL KDFTYSKDDF HRAGLQVEFI NPIFEFSRAM  360
RRLGLDDAEY ALLIAINIFS ADRPNVQEPG RVEALQQPYV EALLSYTRIK RPQDQLRFPR  420
MLMKLVSLRT LSSVHSEQVF ALRLQDKKLP PLLSEIWDVH E                      461

SEQ ID NO: 31          moltype = RNA  length = 1802
FEATURE                Location/Qualifiers
source                 1..1802
                       mol_type = unassigned RNA
                       organism = Homo sapiens
SEQUENCE: 31
tcgtcaagtt tcacgctccg cccctcttcc ggacgtgacg caagggcggg gttgccggaa  60
gaagtggcga agttactttt gagggtattt gagtagcggc ggtgtgtcag gggctaaaga  120
ggaggacgaa gaaaagcaga gcaagggaac ccagggcaac aggagtagtt cactccgcga  180
gaggccgtcc acgagacccc cgcgcgcagc catgagcccc gccccccgct gttgcttgga  240
gaggggcggg acctggagag aggctgctcc gtgaccccac catgtcctct cctaccacga  300
gttccctgga taccccccctg cctggaaatg gcccccctca gcctggcgcc ccttcttctt  360
cacccactgt aaaggaggag ggtccggagc cgtggcccgg gggtccggac cctgatgtcc  420
caggcactga tgaggccagc tcagcctgca gcacagactg gggcgtcctt tctgaagaac  480
agatccggaa gaagaagatt cggaaacaac agcagcagga gtcacagtca cagtcgcagt  540
cacctgtggg gccgcagggc agcagcagct cagcctctgg gcctggggct tcccctggtg  600
gatctgaggc aggcagccag ggctccgggg aaggcgaggg tgtccagcta acagcggctc  660
aagaactaat gatccagcag ttggtggcgg cccaactgca gtgcaacaaa cgctccttct  720
ccgaccagcc caaagtcacg ccctggcccc tgggcgcaga cccccagtcc cgagatgccc  780
gccagcaacg ctttgcccac ttcacggagc tggccatcat ctcagtccag gagatcgtgg  840
acttcgctaa gcaagtgcct ggtttcctgc agctgggccg ggaggaccag atcgccctcc  900
tgaaggcatc cactatcgag atcatgctgc tagagacagc caggcgctac aaccacgaga  960
cagagtgtat caccttcttg aaggacttca cctacagcaa ggacgacttc caccgtgcag  1020
gcctgcaggt ggagttcatc aaccccatct tcgagttctc gcgggccatg cggcggctgg  1080
gcctggacga cgctgagtac gccctgctca tcgccatcaa catcttctcg gccgaccggc  1140
ccaacgtgca ggagccgggc cgcgtggagg cgttgcagca gccctacgtg gaggcgctgc  1200
tgtcctacac gcgcatcaag aggccgcagg accagctgcg cttcccgcgc atgctcatga  1260
agctggtgag cctgcgcacg ctgagctctg tgcactcgga gcaggtcttc gccttgcggc  1320
tccaggacaa gaagctgccg cctctgctgt cggagatctg ggacgtccac gagtgagggg  1380
ctggccaccc agccccacag ccttgcctga ccaccctcca gcagatagac gccggcaccc  1440
cttcctcttc ctagggtgga aggggccctg ggccgagcct gtagacctat cggctctcat  1500
cccttgggat aagccccagt ccaggtccag gaggctccct ccctgcccag cgagtcttcc  1560
agaaggggtg aaagggttgc aggtcccgac cactgaccct tcccggctgc cctccctccc  1620
cagcttacac ctcaagccca gcacgcagtg caccttgaac agagggaggg gaggacccat  1680
```

```
ggctctcccc cctagcccgg gagaccaggg ccttcctctt cctctgcttt tatttaataa  1740
aaactaaaaa cagaaacagg aaaataaaat atgaatacaa tccagcccgg agctggagtg  1800
ca                                                                 1802

SEQ ID NO: 32          moltype = AA  length = 364
FEATURE                Location/Qualifiers
source                 1..364
                       mol_type = protein
                       organism = Homo sapiens
SEQUENCE: 32
MSSPTTSSLD TPLPGNGPPQ PGAPSSSPTV KEEGPEPWPG GPDPDVPGTD EASSACSTDW  60
GVLSEEQIRK KKIRKQQQQE SQSQSQSPVG PQGSSSSASG PGASPGGSEA GSQGSGEGEG  120
VQLTAAQELM IQQLVAAQLQ CNKRSFSDQP KVTPWPLGAD PQSRDARQQR FAHFTELAII  180
SVQEIVDFAK QVPGFLQLGR EDQIALLKAS TIEIMLLETA RRYNHETECI TFLKDFTYSK  240
DDFHRAGLQV EFINPIFEFS RAMRRLGLDD AEYALLIAIN IFSADRPNVQ EPGRVEALQQ  300
PYVEALLSYT RIKRPQDQLR FPRMLMKLVS LRTLSSVHSE QVFALRLQDK KLPPLLSEIW  360
DVHE                                                               364

SEQ ID NO: 33          moltype = RNA  length = 71
FEATURE                Location/Qualifiers
source                 1..71
                       mol_type = unassigned RNA
                       organism = Homo sapiens
SEQUENCE: 33
gccaacccag tgttcagact acctgttcag gaggctctca atgtgtacag tagtctgcac  60
attggttagg c                                                       71

SEQ ID NO: 34          moltype = RNA  length = 110
FEATURE                Location/Qualifiers
source                 1..110
                       mol_type = unassigned RNA
                       organism = Homo sapiens
SEQUENCE: 34
aggaagcttc tggagatcct gctccgtcgc cccagtgttc agactacctg ttcaggacaa  60
tgccgttgta cagtagtctg cacattggtt agactgggca agggagagca             110

SEQ ID NO: 35          moltype = RNA  length = 80
FEATURE                Location/Qualifiers
source                 1..80
                       mol_type = unassigned RNA
                       organism = Homo sapiens
SEQUENCE: 35
cgggaatgcc gcggcgggga cggcgattgg tccgtatgtg tggtgccacc ggccgccggc  60
tccgccccgg cccccgcccc                                              80

SEQ ID NO: 36          moltype = RNA  length = 110
FEATURE                Location/Qualifiers
source                 1..110
                       mol_type = unassigned RNA
                       organism = Homo sapiens
SEQUENCE: 36
ttggatgttg gcctagttct gtgtggaaga ctagtgattt tgttgttttt agataactaa  60
atcgacaaca aatcacagtc tgccatatgg cacaggccat gcctctacag             110

SEQ ID NO: 37          moltype = RNA  length = 110
FEATURE                Location/Qualifiers
source                 1..110
                       mol_type = unassigned RNA
                       organism = Homo sapiens
SEQUENCE: 37
ctggatacag agtggaccgg ctggccccat ctggaagact agtgattttg ttgttgtctt  60
actgcgctca acaacaaatc ccagtctacc taatggtgcc agccatcgca             110

SEQ ID NO: 38          moltype = RNA  length = 110
FEATURE                Location/Qualifiers
source                 1..110
                       mol_type = unassigned RNA
                       organism = Homo sapiens
SEQUENCE: 38
agattagagt ggctgtggtc tagtgctgtg tggaagacta gtgattttgt tgttctgatg  60
tactacgaca acaagtcaca gccggcctca tagcgcagac tcccttcgac             110

SEQ ID NO: 39          moltype = DNA  length = 71
FEATURE                Location/Qualifiers
source                 1..71
                       mol_type = unassigned DNA
                       organism = Homo sapiens
SEQUENCE: 39
gatccgacag tagcctgcac attagtcact tcctgtcagt aaccaatgtg cagactactg  60
```

```
tttttgaat t                                                        71

SEQ ID NO: 40          moltype = DNA  length = 73
FEATURE                Location/Qualifiers
source                 1..73
                       mol_type = unassigned DNA
                       organism = Homo sapiens
SEQUENCE: 40
gatccgccca gtgctcagac tacccgtgcc ttcctgtcag gaacaggtag tctgaacact  60
gggtttttga att                                                     73

SEQ ID NO: 41          moltype = DNA  length = 69
FEATURE                Location/Qualifiers
source                 1..69
                       mol_type = unassigned DNA
                       organism = Homo sapiens
SEQUENCE: 41
gatccgcggc gggaacggcg atcggccctt cctgtcagga ccaatcgccg tccccgccgt  60
ttttgaatt                                                          69

SEQ ID NO: 42          moltype = DNA  length = 73
FEATURE                Location/Qualifiers
source                 1..73
                       mol_type = unassigned DNA
                       organism = Homo sapiens
SEQUENCE: 42
gatccgtgga agattagtga gtttattatc ttcctgtcag acaacaaaat cactagtctt  60
ccatttttga att                                                     73

SEQ ID NO: 43          moltype = AA  length = 14
FEATURE                Location/Qualifiers
source                 1..14
                       mol_type = protein
                       organism = Mus musculus
SEQUENCE: 43
TQQIRLQAEI FQAR                                                    14

SEQ ID NO: 44          moltype = AA  length = 14
FEATURE                Location/Qualifiers
source                 1..14
                       mol_type = protein
                       organism = Homo sapiens
SEQUENCE: 44
AQQIRLQAEA FQAR                                                    14

SEQ ID NO: 45          moltype = AA  length = 14
FEATURE                Location/Qualifiers
REGION                 1..14
                       note = Synthetic
source                 1..14
                       mol_type = protein
                       organism = synthetic construct
SEQUENCE: 45
TAQIRLQAEI FQAR                                                    14

SEQ ID NO: 46          moltype = AA  length = 14
FEATURE                Location/Qualifiers
REGION                 1..14
                       note = Synthetic
source                 1..14
                       mol_type = protein
                       organism = synthetic construct
SEQUENCE: 46
TQAIRLQAEI FQAR                                                    14

SEQ ID NO: 47          moltype = AA  length = 14
FEATURE                Location/Qualifiers
REGION                 1..14
                       note = Synthetic
source                 1..14
                       mol_type = protein
                       organism = synthetic construct
SEQUENCE: 47
TQQARLQAEI FQAR                                                    14

SEQ ID NO: 48          moltype = AA  length = 14
FEATURE                Location/Qualifiers
REGION                 1..14
                       note = Synthetic
```

```
source                  1..14
                        mol_type = protein
                        organism = synthetic construct
SEQUENCE: 48
TQQIALQAEI FQAR                                                   14

SEQ ID NO: 49           moltype = AA  length = 15
FEATURE                 Location/Qualifiers
REGION                  1..15
                        note = Synthetic
source                  1..15
                        mol_type = protein
                        organism = synthetic construct
SEQUENCE: 49
QTQQIRLQAE IFQAR                                                  15

SEQ ID NO: 50           moltype = AA  length = 13
FEATURE                 Location/Qualifiers
REGION                  1..13
                        note = Synthetic
source                  1..13
                        mol_type = protein
                        organism = synthetic construct
SEQUENCE: 50
QQIRLQAEIF QAR                                                    13

SEQ ID NO: 51           moltype = DNA  length = 57
FEATURE                 Location/Qualifiers
misc_feature            1..57
                        note = Synthetic shAPOE
source                  1..57
                        mol_type = other DNA
                        organism = synthetic construct
SEQUENCE: 51
ccgggaagga gttgaaggcc tacaactcga gttgtaggcc ttcaactcct tcttttt     57

SEQ ID NO: 52           moltype = DNA  length = 57
FEATURE                 Location/Qualifiers
misc_feature            1..57
                        note = Synthetic shAPOE
source                  1..57
                        mol_type = other DNA
                        organism = synthetic construct
SEQUENCE: 52
ccgggcagac actgtctgag caggtctcga gacctgctca gacagtgtct gcttttt     57

SEQ ID NO: 53           moltype = DNA  length = 57
FEATURE                 Location/Qualifiers
misc_feature            1..57
                        note = Synthetic shDNAJA
source                  1..57
                        mol_type = other DNA
                        organism = synthetic construct
SEQUENCE: 53
ccgggcgaga agtttaaact catatctcga gatatgagtt taaacttctc gcttttt     57

SEQ ID NO: 54           moltype = DNA  length = 57
FEATURE                 Location/Qualifiers
misc_feature            1..57
                        note = Synthetic shDNAJA4
source                  1..57
                        mol_type = other DNA
                        organism = synthetic construct
SEQUENCE: 54
ccggcctcga cagaaagtga ggattctcga gaatcctcac tttctgtcga ggttttt     57

SEQ ID NO: 55           moltype = DNA  length = 30
FEATURE                 Location/Qualifiers
misc_feature            1..30
                        note = Synthetic ApoE Forward Primer
source                  1..30
                        mol_type = other DNA
                        organism = synthetic construct
SEQUENCE: 55
tcatgaggat ccatgaaggt tctgtgggct                                  30

SEQ ID NO: 56           moltype = DNA  length = 29
FEATURE                 Location/Qualifiers
misc_feature            1..29
```

```
                         note = Synthetic ApoE Reverse Primer
source                   1..29
                         mol_type = other DNA
                         organism = synthetic construct
SEQUENCE: 56
tagcagaatt ctcagtgatt gtcgctggg                                      29

SEQ ID NO: 57            moltype = DNA  length = 31
FEATURE                  Location/Qualifiers
misc_feature             1..31
                         note = Synthetic DNAJA4 Forward Primer
source                   1..31
                         mol_type = other DNA
                         organism = synthetic construct
SEQUENCE: 57
atccctggat ccatgtggga aagcctgacc c                                   31

SEQ ID NO: 58            moltype = DNA  length = 31
FEATURE                  Location/Qualifiers
misc_feature             1..31
                         note = Synthetic DNAJA4 Reverse Primer
source                   1..31
                         mol_type = other DNA
                         organism = synthetic construct
SEQUENCE: 58
taccatgtcg actcatgccg tctggcactg c                                   31

SEQ ID NO: 59            moltype = RNA  length = 19
FEATURE                  Location/Qualifiers
misc_feature             1..19
                         note = Synthetic LRP1 target sequence
source                   1..19
                         mol_type = other RNA
                         organism = synthetic construct
SEQUENCE: 59
cgaggacgat gactgctta                                                 19

SEQ ID NO: 60            moltype = RNA  length = 19
FEATURE                  Location/Qualifiers
misc_feature             1..19
                         note = Synthetic LRP1 target sequence
source                   1..19
                         mol_type = other RNA
                         organism = synthetic construct
SEQUENCE: 60
gctatgagtt taagaagtt                                                 19

SEQ ID NO: 61            moltype = RNA  length = 19
FEATURE                  Location/Qualifiers
misc_feature             1..19
                         note = Synthetic LRP8 target sequence
source                   1..19
                         mol_type = other RNA
                         organism = synthetic construct
SEQUENCE: 61
cgaggacgat gactgctta                                                 19

SEQ ID NO: 62            moltype = RNA  length = 19
FEATURE                  Location/Qualifiers
misc_feature             1..19
                         note = Synthetic LRP8 target sequence
source                   1..19
                         mol_type = other RNA
                         organism = synthetic construct
SEQUENCE: 62
gaactattca cgcctcatc                                                 19

SEQ ID NO: 63            moltype = DNA  length = 20
FEATURE                  Location/Qualifiers
misc_feature             1..20
                         note = Synthetic ApoE Forward Primer
source                   1..20
                         mol_type = other DNA
                         organism = synthetic construct
SEQUENCE: 63
tgggtcgctt ttgggattac                                                20

SEQ ID NO: 64            moltype = DNA  length = 21
FEATURE                  Location/Qualifiers
```

```
misc_feature          1..21
                      note = Synthetic ApoE Reverse Primer
source                1..21
                      mol_type = other DNA
                      organism = synthetic construct
SEQUENCE: 64
ttcaactcct tcatggtctc g                                        21

SEQ ID NO: 65         moltype = DNA  length = 20
FEATURE               Location/Qualifiers
misc_feature          1..20
                      note = Synthetic DNAJA4 Forward Primer
source                1..20
                      mol_type = other DNA
                      organism = synthetic construct
SEQUENCE: 65
ccagcttctc ttcacccatg                                          20

SEQ ID NO: 66         moltype = DNA  length = 20
FEATURE               Location/Qualifiers
misc_feature          1..20
                      note = Synthetic DNAJA4 Reverse Primer
source                1..20
                      mol_type = other DNA
                      organism = synthetic construct
SEQUENCE: 66
gccaatttct tcgtgactcc                                          20

SEQ ID NO: 67         moltype = DNA  length = 19
FEATURE               Location/Qualifiers
misc_feature          1..19
                      note = Synthetic GAPDH Forward Primer
source                1..19
                      mol_type = other DNA
                      organism = synthetic construct
SEQUENCE: 67
agccacatcg ctcagacac                                           19

SEQ ID NO: 68         moltype = DNA  length = 19
FEATURE               Location/Qualifiers
misc_feature          1..19
                      note = Synthetic GAPDH Synthetic Primer
source                1..19
                      mol_type = other DNA
                      organism = synthetic construct
SEQUENCE: 68
gcccaatacg accaaatcc                                           19

SEQ ID NO: 69         moltype = DNA  length = 21
FEATURE               Location/Qualifiers
misc_feature          1..21
                      note = Synthetic LRP1 Forward Primer
source                1..21
                      mol_type = other DNA
                      organism = synthetic construct
SEQUENCE: 69
tttaacagca ccgagtacca g                                        21

SEQ ID NO: 70         moltype = DNA  length = 19
FEATURE               Location/Qualifiers
misc_feature          1..19
                      note = Synthetic LRP1 Reverse Primer
source                1..19
                      mol_type = other DNA
                      organism = synthetic construct
SEQUENCE: 70
caggcagatg tcagagcag                                           19

SEQ ID NO: 71         moltype = DNA  length = 20
FEATURE               Location/Qualifiers
misc_feature          1..20
                      note = Synthetic LRP8 Forward Primer
source                1..20
                      mol_type = other DNA
                      organism = synthetic construct
SEQUENCE: 71
gctaccctgg ctacgagatg                                          20

SEQ ID NO: 72         moltype = DNA  length = 20
```

```
FEATURE                 Location/Qualifiers
misc_feature            1..20
                        note = Synthetic LRP8 Reverse Primer
source                  1..20
                        mol_type = other DNA
                        organism = synthetic construct
SEQUENCE: 72
gattagggat gggctcttgc                                          20

SEQ ID NO: 73           moltype =   length =
SEQUENCE: 73
000

SEQ ID NO: 74           moltype =   length =
SEQUENCE: 74
000

SEQ ID NO: 75           moltype =   length =
SEQUENCE: 75
000

SEQ ID NO: 76           moltype = DNA  length = 31
FEATURE                 Location/Qualifiers
misc_feature            1..31
                        note = Synthetic Primer
source                  1..31
                        mol_type = other DNA
                        organism = synthetic construct
SEQUENCE: 76
agtacctcga ggggatcctt gagtcctact c                             31

SEQ ID NO: 77           moltype = DNA  length = 34
FEATURE                 Location/Qualifiers
misc_feature            1..34
                        note = Synthetic Primer
source                  1..34
                        mol_type = other DNA
                        organism = synthetic construct
SEQUENCE: 77
taattgcggc cgctcagaca gtgtctgcac ccag                          34

SEQ ID NO: 78           moltype = DNA  length = 31
FEATURE                 Location/Qualifiers
misc_feature            1..31
                        note = Synthetic Primer
source                  1..31
                        mol_type = other DNA
                        organism = synthetic construct
SEQUENCE: 78
taatatctcg agatgtggga aagcctgacc c                             31

SEQ ID NO: 79           moltype = DNA  length = 32
FEATURE                 Location/Qualifiers
misc_feature            1..32
                        note = Synthetic Primer
source                  1..32
                        mol_type = other DNA
                        organism = synthetic construct
SEQUENCE: 79
caattgcggc cgctcatgcc gtctggcact gc                            32

SEQ ID NO: 80           moltype = DNA  length = 30
FEATURE                 Location/Qualifiers
misc_feature            1..30
                        note = Synthetic Primer
source                  1..30
                        mol_type = other DNA
                        organism = synthetic construct
SEQUENCE: 80
ttagcctcga gacgccgaag cctgcagcca                               30

SEQ ID NO: 81           moltype = DNA  length = 35
FEATURE                 Location/Qualifiers
misc_feature            1..35
                        note = Synthetic Primer
source                  1..35
                        mol_type = other DNA
                        organism = synthetic construct
SEQUENCE: 81
```

```
ttactgcggc cgctgcgtga aacttggtga atctt                       35

SEQ ID NO: 82          moltype = DNA  length = 30
FEATURE                Location/Qualifiers
misc_feature           1..30
                       note = Synthetic Primer
source                 1..30
                       mol_type = other DNA
                       organism = synthetic construct
SEQUENCE: 82
taatatctcg agcgtggtgc ggggcagcgt                             30

SEQ ID NO: 83          moltype = DNA  length = 35
FEATURE                Location/Qualifiers
misc_feature           1..35
                       note = Synthetic Primer
source                 1..35
                       mol_type = other DNA
                       organism = synthetic construct
SEQUENCE: 83
caattgcggc cgcttatctc tcataccagc tcaat                       35

SEQ ID NO: 84          moltype = DNA  length = 43
FEATURE                Location/Qualifiers
misc_feature           1..43
                       note = Synthetic Primer
source                 1..43
                       mol_type = other DNA
                       organism = synthetic construct
SEQUENCE: 84
gccagcgctg ggaactggca actggtcgct tttgggatta cct              43

SEQ ID NO: 85          moltype = DNA  length = 43
FEATURE                Location/Qualifiers
misc_feature           1..43
                       note = Synthetic Primer
source                 1..43
                       mol_type = other DNA
                       organism = synthetic construct
SEQUENCE: 85
cagcgggaga ccctgtcccc ataccagccg tcctcctggg gtg              43

SEQ ID NO: 86          moltype = DNA  length = 43
FEATURE                Location/Qualifiers
misc_feature           1..43
                       note = Synthetic Primer
source                 1..43
                       mol_type = other DNA
                       organism = synthetic construct
SEQUENCE: 86
tccccgcccc agccgtcctc acagggtgga ccctagttta ata              43

SEQ ID NO: 87          moltype = DNA  length = 43
FEATURE                Location/Qualifiers
misc_feature           1..43
                       note = Synthetic Primer
source                 1..43
                       mol_type = other DNA
                       organism = synthetic construct
SEQUENCE: 87
gggatcggtg gagaagtgcc tattgtgcaa ggggcggggg atg              43

SEQ ID NO: 88          moltype = DNA  length = 43
FEATURE                Location/Qualifiers
misc_feature           1..43
                       note = Synthetic Primer
source                 1..43
                       mol_type = other DNA
                       organism = synthetic construct
SEQUENCE: 88
gtagggggcg gggaacgtgt tatccgtgaa gaggtggcta ggg              43

SEQ ID NO: 89          moltype = DNA  length = 43
FEATURE                Location/Qualifiers
misc_feature           1..43
                       note = Synthetic Primer
source                 1..43
                       mol_type = other DNA
                       organism = synthetic construct
```

```
SEQUENCE: 89
cagggccaac ttagttccta acattctgtg cccttcagtg gat                    43

SEQ ID NO: 90          moltype = DNA  length = 43
FEATURE                Location/Qualifiers
misc_feature           1..43
                       note = Synthetic Primer
source                 1..43
                       mol_type = other DNA
                       organism = synthetic construct
SEQUENCE: 90
acagtttgta tggactacta tcttaaatta tagcttgttt gga                    43

SEQ ID NO: 91          moltype = DNA  length = 43
FEATURE                Location/Qualifiers
misc_feature           1..43
                       note = Synthetic Primer
source                 1..43
                       mol_type = other DNA
                       organism = synthetic construct
SEQUENCE: 91
taattattgc taaagaacta tgttttagtt ggtaatggtg taa                    43

SEQ ID NO: 92          moltype = DNA  length = 45
FEATURE                Location/Qualifiers
misc_feature           1..45
                       note = Synthetic Primer
source                 1..45
                       mol_type = other DNA
                       organism = synthetic construct
SEQUENCE: 92
cagctgcacg gaccaggttc cataaaaaca ttgccagcta gtgag                  45

SEQ ID NO: 93          moltype = DNA  length = 22
FEATURE                Location/Qualifiers
misc_feature           1..22
                       note = Synthetic primer
source                 1..22
                       mol_type = other DNA
                       organism = synthetic construct
SEQUENCE: 93
tgagtatttt tgtggcaact gc                                           22

SEQ ID NO: 94          moltype = DNA  length = 18
FEATURE                Location/Qualifiers
misc_feature           1..18
                       note = Synthetic primer
source                 1..18
                       mol_type = other DNA
                       organism = synthetic construct
SEQUENCE: 94
ctctgctggg aaagcggc                                                18

SEQ ID NO: 95          moltype = DNA  length = 20
FEATURE                Location/Qualifiers
misc_feature           1..20
                       note = Synthetic primer
source                 1..20
                       mol_type = other DNA
                       organism = synthetic construct
SEQUENCE: 95
caagcactct gcgaactgag                                              20

SEQ ID NO: 96          moltype = DNA  length = 21
FEATURE                Location/Qualifiers
misc_feature           1..21
                       note = Synthetic primer
source                 1..21
                       mol_type = other DNA
                       organism = synthetic construct
SEQUENCE: 96
aagtttttga aggcaagatg c                                            21

SEQ ID NO: 97          moltype = DNA  length = 23
FEATURE                Location/Qualifiers
misc_feature           1..23
                       note = Synthetic primer
source                 1..23
                       mol_type = other DNA
```

```
                       organism = synthetic construct
SEQUENCE: 97
gcggtctggc agtaaaaact atc                                            23

SEQ ID NO: 98          moltype = DNA  length = 23
FEATURE                Location/Qualifiers
misc_feature           1..23
                       note = Synthetic primer
source                 1..23
                       mol_type = other DNA
                       organism = synthetic construct
SEQUENCE: 98
gtgaaacagc attgctgtca ctt                                            23

SEQ ID NO: 99          moltype = DNA  length = 24
FEATURE                Location/Qualifiers
misc_feature           1..24
                       note = Synthetic primer
source                 1..24
                       mol_type = other DNA
                       organism = synthetic construct
SEQUENCE: 99
ctaggccaca gaattgaaag atct                                           24

SEQ ID NO: 100         moltype = DNA  length = 25
FEATURE                Location/Qualifiers
misc_feature           1..25
                       note = Synthetic primer
source                 1..25
                       mol_type = other DNA
                       organism = synthetic construct
SEQUENCE: 100
gtaggtggaa attctagcat catcc                                          25

SEQ ID NO: 101         moltype = DNA  length = 20
FEATURE                Location/Qualifiers
misc_feature           1..20
                       note = Synthetic primer
source                 1..20
                       mol_type = other DNA
                       organism = synthetic construct
SEQUENCE: 101
gcctagccga gggagagccg                                                20

SEQ ID NO: 102         moltype = DNA  length = 22
FEATURE                Location/Qualifiers
misc_feature           1..22
                       note = Synthetic primer
source                 1..22
                       mol_type = other DNA
                       organism = synthetic construct
SEQUENCE: 102
tgtgacttgg gagctctgca gc                                             22

SEQ ID NO: 103         moltype = DNA  length = 18
FEATURE                Location/Qualifiers
misc_feature           1..18
                       note = Synthetic primer
source                 1..18
                       mol_type = other DNA
                       organism = synthetic construct
SEQUENCE: 103
gccgccccga ctgcatct                                                  18

SEQ ID NO: 104         moltype = DNA  length = 20
FEATURE                Location/Qualifiers
misc_feature           1..20
                       note = Synthetic primer
source                 1..20
                       mol_type = other DNA
                       organism = synthetic construct
SEQUENCE: 104
tcagtggagg gaaggaaatg                                                20

SEQ ID NO: 105         moltype = DNA  length = 20
FEATURE                Location/Qualifiers
misc_feature           1..20
                       note = Synthetic primer
source                 1..20
```

```
                        mol_type = other DNA
                        organism = synthetic construct
SEQUENCE: 105
ttcctgccct ggacacttac                                           20

SEQ ID NO: 106          moltype = DNA  length = 22
FEATURE                 Location/Qualifiers
misc_feature            1..22
                        note = Synthetic primer
source                  1..22
                        mol_type = other DNA
                        organism = synthetic construct
SEQUENCE: 106
ttgtgcccag tcatagccga at                                        22

SEQ ID NO: 107          moltype = DNA  length = 19
FEATURE                 Location/Qualifiers
misc_feature            1..19
                        note = Synthetic primer
source                  1..19
                        mol_type = other DNA
                        organism = synthetic construct
SEQUENCE: 107
ccttttctcc ctgacaccg                                            19

SEQ ID NO: 108          moltype = DNA  length = 19
FEATURE                 Location/Qualifiers
misc_feature            1..19
                        note = Synthetic primer
source                  1..19
                        mol_type = other DNA
                        organism = synthetic construct
SEQUENCE: 108
gcatccatct ggcaggttc                                            19

SEQ ID NO: 109          moltype = DNA  length = 20
FEATURE                 Location/Qualifiers
misc_feature            1..20
                        note = Synthetic primer
source                  1..20
                        mol_type = other DNA
                        organism = synthetic construct
SEQUENCE: 109
aggtgagatg acaggagatc                                           20

SEQ ID NO: 110          moltype = DNA  length = 57
FEATURE                 Location/Qualifiers
misc_feature            1..57
                        note = Synthetic
source                  1..57
                        mol_type = other DNA
                        organism = synthetic construct
SEQUENCE: 110
ccggccgact gatgttccca cggatctcga gatccgtggg aacatcagtc ggttttt  57

SEQ ID NO: 111          moltype = DNA  length = 57
FEATURE                 Location/Qualifiers
misc_feature            1..57
                        note = Synthetic
source                  1..57
                        mol_type = other DNA
                        organism = synthetic construct
SEQUENCE: 111
ccgggcaact caatgatgcc gagttctcga gaactcggca tcattgagtt gcttttt  57

SEQ ID NO: 112          moltype = DNA  length = 57
FEATURE                 Location/Qualifiers
misc_feature            1..57
                        note = Synthetic
source                  1..57
                        mol_type = other DNA
                        organism = synthetic construct
SEQUENCE: 112
ccggagagtg tatcaccttc ttgaactcga gttcaagaag gtgatacact ctttttt  57

SEQ ID NO: 113          moltype = DNA  length = 57
FEATURE                 Location/Qualifiers
misc_feature            1..57
                        note = Synthetic
```

```
source                  1..57
                        mol_type = other DNA
                        organism = synthetic construct
SEQUENCE: 113
ccgggaaggc atccactatc gagatctcga gatctcgata gtggatgcct tcttttt     57

SEQ ID NO: 114          moltype = DNA  length = 57
FEATURE                 Location/Qualifiers
misc_feature            1..57
                        note = Synthetic
source                  1..57
                        mol_type = other DNA
                        organism = synthetic construct
SEQUENCE: 114
ccgggcagac actgtctgag caggtctcga gacctgctca gacagtgtct gcttttt     57

SEQ ID NO: 115          moltype = DNA  length = 57
FEATURE                 Location/Qualifiers
misc_feature            1..57
                        note = Synthetic
source                  1..57
                        mol_type = other DNA
                        organism = synthetic construct
SEQUENCE: 115
ccgggcaact caatgatgct gagttctcga gaactcagca tcattgagtt gcttttt     57

SEQ ID NO: 116          moltype = DNA  length = 58
FEATURE                 Location/Qualifiers
misc_feature            1..58
                        note = Synthetic
source                  1..58
                        mol_type = other DNA
                        organism = synthetic construct
SEQUENCE: 116
ccggtgagat catgttgcta gaaacctcga ggtttctagc aacatgatct catttttg    58

SEQ ID NO: 117          moltype = DNA  length = 57
FEATURE                 Location/Qualifiers
misc_feature            1..57
                        note = Synthetic
source                  1..57
                        mol_type = other DNA
                        organism = synthetic construct
SEQUENCE: 117
ccgggaggac actatgacgg aagtactcga gtacttccgt catagtgtcc tcttttt     57

SEQ ID NO: 118          moltype = DNA  length = 20
FEATURE                 Location/Qualifiers
misc_feature            1..20
                        note = Synthetic primer
source                  1..20
                        mol_type = other DNA
                        organism = synthetic construct
SEQUENCE: 118
tgggtcgctt ttgggattac                                              20

SEQ ID NO: 119          moltype = DNA  length = 21
FEATURE                 Location/Qualifiers
misc_feature            1..21
                        note = Synthetic primer
source                  1..21
                        mol_type = other DNA
                        organism = synthetic construct
SEQUENCE: 119
ttcaactcct tcatggtctc g                                            21

SEQ ID NO: 120          moltype = DNA  length = 19
FEATURE                 Location/Qualifiers
misc_feature            1..19
                        note = Synthetic primer
source                  1..19
                        mol_type = other DNA
                        organism = synthetic construct
SEQUENCE: 120
agccacatcg ctcagacac                                               19

SEQ ID NO: 121          moltype = DNA  length = 19
FEATURE                 Location/Qualifiers
misc_feature            1..19
```

-continued

```
                       note = Synthetic primer
source                 1..19
                       mol_type = other DNA
                       organism = synthetic construct
SEQUENCE: 121
gcccaatacg accaaatcc                                        19

SEQ ID NO: 122         moltype = DNA  length = 22
FEATURE                Location/Qualifiers
misc_feature           1..22
                       note = Synthetic primer
source                 1..22
                       mol_type = other DNA
                       organism = synthetic construct
SEQUENCE: 122
gttataaccg ggaagacttt gc                                    22

SEQ ID NO: 123         moltype = DNA  length = 21
FEATURE                Location/Qualifiers
misc_feature           1..21
                       note = Synthetic primer
source                 1..21
                       mol_type = other DNA
                       organism = synthetic construct
SEQUENCE: 123
aaactcggca tcattgagtt g                                     21

SEQ ID NO: 124         moltype = DNA  length = 22
FEATURE                Location/Qualifiers
misc_feature           1..22
                       note = Synthetic primer
source                 1..22
                       mol_type = other DNA
                       organism = synthetic construct
SEQUENCE: 124
tttgagggta tttgagtagc gg                                    22

SEQ ID NO: 125         moltype = DNA  length = 19
FEATURE                Location/Qualifiers
misc_feature           1..19
                       note = Synthetic primer
source                 1..19
                       mol_type = other DNA
                       organism = synthetic construct
SEQUENCE: 125
ctctcgcgga gtgaactac                                        19

SEQ ID NO: 126         moltype = DNA  length = 20
FEATURE                Location/Qualifiers
misc_feature           1..20
                       note = Synthetic primer
source                 1..20
                       mol_type = other DNA
                       organism = synthetic construct
SEQUENCE: 126
gaccctggag gctaaggact                                       20

SEQ ID NO: 127         moltype = DNA  length = 20
FEATURE                Location/Qualifiers
misc_feature           1..20
                       note = Synthetic primer
source                 1..20
                       mol_type = other DNA
                       organism = synthetic construct
SEQUENCE: 127
agagccttca tcttcgcaat                                       20

SEQ ID NO: 128         moltype = DNA  length = 20
FEATURE                Location/Qualifiers
misc_feature           1..20
                       note = Synthetic primer
source                 1..20
                       mol_type = other DNA
                       organism = synthetic construct
SEQUENCE: 128
gcacagtcaa ggccgagaat                                       20

SEQ ID NO: 129         moltype = DNA  length = 20
FEATURE                Location/Qualifiers
```

```
misc_feature          1..20
                      note = Synthetic primer
source                1..20
                      mol_type = other DNA
                      organism = synthetic construct
SEQUENCE: 129
gccttctcca tggtggtgaa                                         20

SEQ ID NO: 130        moltype = DNA  length = 19
FEATURE               Location/Qualifiers
misc_feature          1..19
                      note = Synthetic primer
source                1..19
                      mol_type = other DNA
                      organism = synthetic construct
SEQUENCE: 130
gcgctcagct cttgtcact                                          19

SEQ ID NO: 131        moltype = DNA  length = 20
FEATURE               Location/Qualifiers
misc_feature          1..20
                      note = Synthetic primer
source                1..20
                      mol_type = other DNA
                      organism = synthetic construct
SEQUENCE: 131
ctccagccac aaggacatct                                         20

SEQ ID NO: 132        moltype = DNA  length = 20
FEATURE               Location/Qualifiers
misc_feature          1..20
                      note = Synthetic primer
source                1..20
                      mol_type = other DNA
                      organism = synthetic construct
SEQUENCE: 132
gctctgccta catcgtggtc                                         20

SEQ ID NO: 133        moltype = DNA  length = 18
FEATURE               Location/Qualifiers
misc_feature          1..18
                      note = Synthetic primer
source                1..18
                      mol_type = other DNA
                      organism = synthetic construct
SEQUENCE: 133
ctcatggccc agcatctt                                           18

SEQ ID NO: 134        moltype = DNA  length = 19
FEATURE               Location/Qualifiers
misc_feature          1..19
                      note = Synthetic primer
source                1..19
                      mol_type = other DNA
                      organism = synthetic construct
SEQUENCE: 134
atggagcagg gaagaccac                                          19

SEQ ID NO: 135        moltype = DNA  length = 19
FEATURE               Location/Qualifiers
misc_feature          1..19
                      note = Synthetic primer
source                1..19
                      mol_type = other DNA
                      organism = synthetic construct
SEQUENCE: 135
gtaggccgtg ccagaagtt                                          19

SEQ ID NO: 136        moltype = DNA  length = 34
FEATURE               Location/Qualifiers
misc_feature          1..34
                      note = Synthetic primer
source                1..34
                      mol_type = other DNA
                      organism = synthetic construct
SEQUENCE: 136
tcatagctag cgcagagcca ggattcacgc cctg                         34

SEQ ID NO: 137        moltype = DNA  length = 35
```

-continued

```
FEATURE                Location/Qualifiers
misc_feature           1..35
                       note = Synthetic primer
source                 1..35
                       mol_type = other DNA
                       organism = synthetic construct
SEQUENCE: 137
tggtcctcga ggaaccttca tcttcctgcc tgtga                             35

SEQ ID NO: 138         moltype = DNA  length = 30
FEATURE                Location/Qualifiers
misc_feature           1..30
                       note = Synthetic primer
source                 1..30
                       mol_type = other DNA
                       organism = synthetic construct
SEQUENCE: 138
tagttacgcg tagtagcccc catctttgcc                                   30

SEQ ID NO: 139         moltype = DNA  length = 29
FEATURE                Location/Qualifiers
misc_feature           1..29
                       note = Synthetic primer
source                 1..29
                       mol_type = other DNA
                       organism = synthetic construct
SEQUENCE: 139
aatcagctag cccctcagct gcaaagctc                                    29

SEQ ID NO: 140         moltype = DNA  length = 29
FEATURE                Location/Qualifiers
misc_feature           1..29
                       note = Synthetic primer
source                 1..29
                       mol_type = other DNA
                       organism = synthetic construct
SEQUENCE: 140
tagttacgcg tagtagcccc ctctttgcc                                    29

SEQ ID NO: 141         moltype = DNA  length = 31
FEATURE                Location/Qualifiers
misc_feature           1..31
                       note = Synthetic primer
source                 1..31
                       mol_type = other DNA
                       organism = synthetic construct
SEQUENCE: 141
aatcagctag cccttcagct gcaaagctct g                                 31
```

TREATMENT AND DIAGNOSIS OF MELANOMA

CROSS REFERENCE TO RELATED APPLICATIONS

This application is a Divisional of U.S. application Ser. No. 17/201,493, filed Mar. 15, 2021, issuing Jan. 9, 2024 as U.S. Pat. No. 11,865,094, which is a Divisional of U.S. application Ser. No. 16/725,493, filed Dec. 23, 2019, now U.S. Pat. No. 10,945,978, issued Mar. 16, 2021, which is a Continuation of U.S. patent application Ser. No. 15/881,231, filed Jan. 26, 2018, now U.S. Pat. No. 10,543,183, issued Jan. 28, 2020. which is a Continuation of U.S. patent application Ser. No. 15/650,480, filed Jul. 14, 2017, now U.S. Pat. No. 9,962,348, which is a Continuation of U.S. application Ser. No. 15/228,643, filed Aug. 4, 2016, Now U.S. Pat. No. 9,707,195, which is a Continuation of U.S. patent application Ser. No. 14/486,477, filed Sep. 15, 2014, now U.S. Pat. No. 9,526,710, which is a Continuation of International Application No. PCT/US2013/54690 filed Aug. 13, 2013, which claims priority to U.S. Provisional Application No. 61/682,339 filed Aug. 13, 2012 and U.S. Provisional Application No. 61/784,057 filed Mar. 14, 2013. The contents of the applications are incorporated herein by reference in their entirety.

REFERENCE TO A SEQUENCE LISTING

This instant application contains a Sequence Listing which has been submitted electronically in XML format and is hereby incorporated by reference in its entirety. Said XML copy, created on Dec. 27, 2023, is named SeqList-070413-20782 and is 240,567 bytes in size.

FIELD OF THE INVENTION

This invention relates to diagnosis and treatment of migrating cancers and melanoma.

BACKGROUND OF THE INVENTION

Melanoma, a malignant tumor, develops from abnormal melanocytes in the lower epidermis and can metastasize to distant sites in the body via the blood and lymph systems. Although it accounts for less than 5% of skin cancer cases, melanoma is much more dangerous and responsible for a large majority of the deaths associated with skin cancer. Across the world the incidence of melanoma has been increasing at an alarming rate, with a lifetime risk of developing melanoma as high as 1/58 for males in the U.S. (Jemal et al., 2008, CA: Cancer J. Clin. 58:71-96). The mortality rate of malignant melanoma also continues to rise dramatically throughout the world. According to a 2006 WHO report, about 48,000 melanoma related deaths occur worldwide per year (Lucas et al. (2006) Environmental Burden of Disease Series. 13. World Health Organization. ISBN 92-4-159440-3). In the United States, it was estimated that almost 70,000 people were diagnosed with melanoma during 2010 and approximately 9,000 people would be expected to die from the disease (American Cancer Society; www.cancer.org).

Although some conventional cancer therapies have been used in treating metastatic melanoma, they are not effective. Metastatic melanoma therefore remains one of the most difficult cancers to treat and one of the most feared neoplasms. Accordingly, there is a need for new agents and methods for diagnosis and treatment of melanoma.

SUMMARY OF INVENTION

This invention addresses the above-mentioned need by providing agents and methods for diagnosis and treatment of melanoma. The invention is based, at least in part, on an unexpected discovery of a cooperative miRNA-protein network deregulated in metastatic melanoma. This network includes a number of metastasis suppressor factors and metastasis promoter factors.

In one aspect, the invention features a method for treating cancer, including administering to a subject in need thereof, a LXR agonist, wherein the LXR agonist is administered in an amount sufficient to increase the expression level or activity level of ApoE to a level sufficient to slow the spread of metastasis of the cancer.

In another aspect, the invention features a method for treating cancer, including administering to a subject in need thereof, an ApoE polypeptide in an amount sufficient to treat the cancer.

In another aspect, the invention features a method of slowing the spread of a migrating cancer, comprising administering to a subject in need thereof, a LXR agonist or an ApoE polypeptide.

In some embodiments of any of the aforementioned methods, the LXR agonist is a LXRβ agonist. In certain embodiments, the LXR agonist increases the expression level of ApoE at least 2.5-fold in vitro. In certain embodiments, the LXRβ agonist is selective for LXRβ over LXRα. In other embodiments, the LXRβ agonist has activity for LXRβ that is at least 2.5-fold greater than the activity of said agonist for LXRα. In some embodiments, the LXRβ agonist has activity for LXRβ that is at least 10-fold greater than the activity of said agonist for LXRα. In further embodiments, the LXRβ agonist has activity for LXRβ that is at least 100-fold greater than the activity of said agonist for LXRα. In certain embodiments, the LXR agonist has activity for LXRβ that is at least within 2.5-fold of the activity of said agonist for LXRα.

In some embodiments the migrating cancer is metastatic cancer. The metastatic cancer can include cells exhibiting migration and/or invasion of migrating cells and/or include cells exhibiting endothelial recruitment and/or angiogenesis. In other embodiments, the migrating cancer is a cell migration cancer. In still other embodiments, the cell migration cancer is a non-metastatic cell migration cancer.

The migrating cancer can be a cancer spread via seeding the surface of the peritoneal, pleural, pericardial, or subarachnoid spaces. Alternatively, the migrating cancer can be a cancer spread via the lymphatic system, or a cancer spread hematogenously.

In particular embodiments, the migrating cancer is a cell migration cancer that is a non-metastatic cell migration cancer, such as ovarian cancer, mesothelioma, or primary lung cancer.

In a related aspect, the invention provides a method for inhibiting or reducing metastasis of cancer comprising administering a LXR agonist or an ApoE polypeptide.

In another aspect, the invention provides a method for inhibiting proliferation or growth of cancer stem cells or cancer initiating cells, including contacting the cell with a LXR agonist or an ApoE polypeptide in an amount sufficient to inhibit proliferation or growth of said cell.

In yet another aspect, the invention provides a method of reducing the rate of tumor seeding of a cancer including administering to a subject in need thereof a LXR agonist or an ApoE polypeptide in an amount sufficient to reduce tumor seeding.

In still a further aspect, the invention provides a method of reducing or treating metastatic nodule-forming of cancer including administering to a subject in need thereof a LXR agonist or an ApoE polypeptide in an amount sufficient to treat said metastatic nodule-forming of cancer.

In other embodiments, the cancer is breast cancer, colon cancer, renal cell cancer, non-small cell lung cancer, hepatocellular carcinoma, gastric cancer, ovarian cancer, pancreatic cancer, esophageal cancer, prostate cancer, sarcoma, or melanoma. In some embodiments, the cancer is melanoma. In other embodiments, the cancer is breast cancer. In certain embodiments, the cancer is renal cell cancer. In further embodiments, the cancer is pancreatic cancer. In other embodiments, the cancer is non-small cell lung cancer. In some embodiments the cancer is colon cancer. In further embodiments, the cancer is ovarian cancer.

In other embodiments, the cancer is a drug resistant cancer. In further embodiments, the cancer is resistant to vemurafenib, dacarbazine, a CTLA4 inhibitor, a PD1 inhibitor, or a PDL1 inhibitor.

In some embodiments, the method comprises administering an LXR agonist selected from the list consisting of a compound of any one of Formula I-IV or any of compound numbers 1-39, or pharmaceutically acceptable salts thereof. In some embodiments, the LXR agonist is compound 1 or a pharmaceutically acceptable salt thereof. In other embodiments, the LXR agonist is compound 2 or a pharmaceutically acceptable salt thereof. In certain embodiments, the LXR agonist is compound 3 or a pharmaceutically acceptable salt thereof. In further embodiments, the LXR agonist is compound 12 or a pharmaceutically acceptable salt thereof. In some embodiments, the LXR agonist is compound 25 or a pharmaceutically acceptable salt thereof. In other embodiments, the LXR agonist is compound 38 or a pharmaceutically acceptable salt thereof. In further embodiments, the LXR agonist is compound 39 or a pharmaceutically acceptable salt thereof.

The method can further include administering an antiproliferative, wherein said LXR agonist and said antiproliferative are administered in an amount that together, is sufficient to slow the progression of migrating cancer. For example, the antiproliferative and LXR agonist can be administered within 28 days of each (e.g., within 21, 14, 10, 7, 5, 4, 3, 2, or 1 days) or within 24 hours (e.g., 12, 6, 3, 2, or 1 hours; or concomitantly) other in amounts that together are effective to treat the subject.

In some embodiments, the method comprises administering an ApoE polypeptide. The ApoE polypeptide fragment can increase the activity level or expression level of LRP1 or LRP8, and/or the ApoE polypeptide can bind to LRP1 or LRP8, the ApoE polypeptide can be the receptor binding region (RBR) of ApoE. The method can further include administering an antiproliferative, wherein said ApoE polypeptide and said antiproliferative are administered in an amount that together, is sufficient to slow the progression of migrating cancer. For example, the antiproliferative and ApoE polypeptide can be administered within 28 days of each (e.g., within 21, 14, 10, 7, 5, 4, 3, 2, or 1 days) or within 24 hours (e.g., 12, 6, 3, 2, or 1 hours; or concomitantly) other in amounts that together are effective to treat the subject.

In some embodiments, the pharmaceutical composition may further comprise an additional compound having antiproliferative activity. The additional compound having antiproliferative activity can be selected from the group of compounds such as chemotherapeutic and cytotoxic agents, differentiation-inducing agents (e.g. retinoic acid, vitamin D, cytokines), hormonal agents, immunological agents and anti-angiogenic agents. Chemotherapeutic and cytotoxic agents include, but are not limited to, alkylating agents, cytotoxic antibiotics, antimetabolites, vinca alkaloids, etoposides, and others (e.g., paclitaxel, taxol, docetaxel, taxotere, cis-platinum). A list of additional compounds having antiproliferative activity can be found in L. Brunton, B. Chabner and B. Knollman (eds). Goodman and Gilman's The Pharmacological Basis of Therapeutics, Twelfth Edition, 2011, McGraw Hill Companies, New York, NY.

The method may further include administering a antiproliferative compound selected from the group consisting of alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelin A receptor antagonist, retinoic acid receptor agonists, immuno-modulators, hormonal and antihormonal agents, photodynamic agents, tyrosine kinase inhibitors, antisense compounds, corticosteroids, HSP90 inhibitors, proteosome inhibitors (for example, NPI-0052), CD40 inhibitors, anti-CSI antibodies, FGFR3 inhibitors, VEGF inhibitors, MEK inhibitors, cyclin DI inhibitors, NF-kB inhibitors, anthracyclines, histone deacetylases, kinesin inhibitors, phosphatase inhibitors, COX2 inhibitors, mTOR inhibitors, calcineurin antagonists, IMiDs, or other agents used to treat proliferative diseases. Examples of such compounds are provided in Tables 1.

In another aspect, the invention features a method for treating melanoma (e.g., metastatic melanoma) in a subject in need thereof. The method includes (a) increasing in the subject the expression level or activity level of a metastasis suppressor factor selected from the group consisting of DNAJA4, Apolipoprotein E (ApoE), LRP1, LRP8, Liver X Receptor (LXR, e.g., both LXR-alpha and LXR-beta), and miR-7 or (b) decreasing in the subject the expression level or activity level of a metastasis promoter factor selected from the group consisting of miR-199a-3p, miR-199a-5p, miR-1908, and CTGF.

In the method, the increasing step can be carried out by administering to the subject one or more of the followings: (i) a polypeptide having a sequence of DNAJA4, ApoE or an ApoE fragment, LRP1, LRP8, or LXR; (ii) a nucleic acid having a sequence encoding DNAJA4, ApoE, LRP1, LRP8, or LXR; (iii) a ligand for LRP1, LRP8, or LXR; and (iv) an RNAi agent encoding miR-7. Examples of the LRP1 or LRP8 ligand include the receptor binding portion of ApoE, anti-LRP1 or anti-LRP8 antibodies, and small molecule ligands. In one example, increasing the ApoE expression level can be carried out by increasing the activity level or expression level of LXR. Increasing the DNAJA4 expression level can also be carried out by increasing the activity level or expression level of LXR. The LXR activity level can be increased by administering to the subject a ligand of LXR, such as compounds of Formula I-IV as disclosed below. The increasing step can also be carried out by decreasing the expression level or activity level of a microRNA selected from the group consisting of miR-199a-3p, miR-199a-5p, and miR-1908. To this end, one can use a number of techniques known in the art, including, but not limited to, the miR-Zip technology, Locked Nucleic Acid (LNA), and antagomir technology as described in the examples below.

In another aspect, the invention provides a method for determining whether a subject has, or is at risk of having, metastatic melanoma. The method includes obtaining from the subject a sample; measuring in the sample (i) a first expression level of a metastasis promoter factor selected from the group consisting of miR-199a-3p, miR-199a-5p, miR-1908, and CTGF, or (ii) a second expression level of a metastasis suppressor factor selected from the group consisting of DNAJA4, ApoE, LRP1, LRP8, LXR, and miR-7; and comparing the first expression level with a first predetermined reference value, or the second expression level with a second predetermined reference value. The subject is determined to have, or to be at risk of having, metastatic melanoma if (a) the first expression level is above a first predetermined reference value or (b) the second expression level is below a second predetermined reference value. The first and second predetermined reference values can be obtained from a control subject that does not have metastatic melanoma. In one embodiment, the measuring step includes measuring both the first expression level and the second expression level. The sample can be a body fluid sample, a tumor sample, a nevus sample, or a human skin sample.

In a another aspect, the invention provides an array having a support having a plurality of unique locations, and any combination of (i) at least one nucleic acid having a sequence that is complementary to a nucleic acid encoding a metastasis promoter factor selected from the group consisting of miR-199a-3p, miR-199a-5p, miR-1908, and CTGF or a complement thereof, or (ii) at least one nucleic acid having a sequence that is complementary to a nucleic acid encoding a metastasis suppressor factor selected from the group consisting of DNAJA4, ApoE, LRP1, LRP8, LXR, and miR-7 or a complement thereof. Preferably, each nucleic acid is immobilized to a unique location of the support. This array can be used for metastatic melanoma diagnosis and prognosis.

Accordingly, the invention also provides a kit for diagnosing a metastatic potential of melanoma in a subject. The kit includes a first reagent that specifically binds to an expression product of a metastasis suppressor gene selected from the group consisting of DNAJA4, ApoE, LRP1, LRP8, LXR, and miR-7; or a second reagent that specifically binds to an expression product of a metastasis promoter gene selected from the group consisting of miR-199a-3p, miR-199a-5p, miR-1908, and CTGF. The second agent can be a probe having a sequence complementary to the suppressor or promoter gene or a complement thereof. The kit can further contain reagents for performing an immunoassay, a hybridization assay, or a PCR assay. In one embodiment, the kit contained the above-mentioned array.

In a another aspect, the invention provides a method of identifying a compound useful for treating melanoma or for inhibiting endothelial recruitment, cell invasion, or metastatic angiogenesis. The method includes (i) obtaining a test cell expressing a reporter gene encoded by a nucleic acid operatively liked to a promoter of a marker gene selected from the group consisting of miR-199a-3p, miR-199a-5p, miR-1908, and CTGF; (ii) exposing the test cell to a test compound; (iii) measuring the expression level of the reporter gene in the test cell; (iv) comparing the expression level with a control level; and (v) selecting the test compound as a candidate useful for treating melanoma or for inhibiting endothelial recruitment, cancer cell invasion, or metastatic angiogenesis, if the comparison indicates that the expression level is lower than the control level.

The invention provides another method of identifying a compound useful for treating melanoma or for inhibiting endothelial recruitment, cell invasion, or metastatic angiogenesis. The method includes (i) obtaining a test cell expressing a reporter gene encoded by a nucleic acid operatively liked to a promoter of a marker gene selected from the group consisting of DNAJA4, ApoE, LRP1, LRP8, LXR, and miR-7; (ii) exposing the test cell to a test compound; (iii) measuring the expression level of the reporter gene in the test cell; (iv) comparing the expression level with a control level; and (v) selecting the test compound as a candidate useful for treating melanoma or for inhibiting endothelial recruitment, cancer cell invasion, or metastatic angiogenesis, if the comparison indicates that the expression level is higher than the control level.

In the above-mentioned identification methods, the reporter gene can be a standard reporter gene (such as LaxZ, GFP, or luciferase gene, or the like), known in the art, or one of the aforementioned metastasis suppressor genes or metastasis promoter genes. In the methods, the control level can be obtained from a control cell that is the same as the test cell except that the control cell has not be exposed to the test compound.

In a another aspect, the invention provides a method for inhibiting endothelial recruitment, inhibiting tumor cell invasion, or treating metastatic cancer in a subject in need thereof, by administering to the subject an agent that inhibits expression or activity of CTGF. The subject can be one having a disorder characterized by pathological angiogenesis, including but not limited to cancer (e.g., metastatic melanoma), an eye disorder, and an inflammatory disorder. An example of the tumor cell is a metastatic melanoma cell. Examples of the agent include an antibody, a nucleic acid, a polypeptide, and a small molecule compound. In a preferred embodiment, the antibody is a monoclonal antibody.

In a another aspect, the invention provides a method for inhibiting endothelial recruitment, inhibiting tumor cell invasion, or treating metastatic cancer in a subject in need thereof, by administering to the subject an agent that increases expression or activity of miR-7. An example of the tumor cell is a metastatic melanoma cell. Examples of the agent include an antibody, a nucleic acid, a polypeptide, and a small molecule compound. In one example, the agent has miR-7 activity. The nucleic acid can be an oligonucleotide. And, the oligonucleotide can include a sequence selected from the group consisting of SEQ ID Nos. 36-38.

As used herein, "migrating cancer" refers to a cancer in which the cancer cells forming the tumor migrate and subsequently grow as malignant implants at a site other than the site of the original tumor. The cancer cells migrate via seeding the surface of the peritoneal, pleural, pericardial, or subarachnoid spaces to spread into the body cavities; via invasion of the lymphatic system through invasion of lymphatic cells and transport to regional and distant lymph nodes and then to other parts of the body; via hematogenous spread through invasion of blood cells; or via invasion of the surrounding tissue. Migrating cancers include metastatic tumors and cell migration cancers, such as ovarian cancer, mesothelioma, and primary lung cancer, each of which is characterized by cellular migration.

As used herein, "slowing the spread of migrating cancer" refers to reducing or stopping the formation of new loci; or reducing, stopping, or reversing the tumor load.

As used herein, "metastatic tumor" refers to a tumor or cancer in which the cancer cells forming the tumor have a high potential to or have begun to, metastasize, or spread from one location to another location or locations within a subject, via the lymphatic system or via hematogenous spread, for example, creating secondary tumors within the subject. Such metastatic behavior may be indicative of malignant tumors. In some cases, metastatic behavior may be associated with an increase in cell migration and/or invasion behavior of the tumor cells.

As used herein, "slowing the spread of metastasis" refers to reducing or stopping the formation of new loci; or reducing, stopping, or reversing the tumor load.

The term "cancer" refers to any cancer caused by the proliferation of malignant neoplastic cells, such as tumors, neoplasms, carcinomas, sarcomas, leukemias, lymphomas, and the like.

As used herein, "drug resistant cancer" refers to any cancer that is resistant to an antiproliferative in Table 2.

Examples of cancers that can be defined as metastatic include but are not limited to non-small cell lung cancer, breast cancer, ovarian cancer, colorectal cancer, biliary tract cancer, bladder cancer, brain cancer including glioblastomas and medulloblastomas, cervical cancer, choriocarcinoma, endometrial cancer, esophageal cancer, gastric cancer, hematological neoplasms, multiple myeloma, leukemia, intraepithelial neoplasms, livercancer, lymphomas, neuroblastomas, oral cancer, pancreatic cancer, prostate cancer, sarcoma, skin cancer including melanoma, basocellular cancer, squamous cell cancer, testicular cancer, stromal tumors, germ cell tumors, thyroid cancer, and renal cancer.

"Proliferation" as used in this application involves reproduction or multiplication of similar forms (cells) due to constituting (cellular) elements.

"Cell migration" as used in this application involves the invasion by the cancer cells into the surrounding tissue and the crossing of the vessel wall to exit the vasculature in distal organs of the cancer cell.

By "cell migration cancers" is meant cancers that migrate by invasion by the cancer cells into the surrounding tissue and the crossing of the vessel wall to exit the vasculature in distal organs of the cancer cell.

"Non-metastatic cell migration cancer" as used herein refers to cancers that do not migrate via the lymphatic system or via hematogenous spread.

As used herein, "cell to cell adhesion" refers to adhesion between at least two cells through an interaction between a selectin molecule and a selectin specific ligand. Cell to cell adhesion includes cell migration.

A "cell adhesion related disorder" is defined herein as any disease or disorder which results from or is related to cell to cell adhesion or migration. A cell adhesion disorder also includes any disease or disorder resulting from inappropriate, aberrant, or abnormal activation of the immune system or the inflammatory system. Such diseases include but are not limited to, myocardial infarction, bacterial or viral infection, metastatic conditions, e.g. cancer. The invention further features methods for treating a cell adhesion disorder by administering a LXR agonist or ApoE polypeptide.

As used herein, "cancer stem cells" or "cancer initiating cells" refers to cancer cells that possess characteristics associated with normal stem cells, specifically the ability to give rise to all cell types found in a particular cancer sample. Cancer stem cells are therefore tumorgenic or tumor forming, perhaps in contrast to other non-tumorgenic cancer cells. Cancer stem cells may persist in tumors as a distinct population and cause cancer recurrence and metastasis by giving rise to new tumors.

As used herein, "tumor seeding" refers to the spillage of tumor cell clusters and their subsequent growth as malignant implants at a site other than the site of the original tumor.

As used herein, "metastatic nodule" refers to an aggregation of tumor cells in the body at a site other than the site of the original tumor.

The details of one or more embodiments of the invention are set forth in the description below. Other features, objects, and advantages of the invention will be apparent from the description and from the claims.

FIGS. 21A, 21B, 21C, 21D, 21E, 21F, 21G, 21H, 21I, 21J, 21K and 21L. Therapeutic LXR Activation Inhibits Melanoma Tumor Growth. (21A-21B) Primary tumor growth by 5×104 B16F10 mouse melanoma cells subcutaneously injected into C57BL/6-WT mice. Following tumor growth to 5-10 mm3 in volume, mice were continuously fed a control chow or a chow supplemented with GW3965 (20 mg/kg/day or 100 mg/kg/day) (21A) or T0901317 (20 mg/kg/day) (21B). Representative tumor images shown correspond to tumors extracted at the final day (d12). n=10-18 (21A), 8-10 (21B). (21C-21E) Primary tumor growth by 1×106 MeWo (21C), 7.5×105 SK-Mel-334.2 (21D), and 2× 106 SK-Mel-2 (21E) human melanoma cells subcutaneously injected into immunocompromised mice. Following tumor growth to 5-10 mm3 in volume, mice were randomly assigned to a control diet or a diet supplemented with GW3965 (20 mg/kg or 100 mg/kg, as indicated). Tumor images shown correspond to last day of measurements. n=6-34 (21C), 8 (21D), 5 (21E). (21F) 5×104 B16F10 cells were injected subcutaneously into C57BL/6-WT mice. Upon tumor growth to 150 mm3, mice were fed continuously with a control chow or a chow containing GW3965 (150 mg/kg), and tumor growth was measured daily. n=6-13. (21G-21I) Mouse overall survival following subcutaneous grafting of 5×104 B16F10 (21G), 1× 106 MeWo (21H), and 7.5×105 SK-Mel-334.2 cells (21I) into mice that were administered a normal chow or a chow supplemented with GW3965 (100 mg/kg) upon formation of tumors measuring 5-10 mm3 in volume. n=6-9 (21F), 4-7 (21H), 3-6 (21I). (21J, 21K, 21L) Tumor endothelial cell density, determined by immunohistochemical staining for the mouse endothelial cell antigen MECA-32 (21J), tumor cell proliferation, determined by staining for the proliferative marker Ki-67 (21K), and tumor cell apoptosis, determined by staining for cleaved caspase-3 (21L), in subcutaneous melanoma tumors formed by 1×106 MeWo human melanoma cells in response to mouse treatment with a control diet or a GW3965-supplemented diet (20 mg/kg) for 35 days. n=5. Tumor volume was calculated as (small diameter)2×(large diameter)/2. All data are represented as mean±SEM. Scale bars, 5 mm (21A, 21B, 21C, 21D), 50 μm (21J, 21K), 25 μm (21L).

Figures 21A, 21B, 21C, 21D, 21E, 21F, 21G, 21H, 21I:
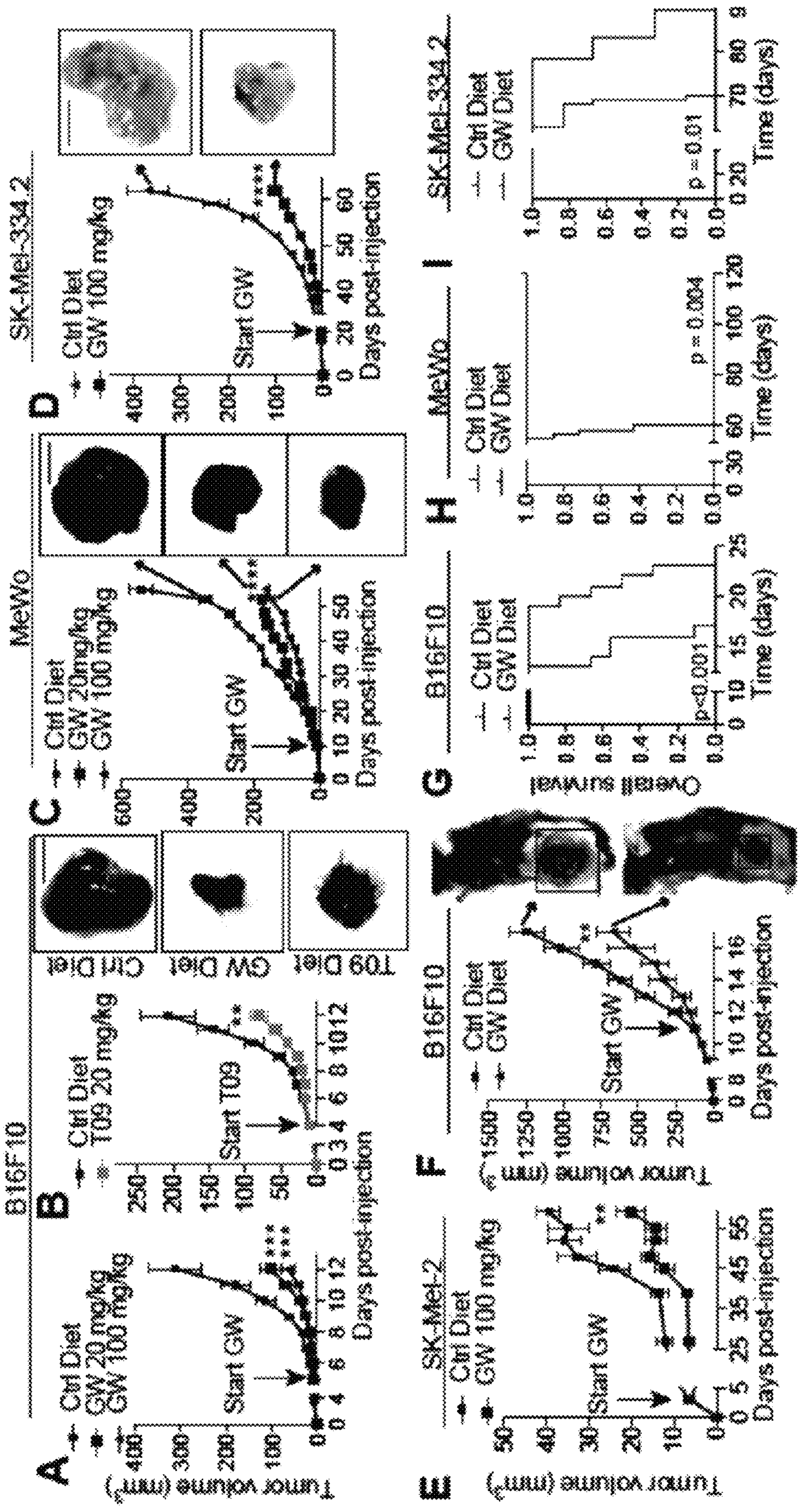
Figures 21J, 21K, 21L:
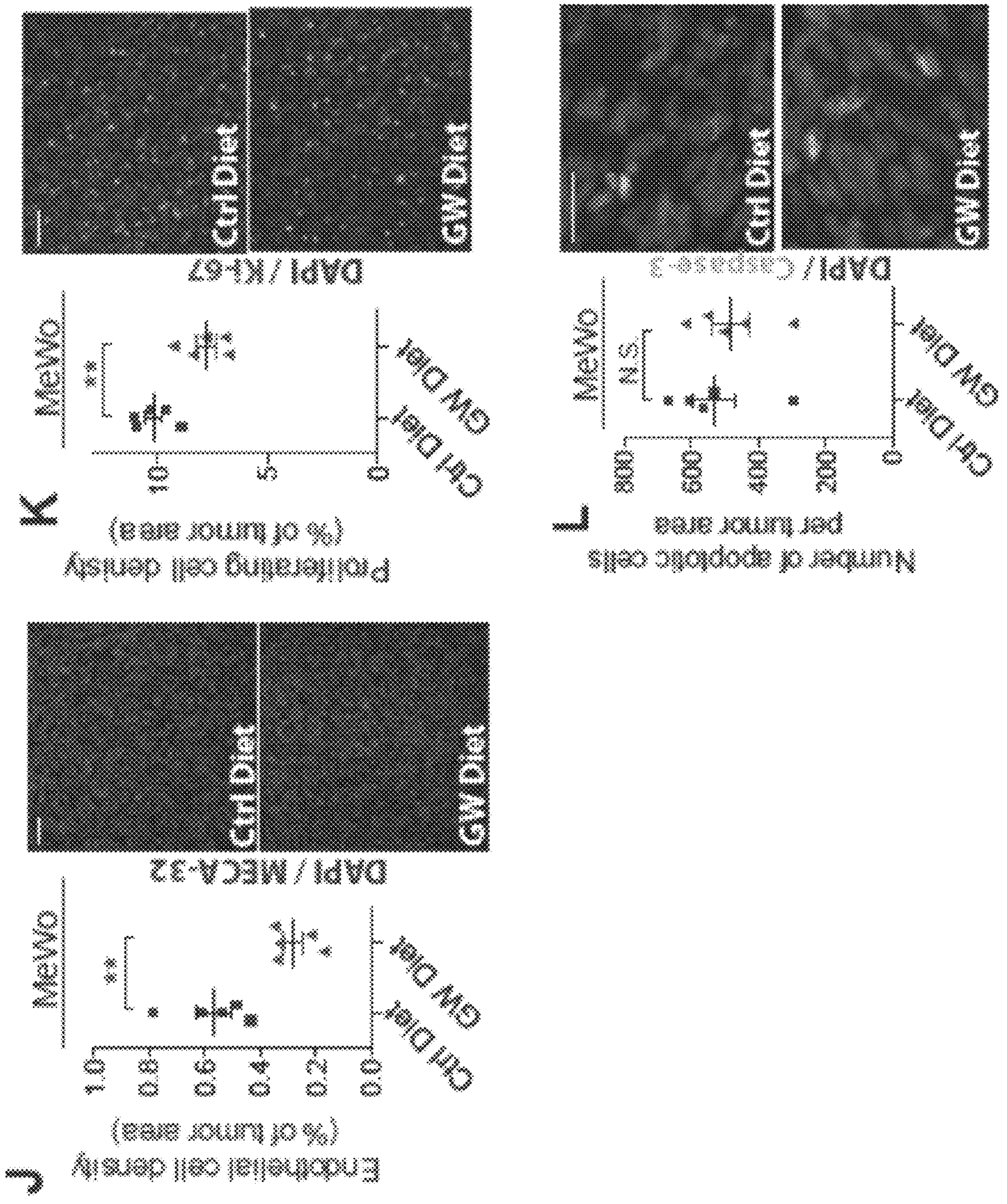
Figure 22:
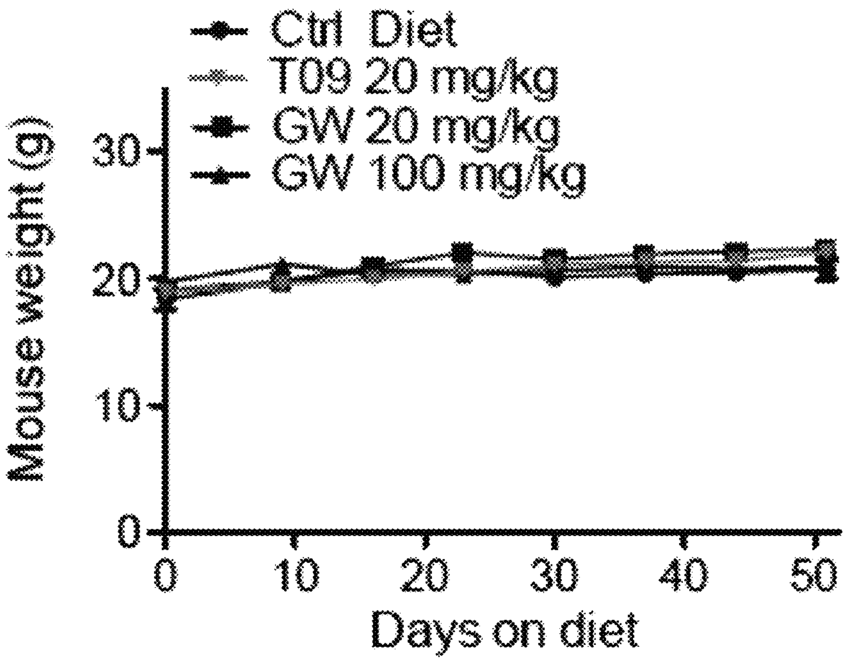

FIG. 22. LXRβ Agonism Suppresses Melanoma Tumor Growth, Related to FIG. 21(A-E). Weight measurements of mice fed a control diet or a diet supplemented with GW3965 (20 mg/kg/day or 100 mg/kg/day) or T0901317 (20 mg/kg) for 65 days. n=5-6.

FIGS. 23A, 23B, 23C, 23D, 23E, 23F, 23G, 23H, 23I, 23J and 23K. LXR Agonism Suppresses Melanoma Metastasis to the Lung and Brain. (23A) MeWo cells were pre-treated with DMSO or GW3965 (1 μM) for 48 hours and 4×104 cells were intravenously injected via the tail-vein into NOD Scid mice. Lung colonization was monitored by weekly bioluminescence imaging. Representative H&E-stained lungs correspond to the final day (d70) are shown. n=4-5. (23B-23C) Bioluminescence imaging of lung metastasis by 4×104 MeWo cells intravenously injected into NOD Scid mice that were fed a control chow or a chow containing GW3965 (20 mg/kg) or T0901317 (20 mg/kg) starting 10 days prior to cancer cell injection. Representative H&E-stained lungs correspond to final imaging day n=5-6. (23B-23C) Bioluminescence imaging of lung metastasis by 4×104 MeWo cells intravenously injected into NOD Scid mice that were fed a control chow or a chow containing GW3965 (20 mg/kg) or T0901317 (20 mg/kg) starting 10 days prior to cancer cell injection. Representative H&E-stained lungs correspond to final imaging day n=5-6. (23F) Systemic and brain photon flux following intracardiac injection of 1× 105 MeWo brain metastatic derivative cells into athymic nude mice that were fed a control diet or a GW3965-supplemented diet (100 mg/kg) starting on day 0 post-injection. n=7. (23G) Schematic of experimental orthotopic metastasis model used to assess the ability of GW3965 treatment to suppress lung metastasis post-tumor excision. (23H) Ex-vivo lung photon flux, determined by bioluminescence imaging, in NOD Scid mice that were administered a control chow or a chow containing GW3965 (100 mg/kg) for 1 month following the excision of size-matched (~300-mm3 in volume) subcutaneous melanoma tumors formed by 1× 106 MeWo melanoma cells. Representative lungs stained for human vimentin are also shown. n=7-9. (23I) 4×104 MeWo cells were intravenously injected into NOD Scid mice. Following initiation of metastases, detected by bioluminescence imaging on d42, mice were administered a control diet or a GW3965 diet (100 mg/kg) as indicated, and lung colonization progression was measured weekly. n=6. (23J) Number of macroscopic metastatic nodules in H&E-stained lungs extracted at the final day (d77) from NOD Scid mice administered a control diet or a diet supplemented with GW3965 (100 mg/kg), as indicated in (23I). n=4-5. (23K) Overall mouse survival following intravenous injection of 4×104 MeWo cells into NOD-Scid mice that were continuously fed a control chow or a GW3965-supplemented chow (20 mg/kg) starting 10 days prior to cancer cell injection. n=5-6. All data are represented as mean±SEM.

FIGS. 24A, 24B, 24C, 24D, 24E and 24F. Suppression of Genetically-Driven Melanoma Progression by LXR Activation Therapy. (24A) Overall survival of Tyr::CreER; BrafV600E/+; Ptenlox/+C57BL/6 mice following general melanoma induction by intraperitoneal administration of 4-HT (25 mg/kg) on three consecutive days. After the first 4-HT injection, mice were randomly assigned to a control diet or a diet supplemented with GW3965 (100 mg/kg). n=10-11. (24B) Melanoma tumor burden, expressed as the percentage of dorsal skin area, measured on day 35 in Tyr::CreER; BrafV600E/+; Ptenlox/lox mice administered a control chow or a chow supplemented with GW3965 (100 mg/kg) upon melanoma induction as described in (24A). n=4-5. (24C) Number of macroscopic metastatic nodules to the salivary gland lymph nodes detected post-mortem in Tyr::CreER; BrafV600E/+; Ptenlox/lox mice that were fed a control chow or a chow containing GW3965 (100 mg/kg) following global induction of melanoma progression as described in (24A). n=7-8. (24D) Tumor growth following subcutaneous injection of 1×105 BrafV600E/+; Pten−/−; CDKN2A−/− primary melanoma cells into syngeneic C57BL/6-WT mice. Upon tumor growth to 5-10 mm3 in volume, mice were fed with a control chow or a chow supplemented with GW3965 (100 mg/kg). n=16-18. (24E) Overall survival of C57BL/6-WT mice subcutaneously injected with 1× 105 BrafV600E/+; Pten−/−; CDKN2A−/− melanoma cells and treated with a GW3965 diet (100 mg/kg) or a control diet following tumor growth to 5-10 mm3 in volume. n=7-8. (24F) Lung colonization by 1× 105 BrafV600E/+; Pten−/−; CDKN2A−/− primary melanoma cells intravenously injected into C57BL/6-WT mice. Immediately following cancer cell injection, mice were randomly assigned to a control diet or a GW3965-supplemented diet (100 mg/kg) for the remainder of the experiment. n=14-15. All data are represented as mean±SEM. Scale bar, 2 mm (24B), 5 mm (24D).

Figures 24A, 24B, 24C, 24D, 24E, 24F:
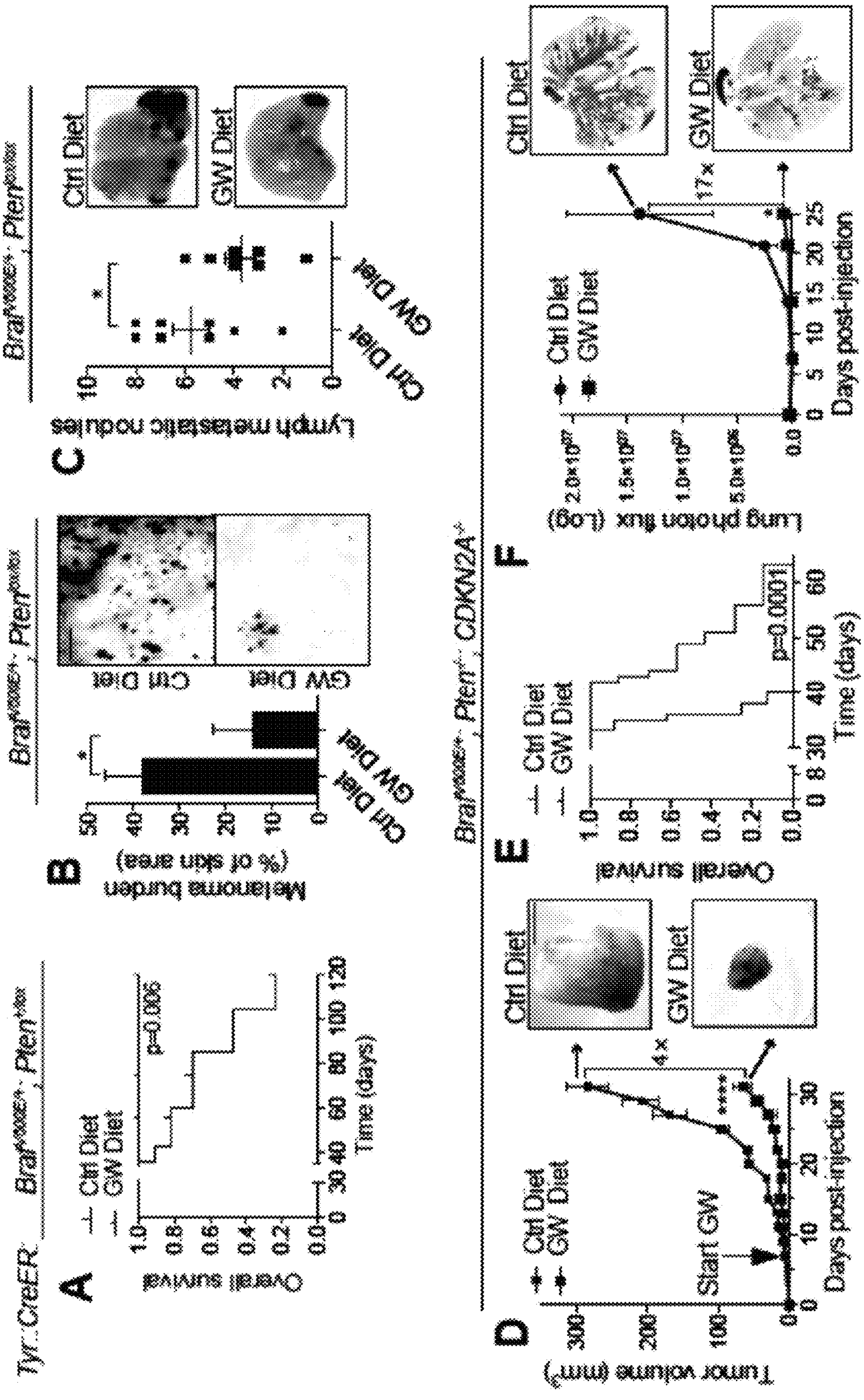
Figures 25A, 25B:
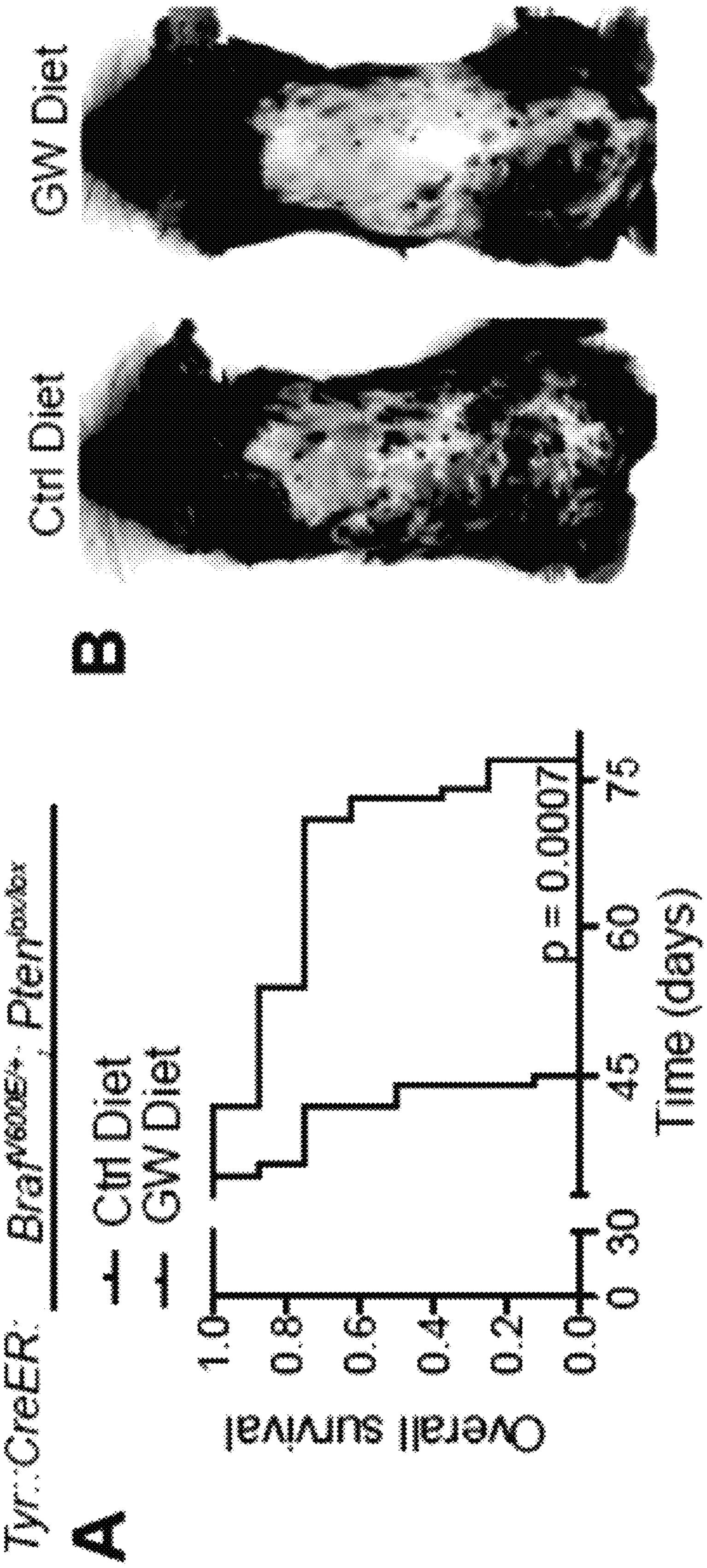

FIGS. 25A and 25B. LXR-Mediated Suppression of Melanoma Progression in a Genetically-Driven Melanoma Mouse Model, Related to FIG. 24(A-C). (25A) Overall survival of Tyr::CreER; BrafV600E/+; Ptenlox/lox C57BL/6 mice following general melanoma induction by intraperitoneal administration of 4-HT (25 mg/kg) on three consecutive days. After the first 4-HT injection, mice were randomly assigned to a control diet or a diet supplemented with GW3965 (100 mg/kg). n=7. (25B) Representative images of Tyr::CreER; BrafV600E/+; Ptenlox/lox C57BL/6 mice fed a control diet of GW3965-supplemented diet (100 mg/kg) taken 43 days following melanoma induction by intraperitoneal 4-HT administration.

FIG. 26. A List of the 50 most upregulated genes in MeWo human melanoma cells in response to GW3965 treatment.

FIGS. 27A, 27B, 27C, 27D, 27E, 27F, 27G, 27H, 27I, 27J and 27K. LXRβ Activation Induces ApoE Expression in Melanoma Cells; ApoE mediates LXRβ-Dependent Suppression of In Vitro Melanoma Progression Phenotypes. (27A, 27B, 27C) MeWo (27A), HT-144 (27B), and WM-266-4 (27C) human melanoma cells were treated with GW3965 or T0901317 at the indicated concentrations for 48 hours, and the expression levels of ApoE were analysed by qRT-PCR. n=3. (27D) Extracellular ApoE protein levels, quantified by ELISA, in serum-free conditioned media collected from HT-144 human melanoma cells treated with DMSO, GW3965, or T0901317 at 1 μM for 72 hours. n=3-4. (27E-27F) 5×104 HT-144 cells, treated with DMSO, GW3965, or T0901317 at 1 μM for 72 hours, were tested for the cell invasion (27E) and endothelial recruitment phenotypes (27F) in the presence of an ApoE neutralization antibody (1D7) or an IgG control antibody added at 40 μg/mL to each trans-well at the start of the assay. n=4. (27G-27H) Cell invasion (27G) and endothelial recruitment (27F) by 1× 105 and 5×104 MeWo cells, respectively, expressing a control shRNA or an shRNA targeting ApoE and treated with DMSO or GW3965 at 1 μM for 72 hours prior to each assay. n=7-8. (27I-27J) Relative ApoE expression, quantified by qRT-PCR, in MeWo (I) and HT-144 (27J) cells transduced with a control shRNA or shRNAs targeting LXRα or LXRβ and subsequently treated with DMSO, GW3965, or T0901317 at 1 μM for 48 hours. n=3-9. (27K) Extracellular ApoE protein levels, measured by ELISA, in serum-free conditioned media harvested from HT-144 cells transduced with a control shRNA or an shRNA targeting LXRα or LXRβ and treated with DMSO or GW3965 at 1 μM for 72 hours. n=3. All data are represented as mean±SEM. Scale bar, 50 μm.

FIGS. 28A, 28B, 28C, 28D, 28E, 28F, 28G, 28H and 28I. LXRβ Activation Suppresses Melanoma Invasion and Endothelial Recruitment by Transcriptionally Enhancing Melanoma-Cell ApoE Expression. (28A) Luciferase activity driven off the ApoE promoter fused downstream of multi-enhancer element 1 (ME.1) or multi-enhancer element 2 (ME.2) sequences and transfected into MeWo cells treated with DMSO, GW3965, or T0901317 at 1 μM for 24 hours. n=4-8. (28B) Extracellular ApoE protein levels were quantified by ELISA in serum-free conditioned media harvested from MeWo cells treated with DMSO, GW3965, or T0901317 at 1 μM for 72 hours. n=3-4. (28C) Cell invasion by 1× 105 MeWo cells pre-treated with DMSO, GW3965, or T0901317 at 1 μM for 72 hours. At the start of the assay, an ApoE neutralization antibody (1D7) or an IgG control antibody was added at 40 μg/mL to each trans-well, as indicated. n=7-8. (28D) 5×104 MeWo cells, pre-treated with DMSO, GW3965, or T0901317 at 1 μM for 72 hours, were tested for their ability to recruit 1×105 endothelial cells in the presence of 1D7 or IgG antibodies at 40 μg/mL. n=6-8. (28E) Extracellular ApoE protein levels, quantified by ELISA, in serum-free conditioned media from SK-Mel-334.2 primary human melanoma cells treated with DMSO or GW3965 at 1 μM for 72 hours. n=4. (28F-28G) 5×104 SK-Mel-334.2 cells, pre-treated with GW3965 at 1 μM for 72 hours, were subjected to the cell invasion (28F) and endothelial recruitment (28G) assays in the presence of 1D7 or IgG antibodies at 40 μg/mL. n=7-8. (28H) Activity of the ApoE promoter fused to ME. 1 or ME.2 enhancer elements was determined through measuring luciferase reporter activity in MeWo cells expressing a control shRNA or shRNAs targeting LXRα or LXRβ in the presence of DMSO or GW3965 (1 μM) for 24 hours. n=3-8. (28I) Extracellular ApoE protein levels, quantified by ELISA, were assessed in serum-free conditioned media collected from human MeWo melanoma cells expressing a control shRNA or shRNAs targeting LXRα or LXRβ in response to treatment with GW3965 or T0901317 (1 μM) for 72 hours. n=3-8. All data are represented as mean±SEM. Scale bar, 50 μm.

FIGS. 29A, 29B, 29C, 29D, 29E, 29F, 29G, 29H, 29I, 29J and 29K. Therapeutic Delivery of LXR Agonists Upregulates Melanoma-Derived and Systemic ApoE Expression. (29A-29B) ApoE expression levels, quantified by qRT-PCR, in subcutaneous tumors formed by B16F10 mouse melanoma cells injected into C57BL/6 mice. After 5-mm3 tumor formation, mice were fed a control diet or diet containing GW3965 (20 mg/kg) (29A) or T0901317 (20 mg/kg) (29B) for 7 days. n=3-4. (29C, 29D, 29E) ApoE transcript expression in primary tumors (29C), lung metastases (29D), and brain metastases (29E) formed by MeWo human melanoma cells grafted onto NOD Scid mice that were administered control chow or chow supplemented with GW3965 (20 mg/kg). ApoE levels were assessed on day 35 (29C), day 153 (29D), and day 34 (29E) post-injection of the cancer cells. n=3-5. (29F) Relative expression levels of LXRα, LXRβ, and ApoE were determined by qRT-PCR in B16F10 mouse melanoma cells expressing a control hairpin or an shRNA targeting mouse LXRα (sh_mLXRα), mouse LXRβ (sh_mLXRβ), or mouse ApoE (sh_mApoE). (29G-29H) ApoE (29G) and ABCA1 (29H) mRNA levels, measured by qRT-PCR, in B16F10 cells expressing a control shRNA or shRNAs targeting mouse LXRβ or mouse ApoE. The cells were treated with DMSO or GW3965 at 5 μM for 48 hours. n=3. (29I) ABCA1 mRNA levels, measured by qRT-PCR, in systemic white blood cells extracted from LXRα−/− or LXRβ −/− mice fed a control diet or a GW3965-supplemented diet (20 mg/kg) for 10 days. n=3-4. (29J) Relative expression of ApoE mRNA, expressed as the frequency of SAGE tags, in mouse skin and lung tissues was determined using the public mSAGE Expression Matrix database available through the NCI-funded Cancer Genome Anatomy Project (CGAP). (29K) Relative expression of ApoE mRNA, determined by qRT-PCR, in MeWo melanoma cells dissociated from lung metastatic nodules (LM2) or primary tumors relative to control unselected MeWo parental cells. n=3.

FIGS. 30A, 30B, 30C, 30D, 30E, 30F, 30G, 30H and 30I. LXRβ Agonism Suppresses Melanoma Tumor Growth and Metastasis by Inducing Melanoma-Derived and Systemic ApoE Expression. (30A) Western blot measurements of ApoE protein levels in adipose, lung, and brain tissue lysates extracted from wild-type mice fed with a control chow or a chow supplemented with GW3965 (20 mg/kg) or T0901317 (20 mg/kg) for 10 days. (30B) Quantification of ApoE protein expression based on western blots shown in (30A). Total tubulin was used as an endogenous control for normalization. n=3-5. (30C) Expression levels of ApoE, determined by qRT-PCR, in systemic white blood cells from mice fed a control diet or a diet supplemented with GW3965 or T0901317 at 20 mg/kg for 10 days. n=3-6. (30D) B16F10 control cells or B16F10 cells expressing shRNAs targeting mouse LXRα (sh_mLXRα) or mouse LXRβ (sh_mLXRβ) were subcutaneously injected into C57BL/6-WT, LXRα−/−, or LXRβ−/− mice. Once the tumors reached 5-10 mm3 in volume, mice were fed a control diet or a diet supplemented with GW3965 (20 mg/kg) for 7 days, after which final tumor volume was measured. Representative tumor images extracted at the end point are shown in the right panel. n=6-18. (30E) ApoE transcript levels, quantified by qRT-PCR, in systemic white blood cells extracted from LXRα−/− or LXRβ−/− mice fed a control diet or a GW3965-supplemented diet (20 mg/kg) for 10 days. n=3-5. (30F) Subcutaneous tumor growth by 5×104 B16F10 control cells or B16F10 cells expressing an shRNA targeting mouse ApoE (sh_mApoE) in C57BL/6-WT or ApoE−/− mice. Following the formation of tumors measuring 5-10 mm3 in volume, mice were fed a control diet or a diet supplemented with GW3965 (20 mg/kg) for 7 days, and final tumor volume was quantified. Representative images of tumors extracted at the final day of measurement (d12) are shown on the right. n=8-18. (30G) Lung colonization by 5×104 B16F10 cells transduced with a control shRNA or sh_mApoE and intravenously injected into C57BL/6-WT or ApoE−/− mice. Starting 10 days prior to cancer cell injection, mice were assigned to a control diet or a GW3965-supplemented diet (20 mg/kg) treatment. Lung metastasis was quantified on d22 by bioluminescence imaging. Representative lungs extracted at the end point (d22) are shown in the right panel. n=5-10. (30H) ApoE protein expression, determined by blinded immunohistochemical analysis, in non-metastatic (n=39) and metastatic (n=34) primary melanoma skin lesion samples obtained from patients at MSKCC. The fraction of ApoE-positively staining cell area was quantified as a percentage of total tumor area. (30I) Kaplan-Meier curves for the MSKCC cohort (n=71) depicting the metastasis-free survival of patients as a function of ApoE protein expression in patients' primary melanoma lesions. Melanomas that had ApoE levels above the median of the population were classified as ApoE-positive (pos), whereas tumors with ApoE expression below the median were classified as ApoE-negative (neg). All data are represented as mean±SEM. Scale bar, 5 mm (30D and 30F), 100 μm (30H).

FIGS. 31A, 31B, 31C, 31D, 31E, 31F, 31G, 31H and 31I. Activation of LXR Suppresses the In Vivo Growth of Melanoma Lines Resistant to Dacarbazine and Vemurafenib. (31A) In vitro cell growth by 2.5×104 B16F10 parental cells and in vitro-derived B16F10 DTIC-resistant cells in response to varying doses of dacarbazine (DTIC) added to the cell media for 4 days. n=3. (31B-31D) Tumor growth by 5×104 DTIC-sensitive B16F10 parental cells (31B) or 5×104 DTIC-resistant B16F10 cells (31C) subcutaneously injected into C57BL/6-WT mice. Following tumor growth to 5-10 mm3 in volume, mice were treated with dacarbazine (50 mg/kg, i.p., daily) or a control vehicle and randomly assigned to regular chow or a chow supplemented with GW3965 (100 mg/kg). Final day tumor volume measurements are shown in (31D). n=8-16 (31B), 7-8 (31C). (31E-31F) Tumor growth by DTIC-sensitive MeWo parental cells and in vivo-derived DTIC-resistant MeWo human melanoma cells in response to DTIC or GW3965 treatments. 5×105 cells were subcutaneously injected into NOD Scid gamma mice. After formation of tumors measuring 5-10 mm3 in volume, mice were blindedly assigned to a control treatment, a DTIC treatment (50 mg/kg, i.p., administered daily in 5-day cycles with 2-day off-treatment intervals), or a GW3965-supplemented diet treatment (100 mg/kg). Final day tumor measurements are show in (31F). n=6-8. (31G) Tumor growth by 2× 106 SK-Mel-239 vemurafenib-resistant clone cells subcutaneously injected into NOD Scid gamma mice that were assigned to a control diet or a diet supplemented with GW3965 (100 mg/kg) subsequent to growth of tumors to 5-10 mm3 in volume. n=7-8. (31H) Overall mouse survival post-grafting of 2×106 SK-Mel-239 vemurafenib-resistant cells. Upon the growth of tumors to 5-10 mm3 in volume, mice were continuously fed a control diet or a diet supplemented with GW3965 (100 mg/kg). n=7. (31I) Experimentally derived model depicting the engagement of systemic and melanoma-autonomous ApoE by LXRβ activation therapy in mediating the suppression of melanoma progression phenotypes. Extracellular ApoE suppresses melanoma metastasis by coordinately inhibiting melanoma cell invasion and non-cell-autonomous endothelial recruitment through targeting melanoma-cell LRP1 and endothelial-cell LRP8 receptors, respectively. All data are represented as mean±SEM. Scale bar, 5 mm.

Figure 32:
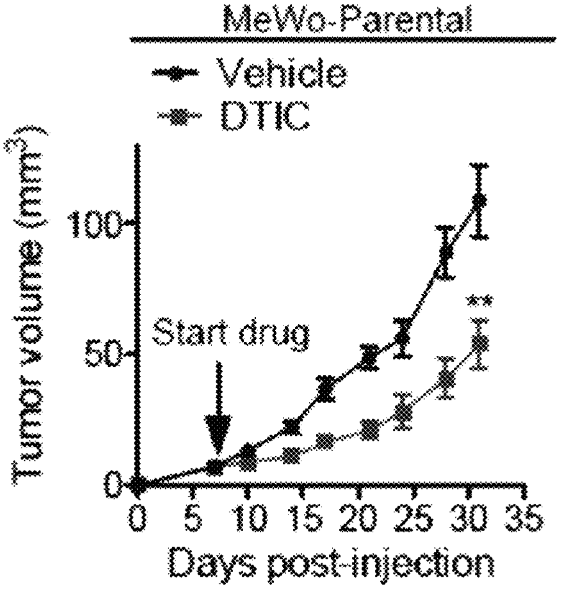
Figures 33A, 33B, 33C, 33D, 33E, 33F, 33G, 33H, 33I:
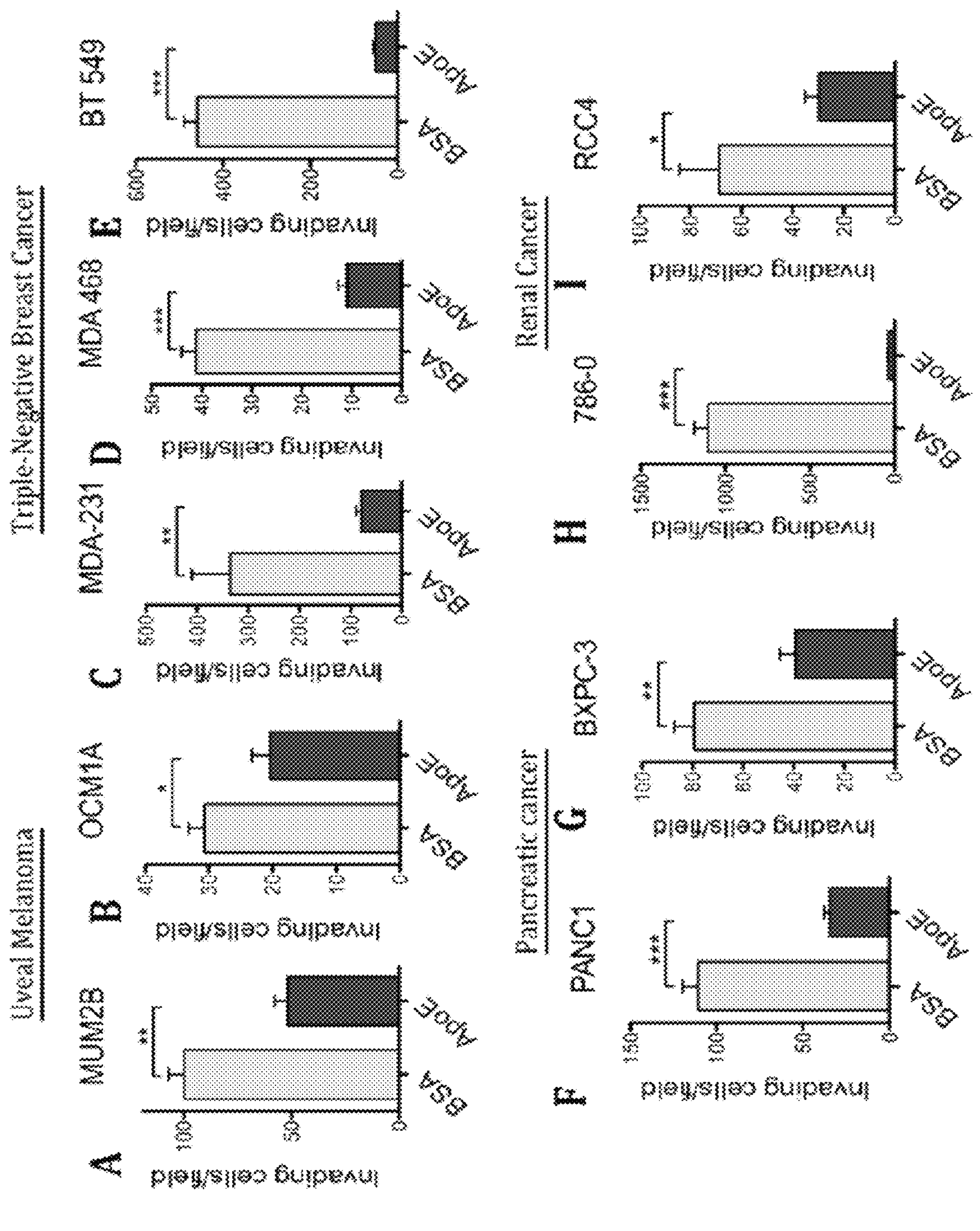

FIG. 32. Dacarbazine-Induced Suppression of Tumor Growth by Human Melanoma Cells. Tumor growth by 5×105 DTIC-sensitive MeWo parental cells subcutaneously injected into Nod SCID gamma mice. When tumors reached 5-10 mm3 volume, mice were treated with a control vehicle or DTIC (50 mg/kg, i.p., administered daily in 5-day cycles with 2-day off-treatment intervals), and tumor volume was measured twice a week. n=6.

FIGS. 33A, 33B, 33C, 33D, 33E, 33F, 33G, 33H and 33I. ApoE-mediated suppression of cell invasion across multiple cancer types. (33A-33B) 5×104 MUM2B and OCM1 human uveal melanoma cells, (33C-33E) 5×104 MDA-231, MDA-468, and BT 549 human triple-negative breast cancer cells, (33F-33G) 5×104 PANC1 and BXPC-3 human pancreatic cancer cells, and (33H-33I) 5×104 786-00 and RCC4 human renal cancer cells were tested for their ability to invade through matrigel-coated trans-well inserts in vitro. BSA or recombinant ApoE were added to the cell media at 100 μg/mL at the start of the assay. n=4. All data are represented as mean±SEM; *p<0.05, p<0.01, *p<0.001.

FIGS. 34A, 34B, 34C and 34D. Effects of LXR agonists LXR-623, WO-2007-002563 Ex. 19, WO-2010-0138598 Ex. 9, and SB742881 on ApoE expression in human melanoma cells. (34A-34D) MeWo human melanoma cells were treated with DMSO or the LXR agonists LXR-623 (34A), WO-2007-002563 (34B), WO-2010-0138598 (34C), or SB742881 (34D) at 500 nM, 1 μM, or 2 μM for 48 hours. The expression levels of ApoE were subsequently quantified by qRT-PCR. n=3. All data are represented as mean±SEM. *p<0.05, **p<0.01.

Figures 35A, 35B, 35C:
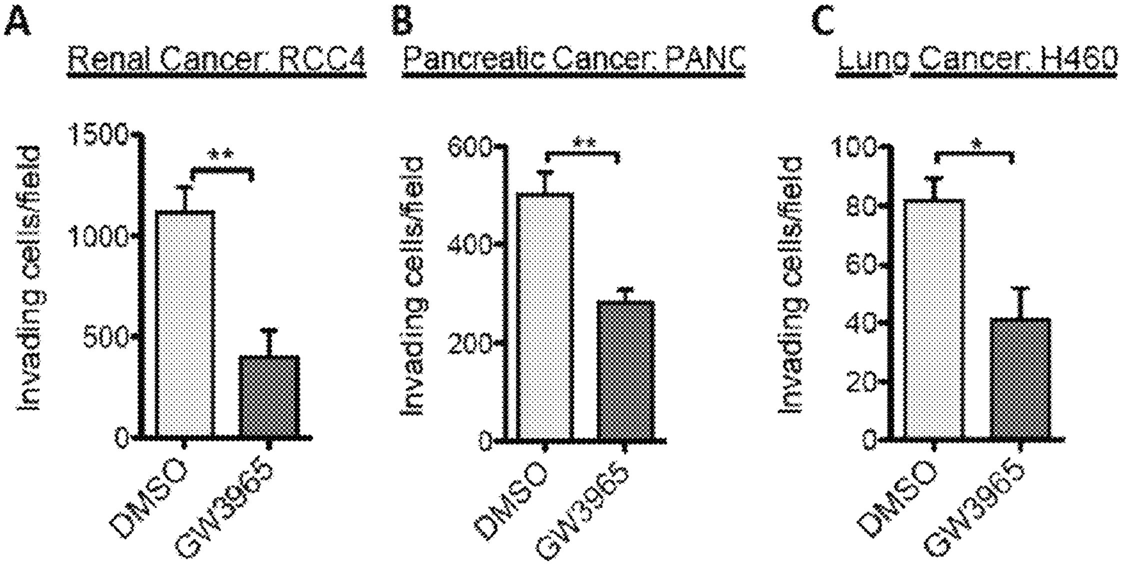

FIGS. 35A, 35B and 35C. Treatment with the LXR agonist GW3965 inhibits In Vitro tumor cell invasion of renal cancer, pancreatic cancer, and lung cancer. (35A, 35B, 35C) Trans-well matrigel invasion by 5×104 RCC human renal cancer cells (35A), 5×104 PANC1 human pancreatic cancer cells (35B), and 5×104 H460 human lung cancer cells (35C) that were treated with DMSO or GW3965 at 1 μM for 72 hours prior to the assay. n=4. All data are represented as mean±SEM. *p<0.05, **p<0.01.

Figure 36:
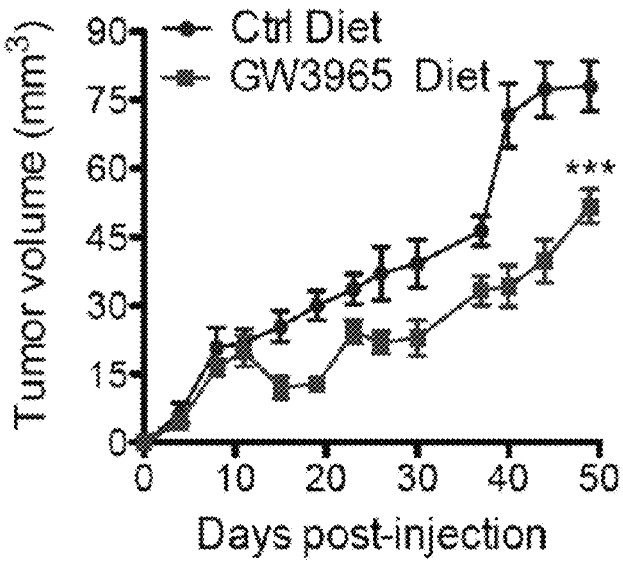

FIG. 36. Treatment with the LXR agonist GW3965 inhibits breast cancer tumor growth In Vivo. Primary tumor growth by 2×106 MDA-468 human breast cancer cells injected into the mammary fat pads of NOD Scid gamma mice. Two days prior to cancer cell injection, the mice were assigned to a control diet treatment or a diet supplemented with GW3965 (75 mg/kg) and maintained on the corresponding diet throughout the experiment. n=8. All data are represented as mean±SEM. ***p<0.001.

Figures 37A, 37B:
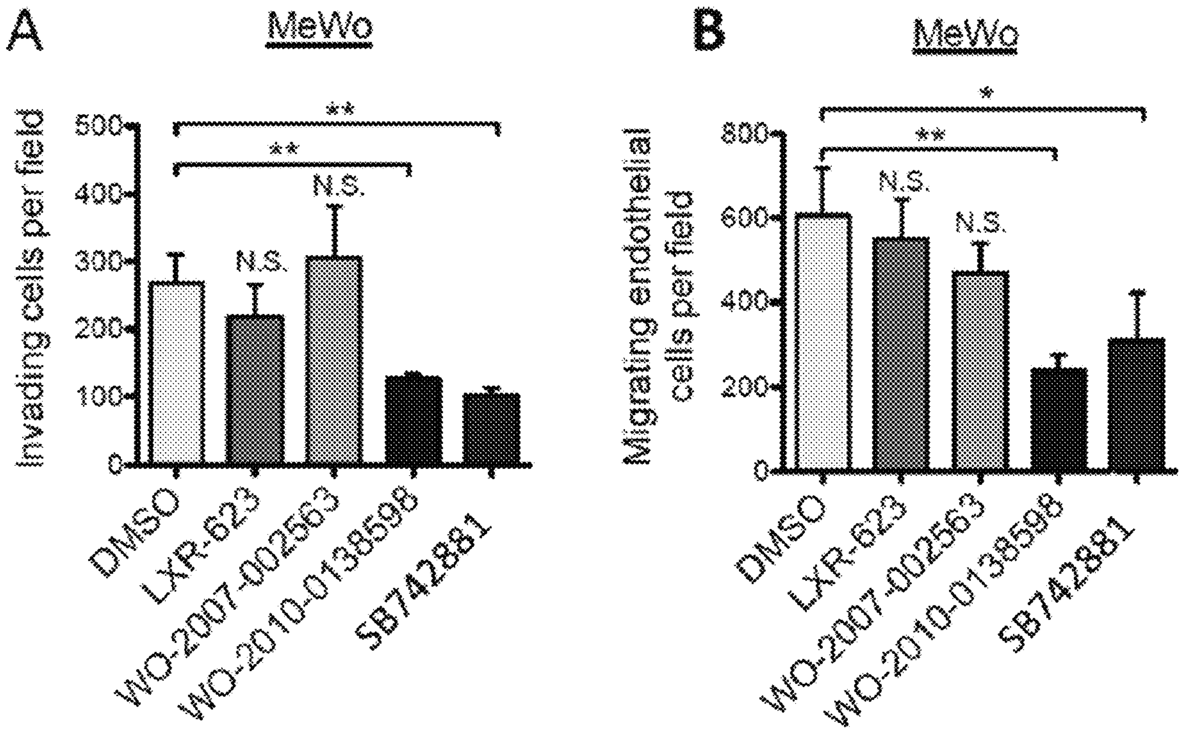
Figures 38A, 38B, 38C, 38D:
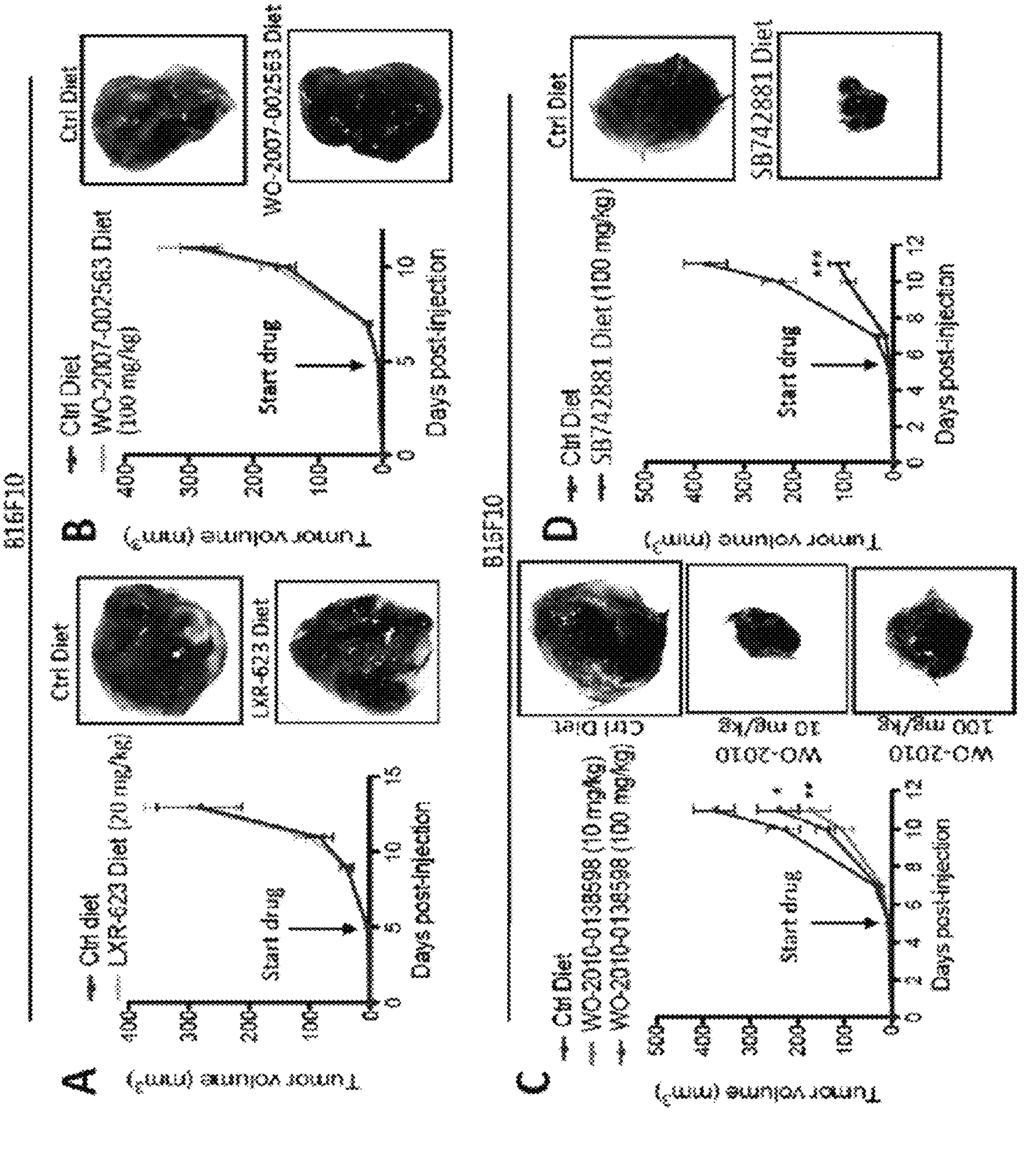

FIGS. 37A and 37B. Effects of LXR agonists LXR-623, WO-2007-002563 Ex. 19, WO-2010-0138598 Ex. 9, and SB742881 on in vitro melanoma progression phenotypes. (37A) Cell invasion by 1×105 MeWo human melanoma cells pre-treated with DMSO, LXR-623, WO-2007-002563 Ex. 19, WO-2010-0138598 Ex. 9, or SB742881 at 1 μM each for 72 hours. The number of cells invading into the basal side of matrigel-coated trans-well inserts was quantified. n=5. (37B) Endothelial recruitment by 5×104 MeWo cells pre-treated with DMSO, LXR-623, WO-2007-002563 Ex. 19, WO-2010-0138598 Ex.9, or SB742881 at 1 μM each for 72 hours. Cancer cells were seeded at the bottom of a 24-well plate. Endothelial cells were seeded in a trans-well insert fitted into each well and allowed to migrate towards the cancer cells. The number of endothelial cells migrating to the basal side of each trans-well insert was quantified. n=4-5. All data are represented as mean±SEM. *p<0.05, **p<0.01.

FIGS. 38A, 38B, 38C and 38D. Effects of LXR agonists LXR-623, WO-2007-002563 Ex. 19, WO-2010-0138598 Ex. 9, and SB742881 on in vivo tumor growth. (38A, 38B, 38C, 38D) Tumor growth by 5×104 B16F10 mouse melanoma cells subcutaneously injected into 7-week-old C57BL/6 mice. After tumors reached 5-10 mm3 in volume, the mice were randomly assigned to a control diet treatment, an LXR-623-supplemented diet treatment at 20 mg/kg/day (38A) a WO-2007-002563 Ex. 19-supplemented diet treatment at 100 mg/kg/day (38B), a WO-2010-0138598 Ex. 19-supplemented diet treatment at 10 mg/kg/day or 100 mg/kg/day (38C), or an SB742881-supplemented diet treatment at 100 mg/kg/day (38D). n=8-10. All data are represented as mean±SEM.

DETAILED DESCRIPTION OF THE INVENTION

The present invention features methods for preventing or reducing aberrant proliferation, differentiation, or survival of cells. For example, compounds of the invention may be useful in reducing the risk of, or preventing, tumors from increasing in size or from reaching a metastatic state. The subject compounds may be administered to halt the progression or advancement of cancer. In addition, the instant invention includes use of the subject compounds to reduce the risk of, or prevent, a recurrence of cancer.

Metastatic progression requires that sets of effector proteins involved in common cellular phenotypes be coherently expressed (Gupta and Massagué, 2006 Cell 127, 679-695; Hanahan and Weinberg, 2011 Cell 144, 646-674; Talmadge and Fidler, 2010 Cancer Res. 70, 5649-5669; Hynes, 2003 Cell 113, 821-823). Such concerted expression states are apparent in gene expression profiles of primary breast cancers that metastasize (Wang et al., 2005 Lancet 365, 671-679), as well as profiles of human cancer cell clones that display enhanced metastatic activity (Kang et al., 2003 Cancer Cell 3, 537-549; Minn et al., 2005 Nature 436, 518-524). In recent years, post-transcriptional regulation has emerged as a pervasive and robust mode of concerted expression-state and phenotype-level control. The most studied class of post-transcriptional regulators with metastatic regulatory activity are small non-coding RNAs (miRNAs) (Bartel, 2009 Cell 136, 215-233; Fabian et al., 2010 Annu. Rev. Biochem, 79, 351-379; Filipowicz et al., 2008 Nat. Rev. Genet. 9, 102-114). Metastasis promoter miRNAs (Ma et al., 2007 Nature 449, 682-688; Huang et al., 2008 Nat. Cell Biol. 10, 202-210) and suppressor miRNAs (Tavazoie et al., 2008 Nature 451, 147-152) were originally discovered in breast cancer. Subsequent studies revealed many more miRNAs with regulatory roles in the tumorigenesis and metastasis of other cancer types (Hatziapostolou et al., 2011 Cell 147, 1233-1247; Hurst et al., 2009 Cancer Res. 69, 7495-7498; Olson et al., 2009 Genes Dev. 23, 2152-2165; Zhang et al., 2010 Oncogene 29, 937-948) In many cases, the expression levels of these miRNAs in human cancer samples have supported their experimental roles in metastasis. Thus, deregulated miRNA expression (Garzon et al., 2010 Nat. Rev. Drug Discov. 9, 775-789; Lujambio and Lowe, 2012 Nature 482, 347-355) and, more recently, deregulated expression of long non-coding RNAs (Calin et al., 2007 Nat. Rev. Cancer 6, 857-866; Gupta et al., 2010 Nature 464, 1071-1076; Guttman et al., 2009 Nature 458, 223-227; Huarte et al., 2010. Cell 142, 409-419; Loewer et al., 2010 Nat. Genet. 42, 1113-1117) as well as non-coding pseudogenes competing for endogenous miRNA binding (Poliseno et al., 2010 Nature 465, 1033-1038) appear to be pervasive features of human cancer. Clues regarding the robust control exerted by specific miRNAs on metastatic progression came from early work showing that concerted targeting of multiple metastasis genes by a single metastasis suppressor miRNA was responsible for the dramatic metastasis suppression effects (Tavazoie et al., 2008 Nature 451, 147-152). Such divergent gene targeting by miRNAs has appeared to be a defining feature of these regulators.

At a conceptual level, the need for divergent regulation of gene expression in cancer is readily understood. A miRNA could exert robust metastatic suppression by virtue of its ability to target multiple genes required for metastasis. The miRNA's silencing through genetic or epigenetic mechanisms would readily promote cancer progression by derepressing multiple promoters of metastasis (Png et al., 2011 Nature 481, 190-194). A role for convergent regulation of a single gene by multiple metastasis regulatory miRNAs is more nuanced. This scenario would emerge if there existed a key gene that acted as a robust suppressor of metastatic progression. Convergent and cooperative targeting of this gene by multiple miRNAs could achieve maximal silencing of such a key metastasis suppressor gene. This scenario, as opposed to genetic deletion, may be seen in cases where complete loss of a target gene could not be tolerated by the cell, and the gene would be required at low levels to mediate metabolic actions, for example. Given this possibility, a search for cooperative metastasis promoter miRNAs may uncover novel genes that are pivotal for metastasis suppression and may provide therapeutic insights into more effective treatments for metastasis prevention.

As disclosed herein, via a systematic, in vivo selection-based approach, a set of miRNAs were identified to be deregulated in multiple independent metastatic lines derived from multiple patients with melanoma—a highly prevalent cancer with increasing incidence (Garbe and Leiter, 2009 Clin. Dermatol. 27, 3-9). As disclosed herein, miR-1908, miR-199a-3p, and miR-199a-5p act as robust endogenous promoters of melanoma metastasis through convergent targeting of the metabolic gene ApoE and the heat-shock protein DNAJA4. Through loss-of-function, gain-of-function, and epistatic analyses, a cooperative miRNA network that maximally silences ApoE signaling is delineated. Cancer cell-secreted ApoE inhibits metastatic invasion and endothelial recruitment, which is mediated through its actions on distinct receptors on melanoma and endothelial cells. These miRNAs display significant prognostic capacity in identifying patients that develop melanoma metastatic relapse, while therapeutic delivery of LNAs targeting these miRNAs significantly inhibits melanoma metastasis. The current lack of effective therapies for the prevention of melanoma metastasis after surgical resection (Garbe et al., 2011 Oncologist 16, 5-24) requires an improved molecular and mechanistic understanding of melanoma metastatic progression. To this end, the findings disclosed herein reveal a number of key novel non-coding and coding genes involved in melanoma progression and offer a novel avenue for both identifying patients at high-risk for melanoma metastasis and treating them.

Listed below are the nucleic acid and amino acid sequences of the members of the above-mentioned network and a number of other sequences.

```
APOE-RNA sequence
                                          (SEQ ID NO: 1)
gggatccttgagtcctactcagccccagcggaggtgaaggacgtccttcc

ccaggagccgactggccaatcacaggcaggaagatgaaggttctgtgggc

tgcgttgctggtcacattcctggcaggatgccaggccaaggtggagcaag

cggtggagacagagccggagcccgagctgcgccagcagaccgagtggcag

agcggccagcgctgggaactggcactgggtcgcttttgggattacctgcg

ctgggtgcagacactgtctgagcaggtgcaggaggagctgctcagctccc

aggtcacccaggaactgagggcgctgatggacgagaccatgaaggagttg

aaggcctacaaatcggaactggaggaacaactgaccccggtggcggagga

gacgcgggcacggctgtccaaggagctgcaggcggcgcaggcccggctgg

gcgcggacatggaggacgtgtgcggccgcctggtgcagtaccgcggcgag

gtgcaggccatgctcggccagagcaccgaggagctgcgggtgcgcctcgc

ctcccacctgcgcaagctgcgtaagcggctcctccgcgatgccgatgacc

tgcagaagcgcctggcagtgtaccaggccggggcccgcgagggcgccgag

cgcggcctcagcgccatccgcgagcgcctggggcccctggtggaacaggg

ccgcgtgcgggccgccactgtgggctccctggccggccagccgctacagg

agcgggcccaggcctggggcgagcggctgcgcgcgcggatggaggagatg

ggcagccggacccgcgaccgcctggacgaggtgaaggagcaggtggcgga

ggtgcgcgccaagctggaggagcaggcccagcagatacgcctgcaggccg

aggccttccaggcccgcctcaagagctggttcgagcccctggtggaagac

atgcagcgccagtgggccgggctggtggagaaggtgcaggctgccgtggg

caccagcgccgcccctgtgcccagcgacaatcactgaacgccgaagcctg

cagccatgcgaccccacgccaccccgtgcctcctgcctccgcgcagcctg

cagcgggagaccctgtccccgccccagccgtcctcctggggtggacccta

gtttaataaagattcaccaagtttcacgcaaaaaaaaaaaaaaaaaaaaa

aaaaaaaaaaaaaaaaaaaaaa
```

-continued

```
APOE-Amino acid sequence
                                          (SEQ ID NO: 2)
mkvlwaallv tflagcqakv eqavetepep elrqqtewqs

gqrwelalgr fwdylrwvqt lseqvqeell ssqvtqelra

lmdetmkelk aykseleeql tpvaeetrar lskelqaaqa

rlgadmedvc grlvqyrgev qamlgqstee lrvrlashlr

klrkrllrda ddlqkrlavy qagaregaer glsairerlg

plveqgrvra atvgslagqp lqeraqawge rlrarmeemg

srtrdrldev keqvaevrak leeqaqqirl qaeafqarlk

swfeplvedm qrqwaglvek vqaavgtsaa pvpsdnh
(Underlined residues 136-150 represent the LRP-
binding domain of Apo E)

DNAJA4 isoform 1-RNA sequence
                                          (SEQ ID NO: 3)
agucccacccuucggcgcagggcuccggccaacacagcccuccaggccgc

cuacucuccagccagccggcuccacggacccacggaagggcaagggggcg

gccucggggcggcgggacaguugucggagggcgcccuccaggcccaagcc

gccuucuccggcccccgccauggcccggggcggcagucagagcuggagcu

ccggggaaucagacgggcagccaaaggagcagacgcccgagaagcccaga

cacaagauggugaaggagacccaguacuaugacauccugggcgugaagcc

cagcgcguccccggaggagaucaagaaggccuaucggaagcuggcgcuca

aguaccacccggacaagaacccggaugagggcgagaaguuuaaacucaua

ucccaggcauaugaagugcuuucagauccaaagaaaagggauguuuauga

ccaaggcggagagcaggcaauuaaagaaggaggcucaggcagccccagcu

ucucuucacccauggacaucuuugacauguucuuugguggugguggacgg

auggcuagagagagaagaggcaagaauguuguacaccaguuaucuguaac

ucuugaagaucuauauaauggagucacgaagaaauuggcccuccagaaaa

auguaauuugugagaaaugugaagguguuggugggaagaagggaucggug

gagaagugcccgcugugcaaggggcgggggaugcagauccacauccagca

gaucgggccgggcaugguacagcagauccagaccgugugcaucgagugca

agggccagggugagcgcaucaaccccaaggaccgcugcgagagcugcagc

ggggccaaggugauccgugagaagaagauuaucgagguacauguugaaaa

agguaugaaagaugggcaaaagauacuauuucauggagaaggagaucagg

agccugagcuggagccuggugaugucauaauugugcuugaucagaaggau

cauagugucuuucagagacgaggccaugacuugaucaugaaaaugaaaau

ucagcuuucugaagcucuuuguggcuucaagaagacgauaaaaacauugg

acaaucgaauucuuguuauuacauccaaagcaggugaggugauaaagcac

ggggaccugagaugcgugcgcgaugaaggaaugcccaucuacaaagcacc

ccuggaaaaagggauucugaucauacaguuuuuaguaaucuuuccugaaa

aacacuggcuuucucuggaaaagcuuccucagcuggaagcuuuacucccu

ccucgacagaaagugaggauuacagaugacauggaucagguggagcugaa

ggaguuuugucccaaugagcagaacuggcgucagcacagggaggccuacg

aggaggacgaagacgggccccaggcuggagugcagugccagacggcauga

cguggugcggggcagcguggccccaccggacuagcacaugaugaauguaa
```

-continued aguuggcacaaugaaaaugacaucgcuuuaauggccuuguguuugggaug uccuguguauguguucagcauucuuaauugcugagugucuuuuuggcuuu ucuuuugguuguaacuuaaguuauagcuuaauuuauauuuaaauguuuua aguauaaaucaccucuagucugcauauggaaucuguucauuucuauuuuc aggauauacuuuugagaugucagugauugcaccaauacuuugugcuucua guggcuuugccauaauucagugucaccaauaaggcacagcccaguuagca gcuuagcccccuagcaaaccccaaggcacaaaguggcauccugacuca ucucuaggucugugguuucucccucuucccuuggcagaguuauugaggg caugaucucagggcugcuaagauaacauuucugaggauucuagaugaucc ucuuaaagaauaaaagcacauccguggaucggacauggcugcaugugccu gcuuaacagggccaacuuaguuccuacuguucugugcccuucaguggaug gaacgugagugucugaucaucucucuuggaaguuuucugaaccuuccaag cucugguggugaggacaaaccaguguuugaaucauaugcugauaacuguuu gccugugacccucacaccuuguucuucaggguuuuaaugauuuucuguug acaacuuuugcaaugcuuucccaccaaagugcuuacuuguaaagaaaacu aaauccuucuguguccccggcagccucagugcagcaacagaagccaaggg agaaugcugcugguuuggcccauggcacagccagcuucucugaccaguaa uccgggugacuugagggucugcaaaggcauagaacuccccaguguuuuc caccucauucucccagauugagcucccuuccaaaggaucguuccucucau ugcacagccauauuacaaaggguuuccugcucaagugauguuuugguaag aacuucgcugaguuccacuguggauuacaguuuguauggacuacuacugu aaauuauagcuuguuuggagggauauuagucauuauuuuauucaugacag guagacuacaauucgaacuuaggguuaccucagucuuuagccauuacugc uuauuucuuuuccccaagucacaaaaaacuuguaagcugcugguuaaag cagaggccaccugucagaucuacccuacccuuauuugguuacauggcacc ugagaguuucacucagaccagggaucuuccuuaggagggucaaagugcag aucagaccaugcagguaaggugaaccagcugcacggaccagguucccgca aaacauugccagcuagugaggcauaauuugcucaaguauagaaacagcc caccugugcccacuuugaccauuggugaggauagauauaaaaucacuucu uccaacgaagccuaggugaaaaucuauuuauaaauggaccacaacucugg ggugucguuuuugugcugugacuuccuaauuauugcuaaagaacuacugu uuaguugguaaugguguaaaauuacauucagcuccuucuugucauauaaa aggaauuuggagggugucgcuuaaaauuuuauuccaccuguacauuuguc acuuuaaaauuaaaauugagcugguaugagagauaaaaaaaaaaaaaaaa aaa DNAJA4 isoform 1-Amino acid sequence (SEQ ID NO: 4)

marggsqsws sgesdgqpke qtpekprhkm vketqyydil gvkpsaspee ikkayrklal kyhpdknpde gekfldisqa yevlsdpkkr dvydqggeqa ikeggsgsps fsspmdifdm ffggggrmar errgknvvhq lsvtledlyn gvtkklalqk -continued nvicekcegv ggkkgsvekc plckgrgmqi hiqqigpgmv qqiqtvciec kgqgerinpk drcescsgak virekkiiev hvekgmkdgq kilfhgegdq epelepgdvi ivldqkdhsv fqrrghdlim kmkiqlseal cgfkktikti dnrilvitsk agevikhgdl revrdegmpi ykaplekgil iiqflvifpe khwlsleklp qleallpprq kvritddmdq velkefcpne qnwrqhreay eededgpqag vqcqta DNAJA4 isoform 2-RNA sequence (SEQ ID NO: 5)

gugaccgugacgcgcgagcgggcggcgggggcgcgggccaggggcgcggg ccagggugccggcaggggcguccggggcgcucugaccggccucgcccgcc cccccgcagacacaagauggugaaggagacccaguacuaugacauccug ggcgugaagcccagcgcguccccggaggagaucaagaaggccuaucggaa gcuggcgcucaaguaccacccggacaagaacccggaugagggcgagaagu uuaaacucauaucccaggcauaugaagugcuuucagauccaaagaaaagg gauguuuaugaccaaggcggagagcaggcaauuaaagaaggaggcucagg cagccccagcuucucuucacccauggacaucuuugacauguucuuuggug gugguggacggauggcuagagagagaagaggcaagaauguuguacaccag uuaucuguaacucuugaagaucuauauaauggagucacgaagaaauuggc ccuccagaaaaauguaauuugugagaaaugugaagguguuggugggaaga agggaucgguggagaagugcccgcugugcaaggggcgggggaugcagauc cacauccagcagaucgggccgggcaugguacagcagauccagaccgugug caucgagugcaagggccagggugagcgcaucaaccccaaggaccgcugcg agagcugcagcggggccaaggugauccgugagaagaagauuaucgaggua cauguugaaaaagguaugaaagaugggcaaaagauacuauuucauggaga aggagaucaggagccugagcuggagccuggugaugucauaauugugcuug aucagaaggaucauagugucuuucagagacgaggccaugacuugaucaug aaaaugaaaauucagcuuucugaagcucuuuguggcuucaagaagacgau aaaaacauuggacaaucgaauucuuguuauuacauccaaagcaggugagg ugauaaagcacggggaccugagaugcgugcgcgaugaaggaaugcccauc uacaaagcaccccuggaaaaagggauucugaucauacaguuuuuaguaau cuuuccugaaaaacacuggcuuucucuggaaaagcuuccucagcuggaag cuuuacucccuccucgacagaaagugaggauuacagaugacauggaucag guggagcugaaggaguuuugucccaaugagcagaacuggcgucagcacag ggaggccuacgaggaggacgaagacgggccccaggcuggagugcagugcc agacggcaugacguggugcggggcagcguggccccaccggacuagcacau gaugaauguaaaguuggcacaaugaaaaugacaucgcuuuaauggccuug uguuugggauguccuguguauguguucagcauucuuaauugcugaguguc uuuuuggcuuuucuuuugguuguaacuuaaguuauagcuuaauuuauauu uaaauguuuuaaguauaaaucaccucuagucugcauauggaaucuguuca uuucuauuuucaggauauacuuuugagaugucagugauugcaccaauacu uugugcuucuaguggcuuugccauaauucagugucaccaauaaggcacag -continued cccaguuagcagcuuagcccccuagcaaaccccaaggcacaaagugggc auccugacucaucucuaggucugugguuucuccccucuucccuuggcaga guuauugagggcaugaucucagggcugcuaagauaacauuucugaggauu cuagaugauccucuuaaagaauaaaagcacauccguggaucggacauggc ugcaugugccugcuuaacagggccaacuuaguuccuacuguucugugccc uucaguggauggaacgugagugucugaucaucucucuuggaaguuuucug aaccuuccaagcucuguggugaggacaaaccaguguuugaaucauaugcu gauaacuguuugccugugacccucacaccuuguucuucaggguuuuaaug auuuucuguugacaacuuuugcaaugcuuucccaccaaagugcuuacuug uaaagaaaacuaaauccuucuguguccccggcagccucagugcagcaaca gaagccaagggagaaugcugcugguuuggcccauggcacagccagcuucu cugaccaguaauccggggugacuugagggucugcaaaggcauagaacucc ccaguguuuccaccucauucucccagauugagcucccuuccaaaggauc guuccucucauugcacagccauauuacaaaggguuuccugcucaagugau guuuugguaagaacuucgcugaguuccacuguggauuacaguuuguaugg acuacuacuguaaauuauagcuuguuuggagggauauuagucauuauuuu auucaugacagguagacuacaauucgaacuuaggguuaccucagucuuua gccauuacugcuuauuucuuuuccccaagucacaaaaaacuuguaagcug cuggguuaaagcagaggccaccugucagaucuacccuacccuuauuuggu uacauggcaccugagaguuucacucagaccagggaucuuccuuaggaggg ucaaagugcagaucagaccaugcagguaaggugaaccagcugcacggacc agguucccgcaaaacauugccagcuagugaggcauaauuugcucaaagua uagaaacagcccaccugugcccacuuugaccauuggugaggauagauaua aaaucacuucuuccaacgaagccuaggugaaaaucuauuuauaaauggac cacaacucuggggugucguuuuugugcugugacuuccuaauuauugcuaa agaacuacuguuuaguugguaaugguguaaaauuacauucagcuccuucu ugucauauaaaaggaauuuggagggugucgcuuaaaauuuuauuccaccu guacauuugucacuuuaaaauuaaaauugagcugguaugagagauaaaaa aaaaaaaaaaaaaa DNAJA4 isoform 2-Amino acid sequence (SEQ ID NO: 6)

mvketqyydi lgvkpsaspe eikkayrkla lkyhpdknpd egekfklisq ayevlsdpkk rdvydqggeq aikeggsgsp sfsspmdifd mffggggrma rerrgknvvh qlsvtledly ngvtkklalq knvicekceg vggkkgsvek cplckgrgmq ihiqqigpgm vqqiqtvcie ckgqgerinp kdrcescsga kvirekkiie vhvekgmkdg qkilfhgegd qepelepgdv iivldqkdhs vfqrrghdli mkmkiqlsea lcgfkktikt ldnrilvits kagevikhgd lrcvrdegmp iykaplekgi liiqflvifp ekhwlslekl pqleallppr qkvritddmd qvelkefcpn eqnwrqhrea yeededgpqa gvqcqta -continued DNAJA4 isoform 3-RNA sequence (SEQ ID NO: 7)

acauuucagcaagcuggcuaaagacaugugggaaagccugacccuggauu caggucaaaucucagcacucacaagauuuaaacucauaucccaggcauau gaagugcuuucagauccaaagaaaagggauguuuaugaccaaggcggaga gcaggcaauuaaagaaggaggcucaggcagccccagcuucucuucaccca uggacaucuuugacauguucuuugguggugguggacggauggcuagagag agaagaggcaagaauguuguacaccaguuaucuguaacucuugaagaucu auauaauggagucacgaagaaauuggcccuccagaaaaauguaauuugug agaaaugugaagguguuggugggaagaagggaucgguggagaagugcccg cugugcaaggggcgggggaugcagauccacauccagcagaucgggccggg caugguacagcagauccagaccgugugcaucgagugcaagggccagggug agcgcaucaaccccaaggaccgcugcgagagcugcagcggggccaaggug auccgugagaagaagauuaucgagguacauguugaaaaagguaugaaaga ugggcaaaagauacuauuucauggagaaggagaucaggagccugagcugg agccuggugaugucauaauugugcuugaucagaaggaucauagugucuuu cagagacgaggccaugacuugaucaugaaaaugaaaauucagcuuucuga agcucuuuguggcuucaagaagacgauaaaaacauuggacaaucgaauuc uuguuauuacauccaaagcaggugaggugauaaagcacggggaccugaga ugcgugcgcgaugaaggaaugcccaucuacaaagcaccccuggaaaaagg gauucugaucauacaguuuuuaguaaucuuuccugaaaaacacuggcuuu cucuggaaaagcuuccucagcuggaagcuuuacucccuccucgacagaaa gugaggauuacagaugacauggaucagguggagcugaaggaguuuugucc caaugagcagaacuggcgucagcacagggaggccuacgaggaggacgaag acgggccccaggcuggagugcagugccagacggcaugacguggugcgggg cagcguggccccaccggacuagcacaugaugaauguaaaguuggcacaau gaaaaugacaucgcuuuaauggccuuguguuugggauguccuguguaugu guucagcauucuuaauugcugagugucuuuuuggcuuuucuuuugguugu aacuuaaguuauagcuuaauuuauauuuaaauguuuuaaguauaaaucac cucuagucugcauauggaaucuguucauuucuauuuucaggauauacuuu ugagaugucagugauugcaccaauacuuugugcuucuaguggcuuugcca uaauucagugucaccaauaaggcacagcccaguuagcagcuuagcccccc uagcaaaccccaaggcacaaagugggcauccugacucaucucuaggucug ugguuucuccccucuucccuuggcagaguuauugagggcaugaucucagg gcugcuaagauaacauuucugaggauucuagaugauccucuuaaagaaua aaagcacauccguggaucggacauggcugcaugugccugcuuaacagggc caacuuaguuccuacuguucugugcccuucaguggauggaacgugagugu cugaucaucucucuuggaaguuuucugaaccuuccaagcucugguggugag gacaaaccaguguuugaaucauaugcugauaacuguuugccugugacccu cacaccuuguucuucaggguuuuaaugauuuucuguugacaacuuuugca augcuuucccaccaaagugcuuacuuguaaagaaaacuaaauccuucugu guccccggcagccucagugcagcaacagaagccaagggagaaugcugcug -continued guuuggcccauggcacagccagcuucucugaccaguaauccggggugacu ugagggucugcaaaggcauagaacuccccaguguuuccaccucauucuc ccagauugagcucccuuccaaaggaucguuccucucauugcacagccaua uuacaaaggguuuccugcucaagugauguuuugguaagaacuucgcugag uuccacuguggauuacaguuuguauggacuacuacuguaaauuauagcuu guuuggagggauauuagucauuauuuuauucaugacagguagacuacaau ucgaacuuaggguuaccucagucuuuagccauuacugcuuauuucuuuuc cccaagucacaaaaaacuuguaagcugcuggguuaaagcagaggccaccu gucagaucuacccuacccuuauuugguuacauggcaccugagaguuucac ucagaccagggaucuucccuuaggagggucaaagugcagaucagaccaugc agguaaggugaaccagcugcacggaccagguucccgcaaaacauugccag cuagugaggcauaaauuugcucaaaguauagaaacagcccaccugugccca cuuugaccauuggugaggauagauauaaaaucacuucuuccaacgaagcc uaggugaaaaucuauuuauaaauggaccacaacucugggguguguuuuu gugcugugacuuccuaauuauugcuaaagaacuacuguuuaguugguaau gguguaaaauuacauucagcuccuucuugucauauaaaaggaauuuggag ggugucgcuuaaaaauuuuauuccaccuguacauuugucacuuuaaaauua aaauugagcugguaugagagauaaaaaaaaaaaaaaaaaaa DNAJA4 isoform 3-Amino acid sequence (SEQ ID NO: 8)

mwesltldsg qisaltrfkl isqayevlsd pkkrdvydqg geqaikeggs gspsfsspmd ifdmffgggg rmarerrgkn vvhqlsvtle dlyngvtkkl alqknvicek cegvggkkgs vekcplckgr gmqihiqqig pgmvqqiqtv cieckgqger inpkdrcesc sgakvirekk iievhvekgm kdgqkilfhg egdqepelep gdviivldqk dhsvfqrrgh dlimkmkiql sealcgfkkt iktldnrilv itskagevik hgdlrcvrde gmpiykaple kgiliiqflv ifpekhwlsl eklpqleall pprqkvritd dmdqvelkef cpneqnwrqh reayeededg pqagvqcqta LRP1-RNA sequence (SEQ ID NO: 9)

cagcggugcgagcuccaggcccaugcacugaggaggcggaaacaaggga gcccccagagcuccaucaagccccccuccaaaggcuccccuacccggucca cgcccccaccccccucccgccuccucccaauugugcauuuuugcagc cggaggcggcuccgagauggggcugugagcuucgcccggggagggggaaa gagcagcgaggagugaagcgggggggugggggugaaggguuuggauuucgg ggcagggggcgcaccccgucagcaggcccuccccaaggggcucggaacu cuaccucuucacccacgccccuggugcgcuuugccgaaggaaagaauaag aacagagaaggaggagggggaaaggaggaaaaggggggacccccaacugg gggggugaaggagagaaguagcaggaccagaggggaaggggcugcugcu ugcaucagcccacaccaugcugaccccgccguugcuccugcugcugcccc -continued ugcucucagcucuggucgcggcggcuaucgacgccccuaagacuugcagc cccaagcaguuugccugcagagaucaaauaaccuguaucucaaagggcug gcggugcgacggugagagggacugcccagacggaucugacgaggccccug agauuuguccacagaguaaggcccagcgaugccagccaaacgagcauaac ugccugggguacugagcuguguguucccaugucccgccucugcaaugggu ccaggacugcauggacggcucagaugaggggccccacugccgagagcucc aaggcaacugcucucgccugggcugccagcaccauugugucccccacacuc gaugggcccaccugcuacugcaacagcagcuuucagcuucaggcagaugg caagaccugcaaagauuuugaugagugcucaguguacggcaccugcagcc agcuaugcaccaacacagacggcuccuucauauguggcuguguugaagga uaccuccugcagccggauaaccgcuccugcaaggccaagaacgagccagu agaccggcccccugugcuguugauagccaacucccagaacaucuuggcca cguaccugagugggggcccaggugucuaccaucacaccuacgagcacgcgg cagaccacagccauggacuucagcuaugccaacgagaccguaugcugggu gcauguuggggacagugcugcucagacgcagcucaagugugcccgcaugc cuggccuaaagggcuucguggaugagcacaccaucaacaucucccucagu cugcaccacguggaacagauggccaucgacuggcugacaggcaacuucua cuuuguggaugacaucgaugauaggaucuuugucugcaacagaaaugggg acacaugugucacauugcuagaccuggaacucuacaaccccaagggcauu gcccuggacccugccauggggaagguguuuuucacugacuaugggcagau cccaaagguggaacgcugugacauggaugggcagaaccgcaccaagcucg ucgacagcaagauuguguuuccucauggcaucacgcuggaccuggucagc cgccuugucuacugggcagaugccuaucuggacuauauugaaguggugga cuaugagggcaagggccgccagaccaucauccagggcauccugauugagc accuguacggccugacuguguuugagaauuaucucuaugccaccaacucg gacaaugccaaugcccagcagaagacgagugugauccgugugaaccgcuu uaacagcaccgaguaccagguugucacccggguggacaaggguggugccc uccacaucuaccaccagaggcgucagccccgagugaggagccaugccugu gaaaacgaccaguaugggaagccggguggcugcucugacaucugccugcu ggccaacagccacaaggcgcggaccugccgcugccguuccggcuucagcc ugggcagugacgggaagucaugcaagaagccggagcaugagcuguuccuc guguauggcaagggccggccaggcaucauccggggcauggauaugggggc caagguccccggaugagcacaugauccccauugaaaaccucaugaaccccc gagcccuggacuuccacgcugagaccggcuucaucuacuuugccgacacc accagcuaccucauuggccgccagaagauugauggcacugagcgggagac cauccugaaggacggcauccacaauguggaggguguggccguggacugga ugggagacaaucuguacuggacggacgaugggcccaaaaagacaaucagc guggccaggcuggagaaagcugcucagacccgcaagacuuuaaucgaggg caaaaugacacaccccagggcuauugugguggauccacucaaugggugga uguacuggacagacugggaggaggaccccaaggacagucggcgugggcgg cuggagagggcguggauggauggcucacaccgagacaucuuugucaccuc -continued caagacagugcuuuggcccaaugggcuaagccuggacaucccggcugggc gccucuacuggguggaugccuucuacgaccgcaucgagacgauacugcuc aauggcacagaccggaagauuguguaugaagguccugagcugaaccacgc cuuuggccugugucaccauggcaacuaccucuucuggacugaguaucgga guggcagugucuaccgcuuggaacgggguguaggaggcgcacccccacu gugacccuucugcgcagugagcggcccccaucuuugagauccgaaugua ugaugcccagcagcagcaaguuggcaccaacaaaugccgggugaacaaug gcggcugcagcagccugugcuuggccaccccugggagccgccagugcgcc ugugcugaggaccagguguuggacgcagacggcgucacuugcuuggcgaa cccauccuacgugccuccaccccagugccagccaggcgaguuugccugug ccaacagccgcugcauccaggagcgcuggaagugugacggagacaacgau ugccuggacaacagugaugaggccccagcccucugccaucagcacaccug ccccucggaccgauucaagugcgagaacaaccggugcauccccaaccgcu ggcucugcgacggggacaaugacugugggaacagugaagaugaguccaau gccacuuguucagcccgcaccugcccccccaaccaguucuccugugccag uggccgcugcauccccaucuccuggacgugugaucuggaugacgacugug gggaccgcucugaugagucugcuucgugugccuaucccaccugcuucccc cugacucaguuuaccugcaacaauggcagauguaucaacaucaacuggag augcgacaaugacaaugacuguggggacaacagugacgaagccggcugca gccacuccuguucuagcacccaguucaagugcaacagcgggcguugcauc cccgagcacuggaccugcgauggggacaaugacugcggagacuacaguga ugagacacacgccaacugcaccaaccaggccacgaggcccccugguggcu gccacacugaugaguuccagugccggcuggauggacuaugcaucccccug cgguggcgcugcgauggggacacugacugcauggacuccagcgaugagaa gagcugugagggagugacccacgucugcgaucccagugucaaguuuggcu gcaaggacucagcucggugcaucagcaaagcguggguguguggauggcgac aaugacugugaggauaacucggacgaggagaacugcgagucccuggccug caggccacccucgcacccuugugccaacaacaccucagucugccugcccc cugacaagcugugugauggcaacgacgacuguggcgacggcucagaugag ggcgagcucugcgaccagugcucucugaauaacgguggcugcagccacaa cugcucaguggcaccuggcgaaggcauuguguguuccugcccucugggca uggagcuggggcccgacaaccacaccugccagauccagagcuacugugcc aagcaucucaaaugcagccaaaagugcgaccagaacaaguucagcgugaa gugcuccugcuacgagggcuggguccuggaaccugacggcgagagcugcc gcagccuggaccccuucaagccguucaucauuuucuccaaccgccaugaa auccggcgcaucgaucuucacaaaggagacuacagcguccuggugcccgg ccugcgcaacaccaucgcccuggacuuccaccucagccagagcgcccucu acuggaccgacgugguggaggacaagaucuaccgcgggaagcugcuggac aacggagcccugacuaguuucgagguggugauucaguauggccuggccac acccgagggccuggcuguagacuggauugcaggcaacaucuacugggugg -continued agaguaaccuggaucagaucgagguggccaagcuggaugggacccuccgg accacccugcuggccggugacauugagcacccaagggcaaucgcacugga uccccgggaugggauccuguuuuggacagacugggaugccagccugcccc gcauugaggcagccuccaugagugggggcugggcgccgcaccgugcaccgg gagaccggcucugggggcuggcccaacgggcucaccguggacuaccugga gaagcgcauccuuuggauugacgccaggucagaugccauuuacucagccc guuacgacggcucuggccacauggaggugcuucggggacacgaguuccug ucgcacccguuugcagugacgcuguacggggggggaggucuacuggacuga cuggcgaacaaacacacuggcuaaggccaacaaguggaccggccacaaug ucaccgugguacagaggaccaacacccagcccuuugaccugcagguguac caccccucccgccagcccauggcucccaaucccugugaggccaaugggg ccagggccccugcucccaccugugucucaucaacuacaaccggaccgugu ccugcgccugcccccaccucaugaagcuccacaaggacaacaccaccugc uaugaguuuaagaaguuccugcuguacgcacgucagauggagauccgagg uguggaccuggaugcucccuacuacaacuacaucaucuccuucacggugc ccgacaucgacaacgucacagugcuagacuacgaugcccgcgagcagcgu guguacuggucugacgugcggacacaggccaucaagcgggccuucaucaa cggcacaggcguggagacagucgucucugcagacuugccaaaugcccacg ggcuggcuguggacugggucucccgaaaccuguucuggacaagcuaugac accaauaagaagcagaucaauguggcccggcuggauggcuccuucaagaa cgcagugguggcagggccuggagcagccccauggccuugucguccacccuc ugcgugggaagcucuacuggaccgauggugacaacaucagcauggccaac auggauggcagcaaucgcacccugcucuucaguggccagaagggccccgu gggccuggcuauugacuucccugaaagcaaacucuacuggaucagcuccg ggaaccauaccaucaaccgcugcaaccuggaugggagugggcuggagguc aucgaugccaugcggagccagcugggcaaggccaccgcccuggccaucau gggggacaagcugugguggcugaucaggugucggaaaagauggcacau gcagcaaggcugacggcucgggcuccgugguccuucggaacagcaccacc cuggugaugcacaugaaggucuaugacgagagcauccagcuggaccauaa gggcaccaaccccugcagugucaacaacggugacugcucccagcucugcc ugcccacgucagagacgacccgcuccugcaugugcacagccggcuauagc cuccggaguggccagcaggccugcgagggcguagguuccuuucuccugua cucugugcaugagggaaucaggggaauuccccuggaucccaaugacaagu cagaugcccuggucccaguguccgggaccucgcuggcugucggcaucgac uuccacgcugaaaaugacaccaucuacuggguggacaugggccugagcac gaucagccgggccaagcgggaccagacguggcgugaagacgugguggacca auggcauuggccguguggagggcauugcaguggacuggaucgcaggcaac aucuacuggacagaccagggcuuugaugucaucgaggucgcccggcucaa uggcuccuuccgcuacguggugaucucccagggucuagacaagccccggg ccaucaccguccacccggagaaaggguacuuguucuggacugagugggu caguauccgcguauugagcggucucggcuagauggcacggagcgugugguu -continued gcuggucaacgucagcaucagcuggcccaacggcaucucaguggacuacc aggaugggaagcuguacuggugcgaugcacggacagacaagauugaacgg aucgaccuggagacaggugagaaccgcgagguggu ucuguccagcaacaa cauggacauguuuucagugucuguguuugaggauuucaucuacuggagug acaggacucaugccaacggcucuaucaagcgcgggagcaaagacaaugcc acagacuccgugccccugcgaaccggcaucggcguccagcuuaaagacau caaagucuucaaccgggaccggcagaaaggcaccaacgugugcgcggugg ccaauggcgggugccagcagcugugccuguaccggggccgugggcagcgg gccugcgccugugcccacgggaugcuggcugaagacggagcaucgugccg cgaguaugccggcuaccugcucuacucagagcgcaccauucucaagagua uccaccugucggaugagcgcaaccucaaugcgcccgugcagcccuucgag gacccugagcacaugaagaacgucaucgcccuggccuuugacuaccgggc aggcaccucuccgggcacccccaaucgcaucuucuucagcgacauccacu uugggaacauccaacagaucaacgacgauggcuccaggaggaucaccauu guggaaaacgugggcuccguggaaggccuggccuaucaccguggcuggga cacucucuauuggacaagcuacacgacauccaccaucacgcgccacacag uggaccagacccgcccaggggccuucgagcgugagaccgucaucacuaug ucuggagaugaccacccacgggccuucguuuggacgagugccagaaccu cauguucuggaccaacuggaaugagcagcaucccagcaucaugcgggcgg cgcucucgggagccaauguccugacccuuaucgagaaggacauccguacc cccaauggccuggccaucgaccaccgugccgagaagcucuacuucucuga cgccacccuggacaagaucgagcggugcgaguaugacggcucccaccgcu augugauccuaaagucagagccuguccaccccuucgggcuggccguguau ggggagcacauuuucuggacugacugggugcggcgggcagugcagcgggc caacaagcacgugggcagcaacaugaagcugcugcgcguggacaucccc c agcagcccaugggcaucaucgccguggccaacgacaccaacagcugugaa cucucuccaugccgaaucaacaacgguggcugccaggaccugugucugcu cacucaccagggccaugucaacugcucaugccgagggggccgaauccucc aggaugaccucaccugccgagcggugaauuccucuugccgagcacaagau gaguuugagugugccaauggcgagugcaucaacuucagccugaccugcga cggcguccccca cugcaaggacaaguccgaugagaagccauccuacugca acucccgccgcugcaagaagacuuuccggcagugcagcaaugggcgcugu guguccaacaugcuguggugcaacggggccgacgacuguggggauggcuc ugacgagaucccuugcaacaagacagccugugguguggg cgaguuccgcu gccgggacgggaccugcaucgggaacuccagccgcugcaaccaguuugug gauugugaggacgccucagaugagaugaacugcagugccaccgacugcag cagcuacuuccgccugggcgugaagggcgugcucuuccagcccugcgagc ggaccucacucugcuacgcacccagcugggugugugauggcgccaaugac uguggggacuacagugaugagcgcgacugcccaggugugaaacgccccag augcccucugaauuacuucgccugcccuagugggcgcugcauccccauga gcuggacgugugacaaagaggaugacugugaacauggcgaggacgagacc cacugcaacaaguucugcucagaggcccaguuugagugccagaaccaucg cugcaucuccaagcaguggcugugugacggcagcgaugacuguggggaug gcucagacgaggcugcucacugugaaggcaagacgugcggccccuccucc uucuccugcccuggcacccacgugugcguccccgagcgcuggcucuguga cggugacaaagacugugcugauggugcagacgagagcaucgcagcugguu gcuuguacaacagcacuugugacgaccgugaguucaugugccagaaccgc cagugcauccccaagcacuucgugugugaccacgaccgugacugugcaga uggcucugaugaguccccgagugugaguacccgaccugcggccccagug aguuccgcugugccaaugggcgcugucugagcucccgccagugggagugu gauggcgagaaugacugccacgaccagagugacgaggcucccaagaaccc acacugcaccagccaagagcacaagugcaaugccucgucacaguuccugu gcagcagugggcgcuguguggcugaggcacugcucugcaacggccaggau gacuguggcgacagcucggacgagcguggcugccacaucaaugagugucu cagccgcaagcucaguggcugcagccaggacugugaggaccucaagaucg gcuucaagugccgcugucgcccuggcuuccggcugaaggacgacggccgg acgugugcugauguggacgagugcagcaccaccuuccccugcagccagcg cugcaucaacacucauggcagcuauaagugucugugugugg agggcuaug caccccgcggcggcgacccccacagcugcaaggcugugacugacgaggaa ccguuucugaucuucgccaaccgguacuaccugcgcaagcucaaccugga cggguccaacuacacguuacuuaagcagggccugaacaacgccguugccu uggauuuugacuaccgagagcagaugaucuacuggacagaugugaccacc cagggcagcaugauccgaaggaugcaccuuaacgggagcaaugugcaggu ccuacaccguacaggccucagcaaccccgaugggcuggcuguggacuggg uggguggcaaccuguacuggugcgacaaaggccgggacaccaucgaggug uccaagcucaauggggccuaucggacggugcuggucagcucuggccuccg ugagcccagggcucugguggugg augugcagaaugg guaccuguacugga cagacuggggugaccauucacugaucggccgcaucggcauggaugggucc agccgcagcgucaucguggacaccaagaucacauggcccaauggccugac gcuggacuaugucacugagcgcaucuacugggccgacgcccgcgaggacu acauugaauuugccagccuggauggcuccaaucgccacguugugcugagc caggacaucccgcacaucuuugcacugacccuguuugaggacuacgucua cuggaccgacugggaaacaaaguccauuaaccgagcccacaagaccacgg gcaccaacaaaacgcuccucaucagcacgcugcaccggcccauggaccug caugucuuccaugcccugcgccagccagacgugcccaaucaccccugcaa ggucaacaaugguggcugcagcaaccugugccugcuguccccgggggag ggcacaaaugugccugccccaccaacuucuaccugggcagcgaugggcgc accuguguguccaacugcacggcuagccaguuuguaugcaagaacgacaa gugcauccccuucugguggaagugugacaccgaggacgacugcggggacc acucagacgagcccccggacugcccugaguucaagugccggcccggacag uuccagugcuccacagguaucugcacaaacccugccuucaucugcgaugg -continued cgacaaugacugccaggacaacagugacgaggccaacugugacauccacg
ucugcuugcccagucaguucaaaugcaccaacaccaaccgcuguauuccc
ggcaucuuccgcugcaaugggcaggacaacugcggagauggggaggauga
gagggacugccccgaggugaccugcgcccccaaccaguuccagugcucca
uuaccaaacggugcaucccccgggucugggucugcgaccgggacaaugac
ugugugggauggcagugaugagcccgccaacugcacccagaugaccugugg
uguggacgaguuccgcugcaaggauucgggccgcugcaucccagcgcguu
ggaagugugacggagaggaugacugugggggauggcucggaugagcccaag
gaagagugugaugaacgcaccugugagccauaccaguuccgcugcaagaa
caaccgcugcgugcccggccgcuggcagugcgacuacgacaacgauugcg
gugacaacuccgaugaagagagcugcaccccucggcccugcuccgagagu
gaguucuccugugccaacggccgcugcaucgcggggcgcuggaaaugcga
uggagaccacgacugcgcggacggcucggacgagaaagacugcaccccccc
gcugugacauggaccaguuccagugcaagagcggccacugcaucccccug
cgcuggcgcugugacgcagacgccgacugcauggacggcagcgacgagga
ggccugcggcacuggcgugcggaccugccccuggacgaguuccagugca
acaacaccuugugcaagccgcuggccuggaagugcgauggcgaggaugac
uguggggacaacucagaugagaaccccgaggagugugcccgguucgugug
cccucccaaccggcccuuccguugcaagaaugaccgcgucugucugugga
ucgggcgccaaugcgauggcacggacaacugugggggaugggacugaugaa
gaggacugugagcccccacagcccacaccacccacugcaaagacaagaa
ggaguuucugugccggaaccagcgcugccucuccuccucccugcgcugca
acauguucgaugacugcggggacggcucugacgaggaggacugcagcauc
gaccccaagcugaccagcugcgccaccaaugccagcaucuguggggacga
ggcacgcugcgugcgcaccgagaaagcggccuacugugccugccgcucgg
gcuuccacaccgugcccggccagcccggaugccaagacaucaacgagugc
cugcgcuucggcaccugcucccagcucugcaacaacaccaagggcggcca
ccucugcagcugcgcucggaacuucaugaagacgcacaacaccugcaagg
ccgaaggcucugaguaccagguccuguacaucgcugaugacaaugagauc
cgcagccuguuccccggccacccccauucggcuuacgagcaggcauucca
gggugacgagaguguccgcauugaugcuauggauguccaugucaaggcug
gccgugucuauuggaccaacuggcacacgggcaccaucuccuaccgcagc
cugccaccugcugcgccuccuaccacuuccaaccgccaccggcgacagau
ugaccgggguguucacccaccucaacauuucagggcugaagaugcccagag
gcaucgccaucgacuggguggccggaaacguguacuggaccgacucgggc
cgagaugugauugagguggcgcagaugaagggcgagaaccgcaagacgcu
caucucgggcaugauugacgagccccacgccauugugguggacccacuga
gggggaccauguacuggucagacuggggcaaccaccccaagauugagacg
gcagcgauggaugggacgcuucgggagacacuggugcaggacaacauuca
guggcccacaggccuggccguggauuaucacaaugagcggcuguacuggg -continued cagacgccaagcuuucagucaucggcagcauccggcucaauggcacggac
cccauuguggcugcugacagcaaacgaggccuaagucaccccuucagcau
cgacgucuuugaggauuacaucuauggugucaccuacaucaauaaucgug
ucuucaagauccauaaguuuggccacagccccuuggucaaccugacaggg
ggccugagccacgccucugacgugguccuuuaccaucagcacaagcagcc
cgaagugaccaacccaugugaccgcaagaaaugcgaguggcucugccugc
ugagccccagugggccugucugcaccugucccaaugggaagcggcuggac
aacggcacaugcgugccugugcccucuccaacgcccccccagaugcucc
ccggccuggaaccuguaaccugcagugcuucaacgguggcagcuguuucc
ucaaugcacggaggcagcccaagugccgcugccaaccccgcuacacgggu
gacaagugugaacuggaccagugcugggagcacugucgcaauggggggcac
cugugcugccucccccucuggcaugcccacgugccggugccccacgggcu
ucacgggccccaaaugcacccagcaggugugugcgggcuacugugccaac
aacagcaccugcacugucaaccagggcaaccagccccagugccgaugccu
acccggcuuccugggcgaccgcugccaguaccggcagugcucuggcuacu
gugagaacuuuggcacaugccagauggcugcugauggcucccgacaaugc
cgcugcacugccuacuuugagggaucgaggugugaggugaacaagugcag
ccgcugucucgaaggggccuguguggucaacaagcagaguggggauguca
ccugcaacugcacggauggccggguggcccccagcugucugaccugcguc
ggccacugcagcaauggcggcuccuguaccaugaacagcaaaaugaugcc
ugagugccagugcccaccccacaugacagggccccggugugaggagcacg
ucuucagccagcagcagccaggacauauagccuccauccuaaucccucug
cuguugcugcugcugcugguucugguggccggagugguauucugguauaa
gcggcgaguccaaggggcuaagggcuuccagcaccaacggaugaccaacg
gggccaugaacguggagauuggaaaccccaccuacaagauguacgaaggc
ggagagccugaugaugugggaggccuacuggacgcugacuuugcccugga
cccugacaagcccaccaacuucaccaaccccguguaugccacacucuaca
ugggggccauggcagucgccacucccuggccagcacggacgagaagcga
gaacuccugggccggggcccugaggacgagauaggggaccccuuggcaua
gggcccugccccgucggacugcccccagaaagccuccugccccccugccgg
ugaaguccuucagugagccccuccccagccagcccuucccuggccccgcc
ggauguauaaauguaaaaaugaaggaauuacauuuuauaugugagcgagc
aagccggcaagcgagcacaguauuauuucuccauccccucccugccugcu
ccuuggcacccccaugcugccuucagggagacaggcagggagggcuuggg
gcugcaccuccuacccucccaccagaacgcaccccacugggagagcuggu
ggugcagccuuccccucccuguauaagacacuuugccaaggcucuccccu
cucgccccaucccugcuugcccgcucccacagcuuccugagggcuaauuc
ugggaagggagaguucuuugcugccccugucuggaagacguggcucuggg
ugagguaggcgggaaaggauggaguguuuaguucuuggggggaggccacc
ccaaaccccagccccaacuccaggggcaccuaugagauggccaugcucaa
ccccccucccagacaggcccucccugucuccagggcccccaccgagguuc -continued ccagggcuggagacuuccucugguaaacauuccuccagccucccccucccc uggggacgccaaggaggugggccacacccaggaagggaaagcgggcagcc ccguuuuggggacgugaacguuuuaauaauuuuugcugaauuccuuuaca acuaaauaacacagauauuguuauaaauaaaauuguaaaaaaaaaaaaaa aaaaa LRP1-Amino acid sequence (SEQ ID NO: 10)

mltppllll pllsalvaaa idapktcspk qfacrdqitc
iskgwrcdge rdcpdgsdea peicpqskaq rcqpnehncl
gtelcvpmsr lcngvqdcmd gsdegphcre lqgncsrlgc
qhhcvptldg ptcycnssfq lqadgktckd fdecsvygtc
sqlctntdgs ficgcvegyl lqpdnrscka knepvdrppv
llianwsqnil atylsgaqvs titptstrqt tamdfsyane
tvcwvhvgds aaqtqlkcar mpglkgfvde htinislslh
hveqmaidwl tgnfyfvddi ddrifvenrn gdtcvtlldl
elynpkgial dpamgkvfft dygqipkver cdmdgqnrtk
lvdskivfph gitldlvsrl vywadayldy ievvdyegkg
rqtiiqgili ehlygltvfe nylyatnsdn anaqqktsvi
rvnrfnstey qvvtrvdkgg alhiyhqrrq prvrshacen
dqygkpggcs dicllanshk artcrcrsgf slgsdgksck
kpehelflvy gkgrpgiirg mdmgakvpde hmipienlmn
praldfhaet gfiyfadtts yligrqkidg teretilkdg
ihnvegvavd wmgdnlywtd dgpkktisva rlekaaqtrk
tliegkmthp raivvdping wmywtdweed pkdsrrgrle
rawmdgshrd ifytsktylw pnglsldipa grlywydafy
drietillng tdrkivyegp elnhafglch hgnylfwtey
rsgsvyrler gvggapptvt lirserppif eirmydaqqq
qvgtnkcrvn nggcsslcla tpgsrqcaca edqvldadgv
tclanpsyvp ppqcqpgefa cansrciqer wkcdgdndcl
dnsdeapalc hqhtcpsdrf kcennrcipn rwlcdgdndc
gnsedesnat csartcppnq fscasgrcip iswtcdlddd
cgdrsdesas cayptcfplt qftcnngrci ninwrcdndn
dcgdnsdeag cshscsstqf kcnsgrcipe hwtcdgdndc
gdysdethan ctnqatrppg gchtdefqcr ldglciplrw
rcdgdtdcmd ssdekscegv thvcdpsvkf gckdsarcis
kawvcdgdnd cednsdeenc eslacrppsh pcanntsycl
ppdklcdgnd dcgdgsdege lcdqcslnng gcshncsvap
gegivcscpl gmelgpdnht cqiqsycakh lkcsqkcdqn
kfsvkcscye gwvlepdges crsldpfkpf iifsnrheir
ridlhkgdys vlvpglrnti aldfhlsqsa lywtdvvedk
iyrgklldng altsfevviq yglatpegla vdwiagniyw
vesnldqiev akldgtirtt llagdiehpr aialdprdgi
lfwtdwdasl prieaasmsg agrrtvhret gsggwpnglt
vdylekrilw idarsdaiys arydgsghme vlrghefish
pfavtlygge vywtdwrtnt lakankwtgh nytyvqrtnt
qpfdlqvyhp srqpmapnpc eanggqgpcs hiclinynrt
vscacphlmk lhkdnttcye fkkfflyarq meirgvdlda
pyynyiisft vpdidnytvl dydareqrvy wsdvrtqaik
rafingtgve tvvsadlpna hglavdwvsr nlfwtsydtn
kkqinvarld gsfknavvqg leqphglvvh plrgklywtd
gdnismanmd gsnrtllfsg qkgpvglaid fpesklywis
sgnhtinrcn ldgsglevid amrsqlgkat alaimgdklw
wadqvsekmg tcskadgsgs vvirnsttly mhmkvydesi
qldhkgtnpc synngdcsql clptsettrs cmctagyslr
sgqqacegvg sfllysvheg irgipldpnd ksdalvpvsg
tslavgidfh aendtiywvd mglstisrak rdqtwredvy
tngigrvegi avdwiagniy wtdqgfdvie varingsfry
vvisqgldkp raitvhpekg ylfwtewgqy priersrldg
tervylvnys iswpngisvd yqdgklywcd artdkierid
letgenrevy lssnnmdmfs vsvfedfiyw sdrthangsi
krgskdnatd svplrtgigy qlkdikvfnr drqkgtnvca
vanggcqqlc lyrgrgqrac acahgmlaed gascreyagy
llysertilk sihlsdernl napvqpfedp ehmknviala
fdyragtspg tpnriffsdi hfgniqqind dgsrritive
nvgsveglay hrgwdtlywt syttstitrh tvdqtrpgaf
eretvitmsg ddhprafvld ecqnlmfwtn wneqhpsimr
aalsganylt liekdirtpn glaidhraek lyfsdatldk
ierceydgsh ryvilksepv hpfglavyge hifwtdwvrr
avqrankhvg snmkllrvdi pqqpmgiiav andtnscels
perinnggcq dlcllthqgh vncscrggri lqddltcrav
nsscraqdef ecangecinf sltcdgvphc kdksdekpsy
cnsrrckktf rqcsngrcvs nmlwcngadd cgdgsdeipc
nktacgvgef rcrdgtcign ssrcnqfvdc edasdemncs
atdcssyfrl gykgylfqpc ertslcyaps wvcdgandcg
dysderdcpg vkrprcpiny facpsgrcip mswtcdkedd
cehgedethc nkfcseaqfe cqnhrciskq wlcdgsddcg
dgsdeaahce gktcgpssfs cpgthycype rwlcdgdkdc
adgadesiaa gclynstcdd refmcqnrqc ipkhfvcdhd
rdcadgsdes peceyptcgp sefrcangrc lssrqwecdg
endchdqsde apknphctsq ehkcnassqf lcssgrcvae
allcngqddc gdssdergch ineclsrkls gcsqdcedlk
igfkercrpg frlkddgrtc advdecsttf pcsqrcinth -continued gsykcicveg yaprggdphs ckavtdeepf lifanryylr klnldgsnyt llkqglnnav aldfdyreqm iywtdvttqg smirrmhlng snvqvlhrtg lsnpdglavd wvggnlywcd kgrdtievsk ingayrtylv ssglrepral vvdvqngyly wtdwgdhsli grigmdgssr svivdtkitw pngltldyvt eriywadare dyiefasldg snrhyvlsqd iphifaltlf edyvywtdwe tksinrahkt tgtnktllis tlhrpmdlhv fhalrqpdvp nhpckvnngg csnlcllspg gghkcacptn fylgsdgrtc vsnctasqfv ckndkcipfw wkcdteddcg dhsdeppdcp efkcrpgqfq cstgictnpa ficdgdndcq dnsdeancdi hvclpsqfkc tntnrcipgi frcngqdncg dgederdcpe vtcapnqfqc sitkrcipry wvcdrdndcv dgsdepanct qmtcgvdefr ckdsgrcipa rwkcdgeddc gdgsdepkee cdertcepyq frcknnrcvp grwqcdydnd cgdnsdeesc tprpcsesef scangrciag rwkcdgdhdc adgsdekdct prcdmdqfqc ksghciplrw rcdadadcmd gsdeeacgtg vrtcpldefq cnntickpla wkcdgeddcg dnsdenpeec arfvcppnrp frckndrycl wigrqcdgtd ncgdgtdeed cepptahtth ckdkkeficr nqrclssslr cnmfddcgdg sdeedcsidp kltscatnas icgdearcvr tekaaycacr sgfhtvpgqp gcqdineclr fgtcsqlcnn tkgghlcsca rnfmkthntc kaegseyqvl yiaddneirs lfpghphsay eqafqgdesv ridamdvhvk agrvywtnwh tgtisyrslp paappttsnr hrrqidrgvt hlnisglkmp rgiaidwvag nvywtdsgrd vievaqmkge nrktlisgmi dephaivvdp lrgtmywsdw gnhpkietaa mdgtlretly qdniqwptgl avdyhnerly wadaklsvig siringtdpi vaadskrgls hpfsidvfed yiygvtyinn rvfkihkfgh splvnitggl shasdvvlyh qhkqpevtnp cdrkkcewlc llspsgpvct cpngkrldng tcypvpsptp ppdaprpgtc nlqcfnggsc flnarrqpkc rcqprytgdk celdqcwehc rnggtcaasp sgmptcrept gftgpkctqq vcagycanns tctvnqgnqp qcrclpgflg drcqyrqcsg ycurlicqnl aadgsrqcrc tayfegsrce vnkcsrcleg acvvnkqsgd vtcnctdgry apscltcvgh csnggsctmn skmmpecqcp phmtgprcee hvfsqqqpgh iasiliplll llllvlvagv vfwykrrvqg akgfqhqrmt ngamnveign ptykmyegge pddvgglida dfaldpdkpt nftnpvyatl ymgghgsrhs lastdekrel lgrgpedeig dpla -continued LRP8 isoform 1-RNA sequence (SEQ ID NO: 11)

gcuggcggcggccgcccagggccggggccgcgcgcccagccugagcccgc cccgccgccgagcgucaccgaaccugcuugaaaugcagccgaggagccgg ggcgggcggcagcggcggcggcggcggcggcgggggcagcggcaaccccg gcgccgcggcaaggacucggagggcugagacgcggcggcggcggcgcggg gagcgcggggcgcggcggccggagccccgggcccgccaugggccuccccg agccgggcccucuccggcuucuggcgcugcugcugcugcugcugcugcug cugcugcugcagcuccagcaucuugcggcggcagcggcugauccgcugcu cggcggccaagggccggccaaggauugcgaaaaggaccaauuccagugcc ggaacgagcgcugcauccccucuguguggagaugcgacgaggacgaugac ugcuuagaccacagcgacgaggacgacugccccaagaagaccugugcaga cagugacuucaccugugacaacggccacugcauccacgaacgguggaagu gugacggcgaggaggaguguccugauggcuccgaugaguccgaggccacu ugcaccaagcagguguguccugcagagaagcugagcuguggacccaccag ccacaagugugugaccugccucguggcgcugcgacggggagaaggacugcg agggugggagcggaugaggccggcugugcuaccuugugcgccccgcacgag uuccagugcggcaaccgcucgugccuggccgccguguucgugugcgacgg cgacgacgacuguggugacggcagcgaugagcgcggcugugcagacccgg ccugcgggccccgcgaguuccgcugcggcggcgauggcggcggcgccugc aucccggagcgcugggucugcgaccgccaguuugacugcgaggaccgcuc ggacgaggcagccgagcucugcggccguccgggccccggggccacguccg cgcccgccgccugcgccaccgccucccaguucgccugccgcagcggcgag ugcgugcaccugggcuggcgcugcgacggcgaccgcgacugcaaagacaa aucggacgaggccgacugcccacugggcaccugccguggggacgaguucc agugugggaugggacauguguccuugcaaucaagcacugcaaccaggag caggacuguccagaugggagugaugaagcuggcugccuacaggggcugaa cgagugucugcacaacaauggcggcugcucacacaucugcacugaccuca agauuggcuuugaaugcacgugcccagcaggcuuccagcuccuggaccag aagaccuguggcgacauugaugagugcaaggacccagaugccugcagcca gaucugugucaauuacaagggcuauuuaagugugagugcuacccuggcu acgagauggaccuacugaccaagaacugcaaggcugcugcuggcaagagc ccaucccuaaucuucaccaaccggcacgaggugcggaggaucgaccuggu gaagcggaacuauucacgccucauccccaugcucaagaaugucguggcac uagauguggaaguugccaccaaucgcaucuacuggugugaccucuccuac cguaagaucuauagcgccuacauggacaaggccagugacccgaaagagca ggagguccucauugacgagcaguugcacucuccagagggccuggcagugg acuggguccacaagcacaucuacuggacugacucgggcaauaagaccauc ucaguggccacaguugaugguggccgccgacgcacucucuucagccguaa ccucagugaaccccgggccaucgcuguugacccccugcgaggguucaugu auuggucugacugggggaccaggccaagauugagaaaucugggcucaac -continued ggugugggaccggcaaacacuggugucagacaauauugaauggcccaacgg aaucacccuggaucugcugagccagcgcuuguacuggguagacuccaagc uacaccaacuguccagcauugacuucaguggaggcaacagaaagacgcug aucuccuccacugacuuccugagccacccuuuugggauagcuguguuuga ggacaagguguucuggacagaccuggagaacgaggccauuuucagugcaa aucggcucaauggccuggaaaucuccauccuggcugagaaccucaacaac ccacaugacauugucaucuuccaugagcugaagcagccaagagcuccaga ugccugugagcugaguguccagccuaauggaggcugugaauaccugugcc uuccugcuccucagaucuccagccacucucccaaguacacaugugccugu ccugacacaauguggcuggguccagacaugaagaggugcuaccgagcacc ucaaucuaccucaacuacgacguuagcuucuaccaugacgaggacaguac cugccaccacaagagcccccgggaccaccguccacagauccaccuaccag aaccacagcacagagacaccaagccugacagcugcagucccaagcucagu uaguguccccagggcucccagcaucagcccgucuacccuaagcccugcaa ccagcaaccacucccagcacuaugcaaaugaagacaguaagaugggcuca acagucacugccgcuguuaucgggaucaucgugcccauaguggugauagc ccuccugugcaugaguggauaccugaucuggagaaacuggaagcggaaga acaccaaaagcaugaauuuugacaacccagucuacaggaaaacaacagaa gaagaagacgaagaugagcuccauauagggagaacugcucagauuggcca ugucuauccugcagcaaucagcagcuuugaucgcccacugugggcagagc ccugucuuggggagaccagagaaccggaagacccagccccugcccucaag gagcuuuuugucuugccgggggaaccaaggucacagcugcaccaacuccc gaagaacccucuuuccgagcugccugucgucaaauccaagcgaguggcau uaagccuugaagaugauggacuacccugaggaugggaucaccccuucgu gccucauggaauucagucccaugcacuacacucuggaugguguaugacug gaugaauggguuucuauauaugggucugugugaguguaugugugugugug auuuuuuuuuaaauuuauguugcggaaagguaaccacaaaguuaugaug aacugcaaacauccaaaggaugugagaguuuuucuauguauaauguuuua uacacuuuuuaacugguugcacuacccaugaggaauucguggaauggcua cugcugacuaacaugaugcacauaaccaaauggggccaauggcacagua ccuuacucaucauuuaaaaacuauauuuacagaagauguuugguugcugg gggggcuuuuuuagguuuuggggcauuuguuuuuuguaaauaagaugauu augcuuuguggcuauccaucaacauaaguaaaaaaaaaaaaaaaacacuu caacucccucccccauuuagauuauuuauuaacauauuuuaaaaaucaga ugaguucuauaaauaauuuagagaagugagaguauuuauuuuuggcaugu uuggcccaccacacagacucugugugugugauguguguguuuauaugugua ugugugugacagaaaaaucuguagagaagaggcacaucuauggcuacugu ucaaauacauaaagauaaauuuauuuucacacaguccacaaggguauau cuuguaguuuucagaaaagccuuuggaaaucuggaucagaaaauagauac caugguuugugcaauuauguaguaaaaaaggcaaaucuuuucaccucugg cuauuccugagaccccaggaagucaggaaaagccuuucagcucacccaug -continued gcugcugugacuccuaccagggcuuucuuggcuuuggcgaaggucagugu acagacauuccaugguaccagagugcucagaaacucaagauaggauaugc cucacccucagcuacuccuuguuuuaaaguucagcucuuugaguaacuuc uucaauuucuuucaggacacuuggguugaauucaguaaguuuccucugaa gcacccugaagggugccauccuuacagagcuaaguggagacguuuccaga ucagcccaaguuuacuauagagacuggcccaggcacugaaugucuaggac augcuguggaugaagauaaagaugguggaauagguuuuaucacaucucuu auuucucuuuuccccuuacucucuaccauuuccuuuaugugggggaaacau uuuaagguaauaaauagguuacuuaccaucauauguucauauagaugaaa cuaauuuuuggcuuaagucagaacaacuggccaaaauugaagucauauuu gagggggggaaauggcauacgcaauauuauauuauauuggauauuuauguu cacacaggaauuugguuuacugcuuuguaaauaaaaggaaaaacuccggg uauauguauagauguucuucauuauagacaucuucuuugcuuuucuuggc cuuggggggaggaagggagaagugcucuuuucuacuugugggggucucccau uggaaacauaauccuauagucccagaaggauucaguccccaguggcuuuc ccauccaaagagaaagaguuugaguuucuuaacucugcuguucugccacu uacucccacuagacaaccagggacaaggugcaacauggaaguguuugacu uaaguaggagcagaggagcugcaucuaaucucaucauaccuggaacuuga cacacuuaagcaaaugccuucccaucccuaccugccagaugcccccaacu caaugaaguuggaugucucaccagcuugauacccuuugaauuuucaguca gacauucuggaguucuagcauccuguaccuaggaccuucccucugugucac ucuuggccuccuaaacucuaagaaaauaacuauauucuggagcuugggca guguguuuugcauaauccagcaaucuccucaugacaugcauguguugaua guccugaaacauucauugagaggguaaaugcaguugaccuagaaugacca auaccaaacagaauuuuaagaacagguggccaacuccuauggagcuuacu cacauauuacuauucuuuuaagaacggaaaguaaaauuauuuuugacuga agaaaaaugaugacagugaaaaacauggaaauguacucaaaacaagugac uuuuucuguaaccuuccaaagaaacugaauuuuccaaggaauuaaaugau aacaguggcuaaggcauaguuucuaaacuuucaguaagauccuggcauuc acagaaaaaaaugaugaauggggucuggacauacagccugagaucucaaa augacaaugaaauucacaacuuuuucucagagacauucauguuuccugca uaugcuacaacugcaguuugaaagaggcagcaaugggagcaacccuuuac aagaaacaaauugugauauauucauguguuggacggcaguaaauaagaug aaaccugaggagucagauccaccuucccccauucauagaggcuuuucagc cucauuuugagguacaguuacauaucuuuugccuuuugcccccgugcaua gcuaucuacagccaaucacagaucacagagucacuggacuauagagcugg aaggaagcucagagacaaugccaagggggcagaaaauuuaucagaagcca gucccagugcguuuccuccauuuccuucugcaggaagacuauuuugggcu gccugaacauuguaucaaaccugcuaccuauacuauggucuaccuuuccu ccaguggaauuacaaaggcacuaacugaaaugccuucuagaaacagagaa -continued aacgaaacuguacuuauuuacucuugauacacagauuauuuauaaaacag auugaaguaaccuguuaacuggcaaaaagagaaugagaucggauuuaaau guauggcaguaaguccuauugaucccuccaguuaucucaguaugacugca guauauucauucacuaaaaccacucacuagauaccaacuacacaccuggc acugcagauguaaaggucagucacacauguucugacuuuacagaguucac aguagcaguggaggaugauauauguggaaacaaaaaaggcauugauucua uucagagcacuguuagggcucaaaggagagaggggucuuuccaccuaaga aaugaggaauagggucaucauagaagugaccuuaagucuuaaaaaauuaag aaggggauuccaagcugcuucagacagagacacaucgagcuaaaacacag agguaugaaagagcacagggacuuuaggaauugcacaguucauucuaaca ggaacaaaaggcucaaggggggcaagaaaugaggcuguauggaaagagau ucaauguaagcacuuuauaaaauagauuaauuucugauucaaugaagcau uucuugaucauuguguacaaggcacuacaugcaucauggaaaauucauua ggaugcauugccagcacuuugcagaacugauauuauucagccucaagcuu uccaguggccaaagggaaaugcugacugcuuuucauauauuugagucaaa gauuuuuuauauggucaaugaagacuaauauaagggcaguggauuuuca cagaugcaugccauguugucgagagccucuuagauuuucucaacugugag aaagaaaaacgaaaauguugaagacguugagucuggagaggggauacuaa ucacuguccaguugggcacugguggggaaugggggaaauggcacaggaaugc aagccucucccacccuacccccccgaacuccagccauacacucaucguuuca caaaauauaaaugaguuagcauuaaaauguuucagaguaaauaauuccuuu ucccgaaaugcaugaagauagaguaacagacuucucacacuguauuuuua ggguauggagaauuuagaagguuaaagaauuacugcuucaauuuuucagu uaaaaaaaaaucaggaagcucuguucauucaggcuaugcaccaugugcac agucaagaauuagcagaaaccccucugcauuuacaaacacuuugugcuaua aaaaaguaauuuuuaaaaagccacgugugugugugugugauauauauauauau auauauauauuuaaagccaagguuuugauacuuuuuuacaaaaacuacaa gagaaaacaaauauaccuguccaaaccauauacuuuuaaaagagcauuuu uuuuuccauacaagcuguuguuaauuuggggguaaagugcugauuugcaa acuucaucaaauuguucccaaguggauucuccuuguuugucuccccuac caaccccaaaguuaccauauuugauguaagaaucaggcauguuagaaugu ugugucacacuaacugauucugcucuuuuugucuugucauucaaguuccg uuagcuucuguacgcggugcccuuugcagucuggugucucuuccagaggc gagggggcugaggaugggggugcugcaucucacuagcuauacuggcaucau cuugguaaacugaaaaccaaauguggacauuuguaaaaucagugcacugu uucuagagagagauuaaauucauuuaaaaaaaa LRP8 isoform 1-Amino acid sequence (SEQ ID NO: 12)

mglpepgplr llallllllll llllqlqhla aaaadpllgg qgpakdcekd qfqcrnerci psvwrcdedd dcldhsdedd cpkktcadsd ftcdnghcih erwkcdgeee cpdgsdesea tctkqvcpae klscgptshk cvpaswrcdg ekdceggade -continued agcaticaph efqcgnrscl aavfvcdgdd dcgdgsderg cadpacgpre frcggdggga ciperwvcdr qfdcedrsde aaelcgrpgp gatsapaaca tasqfacrsg ecvhlgwrcd gdrdckdksd eadcplgtcr gdefqcgdgt cvlaikhcnq eqdcpdgsde agclqglnec lhnnggcshi ctdlkigfec tcpagfqlld qktcgdidec kdpdacsqic vnykgyfkce cypgyemdll tknckaaagk spsliftnrh evrridlvkr nysrlipmlk nvvaldveva tnriywcdls yrkiysaymd kasdpkeqev lideqlhspe glavdwvhkh iywtdsgnkt isvatvdggr rrtlfsrnls epraiavdpl rgfmywsdwg dqakieksgl ngvdrqtivs dniewpngit ldllsqrlyw vdsklhqlss idfsggnrkt lisstdflsh pfgiavfedk vfwtdlenea ifsanringl eisilaenln nphdivifhe lkqprapdac elsvqpnggc eylclpapqi sshspkytca cpdtmwlgpd mkrcyrapqs tstttlastm trtvpattra pgttvhrsty qnhstetpsl taavpssysv prapsispst lspatsnhsq hyanedskmg stvtaavigi ivpivviall cmsgyliwrn wkrkntksmn fdnpvyrktt eeededelhi grtaqighvy paaissfdrp lwaepclget repedpapal kelfvlpgep rsqlhqlpkn plselpvvks krvalsledd gip LRP8 isoform 2-RNA sequence (SEQ ID NO: 13)

gcuggcggcggccgcccagggccggggccgcgcgcccagccugagcccgc cccgccgccgagcgucaccgaaccugcuugaaaugcagccgaggagccgg ggcgggcggcagcggcggcggcggcggcggcgggggcagcggcaaccccg gcgccgcggcaaggacucggagggcugagacgcggcggcggcggcgcggg gagcgcggggcgcggcggccggagccccgggcccgccaugggccuccccg agccgggcccucuccggcuucuggcgcugcugcugcugcugcugcugcug cugcugcugcagcuccagcaucuugcggcggcagcggcugauccgcugcu cggcggccaagggccggccaaggauugcgaaaaggaccaauuccagugcc ggaacgagcgcugcauccccucuguguggagaugcgacgaggacgaugac ugcuuagaccacagcgacgaggacgacugccccaagaagaccugugcaga cagugacuucaccugugacaacggccacugcauccacgaacgguggaagu gugacggcgaggaggaguguccugauggcucccgaugaguccgaggccacu ugcaccaagcaggugugucccugcagagaagcugagcuguggacccaccag ccacaaguguguaccugccucguggcgcugcgacggggagaaggacugcg aggguggagcggaugaggccggcugugcuaccuggcugaacgagugucug cacaacaauggcggcugcucacacaucugcacugaccucaagauuggcuu ugaaugcacgugcccagcaggcuuccagcuccuggaccagaagaccugug gcgacauugaugagugcaaggacccagaugccugcagccagaucuguguc -continued aauuacaagggcuauuuuaagugugagugcuacccuggcuacgagaugga ccuacugaccaagaacugcaaggcugcugcuggcaagagcccaucccuaa ucuucaccaaccggcacgaggugcggaggaucgaccuggugaagcggaac uauucacgccucauccccaugcucaagaaugucguggcacuagaugugga aguugccaccaaucgcaucuacuggugugaccucuccuaccguaagaucu auagcgccuacauggacaaggccagugacccgaaagagcaggagguccuc auugacgagcaguugcacucuccagagggccuggcaguggacugggucca caagcacaucuacuggacugacucgggcaauaagaccaucucaguggcca caguugaugguggccgccgacgcacucucuucagccguaaccucagugaa ccccgggccaucgcuguugacccccugcgaggguucauguauuggucuga cugggggggaccaggccaagauugagaaaucugggcucaacggugugggacc ggcaaacacugguguucagacaauauugaauggcccaacggaaucacccug gaucugcugagccagcgcuuguacuggguagacuccaagcuacaccaacu guccagcauugacuucaguggaggcaacagaaagacgcugaucuccucca cugacuuccugagccacccuuuugggauagcuguguuugaggacaaggug uucuggacagaccuggagaacgaggccauuuucagugcaaaucggcucaa uggccuggaaaucuccauccuggcugagaaccucaacaacccacaugaca uugucaucuuccaugagcugaagcagccaagagcucccagaugccugugag cugaguguccagccuaauggaggcugugaauaccugugccuuccugcucc ucagaucuccagccacucucccaaguacacaugugccuguccugacacaa uguggcuggguccagacaugaagaggugcuaccgagcaccucaaucuacc ucaacuacgacguuagcuucuaccaugacgaggacaguaccugccaccac aagagcccccgggaccaccguccacagauccaccuaccagaaccacagca cagagacaccaagccugacagcugcagucccaagcucaguuaguguccccc agggcucccagcaucagcccgucuacccuaagcccugcaaccagcaacca cucccagcacuaugcaaaugaagacaguaagaugggcucaacagucacug ccgcuguuaucgggaucaucgugcccauaguggugauagcccuccugugc augaguggauaccugaucuggagaaacuggaagcggaagaacaccaaaag caugaauuuugacaacccagucuacaggaaaacaacagaagaagaagacg aagaugagcuccauauagggagaacugcucagauuggccaugucuauccu gcagcaaucagcagcuuugaucgcccacugugggcagagcccugucuugg ggagaccagagaaccggaagacccagccccugcccucaaggagcuuuuug ucuugccgggggaaccaaggucacagcugcaccaacucccgaagaacccu cuuuccgagcugccugucgucaaauccaagcgaguggcauuaagccuuga agaugauggacuacccugaggaugggaucacccccuucgugccucaugga auucagucccaugcacuacacucuggaugguguaugacuggaugaauggg uuucuauauaugggucugugugaguguaugugugugugugauuuuuuuuu uaaauuuauguugcggaaagguaaccacaaaguuaugaugaacugcaaac auccaaaggaugugagaguuuuucuauguauaauguuuuauacacuuuuu aacugguugcacuacccaugaggaauucguggaauggcuacugcugacua acaugaugcacauaaccaaauggggggccaauggcacaguaccuuacucau -continued cauuuaaaaacuauauuuacagaagauguuugguugcugggggggcuuuu uuagguuuuggggcauuuguuuuuuguaaauaagaugauuaugcuuugug gcuauccaucaacauaaguaaaaaaaaaaaaaaaaacacuucaacucccuc ccccauuuagauuauuuauuaacauauuuuaaaaaucagaugaguucuau aaauaauuuagagaagugagaguauuuauuuuuggcauguuuggcccacc acacagacucuguguguguauguguguguuuauauguguaugugugugac agaaaaaucuguagagaagaggcacaucuauggcuacuguucaaauacau aaagauaaauuuauuuucacacaguccacaagggguauaucuuguaguuu ucagaaaagccuuuggaaaucuggaucagaaaauagauaccaugguuugu gcaauuauguaguaaaaaaggcaaaucuuuucaccucuggcuauuccuga gaccccaggaagucaggaaaagccuuucagcucacccauggcugcuguga cuccuaccagggcuuucuuggcuuuggcgaaggucaguguacagacauuc caugguaccagagugcucagaaacucaagauaggauaugccucacccuca gcuacuccuuguuuuaaaguucagcucuuugaguaacuucuucaauuucu uucaggacacuuggguugaauucaguaaguuuccucugaagcacccugaa gggugccauccuuacagagcuaaguggagacguuuccagaucagcccaag uuuacuauagagacuggcccaggcacugaaugucuaggacaugcugugga ugaagauaaagaugguggaauagguuuuaucacaucucuuauuucucuuu uccccuuacucucuaccauuuccuuuauguggggaaacauuuuaagguaa uaaauagguuacuuaccaucauauguucauauagaugaaacuaauuuuug gcuuaagucagaacaacuggccaaaauugaagucauauuugagggggaa auggcauacgcaauauuauauuauauuggauauuuauguucacacaggaa uuugguuuacugcuuuguaaauaaaaggaaaaacuccggguauauguaua gauguucuucauuauagacaucuucuuugcuuuucuuggccuuggggggag gaagggagaagugcucuuuucuacuugugggggucucccauuggaaacaua auccuauagucccagaaggauucaguccccaguggcuuucccauccaaag agaaagaguuugaguuucuuaacucugcuguucugccacuuacucccacu agacaaccagggacaaggugcaacauggaaguguuugacuuaaguaggag cagaggagcugcaucuaaucucaucauaccuggaacuugacacacuuaag caaaugccuucccaucccuaccugccagaugcccccaacucaaugaaguu ggaugucucaccagcuugauacccuuugaauuuucagucagacauucugg aguucuagcauccuguaccuaggaccuuccucugugucacucuuggccuc cuaaacucuaagaaaauaacuauauucuggagcuugggcagugugguuuug cauaauccagcaaucuccucaugacaugcauguguugauaguccugaaac auucauugagagggguaaaugcaguugaccuagaaugaccaauaccaaaca gaauuuuaagaacagguggccaacuccuauggagcuuacucacauauuac uauucuuuuaagaacggaaaguaaaauuauuuuugacugaagaaaaauga ugacagugaaaaacauggaaauguacucaaaacaagugacuuuuucugua accuuccaaagaaacugaauuuuccaaggaauuaaaugauaacaguggcu aaggcauaguuucuaaacuuucaguaagauccuggcauucacagaaaaaa -continued augaugaauggggucuggacauacagccugagaucucaaaaugacaauga aauucacaacuuuuucucagagacauucauguuuccugcauaugcuacaa cugcaguuugaaagaggcagcaaugggagcaacccuuuacaagaaacaaa uugugauauauucauguguuggacggcaguaaauaagaugaaaccugagg agucagauccaccuucccccauucauagaggcuuuucagccucauuuuga gguacaguuacauaucuuuugccuuuugcccccgugcauagcuaucuaca gccaaucacagaucacagagucacuggacuauagagcuggaaggaagcuc agagacaaugccaagggggcagaaaauuuaucagaagccagucccagugc guuuccuccauuuccuucugcaggaagacuauuuugggcugccugaacau uguaucaaaccugcuaccuauacuauggucuaccuuuccuccaguggaau uacaaaggcacuaacugaaaugccuucuagaaacagagaaaacgaaacug uacuuauuuacucuugauacacagauuauuuauaaaacagauugaaguaa ccuguuaacuggcaaaaagagaaugagaucggauuuaaauguauggcagu aaguccuauugaucccuccaguuaucucaguaugacugcaguauauucau ucacuaaaaccacucacuagauaccaacuacacaccuggcacugcagaug uaaaggucagucacacauguucugacuuuacagaguucacaguagcagug gaggaugauauauguggaaacaaaaaaggcauugauucuauucagagcac uguuagggcucaaaggagagaggggucuuuccaccuaagaaaugaggaau agggucaucauagaagugaccuuaagucuuaaaaauuaagaaggggauuc caagcugcuucagacagagacacaucgagcuaaaacacagagguaugaaa gagcacagggacuuuaggaauugcacaguucauucuaacaggaacaaaag gcucaagggggcaagaaaugaggcuguauggaaagagauucaauguaag cacuuuauaaaauagauuaauuucugauucaaugaagcauuucuugauca uuguguacaaggcacuacaugcaucauggaaaauucauuaggaugcauug ccagcacuuugcagaacugauauuauucagccucaagcuuuccaguggcc aaagggaaaugcugacugcuuuucauauauuugagucaaagauuuuuuau auggucaaugaagacuaauauaagggcaguggggauuuucacagaugcaug ccauguugucgagagccucuuagauuuucucaacugugagaaagaaaaac gaaaauguugaagacguugagucuggagaggggauacuaaucacugucca guugggcacugguggggaauggggaaauggcacaggaaugcaagccucucc acccuacccccccgaacuccagccauacacucaucguuucacaaaauauaa augaguuagcauuaaauguuucagaguaaauaauuccuuuucccgaaaug caugaagauagaguaacagacuucucacacuguauuuuuagggguauggag aauuuagaagguuaaagaauuacugcuucaauuuuucaguuaaaaaaaaa ucaggaagcucuguucauucaggcuaugcaccaugugcacagucaagaau uagcagaaacccucugcauuuacaaacacuuugugcuauaaaaaaguaau uuuuaaaaagccacgugugugugugugugauauauauauauauauauauau uuaaagccaagguuuugauacuuuuuuacaaaaacuacaagagaaaacaa auauaccuguccaaaccauauacuuuuaaaagagcauuuuuuuuuccaua caagcuguuguuaauuuggggguaaagugcugauuugcaaacuucaucaa auuguucccaaguggauucuccuuguuugucucccccuaccaaccccaaa guuaccauauuugauguaagaaucaggcauguuagaauguugugucacac uaacugauucugcucuuuuugucuugucauucaaguuccguuagcuucug uacgcggugcccuuugcagucuggugucucuuccagaggcgagggggcug aggauggggugcugcaucucacuagcuauacuggcaucaucuugguaaac ugaaaaccaaauguggacauuuguaaaaucagugcacuguuucuagagag agauuaaauucauuuaaaaaaaa LRP8 isoform 2-Amino acid sequence (SEQ ID NO: 14)

mglpepgplr llalllllll llllqlqhla aaaadpllgg qgpakdcekd qfqcrnerci psywrcdedd dcldhsdedd cpkktcadsd ftcdnghcih erwkcdgeee cpdgsdesea tctkqvcpae klscgptshk cvpaswrcdg ekdceggade agcatwlnec lhnnggcshi ctdlkigfec tcpagfqlld qktcgdidec kdpdacsqic vnykgyfkce cypgyemdll tknckaaagk spsliftnrh evrridlvkr nysrlipmlk nvvaldveva tnriywcdls yrkiysaymd kasdpkeqev lideqlhspe glavdwvhkh iywtdsgnkt isvatvdggr rrtlfsrnls epraiavdpl rgfmywsdwg dqakieksgl ngvdrqtivs dniewpngit ldllsqrlyw vdsklhqlss idfsggnrkt lisstdflsh pfgiavfedk vfwtdlenea ifsanringl eisilaenln nphdivifhe lkqprapdac elsvqpnggc eylclpapqi sshspkytca cpdtmwlgpd mkrcyrapqs tstttlastm trtvpattra pgttvhrsty qnhstetpsl taavpssysy prapsispst lspatsnhsq hyanedskmg stvtaavigi ivpivviall cmsgyliwrn wkrkntksmn fdnpvyrktt eeededelhi grtaqighvy paaissfdrp lwaepclget repedpapal kelfylpgep rsqlhqlpkn plselpvvks krvalsledd glp LRP8 isoform 3-RNA sequence (SEQ ID NO: 15)

gcuggcggcggccgcccagggccggggccgcgcgcccagccugagcccgc cccgccgccgagcgucaccgaaccugcuugaaaugcagccgaggagccgg ggcgggcggcagcggcggcggcggcggcgggggcagcggcaaccccg gcgccgcggcaaggacucggagggcugagacgcggcggcggcggcgcggg gagcgcggggcgcggcggccggagccccgggcccgccaugggccuccccg agccgggcccucuccggcuucuggcgcugcugcugcugcugcugcugcug cugcugcugcagcuccagcaucuugcggcggcagcggcugauccgcugcu cggcggccaagggccggccaaggauugcgaaaaggaccaauuccagugcc ggaacgagcgcugcauccccucuguguggagaugcgacgaggacgaugac ugcuuagaccacagcgacgaggacgacugccccaagaagaccugugcaga cagugacuucaccugugacaacggccacugcauccacgaacgguggaagu gugacggcgaggaggaguguccugauggcuccgaugaguccgaggccacu -continued ugcaccaagcaggugugucccugcagagaagcugagcuguggacccaccag ccacaagugugugaccugccucguggcgcugcgacggggagaaggacugcg aggguggagcggaugaggccggcugugcuaccucacugggcaccugccgu ggggacgaguuccagugugggggaugggacauguguccuugcaaucaagca cugcaaccaggagcaggacuguccagaugggagugaugaagcuggcugcc uacaggggcugaacgagugucugcacaacaauggcggcugcucacacauc ugcacugaccucaagauuggcuuugaaugcacgugcccagcaggcuucca gcuccuggaccagaagaccuguggcgacauugaugagugcaaggacccag augccugcagccagaucugugucaauuacaagggcuauuuuaagugugag ugcuacccuggcuacgagauggaccuacugaccaagaacugcaaggcugc ugcuggcaagagcccaucccuaaucuucaccaaccggcacgaggugcgga ggaucgaccuggugaagcggaacuauucacgccucauccccaugcucaag aaugucguggcacuagauguggaaguugccaccaaucgcaucuacuggug ugaccucuccuaccguaagaucuauagcgccuacauggacaaggccagug acccgaaagagcaggagguccucauugacgagcaguugcacucuccagag ggccuggcaguggacugggguccacaagcacaucuacuggacugacucggg caauaagaccaucucaguggccacaguugaugguggccgccgacgcacuc ucuucagccguaaccucagugaaccccgggccaucgcuguugaccccug cgaggguucauguauuggucugacugggggggaccaggccaagauugagaa aucugggcucaacgguguggaccggcaaacacuggugucagacaauauug aauggcccaacggaaucacccuggaucugcugagccagcgcuuguacugg guagacuccaagcuacaccaacuguccagcauugacuucaguggaggcaa cagaaagacgcugaucuccuccacugacuuccugagccacccuuuuggga uagcuguguuugaggacaagguguucuggacagaccuggagaacgaggcc auuuucagugcaaaucggcucaauggccuggaaaucuccauccuggcuga gaaccucaacaacccacaugacauugucaucuuccaugagcugaagcagc caagagcuccagaugccugugagcugaguguccagccuaauggaggcugu gaauaccugugccuuccugcuccucagaucuccagccacucucccaagua cacaugugccuguccugacacaauguggcugggguccagacaugaagaggu gcuaccgagaugcaaaugaagacaguaagaugggcucaacagucacugcc gcuguuaucgggaucaucgugcccauagugggugauagcccuccugugcau gaguggauaccugaucuggagaaacuggaagcggaagaacaccaaaagca ugaauuuugacaacccagucuacaggaaaacaacagaagaagaagacgaa gaugagcuccauauagggagaacugcucagauuggccaugucuauccugc acgaguggcauuaagccuugaagaugauggacuacccugaggaugggauc accccccuucgugccucauggaauucagucccaugcacuacacucuggaug guguaugacuggaugaauggguuucuauauaugggucugugugaguguau gugugugugugauuuuuuuuuuuaaauuuauguugcggaaagguaaccaca aaguuaugaugaacugcaaacauccaaaggaugugagaguuuuucuaugu auaauguuuuauacacuuuuuaacugguugcacuacccaugaggaauucg uggaauggcuacugcugacuaacaugaugcacauaaccaaaugggggcca -continued auggcacaguaccuuacucaucauuuaaaaacuauauuuacagaagaugu uugguugcugggggggcuuuuuuagguuuuggggcauuuguuuuuuguaa auaagaugauuaugcuuuguggcuauccaucaacauaaguaaaaaaaaaa aaaaaacacuucaacucccucccccauuuagauuauuuauuaacauauuu uaaaaaucagaugaguucuauaaauaauuuagagaagugagaguauuuau uuuuggcauguuuggcccaccacacagacucugugugugugugugugu uuauauguguaugugugugacagaaaaaucuguagagaagaggcacaucu auggcuacuguucaaauacauaaagauaaauuuauuuucacacaguccac aagggguauaucuuguaguuuucagaaaagccuuuggaaaucuggaucag aaaauagauaccaugguuugugcaauuauguaguaaaaaaggcaaaucuu uucaccucuggcuauuccugagaccccaggaagucaggaaaagccuuuca gcucacccauggcugcugugacuccuaccagggcuuucuuggcuuuggcg aaggucaguguacagacauuccaugguaccagagugcucagaaacucaag auaggauaugccucacccucagcuacuccuuguuuuaaaguucagcucuu ugaguaacuucuucaauuucuuucaggacacuugguugaauucaguaag uuuccucugaagcacccugaagggugccauccuuacagagcuaaguggag acguuuccagaucagcccaaguuuacuauagagacuggcccaggcacuga augucuaggacaugcuguggaugaagauaaagaugguggaauagguuuua ucacaucucuuauuucucuuuuccccuuacucucuaccauuuccuuuaug uggggaaacauuuuaagguaauaaauagguuacuuaccaucauauguuca uauagaugaaacuaauuuuuggcuuaagucagaacaacuggccaaaauug aagucauauuugagggggaaauggcauacgcaauauuauauuauauugg auauuuauguucacacaggaauuugguuuacugcuuuguaaauaaaagga aaaacuccggguauauguauagauguucuucauuauagacaucuucuuug cuuuucuuggccuuggggggaggaagggagaagugcucuuuucuacuugug gggucucccauuggaaacauaauccuauagucccagaaggauucaguccc caguggcuuucccauccaaagagaaagaguuugaguuucuuaacucugcu guucugccacuuacucccacuagacaaccagggacaaggugcaacaugga aguguuugacuuaaguaggagcagaggagcugcaucuaaucucaucauac cuggaacuugacacacuuaagcaaaugccuucccaucccuaccugccaga ugcccccaacucaaugaaguuggaugucucaccagcuugauacccuuuga auuuucagucagacauucuggaguucuagcauccuguaccuaggaccuuc cucugugucacucuuggccuccuaaacucuaagaaaauaacuauauucug gagcuugggcagugugguuuugcauaauccagcaaucuccucaugacaugc auguguugauaguccugaaacauucauugagagguaaaugcaguugacc uagaaugaccaauaccaaacagaauuuuaagaacagguggccaacuccua uggagcuuacucacauauuacuauucuuuuaagaacggaaaguaaaauua uuuuugacugaagaaaaaugaugacagugaaaaacauggaaauguacuca aaacaagugacuuuuucuguaaccuuccaaagaaacugaauuuuccaagg aauuaaaugauaacaguggcuaaggcauaguuucuaaacuuucaguaaga -continued

```
uccuggcauucacagaaaaaaaugaugaauggggucuggacauacagccu
gagaucucaaaaugacaaugaaauucacaacuuuuucucagagacauuca
uguuuccugcauaugcuacaacugcaguuugaaagaggcagcaaugggag
caacccuuuacaagaaacaaauugugauauauucauguguuggacggcag
uaaauaagaugaaaccugaggagucagauccaccuucccccauucauaga
ggcuuuucagccucauuuugagguacaguuacauaucuuuugccuuuugc
ccccgugcauagcuaucuacagccaaucacagaucacagagucacuggac
uauagagcuggaaggaagcucagagacaaugccaagggggcagaaaauuu
aucagaagccagucccagugcguuuccuccauuuccuucugcaggaagac
uauuuugggcugccugaacauuguaucaaaccugcuaccuauacuauggu
cuaccuuuccuccaguggaauuacaaaggcacuaacugaaaugccuucua
gaaacagagaaaacgaaacuguacuuauuuacucuugauacacagauuau
uuauaaaacagauugaaguaaccuguuaacuggcaaaaagagaaugagau
cggauuuaaauguauggcaguaaguccuauugaucccuccaguuaucuca
guaugacugcaguauauucauucacuaaaaccacucacuagauaccaacu
acacaccuggcacugcagauguaaaggucagucacacauguucugacuuu
acagaguucacaguagcaguggaggaugauauauguggaaacaaaaaagg
cauugauucuauucagagcacuguuagggcucaaaggagagaggggucuu
uccaccuaagaaaugaggaauagggucaucauagaagugaccuuaagucu
uaaaaauuaagaaggggauuccaagcugcuucagacagagacacaucgag
cuaaaacacagagguaugaaagagcacagggacuuuaggaauugcacagu
ucauucuaacaggaacaaaaggcucaagggggggcaagaaaugaggcugua
uggaaagagauucaauguaagcacuuuauaaaauagauuaauuucugauu
caaugaagcauuucuugaucauuguguacaaggcacuacaugcaucaugg
aaaauucauuaggaugcauugccagcacuuugcagaacugauauuauuca
gccucaagcuuuccaguggccaaagggaaaugcugacugcuuuucauaua
uuugagucaaagauuuuuuauauggucaaugaagacuaauauaagggcag
ugggauuuucacagaugcaugccauguugucgagagccucuuagauuuuc
ucaacugugagaaagaaaaacgaaaauguugaagacguugagucuggaga
ggggauacuaaucacuguccaguugggcacugguggggaauggggaaaugg
cacaggaaugcaagccucuccacccuacccccccgaacuccagccauacac
ucaucguuucacaaaauauaaaugaguuagcauuaaauguuucagaguaa
auaauuccuuuucccgaaaugcaugaagauagaguaacagacuucucaca
cuguauuuuuagguauggagaauuuagaagguuaaagaauuacugcuuc
aauuuuucaguuaaaaaaaaaaucaggaagcucuguucauucaggcuaugc
accaugugcacagucaagaauuagcagaaacccucugcauuuacaaacac
uuugugcuauaaaaaaguaauuuuuaaaaagccacgugugugugugugua
uauauauauauauauauauauuuaaagccaagguuuugauacuuuuuuac
aaaaacuacaagagaaaacaaauauaccuguccaaaccauauacuuuuaa
aagagcauuuuuuuuuccauacaagcuguuguuaauuugggguaaagug
cugauuugcaaacuucaucaaauuguucccaaguggauucuccuuguuug
```

-continued

```
ucucccccuaccaaccccaaaguuaccauauuugauguaagaaucaggca
uguuagaauguugugucacacuaacugauucugcucuuuuugucuuguca
uucaaguuccguuagcuucuguacgcggugcccuuugcagucuggugucu
cuuccagaggcgagggggcugaggauggggugcugcaucucacuagcuau
acuggcaucaucuugguaaacugaaaaccaaauguggacauuuguaaaau
cagugcacuguuucuagagagagauuaaauucauuuaaaaaaaa
```

LRP8 isoform 3-Amino acid sequence (SEQ ID NO: 16)

```
mglpepgplr llalllllll llllqlqhla aaaadpllgg
qgpakdcekd qfqcrnerci psvwrcdedd dcldhsdedd
cpkktcadsd ftcdnghcih erwkcdgeee cpdgsdesea
tctkqvcpae klscgptshk cvpaswrcdg ekdceggade
agcatslgtc rgdefqcgdg tcvlaikhcn qeqdcpdgsd
eagclqglne clhnnggcsh ictdlkigfe ctcpagfqll
dqktcgdide ckdpdacsqi cvnykgyfkc ecypgyemdl
ltknckaaag kspsliftnr hevrridlvk rnysrlipml
knvvaldvev atnriywcdl syrkiysaym dkasdpkeqe
vlideqlhsp eglavdwvhk hiywtdsgnk tisvatvdgg
rrrtlfsrnl sepraiavdp lrgfmywsdw gdqakieksg
lngvdrqtiv sdniewpngi tldllsqrly wvdsklhqls
sidfsggnrk tlisstdfls hpfgiavfed kvfwtdlene
aifsanring leisilaenl nnphdivifh elkqprapda
celsvqpngg ceylclpapq isshspkytc acpdtmwlgp
dmkrcyrdan edskmgstvt aavigiivpi vviallcmsg
yliwrnwkrk ntksmnfdnp vyrktteeed edelhigrta
qighvypary alsleddglp
```

LRP8 isoform 4-RNA sequence (SEQ ID NO: 17)

```
gcuggcggcggccgcccagggccggggccgcgcgcccagccugagcccgc
cccgccgccgagcgucaccgaaccugcuugaaaugcagccgaggagccgg
ggcgggcggcagcggcggcggcggcggcgggggcagcggcaaccccg
gcgccgcggcaaggacucggagggcugagacgcggcggcggcggcgcggg
gagcgcggggcgcggcggccggagccccgggcccgccaugggccuccccg
agccgggcccucuccggcuucuggcgcugcugcugcugcugcugcugcug
cugcugcugcagcuccagcaucuugcggcggcagcggcugauccgcugcu
cggcggccaagggccggccaaggauugcgaaaaggaccaauuccagugcc
ggaacgagcgcugcauccccucuguguggagaugcgacgaggacgaugac
ugcuuagaccacagcgacgaggacgacugccccaagaagaccugugcaga
cagugacuucaccugugacaacggccacugcauccacgaacgguggaagu
gugacggcgaggaggaguguccugauggcuccgaugaguccgaggccacu
ugcaccaagcagguguguccugcagagaagcugagcuguggacccaccag
ccacaaguguguaccugccucguggcgcugcgacggggagaaggacugcg
```

-continued agggugggagcggaugaggccggcugugcuaccuugugcgccccgcacgag
uuccagugcggcaaccgcucgugccuggccgccguguucgugugcgacgg
cgacgacgacugugguggacggcagcgaugagcgcggcugugcagacccgg
ccugcgggccccgcgaguuccgcugcggcggcgauggcggcggcgccugc
aucccggagcgcugggucugcgaccgccaguuugacugcgaggaccgcuc
ggacgaggcagccgagcucugcggccguccgggccccggggccacguccg
cgcccgccgccugcgccaccgccucccaguucgccugccgcagcggcgag
ugcgugcaccugggcuggcgcugcgacggcgaccgcgacugcaaagacaa
aucggacgaggccgacugcccacugggcaccugccguggggacgaguucc
aguguggggaugggacauguguccuugcaaucaagcacugcaaccaggag
caggacuguccagaugggagugaugaagcuggcugccuacaggggcugaa
cgagugucugcacaacaauggcggcugcucacacaucugcacugaccuca
agauuggcuuugaaugcacgugcccagcaggcuuccagcuccuggaccag
aagaccuguggcgacauugaugagugcaaggacccagaugccugcagcca
gaucugugucaauuacaagggcuauuuaagugugagugcuacccuggcu
acgagauggaccuacugaccaagaacugcaaggcugcugcuggcaagagc
ccaucccuaaucuucaccaaccggcacgaggugcggaggaucgaccuggu
gaagcggaacuauucacgccucauccccaugcucaagaaugucguggcac
uagauguggaaguugccaccaaucgcaucuacuggugugaccucuccuac
cguaagaucuauagcgccuacauggacaaggccagugacccgaaagagca
ggagguccucauugacgagcaguugcacucuccagagggccuggcagugg
acuggguccacaagcacaucuacuggacugacucgggcaauaagaccauc
ucaguggccacaguugaugguggccgccgacgcacucucuucagccguaa
ccucagugaaccccgggccaucgcuguugaccccugcgagguucaugu
auuggucugacugggggaccaggccaagauugagaaaucugggcucaac
gguguggaccggcaaacacuggugucagacaauauugaauggcccaacgg
aaucacccuggaucugcugagccagcgcuuguacugguagacuccaagc
uacaccaacuguccagcauugacuucaguggaggcaacagaaagacgcug
aucuccuccacugacuuccugagccacccuuugggauagcuguguuuga
ggacaagguguucuggacagaccuggagaacgaggccauuuucagugcaa
aucggcucaauggccuggaaaucuccauccuggcugagaaccucaacaac
ccacaugacauugucaucuuccaugagcugaagcagccaagagcuccaga
ugccugugagcugaguguccagccuaauggaggcugugaauaccugugcc
uuccugcuccucagaucuccagccacucucccaaguacacaugugccugu
ccugacacaauguggcuggguccagacaugaagaggugcuaccgagcacc
ucaaucuaccucaacuacgacguuagcuucuaccaugacgaggacaguac
cugccaccacaagagcccccgggaccaccguccacagauccaccuaccag
aaccacagcacagagacaccaagccugacagcugcagucccaagcucagu
uagugucccccagggcucccagcaucagcccgucuacccuaagcccugcaa
ccagcaaccacucccagcacuaugcaaaugaagacaguaagaugggcuca
acagucacugccgcuguuaucgggaucaucgugcccauagugguggauagc -continued ccuccugugcaugaguggauaccugaucuggagaaacuggaagcggaaga
acaccaaaagcaugaauuuugacaacccagucuacaggaaaacaacagaa
gaagaagacgaagaugagcuccauauagggagaacugcucagauuggcca
ugucuauccugcacgaguggcauuaagccuugaagaugauggacuacccu
gaggaugggaucacccccuucgugccucauggaauucagucccaugcacu
acacucuggaugguguaugacuggaugaaugggguuucuauauaugggucu
gugugaguguaugugugugugugauuuuuuuuuuuaaauuuauguugcgga
aagguaaccacaaaguuaugaugaacugcaaacauccaaaggaugugaga
guuuuucuauguauaaauguuuuauacacuuuuuaacugguugcacuaccc
augaggaauucguggaauggcuacugcugacuaacaugaugcacauaacc
aaaugggggccaauggcacaguaccuuacucaucauuuaaaaacuauauu
uacagaagauguuugguugcugggggggcuuuuuuagguuuuggggcauu
uguuuuuuguaaauaaagaugauuaugcuuuguggcuauccaucaacauaa
guaaaaaaaaaaaaaaaacacuucaacucccucccccauuuagauuauuu
auuaacauauuuuaaaaaucagaugaguucuauaaauaauuuagagaagu
gagaguauuuauuuuuggcauguuuggcccaccacacagacucugugugu
guaugugugugugguuuauauguguaugugugugacagaaaaaucuguagaga
agaggcacaucuauggcuacuguucaaauacauaaagauaaauuuauuuu
cacacaguccacaaggggguauaucuuguaguuucagaaaagccuuugga
aaucuggaucagaaaauagauaccaugguuugugcaauuauguaguaaaa
aaggcaaaucuuuucaccucuggcuauuccugagaccccaggaagucagg
aaaagccuuucagcucacccauggcugcugugacuccuaccagggcuuuc
uuggcuuuggcgaaggucaguguacagacauuccaugguaccagagugcu
cagaaacucaagauaggauaugccucacccucagcuacuccuuguuuuaa
aguucagcucuuugaguaacuucuucaauuucuuucaggacacuuggguu
gaauucaguaaguuuccucugaagcacccugaagggugccauccuuacag
agcuaaguggagacguuuccagaucagcccaaguuuacuauagagacugg
cccaggcacugaaugucuaggacaugcuguggaugaagauaaagauggug
gaauagguuuuaucacaucucuuauuucucuuuuccccuuacucucuacc
auuuccuuuauguggggaaacauuuuaagguaauaaauagguuacuuacc
aucauauguucauauagaugaaacuaauuuuuggcuuaagucagaacaac
uggccaaaauugaagucauauuugagggggaaauggcauacgcaauauu
auauuauauuggauauuuauguucacacaggaauuugguuuacugcuuug
uaaauaaaaggaaaaacuccggguauauguauagauguucuucauuauag
acaucuucuuugcuuuucuuggccuuggggggaggaagggagaagugcucu
uuucuacuuguggggucucccauuggaaacauaauccuauagucccagaa
ggauucaguccccaguggcuuucccauccaaagagaaagaguuugaguuu
cuuaacucugcuguucugccacuuacucccacuagacaaccagggacaag
gugcaacauggaaguguuugacuuaaguaggagcagaggagcugcaucua
aucucaucauaccuggaacuugacacacuuaagcaaaugccuucccaucc -continued cuaccugccagaugcccccaacucaaugaaguuggaugucucaccagcuu gauacccuuugaauuuucagucagacauucuggaguucuagcauccugua ccuaggaccuuccucugugucacucuuggccuccuaaacucuaagaaaau aacuauauucuggagcuugggcagugugupuugcauaauccagcaaucuc cucaugacaugcauguguugauaguccugaaacauucauugagagguaa augcaguugaccuagaaugaccaauaccaaacagaauuuuaagaacaggu ggccaacuccuauggagcuuacucacauuacuauucuuuuaagaacgg aaaguaaaauuauuuuugacugaagaaaaaugaugacagugaaaaacaug gaaauguacucaaaacaagugacuuuuucuguaaccuuccaaagaaacug aauuuuccaaggaauuaaaugauaacaguggcuaaggcauaguuucuaaa cuuucaguaagauccuggcauucacagaaaaaaaugaugaaugggucug gacauacagccugagaucucaaaaugacaaugaaauucacaacuuuuucu cagagacauucauguuuccugcauaugcuacaacugcaguuugaaagagg cagcaaugggagcaacccuuuacaagaaacaaauugugauauauucaugu guuggacggcaguaaauaagaugaaaccugaggagucagauccaccuucc cccauucauagaggcuuuucagccucauuugagguacaguuacauaucu uuugccuuuugcccccgugcauagcuaucuacagccaaucacagaucaca gagucacuggacuauagagcuggaaggaagcucagagacaaugccaaggg ggcagaaaauuuaucagaagccagucccagugcguuuccuccauuuccuu cugcaggaagacuauuuugggcugccugaacauuguaucaaaccugcuac cuauacuauggucuaccuuuccuccaguggaauuacaaaggcacuaacug aaaugccuucuagaaacagagaaaacgaaacuguacuuauuuacucuuga uacacagauuauuuauaaaacagauugaaguaaccuguuaacuggcaaaa agagaaugagaucggauuuaaauguauggcaguaaguccuauugaucccu ccaguuaucucaguaugacugcaguauauucauucacuaaaaccacucac uagauaccaacuacacaccuggcacugcagauguaaaggucagucacaca uguucugacuuuacagaguucacaguagcaguggaggaugauauaugugg aaacaaaaaaggcauugauucuauucagagcacuguuagggcucaaagga gagaggggucuuuccaccuaagaaaugaggaauagggucaucauagaagu gaccuuaagucuuaaaaauuaagaaggggauuccaagcugcuucagacag agacacaucgagcuaaaacacagagguaugaaagagcacagggacuuuag gaauugcacaguucauucuaacaggaacaaaaggcucaagggggcaaga aaugaggcuguauggaaagagauucaauguaagcacuuuauaaaauagau uaauuucugauucaaugaagcauuucuugaucauuguguacaaggcacua caugcaucauggaaaauucauuaggaugcauugccagcacuuugcagaac ugauauuauucagccucaagcuuuccaguggccaaagggaaaugcugacu gcuuuucauauauuugagucaaagauuuuuuauauggucaaugaagacua auauaagggcaguggguuuucacagaugcaugccauguugucgagagcc ucuuagauuuucucaacugugagaaagaaaaacgaaaauguugaagacgu ugagucuggagaggggauacuaaucacuguccaguugggcacuggugga auggggaaauggcacaggaaugcaagccucuccacccuacccccgaacu -continued ccagccauacacucaucguuucacaaaauauaaaugaguuagcauuaaau guuucagaguaaauaauuccuuuucccgaaaugcaugaagauagaguaac agacuucucacacuguauuuuuagguauggagaauuuagaagguuaaag aauuacugcuucaauuuuucaguuaaaaaaaaaucaggaagcucuguuca uucaggcuaugcaccaugugcacagucaagaauuagcagaaacccucugc auuuacaaacacuuugugcuauaaaaaaguaauuuuuaaaaagccacgug ugugugugugauauauauauauauauauauauuuaaagccaagguuuug auacuuuuuuacaaaaacuacaagagaaaacaaauauaccuguccaaacc auauacuuuuaaaagagcauuuuuuuuuccauacaagcuguuguuaauuu gggguaaagugcugauuugcaaacuucaucaaauuguucccaaguggau ucuccuuguuugucucccccuaccaaccccaaaguuaccauauuugaugu aagaaucaggcauguuagaauguugugucacacuaacugauucugcucuu uuugucuugucauucaaguuccguuagcuucuguacgcggugcccuuugc agucuggugucucuuccagaggcgagggggcugaggauggggugcugcau cucacuagcuauacuggcaucaucuugguaaacugaaaaccaaaugugga cauuuguaaaaucagugcacuguuucuagagagagauuaaaauucauuuaa aaaaaa LRP8 isoform 4-Amino acid sequence (SEQ ID NO: 18)

mglpepgplr llalllllll llllqlqhla aaaadpllgg qgpakdcekd qfqcrnerci psvwrcdedd dcldhsdedd cpkktcadsd ftcdnghcih erwkcdgeee cpdgsdesea tctkqvcpae klscgptshk cvpaswrcdg ekdceggade agcaticaph efqcgnrscl aavfvcdgdd dcgdgsderg cadpacgpre frcggdggga ciperwvcdr qfdcedrsde aaelcgrpgp gatsapaaca tasqfacrsg ecvhlgwrcd gdrdckdksd eadcplgtcr gdefqcgdgt cvlaikhcnq eqdcpdgsde agclqglnec lhnnggcshi ctdlkigfec tcpagfqlld qktcgdidec kdpdacsqic vnykgyfkce cypgyemdll tknckaaagk spsliftnrh evrridlvkr nysrlipmlk nvvaldveva tnriywcdls yrkiysaymd kasdpkeqev lideqlhspe glavdwvhkh iywtdsgnkt isvatvdggr rrtlfsrnls epraiavdpl rgfmywsdwg dqakieksgl ngvdrqtivs dniewpngit ldllsqrlyw vdsklhqlss idfsggnrkt lisstdflsh pfgiavfedk vfwtdlenea ifsanringl eisilaenln nphdivifhe lkqprapdac elsvqpnggc eylclpapqi sshspkytca cpdtmwlgpd mkrcyrapqs tstttlastm trtvpattra pgttvhrsty qnhstetpsl taavpssysv prapsispst -continued lspatsnhsq hyanedskmg stvtaavigi ivpivviall cmsgyliwrn wkrkntksmn fdnpvyrktt eeededelhi grtaqighvy parvalsled dglp CTGF-RNA sequence (SEQ ID NO: 19)

aaacucacacaacaacucuuccccgcugagaggagacagccagugcgacu ccacccuccagcucgacggcagccgccccggccgacagccccgagacgac agcccggcgcgucccgguccccaccuccgaccaccgccagcgcuccaggc cccgccgcuccccgcucgccgccaccgcgcccuccgcuccgcccgcagug ccaaccaugaccgccgccaguaugggccccguccgcgucgccuucguggu ccuccucgcccucugcagccggccggccgucggccagaacugcagcgggc cgugccggugcccggacgagccggcgccgcgcugcccggcgggcgugagc cucgugcuggacggcugcggcugcugccgcgucugcgccaagcagcuggg cgagcugugcaccgagcgcgaccccugcgacccgcacaagggccucuucu gugacuucggcuccccggccaaccgcaagaucggcgugugcaccgccaaa gauggugcucccugcaucuucggugguacgguguaccgcagcggagaguc cuuccagagcagcugcaaguaccagugcacgugccuggacggggcggugg gcugcaugccccugugcagcauggacguucgucugcccagcccugacugc cccuucccgaggagggucaagcugcccgggaaaugcugcgaggagugggu gugugacgagcccaaggaccaaaccgugguugggccugcccucgcggcuu accgacuggaagacacguuuggcccagacccaacuaugauuagagccaac ugccugguccagaccacagaguggagcgccuguuccaagaccugugggau gggcaucuccacccggguuaccaaugacaacgccuccugcaggcuagaga agcagagccgccugugcauggucaggccuugcgaagcugaccuggaagag aacauuaagaagggcaaaaagugcauccguacucccaaaaucuccaagcc uaucaaguuugagcuuucuggcugcaccagcaugaagacauaccgagcua aauucuguggaguauguaccgacggccgaugcugcacccccacagaacc accacccugccgguggaguucaagugcccugacggcgaggucaugaagaa gaacaugauguucaucaagaccugugccugccauuacaacugucccggag acaaugacaucuuugaaucgcuguacuacaggaagauguacggagacaug gcaugaagccagagagugagagacauuaacucauuagacuggaacuugaa cugauucacaucucauuuuuccguaaaaaugauuucaguagcacaaguua uuuaaaucuguuuuucuaacuggggggaaaagauucccacccaauucaaaa cauugugccaugucaaacaaauagucuaucaaccccagacacugguuuga agaauguuaagacuugacaguggaacuacauuaguacacagcaccagaau guauauuaagguguggcuuuaggagcagugggaggguaccagcagaaagg uuaguaucaucagauagcaucuuauacgaguaauaugccugcuauuugaa guguaauugagaaggaaaauuuuagcgugcucacugaccugccuguagcc ccagugacagcuaggaugugcauucuccagccaucaagagacugagucaa guuguuccuuaagucagaacagcagacucagcucugacauucugauucga augacacuguucaggaaucggaauccugucgauuagacuggacagcuugu ggcaagugaauuugccuguaacaagccagauuuuuuaaaauuuauauugu -continued aaauauugugugugugugugugugugugugauauauauauauauauguacaguua ucuaaguuaauuuaaaguuguuugugccuuuuuauuuuuguuuuuaaugc uuugauauuucaauguuagccucaauuucugaacaccauagguagaaugu aaagcuugucugaucguucaaagcaugaaauggauacuuauauggaaauu cugcucagauagaaugacaguccgucaaaacagauuguuugcaaaggga ggcaucaguguccuuggcaggcugauuucuagguaggaaaugugguagcc ucacuuuuaaugaacaaauggccuuuauuaaaaacugagugacucuauau agcugaucaguuuuuucaccuggaagcauuuguuucuacuuugauaugac uguuuuucggacaguuuauuuguugagagugugaccaaaaguuacauguu ugcaccuuucuaguugaaaauaaaguguauauuuuuucuauaaaaaaaaa aaaaaaa CTGF-Amino Acid sequence (SEQ ID NO: 20)

mtaasmgpvr vafvvllalc srpavgqncs gpercpdepa prcpagvslv ldgcgccrvc akqlgelcte rdpcdphkgl fcdfgspanr kigvctakdg apcifggtvy rsgesfqssc kyqctcldga vgcmplcsmd vrlpspdcpf prrvklpgkc ceewvcdepk dqtvvgpala ayrledtfgp dptmirancl vqttewsacs ktcgmgistr vtndnascrl ekqsrlcmvr pceadleeni kkgkkcirtp kiskpikfel sgctsmktyr akfcgvctdg rcctphrttt lpvefkcpdg evmkknmmfi ktcachyncp gdndifesly yrkmygdma LXR-a isoform 1: RNA sequence (SEQ ID NO: 21)

aggaaggagggguggccugaccccucggcagucccuccccucagccuuuc cccaaauugcuacuucucuggggcuccagguccugcuugugcucagcucc agcucacuggcuggccaccgagacuucuggacaggaaacugcaccauccu cuucucccagcaagggggcuccagagacugcccacccaggaagucuggug gccuggggauuuggacagugccuugguaaugaccagggcuccaggaagag auguccuuguggcugggggccccugugccugacauuccuccugacucugc gguggagcuguggaagccaggcgcacaggaugcaagcagccaggcccagg gaggcagcagcugcauccucagagaggaagccaggaugccccacucugcu gggguacugcagggguggggcuggaggcugcagagcccacagcccugcu caccagggcagagcccccuucagaacccacagagauccguccacaaaagc ggaaaaaggggccagcccccaaaaugcuggggaacgagcuaugcagcgug uguggggacaaggccucgggcuuccacuacaauguucugagcugcgaggg cugcaagggauucuuccgccgcagcgucaucaagggagcgcacuacaucu gccacaguggcggccacugccccauggacaccuacaugcgucgcaagugc caggagugucggcuucgcaaaugccgucaggcuggcaugcgggaggagug uguccugucagaagaacagauccgccugaagaaacugaagcggcaagagg aggaacaggcucaugccacauccuugcccccccagggcuuccucacccccc caaauccugccccagcucagcccggaacaacugggcaugaucgagaagcu -continued cgucgcugcccagcaacaguguaaccggcgcuccuuuucugaccggcuuc
gagucacgccuuggcccauggcaccagauccccauagccgggaggcccgu
cagcagcgcuuugcccacuucacugagcuggccaucgucucugugcagga
gauaguugacuuugcuaaacagcuacccggcuuccugcagcucagccggg
aggaccagauugcccugcugaagaccucugcgaucgaggugaugcuucug
gagacaucucggagguacaacccugggagugagaguaucaccuuccucaa
ggauuucaguuauaaccgggaagacuuugccaaagcagggcugcaagugg
aauucaucaaccccaucuucgaguucuccagggccaugaaugagcugcaa
cucaaugaugccgaguuugccuugcucauugcuaucagcaucuucucugc
agaccggcccaacgugcaggaccagcuccagguagagaggcugcagcaca
cauauguggaagcccugcaugccuacgucuccauccaccauccccaugac
cgacugauguucccacggaugcuaaugaaacuggugagccuccggacccu
gagcagcguccacucagagcaaguguuugcacugcgucugcaggacaaaa
agcucccaccgcugcucucugagaucugggaugugcacgaaugacuguuc
ugucccauauuuucuguuuucuuggccggauggcugaggccugguggcu
gccuccuagaaguggaacagacugagaagggcaaacauuccugggagcug
ggcaaggagauccucccguggcauuaaaagagagucaaagguugcgagu
uuguggcuacugagcaguggagcccucgcuaacacugugcugugucuga
agaucaugcugaccccacaaacggaugggccuggggggccacuuugcacag
gguucuccagagcccugcccauccugccuccaccacuuccuguuuuuccc
acagggccccaagaaaauucuccacugucaaaaaaaaa LXR-a (NR1H3) isoform 1: Amino acid sequence
(SEQ ID NO: 22)

mslwlgapvp dippdsavel wkpgaqdass qaqggsscil
reearmphsa ggtagvglea aeptalltra eppsepteir
pqkrkkgpap kmlgnelcsv cgdkasgfhy nvlscegckg
ffrrsvikga hyichsgghc pmdtymrrkc qecrlrkcrq
agmreecvls eeqirlkklk rqeeeqahat slpprasspp
qilpqlspeq lgmieklvaa qqqcnrrsfs drirvtpwpm
apdphsrear qqrfahftel aivsvqeivd fakqlpgflq
lsredqiall ktsaievmll etsrrynpgs esitflkdfs
ynredfakag lqvefinpif efsramnelq lndaefalli
aisifsadrp nvqdqlqver lqhtyvealh ayvsihhphd
rlmfprmlmk lvslrtlssv hseqvfalrl qdkklpplls
eiwdvhe LXR-a (NR1H3) isoform 2: RNA sequence
(SEQ ID NO: 23)

aggaaggagggguggccugaccccucggcagucccucccccucagccuuuc
cccaaauugcuacuucucuggggcuccagguccugcuugugcucagcucc
agcucacuggcuggccaccgagacuucuggacaggaaacugcaccauccu
cuucucccagcaagggggcuccagagacugcccacccaggaagucuggug
gccuggggauuuggacagugccuugguaaugaccagggcuccaggaagag
auguccuuguggcugggggccccugugccugacauuccuccugacucugc -continued gguggagcuguggaagccaggcgcacaggaugcaagcagccaggcccagg
gaggcagcagcugcauccucagagaggaagccaggaugccccacucugcu
gggguacugcagggguggggcuggaggcugcagagcccacagcccugcu
caccagggcagagccccccuucagaacccacagagauccguccacaaaagc
ggaaaaaggggccagcccccaaaaugcuggggaacgagcuaugcagcgug
uguggggacaaggccucgggcuuccacuacaauguucugagcugcgaggg
cugcaagggauucuuccgccgcagcgucaucaagggagcgcacuacaucu
gccacaguggcggccacugccccauggacaccuacaugcgucgcaagugc
caggagugucggcuucgcaaaugccgucaggcuggcaugcgggaggagug
uguccugucagaagaacagauccgccugaagaaacugaagcggcaagagg
aggaacaggcucaugccacauccuugccccccagggcuuccucaccccccc
caaauccugccccagcucagcccggaacaacugggcaugaucgagaagcu
cgucgcugcccagcaacaguguaaccggcgcuccuuuucugaccggcuuc
gagucacggugaugcuucuggagacaucucggagguacaacccugggagu
gagaguaucaccuuccucaaggauuucaguuauaaccgggaagacuuugc
caaagcagggcugcaaguggaauucaucaaccccaucuucgaguucucca
gggccaugaaugagcugcaacucaaugaugccgaguuugccuugcucauu
gcuaucagcaucuucucugcagaccggcccaacgugcaggaccagcucca
gguagagaggcugcagcacacauauguggaagcccugcaugccuacgucu
ccauccaccauccccaugaccgacugauguucccacggaugcuaaugaaa
cuggugagccuccggacccugagcagcguccacucagagcaaguguuugc
acugcgucugcaggacaaaaagcucccaccgcugcucucugagaucuggg
augugcacgaaugacuguucugucccauauuuucuguuuucuuggccgg
auggcugaggccugguggcugccuccuagaaguggaacagacugagaagg
gcaaacauuccugggagcugggcaaggagauccucccguggcauuaaaag
agagucaaagguugcgaguuuuguggcuacugagcaguggagcccucgc
uaacacugugcugugucugaagaucaugcugaccccacaaacggaugggc
cugggggccacuuugcacaggguucuccagagcccugcccauccugccuc
caccacuuccuguuuuucccacagggccccaagaaaauucuccacuguc
aaaaaaaaa LXR-a (NR1H3) isoform 2: Amino acid sequence
(SEQ ID NO: 24)

mslwlgapvp dippdsavel wkpgaqdass qaqggsscil
reearmphsa ggtagvglea aeptalltra eppsepteir
pqkrkkgpap kmlgnelcsv cgdkasgfhy nvlscegckg
ffrrsvikga hyichsgghc pmdtymrrkc qecrlrkcrq
agmreecvls eeqirlkklk rqeeeqahat slpprasspp
qilpqlspeq lgmieklvaa qqqcnrrsfs drlrvtvmll
etsrrynpgs esitflkdfs ynredfakag lqvefinpif -continued efsramnelq lndaefalli aisifsadrp nvqdqlqver lqhtyvealh ayvsihhphd rlmfprmlmk lvslrtlssv hseqvfalrl qdkklpplls eiwdvhe LXR-a (NR1H3) isoform 3: RNA sequence
(SEQ ID NO: 25)

aucuuacuuagggaccugcuggggugcggggaaaaggcgcagucucggug ggauugcgugcaggagggucguggucuggcuguggcggaggagcauaaga agacucugcgguggagcuguggaagccaggcgcacaggaugcaagcagcc aggcccagggaggcagcagcugcauccucagagaggaagccaggaugccc cacucugcugggguacugcaggggugggcuggaggcugcagagcccac agcccugcucaccagggcagagcccccuucagaacccacagagauccguc cacaaaagcggaaaaaggggccagcccccaaaaugcuggggaacgagcua ugcagcgugugugggacaaggccucgggcuuccacuacaauguucugag cugcgagggcugcaagggauucuuccgccgcagcgucaucaagggagcgc acuacaucugccacaguggcggccacugccccauggacaccuacaugcgu cgcaagugccaggagugucggcuucgcaaaugccgucaggcuggcaugcg ggaggagugugucugucagaagaacagauccgccugaagaaacugaagc ggcaagaggaggaacaggcucaugccacauccuugcccccagggcuucc ucacccccccaaauccugccccagcucagcccggaacaacugggcaugau cgagaagcucgucgcugcccagcaacaguguaaccggcgcuccuuuucug accggcuucgagucacgccuuggcccauggcaccagauccccauagccgg gaggcccgucagcagcgcuuugcccacuucacugagcuggccaucgucuc ugugcaggagauaguugacuuugcuaaacagcuacccggcuuccugcagc ucagccgggaggaccagauugcccugcugaagaccucugcgaucgaggug augcuucuggagacaucucggagguacaacccugggagugagaguaucac cuuccucaaggauuucaguuauaaccgggaagacuuugccaaagcagggc ugcaaguggaauucaucaaccccaucuucgaguucuccagggccaugaau gagcugcaacucaaugaugccgaguuugccuugcucauugcuaucagcau cuucucugcagaccggcccaacgugcaggaccagcuccagguagagaggc ugcagcacacauauguggaagcccugcaugccuacgucuccauccaccau ccccaugaccgacugauguucccacggaugcuaaugaaacuggugagccu ccggacccugagcagcguccacucagagcaaguguuugcacugcgucugc aggacaaaaagcucccaccgcugcucucugagaucugggaugugcacgaa ugacuguucuguccccauauuuucuguuuucuuggccggauggcugaggc cugguggcugccuccuagaaguggaacagacugagaagggcaaacauucc ugggagcugggcaaggagauccucccguggcauuaaaagagagucaaagg guugcgaguuuuguggcuacugagcaguggagcccucgcuaacacugugc ugugucugaagaucaugcugaccccacaaacggaugggccugggggccac uuugcacaggguucuccagagcccugcccauccugccuccaccacuuccu guuuuucccacagggccccaagaaaaauucuccacugucaaaaaaaaa LXR-a (NR1H3) isoform 3: Amino acid sequence
(SEQ ID NO: 26)

mphsaggtag vgleaaepta lltraeppse pteirpqkrk kgpapkmlgn elcsvcgdka sgfhynvlsc egckgffrrs vikgahyich sgghcpmdty mrrkcqecrl rkcniagmre ecvlseeqir lkklkrqeee qahatslppr assppqilpq lspeqlgmie klvaaqqqcn rrsfsdrlry tpwpmapdph srearqqrfa hftelaivsv qeivdfakql pgfiqlsred qiallktsai evmlletsrr ynpgsesitf lkdfsynred fakaglqvef inpifefsra mnelqlndae falliaisif sadrpnvqdq lqverlqhty vealhayvsi hhphdrlmfp rmlmklvslr tlssvhseqv falrlqdkkl pplkseiwdv he LXR-a (NR1H3) isoform 4: RNA sequence
(SEQ ID NO: 27)

gauucuaacuuagcuaagcaaugcuacuggagaccauaggcaaagccaag guacagcuucagggaagucuuuggugagcccaucucucauuaccaaggua acgaagcgcagacuccgggcccgggugggcggcaucaccaccagguucac gccgagaaggagcuggaggagagccgcccggcuccagccggaccgcuugc ccgccaucaccguuguaaucuaugcagcaaacaagcuggaacccgcuggg uggcaccugcaagcagccgcccggacgcacccacucugegguggagcugu ggaagccaggcgcacaggaugcaagcagccaggcccagggaggcagcagc ugcauccucagagaggaagccaggaugccccacucugcugggguacugc aggggugggcuggaggcugcagagcccacagcccugcucaccagggcag agcccccuucagaacccacagagauccguccacaaaagcggaaaaagggg ccagcccccaaaaugcuggggaacgagcuaugcagcgugugugggacaa ggccucgggcuuccacuacaauguucugagcugcgagggcugcaagggau ucuuccgccgcagcgucaucaagggagcgcacuacaucugccacagugge ggccacugccccauggacaccuacaugcgucgcaagugccaggagugucg gcuucgcaaaugccgucaggcuggcaugcgggaggagugugucugucag aagaacagauccgccugaagaaacugaagcggcaagaggaggaacaggcu caugccacauccuugcccccagggcuuccucacccccccaaauccugcc ccagcucagcccggaacaacugggcaugaucgagaagcucgucgcugccc agcaacaguguaaccggcgcuccuuuucugaccggcuucgagucacgccu uggcccauggcaccagauccccauagccgggaggcccgucagcagcgcuu ugcccacuucacugagcuggccaucgucucugugcaggagauaguugacu uugcuaaacagcuacccggcuuccugcagcucagccgggaggaccagauu gcccugcugaagaccucugcgaucgaggugaugcuucuggagacaucucg gagguacaacccugggagugagaguaucaccuuccucaaggauuucaguu auaaccgggaagacuuugccaaagcagggcugcaaguggaauucaucaac cccaucuucgaguucuccagggccaugaaugagcugcaacucaaugaugc -continued cgaguuugccuugcucauugcuaucagcaucuucucugcagaccggccca acgugcaggaccagcuccagguagagaggcugcagcacacauauguggaa gcccugcaugccuacgucuccauccaccauccccaugaccgacugauguu cccacggaugcuaaugaaacuggugagccuccggacccugagcagcgucc acucagagcaaguguuugcacugcgucugcaggacaaaagcucccaccg cugcucucugagaucugggaugugcacgaaugacuguucuguccccauau uuucuguuuucuuggccggauggcugaggccugguggcugccuccuagaa guggaacagacugagaagggcaaacauuccugggagcugggcaaggagau ccucccguggcauuaaaagagagucaaaggguugcgaguuuguggcuac ugagcaguggagcccucgcuaacacugugcugugucugaagaucaugcug accccacaaacggaugggccugggggccacuuugcacaggguucuccaga gcccugcccauccugccuccaccacuuccuguuuucccacagggcccca agaaaaauucuccacugucaaaaaaaaa LXR-a (NR1H3) isoform 4: Amino acid sequence (SEQ ID NO: 28)

mqqtswnplg gtckqppgrt hsavelwkpg aqdassqaqg gsscilreea rmphsaggta gvgleaaept alltraepps epteirpqkr kkgpapkmlg nelcsvcgdk asgfhynvls cegckgffrr svikgahyic hsgghcpmdt ymrrkcqecr lrkcrqagmr eecvlseeqi rlkklkrqee eqahatslpp rassppqilp qlspeqlgmi eklvaaqqqc nrrsfsdrlr vtpwpmapdp hsrearqqrf ahftelaivs vqeivdfakq lpgflqlsre dqiallktsa ievmlletsr rynpgsesit flkdfsynre dfakaglqve finpifefsr amnelqlnda efalliaisi fsadrpnvqd qlqverlqht yvealhayvs ihhphdrlmf prmlmklvsl rtlssvhseq vfalrlqdkk lppllseiwd vhe LXR-b (NR1H2) isoform 1: RNA sequence (SEQ ID NO: 29)

ucgucaaguuucacgcuccgccccucuuccggacgugacgcaagggcggg guugccggaagaaguggcgaaguuacuuuugaggguauuugaguagcggc ggugugucaggggcuaaagaggaggacgaagaaaagcagagcaagggaac ccagggcaacaggaguaguucacuccgcgagaggccguccacgagacccc cgcgcgcagccaugagccccgcccccgcuguugcuuggagaggggcggg accuggagagaggcugcuccgugaccccaccauguccucuccuaccacga guucccuggauacccccugccuggaaauggcccccucagccuggcgcc ccuucuucuucacccacuguaaaggaggaggguccggagccguggcccgg ggguccggacccugaugucccaggcacugaugaggccagcucagccugca gcacagacugggucaucccagaucccgaagaggaaccagagcgcaagcga aagaagggcccagccccgaagaugcugggccacgagcuuugccgugucug uggggacaaggccuccggcuuccacuacaacgugcucagcugcgaaggcu gcaagggcuucuuccggcgcagugugguccgugguggggccaggcgcuau -continued gccugccggggguggcggaaccugccagauggacgcuuucaugcggcgcaa gugccagcagugccggcugcgcaagugcaaggaggcagggaugagggagc agugcguccuuucugaagaacagauccggaagaagaagauucggaaacaa cagcagcaggagucacagucacagucgcagucaccugugggccgcaggg cagcagcagcucagccucugggccuggggcuuccccugguggaucugagg caggcagccagggcuccggggaaggcgaggguguccagcuaacagcggcu caagaacuaaugauccagcaguugguggcggcccaacugcagugcaacaa acgcuccuucuccgaccagcccaaagucacgcccuggccccugggcgcag accccaguccccgagaugcccgccagcaacgcuuugcccacuucacggag cuggccaucaucucaguccaggagaucguggacuucgcuaagcaagugcc ugguuuccugcagcugggccgggaggaccagaucgcccuccugaaggcau ccacuaucgagaucaugcugcuagagacagccaggcgcuacaaccacgag acagaguguaucaccuucuugaaggacuucaccuacagcaaggacgacuu ccaccgugcaggccugcagguggaguucaucaaccccaucuucgaguucu cgcgggccaugcggcggcugggccuggacgacgcugaguacgcccugcuc aucgccaucaacaucuucucggccgaccggcccaacgugcaggagccggg ccgcguggaggcguugcagcagcccuacguggaggcgcugcuguccuaca cgcgcaucaagaggccgcaggaccagcugcgcuucccgcgcaugcucaug aagcuggugagccugcgcacgcugagcucugugcacucggagcaggucuu cgccuugcggcuccaggacaagaagcugccgccucugcugucggagaucu gggacguccacgagugaggggcuggccacccagccccacagccuugccug accacccuccagcagauagacgccggcaccccuuccucuuccuagggugg aaggggcccugggccgagccuguagaccuaucggcucucaucccuugga uaagccccaguccagguccaggaggcucccucccugcccagcgagucuuc cagaaggggugaaaggguugcaggucccgaccacugacccuucccggcug cccucccuccccagcuuacaccucaagcccagcacgcagugcaccuugaa cagagggaggggaggacccauggcucuccccccuagcccgggagaccagg gccuuccucuuccucugcuuuuauuuaauaaaaacuaaaaacagaaacag gaaaauaaaauaugaauacaauccagcccggagcuggagugca LXR-b (NR1H2) isoform 1: Amino acid sequence (SEQ ID NO: 30)

msspttssld tplpgngppq pgapsssptv keegpepwpg gpdpdvpgtd eassacstdw vipdpeeepe rkrkkgpapk mlghelcrvc gdkasgfhyn vlscegckgf frrsvvrgga rryacrgggt cqmdafmrrk cqqcrlrkck eagmreqcvl seeqirkkki rkqqqqesqs qsqspvgpqg ssssasgpga spggseagsq gsgegegvql taaqelmiqq lvaaqlqcnk rsfsdqpkvt pwplgadpqs rdarqqrfah ftelaiisvq eivdfakqvp gflqlgredq iallkastie imlletarry nhetecitfl kdftyskddf hraglqvefi npifefsram -continued rrlglddaey alliainifs adrpnvqepg rvealqqpyv eallsytrik rpqdqlrfpr mlmklvslrt lssvhseqvf alrlqdkklp pllseiwdvh e LXR-b (NR1H2) isoform 2: RNA sequence (SEQ ID NO: 31)

ucgucaaguuucacgcuccgccccucuuccggacgugacgcaagggcggg guugccggaagaaguggcgaaguuacuuuugaggguauuugaguagcggc ggugugucaggggcuaaagaggaggacgaagaaaagcagagcaagggaac ccagggcaacaggaguaguucacuccgcgagaggccguccacgagacccc cgcgcgcagccaugagccccgcccccgcuguugcuuggagaggggcggg accuggagagaggcugcuccgugaccccaccauguccucuccuaccacga guucccuggauacccccugccuggaaauggcccccucagccuggcgcc ccuucuucuucacccacuguaaaggaggaggguccggagccguggcccgg ggguccggacccugaugucccaggcacugaugaggccagcucagccugca gcacagacuggggcguccuuucugaagaacagauccggaagaagaagauu cggaaacaacagcagcaggagucacagucacagucgcagucaccuguggg gccgcagggcagcagcagcucagccucugggccuggggcuuccccuggug gaucugaggcaggcagccagggcuccggggaaggcgaggguguccagcua acagcggcucaagaacuaaugauccagcaguugguggcggcccaacugca gugcaacaaacgcuccuucuccgaccagcccaaagucacgcccuggcccc ugggcgcagacccccagucccgagaugcccgccagcaacgcuuugcccac uucacggagcuggccaucaucucaguccaggagaucguggacuucgcuaa gcaagugccugguuuccugcagcugggccgggaggaccagaucgcccucc ugaaggcauccacuaucgagaucaugcugcuagagacagccaggcgcuac aaccacgagacagaguguaucaccuucuugaaggacuucaccuacagcaa ggacgacuuccaccgugcaggccugcagguggaguucaucaaccccaucu ucgaguucucgcgggccaugcggcggcugggccuggacgacgcugaguac gcccugcucaucgccaucaacaucuucucggccgaccggcccaacgugca ggagccgggccgcguggaggcguugcagcagcccuacguggaggcgcugc uguccuacacgcgcaucaagaggccgcaggaccagcugcgcuucccgcgc augcucaugaagcuggugagccugcgcacgcugagcucugugcacucgga gcaggucuucgccuugcggcuccaggacaagaagcugccgccucugcugu cggagaucugggacguccacgagugaggggcuggccacccagccccacag ccuugccugaccacccuccagcagauagacgccggcaccccuuccucuuc cuaggguggaaggggcccugggccgagccuguagaccuaucggcucucau cccuugggauaagccccaguccagguccaggaggcucccucccugcccag cgagucuuccagaaggggugaaagguugcaggucccgaccacugacccu ucccggcugcccucccuccccagcuuacaccucaagcccagcacgcagug caccuugaacagagggaggggaggacccauggcucuccccccuagcccgg gagaccagggccuuccucuuccucugcuuuuauuuaauaaaaacuaaaaa cagaaacaggaaaauaaaauaugaauacaauccagcccggagcuggagug ca -continued LXR-b (NR1H2) isoform 2: Amino acid sequence (SEQ ID NO: 32)

msspttssld tplpgngppq pgapssspt v keegpepwpg gpdpdvpgtd eassacstdw gvlseeqirk kkirkqqqqe sqsqsqspvg pqgssssasg pgaspggsea gsqgsgegeg vqltaaqelm iqqlvaaqlq cnkrsfsdqp kvtpwplgad pqsrdarqqr fahftelaii svqeivdfak qvpgflqlgr edqiallkas tieimlleta rrynheteci tflkdftysk ddfhraglqv efinpifefs ramrrlgldd aeyalliain ifsadrpnvq epgrvealqq pyveallsyt rikrpqdqlr fprmlmklvs lrtlssvhse qvfalrlqdk klpplls eiw dvhe has-miR-199a-1 sequence (SEQ ID NO: 33)

GCCAACCCAGUGUUCAGACUACCUGUUCAGGAGGCUCUCAAUGUGUACAG

UAGUCUGCACAUUGGUUAGGC has-miR-199a-2 sequence (SEQ ID NO: 34)

AGGAAGCUUCUGGAGAUCCUGCUCCGUCGCCCCAGUGUUCAGACUACCUG

UUCAGGACAAUGCCGUUGUACAGUAGUCUGCACAUUGGUUAGACUGGGCA

AGGGAGAGCA has-miR-1908 sequence (SEQ ID NO: 35)

CGGGAAUGCCGCGGCGGGGACGGCGAUUGGUCCGUAUGUGUGGUGCCACC

GGCCGCCGGCUCCGCCCCGGCCCCCGCCCC has-miR-7-1 sequence (SEQ ID NO: 36)

UUGGAUGUUGGCCUAGUUCUGUGUGGAAGACUAGUGAUUUUGUUGUUUUU

AGAUAACUAAAUCGACAACAAAUCACAGUCUGCCAUAUGGCACAGGCCAU

GCCUCUACAG has-miR-7-2 sequence (SEQ ID NO: 37)

CUGGAUACAGAGUGGACCGGCUGGCCCCAUCUGGAAGACUAGUGAUUUUG

UUGUUGUCUUACUGCGCUCAACAACAAAUCCCAGUCUACCUAAUGGUGCC

AGCCAUCGCA has-miR-7-3 sequence (SEQ ID NO: 38)

AGAUUAGAGUGGCUGUGGUCUAGUGCUGUGUGGAAGACUAGUGAUUUUGU

UGUUCUGAUGUACUACGACAACAAGUCACAGCCGGCCUCAUAGCGCAGAC

UCCCUUCGAC miR-Zip 199a-3p sequence (SEQ ID NO: 39)

GATCCGACAGTAGCCTGCACATTAGTCACTTCCTGTCAGTAACCAATGTG

CAGACTACTGTTTTTTGAATT miR-Zip 199a-5p sequence (SEQ ID NO: 40)

GATCCGCCCAGTGCTCAGACTACCCGTGCCTTCCTGTCAGGAACAGGTAG

TCTGAACACTGGGTTTTTGAATT

-continued miR-Zip 1908 sequence (SEQ ID NO: 41)

GATCCGCGGCGGGAACGGCGATCGGCCCTTCCTGTCAGGACCAATCGCCG

TCCCCGCCGTTTTTGAATT miR-Zip 7 sequence (SEQ ID NO: 42)

GATCCGTGGAAGATTAGTGAGTTTATTATCTTCCTGTCAGACAACAAAAT

CACTAGTCTTCCATTTTTGAATT

The members of this network can be used as targets for treating metastatic melanoma. In addition, the members can be used a biomarkers for determining whether a subject has, or is at risk of having, a metastatic melanoma or for determining a prognosis or surveillance of patient having the disorder. Accordingly, the present invention encompasses methods of treating metastatic melanoma by targeting one or more of the members, methods of determining the efficacy of therapeutic regimens for inhibiting the cancer, and methods of identifying anti-cancer agent. Also provided are methods of diagnosing whether a subject has, or is at risk for having, metastatic melanoma, and methods of screening subjects who are thought to be at risk for developing the disorder. The invention also encompasses various kits suitable for carrying out the above mentioned methods.

ApoE Polypeptides

The term "polypeptide or peptide" as used herein includes recombinantly or synthetically produced fusion or chimeric versions of any of the aforementioned metastasis suppressors, having the particular domains or portions that are involved in the network. The term also encompasses an analog, fragment, elongation or derivative of the peptide (e.g. that have an added amino-terminal methionine, useful for expression in prokaryotic cells).

"Apolipoprotein polypeptide or ApoE polypeptide" as used herein means a peptide, drug, or compound that mimics a function of the native apolipoprotein either in vivo or in vitro including apolipoprotein analogs, fragments, elongations or derivatives that are a peptide of between 10 and 200 amino acid residues in length, such peptides can contain either natural, or non-natural amino acids containing amide bonds. Apolipoprotein peptide fragments may be modified to improve their stability or bioavailability in vivo as known in the art and may contain organic compounds bound to the amino acid side chains through a variety of bonds.

In one aspect, our invention is a method for using an isolated apoEp1.B peptide having the amino acid sequence TQQIRLQAEIFQAR (murine) (SEQ. ID. No. 43) or AQQIRLQAEAFQAR (human)(SEQ. ID. No. 44) or an analog, fragment, elongation or derivative of the peptide. The invention also includes a nucleic acid molecule encoding the apoEpI.B peptide, or an analog, fragment, elongation or derivative thereof.

The term "analog" includes any peptide having an amino acid residue sequence substantially identical to the native peptide in which one or more residues have been conservatively substituted with a functionally similar residue and which displays the ability to mimic the native peptide. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite activity. Analogs of the peptides include peptides having the following sequences:

(SEQ. ID. NO.: 45)

TAQIRLQAEIFQAR;

(SEQ. ID. NO.: 46)

TQAIRLQAEIFQAR;

(SEQ. ID. NO.: 47)

TQQARLQAEIFQAR and (SEQ. ID. NO.: 48)

TQQIALQAEIFQAR.

"Derivative" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject peptide having an amino acid residue sequence shorter than that of a peptide whose amino acid residue sequence is shown herein.

The term "elongation" refers to any subject peptide having an amino acid sequence longer by one or two amino acids (either at the carboxy or amino terminal end) than that of a peptide of the present invention. Preferably, the elongation occurs at the amino terminal end. Fragments and elongations of the peptides include peptides that have the following sequences:

(SEQ. ID. NO.: 49)

QTQQIRLQAEIFQAR and (SEQ. ID. NO.: 50)

QQIRLQAEIFQAR.

ApoE polypeptides and methods for their preparation are described in U.S. Pat. No. 6,652,860, incorporated herein by reference.

LXR Agonists

The methods of the invention can include administering a LXR agonist for the prevention and treatment of metastasis.

The LXR agonist can be a compound according to the Formula I, II, III, or IV shown below.

Formula I is provided below:

Formula I

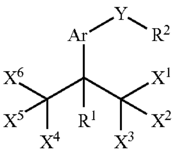

or a pharmaceutically acceptable salt thereof, wherein

Ar is an aryl group;

$R^1$ is a member selected from the group consisting of

—OH, —$CO_2H$, —O—($C_1$-$C_7$)alkyl, —OC(O)—, —($C_1$-$C_7$)alkyl, —O—($C_1$-$C_7$)heteroalkyl, —OC(O)—($C_1$-$C_7$)heteroalkyl, —$NH_2$, —NH($C_1$-$C_7$) alkyl, —N(($C_1$-$C_7$)alkyl)$_2$ and —NH—S(O)$_2$($C_1$-$C_5$)alkyl;

$R^2$ is a member selected from the group consisting of ($C_1$-$C_7$)alkyl, ($C_1$-$C_7$)heteroalkyl, aryl and aryl ($C_1$-$C_7$) alkyl;

$X^1$, $X^2$, $X^3$, $X^4$, $X^5$ and $X^6$ are each independently a member selected from the group consisting of:

H, ($C_1$-$C_5$)alkyl, ($C_1$-$C_5$)heteroalkyl, F and CI, with the proviso that no more than three of $X^1$ through $X^6$ are H, ($C_1$-$C_5$)alkyl, ($C_1$-$C_5$)heteroalkyl; and Y is a divalent linking group selected from the group consisting of:

—N($R^{12}$)S(O)$_m$—, —N($R^{12}$)S(O)$_m$N($R^{13}$)—, —N($R^{12}$)C(O)—, —N($R^{12}$)C(O)N($R^{13}$)—, —N($R^{12}$)C(S)— and —N($R^{12}$)C(O)O—;

wherein $R^{12}$ and $R^{13}$ are each independently selected from the group consisting of:

H, ($C_1$-$C_7$)alkyl, ($C_1$-$C_7$)heteroalkyl, aryl and aryl($C_1$-$C_7$) alkyl, and optionally when Y is —N($R^{12}$)S(O)$_m$— or —N($R^{12}$)S(O)$_m$N($R^{13}$)—, $R^{12}$ forms a five- or six-membered ring fused to Ar or to $R^2$ through covalent attachment to Ar or to $R^2$, respectively; and the subscript m is an integer of from 1 to 2;

with the proviso that when $R^1$ is OH, and —Y—$R^2$ is —N($R^{12}$)S(O)$_m$—$R^2$ or —N($R^{12}$)C(O)N($R^{13}$)—$R^2$ and is attached to a position para to the quaternary carbon attached to Ar, and when $R^2$ is phenyl, benzyl, or benzoyl, then i) at least one of $R^{12}$ or $R^{13}$ is other than hydrogen and contains an electron-withdrawing substituent, or ii) $R^2$ is substituted with a moiety other than amino, acetamido, di($C_1$-$C_7$)alkylamino, ($C_1$-$C_7$)alkylamino, halogen, hydroxy, nitro, or ($C_1$-$C_7$)alkyl, or iii) the benzene ring portion of $R^2$ is substituted with at least three independently selected groups in addition to the Y group or point of attachment to Y.

In some embodiments, Y is —N(R12)S(O)2- and R1 is OH.

Accordingly, the compounds of Formula I include but are not limited the compound with the structure shown below:

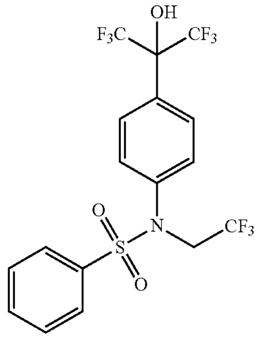

Compounds of Formula I can be synthesized as described by U.S. Pat. No. 6,316,503, incorporated herein by reference.

Formula II is provided below:

Formula II

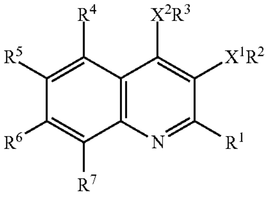

wherein:

$R^1$ is —H;

$X^1$ is a bond, $C_1$ to $C_5$ alkyl, —C(O)—, —C(=$CR^8R^9$)—, —O—, —S(O)$_t$—, —$NR^8$—, —$CR^8R^9$—, —$CHR^{23}$, —$CR^8$($CR^9$)—, —C($CR^8$)$_2$—, —$CR^8$(OC(O)$R^9$)—, —C=$NOR^9$—, —C(O)$NR^8$—, —$CH_2O$—, —$CH_2S$—, —$CH_2NR^8$—, —$OCH_2$—, —$SCH_2$—, —$NR^8CH_2$—, or

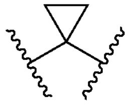 ;

$R^2$ is H, $C_1$ to $C_6$alkyl, $C_2$ to $C_6$alkenyl, $C_2$ to $C_6$alkynyl, $C_3$ to $C_6$ cycloalkyl, —$CH_2OH$, C7 to $C_{11}$ arylalkyl, phenyl, naphthyl, $C_1$ to $C_3$ perfluoroalkyl, CN, C(O)$NH_2$, $CO_2R^{12}$ or phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, -$NO_2$, —$NR^8R^9$, —CN, —OH, and $C_1$ to $C_3$alkyl substituted with 1 to 5 fluorines, or $R^2$ is a heterocycle selected from the group consisting of pyridine, thiophene, benzisoxazole, benzothiophene, oxadiazole, pyrrole, pyrazole, imidazole, and furan, each of which may be optionally substituted with one to three groups independently selected from $C_1$ to $C_3$alkyl, $C_1$ to $C_3$ alkoxy, $C_1$ to $C_3$ perfluoroalkyl, halogen, —$NO_2$, —$NR^8R^9$, —CN, and $C_1$ to $C_3$alkyl substituted with 1 to 5 fluorines;

$X^2$ is a bond or —$CH_2$—;

$R^3$ is phenyl, naphthyl, or phenyl or naphthyl substituted independently by one to four groups independently selected from $C_1$ to $C_3$ alkyl, hydroxy, phenyl, acyl, halogen, —$NH_2$, —CN, —$NO_2$, $C_1$ to $C_3$ alkoxy, $C_1$ to $C_3$perfluoroalkyl, $C_1$ to $C_3$ alkyl substituted with 1 to 5 fluorines, $NR^{14}R^{15}$—$C(O)R^{10}$, —$C(O)NR^{10}R^{11}$, —$C(O)NR^{11}A$, —C≡$CR^8$, —CH═$CHR^8$, —WA, —C≡CA, —CH═CHA, —WYA, —$WYNR^{11}$-A, —$WYR^{10}$, —$WY(CH2)_jA$, —$WCHR^{11}(CH2)_jA$, —$W(CH2)_jA$, —$W(CH2)_jR^{10}$, —$CHR^{11}W(CH_2)_jR^{10}$, —$CHR^{11}W(CH_2)_jA$, —$CHR^{11}NR^{12}YA$, —$CHR^{11}NR^{12}YR^{10}$, pyrrole, —$W(CH_2)_jA(CH_2)_kD(CH2)_pZ$, —$W(CR^{18}R^{19})A(CH_2)_kD(CH_2)_pZ$, —$(CH_2)_jWA(CH_2)_kD(CH_2)_pZ$, —CH═$CHA(CH_2)_kD(CH2)pZ$, —C≡$CA(CH_2)_kD(CH_2)_pZ$, —$W(CH_2)_j$C≡$CA(CH_2)_kD(CH_2)_pZ$, and —$W(CH_2)_jZ$, or $R^3$ is a heterocycle selected from pyrimidine, thiophene, furan, benzothiophene, indole, benzofuran, benzimidazole, benzothiazole, benzoxazole, and quinoline, each of which may be optionally substituted with one to three groups independently selected from $C_1$ to $C_3$alkyl, $C_1$ to $C_3$ alkoxy, hydroxy, phenyl, acyl, halogen, —$NH_2$, —CN, —$NO_2$, $C_1$ to $C_3$ perfluoroalkyl, $C_1$ to $C_3$ alkyl substituted with 1 to 5 fluorines, —$C(O)R^{10}$, —C(O) $NR^{10}R^{11}$, —$C(O)NR^{11}A$, —C≡$CR^8$, —CH═$CHR^8$, —WA, —C≡CA, —CH═CHA, —WYA, —$WYR^{10}$, —$WY(CH_2)_jA$, —$W(CH_2)_jA$, —$W(CH_2)_jR^{10}$, —$CHR^{11}W(CH_2)_jR^{10}$, —$CHR^{11}W(CH_2)_jA$, —$CHR^{11}NR^{12}YA$, —$CHR^{11}NR^{12}YR^{10}$, —$WCHR^{11}(CH_2)_jA$, —$W(CH_2)_jA(CH_2)_kD(CH_2)_pZ$, —$W(CR^{18}R^{19})A(CH_2)_kD(CH_2)_pZ$, —$(CH_2)_j$ $WA(CH_2)_kD(CH_2)_pZ$, —CH═$CHA(CH_2)_kD(CH_2)_pZ$, —C≡$CA(CH_2)_kD(CH_2)_pZ$, —$W(CH_2)_j$C≡$CA(CH_2)_kD(CH_2)_pZ$, and —$W(CH_2)_jZ$;

W is a bond, —O—, —S—, —S(O)—, —$S(O)_2$—, —$NR^{11}$—, or —$N(COR^{12})$—;

Y is —CO—, —$S(O)^2$—, —$CONR^{13}$, —$CONR^{13}CO$—, —$CONR^{13}SO_2$—, —C(NCN)—, —$CSNR^{13}$, —$C(NH)NR^{13}$, or —C(O)O—;

j is 0 to 3;

k is 0 to 3;

t is 0 to 2;

D is a bond, —CH═CH—, —C≡C—, —C═, —C(O)—, phenyl, —O—, —NH—, —S—, —$CHR^{14}$—, —$CR^{14}R^{15}$—$OCHR^{14}$, —$OCR^{14}R^{15}$—, or —CH(OH)CH(OH)—;

p is 0 to 3;

Z is —$CO_2R^{11}$, —$CONR^{10}R^{11}$, —$C(NR^{10})NR^{11}R^{12}$, —$CONH_2NH_2$, —CN, —$CH_2OH$, —$NR^{16}R^{17}$, phenyl, $CONHCH(R^{20})COR^{12}$, phthalimide, pyrrolidine-2,5dione, thiazolidine-2,4-dione, tetrazolyl, pyrrole, indole, oxazole, 2-thioxo-1,3-thiazolinin-4-one, $C_1$ to $C_7$ amines, $C_3$ to $C_7$ cyclic amines, or $C_1$ to $C_3$ alkyl substituted with one to two OH groups; wherein said pyrrole is optionally substituted with one or two substituents independently selected from the group consisting of—$CO_2CH_3$, —$CO_2H$, —$COCH_3$, —$CONH_2$, and —CN;

wherein said $C_1$ to $C_7$ amines are optionally substituted with one to two substituents independently selected from the group consisting of —OH, halogen, —$OCH_3$, and —C≡CH;

wherein said phenyl is optionally substituted with $CO_2R^{11}$, and wherein said $C_3$ to $C_7$ cyclic amines are optionally substituted with one or two substituents independently selected from the group consisting of —OH —$CH_2OH$, $C_1$ to $C_3$ alkyl, —$CH_2OCH_3$, —$CO_2CH_3$, and —$CONH_2$, and wherein said oxazole is optionally substituted with $CH_2CO_2R^{11}$;

A is phenyl, naphthyl, tetrahydronaphthyl, indan or biphenyl, each of which may be optionally substituted by one to four groups independently selected from halogen, $C_1$ to $C_3$ alkyl, $C_2$ to $C_4$ alkenyl, $C_2$ to $C_4$ alkynyl, acyl, hydroxy, halogen, —CN, —$NO_2$, —$CO_2R^{11}$, —$CH_2CO_2R^{11}$, phenyl, $C_1$ to $C_3$perfluoroalkoxy, $C_1$ to $C_3$ perfluoroalkyl, —$NR^{10}R^{11}$, —$CH_2NR^{10}R^{11}$, —$SR^{11}$, $C_1$ to $C_6$ alkyl substituted with 1 to 5 fluorines, $C_1$ to $C_3$alkyl substituted with 1 to 2-OH groups, $C_1$ to $C_6$ alkoxy optionally substituted with 1 to 5 fluorines, or phenoxy optionally substituted with 1 to 2 $CF_3$ groups; or A is a heterocycle selected from pyrrole, pyridine, pyridine-N-oxide, pyrimidine, pyrazole, thiophene, furan, quinoline, oxazole, thiazole, imidazole, isoxazole, indole, benzo[1,3]-dioxole, benzo[1,2,5]-oxadiazole, isochromen-1-one, benzothiophene, benzofuran, 2,3-di-5 hydrobenzo[1,4]-dioxine, bithienyl, quinazolin-2, 4-9[3H]dione, and 3-H-isobenzofuran-1-one, each of which may be optionally substituted by one to three groups independently selected from halogen, $C_1$ to $C_3$ alkyl, acyl, hydroxy, —CN, —$NO_2$, $C_1$ to $C_3$perfluoroalkyl, —$NR^{10}R^{11}$, —$CH_2NR^{10}R^{11}$, —$SR^{11}$, $C_1$ to $C_3$ alkyl substituted with 1 to 5 fluorines, and $C_1$ to $C_3$ alkoxy optionally substituted with 1 to 5 fluorines;

$R^4$, $R^5$, and $R^6$ are each, independently, —H or —F;

$R^7$ is $C_1$ to $C_4$ alkyl, $C_1$ to $C_4$ perfluoroalkyl, halogen, —$NO_2$, —CN, phenyl or phenyl substituted with one or two groups independently selected from halogen, $C_1$ to $C_2$alkyl and OH;

provided that if $X_1R^2$ forms hydrogen, then $R^3$ is selected from:

(a) phenyl substituted by —$W(CH_2)_jA(CH_2)_kD(CH_2)_pZ$, —$W(CR^{18}R^{19})A(CH_2)_kD(CH_2)_pZ$, —$(CH_2)_j$ $WA(CH_2)_kD(CH_2)_pZ$, —CH═$CHA(CH_2)_kD(CH_2)_pZ$, —C≡$CA(CH_2)_kD(CH_2)_pZ$, or —$W(CH_2)_j$C≡$CA(CH_2)_kD(CH_2)_pZ$, wherein the phenyl moiety is further optionally substituted with one or two groups independently selected from $C_1$ to $C_2$ alkyl, $C_1$ to $C_2$perfluoroalkyl, halogen, and CN; and (b) a heterocycle selected from pyrimidine, thiophene, and furan, each of which is substituted by one of —$W(CH_2)_jA(CH_2)_kD(CH_2)_pZ$, —$W(CR^{18}R^{19})A(CH_2)_kD(CH_2)_pZ$, —$(CH_2)_jWA(CH_2)_kD(CH_2)_pZ$, —CH═$CHA(CH_2)_kD(CH_2)_pZ$, —C≡$CA(CH_2)_kD(CH_2)_pZ$, or —$W(CH_2)_j$C≡$CA(CH_2)_kD(CH_2)_pZ$;

each $R^8$ is independently-H, or $C_1$ to $C_3$alkyl;

each $R^9$ is independently-H, or $C_1$ to $C_3$alkyl;

each $R^{10}$ is independently-H, —CH, $C_1$ to $C_3$alkoxy, $C_1$ to $C_7$ alkyl, $C_3$ to $C_7$ alkenyl, $C_3$ to $C_7$ alkynyl, $C_3$ to $C_7$ cycloalkyl, —$CH_2CH_2OCH_3$, 2-methyl-tetrahydro-furan, 2-methyl-tetrahydro-pyran, 4-methyl-piperidine, morpholine, pyrrolidine, or phenyl optionally substituted with one or two $C_1$ to $C_3$alkoxy groups, wherein said $C_1$ to $C_7$ alkyl is optionally substituted with 1, 2 or 3 groups independently selected from $C_1$ to $C_3$ alkoxy, $C_1$ to $C_3$thioalkoxy, and CN;

each $R^{11}$ is independently-H, $C_1$ to $C_3$alkyl or $R^{22}$; or $R^{10}$ and $R^{11}$, when attached to the same atom, together with said atom form:

a 5 to 7 membered saturated ring, optionally substituted by 1 to 2 groups independently selected from $C_1$ to $C_3$ alkyl, OH and $C_1$-$C_3$alkoxy; or a 5 to 7 membered ring containing 1 or 2 heteroatoms, optionally substituted by 1 to 2 groups independently selected from $C_1$ to $C_3$alkyl, OH and $C_1$-$C_3$ alkoxy;

each $R^{12}$ is independently-H, or $C_1$ to $C_3$alkyl;

each $R^{13}$ is independently-H, or $C_1$ to $C_3$alkyl;

each $R^{14}$ and $R^{15}$ is, independently, $C_1$ to $C_7$ alkyl, $C_3$ to $C_8$ cycloalkyl, $C_2$ to $C_7$ alkenyl, $C_2$ to $C_7$ alkynyl, —CH, —F, $C_7$ to $C_{14}$arylalkyl, where said arylalkyl is optionally substituted with 1 to 3 groups independently selected from $NO_2$, $C_1$ to $C_6$ alkyl, $C_1$ to $C_3$perhaloalkyl, halogen, $CH_2CO_2R^{11}$, phenyl and $C_1$ to $C_3$ alkoxy, or $R^{12}$ and $R^{15}$ together with the atom to which they are attached can form a 3 to 7 membered saturated ring;

each $R^{16}$ and $R^{17}$ is, independently, hydrogen, $C_1$ to $C_3$ alkyl, $C_1$ to $C_3$alkenyl, $C_1$ to $C_3$ alkynyl, phenyl, benzyl or $C_3$ to $C_8$ cycloalkyl, wherein said $C_1$ to $C_3$ alkyl is optionally substituted with one OH group, and wherein said benzyl is optionally substituted with 1 to 3 groups selected from $C_1$ to $C_3$alkyl and $C_1$ to $C_3$alkoxy; or $R^{16}$ and $R^{17}$, together with the atom to which they are attached, can form a 3 to 8 membered heterocycle which is optionally substituted with one or two substituents independently selected from the group consisting of $C_1$ to $C_3$alkyl, —OH, $CH_2OH$, —$CH_2OCH_3$, —$CO_2CH_3$, and —$CONH_2$;

each $R^{18}$ and $R^{19}$ is, independently, $C_1$ to $C_3$alkyl;

each $R^{20}$ is independently H, phenyl, or the side chain of a naturally occurring alpha amino acid;

each $R^{22}$ is independently arylalkyl optionally substituted with $CH_2COOH$; and each $R^{23}$ is phenyl;

or a pharmaceutically acceptable salt thereof.

Compounds of Formula II can be synthesized as described in U.S. Pat. No. 7,576,215, incorporated herein by reference. The compound of formula II can be any of compounds 26-32, or a pharmaceutically acceptable salt thereof.

26

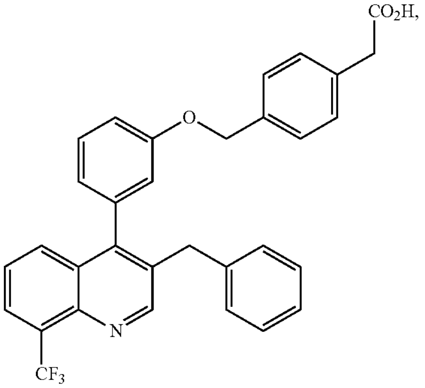

27

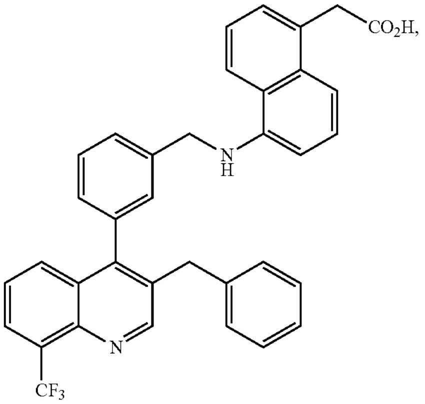

-continued

28

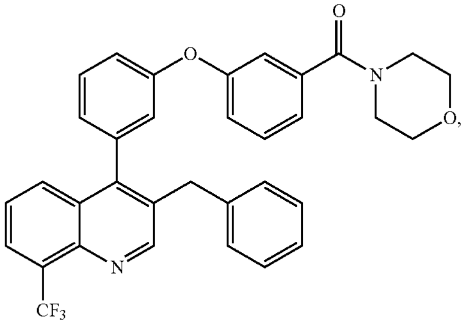

29

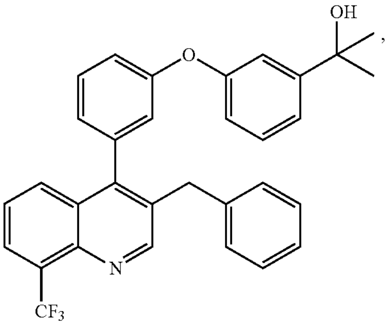

30

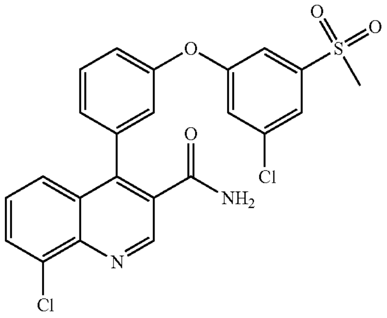

31

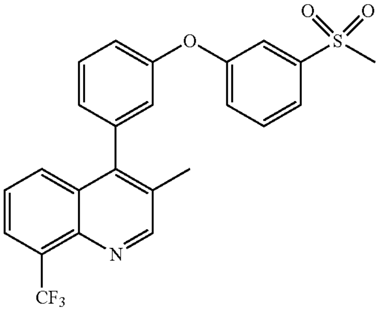

32

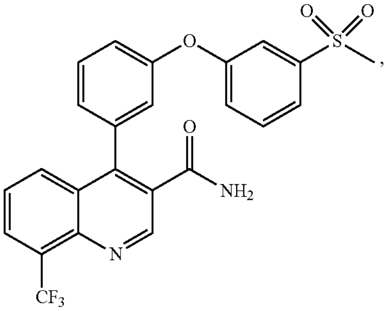

Formula III is provided below:

Formula III

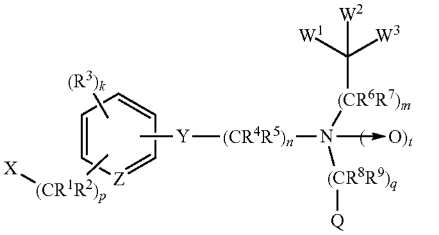

wherein:

X is selected from hydrogen, $C_1$-$C_8$ alkyl, halo, —$OR^{10}$, —$NR^{10}R^{11}$, nitro, cyano, —$COOR^{10}$, or —$COR^{10}$.

Z is CH, $CR^3$ or N, wherein when Z is CH or $CR^3$, k is 0-4 and t is 0 or 1, and when Z is N, k is 0-3 and t is 0;

Y is selected from —O—, —S—, —$N(R^{12})$—, and —$C(R^4)(R^5)$—;

$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$alkyl-C(O)$SR^{12}$, —$C_0$-$C_6$alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$alkyl-$OR^{12}$, —$C_0$-$C_6$alkyl-$SO_3H$, —$C_0$-$C_6$alkyl-$SO_2NR^{13}R^{14}$, —$C_0$-$C_6$alkyl-$SO_2R^{12}$, —$C_0$-$C_6$alkyl-$SOR^{15}$, —$C_0$-$C_6$alkyl$OCOR^{15}$, —$C_0$-$C_6$alkyl-OC(O)$NR^{13}R^{14}$, —$C_0$-$C_6$alkyl-OC(O)$OR^{15}$, —$C_0$-$C_6$ alkyl-$NR^{13}$C(O)$OR^{15}$, —$C_0$-$C_6$ alkyl-$NR^{13}$C(O)$NR^{13}R^{14}$, and-$C_0$-$C_6$ alkyl-$NR^{13}COR^{15}$, where said $C_1$-$C_6$ alkyl, is optionally unsubstituted or substituted by one or more halo substituents;

$W^2$ is selected from H, halo, $C_1$-$C_6$alkyl, $C_2$-$C_6$alkenyl, $C_2$-$C_6$ alkynyl, —$C_0$-$C_6$ alkyl-$NR^{13}R^{14}$, —$C_0$-$C_6$alkyl-$SR^{12}$, —$C_0$-$C_6$ alkyl-$OR^{12}$, —$C_0$-$C_6$alkyl$CO_2R^{12}$, —$C_0$-$C_6$alkyl-C(O)$SR^{12}$, —$C_0$-$C_6$ alkyl$CONR^{13}R^{14}$, —$C_0$-$C_6$alkyl-$COR^{15}$, —$C_0$-$C_6$ alkyl$OCOR^{15}$, —$C_0$-$C_6$alkyl-$OCONR^{13}R^{14}$, —$C_0$-$C_6$alkyl-$NR^{13}CONR^{13}R^{14}$, —$C_0$-$C_6$ alkyl-$NR^{13}COR^{15}$, —$C_0$-$C_6$alkyl-Het, —$C_0$-$C_6$alkyl-Ar and —$C_0$-$C_6$alkyl-$C_3$-$C_7$ cycloalkyl, wherein said $C_1$-$C_6$ alkyl is optionally unsubstituted or substituted by one or more halo substituents, and wherein the $C_3$-$C_7$cycloalkyl, Ar and Het moieties of said —$C_0$-$C_6$alkyl-Het, —$C_0$-$C_6$alkyl-Ar and —$C_0$-$C_6$alkyl-$C_3$-$C_7$cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$alkyl-$CO_2R^{12}$, —$C_0$-$C_6$ alkyl-C(O)$SR^{12}$, —$C_0$-$C_6$alkyl-$CONR^{13}R^{14}$, —$C_0$-$C_6$alkyl-$COR^{15}$, —$C_0$-$C_6$alkyl-$NR^{13}R^{14}$, —$C_0$-$C_6$alkyl-$SR^{12}$, —$C_0$-$C_6$alkyl-$OR^{12}$, —$C_0$-$C_6$ alkyl-$SO_3H$, —$C_0$-$C_6$alkyl-$SO_2NR^{13}R^{14}$, —$C_0$-$C_6$alkyl-$SO_2R^{12}$, —$C_0$-$C_6$alkyl-$SOR^{15}$, —$C_0$-$C_6$alkyl-$OCOR^{15}$, —$C_0$-$C_6$alkylOC(O)$NR^{13}R^{14}$, —$C_0$-$C_6$alkyl-OC(O)$OR^{15}$, —$C_0$-$C_6$alkyl-$NR^{13}$C(O)$OR^{15}$, —$C_0$-$C_6$alkyl-$NR^{13}$C(O)$NR^{13}R^{14}$, and —$C_0$-$C_6$alkyl-$NR^{13}COR^{15}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{13}R^{14}$, —$C_0$-$C_6$alkyl$SR^{12}$, —$C_0$-$C_6$alkyl-$OR^{12}$, —$C_0$-$C_6$alkyl-$CO_2R^{12}$, —$C_0$-$C_6$alkyl-C(O)$SR^{12}$, —$C_0$-$C_6$alkyl-$CONR^{13}R^{14}$, —$C_0$-$C_6$alkyl-$COR^{15}$, —$C_0$-$C_6$alkyl-$OCOR^{15}$, —$C_0$-$C_6$ alkyl-$OCONR^{13}R^{14}$, —$C_0$-$C_6$alkyl$NR^{13}CONR^{13}R^{14}$ —$C_0$-$C_6$alkyl-$NR^{13}COR^{15}$, —$C_0$-$C_6$alkyl-Het, —$C_1$-$C_6$alkyl-Ar and —$C_1$-$C_6$alkyl-$C_3$-$C_7$cycloalkyl, wherein said $C_1$-$C_6$ alkyl is optionally unsubstituted or substituted by one or more halo substituents;

Q is selected from $C_3$-$C_8$cycloalkyl, Ar and Het; wherein said $C_3$-$C_8$cycloalkyl, Ar and Het are optionally unsubstituted or substituted with one or more groups independently selected from halo, cyano, nitro, $C_1$-$C_6$alkyl, $C_3$-$C_6$alkenyl, $C_3$-$C_6$alkynyl, —$C_0$-$C_6$alkyl$CO_2R^{12}$, —$C_0$-$C_6$ alkyl-C(O)$SR^{12}$, —$C_0$-$C_6$alkyl$CONR^{13}R^{14}$, —$C_0$-$C_6$ alkyl-$COR^{15}$, —$C_0$-$C_6$alkyl$NR^{13}R^{14}$, —$C_0$-$C_6$alkyl-$SR^{12}$, —$C_0$-$C_6$alkyl-$OR^{12}$, —$C_0$-$C_6$ alkyl-$SO_3H$, —$C_0$-$C_6$ alkyl-$SO_2NR^{13}R^{14}$, —$C_0$-$C_6$alkyl-$SO_2R^{12}$, —$C_0$-$C_6$alkyl-$SOR^{15}$, —$C_0$-$C_6$alkyl-$OCOR^{15}$, —$C_0$-$C_6$alkyl-OC(O)$NR^{13}R^{14}$, —$C_0$-$C_6$alkyl-OC(O)$OR^{15}$, —$C_0$-$C_6$alkyl$NR^{13}$C(O)$OR^{15}$, —$C_0$-$C_6$ alkyl-$NR^{13}$C(O)$NR^{13}R^{14}$, and —$C_0$-$C_6$alkyl-$NR^{13}COR^{15}$, where said $C_1$-$C_6$alkyl is optionally unsubstituted or substituted by one or more halo substituents;

p is 0-8;

n is 2-8;

m is 0 or 1;

q is 0 or 1;

t is 0 or 1;

each $R^1$ and $R^2$ are independently selected from H, halo, $C_1$-$C_6$alkyl, $C_3$-$C_6$alkenyl, $C_3$-$C_6$ alkynyl, —$C_0$-$C_6$alkyl-$NR^{13}R^{14}$, —$C_0$-$C_6$alkyl-$OR^{12}$, —$C_0$-$C_6$ alkyl-$SR^{12}$, —$C_1$-$C_6$alkyl-Het, —$C_1$-$C_6$alkyl-Ar and —$C_1$-$C_6$alkyl-$C_3$-$C_7$cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$alkenyl, $C_3$-$C_6$alkynyl, —$C_0$-$C_6$alkyl-Ar, —$C_0$-$C_6$alkyl-Het, —$C_0$-$C_6$alkyl-$C_3$-$C_7$cycloalkyl, —$C_0$-$C_6$alkyl-$CO_2R^{12}$, —$C_0$-$C_6$alkyl-C(O)$SR^{12}$, —$C_0$-$C_6$alkyl-$CONR^{13}R^{14}$, —$C_0$-$C_6$alkyl-$COR^{15}$, —$C_0$-$C_6$alkyl-$NR^{13}R^{14}$, —$C_0$-$C_6$alkyl-$SR^{12}$, —$C_0$-$C_6$alkyl-$OR^{12}$, —$C_0$-$C_6$alkyl-$SO_3H$, —$C_0$-$C_6$alkyl$SO_2NR^{13}R^{14}$, —$C_0$-$C_6$ alkyl-$SO_2R^{12}$, —$C_0$-$C_6$alkyl$SOR^{15}$, —$C_0$-$C_6$alkyl-$OCOR^{15}$, —$C_0$-$C_6$ alkyl-OC(O)$NR^{13}R^{14}$, —$C_0$-$C_6$alkyl-OC(O)$OR^{15}$, —$C_0$-$C_6$alkyl-$NR^{13}$C(O)$OR^{15}$, —$C_0$-$C_6$alkyl-$NR^{13}$C(O)$NR^{13}R^{14}$, and —$C_0$-$C_6$alkyl-$NR^{13}COR^{15}$, wherein said $C_1$-$C_6$alkyl is optionally unsubstituted or substituted by one or more halo substituents;

each $R^4$ and $R^5$ is independently selected from H, halo, $C_1$-$C_6$alkyl, —$C_0$-$C_6$alkyl-Het, —$C_0$-$C_6$alkyl-Ar and —$C_0$-$C_6$alkyl-$C_3$-$C_7$cycloalkyl;

$R^6$ and $R^7$ are each independently selected from H, halo, $C_1$-$C_6$ alkyl, —$C_0$-$C_6$alkyl-Het, —$C_0$-$C_6$ alkyl-Ar and —$C_0$-$C_6$alkyl-$C_3$-$C_7$cycloalkyl;

$R^8$ and $R^9$ are each independently selected from H, halo, $C_1$-$C_6$ alkyl, —$C_0$-$C_6$alkyl-Het, —$C_0$-$C_6$ alkyl-Ar and —$C_0$-$C_6$alkyl-$C_3$-$C_7$ cycloalkyl;

$R^{10}$ and $R^{11}$ are each independently selected from H, $C_1$-$C_{12}$ alkyl, $C_3$-$C_{12}$alkenyl, $C_3$-$C_{12}$alkynyl, —$C_0$-$C_8$alkyl-Ar, —$C_0$-$C_8$ alkyl-Het, —$C_0$-$C_8$ alkyl-$C_3$-$C_7$ cycloalkyl, —$C_0$-$C_8$ alkyl-O—Ar, —$C_0$-$C_8$alkyl-O-Het, —$C_0$-$C_8$ alkyl-O—$C_3$-$C_7$cycloalkyl, —$C_0$-$C_8$alkyl-S(O)$_x$— $C_0$-$C_6$alkyl, —$C_0$-$C_8$alkyl-S(O)$_x$—Ar, —$C_0$-$C_8$ alkyl-S(O)$_x$-Het, —$C_0$-$C_8$ alkyl-S(O)$_x$—$C_3$-$C_7$cycloalkyl, —$C_0$-$C_8$alkyl-NH—Ar, —$C_0$-$C_8$alkyl-NH-Het, —$C_0$-$C_8$alkyl-NH—$C_3$-$C_7$cycloalkyl, —$C_0$-$C_8$alkyl-N($C_1$-$C_4$ alkyl)-Ar, —$C_0$-$C_8$alkyl-N($C_1$-$C_4$alkyl)-Het, —$C_0$-$C_8$alkyl-N($C_1$-$C_4$alkyl-$C_3$-$C_7$cycloalkyl, —$C_0$-$C_8$alkyl-Ar, —$C_0$-$C_8$alkyl-Het and —$C_0$-$C_8$alkyl-$C_3$-$C_7$cycloalkyl, where x is 0, 1, or 2, or $R^{10}$ and $R^{11}$, together with the nitrogen to which they are attached, form a 4-7 membered heterocyclic ring which optionally contains one or more additional heteroatoms selected from N, O, and S, wherein said $C_1$-$C_{12}$alkyl, $C_3$-$C_{12}$ alkenyl, or $C_3$-$C_{12}$alkynyl is optionally substituted by one or more of the substituents independently selected from the group halo, —OH, —SH, —$NH_2$, —NH(unsubstituted $C_1$-$C_6$alkyl), —N(unsubstituted $C_1$-$C_6$ alkyl)(unsubstituted $C_1$-$C_6$alkyl), unsubstituted —$OC_1$-$C_6$ alkyl, —$CO_2$H, —$CO_2$(unsubstituted $C_1$-$C_6$ alkyl), —$CONH_2$, —CONH (unsubstituted $C_1$-$C_6$ alkyl), —CON(unsubstituted $C_1$-$C_6$ alkyl)(unsubstituted $C_1$-$C_6$ alkyl), —$SO_3$H, —$SO_2NH_2$, —$SO_2$NH(unsubstituted $C_1$-$C_6$alkyl) and —$SO_2$N(unsubstituted $C_1$-$C_6$alkyl)(unsubstituted $C_1$-$C_6$ alkyl);

$R^{12}$ is selected from H, $C_1$-$C_6$ alkyl, $C_3$-$C_6$alkenyl, $C_3$-$C_6$alkynyl, —$C_0$-$C_6$alkyl-Ar, —$C_0$-$C_6$alkyl-Het and —$C_0$-$C_6$alkyl-$C_3$-$C_7$cycloalkyl;

each $R^{13}$ and each $R^{14}$ are independently selected from H, $C_1$-$C_6$alkyl, $C_3$-$C_6$alkenyl, $C_3$-$C_6$alkynyl, —$C_0$-$C_6$alkyl-Ar, —$C_0$-$C_6$alkyl-Het and-$C_0$-$C_6$alkyl-$C_3$-$C_7$cycloalkyl, or $R^{13}$ and $R^{14}$ together with the nitrogen to which they are attached form a 4-7 membered heterocyclic ring which optionally contains one or more additional heteroatoms selected from N, O, and S;

and $R^{15}$ is selected from $C_1$-$C_6$alkyl, $C_3$-$C_6$ alkenyl, $C_3$-$C_6$alkynyl, —$C_0$-$C_6$alkyl-Ar, —$C_0$-$C_6$ alkyl-Het and —$C_0$-$C_6$ alkyl-$C_3$-$C_7$ cycloalkyl;

or a pharmaceutically acceptable salt thereof.

In some embodiments, X is hydrogen, p is 0, t is 0, Z is CH, and Y is —O—.

In further embodiments, X is hydrogen, p is 0, t is 0, Z is CH, and Y is —O—, $W^1$ and $W^2$ are phenyl, $W^3$ is hydrogen, q is 1, and $R^8$ and $R^9$ are hydrogen.

In other embodiments, X is hydrogen, p is 0, t is 0, Z is CH, and Y is —O—, $W^1$ and $W^2$ are phenyl, $W^3$ is hydrogen, q is 1, $R^8$ and $R^9$ are hydrogen, and Q is Ar.

Accordingly, the compounds of Formula III include but are not limited the compounds with structures shown below GW3965 2 and SB742881 25:

2

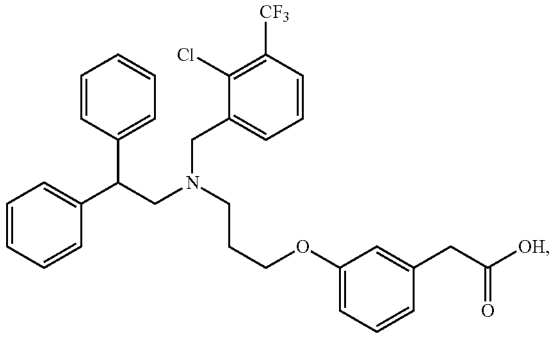

-continued

25

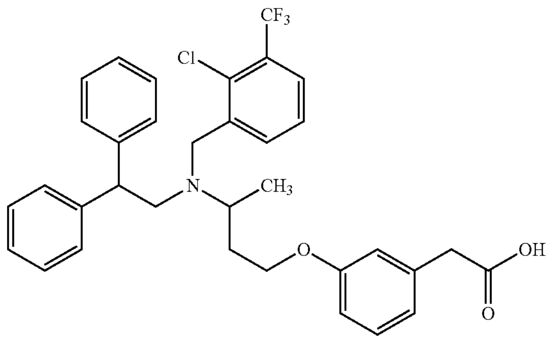

Compounds of Formula III can be synthesized as described in U.S. Pat. Nos. 7,365,085 and 7,560,586 incorporated herein by reference.

Formula IV is shown below:

Formula IV

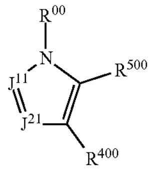

or a pharmaceutically acceptable salt thereof, wherein:

$J^{11}$ is —N= and $J^{21}$ is —$CR^{300}$—, or $J^{11}$ is —$CR^{200}$— and $J^{21}$ is =N—;

$R^{00}$ is $G^1$, $G^{21}$, or $R^N$;

$R^{200}$ is $G^1$, $G^{21}$, or $R^C$;

$R^{300}$ and $R^{400}$ are independently $R^C$ or Q, provided one and only one of $R^{300}$, $R^{400}$, and $R^{500}$ is

Q;

Q is $C_{3-6}$ cycloalkyl, heteroaryl or heterocyclyl, each optionally substituted with 1 to 4$R^Q$, or Q is —X— Y—Z; wherein each $R^Q$ is independently aryloxy, aralkyloxy, aryloxyalkyl, aryl$C_0$-$C_6$alkylcarboxy, $C(R^{110})$=$C(R^{110})$— COOH, oxo, =S, —Z, —Y'—Z, or —X—Y—Z, wherein each $R^Q$ is optionally substituted with 1 to 4 $R^{80}$;

$R^{500}$ is $G^1$ $G^{21}$, Q, or $R^C$; provided that only one of $R^{00}$, $R^{200}$, and $R^{500}$ is $G^1$ and only one of $R^{00}$, N=, and $R^{500}$ is $G^{21}$;

$G^{21}$ is -$J^0$-$K^o$, wherein $J^0$and $K^0$ are independently aryl or heteroaryl, each optionally substituted with one to four $R^K$ groups; each $R^K$ is independently hydrogen, halogen, $CR^{110}$=$CR^{110}COOR^{110}$, nitro, —Z, —Y—Z, or —X—Y—Z;

$G^1$ is -$L^{10}$-R, wherein $L^{10}$ is a bond, $L^{50}$, $L^{60}$, -$L^{50}$-$L^{60}$-$L^{50}$-, or -$L^{60}$-$L^{50}$-$L^{50}$-, wherein each $L^{50}$ is independently —$[C(R^{150})_2]_m$—;

each $L^{60}$ is independently —CS—, —CO—, —$SO_2$—, —O—, —CON($R^{110}$)—, —$CONR^{110}N(R^{110})$—, —C(=$NR^{110}$)—, —C($NOR^{11}$)—, —C(=N—N($R^{110}$)$_2$)—, —$C_3$-$C_8$cycloalkyl-, or -heterocyclyl-, wherein the cycloalkyl or heterocyclyl is optionally substituted with one to 4 $R^{140}$ groups; or or each $L^{60}$ is independently $C_2$-$C_6$ alidiyl, wherein the alidiyl chain is optionally interrupted by —$C(R^{100})_2$—, —C($R^{110}$)$_2$C($R^{110}$)$_2$—, —C($R^{11}$)C($R^{110}$)—, —C($R^{110}$)$_2$O—, —C($R^{110}$)$_2$NR$^{110}$—, —C C—, —O—, —S—, —N(RO)CO—, —N($R^{100}$)CO$_2$—, —CON($R^{110}$)—, —CO—, —CO$_2$—, —OC(═O)—, —OC(═O)N($R^{100}$)—, —SO$_2$—, —N($R^{100}$)SO$_2$—, or —SO$_2$N($R^{100}$);

R is aryl, heterocyclyl, heteroaryl or —($C_3$-$C_6$)cycloalkyl, wherein R is optionally substituted with 1 to 4 $R^4$, wherein each $R^A$ is independently halogen, nitro, heterocyclyl, $C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_1C_6$ alkenyl-, arylalkyl, aryloxy, aryl$C_{1-6}$ alkoxy, $C_1$-$C_6$ haloalkyl, SO$_2$R$^{110}$, OR$^{110}$, SR$^{110}$, N$_3$, SOR$^{110}$, COR$^{110}$, SO$_2$N($R^{110}$)$_2$, SO$_2$NR$^{110}$COR$^{110}$, C═N, C(O)OR$^{110}$, CON($R^{110}$)$_2$, —CON($R^{110}$)OR$^{110}$, OCON($R^{110}$)$_2$, —NR$^{110}$COR$^{110}$, NR$^{110}$CON($R^{110}$)$_2$, NR$^{110}$COOR$^{110}$, —C(═N—OH)R$^{110}$, —C(═S)N($R^{110}$)$_2$, —S(═O)N($R^{110}$)$_2$, —S(═O)OR$^{110}$, —N($R^{110}$)S(═O)$_2$R$^{110}$, —C(═O)N($R^{110}$)N($R^{110}$)$_2$, —OC(═O)—R$^{110}$, —OC(═O)—OR$^{110}$ or N($R^{11}$)$_2$, wherein each $R^A$ is optionally substituted with 1 to 4 groups which independently are -halogen, —$C_1$-$C_6$ alkyl, aryloxy, $C_{0-6}$ alkylSO$_2$R$^{110}$, $C_{0-6}$ alkylCOOR$^{110}$, $C_{1-6}$ alkoxyaryl, $C_1$-$C_6$ haloalkyl, —SO$_2$R$^{110}$, —OR$^{110}$, —SR$^{110}$, —N$_3$, —SO$_2$R$^{110}$, —COR$^{110}$, —SO$_2$N($R^{110}$)$_2$, —SO$_2$NR$^{110}$COR$^{110}$, —C≡N, —C(O)OR$^{110}$, —CON($R^{110}$)$_2$, —CON($R^{110}$)OR$^{110}$, —OCON($R^{110}$)$_2$, —NR$^{110}$COR$^{110}$, —NR$^{110}$CON($R^{110}$)$_2$, —NR$^{110}$COOR$^{110}$, or —N($R^{110}$)$_2$;

$R^N$ is -$L^{31}$-$R^{60}$, wherein $L^{31}$ is a bond, —$X^3$(CH$_z$)$_n$—$X^3$—, —(CH$_2$)$_m$—$X^3$—(CH$_2$)$_n$— or —(CH$_2$)$_{1+w}$, —$Y^3$—(CH$_2$)$_w$—, wherein each w is independently 0-5; and each $X^3$ is independently a bond, —C($R^{110}$)$_2$—, —C($R^{110}$)$_2$C($R^{110}$)$_2$—, —C($R^{110}$)═C($R^{110}$)—, —C≡C—, —CO—, —CS—, —CONR$^{100}$—, —C(═N)($R^{100}$)—, —C(═N—OR$^{110}$)—, —C[═N—N($R^{110}$)$_2$], —CO$_2$—, —SO$_2$—, or —SO$_2$N($R^{110}$)—; and $Y^3$ is —O—, —S—, —NR$^{70}$—, —N($R^{100}$)CO—, —N($R^{110}$)CO$_2$—, —OCO—, —OC(═O)N($R^{100}$)—, —NR$^{100}$CONR$^{100}$—, —N($R^{110}$)SO$_2$—, or —NR$^{100}$CSNR$^{100}$—;

or $L^{31}$ is $C_2$-6 alidiyl chain wherein the alidiyl chain is optionally interrupted by —C($R^{110}$)$_2$—, —C($R^{110}$)$_2$C($R^{110}$)$_2$—, —C($R^{110}$)═C($R^{110}$)—, —C($R^{110}$)$_2$O—, —C($R^{110}$)$_2$NR$^{110}$—, —C≡C—, —O—, —S—, —N($R^{100}$)CO—, —N($R^{100}$)CO$_2$—, —CON($R^{100}$)—, —CO—, —CO$_2$—, —OC(═O)—, —OC(═O)N($R^{110}$)—, —SO$_2$—, —N($R^{100}$)SO$_2$—, or —SO$_2$N($R^{100}$); and $R^{60}$ is $C_1$-$C_6$ alkyl, $C_1$-$C_6$ halo alkyl, aryl, $C_3$-$C_8$ cycloalkyl, heteroaryl, heterocyclyl, —CN, —C(═O)R$^{110}$, —C(═O)OR$^{110}$, —C(═O)N($R^{110}$)$_2$, —N($R^{110}$)$_2$, —SO$_2$R$^{110}$, —S(═O)$_2$N($R^{110}$)$_2$, —C(═O)N($R^{110}$)N($R^{110}$)$_2$, or —C(═O)N($R^{11}$)(OR$^{110}$), wherein the aryl, heteroaryl, cycloalkyl, or heterocyclyl is optionally substituted with 1 to 4 $R^{60a}$, wherein each $R^{60a}$ is independently —Z, —Y'—Z, or —X—Y—Z;

each $R^C$ is independently -$L^{30}$-$R^{70}$, wherein each $L^{30}$ is independently a bond or —(CH$_2$)$_m$—$V^{10}$—(CH$_2$)$_n$—, wherein $V^{10}$ is —C($R^{110}$)$_2$—, —C($R^{110}$)$_2$C($R^{110}$)$_2$, —C($R^{110}$)═C($R^{110}$)—, —C($R^{110}$)$_{20}$—, —C($R^{110}$)$_2$NR$^{110}$—, —C≡C—, —O—, —S—, —NR$^{10}$—, —N($R^{100}$)CO—, —N($R^{100}$)CO$_2$—, —OCO—, —CO—, —CS—, —CONR$^{100}$—, —C(═N—R$^{110}$)—, —C(═N—OR$^{110}$)—, —C[═N—N($R^{110}$)$_2$], —CO$_2$—, —OC(═O)—, —OC(═O)N($R^{100}$)—, SO$_2$—, —N($R^{100}$)SO$_2$—, —SO$_2$N($R^{100}$)—, —NR$^{100}$CONR$^{100}$—, —NR$^{100}$CSNR$^{100}$, $C_3$-$C_6$cyclo alkyl, or $C_3$-$C_6$ cyclohaloalkyl; or each $L^{30}$ is independently $C_2$-$C_6$ alidiyl, wherein the alidiyl chain is optionally interrupted by —C($R^{110}$)$_2$—, —C($R^{110}$)$_2$C($R^{110}$)$_2$—, —C($R^{110}$)C($R^{110}$)—, —C($R^{110}$)$_{20}$—, —C($R^{110}$)$_2$NR$^{110}$—, —C≡C—, —O—, —S—, —N($R^{100}$)CO—, —N($R^{100}$)CO$_2$—, —NR$^{110}$—, —CON($R^{100}$)—, —CO—, —CO$_2$—, —O(C═O)—, —O(C—O)N($R^{100}$)—, —SO$_2$—, —N($R^{100}$)SO$_2$—, or —SO$_2$N($R^{100}$)—;

each $R^{70}$ is independently hydrogen, halogen, nitro, aryl, heteroaryl, heterocyclyl, —Z, —Y—Z, or —X—YZ, wherein the aryl, heteroaryl, and heterocyclyl, are each optionally substituted with 1 to 4 $R^{70a}$, wherein each $R^{70a}$ is independently aryloxy, aralkyloxy, aryloxyalkyl, aryl$C_o$-$C_6$alkylcarboxy, C($R^{110}$)═C($R^{110}$)COOH, oxo, —Z, —Y'—Z, or —X— Y—Z, wherein each $R^{70a}$ $^{a}$ *is optionally substituted with* 1 to 4 $R^{80}$, and wherein each $R^{80}$ is independently halogen, $C_1$-$C_6$ alkyl, $C_1$-$C_6$ alkoxy, $C_1$-$C_8$haloalkyl, $C_1$-$C_8$ haloalkyl(OR$^{110}$), $C_0$-$C_6$ alkylOR$^{110}$, $C_0$-$C_6$ alkylCON($R^{110}$)$_2$, $C_0$-$C_6$ alkylCOR$^{110}$, $C_0$-$C_6$ alkylCOOR$^{110}$, or $C_0$-$C_6$ alkylSO$_2$R$^{110}$, each $R^{100}$ is independently —R$^{110}$, —C(═O)R$^{110}$, —CO$_2$R$^{110}$, or —SO$_2$R$^{110}$;

each $R^{110}$ is independently -hydrogen, —$C_1$-$C_6$ alkyl, $C_2$-$C_6$ alkenyl, $C_1$-$C_6$ alkynyl, —$C_1$-$C_6$ haloalkyl, or —N($R^{12}$)$_2$, wherein any of $R^{110}$ is optionally substituted with 1 to 4 radicals of $R^{120}$;

each $R^{120}$ is independently halogen, cyano, nitro, oxo, —B(OR$^{130}$), $C_0$-$C_6$ alkylN($R^{13}$)$_2$, $C_1$-$C_6$haloalkyl, $C_1$-$C_6$ alkyl, $C_1$-$C_6$ alkoxy, ($C_0$-$C_6$ alkyl)C—O(OR$^{130}$), $C_0$-$C_6$ alkylOR$^{130}$, $C_0$-$C_6$ alkylCOR$^{130}$, $C_0$-$C_6$alkylSO$_2$R$^{130}$, $C_0$-$C_6$alkylCON($R^{13}$)$_2$, $C_0$-$C_6$alkylCONR$^{130}$OR$^{130}$, $C_0$-$C_6$alkylSO$_2$N($R^{130}$)$_2$, $C_0$-$C_6$alkylSR$^{130}$, $C_0$-$C_6$ haloalkylOR$^{130}$, $C_0$-$C_6$alkylCN, —$C_0$-$C_6$alkyN($R^{13}$)$_2$, —NR$^{13}$SO$_2$R$^{13}$, or —O$C_{0-6}$ alkylCOOR$^{130}$;

each $R^{130}$ is independently hydrogen, $C_1$-$C_6$ alkyl, $C_2$-$C_6$ alkenyl, or $C_2$-$C_6$ alkynyl;

each $R^{140}$ is independently $C_1$-$C_6$ alkyl, $C_1$-$C_6$ alkoxy, halogen, $C_1$-$C_6$ haloalkyl, $C_0$-$C_6$ alkylCON($R^{110}$)$_o$, $C_0$-$C_6$ alkylCONR$^{110}$R$^{10}$, $C_0$-$C_6$ alkylOR$^{110}$, or $C_0$-$C_6$ alkylCOOR$^{110}$; and each $R^{150}$ is independently hydrogen, halogen, OR$^{130}$, ($C_1$-$C_6$)alkyl or ($C_1$-$C_6$)haloalkyl, wherein each alkyl is optionally substituted with at least one group which are each independently halogen, cyano, nitro, azido, OR$^{130}$, C(O)R$^{130}$, C(O)OR$^{13}$C(O)N($R^{130}$)$_2$, N($R^{130}$)$_2$, N($R^{130}$)C(O)R$^{130}$, N($R^{130}$)S(O)$_2$R$^{130}$, —OC(O)OR$^{130}$, OC(O)N($R^{130}$)$_2$, N($R^{130}$)C(O)OR$^{130}$, N($R^{130}$)C(O)N($R^{130}$), SR$^{130}$, S(O)R$^{130}$, S(O)$_2$R', or S(O)$_2$N($R^{130}$)$_2$; or two $R^{150}$ (bonded to same or different atoms) can be taken together to form a C3-C6 cycloalkyl;

each X is independently —O—, —S—, or —N($R^{100}$)—;

each Y is independently —[C($R^{150}$)$_2$]$_p$—, or —$C_2$-$C_6$ alkenyl, wherein p is 1, 2, 3, 4, 5, or 6;

each Y' is independently —[C($R^{150}$)$_2$]$_p$—, —$C_2$-$C_6$ alkenyl $C_3$-$C_8$ cycloalkyl, or heterocyclyl, wherein the cycloalkyl or heterocyclyl is optionally substituted with 1 to 3 Z groups;

each Z is independently —H, halogen, —OR$^{110}$, —SR$^{110}$, —C(═O)R$^{110}$, —C(═O)OR$^{110}$, —C(═O)N($R^{110}$)$_2$, $—N(R^{100})_2$, $—N_3$, $—NO_2$, $—C(=N—OH)R^{110}$, $—C(=S)N(R^{110})_2$, —CN, $—S(=O)R^{110}$, $—S(=O)N(R^{110})_2$, $—S(=O)OR^{110}$, $—S(=O)_2R^{110}$, $S(=O)_2N(R^{110})_2$, $—NR^{110}COR^{110}$, $—N(R^{110})C(=O)N(R^{110})_2$, $—N(R^{110})COOR^{110}$, $—N(R^{110})S(=O)_2R^{110}$, $—C(=O)N(R^{110})N(R^{110})_2$, $—C(=O)N(R^{110})(OR^{110})$, $—OC(=O)—R^{110}$, $—OC(=O)—OR^{110}$, or $—OC(=O)—N(R^{110})_2$; and each m and n is independently 0, 1, 2, 3, 4, 5, or 6.

In some embodiments the compound of Formula IV has a structure of Formula V or VI:

Formula V

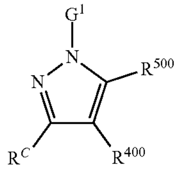

Formula VI

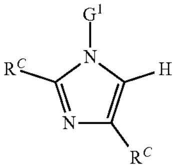

In other embodiments the compound of Formula VI has a structure of Formula VII:

Formula VII

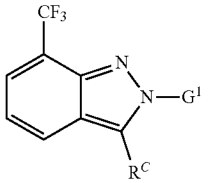

In yet other embodiments the compound of Formula VI has a structure of Formula VIII:

Formula VIII

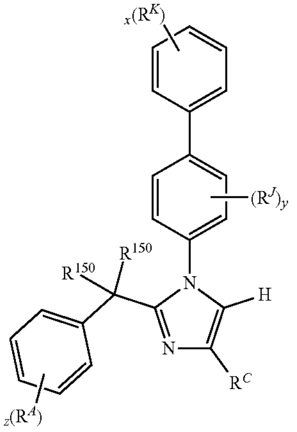

In still further embodiments the compound of Formula VI has a structure of Formula IX:

Formula IX

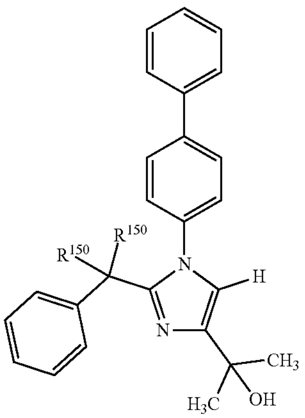

Accordingly, the compounds of Formula IV which can be useful in the methods of the invention include, but are not limited to, compounds having the structures are shown below, and pharmaceutically acceptable salts thereof:

3

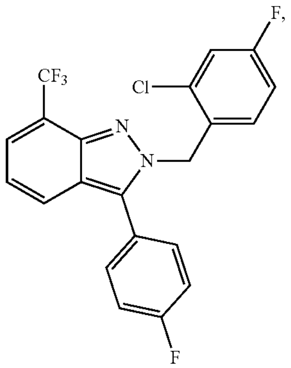

4

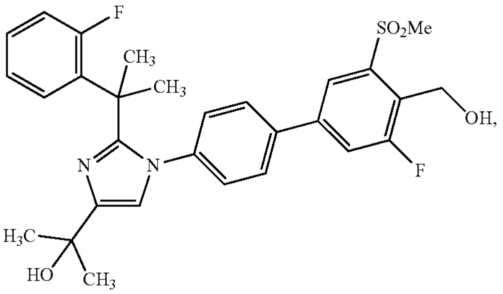

5

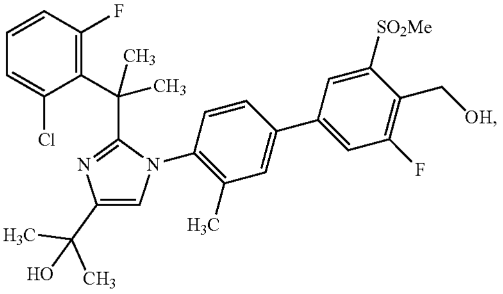

-continued
6
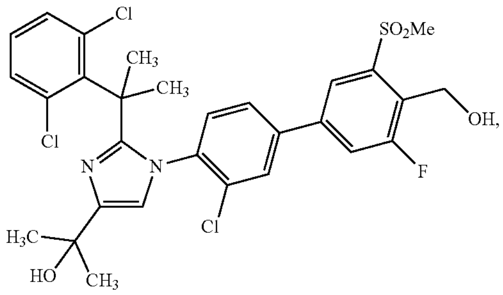
7
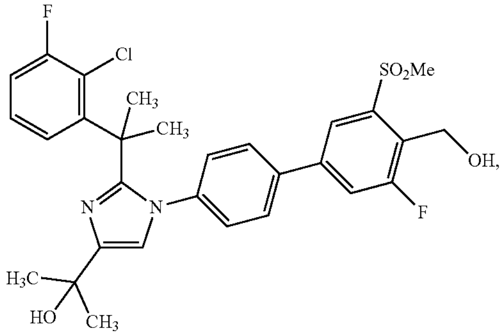
8
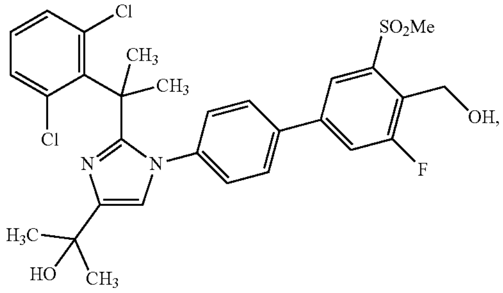
9
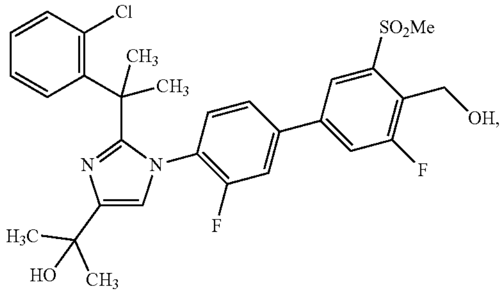
10
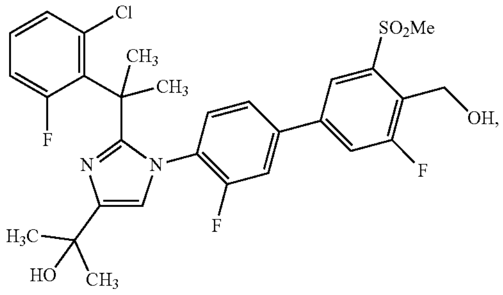
-continued
11
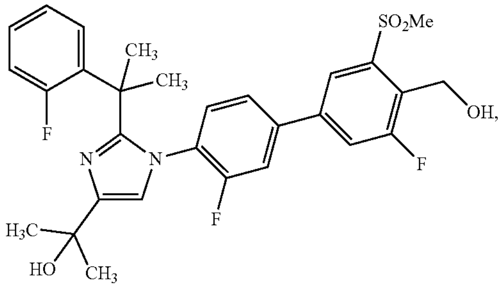
12
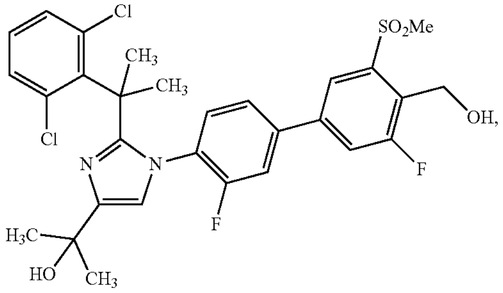
13
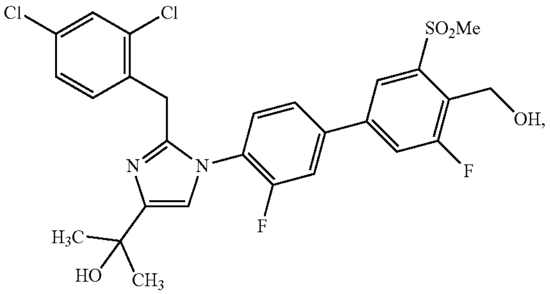
14
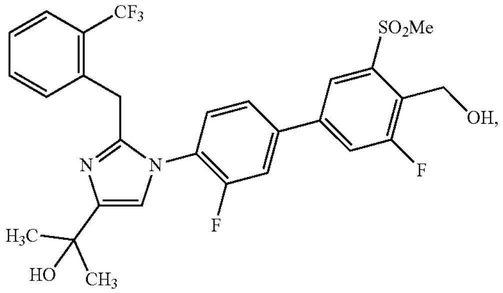
15
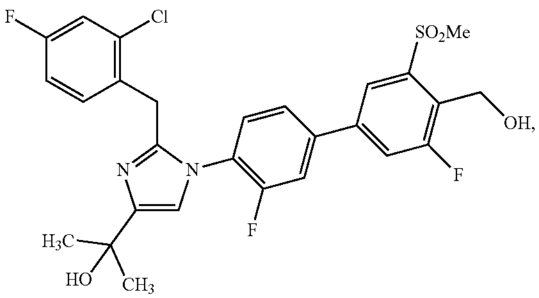

-continued
16
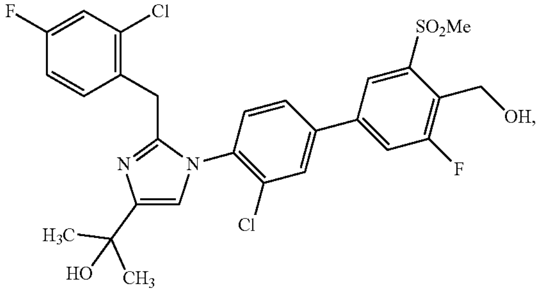
17
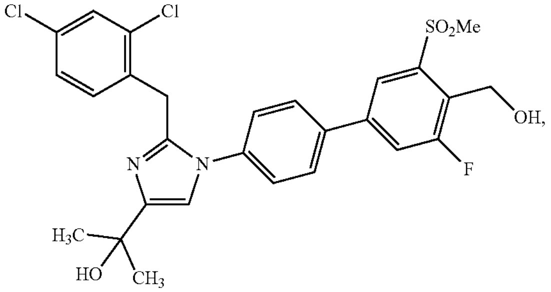
18
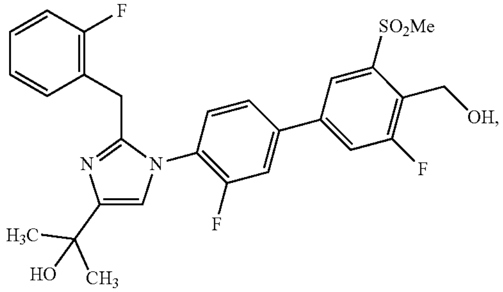
19
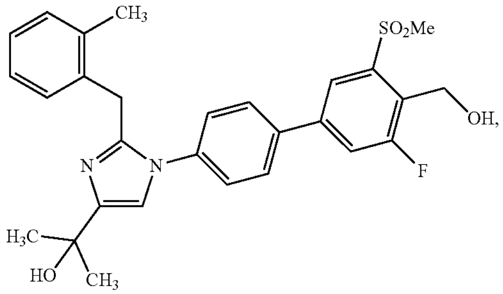
20
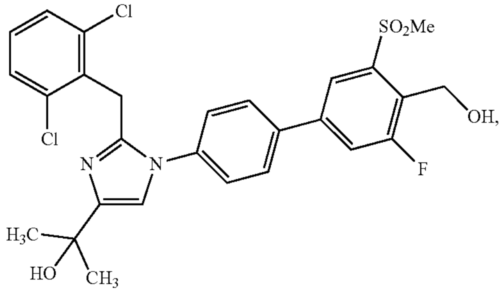
-continued
21
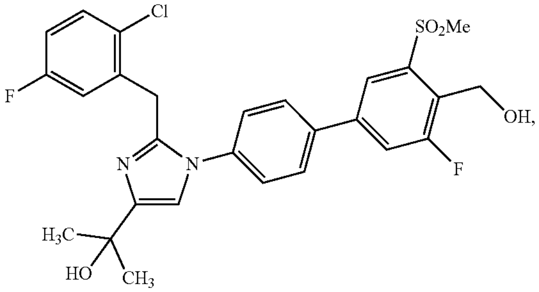
22
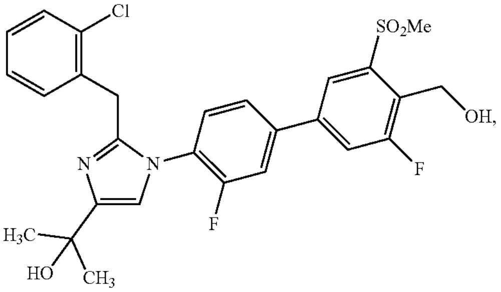
23
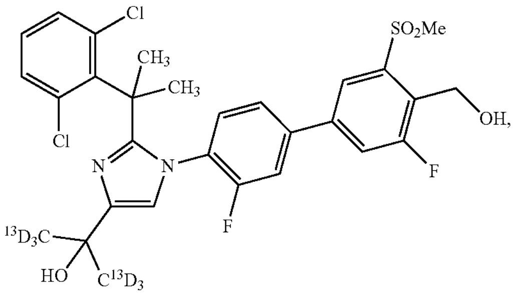
38
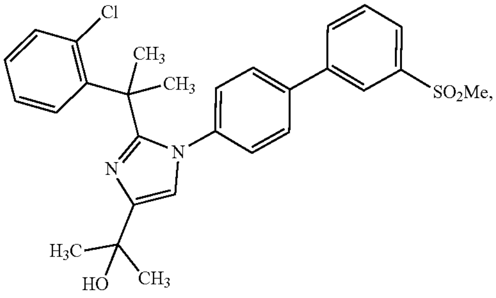

-continued

39

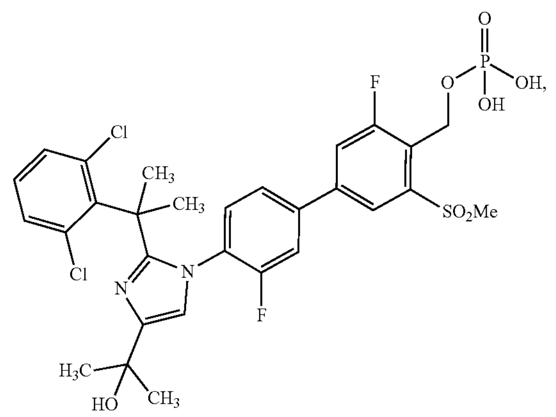

and selected from the list comprising:

33 2-(1-(3chloro-3'-fluoro-4'-(hydroxymethyl)-5'-(methylsulfonyl)biphenyl-4-yl)-2-(2-(2,6dichlorophenyl)propan-2-yl)-1H-imidazol-4-yl)propan-2-ol; 34 2-(2-(2(2-chloro-3-fluorophenyl)propan-2-yl)-1-(3'-fluoro-4'-(hydroxymethyl)-5'(methylsulfonyl)biphenyl-4-yl)-1H-imidazol-4-yl)propan-2-ol; 35 2-(2-(2(2,6-dichlorophenyl)propan-2-yl)-1-(3'-fluoro-4'-(hydroxymethyl)-5'(methylsulfonyl)biphenyl-4-yl)-1H-imidazol-4-yl)propan-2-ol; 36 2-(2-(2(2,6-dichlorophenyl)propan-2-yl)-1-(3,3'-difluoro-4'-(hydroxymethyl)-5'(methylsulfonyl)biphenyl-4-yl)-1H-imidazol-4-yl)propan-2-ol; and 37 2-(2-[1(2,6-dichlorophenyl)ethyl]-1-[3,3'-difluoro-4'-(hydroxymethyl)-5'(methylsulfonyl)biphenyl-4-yl]-1H-imidazol-4-yl)propan-2-ol. Compound 12 is also known as WO2010 0138598 Ex. 9. Compound 38 is also known WO2007 002563 Ex. 19. Compound 39 is also known as WO2012 0135082.

Compounds of Formula IV can be synthesized as described in PCT publication No. US2010/0069367 and WO2010/138598 incorporated herein by reference.

The LXR agonist that can be used for the treatment and/or prevention of metastasis can be compound 24, or a pharmaceutically acceptable salt thereof.

24

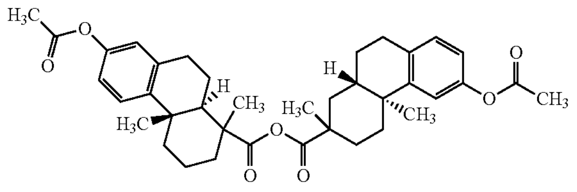

In further embodiments compounds that can be used for the treatment and/or prevention of metastasis can be found in the PCT publications in the list consisting of: WO2006/094034, WO2008/049047, WO2009/020683, WO2009/086138, WO2009/086123, WO2009/086130, WO2009/086129, WO2007/002559, WO2007/002563, WO2007/081335, WO2006/017055, WO2006/102067, WO2009/024550, US2006/0074115, US2006/0135601, WO2009/021868, WO2009/040289, WO2007/047991, WO2007/

050425, WO2006/073363, WO2006/073364, WO2006/073365, WO2006/073366, WO2006/073367, US2009/0030082, WO2008/065754, JP2008/179562, WO2007/092065, US2010/0069367, U.S. Pat. Nos. 7,998,995, 7,247,748, WO2010/138598, U.S. Pat. Nos. 7,365,085, 75,776,215, U.S. 63/136,503, US2004/0072868, US2005/0107444, US2005/0113580, US2005/0131014, US2005/0282908, US2009/0286780, incorporated herein by reference.

LXRα and LXRβ, initially discovered by multiple groups at roughly the same time (Apfel et al., 1994; Willy et al., 1995; Song et al., 1994; Shinar et al., 1994; Teboul et al., 1995), belong to a family of nuclear hormone receptors that are endogenously activated by cholesterol and its oxidized derivatives to mediate transcription of genes involved in maintaining glucose, cholesterol, and fatty acid metabolism (Janowski et al., 1996; Calkin and Tontonoz, 2012). Given the intricate link between lipid metabolism and cancer cell growth (Cairns et al., 2011), the ubiquitous expression of LXRβ in melanoma is unlikely to be coincidental, allowing melanoma cells to synthesize lipids and lipoprotein particles to sustain their growth. At the same time, however, such stable basal expression levels make LXRβ an ideal therapeutic target, as exemplified by the broad-ranging responsiveness of melanoma cells to LXRβ activation therapy.

Compounds have been shown to have selectivity for LXRβ or LXRα. This selectivity may allow for increased activity and/or decreased off target effects. Examples of compounds with selectivity towards LXRβ or LXRα are shown in Table 1.

TABLE 1

EC$_{50}$ values for selected compounds against LXRα and LXRβ

| Compound | EC$_{50}$-LXRα (nM) | EC$_{50}$-LXRβ (nM) |
|---|---|---|
| GW3965 2 | 200 | 40 |
| SB742881 25 | 74 | 25 |
| TO9013171 | 20 | 50 |
| LXR-623 3 | 179 | 24 |
| 12 | <100 | 11 |
| 38 | 101-1000 | 630 |

As used herein, reference to the activity of an LXR agonist at LXRα and LXRβ refer to the activity as measured using the ligand sensing assay (LiSA) described in Spencer et al. Journal of Medicinal Chemistry 2001, 44, 886-897, incorporated herein by reference. In some embodiments, the LXR agonist has an EC50 of less than 1 μM in the ligand sensing assay (e.g., 0.5 nm to 500 nM, 10 nM to 100 nM). For example, the methods of the invention can be performed using an LXRβ agonist having activity for LXRβ that is at least 3-fold greater than the activity of the agonist for LXRα, or having activity for LXRβ that is at least 10-fold greater than the activity of the agonist for LXRα, or having activity for LXRβ that is at least 100-fold greater than the activity of said agonist for LXRα, or having activity for LXRβ that is at least within 3-fold of the activity of the agonist for LXRα. The term "greater activity" in the LiSA assay assay refers to a lower EC50. For example, GW3965 2 has approximately 6-fold greater activity for LXRβ (EC50-30) compared to LXRα (EC50=190).

As used herein, the term "increases the level of ApoE expression in vitro" refers to certain LXR agonists capable of increasing the level of ApoE expression 2.5-fold in the qPCR assay of Example 21 at a concentration of less than 5 μM (e.g., at a concentration of 100 nM to 2 μM, at a concentration of less than or equal to 1 μM). The LXR agonists exhibiting this in vitro effect can be highly efficacious for use in the methods of the invention.

The term "alkyl" used is the present application relates a saturated branched or unbranched aliphatic univalent substituent. The alkyl substituent has 1 to 100 carbon atoms, (e.g., 1 to 22 carbon atoms, 1 to 10 carbon atoms 1 to 6 carbon atoms, 1 to 3 carbon atoms). Accordingly, examples of the alkyl substituent include methyl, ethyl, n-propyl, isopropyl, n-butyl, isobutyl, sec-butyl, tert-butyl, n-pentyl and n-hexyl.

The term "alkoxy" represents a chemical substituent of formula —OR, where R is an optionally substituted $C_1$-$C_6$ alkyl group, unless otherwise specified. In some embodiments, the alkyl group can be substituted, e.g., the alkoxy group can have 1, 2, 3, 4, 5 or 6 substituent groups as defined herein.

The term "alkoxyalkyl" represents a heteroalkyl group, as defined herein, that is described as an alkyl group that is substituted with an alkoxy group. Exemplary unsubstituted alkoxyalkyl groups include between 2 to 12 carbons. In some embodiments, the alkyl and the alkoxy each can be further substituted with 1, 2, 3, or 4 substituent groups as defined herein for the respective group.

As used herein, the term "cycloalkyl" refers to a monocyclic, bicyclic, or tricyclic substituent, which may be saturated or partially saturated, i.e. possesses one or more double bonds. Monocyclic substituents are exemplified by a saturated cyclic hydrocarbon group containing from 3 to 8 carbon atoms. Examples of monocyclic cycloalkyl substituents include cyclopropyl, cyclobutyl, cyclopentyl, cyclopentenyl, cyclohexyl, cyclohexenyl, cycloheptyl and cyclooctyl. Bicyclic fused cycloalkyl substituents are exemplified by a cycloalkyl ring fused to another cycloalkyl ring. Examples of bicyclic cycloalkyl substituents include, but are not limited to decalin, 1,2,3,7,8,8a-hexahydro-naphthalene, and the like. Tricyclic cycloalkyl substituents are exemplified by a cycloalkyl bicyclic fused ring fused to an additional cycloalkyl substituent.

The term "alkylene" used is the present application relates a saturated branched or unbranched aliphatic bivalent substituent (e.g. the alkylene substituent has 1 to 6 carbon atoms, 1 to 3 carbon atoms). Accordingly, examples of the alkylene substituent include methylene, ethylene, trimethylene, propylene, tetramethylene, isopropylidene, pentamethylene and hexamethylene.

The term "alkenylene or alkenyl" as used in the present application is an unsaturated branched or unbranched aliphatic bivalent substituent having a double bond between two adjacent carbon atoms (e.g. the alkenylene substituent has 2 to 6 carbon atoms, 2 to 4 carbon atoms). Accordingly, examples of the alkenylene substituent include but are not limited to vinylene, 1-propenylene, 2-propenylene, methylvinylene, 1-butenylene, 2-butenylene, 3-butenylene, 2-methyl-1-propenylene, 2-methyl-2-propenylene, 2-pentenylene, 2-hexenylene.

The term "alkynylene or alkynyl" as used is the present application is an unsaturated branched or unbranched aliphatic bivalent substituent having a triple bond between two adjacent carbon atoms (e.g. the alkynylene substituent has 2 to 6 carbon atoms 2 to 4 carbon atoms). Examples of the alkynylene substituent include but are not limited to ethynylene, 1-propynylene, 1-butynylene, 2-butynylene, 1-pentynylene, 2-pentynylene, 3-pentynylene and 2-hexynylene.

The term "alkadienylene" as used is the present application is an unsaturated branched or unbranched aliphatic bivalent substituent having two double bonds between two adjacent carbon atoms (e.g. the alkadienylene substituent has 4 to 10 carbon atoms). Accordingly, examples of the alkadienylene substituent include but are not limited to 2,4-pentadienylene, 2,4-hexadienylene, 4-methyl-2,4-pentadienylene, 2,4-heptadienylene, 2,6-heptadienylene, 3-methyl-2,4-hexadienylene, 2,6-octadienylene, 3-methyl-2,6-heptadienylene, 2-methyl-2,4-heptadienylene, 2,8-nonadienylene, 3-methyl-2,6-octadienylene, 2,6-decadienylene, 2,9-decadienylene and 3,7-dimethyl-2,6-octadienylene substituents.

The term "heteroaliphatic substituent or heteroalkyl", as used herein, refers to a monovalent or a bivalent substituent, in which one or more carbon atoms have been substituted with a heteroatom, for instance, with an oxygen, sulfur, nitrogen, phosphorus or silicon atom, wherein the nitrogen and sulfur atoms may optionally be oxidized, and the nitrogen heteroatom may optionally be quaternized. The heteroatom(s) O, N and S may be placed at any interior position of the heteroaliphatic substituent. Examples include —CH2-CH2-O—CH3, —CH2-CH2-NH—CH3, —CH2-CH2-N(CH3)-CH3, —CH2-S—CH2-CH3, —S(O)—CH3, —CH2-CH2-S(O)2-CH3, —CH—CH—O—CH3, —CH2-CH═N—OCH3, and —CH═CH—N(CH3)-CH3. A heteroaliphatic substituent may be linear or branched, and saturated or unsaturated.

In one embodiment, the heteroaliphatic substituent has 1 to 100, (e.g 1 to 42 carbon atoms). In yet another embodiment, the heteroaliphatic substituent is a polyethylene glycol residue.

As used herein, "aromatic substituent or aryl" is intended to mean any stable monocyclic, bicyclic or polycyclic carbon ring of up to 10 atoms in each ring, wherein at least one ring is aromatic, and may be unsubstituted or substituted. Examples of such aromatic substituents include phenyl, p-toluenyl (4-methylphenyl), naphthyl, tetrahydronaphthyl, indanyl, biphenyl, phenanthryl, anthryl or acenaphthyl. In cases where the aromatic substituent is bicyclic and one ring is non-aromatic, it is understood that attachment is via the aromatic ring.

The term "alkylaryl substituents or arylalkyl" refers to alkyl substituents as described above wherein one or more bonds to hydrogen contained therein are replaced by a bond to an aryl substituent as described above. It is understood that an arylalkyl substituents is connected to the carbonyl group if the compound of the invention through a bond from the alkyl substituent. Examples of arylalkyl substituents include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaromatic substituent or heteroaryl" as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic heteroaromatic substituents include phenyl, pyridine, pyrimidine or pyridazine rings that are a) fused to a 6-membered aromatic (unsaturated) heterocyclic ring having one nitrogen atom;
b) fused to a 5- or 6-membered aromatic (unsaturated) heterocyclic ring having two nitrogen atoms;
c) fused to a 5-membered aromatic (unsaturated) heterocyclic ring having one nitrogen atom together with either one oxygen or one sulfur atom; or
d) fused to a 5-membered aromatic (unsaturated) heterocyclic ring having one heteroatom selected from O, N or S.

Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The aliphatic, heteroaliphatic, aromatic and heteroaromatic substituents can be optionally substituted one or more times, the same way or differently with any one or more of the following substituents including, but not limited to: aliphatic, heteroaliphatic, aromatic and heteroaromatic substituents, aryl, heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; CI; Br; I; —OH; —NO2; —CN; —CF3; —CH2CF3; —CHCl2; —CH2OH; —CH2CH2OH; —CH2NH2; —CH2SO2CH3; —C(O)Rx; —CO2(Rx); —CON(Rx)2; —OC(O)Rx; —OCO2Rx; —OCON(Rx)2; —N(RX)2; —S(O)Rx; —S(O)2Rx; —NRx(CO)Rx wherein each occurrence of Rx independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, (alkyl)aryl or (alkyl)heteroaryl substituents described above and herein may be substituted or unsubstituted. Additionally, it will be appreciated, that any two adjacent substituents taken together may represent a 4, 5, 6, or 7-membered substituted or unsubstituted alicyclic or heterocyclic substituents. Additional examples of generally applicable substituents are illustrated by the specific embodiments shown below.

The terms "halo" and "halogen" refer to a halogen atom selected from the group consisting of F, Cl, Br and I.

The term "halogenated alkyl substituent, haloalkyl" refers to an alkyl substituents as defined above which is substituted with at least one halogen atom. In an embodiment, the halogenated alkyl substituent is perhalogenated. In another embodiment, perfluoroalkyl refers to the halogenated alkyl substituent is a univalent perfluorated substituent of formula CnF2n+1. For example, the halogenated alkyl substituent may have 1 to 6 carbon atoms, (e.g. 1 to 3 carbon atoms). Accordingly, examples of the alkyl group include trifluoromethyl, 2,2,2-trifluoroethyl, n-perfluoropropyl, n-perfluorobutyl and n-perfluoropentyl.

The term "amino," as used herein, represents —N(RN1)2, wherein each RN1 is, independently, H, OH, NO2, N(RN2)2, SO2ORN2, SO2RN2, SORN2, an N-protecting group, alkyl, alkenyl, alkynyl, alkoxy, aryl, alkaryl, cycloalkyl, alkcycloalkyl, heterocyclyl (e.g., heteroaryl), alkheterocyclyl (e.g., alkheteroaryl), or two RN1 combine to form a heterocyclyl or an N-protecting group, and wherein each RN2 is, independently, H, alkyl, or aryl. In a preferred embodiment, amino is —NH2, or —NHRN1, wherein RN1 is, independently, OH, NO2, NH2, NRN22, SO2ORN2, SO2RN2, SORN2, alkyl, or aryl, and each RN2 can be H, alkyl, or aryl. The term "aminoalkyl," as used herein, represents a heteroalkyl group, as defined herein, that is described as an alkyl group, as defined herein, substituted by an amino group, as defined herein. The alkyl and amino each can be further substituted with 1, 2, 3, or 4 substituent groups as described herein for the respective group. For example, the alkyl moiety may comprise an oxo (═O) substituent.

As used herein, the term "aryloxy" refers to aromatic or heteroaromatic systems which are coupled to another residue through an oxygen atom. A typical example of an O-aryl is phenoxy. Similarly, "arylalkyl" refers to aromatic and heteroaromatic systems which are coupled to another residue through a carbon chain, saturated or unsaturated, typically of C1-C8, C1-C6, or more particularly C1-C4 or C1-C3 when saturated or C2-C8, C2-C6, C2-C4, or C2-C3 when unsaturated, including the heteroforms thereof. For greater certainty, arylalkyl thus includes an aryl or heteroaryl group as defined above connected to an alkyl, heteroalkyl, alkenyl, heteroalkenyl, alkynyl or heteroalkynyl moiety also as defined above. Typical arylalkyls would be an aryl(C6-C12)alkyl(C1-C8), aryl(C6-C12)alkenyl(C2-C8), or aryl(C6-C12)alkynyl(C2-C8), plus the heteroforms. A typical example is phenylmethyl, commonly referred to as benzyl.

Typical optional substituents on aromatic or heteroaromatic groups include independently halo, CN, NO2, CF3, OCF3, COOR', CONR'2, OR', SR', SOR', SO2R', NR'2, NR'(CO)R',NR'C(O)OR', NR'C(O)NR'2, NR'SO2NR'2, or NR'SO2R', wherein each R' is independently H or an optionally substituted group selected from alkyl, alkenyl, alkynyl, heteroalkyl, heteroalkenyl, heteroalkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl and arylalkyl.

Optional substituents on a non-aromatic group (e.g., alkyl, alkenyl, and alkynyl groups), are typically selected from the same list of substituents suitable for aromatic or heteroaromatic groups, except as noted otherwise herein. A non-aromatic group may also include a substituent selected from ═O and ═NOR' where R' is H or an optionally substituted group selected from alkyl, alkenyl, alkynyl, heteroalkyl, heteroalkenyl, heteralkynyl, heteroaryl, and aryl (all as defined above).

In general, a substituent group (e.g., alkyl, alkenyl, alkynyl, or aryl (including all heteroforms defined above) may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. However, alkyl substituted by aryl, amino, halo and the like would be included. For example, where a group is substituted, the group may be substituted with 1, 2, 3, 4, 5, or 6 substituents. Optional substituents include, but are not limited to: C1-C6 alkyl or heteroaryl, C2-C6 alkenyl or heteroalkenyl, C2-C6 alkynyl or heteroalkynyl, halogen; aryl, heteroaryl, azido (—N3), nitro (—NO2), cyano (—CN), acyloxy(—OC(═O)R'), acyl (—C(═O)R'), alkoxy (—OR'), amido (—NR'C(═O)R" or —C(═O)NRR'), amino (—NRR'), carboxylic acid (—CO2H), carboxylic ester (—CO2R'), carbamoyl (—OC(═O)NR'R" or —NRC(═O)OR'), hydroxy (—OH), isocyano (—NC), sulfonate (—S(═O)2OR), sulfonamide (—S(═O)2NRR' or —NRS(═O)2R'), or sulfonyl (—S(═O)2R), where each R or R' is selected, independently, from H, C1-C6 alkyl or heteroaryl, C2-C6 alkenyl or heteroalkenyl, 2C-6C alkynyl or heteroalkynyl, aryl, or heteroaryl. A substituted group may have, for example, 1, 2, 3, 4, 5, 6, 7, 8, or 9 substituents.

The term "heterocyclyl, heterocyclic, or Het" as used herein represents cyclic heteroalkyl or heteroalkenyl that is, e.g., a 3-, 4-, 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like.

Some of the compounds of the present invention can comprise one or more stereogenic centers, and thus can exist in various isomeric forms, e.g. stereoisomers and/or diastereomers. Thus, the compounds of the invention and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided. Moreover, when compounds of the invention exist in tautomeric forms, each tautomer is embraced herein.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Treatment Methods

As disclosed herein, miR-1908, miR-199a-3p, miR-199a-5p, and CTGF were identified as endogenous metastasis promoters of metastatic invasion, endothelial recruitment, and colonization in melanoma while DNAJA4, ApoE, LRP1, LRP8, LXR, and miR7 function as metastasis suppressors or inhibitors of the same process. In addition, it was found that these miRNAs convergently target ApoE and the heat-shock factor DNAJA4. Cancer-secreted ApoE suppresses invasion and endothelial recruitment by activating melanoma cell LRP1 and endothelial LRP8 receptors, respectively. DNAJA4, in turn, induces ApoE expression. These miRNAs strongly predict human metastatic outcomes. Pre-treatment with locked nucleic acids (LNAs) targeting miR-199a-3p, miR-199a-5p, and miR-1908 inhibits metastasis to multiple organs, while therapeutic delivery of these LNAs significantly suppresses human melanoma cell metastasis in a mouse model.

Accordingly, this invention provides methods for treating melanoma via increasing in the subject the expression level or activity level of one of the metastasis suppressors. This increasing can be achieved by, among others, forced expression of one or more of the metastasis suppressors DNAJA4, ApoE, LRP1, and LRP8, or decreasing the expression level or activity level of one or more miR-199a-3p, miR-199a-5p, and miR-1908. In addition, the treatment can be achieved by decreasing the expression level or activity level of one or more of the metastasis promoters.

The invention also provides methods for treating in a subject an angiogenic disorder or a disorder of angiogenesis. The terms "angiogenic disorder," "disorder of angiogenesis," and "angiogenesis disorder" are used interchangeably herein, and refer to a disorder characterized by pathological angiogenesis. A disorder characterized by pathological angiogenesis refers to a disorder where abnormal or aberrant angiogenesis, alone or in combination with others, contributes to causation, origination, or symptom of the disorder. Examples of this disorder include various cancers (e.g., vascularized tumors), eye disorders, inflammatory disorders, and others.

Typical vascularized tumors that can be treated with the method include solid tumors, particularly carcinomas, which require a vascular component for the provision of oxygen and nutrients. Exemplary solid tumors include, but are not limited to, carcinomas of the lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, Kaposi's sarcoma, and sarcomas.

A number of disorders or conditions, other than cancer, also can be treated with the above-described method. Examples include arthritis, rheumatoid arthritis, psoriasis, atherosclerosis, diabetic retinopathy, age-related macular degeneration, Grave's disease, vascular restenosis (including restenosis following angioplasty), arteriovenous malformations (AVM), meningioma, hemangioma, neovascular glaucoma, chronic kidney disease, diabetic nephropathy, polycystic kidney disease, interstitial lung disease, pulmonary hypertension, chronic obstructive pulmonary disease (COPD), emphysema, autoimmune hepatitis, chronic inflammatory liver disease, hepatic cirrhosis, cutaneous T-cell lymphoma, rosacea, and basal cell carcinoma.

Other treatment targets include those described in, e.g., US Applications 2009004297, 20090175791, and 20070161553, such as angiofibroma, atherosclerotic plaques, corneal graft neovascularization, hemophilic joints, hypertrophic scars, Osler-Weber syndrome, pyogenic granuloma retrolental fibroplasia, scleroderma, trachoma, vascular adhesions, synovitis, dermatitis, various other inflammatory diseases and disorders, and endometriosis.

Forced Expression of Metastasis Suppressors

Both polypeptides of the aforementioned metastasis suppressors (e.g., DNAJA4, ApoE, LRP1, LRP8, and LXR) and nucleic acid encoding the polypeptides can be used to practice the invention. While many polypeptide preparations can be used, a highly purified or isolated polypeptide is preferred. The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (e.g., glycosylation or phosphorylation).

The polypeptide "of this invention" includes recombinantly or synthetically produced fusion or chimeric versions of any of the aforementioned metastasis suppressors, having the particular domains or portions that are involved in the network. The term also encompasses polypeptides that have an added amino-terminal methionine (useful for expression in prokaryotic cells).

Within the scope of this invention are fusion proteins containing one or more of the aforementioned sequences and a heterologous sequence. A "chimeric" or "fusion" refers to the combination of amino acid sequences of different origin in one polypeptide chain by in-frame combination of their coding nucleotide sequences. The term explicitly encompasses internal fusions, i.e., insertion of sequences of different origin within a polypeptide chain, in addition to fusion to one of its termini. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

An "isolated" or "purified" polypeptide refers to a polypeptide that has been separated from other proteins, lipids, and nucleic acids with which it is naturally associated. The polypeptide can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide described in the invention can be purified from a natural source, produced by recombinant DNA techniques, or by chemical methods.

A "recombinant" polypeptide refers to a polypeptide produced by recombinant DNA techniques; i.e., produced from cells transformed by an exogenous DNA construct encoding the desired polypeptide. A "synthetic" polypeptide refers to a polypeptide prepared by chemical synthesis. The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified.

"Overexpression" refers to the expression of a RNA or polypeptide encoded by a nucleic acid introduced into a host cell, wherein the RNA or polypeptide or protein is either not normally present in the host cell, or wherein the RNA or polypeptide is present in said host cell at a higher level than that normally expressed from the endogenous gene encoding the RNA or polypeptide.

The amino acid composition of each of the above-mentioned polypeptides may vary without disrupting their functions—the ability to up-regulate the above-mentioned network (e.g., increase the activation level of the ApoE/LRP signaling pathway), thereby inhibiting metastasis to multiple organs. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in one of the above-described polypeptides (e.g., SEQ ID NOs: 2, 4, 6, 8, 10, 12, 14, 16, and 18) is preferably replaced with another amino acid residue from the same side chain family. Alternatively, mutations can be introduced randomly along all or part of the sequences, such as by saturation mutagenesis, and the resultant mutants can be screened for the ability to up-regulate the above-mentioned network or ApoE/LRP signaling pathway, and trigger the respective cellular response to identify mutants that retain the activity as descried below in the examples.

A functional equivalent of a polypeptide of this invention refers to a derivative of the polypeptide, e.g., a protein having one or more point mutations, insertions, deletions, truncations, a fusion protein, or a combination thereof. It retains substantially the activity to of the above-mentioned polypeptide. The isolated polypeptide of this invention can contain the sequence of one of SEQ ID NOs: 2, 4, 6, 8, 10, 12, 14, 16, and 18, or a functional equivalent or fragment thereof. In general, the functional equivalent is at least 75% (e.g., any number between 75% and 100%, inclusive, e.g., 70%, 80%, 85%, 90%, 95%, and 99%) identical to one of SEQ ID NOs: 2, 4, 6, 8, 10, 12, 14, 16, and 18.

A polypeptide described in this invention can be obtained as a recombinant polypeptide. To prepare a recombinant polypeptide, a nucleic acid encoding it can be linked to another nucleic acid encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention. Alternatively, the polypeptide of the invention can be chemically synthesized (see e.g., Creighton, "Proteins: Structures and Molecular Principles," W.H. Freeman & Co., NY, 1983). For additional guidance, skilled artisans may consult Ausubel et al. (Current Protocols in Molecular Biology and Short Protocols in Molecular Biology, 3rd Ed. 1987 & 1995), Sambrook et al. (Molecular Cloning, A Laboratory Manual, Cold Spring Harbor Press, Cold Spring Harbor, N Y, 1989), and chemical synthesis Gait, M. J. Ed. (Oligonucleotide Synthesis, IRL Press, Oxford, 1984).

Due to their functions as cellular protein or membrane protein, DNAJA4, LRP1, LRP8, and LXR can be associated with, e.g., conjugated or fused to, one or more of an amino acid sequence comprising a cell-penetrating peptide (CPP) sequence, and the like. In this manner, a composition of the invention as discussed below can include a transport enhancer. A cell-penetrating peptide (CPP) generally consists of less than 30 amino acids and has a net positive charge. CPPs internalize in living animal cells in an endocytotic or receptor/energy-independent manner. There are several classes of CPPs with various origins, from totally protein-derived CPPs via chimeric CPPs to completely synthetic CPPs. Examples of CPPs are known in the art. See, e.g., U.S. Application Nos. 20090099066 and 20100279918. It is know that CPPs can delivery an exogenous protein into various cells.

All of naturally occurring versions, genetic engineered versions, and chemically synthesized versions of the above-mentioned polypeptides can be used to practice the invention disclosed therein. Polypeptides obtained by recombinant DNA technology may have the same amino acid sequence as a naturally occurring version (e.g., one of SEQ ID NOs: 2, 4, 6, 8, 10, 12, 14, 16, and 18) or a functionally equivalent thereof. They also include chemically modified versions. Examples of chemically modified polypeptides include polypeptides subjected to conformational change, addition or deletion of a side chain, and those to which a compound such as polyethylene glycol has been bound. Once purified and tested by standard methods or according to the method described in the examples below or other methods known in the art, the polypeptides can be included in suitable composition.

For expressing the above-mentioned factors, the invention provides a nucleic acid that encodes any of the polypeptides mentioned above. Preferably, the nucleotide sequences are isolated and/or purified. A nucleic acid refers to a DNA molecule (e.g., but not limited to, a cDNA or genomic DNA), an RNA molecule (e.g., but not limited to, an mRNA), or a DNA or RNA analog. A DNA or RNA analog can be synthesized from nucleotide analogs. The nucleic acid molecule can be single-stranded or double-stranded. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The terms "RNA," "RNA molecule," and "ribonucleic acid molecule" are used interchangeably herein, and refer to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA also can be chemically synthesized. DNA and RNA can be single-stranded (i.e., ssRNA and ssDNA, respectively) or multi-stranded (e.g., double-stranded, i.e., dsRNA and dsDNA, respectively).

The present invention also provides recombinant constructs having one or more of the nucleotide sequences described herein. Example of the constructs include a vector, such as a plasmid or viral vector, into which a nucleic acid sequence of the invention has been inserted, in a forward or reverse orientation. In a preferred embodiment, the construct further includes regulatory sequences, including a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook et al. (2001, Molecular Cloning: A Laboratory Manual, Cold Spring Harbor Press).

Examples of expression vectors include chromosomal, nonchromosomal and synthetic DNA sequences, e.g., derivatives of or Simian virus 40 (SV40), bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the polypeptides described above can be inserted into an appropriate restriction endonuclease site(s) by procedures known in the art. Such procedures and related sub-cloning procedures are within the scope of those skilled in the art.

The nucleic acid sequence in the aforementioned expression vector is preferably operatively linked to an appropriate transcription control sequence (promoter) to direct mRNA synthesis. Examples of such promoters include: the retroviral long terminal (LTR) or SV40 promoter, the *E. coli* lac or trp promoter, the phage lambda PL promoter, and other promoters known to control expression of genes in prokaryotic or eukaryotic cells or viruses. The expression vector can also contain a ribosome binding site for translation initiation, and a transcription terminator. The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in *E. coli.*

The vector containing the appropriate nucleic acid sequences as described above, as well as an appropriate promoter or control sequence, can be employed to transform an appropriate host to permit the host to express the polypeptides described above. Such vectors can be used in gene therapy. Examples of suitable expression hosts include bacterial cells (e.g., *E. coli, Streptomyces, Salmonella typhimurium*), fungal cells (yeast), insect cells (e.g., *Drosophila* and *Spodoptera frugiperda* (Sf9)), animal cells (e.g., CHO, COS, and HEK 293), adenoviruses, and plant cells. The selection of an appropriate host is within the scope of those skilled in the art. In some embodiments, the present invention provides methods for producing the above mentioned polypeptides by transfecting a host cell with an expression vector having a nucleotide sequence that encodes one of the polypeptides. The host cells are then cultured under a suitable condition, which allows for the expression of the polypeptide.

Decreasing Expression or Activity Level of Metastasis Promoters

As mentioned above, one can use an inhibitory agent that decreases the expression or activity level of miR-199a-3p, miR-199a-5p, miR-1908, or CTGF in treating melanoma. An inhibitory agent (i.e., inhibitor) can be a nucleic acid, a polypeptide, an antibody, or a small molecule compound. In one example, the inhibitor functions at a level of transcription, mRNA stability, translation, protein stability/degradation, protein modification, and protein binding.

A nucleic acid inhibitor can encode a small interference RNA (e.g., an RNAi agent) that targets one or more of the above-mentioned genes, e.g., CTGF, and inhibits its expression or activity. The term "RNAi agent" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein or RNA) is down-regulated. Generally, an interfering RNA ("iRNA") is a double stranded short-interfering RNA (siRNA), short hairpin RNA (shRNA), or single-stranded micro-RNA (miRNA) that results in catalytic degradation of specific mRNAs, and also can be used to lower or inhibit gene expression.

The term "short interfering RNA" or "siRNA" (also known as "small interfering RNAs") refers to an RNA agent, preferably a double-stranded agent, of about 10-50 nucleotides in length, preferably between about 15-25 nucleotides in length, more preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

The term "miRNA" or "microRNA" refers to an RNA agent, preferably a single-stranded agent, of about 10-50 nucleotides in length, preferably between about 15-25 nucleotides in length, more preferably about 17, 18, 19, 20, 21, 22, 23, 24, or 25 nucleotides in length, which is capable of directing or mediating RNA interference. Naturally-occurring miRNAs are generated from stem-loop precursor RNAs (i.e., pre-miRNAs) by Dicer. The term "Dicer" as used herein, includes Dicer as well as any Dicer orthologue or homologue capable of processing dsRNA structures into siRNAs, miRNAs, siRNA-like or miRNA-like molecules. The term microRNA (or "miRNA") is used interchangeably with the term "small temporal RNA" (or "stRNA") based on the fact that naturally-occurring microRNAs (or "miRNAs") have been found to be expressed in a temporal fashion (e.g., during development).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

Within the scope of this invention is utilization of RNAi featuring degradation of RNA molecules (e.g., within a cell). Degradation is catalyzed by an enzymatic, RNA-induced silencing complex (RISC). A RNA agent having a sequence sufficiently complementary to a target RNA sequence (e.g., the above-mentioned CTGF gene) to direct RNAi means that the RNA agent has a homology of at least 50%, (e.g., 50%, 60%, 70%, 80%, 90%, 95%, 98%, 99%, or 100% homology) to the target RNA sequence so that the two are sufficiently complementary to each other to hybridize and trigger the destruction of the target RNA by the RNAi machinery (e.g., the RISC complex) or process. A RNA agent having a "sequence sufficiently complementary to a target RNA sequence to direct RNAi" also means that the RNA agent has a sequence sufficient to trigger the translational inhibition of the target RNA by the RNAi machinery or process. A RNA agent also can have a sequence sufficiently complementary to a target RNA encoded by the target DNA sequence such that the target DNA sequence is chromatically silenced. In other words, the RNA agent has a sequence sufficient to induce transcriptional gene silencing, e.g., to down-modulate gene expression at or near the target DNA sequence, e.g., by inducing chromatin structural changes at or near the target DNA sequence.

The above-mentioned polynucleotides can be delivered using polymeric, biodegradable microparticle or microcapsule delivery devices known in the art. Another way to achieve uptake of the polynucleotides is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of naked DNA (i.e., without a delivery vehicle) to an intramuscular, intradermal, or subcutaneous site is another means to achieve in vivo expression.

siRNA, miRNA, and asRNA (antisense RNA) molecules can be designed by methods well known in the art. siRNA, miRNA, and asRNA molecules with homology sufficient to provide sequence specificity required to uniquely degrade any RNA can be designed using programs known in the art, including, but not limited to, those maintained on websites for AMBION, Inc. and DHARMACON, Inc. Systematic testing of several designed species for optimization of the siRNA, miRNA, and asRNA sequence can be routinely performed by those skilled in the art. Considerations when designing short interfering nucleic acid molecules include, but are not limited to, biophysical, thermodynamic, and structural considerations, base preferences at specific positions in the sense strand, and homology. These considerations are well known in the art and provide guidelines for designing the above-mentioned RNA molecules.

An antisense polynucleotide (preferably DNA) of the present invention can be any antisense polynucleotide so long as it possesses a base sequence complementary or substantially complementary to that of the gene encoding a component of the aforementioned network. The base sequence can be at least about 70%, 80%, 90%, or 95% homology to the complement of the gene encoding the polypeptide. These antisense DNAs can be synthesized using a DNA synthesizer.

The antisense DNA of the present invention may contain changed or modified sugars, bases or linkages. The antisense DNA, as well as the RNAi agent mentioned above, may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like. The inhibitory action of the antisense DNA can be examined using a cell-line or animal based gene expression system of the present invention in vivo and in vitro.

The above-discussed nucleic acids encoding one or more of the polypeptides mentioned above or RNAi agents can be cloned in a vector for delivering to cells in vitro or in vivo. For in vivo uses, the delivery can target a specific tissue or organ (e.g., skin). Targeted delivery involves the use of vectors (e.g., organ-homing peptides) that are targeted to specific organs or tissues after systemic administration. For example, the vector can have a covalent conjugate of avidin and a monoclonal antibody to a liver specific protein.

In certain embodiments, the present invention provides methods for in vivo expression the above-mentioned metastasis suppressors. Such method would achieve its therapeutic effect by introduction of nucleic acid sequences encoding any of the factors into cells or tissues of a human or a non-human animal in need of inhibiting endothelial recruitment, cancer cell invasion, or metastatic angiogenesis. Delivery of the nucleic acid sequences can be achieved using a recombinant expression vector such as a chimeric virus or a colloidal dispersion system. Preferred for therapeutic delivery of the nucleic acid sequences is the use of targeted liposomes.

Various viral vectors which can be utilized for gene therapy disclosed herein include, adenovirus, adeno-associated virus (AAV), herpes virus, vaccinia, or, preferably, an RNA virus such as a retrovirus and a lentivirus. Preferably, the retroviral vector is a lentivirus or a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes.

All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using a target-specific antibody or hormone that has a receptor in the target. Those of skill in the art will recognize that specific polynucleotide sequences can be inserted into the retroviral genome or attached to a viral envelope to allow target specific delivery of the retroviral vector.

Another targeted system for delivery of nucleic acids is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA, and intact virions can be encapsulated within the aqueous interior and delivered to cells in a biologically active form. Methods for efficient gene transfer using a liposome vehicle are known in the art. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Exemplary phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

When used in vivo, it is desirable to use a reversible delivery-expression system. To that end, the Cre-loxP or FLP/FRT system and other similar systems can be used for reversible delivery-expression of one or more of the above-described nucleic acids. See WO2005/112620, WO2005/039643, U.S. Applications 20050130919, 20030022375, 20020022018, 20030027335, and 20040216178. In particular, the reversible delivery-expression system described in US Application NO 20100284990 can be used to provide a selective or emergency shut-off.

In another example, the above-mentioned inhibitory agent can be a polypeptide or a protein complex, such as an antibody. The term "antibody" refers to an immunoglobulin molecule or immunologically active portion thereof, i.e., an antigen-binding portion. Examples include, but are not limited to, a protein having at least one or two, heavy (H) chain variable regions (VH), and at least one or two light (L) chain variable regions (VL). The VH and VL regions can be further subdivided into regions of hypervariability, termed "complementarity determining regions" ("CDR"), interspersed with regions that are more conserved, termed "framework regions" (FR). As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, and IgG4), delta, epsilon and mu constant region genes, as well as the myriad immunoglobulin variable region genes.

The term "antigen-binding portion" of an antibody (or "antibody portion") refers to one or more fragments of an antibody that retain the ability to specifically bind to an antigen (e.g., LRP1, LRP8, and CTGF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

Antibodies that specifically bind to one of the above-mentioned target proteins (e.g., CTGF) can be made using methods known in the art. This antibody can be a polyclonal or a monoclonal antibody. In one embodiment, the antibody can be recombinantly produced, e.g., produced by phage display or by combinatorial methods. In another embodiment, the antibody is a fully human antibody (e.g., an antibody made in a mouse which has been genetically engineered to produce an antibody from a human immunoglobulin sequence), a humanized antibody, or a non-human antibody, for example, but not limited to, a rodent (mouse or rat), goat, primate (for example, but not limited to, monkey), rabbit, or camel antibody. Examples of methods to generate humanized version of antibodies include, but are not limited to, CDR grafting (Queen et al., U.S. Pat. No. 5,585,089; Riechmann et al., Nature 332:323 (1988)), chain shuffling (U.S. Pat. No. 5,565,332); and veneering or resurfacing (EP 592,106; EP 519,596); Padlan, Molecular Immunology 28(415):489-498 (1991); Studnicka et al., Protein Engineering 7(6):805-814 (1994); Roguska. et al., PNAS 91:969-973 (1994)). Examples of methods to generate fully human antibodies include, but are not limited to, generation of antibodies from mice that can express human immunoglobulin genes and use of phage-display technology to generate and screen human immunoglobulin gene libraries.

An "isolated antibody" is intended to refer to an antibody that is substantially free of other antibodies having different antigenic specificities (e.g., an isolated antibody that specifically binds CTGF is substantially free of antibodies that specifically bind antigens other than such an antigen). Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by the heavy chain constant region genes. The phrases "an antibody recognizing an antigen" and "an antibody specific for an antigen" are used interchangeably herein with the term "an antibody which binds specifically to an antigen." As used herein, the term "high affinity" for an IgG antibody refers to an antibody having a KD of 10-7 M or less, preferably 10-8 M or less, more preferably 10-9 M or less and even more preferably 10-10 M or less for a target antigen. However, "high affinity" binding can vary for other antibody isotypes. For example, "high affinity" binding for an IgM isotype refers to an antibody having a KD of 10-7 M or less, more preferably 10-8 M or less.

In one example, a composition contains a monoclonal antibody that neutralizes CTGF. In one embodiment, this antibody can be a fully human antibody, a humanized antibody, or a non-human antibody, for example, but not limited to, a rodent (mouse or rat), goat, primate (for example, but not limited to, monkey), rabbit, or camel antibody. In one embodiment, one or more amino-acids of this monoclonal monoclonal antibody may be substituted in order to alter its physical properties. These properties include, but are not limited to, binding specificity, binding affinity, immunogenicity, and antibody isotype. Pharmaceutical compositions containing fully human or humanized versions of the above described antibodies can be used for treating melanoma or for inhibiting endothelial recruitment, cancer cell invasion, or metastatic angiogenesis.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental animal or animal suitable as a disease model. A subject to be treated for a disorder can be identified by standard diagnosing techniques for the disorder. Optionally, the subject can be examined for mutation, expression level, or activity level of one or more of the miR-199a-3p, miR-199a-5p, miR-1908, and CTGF mentioned above by methods known in the art or described above before treatment. If the subject has a particular mutation in the gene, or if the gene expression or activity level is, for example, greater in a sample from the subject than that in a sample from a normal person, the subject is a candidate for treatment of this invention.

To confirm the inhibition or treatment, one can evaluate and/or verify the inhibition of endothelial recruitment or resulting angiogenesis using technology known in the art before and/or after the administering step. Exemplary technologies include angiography or arteriography, a medical imaging technique used to visualize the inside, or lumen, of blood vessels and organs of the body, can generally be done by injecting a radio-opaque contrast agent into the blood vessel and imaging using X-ray based techniques such as fluoroscopy.

"Treating" or "treatment" as used herein refers to administration of a compound or agent to a subject who has a disorder with the purpose to cure, alleviate, relieve, remedy, delay the onset of, prevent, or ameliorate the disorder, the symptom of a disorder, the disease state secondary to the disorder, or the predisposition toward the disorder. An "effective amount" or "therapeutically effective amount" refers to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The expression "effective amount" as used herein, refers to a sufficient amount of the compound of the invention to exhibit the desired therapeutic effect. The exact amount required will vary from subject to subject, depending on the species, age, and general condition of the subject, the particular therapeutic agent and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the anticancer activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

A therapeutic agent can be administered in vivo or ex vivo, alone or co-administered in conjunction with other drugs or therapy, i.e., a cocktail therapy. As used herein, the term "co-administration" or "co-administered" refers to the administration of at least two agent(s) or therapies to a subject. For example, in the treatment of tumors, particularly vascularized, malignant tumors, the agents can be used alone or in combination with, e.g., chemotherapeutic, radiotherapeutic, apoptotic, anti-angiogenic agents and/or immunotoxins or coaguligands. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In an in vivo approach, a compound or agent is administered to a subject. Generally, the compound is suspended in a pharmaceutically-acceptable carrier (such as, for example, but not limited to, physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) can increase the efficiency of delivery, particularly for oral delivery.

Compositions

Within the scope of this invention is a composition that contains a suitable carrier and one or more of the therapeutic agents described above. The composition can be a pharmaceutical composition that contains a pharmaceutically acceptable carrier, a dietary composition that contains a dietarily acceptable suitable carrier, or a cosmetic composition that contains a cosmetically acceptable carrier.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, sodium lauryl sulfate, and D&C Yellow #10.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M.

Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts, include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; natural and synthetic phospholipids, such as soybean and egg yolk phosphatides, lecithin, hydrogenated soy lecithin, dimyristoyl lecithin, dipalmitoyl lecithin, distearoyl lecithin, dioleoyl lecithin, hydroxylated lecithin, lysophosphatidylcholine, cardiolipin, sphingomyelin, phosphatidylcholine, phosphatidyl ethanolamine, distearoyl phosphatidylethanolamine (DSPE) and its pegylated esters, such as DSPE-PEG750 and, DSPE-PEG2000, phosphatidic acid, phosphatidyl glycerol and phosphatidyl serine. Commercial grades of lecithin which are preferred include those which are available under the trade name Phosal® or Phospholipon® and include Phosal 53 MCT, Phosal 50 PG, Phosal 75 SA, Phospholipon 90H, Phospholipon 90G and Phospholipon 90 NG; soy-phosphatidylcholine (SoyPC) and DSPE-PEG2000 are particularly preferred; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The above-described composition, in any of the forms described above, can be used for treating melanoma, or any other disease or condition described herein. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally comprise one or more excipients or diluents. In some preferred embodiments, the topical formulations include a material that would enhance absorption or penetration of the active agent(s) through the skin or other affected areas.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incompatibility, instability, allergic response, and the like. The carrier enables an active agent and optional component to be delivered to the skin at an appropriate concentration(s). The carrier thus can act as a diluent, dispersant, solvent, or the like to ensure that the active materials are applied to and distributed evenly over the selected target at an appropriate concentration. The carrier can be solid, semi-solid, or liquid. The carrier can be in the form of a lotion, a cream, or a gel, in particular one that has a sufficient thickness or yield point to prevent the active materials from sedimenting. The carrier can be inert or possess dermatological benefits. It also should be physically and chemically compatible with the active components described herein, and should not unduly impair stability, efficacy, or other use benefits associated with the composition.

Combination Therapies

In some embodiments, the pharmaceutical composition may further comprise an additional compound having antiproliferative activity. The additional compound having antiproliferative activity can be selected from a group of antiproliferative agents including those shown in Table 2.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

By "antiproliferative agent" is meant any antiproliferative agent, including those antiproliferative agents listed in Table 2, any of which can be used in combination with a LXR agonist to treat the medical conditions recited herein. Antiproliferative agents also include organo-platine derivatives, naphtoquinone and benzoquinone derivatives, chrysophanic acid and anthroquinone derivatives thereof.

TABLE 2

| | | |
|---|---|---|
| Alkylating agents | Busulfan | Chlorambucil |
| | dacarbazine | procarbazine |
| | ifosfamide | altretamine |
| | hexamethylmelamine | estramustine phosphate |
| | thiotepa | mechlorethamine |
| | dacarbazine | streptozocin |
| | lomustine | temozolomide |
| | cyclophosphamide | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche) |
| | iproplatin | SM-11355 (Sumitomo) |
| | ZD-0473 (AnorMED) | AP-5280 (Access) |
| | oxaliplatin | cisplatin |
| | carboplatin | |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |
| | methotrexate | DMDC (Hoffmann-La Roche) |
| | tomudex | ethynylcytidine (Taiho) |
| | fludarabine | gemcitabine |
| | raltitrexed | capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | | elsamitrucin (Spectrum) |
| | dexrazoxanet (TopoTarget) | J-107088 (Merck & Co) |
| | pixantrone (Novuspharma) | BNP-1350 (BioNumerik) |
| | rebeccamycin analogue | CKD-602 (Chong Kun Dang) |

TABLE 2-continued

| | | |
|---|---|---|
| | (Exelixis)<br>BBR-3576 (Novuspharma)<br>rubitecan (SuperGen)<br>irinotecan (CPT-11)<br>topotecan | KW-2170 (Kyowa Hakko)<br>hydroxycamptothecin (SN-38) |
| Antitumor antibiotics | valrubicin<br>therarubicin<br>idarubicin<br>rubidazone<br>plicamycin<br>porfiromycin<br>mitoxantrone (novantrone)<br>amonafide | azonafide<br>anthrapyrazole<br>oxantrazole<br>losoxantrone<br>MEN-10755 (Menarini)<br>GPX-100 (Gem Pharmaceuticals)<br>Epirubicin<br>mitoxantrone<br>doxorubicin |
| Antimitotic agents | colchicine<br>vinblastine<br>vindesine<br>dolastatin 10 (NCI)<br>rhizoxin (Fujisawa)<br>mivobulin (Warner-Lambert)<br>cemadotin (BASF)<br>RPR 109881A (Aventis)<br>TXD 258 (Aventis)<br>epothilone B (Novartis)<br>T 900607 (Tularik)<br>T 138067 (Tularik)<br>cryptophycin 52 (Eli Lilly)<br>vinflunine (Fabre)<br>auristatin PE (Teikoku Hormone)<br>BMS 247550 (BMS)<br>BMS 184476 (BMS)<br>BMS 188797 (BMS)<br>taxoprexin (Protarga)<br>SB 408075 (GlaxoSmithKline)<br>Vinorelbine<br>Tricho statin A | E7010 (Abbott)<br>PG-TXL (Cell Therapeutics)<br>IDN 5109 (Bayer)<br>A 105972 (Abbott)<br>A 204197 (Abbott)<br>LU 223651 (BASF)<br>D 24851 (ASTAMedica)<br>ER-86526 (Eisai)<br>combretastatin A4 (BMS)<br>isohomohalichondrin-B (PharmaMar)<br>ZD 6126 (AstraZeneca)<br>AZ10992 (Asahi)<br>IDN-5109 (Indena)<br>AVLB (Prescient NeuroPharma)<br>azaepothilone B (BMS)<br>BNP-7787 (BioNumerik)<br>CA-4 prodrug (OXiGENE)<br>dolastatin-10 (NIH)<br>CA-4 (OXiGENE)<br>docetaxel<br>vincristine<br>Paclitaxel |
| Aromatase inhibitors | aminoglutethimide<br>atamestane (BioMedicines)<br>letrozole<br>anastrazole | YM-511 (Yamanouchi)<br>formestane<br>exemestane |
| Thymidylate synthase inhibitors | pemetrexed (Eli Lilly)<br>ZD-9331 (BTG) | nolatrexed (Eximias)<br>CoFactor ™ (BioKeys) |
| DNA antagonists | trabectedin (PharmaMar)<br>glufosfamide (Baxter International)<br>albumin + 32P (Isotope Solutions)<br>thymectacin (NewBiotics) | edotreotide (Novartis)<br>mafosfamide (Baxter International)<br>apaziquone (Spectrum Pharmaceuticals)<br>O6 benzyl guanine (Paligent) |
| Farnesyltransferase inhibitors | arglabin (NuOncology Labs)<br>lonafarnib (Schering-Plough)<br>BAY-43-9006 (Bayer) | tipifarnib (Johnson & Johnson)<br>perillyl alcohol (DOR BioPharma) |
| Pump inhibitors | CBT-1 (CBA Pharma)<br>tariquidar (Xenova)<br>MS-209 (Schering AG) | zosuquidar trihydrochloride (Eli Lilly)<br>biricodar dicitrate (Vertex) |
| Histone acetyltransferase inhibitors | tacedinaline (Pfizer)<br>SAHA (Aton Pharma)<br>MS-275 (Schering AG) | pivaloyloxymethyl butyrate (Titan)<br>depsipeptide (Fujisawa) |
| Metalloproteinase inhibitors | Neovastat (Aeterna Laboratories)<br>marimastat (British Biotech) | CMT-3 (CollaGenex)<br>BMS-275291 (Celltech) |
| Ribonucleoside reductase inhibitors | gallium maltolate (Titan)<br>triapine (Vion) | tezacitabine (Aventis)<br>didox (Molecules for Health) |
| TNF alpha agonists/antagonists | virulizin (Lorus Therapeutics)<br>CDC-394 (Celgene) | revimid (Celgene) |
| Endothelin A receptor antagonist | atrasentan (Abbott)<br>ZD-4054 (AstraZeneca) | YM-598 (Yamanouchi) |
| Retinoic acid receptor agonists | fenretinide (Johnson & Johnson)<br>LGD-1550 (Ligand) | alitretinoin (Ligand) |
| Immuno-modulators | interferon<br>oncophage (Antigenics)<br>GMK (Progenics)<br>adenocarcinoma vaccine (Biomira)<br>CTP-37 (AVI BioPharma)<br>IRX-2 (Immuno-Rx)<br>PEP-005 (Peplin Biotech) | dexosome therapy (Anosys)<br>pentrix (Australian Cancer Technology)<br>ISF-154 (Tragen)<br>cancer vaccine (Intercell)<br>norelin (Bio star)<br>BLP-25 (Biomira)<br>MGV (Progenics) |

TABLE 2-continued

| | | |
|---|---|---|
| | synchrovax vaccines (CTL Immuno) | β-alethine (Dovetail) |
| | melanoma vaccine (CTL Immuno) | CLL therapy (Vasogen) |
| | p21 RAS vaccine (GemVax) | Ipilimumab (BMS), |
| | MAGE-A3 (GSK) | CM-10 (cCam Biotherapeutics) |
| | nivolumab (BMS) | MPDL3280A (Genentech) |
| | abatacept (BMS) | |
| Hormonal and antihormonal agents | estrogens | dexamethasone |
| | conjugated estrogens | prednisone |
| | ethinyl estradiol | methylprednisolone |
| | chlortrianisen | prednisolone |
| | idenestrol | aminoglutethimide |
| | hydroxyprogesterone caproate | leuprolide |
| | medroxyprogesterone | octreotide |
| | testosterone | mitotane |
| | testosterone propionate; | P-04 (Novogen) |
| | fluoxymesterone | 2-methoxyestradiol (EntreMed) |
| | methyltestosterone | arzoxifene (Eli Lilly) |
| | diethylstilbestrol | tamoxifen |
| | megestrol | toremofine |
| | bicalutamide | goserelin |
| | flutamide | Leuporelin |
| | nilutamide | bicalutamide |
| Photodynamic agents | talaporfin (Light Sciences) | Pd-bacteriopheophorbide (Yeda) |
| | Theralux (Theratechnologies) | lutetium texaphyrin (Pharmacyclics) |
| | motexafin gadolinium (Pharmacyclics) | hypericin |
| Kinase Inhibitors | imatinib (Novartis) | EKB-569 (Wyeth) |
| | leflunomide (Sugen/Pharmacia) | kahalide F (PharmaMar) |
| | ZD1839 (AstraZeneca) | CEP-701 (Cephalon) |
| | erlotinib (Oncogene Science) | CEP-751 (Cephalon) |
| | canertinib (Pfizer) | MLN518 (Millenium) |
| | squalamine (Genaera) | PKC412 (Novartis) |
| | SU5416 (Pharmacia) | Phenoxodiol (Novogen) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | EKB-509 (Wyeth) | IMC-1C11 (ImClone) |
| | trastuzumab (Genentech) | Tyrphostins |
| | OSI-774 (Tarceva ™) | Gefitinib (Iressa) |
| | CI-1033 (Pfizer) | PTK787 (Novartis) |
| | SU11248 (Pharmacia) | EMD 72000 (Merck) |
| | RH3 (York Medical) | Emodin |
| | Genistein | Radicinol |
| | Radicinol | Vemurafenib (B-Raf enzyme inhibitor, Daiichi Sankyo) |
| | Met-MAb (Roche) | |
| SR-27897 (CCK A inhibitor, Sanofi-Synthelabo) | ceflatonin (apoptosis promotor, ChemGenex) | |
| tocladesine (cyclic AMP agonist, Ribapharm) | BCX-1777 (PNP inhibitor, BioCryst) | |
| alvocidib (CDK inhibitor, Aventis) | ranpirnase (ribonuclease stimulant, Alfacell) | |
| CV-247(COX-2 inhibitor, Ivy Medical) | galarubicin (RNA synthesis inhibitor, Dong-A) | |
| P54 (COX-2 inhibitor, Phytopharm) | tirapazamine (reducing agent, SRI International) | |
| CapCell ™ (CYP450 stimulant, Bavarian Nordic) | N-acetylcysteine (reducing agent, Zambon) | |
| GCS-100 (gal3 antagonist, GlycoGenesys) | R-flurbiprofen (NF-kappaB inhibitor, Encore) | |
| G17DT immunogen (gastrin inhibitor, Aphton) | 3CPA (NF-kappaB inhibitor, Active Biotech) | |
| efaproxiral (oxygenator, Allos Therapeutics) | seocalcitol (vitamin D receptor agonist, Leo) | |
| PI-88 (heparanase inhibitor, Progen) | 131-I-TM-601 (DNA antagonist, TransMolecular) | |
| tesmilifene (histamine antagonist, YM BioSciences) | eflornithine (ODC inhibitor , ILEX Oncology) | |
| histamine (histamine H2 receptor agonist, Maxim) | minodronic acid (osteoclast inhibitor, Yamanouchi) | |
| tiazofurin (IMPDH inhibitor, Ribapharm) | indisulam (p53 stimulant, Eisai) | |
| cilengitide (integrin antagonist, Merck KGaA) | aplidine (PPT inhibitor, PharmaMar) | |
| SR-31747 (IL-1 antagonist, Sanofi-Synthelabo) | gemtuzumab (CD33 antibody, Wyeth Ayerst) | |
| CCI-779 (mTOR kinase inhibitor, Wyeth) | PG2 (hematopoiesis enhancer, Pharmagenesis) | |
| exisulind (PDE V inhibitor, Cell Pathways) | Immunol ™ (triclosan oral rinse, Endo) | |
| CP-461 (PDE V inhibitor, Cell Pathways) | triacetyluridine (uridine prodrug , Wellstat) | |
| AG-2037 (GART inhibitor, Pfizer) | SN-4071 (sarcoma agent, Signature BioScience) | |
| WX-UK1 (plasminogen activator inhibitor, Wilex) | TransMID-107 ™ (immunotoxin, KS Biomedix) | |
| PBI-1402 (PMN stimulant, ProMetic LifeSciences) | PCK-3145 (apoptosis promotor, Procyon) | |
| bortezomib (proteasome inhibitor, Millennium) | doranidazole (apoptosis promotor, Pola) | |
| SRL-172 (T cell stimulant, SR Pharma) | CHS-828 (cytotoxic agent, Leo) | |
| TLK-286 (glutathione S transferase inhibitor, Telik) | trans-retinoic acid (differentiator, NIH) | |
| PT-100 (growth factor agonist, Point Therapeutics) | MX6 (apoptosis promotor, MAXIA) | |
| | apomine (apoptosis promotor, ILEX Oncology) | |
| | urocidin (apoptosis promotor, Bioniche) | |
| | Ro-31-7453 (apoptosis promotor, La Roche) | |

TABLE 2-continued

| | |
|---|---|
| midostaurin (PKC inhibitor, Novartis) | brostallicin (apoptosis promotor, Pharmacia) |
| bryostatin-1 (PKC stimulant, GPC Biotech) | β-lapachone |
| CDA-II (apoptosis promotor, Everlife) | gelonin |
| SDX-101 (apoptosis promotor, Salmedix) | cafestol |
| rituximab (CD20 antibody, Genentech | kahweol |
| carmustine | caffeic acid |
| Mitoxantrone | Tyrphostin AG |
| Bleomycin | PD-1 inhibitors |
| Absinthin | CTLA-4 inhibitors |
| Chrysophanic acid | sorafenib |
| Cesium oxides | BRAF inhibitors |
| BRAF inhibitors, | |
| PDL1 inhibitors | |
| MEK inhibitors | |
| bevacizumab | |
| angiogenesis inhibitors | |
| dabrafenib | |

Diagnosis and Prognosis Methods

The above-describe genes can be used in determining whether a subject has, or is at risk of having, metastatic melanoma. Alternatively, they can be used for determining a prognosis of such a disorder in a subject.

Diagnosis Methods

In one aspect, the invention provides qualitative and quantitative information to determine whether a subject has or is predisposed to metastatic melanoma or other disease characterized by endothelial recruitment, cancer cell invasion, or metastatic angiogenesis. A subject having such a disorder or prone to it can be determined based on the expression levels, patterns, or profiles of the above-described genes or their products (mRNAs, microRNAs, or polypeptides) in a test sample from the subject. In other words, the products can be used as markers to indicate the presence or absence of the disorder. Diagnostic and prognostic assays of the invention include methods for assessing the expression level of the products. The methods allow one to detect the disorder. For example, a relative increase in the expression level of one or more promoters (i.e., miR-199a-3p, miR-199a-5p, miR-1908, and CTGF) is indicative of presence the disorder. Conversely, a lower expression level or a lack of the expression is indicative lack of the disorder.

The presence, level, or absence of, an mRNA, microRNA, or polypeptide product in a test sample can be evaluated by obtaining a test sample from a test subject and contacting the test sample with a compound or an agent capable of detecting the nucleic acid (e.g., RNA or DNA probe) or polypeptide. The "test sample" includes tissues, cells and biological fluids isolated from a subject, as well as tissues, cells and fluids present within a subject. The level of expression of a gene(s) of interest can be measured in a number of ways, including measuring the RNA encoded by the gene.

Expressed RNA samples can be isolated from biological samples using any of a number of well-known procedures. For example, biological samples can be lysed in a guanidinium-based lysis buffer, optionally containing additional components to stabilize the RNA. In some embodiments, the lysis buffer can contain purified RNAs as controls to monitor recovery and stability of RNA from cell cultures. Examples of such purified RNA templates include the Kanamycin Positive Control RNA from PROMEGA (Madison, WI), and 7.5 kb Poly(A)-Tailed RNA from LIFE TECHNOLOGIES (Rockville, MD). Lysates may be used immediately or stored frozen at, e.g., −80° C.

Optionally, total RNA can be purified from cell lysates (or other types of samples) using silica-based isolation in an automation-compatible, 96-well format, such as the RNEASY purification platform (QIAGEN, Inc., Valencia, CA). Other RNA isolation methods are contemplated, such as extraction with silica-coated beads or guanidinium. Further methods for RNA isolation and preparation can be devised by one skilled in the art.

The methods of the present invention can be performed using crude samples (e.g., blood, serum, plasma, or cell lysates), eliminating the need to isolate RNA. RNAse inhibitors are optionally added to the crude samples. When using crude cellular lysates, it should be noted that genomic DNA can contribute one or more copies of a target sequence, e.g., a gene, depending on the sample. In situations in which the target sequence is derived from one or more highly expressed genes, the signal arising from genomic DNA may not be significant. But for genes expressed at low levels, the background can be eliminated by treating the samples with DNAse, or by using primers that target splice junctions for subsequent priming of cDNA or amplification products.

The level of RNA corresponding to a gene in a cell can be determined both in situ and in vitro. RNA isolated from a test sample can be used in hybridization or amplification assays that include, Southern or Northern analyses, PCR analyses, and probe arrays. A preferred diagnostic method for the detection of RNA levels involves contacting the isolated RNA with a nucleic acid probe that can hybridize to the RNA encoded by the gene. The probe can be a full-length nucleic acid or a portion thereof, such as an oligonucleotide of at least 10 nucleotides in length and sufficient to specifically hybridize under stringent conditions to the RNA.

In one format, RNA (or cDNA prepared from it) is immobilized on a surface and contacted with the probes, for example, by running the isolated RNA on an agarose gel and transferring the RNA from the gel to a membrane, such as nitrocellulose. In another format, the probes are immobilized on a surface and the RNA (or cDNA) is contacted with the probes, for example, in a gene chip array. A skilled artisan can adapt known RNA detection methods for detecting the level of RNA.

The level of RNA (or cDNA prepared from it) in a sample encoded by a gene to be examined can be evaluated with nucleic acid amplification, e.g., by standard PCR (U.S. Pat. No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115:379-402, 1999), or any other nucleic acid amplification method, followed by the detection of the amplified molecules using techniques known in the art. In another embodiment, the methods of the invention further include contacting a control sample with a compound or agent capable of detecting the RNA of a gene and comparing the presence of the RNA in the control sample with the presence of the RNA in the test sample.

The above-described methods and markers can be used to assess the risk of a subject for developing melanoma. In particular, the invention can be applied to those in high risk cohort who already have certain risks so as to gain critical insight into early detection. A change in levels of miR gene products associated with melanoma can be detected prior to, or in the early stages of, the development of transformed or neoplastic phenotypes in cells of a subject. The invention therefore also provides a method for screening a subject who is at risk of developing melanoma, comprising evaluating the level of at least one gene product, or a combination of gene products, associated with melanoma in a biological sample obtained form the subject's skin. Accordingly, an alteration in the level of the gene product, or combination of gene products, in the biological sample as compared to the level of a corresponding gene product in a control sample, is indicative of the subject being at risk for developing melanoma. The biological sample used for such screening can include skin tissue that is either normal or suspected to be cancerous. Subjects with a change in the level of one or more gene products associated with melanoma are candidates for further monitoring and testing. Such further testing can comprise histological examination of tissue samples, or other techniques within the skill in the art.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder, e.g., melanoma.

Prognosis Methods

The diagnostic methods described above can identify subjects having, or at risk of developing, a melanoma. In addition, changes in expression levels and/or trends of the above-mentioned genes in a biological sample, e.g., peripheral blood samples, can provide an early indication of recovery or lack thereof. For example, a further increase (or decline) or persistently-altered gene expression levels of the promoter genes (or inhibitor genes) indicate a poor prognosis, i.e., lack of improvement or health decline. Accordingly, these genes allow one to assess post-treatment recovery of melanoma. The analysis of this select group of genes or a subset thereof indicates outcomes of the conditions.

The prognostic assays described herein can be used to determine whether a subject is suitable to be administered with an agent (e.g., an agonist, antagonist, peptidomimetic, protein, peptide, nucleic acid, small molecule, or other drug candidate) to treat melanoma or other disorders associated with endothelial recruitment, cancer cell invasion, or metastatic angiogenesis. For example, such assays can be used to determine whether a subject can be administered with a chemotherapeutic agent.

Thus, also provided by this invention is a method of monitoring a treatment for a cellular proliferative disorder in a subject. For this purpose, gene expression levels of the genes disclosed herein can be determined for test samples from a subject before, during, or after undergoing a treatment. The magnitudes of the changes in the levels as compared to a baseline level are then assessed. A decrease in the expression of the above-mentioned promoter genes (miR-199a-3p, miR-199a-5p, miR-1908, and CTGF) after the treatment indicates that the subject can be further treated by the same treatment. Similarly, an increase in the inhibitors (DNAJA4, ApoE, LRP1, and LRP8) also indicates that the subject can be further treated by the same treatment. Conversely, further increase or persistent high expression levels of one or more of the promoter genes is indicate lack of improvement or health decline.

Information obtained from practice of the above assays is useful in prognostication, identifying progression of, and clinical management of diseases and other deleterious conditions affecting an individual subject's health status. In preferred embodiments, the foregoing diagnostic assays provide information useful in prognostication, identifying progression of and management of melanoma and other conditions characterized by endothelial recruitment, cancer cell invasion, or metastatic angiogenesis. The information more specifically assists the clinician in designing chemotherapeutic or other treatment regimes to eradicate such conditions from the body of an afflicted subject, a human.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer after treatment, while the average patient with the same cancer has only a 25% probability of being cured.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" a target includes determining the amount of the target present, as well as determining whether it is present or absent.

Arrays

Also provided in the invention is a biochip or array. The biochip/array may contain a solid or semi-solid substrate having an attached probe or plurality of probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

"Attached" or "immobilized" as used herein to refer to a nucleic acid (e.g., a probe) and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

The solid substrate can be a material that may be modified to contain discrete individual sites appropriate for the attachment or association of the probes and is amenable to at least one detection method. Examples of such substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate can be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The array/biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide. The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography. Detailed discussion of methods for linking nucleic acids to a support substrate can be found in, e.g., U.S. Pat. Nos. 5,837,832, 6,087,112, 5,215,882, 5,707,807, 5,807,522, 5,958,342, 5,994,076, 6,004,755, 6,048,695, 6,060,240, 6,090,556, and 6,040,138.

In some embodiments, an expressed transcript (e.g., a transcript of a microRNA gene described herein) is represented in the nucleic acid arrays. In such embodiments, a set of binding sites can include probes with different nucleic acids that are complementary to different sequence segments of the expressed transcript. Examples of such nucleic acids can be of length of 15 to 200 bases, 20 to 100 bases, 25 to 50 bases, 40 to 60 bases. Each probe sequence can also include one or more linker sequences in addition to the sequence that is complementary to its target sequence. A linker sequence is a sequence between the sequence that is complementary to its target sequence and the surface of support. For example, the nucleic acid arrays of the invention can have one probe specific to each target microRNA gene. However, if desired, the nucleic acid arrays can contain at least 2, 5, 10, 100, 200, 300, 400, 500 or more probes specific to some expressed transcript (e.g., a transcript of a microRNA gene described herein).

Kits

In another aspect, the present invention provides kits embodying the methods, compositions, and systems for analysis of the polypeptides and microRNA expression as described herein. Such a kit may contain a nucleic acid described herein together with any or all of the following: assay reagents, buffers, probes and/or primers, and sterile saline or another pharmaceutically acceptable emulsion and suspension base. In addition, the kit may include instructional materials containing directions (e.g., protocols) for the practice of the methods described herein. For example, the kit may be a kit for the amplification, detection, identification or quantification of a target mRNA or microRNA sequence. To that end, the kit may contain a suitable primer (e.g., hairpin primers), a forward primer, a reverse primer, and a probe.

In one example, a kit of the invention includes one or more microarray slides (or alternative microarray format) onto which a plurality of different nucleic acids (each corresponding to one of the above-mentioned genes) have been deposited. The kit can also include a plurality of labeled probes. Alternatively, the kit can include a plurality of polynucleotide sequences suitable as probes and a selection of labels suitable for customizing the included polynucleotide sequences, or other polynucleotide sequences at the discretion of the practitioner. Commonly, at least one included polynucleotide sequence corresponds to a control sequence, e.g., a normalization gene or the like. Exemplary labels include, but are not limited to, a fluorophore, a dye, a radiolabel, an enzyme tag, that is linked to a nucleic acid primer.

In one embodiment, kits that are suitable for amplifying nucleic acid corresponding to the expressed RNA samples are provided. Such a kit includes reagents and primers suitable for use in any of the amplification methods described above. Alternatively, or additionally, the kits are suitable for amplifying a signal corresponding to hybridization between a probe and a target nucleic acid sample (e.g., deposited on a microarray).

In addition, one or more materials and/or reagents required for preparing a biological sample for gene expression analysis are optionally included in the kit. Furthermore, optionally included in the kits are one or more enzymes suitable for amplifying nucleic acids, including various polymerases (RT, Taq, etc.), one or more deoxynucleotides, and buffers to provide the necessary reaction mixture for amplification.

Typically, the kits are employed for analyzing gene expression patterns using mRNA or microRNA as the starting template. The RNA template may be presented as either total cellular RNA or isolated RNA; both types of sample yield comparable results. In other embodiments, the methods and kits described in the present invention allow quantitation of other products of gene expression, including tRNA, rRNA, or other transcription products.

Optionally, the kits of the invention further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

The kits optionally contain distinct containers for each individual reagent and/or enzyme component. Each component will generally be suitable as aliquoted in its respective container. The container of the kits optionally includes at least one vial, ampule, or test tube. Flasks, bottles and other container mechanisms into which the reagents can be placed and/or aliquoted are also possible. The individual containers of the kit are preferably maintained in close confinement for commercial sale. Suitable larger containers may include injection or blow-molded plastic containers into which the desired vials are retained. Instructions, such as written directions or videotaped demonstrations detailing the use of the kits of the present invention, are optionally provided with the kit.

In a further aspect, the present invention provides for the use of any composition or kit herein, for the practice of any method or assay herein, and/or for the use of any apparatus or kit to practice any assay or method herein.

A "test sample" or a "biological sample" as used herein may mean a sample of biological tissue or fluid that comprises nucleic acids. Such samples include, but are not limited to, tissue or body fluid isolated from animals. Biological samples may also include sections of tissues such as biopsy and autopsy samples, frozen sections taken for histological purposes, blood, plasma, serum, sputum, stool, tears, mucus, urine, effusions, amniotic fluid, ascitic fluid, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

The term "body fluid" or "bodily fluid" refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C. Suitable body fluids are acellular fluids. "Acellular" fluids include body fluid samples in which cells are absent or are present in such low amounts that the miRNA level determined reflects its level in the liquid portion of the sample, rather than in the cellular portion. Such acellular body fluids are generally produced by processing a cell-containing body fluid by, for example, centrifugation or filtration, to remove the cells. Typically, an acellular body fluid contains no intact cells however, some may contain cell fragments or cellular debris. Examples of acellular fluids include plasma or serum, or body fluids from which cells have been removed.

The term "gene" used herein refers to a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto. The term also includes pseudogenes, which are dysfunctional relatives of known genes that have lost their protein-coding ability or are otherwise no longer expressed in a cell.

"Expression profile" as used herein refers to a genomic expression profile, e.g., an expression profile of microRNAs. Profiles may be generated by any convenient means for determining a level of a nucleic acid sequence e.g., quantitative hybridization of microRNA, cRNA, etc., quantitative PCR, ELISA for quantification, and the like, and allow the analysis of differential gene expression between two samples. A subject or patient sample, e.g., cells or a collection thereof, e.g., tissues, is assayed. Samples are collected by any convenient method, as known in the art. Nucleic acid sequences of interest are nucleic acid sequences that are found to be predictive, including the nucleic acid sequences of those described herein, where the expression profile may include expression data for 5, 10, 20, 25, 50, 100 or more of, including all of the listed nucleic acid sequences. The term "expression profile" may also mean measuring the abundance of the nucleic acid sequences in the measured samples.

"Differential expression" refers to qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type that may be detectable by standard techniques. Some genes will be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, Northern analysis, and RNase protection.

"Nucleic acid" or "oligonucleotide" or "polynucleotide" as used herein refers to at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypo-xanthine, isocytosine and isoguanine. Nucleic acids may be obtained by chemical synthesis methods or by recombinant methods.

The term "primer" refers to any nucleic acid that is capable of hybridizing at its 3' end to a complementary nucleic acid molecule, and that provides a free 3' hydroxyl terminus which can be extended by a nucleic acid polymerase. As used herein, amplification primers are a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule having the nucleotide sequence flanked by the primers. For in situ methods, a cell or tissue sample can be prepared and immobilized on a support, such as a glass slide, and then contacted with a probe that can hybridize to RNA. Alternative methods for amplifying nucleic acids corresponding to expressed RNA samples include those described in, e.g., U.S. Pat. No. 7,897,750.

The term "probe" as used herein refers to an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

"Stringent hybridization conditions" as used herein refers to conditions under which a first nucleic acid sequence (e.g., probe) hybridizes to a second nucleic acid sequence (e.g., target), such as in a complex mixture of nucleic acids. Stringent conditions are sequence-dependent and be different in different circumstances, and can be suitably selected by one skilled in the art. Stringent conditions may be selected to be about 5-10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° ° C., or, 5×SSC, 1% SDS, incubating at 65° C., with wash in 0.2×SSC, and 0.1% SDS at 65° C. However, several factors other than temperature, such as salt concentration, can influence the stringency of hybridization and one skilled in the art can suitably select the factors to accomplish a similar stringency.

As used herein the term "reference value" refers to a value that statistically correlates to a particular outcome when compared to an assay result. In preferred embodiments, the reference value is determined from statistical analysis of studies that compare microRNA expression with known clinical outcomes. The reference value may be a threshold score value or a cutoff score value. Typically a reference value will be a threshold above (or below) which one outcome is more probable and below which an alternative threshold is more probable.

In one embodiment, a reference level may be one or more circulating miRNA levels expressed as an average of the level of the circulating miRNA from samples taken from a control population of healthy (disease-free) subjects. In another embodiment, the reference level may be the level in the same subject at a different time, e.g., before the present assay, such as the level determined prior to the subject developing the disease or prior to initiating therapy. In general, samples are normalized by a common factor. For example, acellular body fluid samples are normalized by volume body fluid and cell-containing samples are normalized by protein content or cell count. Nucleic acid samples may also be normalized relative to an internal control nucleic acid.

As disclosed herein, the difference of the level of one or more polypeptides or RNAs (mRNAs or microRNAs) is indicative of a disease or a stage thereof. The phrase "difference of the level" refers to differences in the quantity of a particular marker, such as a nucleic acid, in a sample as compared to a control or reference level. For example, the quantity of a particular biomarker may be present at an elevated amount or at a decreased amount in samples of patients with a neoplastic disease compared to a reference level. In one embodiment, a "difference of a level" may be a difference between the quantity of a particular biomarker present in a sample as compared to a control (e.g., reference value) of at least about 1%, 2%, 3%, 5%, 10%, 15%, 20%, 25%, 30%, 35%, 40%, 50%, 60%, 75%, 80% 100%, 150%, 200%, or more. In one embodiment, a "difference of a level" may be a statistically significant difference between the quantities of a biomarker present in a sample as compared to a control. For example, a difference may be statistically significant if the measured level of the biomarker falls outside of about 1.0 standard deviation, about 1.5 standard deviations, about 2.0 standard deviations, or about 2.5 stand deviations of the mean of any control or reference group. With respect to miRNA measurement, the level may be measured from real-time PCR as the Ct value, which may be normalized to a ΔCt value as described in the Examples below.

Drug Screening

The invention provides a method for identifying a compound that are useful for treating melanoma or for inhibiting endothelial recruitment, cell invasion, or metastatic angiogenesis.

Candidate compounds to be screened (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. 1994, J. Med. Chem. 37:2678-2685; and Lam, 1997, Anticancer Drug Des. 12:145. Examples of methods for the synthesis of molecular libraries can be found in, e.g., DeWitt et al., 1993, PNAS USA 90:6909; Erb et al., 1994, PNAS USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89: 1865-1869), or phages (Scott and Smith 1990, Science 249:386-390; Devlin, 1990, Science 249:404-406; Cwirla et al., 1990, PNAS USA 87:6378-6382; Felici 1991, J. Mol. Biol. 222:301-310; and U.S. Pat. No. 5,223,409).

To identify a useful compound, one can contact a test compound with a system containing test cells expressing a reporter gene encoded by a nucleic acid operatively liked to a promoter of a marker gene selected from the above-mentioned metastasis promoters or suppressors. The system can be an in vitro cell line model or an in vivo animal model. The cells can naturally express the gene, or can be modified to express a recombinant nucleic acid. The recombinant nucleic acid can contain a nucleic acid coding a reporter polypeptide to a heterologous promoter. One then measures the expression level of the miRNA, polypeptide, or reporter polypeptide.

For the polypeptide, the expression level can be determined at either the mRNA level or at the protein level. Methods of measuring mRNA levels in a cell, a tissue sample, or a body fluid are well known in the art. To measure mRNA levels, cells can be lysed and the levels of mRNA in the lysates or in RNA purified or semi-purified from the lysates can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out using tissue sections or unlysed cell suspensions, and detectably (e.g., fluorescent or enzyme) labeled DNA or RNA probes. Additional mRNA-quantifying methods include RNA protection assay (RPA) and SAGE. Methods of measuring protein levels in a cell or a tissue sample are also known in the art.

To determine the effectiveness of a candidate compound to treat melanoma or inhibiting endothelial recruitment, cell invasion, or metastatic angiogenesis, one can compare the level obtained in the manner described above with a control level (e.g., one obtained in the absence of the candidate compound). The compound is identified as being effective if (i) a metastasis suppressor's level is lower than a control or reference value or (ii) a metastasis promoter's level is higher than the control or reference value. One can further verify the efficacy of a compound thus-identified using the in vitro cell culture model or an in vivo animal model as disclosed in the example below.

EXAMPLES

Example 1 Materials and Methods

This example describes materials and methods used in EXAMPLES 2-11 below.

Compounds

TABLE 3

| Compound Names | |
|---|---|
| Compound # | Compound Name |
| 1 | T0901317 |
| 2 | GW3965 |
| 3 | LXR-623 |
| 12 | WO-2010-0138598 Ex. 9 or WO-201000138598 |
| 25 | SB742881 |
| 38 | WO-2007-002563 Ex. 19 or WO-2007-002563 |

Animal Studies

All mouse experiments were conducted in agreement with a protocol approved by the Institutional Animal Care and Use Committee (IACUC) at The Rockefeller University. 6-8-week old age-matched and sex-matched mice were used for primary tumor growth and metastasis assays as previously described (Minn et al., 2005; Tavazoie et al., 2008). See Extended Experimental Procedures.

Cell Culture

All cancer cell lines were cultured as previously described (Tavazoie et al., 2008). 293T and human umbilical vein endothelial cells (HUVEC's) were maintained in standard conditions. miRNA and gene knock-down/over-expression studies in cell lines and in vitro functional assays are detailed in Extended Experimental Procedures.

Microarray Hybridization

In order to identify miRNAs deregulated across highly metastatic derivatives, small RNAs were enriched from total RNA derived from MeWo and A375 cell lines and profiled by LC sciences. In order to identify potential gene targets of miR-199a-3p, miR-199a-5p, and miR-1908, total RNA from MeWo cell lines was labeled and hybridized onto Illumina HT-12 v3 Expression BeadChip arrays by The Rockefeller University genomics core facility. See Extended Experimental Procedures for thresholds and criteria used to arrive at miRNA and mRNA targets.

Analysis of miRNA Expression in Human Melanoma Skin Lesions

All human clinical samples used in this study were obtained, processed, and analyzed in accordance with IRB guidelines. Total RNA was extracted from paraffin-embedded cross-sections of primary melanoma skin lesions previously resected from patients at MSKCC, and specific miRNA expression levels were analyzed in a blinded fashion using TaqMan miRNA Assays (Applied Biosystems). Kaplan-Meier curves representing each patient's metastasis-free-survival data as a function of primary tumor miRNA expression values were generated using the GraphPad Prism software package.

In Vivo LNA Therapy

Following tail-vein injection of $4\times10^4$ MeWo-LM2 cells, NOD-SCID mice were treated intravenously twice a week for four weeks with in vivo-optimized LNAs (Exiqon) antisense to miR-199a-3p, miR-199a-5p, and miR-1908 at a combinatorial dose of 12.5 mg/kg delivered in 0.1 mL of PBS.

Histology

For gross macroscopic metastatic nodule visualization, 5-μm-thick lung tissue sections were H&E stained. For in vivo endothelial content analyses, lung sections were double-stained with antibodies against MECA-32 (Developmental Studies Hybridoma Bank, The University of Iowa, IA), which labels mouse endothelial cells, and human vimentin (Vector Laboratories), which labels human melanoma cells. See Extended Experimental Procedures.

Data Analysis

All data are represented as mean #SEM. The Kolmogorov-Smirnov test was used to determine significance of differences in metastatic blood vessel density cumulative distributions. The prognostic power of the miRNAs to predict metastatic outcomes was tested for significance using the Mantel-Cox log-rank test. The one-way Mann-Whitney t-test was used to determine significance values for non-Gaussian bioluminescence measurements. For all other comparisons, the one-sided student's t-test was used. P values<0.05 were deemed to be statistically significant.

In Vivo Selection, Experimental Metastasis, and Primary Tumor Growth Assays

All mouse experiments were conducted in agreement with a protocol approved by the Institutional Animal Care and Use Committee (IACUC) at The Rockefeller University. To generate multiple metastatic derivatives from two independent human melanoma cell lines, in vivo selection was performed as previously described (Minn et al., 2005 Nature 436, 518-524; Pollack and Fidler, 1982 J. Natl. Cancer Inst. 69, 137-141). In brief, $1\times10^6$ pigmented MeWo or non-pigmented A375 melanoma parental cells were resuspended in 0.1 mL of PBS and intravenously injected into 6-8-week old immunocompromised NOD-SCID mice. Following lung metastases formation, nodules were dissociated and cells were propagated in vitro, giving rise to first generation of lung metastatic derivatives (LM1). The LM1 cells were then subjected to another round of in vivo selection by injecting $2\times10^5$ cells via the tail-vein into NOD-SCID mice, giving rise to metastatic nodules, whose subsequent dissociation yielded second generation of lung metastatic derivatives (LM2). For the A375 cell line, a third round of in vivo selection was performed, yielding the highly metastatic A375-LM3 derivatives.

In order to monitor metastasis in vivo through bioluminescence imaging, A375 and MeWo parental cells and their metastatic derivatives were transduced with a retroviral construct expressing a luciferase reporter (Ponomarev et al., 2004 Eur J Nucl Med Mol Imaging 31, 740-751). For all metastasis experiments, lung or systemic colonization was monitored over time and quantified through non-invasive bioluminescence imaging as previously described (Minn et al., 2005). To determine whether in vivo selection had been achieved, $4\times10^4$ MeWo parental or MeWo-LM2 cells and $1\times10^5$ A375 parental or A375-LM3 cells were resuspended in 0.1 mL of PBS and injected via the lateral tail vein into 6-8-week old NOD-SCID mice. For experimental metastasis assays testing the effects of putative promoter miRNAs on lung colonization, $4\times10^4$ MeWo parental cells over-expressing miR-199a, miR-1908, miR-214, or a control hairpin, $4\times10^4$ MeWo-LM2 cells with silenced expression of miR-199a-3p, miR-199a-5p, miR-1908, or a control sequence, and $2\times10^5$ A375-LM3 cells inhibited for miR-199a-3p, miR-199a-5p, miR-1908, or a control sequence were resuspended in 0.1 mL of PBS and tail-vein injected into 6-8-week old NOD-SCID mice. For epistasis experiments, $1\times10^5$ MeWo-LM2 cells expressing an shRNA targeting ApoE, DNAJA4, or a control sequence or siRNA inhibiting LRP1 or a control sequence in the setting of miRNA inhibition were intravenously injected into 6-8-week old NOD-SCID mice. For ApoE pre-treatment experiments, MeWo-LM2 cells were incubated in the presence of ApoE or BSA at 100 μg/mL at 37° C. After 24 hours, $4\times10^4$ cells were injected via the tail-vein into 7-week old NOD-SCID mice. To determine the effect of pre-treating highly metastatic melanoma cells with LNAs targeting miR-199a-3p, miR-199a-5p, and miR-1908 on metastasis, MeWo-LM2 cells were transfected with each LNA individually, a cocktail of LNAs targeting all three miRNAs, or a control LNA. After 48 hours, $1\times10^5$ cells, resuspended in 0.1 mL of PBS, were administered intravenously into 7-week old NOD-SCID mice for lung metastatic colonization studies or through intracardiac injection into 7-week old athymic nude mice for systemic metastasis assays. To determine the effect of genetic deletion of ApoE on metastasis, 8-week old C57BL/6-WT or C57BL/6-ApoE−/− mice were intravenously injected with $5\times10^4$ B16F10 mouse melanoma cells. For primary tumor growth studies, $1\times10^6$ parental MeWo cells over-expressing miR-199a, miR-1908, or a control hairpin were mixed 1:1 with matrigel and subcutaneously injected into the lower right flank of 6-week old immunodeficient NOD-SCID mice. Animals were palpated weekly for tumor formation, after which sizeable tumors were measured twice a week. Tumor volume was calculated as (small diameter)$^2\times$(large diameter)/2.

Lentiviral miRNA Inhibition and Gene Knock-Down 293T cells were seeded in a 10-cm plate and allowed to reach 60% confluency. Prior to transfection, the cell media was replaced with fresh antibiotic-free DMEM media supplemented with 10% FBS. 6 μg of vector A, 12 μg of vector K, and 12 μg of the appropriate miR-Zip (System Biosciences, Mountain View, CA) or shRNA plasmid construct (MSKCC HTS Core Facility, New York, NY) were co-transfected using 60 μL of TransIT-293 transfection reagent (MIR 2700, Mirus Bio LLC, Madison, WI). The cells were incubated at 37° C. for 48 hours, and the virus was harvested by spinning the cell media for 10 minutes at 2000 g followed by virus filtration through a 0.45 μm filter. $1\times10^5$ cancer cells were transduced with 2 mL of the appropriate virus in the presence of 10 μg/mL of polybrene (TR-1003-G, Millipore, Billerica, MA) for 6 hrs. After 48 hours, 2 μg/mL of puromycin (P8833, Sigma-Aldrich, St Louis, MO) was added to the cell media for lentiviral selection. The cells were kept in puromycin selection for 72 hours. The following miR-Zip sequences were used:

```
miR-Zip-199a-3p:
5'-GATCCGACAGTAGCCTGCACATTAGTCACTTCCTGTCAGTAACCAA

TGTGCAGACTACTGTTTTTTGAATT-3'

miR-Zip-199a-5p:
5'-GATCCGCCCAGTGCTCAGACTACCCGTGCCTTCCTGTCAGGAACAG

GTAGTCTGAACACTGGGTTTTTGAATT-3'

miR-Zip-1908
5'-GATCCGCGGCGGGAACGGCGATCGGCCCTTCCTGTCAGGACCAATC

GCCGTCCCCGCCGTTTTTGAATT-3'
```

The following shRNA sequences were used:

```
shAPOE1:
5'CCGGGAAGGAGTTGAAGGCCTACAACTCGAGTTGTAGGCCTTCAACTC

CTTCTTTTT3'

shAPOE2:
5'CCGGGCAGACACTGTCTGAGCAGGTCTCGAGACCTGCTCAGACAGTGT

CTGCTTTTT3'

shDNAJA41:
5'CCGGGCGAGAAGTTTAAACTCATATCTCGAGATATGAGTTTAAACTTC

TCGCTTTTT3'

shDNAJA42:
5'CCGGCCTCGACAGAAAGTGAGGATTCTCGAGAATCCTCACTTTCTGTC

GAGGTTTTT3'
```

Retroviral miRNA and Gene Over-Expression

6 μg of vector VSVG, 12 μg of vector Gag-Pol, and 12 μg of pBabe plasmid containing the coding sequences of human ApoE, DNAJA4, or an empty vector or miR-Vec containing the precursor sequence of miR-199a, miR-214, miR-1908, or a control hairpin were co-transfected into 60%-confluent 293T cells using 60 μL of TransIT-293 transfection reagent. The cells were incubated at 37° C. for 48 hours, after which the virus was harvested and transduced into cancer cells in the presence of 10 μg/mL of polybrene for 6 hours. After 48 hours, 2 μg/mL of puromycin or 10 μg/mL of blasticidin (15205, Sigma-Aldrich, St Louis, MO) were added to the cell media for retroviral selection. The cells were kept in puromycin selection for 72 hours or in blasticidin selection for 7 days. The following cloning primers were used for over-expression of the coding sequences of ApoE and DNAJA4:

```
ApoE_CDS_Fwd:
5'-TCATGAGGATCCATGAAGGTTCTGTGGGCT-3'

ApoE_CDS_Rev:
5'-TAGCAGAATTCTCAGTGATTGTCGCTGGG-3'

DNAJA4_CDS_Fwd:
5'-ATCCCTGGATCCATGTGGGAAAGCCTGACCC-3'
```

-continued

```
DNAJA4_CDS_Rev:
5'-TACCATGTCGACTCATGCCGTCTGGCACTGC-3'
```

LNA-Based miRNA Knock-Down

LNAs complimentary to mature miR-199a-3p, miR-199a-5p, miR-1908, or a control sequence (426917-00, 426918-00, 426878-00, and 1990050, respectively; Exiqon, Vedbaek, Denmark) were transfected at a final concentration of 50 nM into 50% confluent MeWo-LM2 cancer cells cultured in antibiotics-free media using Lipofectamine™ 2000 transfection reagent (11668-09, Invitrogen, Carlsbad, CA). After 8 hours, the transfection media was replaced with fresh media. After 48 hours, $1\times10^5$ cells were injected intravenously into NOD-SCID mice to assess lung metastatic colonization or through intracardiac injection into athymic nude mice to assess systemic metastasis. For cell invasion and endothelial recruitment in vitro assays, the cells were used 96 hours post-transfection.

siRNA-Based mRNA Knock-Down siRNAs targeting LRP1, LRP8, VLDLR, LDLR, or a control sequence were transfected into cancer cells or HUVEC's at a final concentration of 100 nM using Lipofectamine™ 2000 transfection reagent. After 5 hours, the transfection media was replaced with fresh media. The cells were subjected to matrigel invasion and endothelial recruitment assays 96 hours post-transfection. Cells transduced with siRNAs targeting LRP1 or a control sequence in the setting of miRNA inhibition were tail-vein injected for lung colonization assays 72 hours post-transfection. Control non-targeting siRNAs were obtained from Dharmacon. The following LRP1 and LRP8 target sequences were used:

```
siLRP11: 5'-CGAGGACGAUGACUGCUUA-3';

siLRP12: 5'-GCUAUGAGUUUAAGAAGUU-3';

siLRP81: 5'-CGAGGACGAUGACUGCUUA-3';

siLRP82: 5'-GAACUAUUCACGCCUCAUC-3'.
```

Cell Proliferation Assay

To determine the effects of miR-199a or miR-1908 over-expression and combinatorial LNA-induced miRNA inhibition on cell proliferation, $2.5\times10^4$ cells were seeded in triplicate in 6-well plates, and viable cells were counted after 5 days. To assess the effects of recombinant ApoE addition on melanoma cell or endothelial cell proliferation, $3\times10^4$ melanoma MeWo-LM2 cells or endothelial cells were incubated in the presence of ApoE (100 μM) or BSA (100 μM). Viable cells were counted after 8, 24, 48, 72, and 120 hours.

Matrigel Invasion Assay

Cancer cells were serum-starved in 0.2% FBS DMEM-based media for 12 hours. Trans-well invasion chambers (354480, BD Biosciences, Bedford, MA) were pre-equilibrated prior to beginning the assay by adding 0.5 mL of starvation media to the top and bottom chambers. After 30 minutes, the media in the top chamber was removed, and 0.5 mL of media containing $1\times10^5$ cancer cells was added into each matrigel-coated trans-well insert and incubated at 37° C. for 24 hours. For neutralization antibody and/or recombinant protein experiments, antibody/recombinant protein was added to each well at the start of the assay at the following concentrations as indicated in the figures: 5-40 μg/mL anti-ApoE 1D7 (Heart Institute, University of Ottawa), 5-40 μg/mL anti-IgG (AB-108-C, R&D Systems, Minneapolis, MN), 100 μM recombinant human ApoE3

(4696, BioVision, Mountain View, CA), and 100 μM BSA (A2153, Sigma-Aldrich). Upon completion of the assay, matrigel-coated inserts were washed with PBS, the cells at the top side of each insert were scraped off, and the inserts were fixed in 4% paraformaldehyde for 15 minutes. The inserts were then cut out and mounted onto slides using VectaShield mounting medium containing DAPI (H-1000, Vector Laboratories, Burlingame, CA). The basal side of each insert was imaged using an inverted fluorescence microscope (Zeiss Axiovert 40 CFL) at 5× magnification, taking three representative images for each insert. The number of invaded cells was quantified using ImageJ (NIH).

Endothelial Recruitment Assay $5\times10^4$ cancer cells were seeded into 24-well plates approximately 24 hours prior to the start of the assay. HUVEC's were grown to 80% confluency and serum starved in EGM-2 media supplemented with 0.2% FBS for 16 hours. HUVEC's were then pulsed with Cell Tracker Red CMTPX dye (C34552, Invitrogen) for 45 minutes. Meanwhile, cancer cells were washed with PBS, 0.5 mL of 0.2% FBS EGM-2 media was added to each well, and a 3.0 μm HTS Fluoroblock insert (351151, BD Falcon, San Jose, CA) was placed into each well. $1\times10^5$ HUVEC's, resuspended in 0.5 mL of starvation media, were seeded into each trans-well insert, and the recruitment assay was allowed to proceed for 16-18 hours at 37° C. For neutralization antibody and/or recombinant protein experiments, antibody/protein was then added to each well at the appropriate concentration as indicated in the figures: 40 μg/mL anti-ApoE 1D7, 40 μg/mL anti-IgG, 100 μM rhApoE3, and 100 μM BSA. Upon completion of the assay, the inserts were processed and analyzed as described for the matrigel invasion assay above (See Matrigel Invasion Assay).

Endothelial Migration Assay

Serum-starved HUVEC's were pulsed with Cell Tracker Red CMTPX dye for 45 minutes and seeded into HTS Fluoroblock trans-well inserts at a concentration of $1\times10^5$ HUVEC's in 0.5 mL starvation media per each insert. The assay was allowed to proceed for 16-18 hours at 37° C., and the inserts were processed and analyzed as described above (See Matrigel Invasion Assay).

Chemotaxis Assay

HUVEC's were serum-starved in 0.2% FBS EGM-2 media for 16 hours and labeled with Cell Tracker Red CMTPX dye for 45 minutes. Meanwhile, the indicated amounts (1-5 μg) of recombinant human ApoE3 or BSA were mixed with 250 μL of matrigel (356231, BD Biosciences) and allowed to solidify at the bottom of a 24-well plate for 30 min. 250 μL of HUVEC EGM-2 media containing 0.2% FBS was then added to each matrigel-coated well, and 3.0 μM HTS Fluoroblock inserts were fitted into each well. $1\times10^5$ HUVEC's, resuspended in 0.5 mL of starvation media, were seeded into each insert and allowed to migrate along the matrigel gradient for 16-18 hours at 37° C. Upon completion of the assay, the inserts were mounted on slides and analyzed as described above (See Matrigel Invasion Assay).

Endothelial Adhesion Assay

HUVEC's were seeded in 6-well plates and allowed to form monolayers. Cancer cells were serum starved in 0.2% FBS DMEM-based media for 30 minutes and pulsed with Cell Tracker Green CMFDA dye (C7025, Invitrogen) for 45 minutes. $2\times 10^5$ cancer cells, resuspended in 0.5 mL starvation media, were seeded onto each endothelial monolayer. The cancer cells were allowed to adhere to the HUVEC monolayers for 30 minutes at 37° C. The endothelial monolayers were then washed gently with PBS and fixed with 4% paraformaldehyde for 15 minutes. Each well was then coated with PBS, and 8 images were taken for each endothelial monolayer using an inverted Fluorescence microscope (Zeiss Axiovert 40 CFL) at 10× magnification. The number of cancer cells adhering to HUVEC's was quantified using ImageJ.

Anoikis Assay $1\times10^6$ MeWo cells over-expressing miR-199a, miR-1908, or a control hairpin were seeded in low adherent plates containing cell media supplemented with 0.2% methylcellulose. Following 48 hours in suspension, the numbers of dead and viable cells were counted using trypan blue.

Serum Starvation Assay

To determine the effects of miR-199a and miR-1908 on melanoma cell serum starvation capacity, $1\times 10^5$ MeWo parental cells over-expressing miR-199a, miR-1908, or a control hairpin were seeded in quadruplicate into 6-well plates and incubated in 0.2% FBS starvation DMEM-based media for 48 hours, after which the number of viable cells was counted using trypan blue. To determine the effect of recombinant ApoE3 addition on the survival of melanoma cells or endothelial cells in serum starvation conditions, $3\times10^4$ MeWo-LM2 cells or endothelial cells were incubated in the presence of ApoE3 (100 μM) or BSA (100 μM) in low serum conditions (0.2% FBS). The number of viable cells was counter after 8, 16, and 24 hours.

Colony Formation Assay

Fifty MeWo parental cells over-expressing miR-199a, miR-1908, or a control hairpin were seeded in quadruplicate into 6-cm plates. After two weeks, the cells were washed with PBS, fixed with 6% glutaraldehyde, and stained with 0.5% crystal violet. The number of positive-staining colonies was counted.

miRNA Microarray Hybridization

For identification of miRNAs showing deregulated expression across highly metastatic melanoma cell line derivatives, total RNA from multiple independent metastatic derivatives and their respective parental MeWo and A375 cell populations was used to enrich for small RNAs which were then labelled and hybridized onto microfluidic custom microarray platforms by LC sciences. The arrays were designed to detect 894 mature miRNAs corresponding to the miRNA transcripts listed in Sanger miRBase Release 13.0. Out of all the probes analyzed, those corresponding to 169 miRNAs yielded signal above a background threshold across the multiple cell lines analyzed. The raw signal intensities, corresponding to probe hybridization, were median-normalized for each cell line. A threshold of 2-fold or higher up-regulation of median-normalized expression values were used in order to identify miRNAs commonly induced in multiple metastatic derivatives for two independent human melanoma cell lines.

Microarray-Based Gene Target Prediction for miR-199a and miR-1908

In order to identify potential genes targeted by miR-199a-3p, miR-199a-5p, and miR-1908, total RNA was extracted from MeWo cell lines with loss- or gain-of-function of each miRNA and submitted to the genomics core facility at The Rockefeller University for hybridization onto Illumina HT-12 v3 Expression BeadChip microarrays. The raw signal intensities, corresponding to probe hybridization, were then median-normalized for each cell line sample. Three sets of microarray profile comparisons were generated: (1) MeWo control cells relative to MeWo cells over-expressing miR-199a or miR-1908, (2) MeWo-LM2 control cells relative to MeWo-LM2 cells expressing a short hairpin (miR-Zip) targeting miR-199a-3p, miR-199a-5p, or miR-1908, and (3)

MeWo parental cells relative to MeWo-LM2 cells. Based on the median-normalized expression values from these arrays, the following criteria were used to arrive at possible target genes common to miR-199a and miR-1908: (1) Genes down-regulated by more than 1.5 fold upon individual over-expression of each miR-199a and miR-1908, (2) Genes up-regulated by more than 1.5 fold upon inhibition of either both miR-199a-3p and miR-1908 or both miR-199a-5p and miR-1908, and (3) genes down-regulated by more than 1.5 fold in LM2 cells, which express physiologically higher levels of the three miRNAs, relative to MeWo parental cells.

Analysis of miRNA and mRNA Expression in Cell Lines

Total RNA was extracted from various cell lines using the miRvana kit (AM1560, Applied Biosystems, Austin, TX). The expression levels of mature miRNAs were quantified using the Taqman miRNA expression assay (4427975-0002228, Applied Biosystems). RNU44 was used as an endogenous control for normalization. For mRNA expression analyses, 600 ng of total RNA was reverse transcribed using the cDNA First-Strand Synthesis Kit (18080-051, Invitrogen), and roughly 200 ng of the resulting cDNA was then mixed with SYBR green PCR Master Mix (4309155, Applied Biosystems) and the appropriate primers. Each reaction was performed in quadruplicate, and mRNA expression was quantified by performing real-time PCR amplification using an ABI Prism 7900HT Real-Time PCR System (Applied Biosystems). GAPDH was used as an endogenous control for normalization. The following primers were used:

```
ApoE_Fwd:
5'-TGGGTCGCTTTTGGGATTAC-3'

ApoE_Rev:
5'-TTCAACTCCTTCATGGTCTCG-3'

DNAJA4_Fwd:
5'-CCAGCTTCTCTTCACCCATG-3'

DNAJA4_Rev:
5'-GCCAATTTCTTCGTGACTCC-3'

GAPDH_Fwd:
5'-AGCCACATCGCTCAGACAC-3'

GAPDH_Rev:
5'-GCCCAATACGACCAAATCC-3'

LRP1_Fwd:
5'-TTTAACAGCACCGAGTACCAG-3'

LRP1_Rev:
5'CAGGCAGATGTCAGAGCAG-3'

LRP8_Fwd:
5'-GCTACCCTGGCTACGAGATG-3'

LRP8_Rev:
5'-GATTAGGGATGGGCTCTTGC-3'
```

ELISA

Conditioned cancer cell media was prepared by incubating cells in 0.2% FBS serum starvation DMEM-based media for 24 hours. ApoE levels in conditioned media were determined using the APOE ELISA kit (IRAPKT031, Innovative Research, Novi, Michigan).

Luciferase Reporter Assays

Heterologous luciferase reporter assays were performed as previously described (Tavazoie et al., 2008). In brief, full-length 3'UTRs and CDS's of ApoE and DNAJA4 were cloned downstream of a renilla luciferase reporter into the psiCheck2 dual luciferase reporter vector (C8021, Promega, Madison, WI). $5\times10^4$ parental MeWo cells, MeWo-LM2 cells, MeWo cells over-expressing miR-199a, miR-1908, or a control hairpin, and MeWo-LM2 cells expressing a miR-Zip hairpin targeting miR-199a-3p, miR-199a-5p, miR-1908, or a control sequence were transfected with 100 ng of the respective specific reporter constructs using TransiT-293 transfection reagent. Twenty-four hours post-transfection, the cells were lysed, and the ratio of renilla to firefly luciferase expression was determined using the dual luciferase assay (E1910, Promega). Putative miRNA binding sites in each target construct were identified by alignment to the complimentary miRNA seed sequences (miR-199a-3p: 5'-CAGUAGUC-3'; miR-199a-5p: 5'-CCAGUGUU-3'; miR-1908: 5'-GGCGGGGA-3'). The miRNA complimentary sites on each target construct were mutated using the QuickChange Multi Site-Directed Mutagenesis Kit (200514, Agilent Technologies, Santa Clara, CA). Based on miRNA seed sequence complementarity analysis, the CDS of ApoE was mutated at position 141 (CTG to ACT), the 3'UTR of ApoE was mutated at positions 83 (GCC to ATA) and 98 (CTG to ACA), the CDS of DNAJA4 was mutated at positions 373 (CGC to TAT) and 917 (CTG to AGA), and the 3'UTR of DNAJA4 was mutated at positions 576 (CTG to ACA), 1096 (CTG to TCT), 1396 (CGC to TGT), and 1596 (CTG to TGT). The following primers were used to clone the 3'UTR's and CDS's of ApoE and DNAJA4:

```
ApoE_CDS_Fwd:
5'-AGTACCTCGAGGGGATCCTTGAGTCCTACTC-3'

APOE_CDS_Rev:
5'-TAATTGCGGCCGCTCAGACAGTGTCTGCACCCAG-3'

DNAJA4_CDS_Fwd:
5'-TAATATCTCGAGATGTGGGAAAGCCTGACCC-3'

DNAJA4_CDS_Rev:
5'-CAATTGCGGCCGCTCATGCCGTCTGGCACTGC-3'

APOE_3'UTR_Fwd:
5'-TTAGCCTCGAGACGCCGAAGCCTGCAGCCA-3'

APOE_3'UTR_Rev:
5'-TTACTGCGGCCGCTGCGTGAAACTTGGTGAATCTT-3'

DNAJA4_3'UTR_Fwd:
5'-TAATATCTCGAGCGTGGTGCGGGGCAGCGT-3'

DNAJA4_3'UTR_Rev:
5'-CAATTGCGGCCGCTTATCTCTCATACCAGCTCAAT-3'
```

The following primers were used to mutagenize the miRNA binding sites on each target:

```
APOE_CDS_mut:
5'-GCCAGCGCTGGGAACTGGCAACTGGTCGCTTTTGGGATTACCT-3'

APOE_3'UTR_mut1:
5'-CAGCGGGAGACCCTGTCCCCATACCAGCCGTCCTCCTGGGGTG-3'

APOE_3'UTR_mut2:
5'-TCCCCGCCCCAGCCGTCCTCACAGGGTGGACCCTAGTTTAATA-3'

DNAJA4_CDS_mut1:
5'-GGGATCGGTGGAGAAGTGCCTATTGTGCAAGGGGCGGGGGATG-3'

DNAJA4_CDS_mut2:
5'-GTAGGGGGCGGGGAACGTGTTATCCGTGAAGAGGTGGCTAGGG-3'

DNAJA4_3'UTR_mut1:
5'-CAGGGCCAACTTAGTTCCTAACATTCTGTGCCCTTCAGTGGAT-3'

DNAJA4_3'UTR_mut2:
5'-ACAGTTTGTATGGACTACTATCTTAAATTATAGCTTGTTTGGA-3'
```

-continued

```
DNAJA4_3'UTR_mut3:
5'-TAATTATTGCTAAAGAACTATGTTTTAGTTGGTAATGGTGTAA-3'

DNAJA4_3'UTR_mut4:
5'-CAGCTGCACGGACCAGGTTCCATAAAAACATTGCCAGCTAGTGAG-

3'
```

Analysis of miRNA Expression in Human Melanoma Skin Lesions

All human clinical samples used in this study were obtained, processed, and analyzed in accordance with institutional IRB guidelines. Paraffin-embedded cross-sections of primary melanoma skin lesions from 71 human patients were obtained from MSKCC. The samples were de-paraffinized by five consecutive xylene washes (5 minutes each). Following de-paraffinization, the malignancy-containing region was identified by H&E staining, dissected, and total RNA was extracted from it using the RecoverAll Total Nucleic Acid Isolation Kit (AM1975, Applied Biosystems). The expression levels of mature miR-199a-3p, miR-199a-5p, and miR-1908 in each sample were quantified in a blinded fashion using the Taqman miRNA assay. RNU44 was used as an endogenous control for normalization. The expression levels of each miRNA were compared between primary melanomas with propensity to metastasize and primary melanomas that did not metastasize. Kaplan-Meier curves were plotted using metastasis-free survival data of patients as a function of the expression levels for each miRNA in each patient's tumor. Metastatic recurrence to such sites as lung, brain, bone, and soft tissue were previously documented and allowed for a retrospective analysis of the relationship between the expression levels of identified miRNAs and metastatic recurrence.

Histology

Animals were perfused with PBS followed by fixation with 4% paraformaldehyde infused via intracardiac and subsequently intratracheal injection. The lungs were sectioned out, incubated in 4% paraformaldehyde at 4° C. overnight, embedded in paraffin, and sliced into 5-μm-thick increments. For gross macroscopic metastatic nodule visualization, lung sections were H&E stained. For endothelial content analysis in metastatic nodules formed by human melanoma MeWo cells in mice, representative lung sections were double-stained with primary antibodies against MECA-32 (Developmental Studies Hybridoma Bank, The University of Iowa, IA), which labels mouse endothelial cells, and human vimentin (VP-V684, Vector Laboratories), which labels human melanoma cells. Various Alexa Flour dye-conjugated secondary antibodies were used to detect primary antibodies. To determine the blood vessel density within metastatic nodules, fluorescence was measured using a Zeiss laser scanning confocal microscope (LSM 510), and the MECA-32 signal within each metastatic nodule, outlined based on co-staining with human vimentin, was quantified in a blinded fashion using ImageJ (NIH). For endothelial content analysis in metastatic nodules formed by mouse B16F10 mouse melanoma cells in wild type and ApoE genetically null mice, representative lung sections were stained for MECA-32, and the MECA-32 signal within each nodule, demarcated based on cell pigmentation, was quantified in a blinded fashion. The collective vessel area, given as the percentage area covered by blood vessels relative to the total area of each metastatic nodule, was obtained by background subtraction (rolling ball radius of 1 pixel) and use of a pre-determined threshold as a cut-off. A metastatic nodule was defined as any region of greater than 2000 $\mu m^2$ total area. For large nodules, minimum of four representative images were obtained, and their average blood vessel density was calculated.

In Vivo Matrigel Plug Assay

10 μg/mL recombinant human ApoE3 (4696, BioVision), 10 μg/mL BSA (A2153, Sigma Aldrich), or 400 ng/ml VEGF were mixed with matrigel (356231, BD Biosciences) as indicated. 400 μL of matrigel containing the indicated recombinant proteins were injected subcutaneously just above the ventral flank of immunocompromised NOD-SCID mice. Plugs were extracted on day 3 post-injection and fixed in 4% paraformaldehyde for 48 hours. Plugs were then paraffin-embedded and sectioned at 5-μm-thick increments. Plug cross-sectional sections were immunohistochemically stained using a primary antibody against the mouse endothelial antigen MECA-32 (Developmental Studies Hybridoma Bank, The University of Iowa, IA), detected by peroxidase-conjugated secondary antibody, and subsequently visualized by DAB oxidization. To quantify the extent of endothelial cell invasion into each matrigel plug, the number of endothelial cells was counted in 4-5 random fields for each plug, and the average number of endothelial cells per given plug area was calculated.

Tissue Culture

The SK-Mel-334 primary human melanoma line was established from a soft tissue metastasis of a Braf-mutant melanoma of a patient at the MSKCC. Following minimum expansion in vitro, the cells were in vivo selected (Pollack and Fidler, 1982) to generate the lung-metastatic derivatives SK-Mel-334.2. The SK-Mel-239 vemurafenib-resistant clone (C1) was a gift from Poulikos Poulikakos (Mount Sinai Medical School) and the B-Raf$^{V600E/+}$; Pten$^{-/-}$; CDKN2A$^{-/-}$ primary murine melanoma cell line was generously provided by Marcus Rosenberg (Yale University). All other cell lines used were purchased from ATCC.

ApoE Elisa

Extracellular ApoE levels in serum-free conditioned media from melanoma cells treated with DMSO, GW3965, or T0901317 (1 μM each) were quantified using the ApoE ELISA kit (Innovative Research) at 72 hours following treatment.

Western Blotting

Mouse lung and brain tissue samples were homogenized on ice in RIPA buffer (Sigma-Aldrich) supplemented with protease inhibitors (Roche). Mouse adipose tissue was homogenized on ice in TNET buffer (1.5 mM Tris pH 7.5, 150 mM NaCl, 2 mM EDTA 1% triton, protease inhibitors). Total protein lysate (2 μg) was separated by SDS-PAGE, transferred to PVDF membrane, and blotted with an anti-mouse ApoE (ab20874, Abcam) and anti-tubulin α/β (2148, Cell Signaling) antibodies.

ApoE Expression Analysis in Melanoma Clinical Samples

All clinical sample procurement, processing, and analyses were performed in strict agreement with IRB guidelines. Primary melanoma skin lesions were previously resected from patients at the MSKCC, formalin-fixed, paraffin-embedded, and sectioned into 5-μm-thick slides. ApoE protein expression was assessed by double-blinded immunohistochemical analysis using the D6E10 anti-ApoE antibody (ab 1906, Abcam).

Histochemistry

Animals were intracardially perfused with PBS followed by 4% paraformaldehyde (PFA). Fixed lungs were embedded in paraffin and sectioned into 5-μm-thick increments. Macroscopic lung metastatic nodules were visualized by H&E staining. For analysis of tumor endothelial cell content, proliferation, and apoptosis, primary tumor paraffin-embedded sections were stained with antibodies against MECA-32 (Developmental Studies Hybridoma Bank, University of Iowa), KI-67 (ab 15580, Abcam), and cleaved caspase-3 (9661, Cell Signaling), respectively.

Tail-Vein Metastasis Assays

Melanoma cells used for in vivo metastasis assays were transduced with a stably expressed retroviral construct encoding a luciferase reporter gene (Ponomarev et al., 2004), allowing us to monitor the in vivo progression of melanoma cells by bioluminescence imaging. The following numbers of melanoma cells, resuspended in 100 μL of PBS, were injected intravenously via the tail-vein: $4\times10^4$ MeWo cells, $2.5\times10^5$ HT-144 cells, $2\times10^5$ SK-Mel-334.2 cells, $5\times10^4$B16F10 cells, and $1\times10^5$ YUMM cells. The MeWo, HT-144, and SK-Mel-334.2 cells were injected into 6-8 week-old sex-matched NOD scid mice, while the B16F10 and YUMM cells were injected into 6-8 week-old sex-matched C57BL/6 mice. In all experiments assessing at the effects of GW3965 on metastasis formation, mice were pre-treated on a control diet or a GW3965-supplemented diet (20 mg/kg) for 10 days. To assess the effect of GW3965 treatment on brain metastasis, $1\times10^5$ MeWo brain-metastatic derivatives were injected intracardially into athymic nude mice. Immediately following injection, mice were randomly assigned to a control diet or GW3965-supplemented diet (100 mg/kg). To determine whether oral delivery of GW3965 can inhibit the progression of incipient metastasis, NOD Scid mice were intravenously injected with $4\times10^4$ MeWo cells and the cells were allowed to colonize the lungs for 42 days, after which mice were blindedly assigned to a control diet or a GW3965-supplemented diet (100 mg/kg) treatment.

Orthotopic Metastasis Assays

To determine the effect of GW3965 treatment on lung colonization by melanoma cells dissociated from an orthotopic site, $1\times10^6$ MeWo cells expressing a luciferase reporter were subcutaneously injected into both lower flanks of NOD Scid mice. Upon the formation of tumors measuring ~300 $mm^3$ in volume, the tumors were excised and the mice were randomly assigned to a control diet or a GW3965-supplemented diet (100 mg/kg) treatment. One month after tumor excision, the lungs were extracted and lung colonization was measured by ex vivo bioluminescence imaging. To histologically confirm the extent of melanoma lung colonization, lungs were then fixed in 4% PFA overnight, paraffin-embedded, section into 5-μM increments and stained for human vimentin (VP-V684, Vector Laboratories).

Generation of Dacarbazine-Resistant Melanoma Cells

Dacarbazine-resistant B16F10 mouse melanoma cells were generated by continuously culturing the cells in the presence of DTIC (D2390, Sigma-Aldrich, St. Louis, MO). First, the cells were treated with 500 μg/mL DTIC for one week. Following this initial DTIC treatment, the remaining (~10%) viable cells were allowed to recover for one week, after which 750 μg/mL of DTIC was added to the cell media for 5 days. Subsequent to this high-dose treatment, the cells were allowed to recover in the presence of low-dose DTIC (100 μg/mL) for one week. The cells were then continuously cultured in cell media containing 200 μg/mL DTIC for at least one month prior to grafting the cells into mice. DTIC was added to fresh cancer cell media every 3 days. For tumor growth experiments, $5\times10^4$ B16F10 parental and DTIC-resistant cells were subcutaneously injected into the lower flank of 7-week-old C57BL/6 mice. Following formation of small tumors measuring 5-10 $mm^3$ in volume, the mice were randomly assigned to the following treatment groups: (1) control diet+vehicle, i.p.; (2) control diet+DTIC i.p. (50 mg/kg); (3) GW3965-supplemented diet (100 mg/kg)+vehicle i.p. DTIC was dissolved in the presence of citric acid (1:1 by weight) in water and administered daily by intraperitoneal injection.

The DTIC-resistant MeWo human melanoma cell line clone was generated following DTIC treatment of mice bearing MeWo tumors measuring 600-800 $mm^3$ in volume. After initial tumor shrinkage in response to daily DTIC dosing (50 mg/kg, i.p.) during the first two weeks, the tumors eventually developed resistance and resumed growth, at which point tumor cells were dissociated and the DTIC-resistant MeWo cell line was established. The cells were expanded in vitro in the presence of DTIC (200 μg/mL) for one week, after which $5\times10^5$ DTIC-resistant MeWo cells were re-injected into 8-week old Nod SCID gamma mice. Following growth of tumors to 5-10 $mm^3$ in volume, mice were blindedly assigned to the following treatment groups: (1) control diet; (2) control diet+DTIC (50 mg/kg); (3) GW3965-supplemented diet (100 mg/kg). To determine the effect of DTIC on tumor growth by parental unselected MeWo cells, $5\times10^5$ MeWo cells were subcutaneously injected into Nod SCID gamma mice, and the mice were treated with a control vehicle or DTIC (50 mg/kg) subsequent to formation of tumors measuring 5-10 $mm^3$ in volume. DTIC was administered daily, as described above, in cycles consisting of 5 consecutive daily treatments interspersed by 2-day off-treatment intervals. Tumor growth was measured twice a week.

Genetically-Initiated Model of Melanoma Progression

The Tyr::CreER; B-Raf$^{V600E/+}$; Pten$^{lox/+}$/Tyr::CreER; B-Raf$^{V600E/+}$; Pten$^{lox/lox}$ conditional model of melanoma progression was previously established and characterized by Dankort et al. (2009). Briefly, melanoma in these mice was induced at 6 weeks of age by intraperitoneally injecting 4-HT (H6278, 70% isomer, Sigma-Aldrich, St Louis, MO) at 25 mg/kg administered in peanut oil on three consecutive days. The 4-HT stock solution was prepared by dissolving it in 100% EtOH at 50 mg/mL by heating at 45° C. for 5 min and mixing. Once dissolved, the stock 4-HT solution was then diluted by 10-fold in peanut oil, yielding a 5 mg/mL 4-HT working solution that was then injected into mice. After the first 4-HT injection, mice were blindedly assigned to receive either a control diet or a diet supplemented with GW3965 (100 mg/kg). Mice were examined three times a week for the presence and progression of melanoma lesions. At day 35, dorsal skin samples were harvested from control-treated and GW3965-treated mice, fixed in 4% PFA and photographed at 10×. The percentage of pigmented melanoma lesion area out of the total skin area was quantified using ImageJ. For survival analyses, mice were monitored daily for melanoma progression and euthanized according to a standard body condition score, taking into account initial signs of moribund state and discomfort associated with the progression of melanoma burden. Post-mortem, the lungs, brains, and salivary glands were harvested and examined for the presence of macroscopic melanoma lesions.

Mouse Genotyping

All mouse genotyping was performed using standard PCR conditions, as recommended by Jackson Labs. The following genotyping primers were used for the respective PCR reactions:

Tyr::CreER; B-Baf$^{V600E/+}$; Pten$^{lox/+}$ and
Tyr::CreER; B-Raf$^{V600E/+}$; Pten$^{lox/lox}$ mice:

-continued

B-Raf Forward:
5'-TGA GTA TTT TTG TGG CAA CTG C-3'

B-Raf Reverse:
5'-CTC TGC TGG GAA AGC GGC-3'

Pten Forward:
5'-CAA GCA CTC TGC GAA CTG AG-3'

Pten Reverse:
5'-AAG TTT TTG AAG GCA AGA TGC-3'

Cre Transgene Forward:
5'-GCG GTC TGG CAG TAA AAA CTA TC-3'

Cre Transgene Reverse:
5'-GTG AAA CAG CAT TGC TGT CAC TT-3'

Internal Positive Control Forward:
5'-CTA GGC CAC AGA ATT GAA AGA TCT-3'

Internal Positive Control Reverse:
5'-GTA GGT GGA AAT TCT AGC ATC ATC C-3'

ApoE-/- mice:
Common Forward:
5'-GCC TAG CCG AGG GAG AGC CG-3'

Wild-type Reverse:
5'-TGT GAC TTG GGA GCT CTG CAG C-3'

Mutant Reverse:
5'-GCC GCC CCG ACT GCA TCT-3'

LXRα-/- mice:
Common Forward:
5'-TCA GTG GAG GGA AGG AAA TG-3'

Wild-type Reverse:
5'-TTC CTG CCC TGG ACA CTT AC-3'

Mutant Reverse:
5'-TTG TGC CCA GTC ATA GCC GAA T-3'

LXRβ-/- mice:
Common Forward:
5'-CCT TTT CTC CCT GAC ACC G-3'

Wild-type Reverse:
5'-GCA TCC ATC TGG CAG GTT C-3'

Mutant Reverse:
5'-AGG TGA GAT GAC AGG AGA TC-3'

Cell Proliferation and Viability Assay:

To determine the effects of GW3965, T0901317, and Bexarotene on in vitro cell growth, $2.5\times 10^4$ melanoma cells were seeded in triplicate in 6-well plates and cultured in the presence of DMSO, GW3965, T0901317, or Bexarotene at 1 μM each. After 5 days, the number of viable and dead cells was counted using the trypan blue dye (72-57-1, Sigma-Aldrich), which selectively labels dead cells.

Cell Invasion Assay

The cell invasion assay was performed as previously described in detail (Pencheva et al., 2012) using a trans-well matrigel invasion chamber system (354480, BD Biosciences). In brief, various melanoma cells were cultured in the presence of DMSO, GW3965, T0901317, or Bexarotene at 1 μM for 56 hours, after which melanoma cells were switched to starvation media (0.2% FBS) for 16 hours in the presence of each drug. Following starvation, cells were seeded into matrigel-coated trans-well inserts, and the invasion assay was allowed to proceed for 24 hours at 37° C. For ApoE antibody neutralization experiments, 40 μg/mL 1D7 anti-ApoE blocking antibody (Heart Institute, University of Ottawa, Ottawa, Canada) or 40 μg/mL anti-IgG control antibody (AB-108-C, R&D Systems, Minneapolis, MN) was added to each trans-well insert at the start of the assay.

Endothelial Recruitment Assay

The endothelial recruitment assay was carried out as previously described (Pencheva et al., 2012; Png et al., 2012). Melanoma cells were treated with DMSO, GW3965, T0901317, or Bexarotene at 1 μM for 56 hours, after which $5\times10^4$ cells were seeded in a 24-well plate in the presence of each drug and allowed to attach for 16 hours prior to starting the assay. HUVEC cells were serum-starved overnight in EGM-2 media containing 0.2% FBS. The following day, $1\times10^5$ HUVEC cells were seeded into a 3.0 μm HTS Fluoroblock trans-well migration insert (351151, BD Falcon, San Jose, CA) fitted into each well containing cancer cells at the bottom. The HUVEC cells were allowed to migrate towards the cancer cells for 20 hours at 37° C., after which the inserts were processed as previously described (Pencheva et al., 2012). For ApoE antibody neutralization experiments, 40 μg/mL 1D7 anti-ApoE blocking antibody (Heart Institute, University of Ottawa, Ottawa, Canada) or 40 μg/mL anti-IgG control antibody (AB-108-C, R&D Systems, Minneapolis, MN) was added to each trans-well insert at the start of the assay.

Lentiviral shRNA-Based Gene Knockdown shRNAs were integrated into lentiviral particles that were prepared by transfection of 6 μg of vector A, 12 μg of vector K, and 12 μg of shRNA plasmid into HEK-293T packaging cells, as previously described (Pencheva et al., 2012; Png et al., 2012). Lentiviral shRNA transduction was performed in the presence of 10 μg/mL of polybrene (TR-1003-G, Millipore, Billerica, MA) for 6 hours, as described previously (Pencheva et al., 2012). The cells were expanded for 72 hours after transduction and lentiviral selection was performed by culturing the cells in the presence of 2 μg/mL of puromycin (P8833, Sigma-Aldrich) for 72 hours.

The following shRNA sequences were used:

Human:
$sh_1$LXRα:
5'-CCGGCCGACTGATGTTCCCACGGATCTCGAGATCCGTGGGAACATCA
GTCGGTTTTT-3'

$sh_2$LXRα:
5'-CCGGGCAACTCAATGATGCCGAGTTCTCGAGAACTCGGCATCATTGA
GTTGCTTTTT-3'

$sh_1$LXRβ:
5'-CCGGAGAGTGTATCACCTTCTTGAACTCGAGTTCAAGAAGGTGATAC
ACTCTTTTTT-3'

$sh_2$LXRβ:
5'-CCGGGAAGGCATCCACTATCGAGATCTCGAGATCTCGATAGTGGATG
CCTTCTTTTT-3' shApoE:
5'-CCGGGCAGACACTGTCTGAGCAGGTCTCGAGACCTGCTCAGACAGTG
TCTGCTTTTTT-3'

Mouse:
sh_mLXRα:
5'-CCGGGCAACTCAATGATGCTGAGTTCTCGAGAACTCAGCATCATTGA
GTTGCTTTTT-3'

-continued sh_mLXRβ:
5'-CCGGTGAGATCATGTTGCTAGAAACCTCGAGGTTTCTAGCAACATGA

TCTCATTTTTG-3' sh_mApoE:
5'-CCGGGAGGACACTATGACGGAAGTACTCGAGTACTTCCGTCATAGTG

TCCTCTTTTT-3'

Gene Expression Analysis by qRT-PCR:

RNA was extracted from whole cell lysates using the Total RNA Purification Kit (17200, Norgen, Thorold, Canada). 600 ng of total RNA was then reverse transcribed into cDNA using the cDNA First-Strand Synthesis Kit (18080-051, Invitrogen), and quantitative real-time PCR amplification was performed as previously described (Pencheva et al., 2012) using an ABI Prism 7900HT Real-Time PCR System (Applied Biosystems, Austin, TX). Each PCR reaction was carried out in quadruplicates. Gene expression was normalized to GAPDH, which was used as an endogenous control.

The following primers were used:

| | |
|---|---|
| Human: | |
| ApoE Forward: | 5'-TGGGTCGCTTTTGGGATTAC-3' |
| ApoE Reverse: | 5'-TTCAACTCCTTCATGGTCTCG-3' |
| GAPDH Forward: | 5'-AGCCACATCGCTCAGACAC-3' |
| GAPDH Reverse: | 5'-GCCCAATACGACCAAATCC-3' |
| LXRα_Fwd: | 5'- GTTATAACCGGGAAGACTTTGC-3' |
| LXRα_Rev: | 5'- AAACTCGGCATCATTGAGTTG-3' |
| LXRβ_Fwd: | 5'- TTTGAGGGTATTTGAGTAGCGG-3' |
| LXRβ_Rev: | 5'- CTCTCGCGGAGTGAACTAC-3' |
| Mouse: | |
| ApoE Forward: | 5'-GACCCTGGAGGCTAAGGACT-3' |
| ApoE Reverse: | 5'-AGAGCCTTCATCTTCGCAAT-3' |
| GAPDH Forward: | 5'-GCACAGTCAAGGCCGAGAAT-3' |
| GAPDH Reverse: | 5'-GCCTTCTCCATGGTGGTGAA-3' |
| LXRα Forward: | 5'-GCGCTCAGCTCTTGTCACT-3' |
| LXRα Reverse: | 5'-CTCCAGCCACAAGGACATCT-3' |
| LXRβ Forward: | 5'-GCTCTGCCTACATCGTGGTC-3' |
| LXRβ Reverse: | 5'-CTCATGGCCCAGCATCTT-3' |
| ABCA1 Forward: | 5'- ATGGAGCAGGGAAGACCAC-3' |
| ABCA1 Reverse: | 5'- GTAGGCCGTGCCAGAAGTT-3' |

ApoE Promoter Activity Assay

The ApoE promoter, consisting of a sequence spanning 980 base pairs upstream and 93 base pairs downstream of the ApoE gene, was cloned into a pGL3-Basic vector (E1751, Promega Corporation, Madison, WI) upstream of the firefly luciferase gene using NheI and SacI restriction enzymes. Then, multi-enhancer elements 1 (ME.1) and 2 (ME.2) were cloned directly upstream of the ApoE promoter using MluI and SacI restriction enzymes. To assess ApoE promoter- and ME.1/ME.2-driven transcriptional activation by LXR agonists, $5\times10^4$ MeWo cells were seeded into a 24-well plate. The following day, 100 ng of pGL3-ME.1/ME.2-ApoE promoter construct and 2 ng of pRL-CMV renilla luciferase construct (E2261, Promega) were co-transfected into cells in the presence of DMSO, GW3965, or T0901317 at 1 μM, each condition in quadruplicate. To assess transcriptional activation by LXRα or LXRβ, $5\times10^4$ MeWo cells expressing a control shRNA or shRNA targeting LXRα or LXRβ were seeded into a 24-well plate. The following day, 200 ng of pGL3-ME.1/ME.2-ApoE promoter construct and 2 ng of pRL-CMV renilla luciferase were co-transfected into cells in the presence of DMSO, GW3965, or T0901317 at 1 μM, each condition in quadruplicate. After 24 hours, cells were lysed, and cell lysate was analyzed for firefly and *renilla* luciferase activity using the Dual Luciferase Assay System (E1960, Promega) and a Bio-Tek Synergy NEO Microplate Reader. Firefly luciferase signal was normalized to *renilla* luciferase signal and all data are expressed relative to the luciferase activity ratio measured in the DMSO-treated control cells.

The following cloning primers were used:

ApoE-promoter Forward:
5'-TCA TAG CTA GCG CAG AGC CAG GAT TCA CGC CCT

G-3'

ApoE-promoter Reverse:
5'-TGG TCC TCG AGG AAC CTT CAT CTT CCT GCC TGT

GA-3'

ME.1 Forward:
5'-TAG TTA CGC GTA GTA GCC CCC ATC TTT GCC-3'

ME.1 Reverse:
5'-AAT CAG CTA GCC CCT CAG CTG CAA AGC TC-3'

ME.2 Forward:
5'-TAG TTA CGC GTA GTA GCC CCC TCT TTG CC-3'

ME.2 Reverse:
5'-AAT CAG CTA GCC CTT CAG CTG CAA AGC TCT G-3'

Tumor Histochemistry

Tumors were excised from mice and fixed in 4% paraformaldehyde at 4° C. for 48 hours. Then, tumors were paraffin-embedded and sectioned into 5-μm-thick increments. For endothelial cell content analysis in tumors, tumor sections were stained with a primary antibody against the mouse endothelial cell marker MECA-32 (Developmental Studies Hybridoma Bank, The University of Iowa, IA) and counterstained with DAPI nuclear stain. To determine tumor cell proliferation and apoptosis, tumor sections were stained with antibodies against the proliferative marker Ki-67 (Abcam, ab15580, Cambridge, MA) and the apoptotic marker cleaved caspase-3 (9661, Cell Signaling, Danvers, MA), respectively. Various Alexa Flour dye-conjugated secondary antibodies were used to detect primary antibodies. Fluorescence was measured using inverted fluorescence microscope (Zeiss Axiovert 40 CFL) at 5× magnification for MECA-32 and Ki-67 staining and 10× magnification for cleaved caspase-3 staining. Endothelial cell content density and tumor proliferation rate were quantified by calculating the average percentage of MECA-32 or Ki-67 positively-staining area out of the total tumor area. Tumor apoptosis was measured by counting the number of cleaved caspase-3 expressing cells per given tumor area.

Analysis of ApoE Expression in Primary Melanoma Lesions

Human primary melanoma skin samples were resected from melanoma patients at MSKCC, formalin-fixed, embedded in paraffin, and sectioned into 5-μm-thick increments. To determine ApoE protein expression, the samples were first de-paraffinized by two consecutive xylene washes (5 minutes each), and rehydrated in a series of ethanol washes (100%, 95%, 80%, and 70% EtOH). ApoE antigen was retrieved by incubating the samples in the presence of proteinase K (5 μg/mL) for 20 minutes at room temperature. To quench endogenous peroxidase activity, the slides were incubated in 3% $H_2O_2$ solution. The slides were then blocked in three consecutive Avidin, Biotin, and horse serum block solutions for 15 min each at room temperature (SP-2001, Vector Laboratories, Burlingame, CA). ApoE was detected by staining with D6E10 anti-ApoE antibody (ab 1908, Abcam), which was used at a 1:100 dilution in PBS at 4° C. overnight. The primary antibody was then recognized by incubating the slides in a peroxidase-conjugated secondary antibody (PK-4002, Vector Laboratories) and exposed by DAB (SK-4105, Vector Laboratories) oxidation reaction. The slides were imaged at 10× magnification and analysed in a double-blinded manner. ApoE expression was quantified by counting the number of DAB-positive cells and measuring the area of extracellular ApoE staining. Total ApoE staining signal was expressed as the percentage staining area per given tumor area, determined based on matched H&E-stained slides for each sample. Kaplan-Meier curves depicting patients' metastasis-free survival times were generated by plotting each patient's relapse-free survival data as a function of ApoE expression in that patient's primary melanoma lesion. Patients whose tumors had ApoE levels lower than the median ApoE expression of the population were classified as ApoE-negative, whereas patients whose melanomas expressed ApoE above the median were classified as ApoE-positive. Previously documented patients' history of metastatic recurrence to sites such as lung, brain, bone, soft and subcutaneous tissues, and skin enabled us to retrospectively determine the relationship between ApoE expression at a primary melanoma site and metastatic relapse.

Figures 1A, 1B:
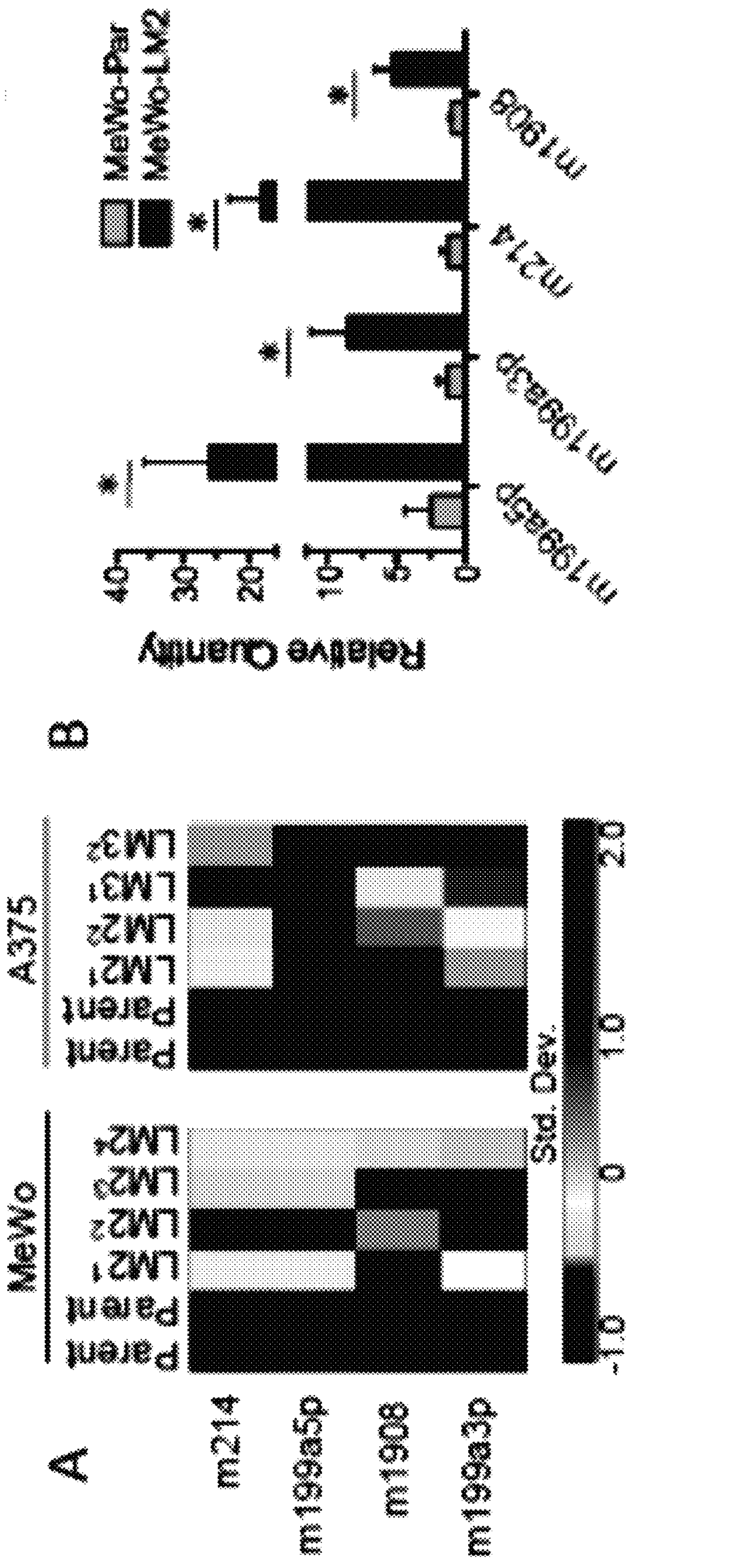
FIGS. 1A, 1B, 1C, 1D, 1E and 1F. Systematic Identification of miR-1908, miR-199a-3p, and miR-199a-5p as Endogenous Promoters of Human Melanoma Metastasis (1A) Heat map illustrating variance-normalized microarray expression values of miRNAs up-regulated in independent MeWo and A375 metastatic derivatives relative to their respective parental cells. Standard deviation changes from the mean of each heat map row are indicated by color map. (1B) miRNAs found to be up-regulated by microarray hybridization were validated by qRT-PCR in MeWo-LM2 metastatic derivatives. n=3. (1C) Bioluminescence imaging plot of lung metastatic colonization following intravenous injection of 4×104 parental MeWo cells over-expressing the precursors for miR-199a, miR-1908, miR-214, or a control hairpin. Lungs were extracted 63 days post-injection and H&E-stained. n=5. (1D) Bioluminescence imaging plot and H&E-stained lungs corresponding to lung metastasis following intravenous injection of 4×104 LM2 cells expressing a short hairpin (miR-Zip) inhibiting miR-1908 (m1908 KD), miR-199a-3p (m199a3p KD), miR-199a-5p (m199a5p KD), or a control sequence (shCTRL). Lungs were extracted and H&E-stained 49 days post-injection n=5-8. (1E) Lung colonization by 2×105 A375-LM3 metastatic derivatives with miR-Zip-induced silencing of miR-1908, miR-199a-3p, miR-199a-5p, or a control sequence was quantified at day 42 by bioluminescence imaging. n=5-8 (1F) The expression levels of miR-199a-3p, miR-199a-5p, and miR-1908 were determined in a blinded fashion by qRT-PCR in a cohort of non-metastatic (n=38) and metastatic (n=33) primary melanoma skin lesions from MSKCC patients. n=71. All data are represented as mean±SEM. $*p<0.05$, $p<0.01$, $*p<0.001$. See also FIG. 12.
Figures 1C, 1D:
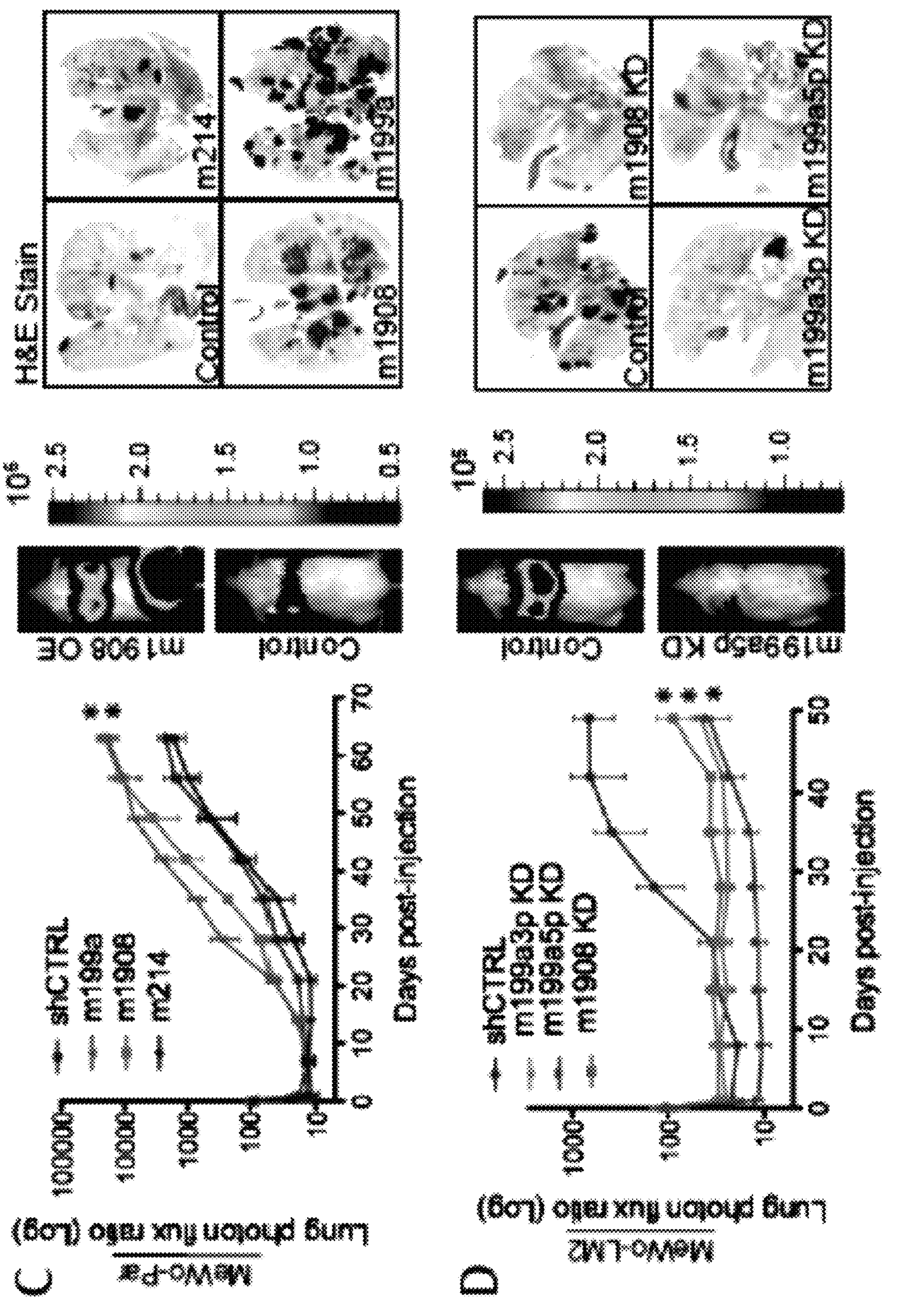
Figures 12A, 12B, 12C, 12D:
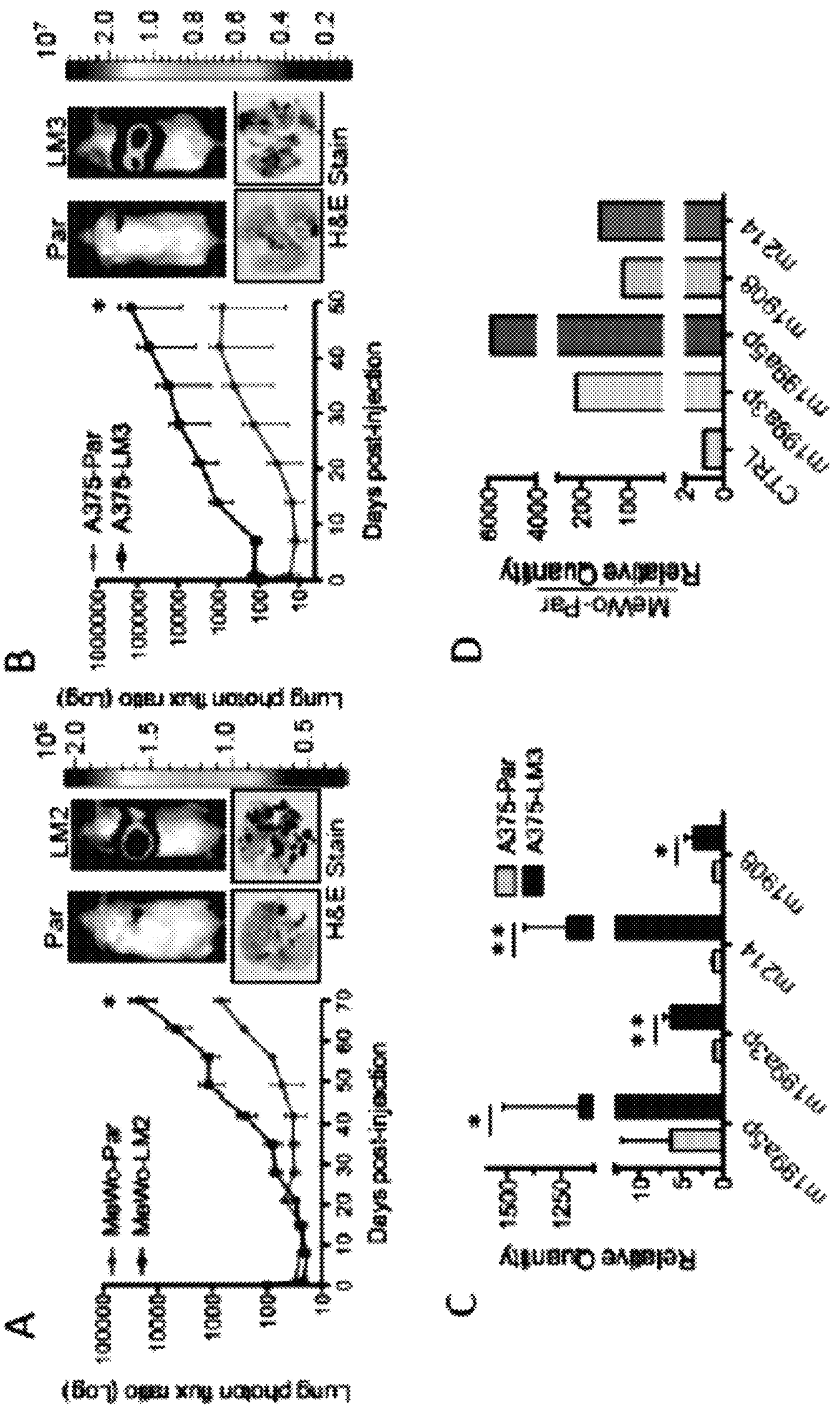
FIGS. 12A, 12B, 12C, 12D, 12E and 12F. In Vivo Selection For Highly Metastatic Human Melanoma Cell Line Derivatives and Identification of miR-199a-3p, miR-199a-5p, and miR-1908 as Metastasis-Promoter miRNAs (12A-12B) Bioluminescence imaging of lung metastasis and representative images of H&E-stained lungs corresponding to MeWo-LM2 (12A) and A375-LM3 metastatic derivatives (12B) and their respective parental cell lines. 4×104 MeWo-Par/MeWo-LM2 cells and 1×105 A375-Par/A375-LM3 cells were intravenously injected into NOD-SCID mice, and lungs were extracted and H&E stained on day 72 and day 49, respectively. n=4-5. (12C) Expression levels of miR-199a-5p, miR-199a-3p, miR-1908, and miR-214 were determined by qRT-PCR in A375-LM3 metastatic derivatives and their parental cells. n=3. (12D) Parental MeWo cells were transduced with retrovirus expressing a control hairpin or a pre-miRNA hairpin construct giving rise to miR-199a (both miR-199a-3p and miR-199a-5p), miR-1908, or miR-214. The expression levels of the target miRNAs were determined by qRT-PCR. 12 n=3. (12E) H&E-stained lung sections from FIG. 1C were analyzed for the number of metastatic nodules resulting from parental MeWo cells over-expressing miR-199a, miR-1908, or a control hairpin. n=3. (12F) The number of metastatic nodules formed by LM2 cells with silenced expression of miR-199a-3p, miR-199a-5p, miR-1908, or a control sequence was analyzed in H&E-stained lung sections from FIG. 1D. n=3. All data are represented as mean±SEM.

Example 2 Endogenous Mir-1908, Mir-199a-3p, and Mir-199a-5p Promote Human Melanoma Metastasis In order to identify miRNA regulators of melanoma metastasis, in vivo selection (Pollack and Fidler, 1982) was utilized with the pigmented MeWo and non-pigmented A375 human melanoma cell lines to generate multiple second (LM2) and third generation (LM3) lung metastatic derivatives. Comparison of the metastatic potential of the MeWo-LM2 and A375-LM3 lines showed these derivatives to metastasize significantly more efficiently than their respective parental populations in lung colonization assays (FIGS. 12A-B). Hybridization-based small RNA profiling of 894 mature miRNAs followed by quantitative stem-loop PCR (qRT-PCR) revealed four miRNAs (miR-1908, miR-199a-3p, miR-199a-5p, and miR-214) to be upregulated greater than two-fold in multiple A375 and MeWo metastatic derivatives relative to their respective parental cells (FIGS. 1A-B, 12C). The significant induction of miR-199a-3p, miR-199a-5p, miR-214, and miR-1908 across multiple metastatic derivatives suggested a metastasis-promoting role for these miRNAs. Retrovirally mediated transduction and over-expression of the precursors for miR-199a-3p and miR-199a-5p (over-expressed concomitantly as the miR-199a hairpin) and miR-1908 lead to a robust increase in lung metastatic colonization based on both bioluminescence signal quantification and gross lung histology (FIG. 1C, 12D; 9.64-fold increase, P=0.016 for miR-1908; 8.62-fold increase, P=0.028 for miR-199a), while miR-214 over-expression did not significantly affect metastasis. Importantly, over-expression of each miR-199a and miR-1908 increased the number of metastatic nodules formed (FIG. 12E), consistent with a role for these miRNAs in metastatic initiation. These findings also revealed miR-199a and miR-1908 to be sufficient for enhanced metastatic colonization.

Figures 12E, 12F:
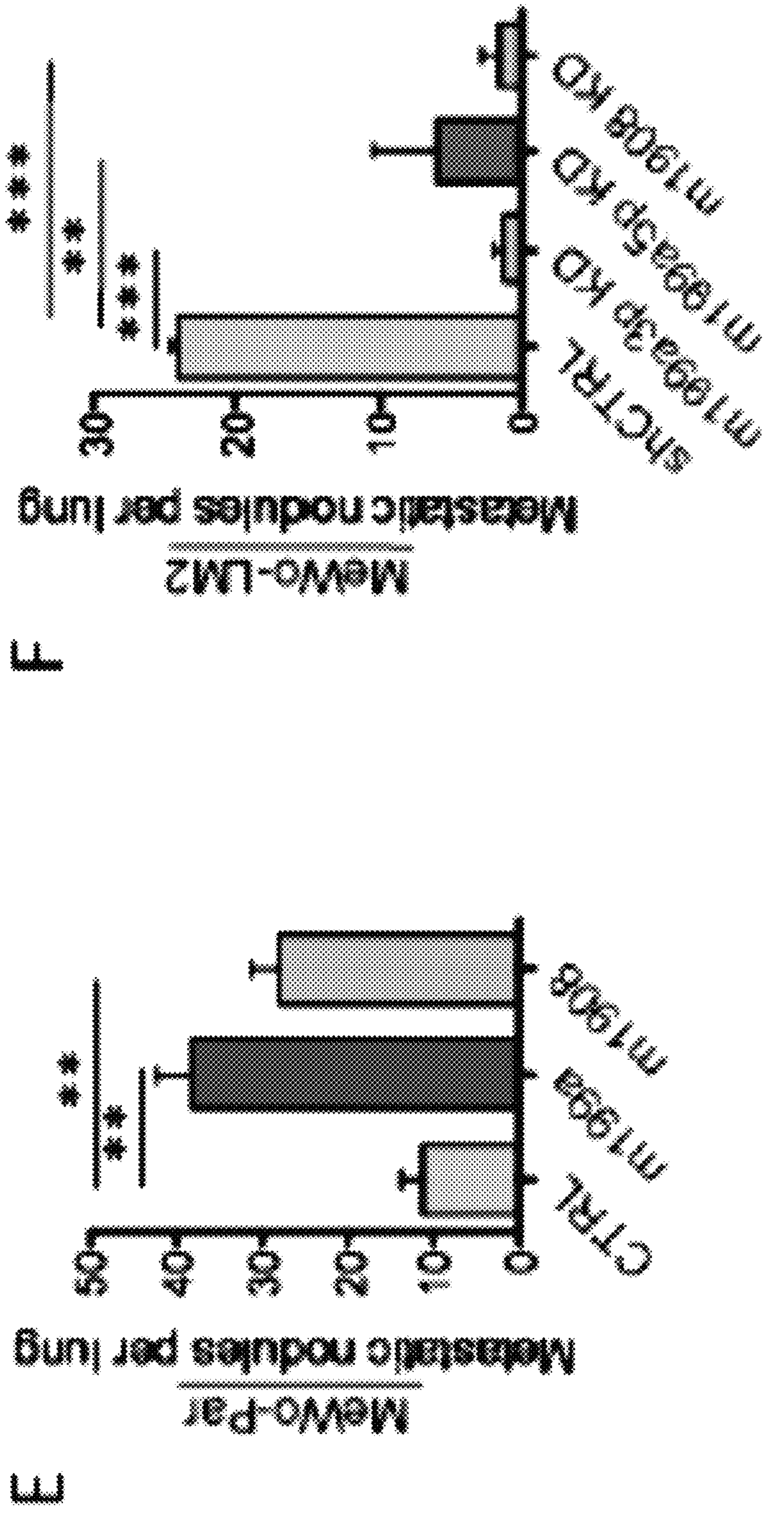

Next, assays were carried out to examine if endogenous levels of these miRNAs promote metastasis. To this end, miR-1908 and each of the two miRNAs arising from the miR-199a hairpin (miR-199a-3p and miR-199a-5p) were inhibited in the highly metastatic cells through miR-Zip technology. Individual inhibition of each of these miRNAs suppressed metastatic colonization by more than 7-fold (FIG. 1D; P=0.047 for miR-1908 inhibition; P=0.010 for miR-199a-3p inhibition; P=0.015 for miR-199a-5p inhibition) and dramatically decreased the number of metastatic nodules formed (FIG. 12F).

Figures 1E, 1F:
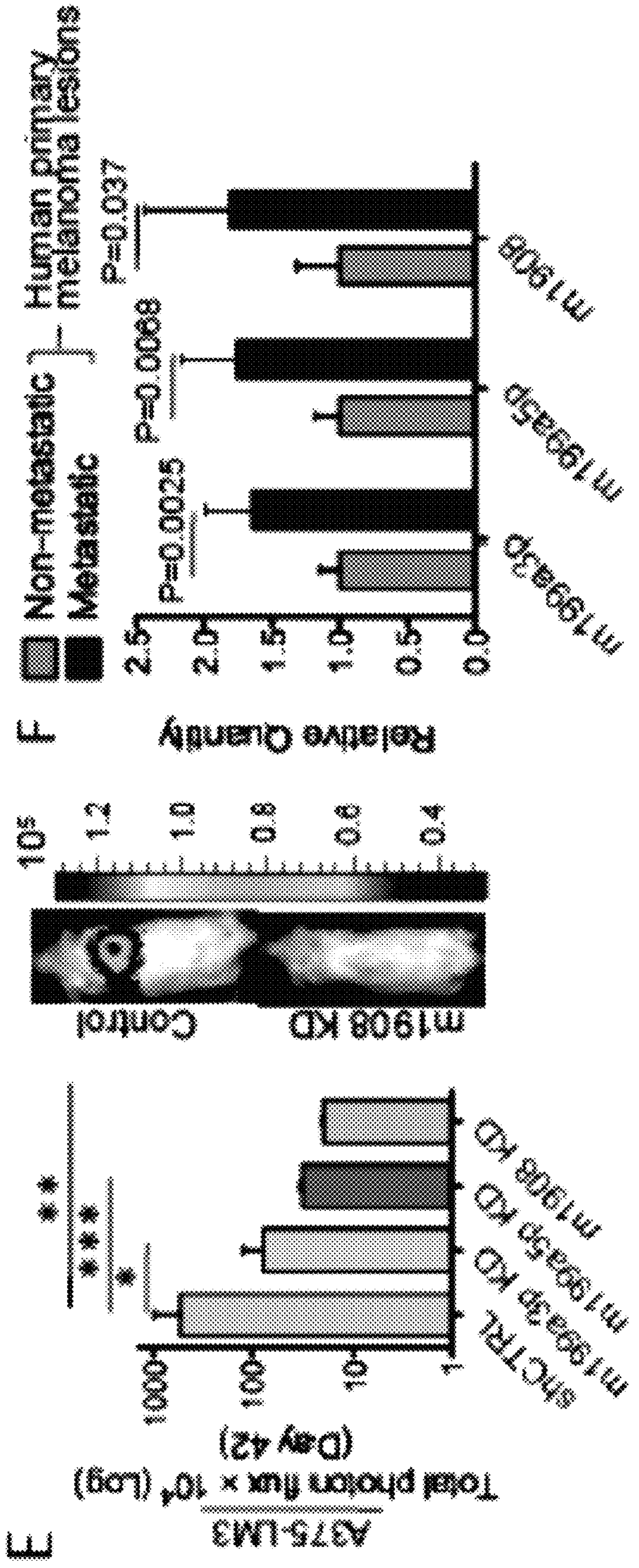

To determine whether these miRNAs also promote metastasis in an independent cell line, their expression was silenced in the A375 metastatic derivative cell line. Indeed, inhibition of miR-1908, miR-199a-3p, or miR-199a-5p significantly reduced the lung colonization capacity of metastatic A375-LM3 cells (FIG. 1E), establishing these three miRNAs as endogenous promoters of metastasis by human melanoma cells.

Given the robust functional roles of miR-1908, miR-199a-3p, and miR-199a-5p in promoting melanoma metastasis in a mouse model of human cell metastasis, further assays were carried out to examine whether expression of these miRNAs correlates with the capacity of human primary melanoma lesions to metastasize. To this end, 71 primary melanoma skin lesions obtained from Memorial Sloan-Kettering Cancer Center (MSKCC) patients were analyzed in a blinded fashion for the expression levels of miR-1908, miR-199a-3p, and miR-199a-5p through qRT-PCR. Consistent with the above functional studies, all three miRNAs were significantly induced in primary melanomas that had metastasized relative to those that had not (FIG. 1F; P=0.037 for miR-1908; P=0.0025 for miR-199a-3p; P=0.0068 for miR-199a-5p), suggesting that upregulated expression of these miRNAs in primary lesions is an early event predictive of melanoma cancer progression.

Example 3 Mir-1908, Mir-199a-3p, and Mir-199a-5p Promote Cell Invasion and Endothelial Recruitment In this Examiner, assays were carried out to determine the cellular mechanisms by which miR-1908, miR-199a-3p, and miR-199a-5p regulate metastasis.

Figures 13A, 13B, 13C, 13D, 13E, 13F, 13G:
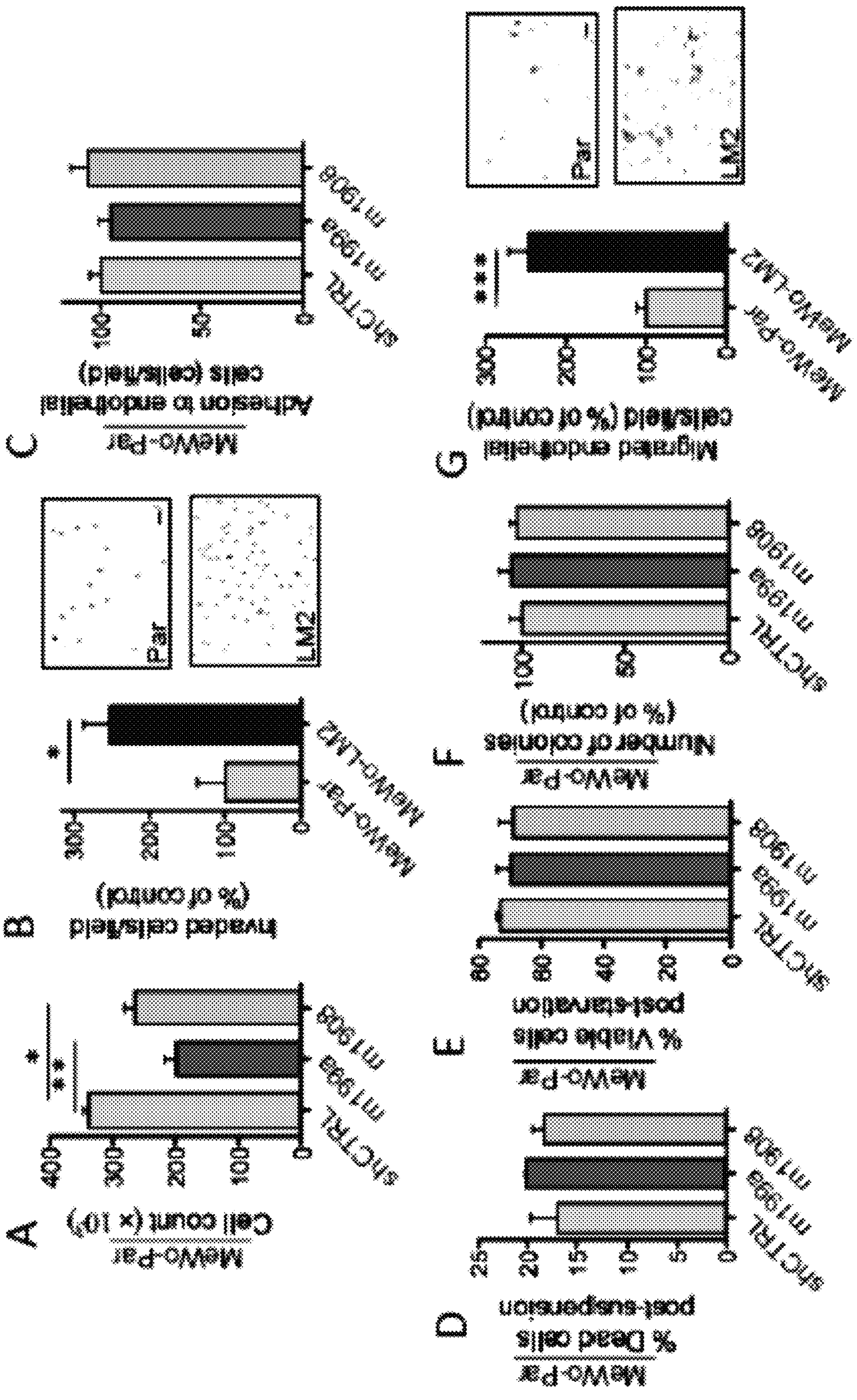
FIGS. 13A, 13B, 13C, 13D, 13E, 13F, 13G and 13H. MiR-199a and miR-1908 Inhibit Proliferation in vitro and Selectively Promote Cell Invasion and Endothelial Recruitment (13A) 2.5×104 MeWo cells over-expressing miR-199a, miR-1908, or a control hairpin were seeded in triplicate, and viable cells were counted after 5 days. n=3. (13B) 1×105 poorly metastatic parental MeWo and highly metastatic LM2 cells were compared for their ability to invade though matrigel in a trans-well assay. n=3-4. (13C) 1×105 endothelial cells were seeded in a 6-well plate and allowed to form a monolayer. 2×105 parental MeWo cells over-expressing miR-199a, miR-1908, or a control hairpin were seeded on top of the endothelial monolayer and incubated for 30 minutes. Each monolayer was subsequently imaged, and the number of cancer cells adhering to endothelial cells was quantified. n=3. (13D) 1×106 parental MeWo cells over-expressing miR-199a, miR-1908, or a control hairpin were seeded in low adherent plates containing cell media supplemented with 0.2% methylcellulose. Following 48 hours in suspension, the numbers of dead and viable cells were quantified. n=3. (13E) 5×105 parental MeWo cells over-expressing miR-199a, miR-1908, or a control hairpin were seeded in a 6-well plate and incubated in low-serum media for 48 hours, after which the number of viable cells was quantified. n=4. (13F) Colony formation by parental MeWo cells over-expressing miR-199a, miR-1908, or a control hairpin. 50 cells were seeded in a 6-cm plate, and the number of colonies formed was quantified 2 weeks later. n=4. (13G) 5×104 parental MeWo and LM2 cells were seeded on the bottom of a well and assessed for their ability to recruit endothelial cells. n=6-8. (13H) Percentage blood vessel density, shown as a cumulative fraction plot, for metastatic nodules formed by parental MeWo cells over-expressing miR-199a, miR-1908, or a control hairpin. Lung sections from FIG. 1C were immunohistochemically double-stained for human vimentin and MECA-32, and the MECA-32 positive area relative to the total nodule area, given by human vimentin staining, was quantified using ImageJ. n=43 nodules (control); n=117 nodules (miR-199a OE); n=55 nodules (miR-1908 OE). All data are represented as mean±SEM. Scale bar, 100 μm.

First, it was examined if these miRNAs promote metastasis by enhancing proliferation or tumor growth. Contrary to this, over-expression of each miRNA reduced cell proliferation (FIG. 13A). More importantly, miR-1908 over-expression did not increase primary tumor growth, while miR-199a over-expression actually lead to a significant decrease (35%; P<0.001) in tumor volume (FIG. 2A), indicating that the pro-metastatic effects of miR-1908 and miR-199a are not secondary to tumor growth promotion or enhanced cell proliferation.

Next, it was examined whether these miRNAs regulate cell invasion, a key metastatic phenotype. Metastatic LM2 cells, which express higher levels of these miRNAs, displayed significantly increased matrigel invasion capacity relative to their less metastatic parental population (FIG. 13B). Accordingly, over-expression of miR-199a and miR-1908 individually enhanced the ability of parental MeWo cells to invade through matrigel (FIG. 2B; three-fold increase for miR-199; two-fold increase for miR-1908). Conversely, individual inhibition of miR-199a-3p, miR-199a-5p, and miR-1908 significantly decreased the invasive capacity of MeWo-LM2 (FIG. 2C) as well as A375-LM3 (FIG. 2D) metastatic melanoma cell derivatives.

Figures 2A, 2B, 2C, 2D, 2E:
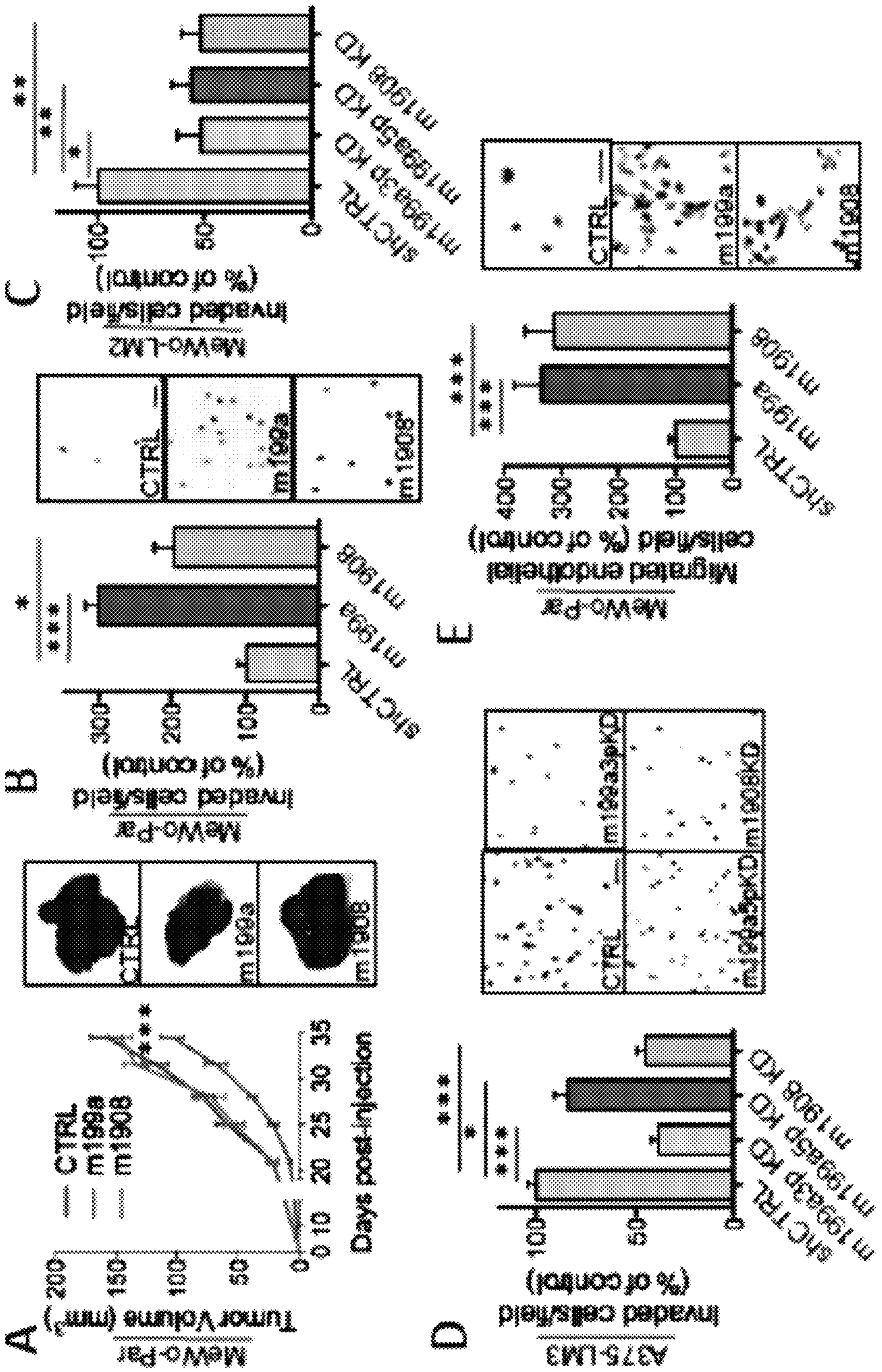
FIGS. 2A, 2B, 2C, 2D, 2E, 2F, 2G and 2H. MiR-1908, miR-199a-3p, and miR-199a-5p Display Dual Cell-Autonomous/Non-Cell-Autonomous Roles in Regulating Melanoma Metastatic Progression (2A) 1×106 parental MeWo cells over-expressing miR-199a, miR-1908, or a control hairpin were injected subcutaneously into immuno-deficient mice, and primary tumor volume was monitored over time. n=4-6. (2B) 1×105 parental MeWo cells over-expressing miR-199a, miR-1908, or a control hairpin were allowed to invade through a trans-well matrigel-coated insert for 24 hours, and the number of cells invaded into the basal side of each insert was quantified. n=7. (2C-2D) 1×105 highly metastatic MeWo-LM2 (2C) and A375-LM3 (2D) cells with miR-Zip-induced inhibition of miR-199a-3p, miR-199a-5p, miR-1908, or a control sequence were subjected to the cell invasion assay. n=6-8. (2E) 5×104 MeWo cells over-expressing miR-199a, miR-1908, or a control hairpin were seeded on the bottom of a well, and 1×105 human umbilical vein endothelial cells (HUVEC's) were allowed to migrate towards the cancer cells for 16 hours through a trans-well insert. Endothelial recruitment capacity was measured by quantifying the number of HUVEC's migrated to the basal side of each insert. n=7. (2F-2G) Endothelial recruitment by 5×104 MeWo-LM2 (2F) and A375-LM3 (2G) cells inhibited for miR-199a-3p, miR-199a-5p, miR-1908, or a control sequence. n=6-10. (2H) Cumulative fraction plot of the percentage blood vessel density distribution for metastatic nodules formed following intravenous injection of 2×105 highly metastatic MeWo-LM2 cells depleted for miR-199-3p, miR-199a-5p, miR-1908, or a control sequence. Lung sections were immunohistochemically double-stained for human vimentin (blue) and MECA-32 (red), and the percentage MECA-32 positive area within each metastatic nodule, demarcated based on vimentin staining, was quantified. n=211 nodules (control KD); n=60 nodules (m199a3p KD); n=138 nodules (m199a5p KD); n=39 nodules (m1908 KD). All data are represented as mean±SEM. Scale bar, 100 μm. See also FIG. 13.
Figures 2F, 2G, 2H:
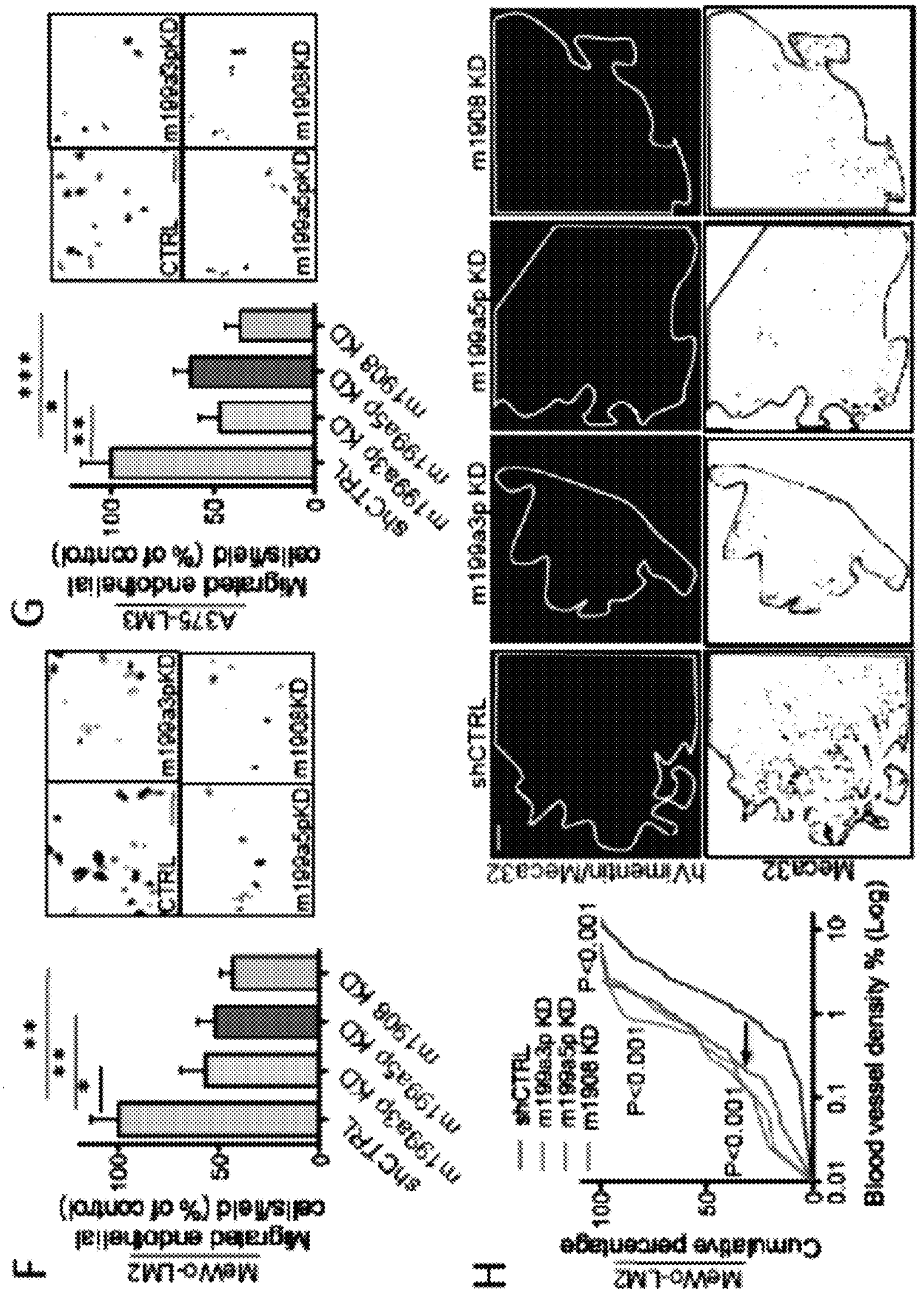

Given the robust effects of these miRNAs on metastatic progression, further analyses were conducted to examiner whether they may regulate any additional pro-metastatic phenotypes. While over-expression of miR-199a or miR-1908 did not modulate melanoma cell adhesion to endothelial cells (FIG. 13C), resistance to anoikis (FIG. 13D), survival in the setting of serum starvation (FIG. 13E), or colony formation (FIG. 13F), each miRNA dramatically enhanced (more than three-fold increase) the ability of parental MeWo cells to recruit endothelial cells in trans-well endothelial recruitment assays (FIG. 2E). Consistent with this, metastatic Mewo-LM2 cells, which physiologically over-express miR-199a and miR-1908, were more efficient at recruiting endothelial cells relative to their parental cells (FIG. 13G). Conversely, inhibition of miR-199a-3p, miR-199a-5p, or miR-1908 in the metastatic MeWo-LM2 (FIG. 2F) as well as A375-LM3 cells (FIG. 2G) suppressed endothelial recruitment, consistent with the requirement and sufficiency of these miRNAs for enhanced endothelial recruitment capacity of metastatic melanoma cells.

Figure 13H:
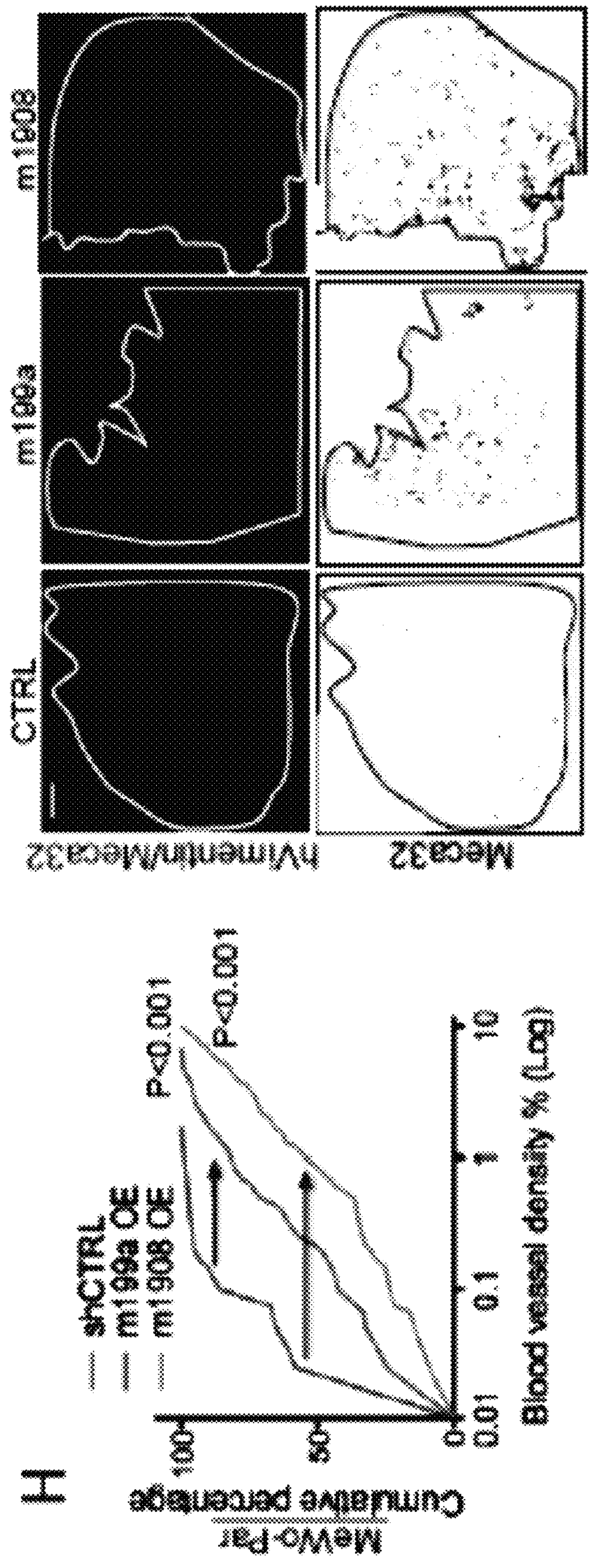

To determine whether endogenous miR-199a-3p, miR-199a-5p, and miR-1908 regulate endothelial recruitment by metastatic cells in vivo, assays were carried out to examine metastatic blood vessel density by performing co-immunostaining for human vimentin, which labels human MeWo melanoma cells, and mouse endothelial cell antigen (MECA-32), which labels mouse endothelial cells. Strikingly, inhibition of miR-199a-3p, miR-199a-5p, or miR-1908 individually led to pronounced decreases (an average of 3-fold for miR-199a-3p and miR-199a-5p and 4.7-fold for miR-1908) in blood vessel density within metastatic nodules (FIG. 2H; $P<0.001$ for miR-199a-3p; $P<0.001$ for miR-199a-5p; and $P<0.001$ for miR-1908), revealing a role for these miRNAs in promoting metastatic endothelial content and metastatic angiogenesis. Conversely, over-expression of each miRNA in poorly metastatic melanoma cells dramatically increased metastatic blood vessel density (FIG. 13H). These findings reveal miR-199a-3p, miR-199a-5p, and miR-1908 as necessary and sufficient for enhanced invasion and endothelial recruitment during melanoma progression.

Example 4 Mir-1908, Mir-199a-3p, and Mir-199a-5p Convergently and Cooperatively Target Apoe and DNAJA4

In this example, a systematic and unbiased approach was employed to identify the direct molecular targets of these miRNAs.

Figures 14A, 14B, 14C, 14D:
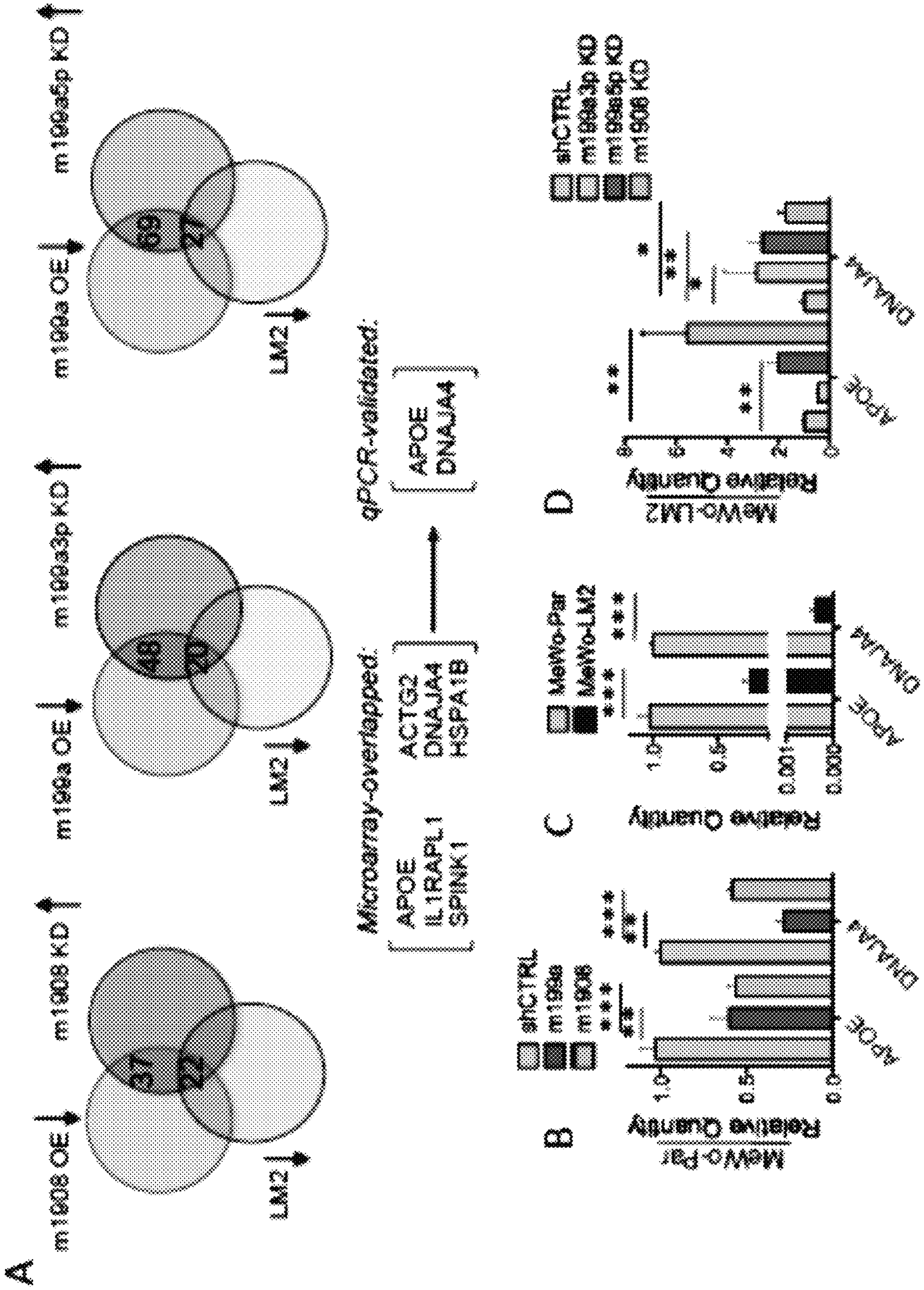
FIGS. 14A, 14B, 14C, 14D, 14E, 14F and 14G. MiR-199a and miR-1908 Convergently and Cooperatively Target ApoE and DNAJA4 (14A) Venn diagram showing the integrative experimental approach that lead to the identification of putative target genes common to miR-199a-3p, miR-199a-5p, and miR-1908. Transcriptomic profiling of genes down-regulated by greater than 1.5-fold upon each miRNA over-expression were overlapped with genes up-regulated by more than 1.5-fold upon each miRNA silencing and with genes down-regulated by more than 1.5-fold in metastatic LM2 cells relative to their parental cell line. (14B, 14C, 14D) Expression levels of ApoE and DNAJA4 measured by qRT-PCR in parental MeWo cells over-expressing miR-199a, miR-1908, or a control hairpin (14B), in parental MeWo cells and their highly metastatic LM2 derivative cell line (14C), and in MeWo-LM2 cells with miR-Zip-based silencing of miR-199a-3p, miR-199a-5p, miR-1908, or a control sequence (14D). n=3. (14E) Heterologous luciferase reporter assays measuring the stability of miR-199a-3p, miR-199a-5p, or miR-1908 target site mutant ApoE and DNAJA4 3'UTR/CDS luciferase fusions in highly metastatic LM2 cells with inhibition of miR-199a-3p, miR-199a-5p, miR-1908, or a control sequence. n=3-4. (14F) MeWo-LM2 cells were transduced with retrovirus expressing a control vector or an over-expression vector giving rise to ApoE or DNAJA4. The expression levels of the target genes were determined by qRT-PCR. (14G) Expression levels of ApoE and DNAJA4, determined by qRT-PCR, in parental MeWo cells were transduced with lentiviral shRNAs targeting ApoE, DNAJA4, or a control sequence. All data are represented as mean±SEM.

Since miR-1908, miR-199a-3p, and miR-199a-5p mediate the same sets of in vitro and in vivo phenotypes and miR-199a-5p and miR-199a-3p arise from the same precursor hairpin, it was hypothesized that the pro-metastatic phenotypes of these miRNAs may arise through silencing of common target genes. Given that mammalian miRNAs act predominantly by destabilizing target mRNA transcripts (Guo et al., 2010 Nature 466, 835-840), transcriptomic profiling of melanoma cells was performed in the context of both loss- and gain-of-function for each miRNA. This revealed a small set of genes that were repressed by both miR-199a and miR-1908 and that also displayed lower levels in the metastatic LM2 derivatives, which express higher endogenous levels of these miRNAs (FIG. 14A). Quantitative RT-PCR validated two genes, the metabolic gene Apolipoprotein E (ApoE) and the heat-shock protein DNAJA4, as significantly modulated by miR-199a and miR-1908 and dramatically silenced in the highly metastatic LM2 cells (FIGS. 3A and 14B-D).

Figures 3A, 3B, 3C, 3D:
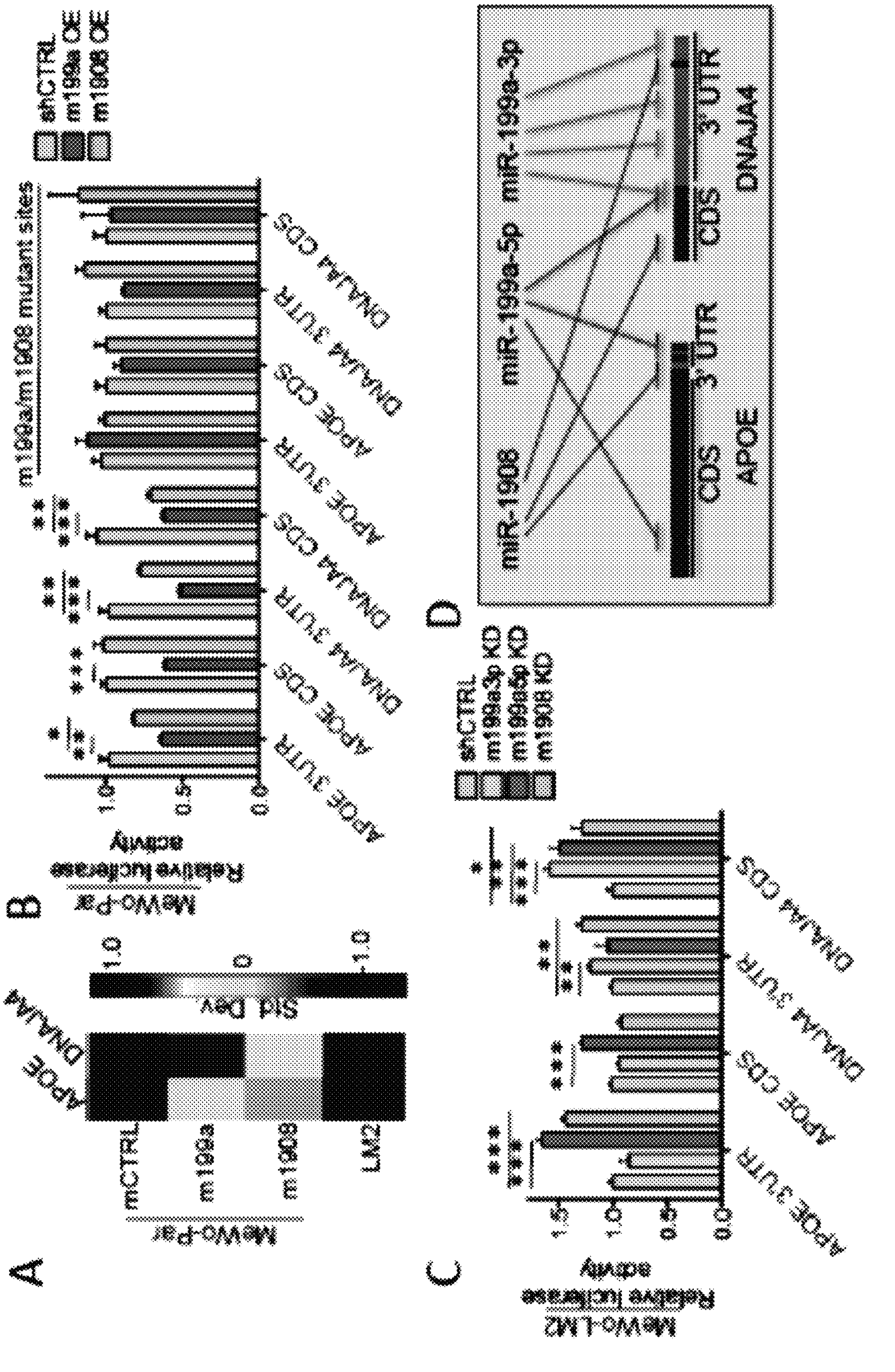
FIGS. 3A, 3B, 3C, 3D, 3E, 3F, 3G, 3H and 3I. Identification of ApoE and DNAJA4 as Common Target Genes of miR-199a and miR-1908 (3A) Heat map depicting mRNA levels of ApoE and DNAJA4, measured by qRT-PCR, in poorly metastatic MeWo cells over-expressing miR-199a, miR-1908, or a control hairpin and in highly metastatic MeWo-LM2 cells. Color map illustrates standard deviation changes from the mean of each heat map column. (3B) Heterologous luciferase reporter assays measuring the stability of wild-type ApoE and DNAJA4 3'UTR/CDS luciferase fusions or miRNA target-site mutant ApoE and DNAJA4 3'UTR/CDS fusions in parental MeWo cells over-expressing miR-199a, miR-1908, or a control hairpin. n=3-4. (3C) Stability of wild-type ApoE and DNAJA4 3'UTR/CDS luciferase fusions in MeWo-LM2 cells with silenced expression of miR-199a-3p, miR-199a-5p, miR-1908, or a control sequence. n=4. (3D) Schematic of experimentally derived model of ApoE and DNAJA4 3'UTR/CDS targeting by miR-199a-3p, miR-199a-5p, and miR-1908. (3E) Luciferase activity of wild-type and miRNA target-site mutant ApoE and DNAJA4 3'UTR/CDS luciferase fusions in highly metastatic MeWo-LM2 derivatives and their poorly metastatic parental cell line. n=4. (3F) Matrigel invasion capacity by 1×105 MeWo-LM2 cells expressing a control vector or over-expressing ApoE or DNAJA4. n=4. (3G) Endothelial recruitment ability by 5×104 MeWo-LM2 cells transduced with a control vector or an over-expression vector for ApoE or DNAJA4. n=6. (3H-3I) Poorly metastatic parental MeWo cells transduced with lentiviral short hairpins targeting ApoE, DNAJA4, or a control sequence were assessed for their matrigel invasion capacity (3H) and ability to recruit endothelial cells (3I). n=6-8. All data are represented as mean±SEM. Scale bar, 100 μm. See also FIG. 14.
Figures 3E, 3F, 3G, 3H, 3I:
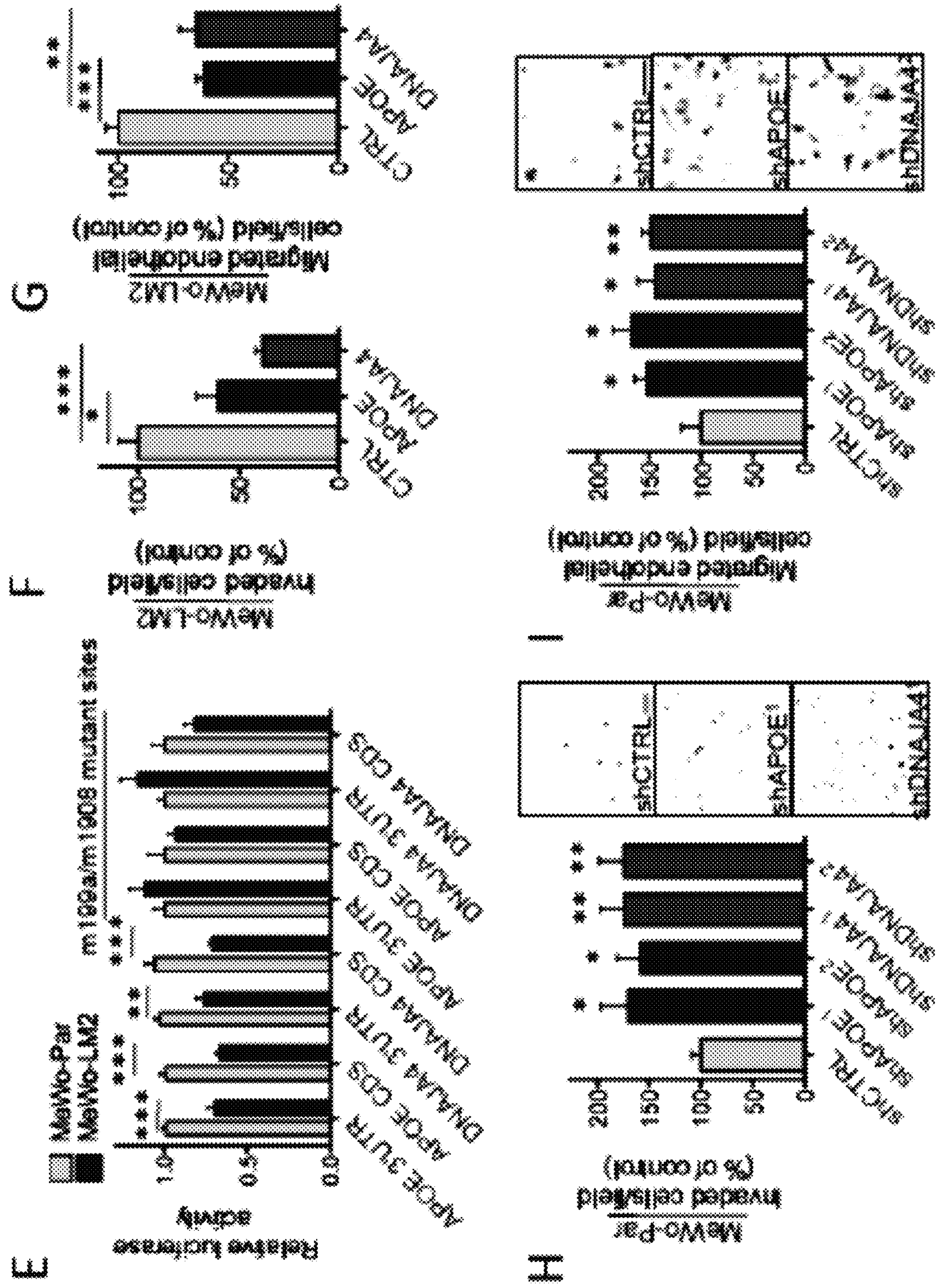

To determine whether ApoE and DNAJA4 are directly targeted by miR-1908, miR-199a-3p, and miR-199a-5p, the effects of each miRNA on the stability of its putative targets were examined through heterologous luciferase reporter assays. Interestingly, over-expression of miR-199a repressed the stability of the 3' untranslated region (UTR) and coding sequence (CDS) of both ApoE and DNAJA4, while over-expression of miR-1908 destabilized the 3'UTR of ApoE and the 3'UTR and CDS of DNAJA4. Consistent with direct targeting, mutating the miRNA complementary sequences on each target abrogated miRNA-mediated regulation (FIG. 3B). In a direct test of endogenous targeting, individual miRNA inhibition in metastatic LM2 cells resulted in increased target stability (FIG. 3C) that was abrogated upon mutating the miRNA target sites (FIG. 14E), revealing ApoE to be directly targeted by miR-1908 and miR-199a-5p and DNAJA4 to be directly targeted by all three miRNAs (FIG. 3D). Importantly, the CDS's and 3'UTR's of both of these genes were less stable in the highly metastatic LM2 cells, which express physiologically higher levels of the three regulatory miRNAs, indicating that endogenous targeting of ApoE and DNAJA4 by these miRNAs is relevant to melanoma metastasis (FIG. 3E).

Figures 14E, 14F, 14G:
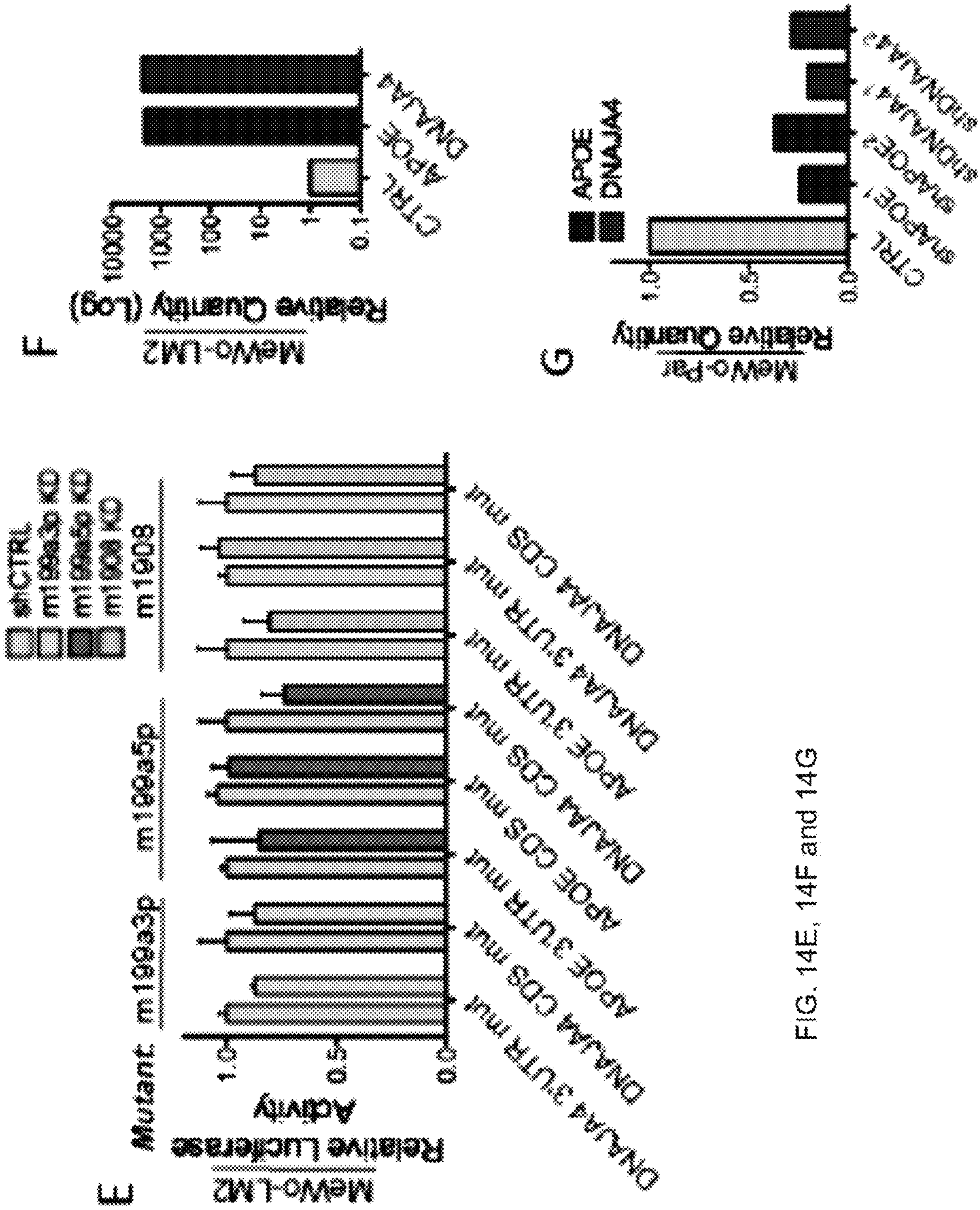

Given the molecular convergence of miR-199a-3p, miR-199a-5p, and miR-1908 onto common target genes, it was next examined whether these targets, ApoE and DNAJA4, could mediate the metastatic phenotypes conferred by these miRNAs. Over-expression of each gene in the metastatic LM2 cells led to pronounced reductions in cell invasion and endothelial recruitment phenotypes (FIGS. 3F-G, 14F). Conversely, knock-down of ApoE or DNAJA4 in the poorly metastatic cells using independent hairpins significantly enhanced cell invasion and endothelial recruitment (FIGS. 3H-I, 14G), revealing ApoE and DNAJA4 to act as endogenous suppressors of these pro-metastatic phenotypes-consistent with their targeting by the above mentioned metastasis-promoting miRNAs.

Figures 4A, 4B, 4C, 4D, 4E, 4F:
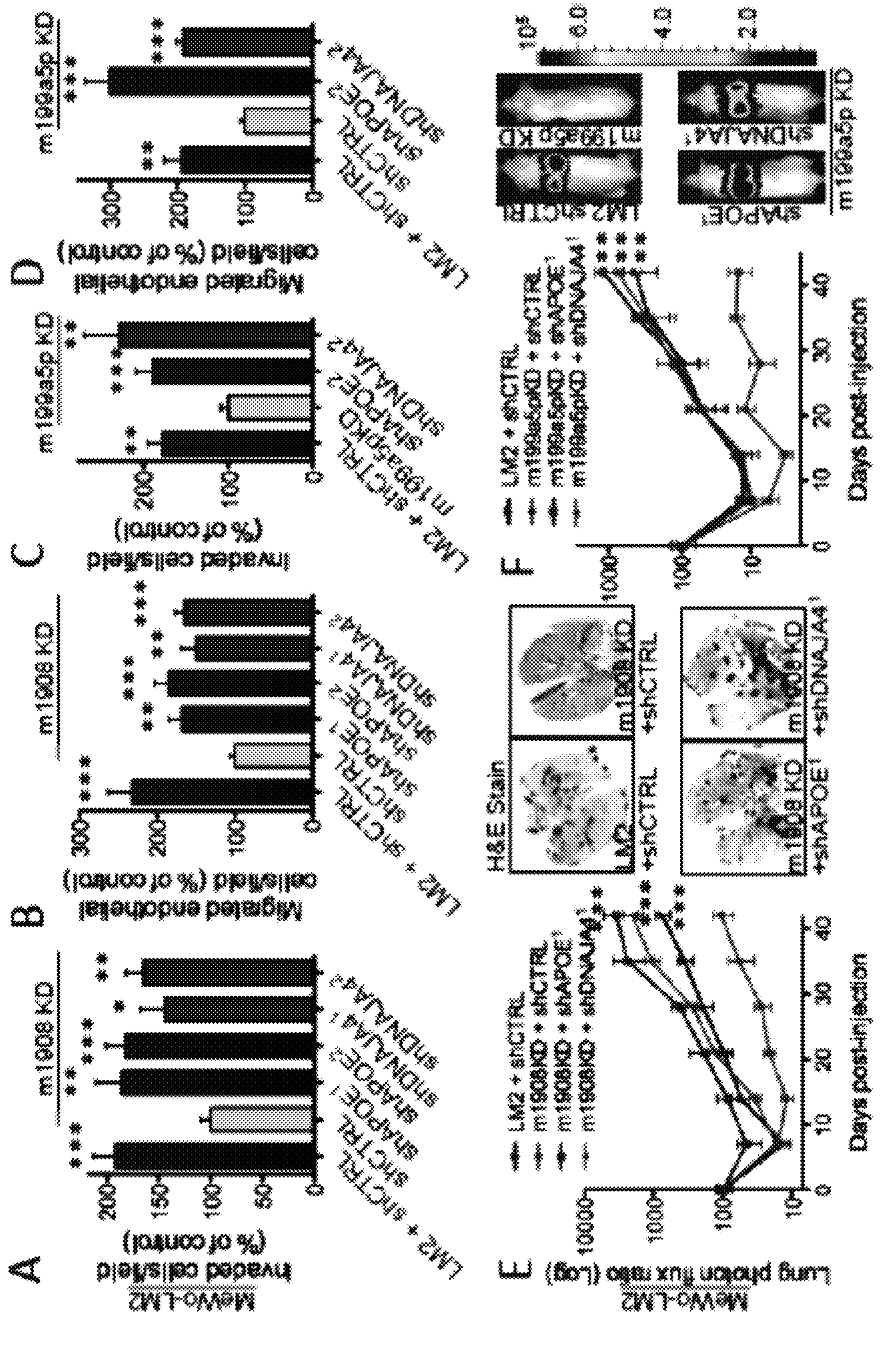
FIGS. 4A, 4B, 4C, 4D, 4E, 4F, 4G, 4H, 4I, 4J and 4K. Direct Targeting of ApoE and DNAJA4 by miR-199a and miR-1908 Promotes Metastatic Invasion, Endothelial Recruitment, and Colonization (4A-4D) Highly metastatic LM2 cells expressing a control shRNA or shRNAs targeting ApoE or DNAJA4 in the context of miR-1908 inhibition (m1908 KD; 4A, 4B) or miR-199a-5p inhibition (m199a5p KD; 4C, 4D) were subjected to the cell invasion (4A, 4C) and endothelial recruitment assays (4B, 4D). n=6-8. (4E-4F) Bioluminescence imaging plot and H&E-stained lungs representative of lung metastasis after intravenous injection of 1× 105 LM2 cells expressing a control hairpin or hairpins targeting ApoE, DNAJA4, or a control sequence in the setting of miR-1908 silencing (4E) or miR-199a-5p silencing (4F). n=5. (4G-4H) Parental MeWo cells over-expressing ApoE or DNAJA4 or expressing a control vector in the context of miR-1908 over-expression were analyzed for the matrigel invasion (4G) and endothelial recruitment (4H) phenotypes. (4I-4J) A375-LM3 derivatives expressing a control shRNA or shRNAs targeting ApoE and DNAJA4 were transduced with a cocktail of LNAs targeting miR-199a-3p, miR-199a-5p, and miR-1908 or a control LNA and analyzed in the matrigel invasion (4I) and endothelial recruitment (4J) assays. n=4. (4K) Blood vessel density distribution, represented in a cumulative fraction plot, for metastatic nodules formed by MeWo-LM2 cells inhibited for miR-1908 and transduced with shRNAs targeting ApoE, DNAJA4, or a control sequence. Lung sections from FIG. 4E were immunocytochemically double-stained for human vimentin (blue) and the endothelial marker MECA-32 (red). The percentage MECA-32 positive area within each vimentin-positive nodule was quantified. n=39 nodules (shCTRL); n=97 (shAPOE1); n=38 (shAPOE2); n=200 (shDNAJA41); n=19 (shDNAJA42). All data are represented as mean±SEM. Scale bar, 100 μm. See also FIG. 15.
Figures 4G, 4H, 4I, 4J, 4K:
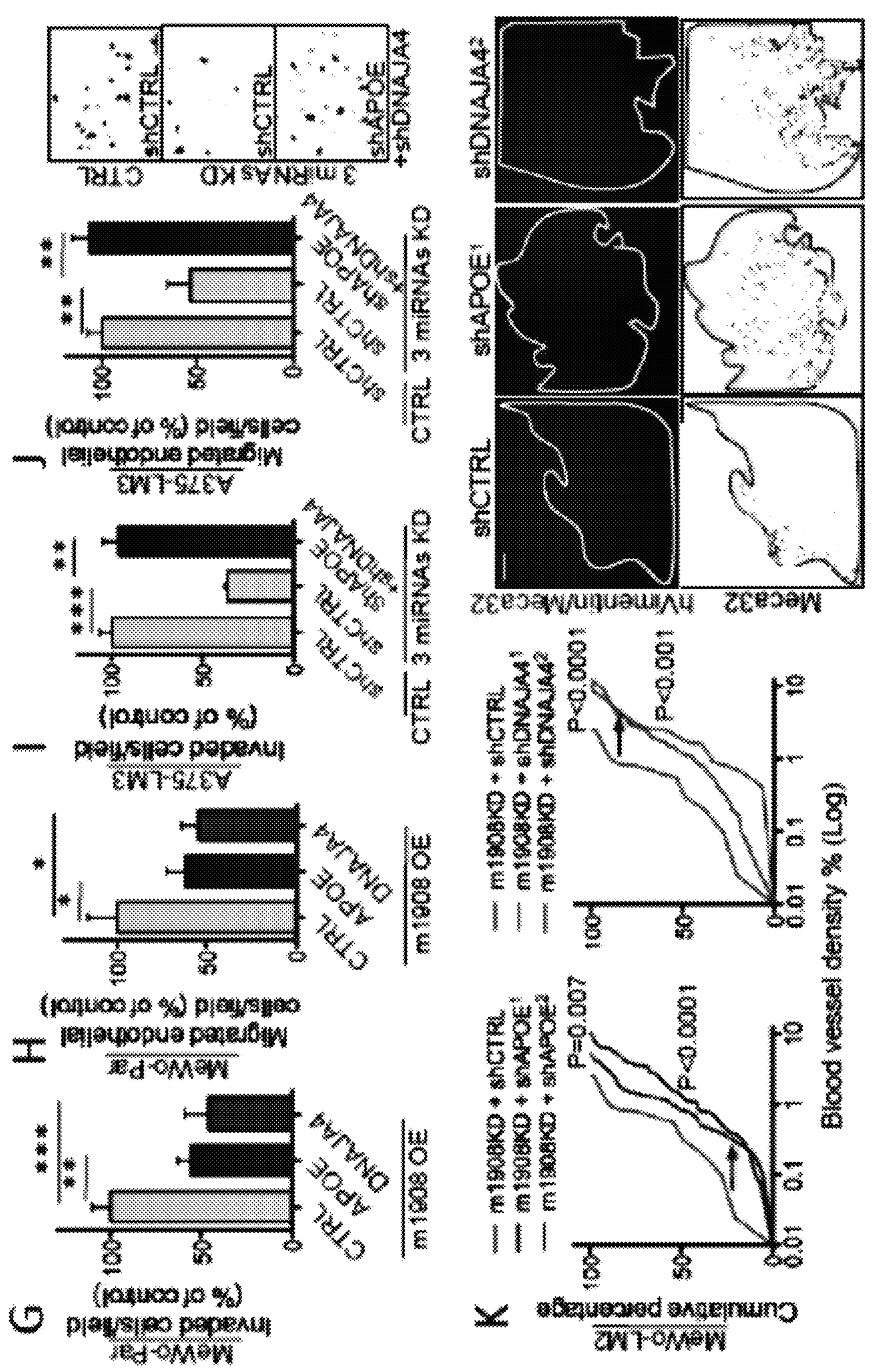
Figures 15A, 15B, 15C, 15D, 15E, 15F, 15G:
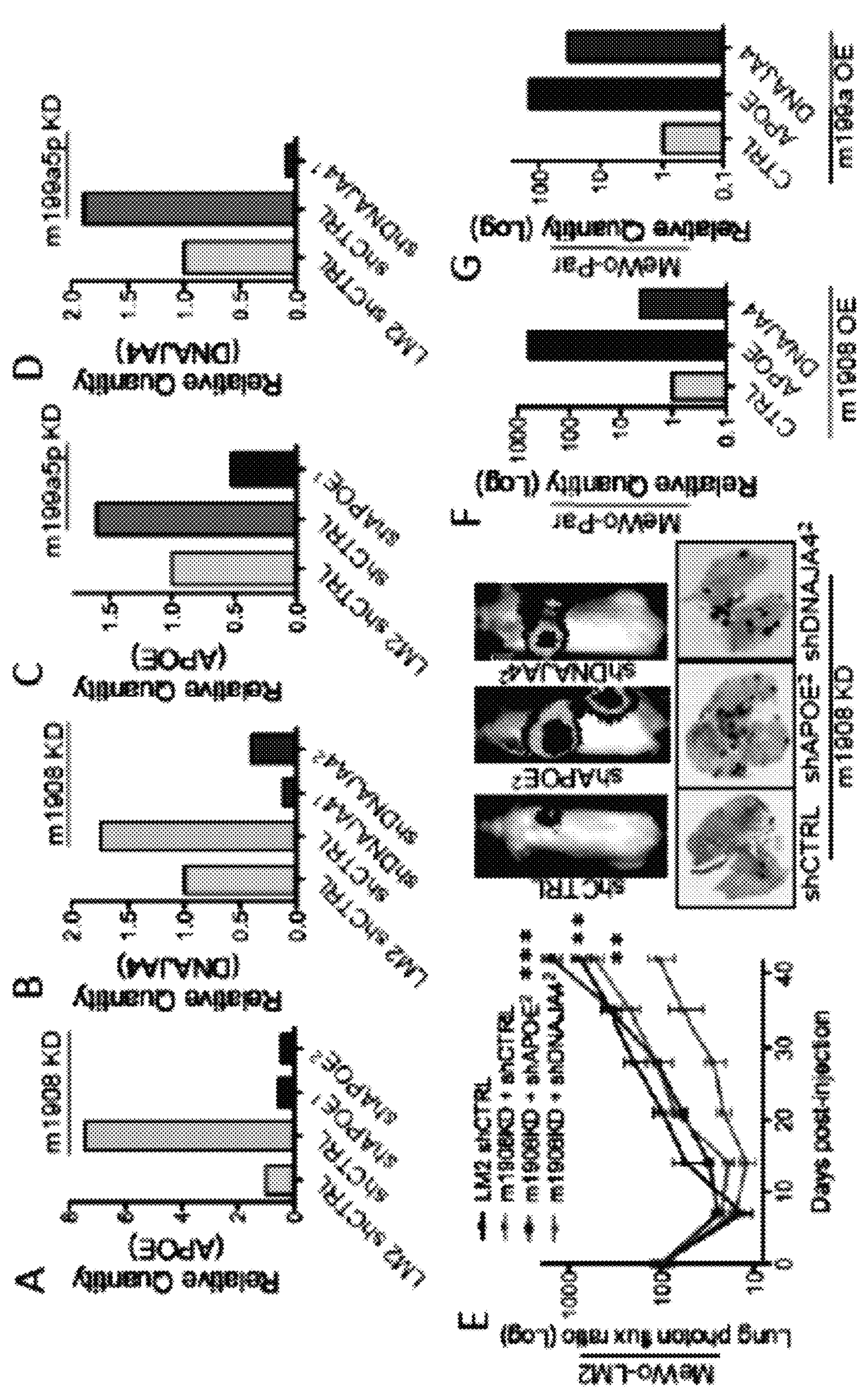
FIGS. 15A, 15B, 15C, 15D, 15E, 15F, 15G, 15H, 15I, 15J and 15K. Epistatic Interactions between miR-199a/miR-1908 and ApoE/DNAJA4 (15A, 15B, 15C and 15D). MeWo-LM2 cells were transduced with lentiviral shRNAs targeting ApoE (15A, 15C), DNAJA4 (15B, 15D), or a control shRNA in the setting of miR-Zip-induced silencing of miR-1908 (15A, 15B), miR-199a-5p (15C, 15D), or a control sequence. The levels of the target genes were analyzed by qRT-PCR. (15E) Bioluminescence imaging of lung metastasis by 1×105 LM2 cells expressing a control hairpin or shRNAs (independent from the shRNAs used in FIG. 4E) targeting ApoE, DNAJA4, or a control sequence in the setting of miR-1908 inhibition. Representative bioluminescence images and H&E-stained lungs correspond to day 42 post-injection. n=5. (15F-15G) The expression levels of ApoE and DNAJA4 were analyzed by qRT-PCR in parental MeWo cells transduced with retrovirus expressing a control vector or an over-expression vector for ApoE or DNAJA4 in the setting of miR-1908 (15F) or miR-199a (15G) over-expression. (15H-15I). Parental MeWo cells over-expressing ApoE or DNAJA4 or expressing a control vector in the setting of miR-199a over-expression were examined for the invasion (15H) and endothelial recruitment (15I) phenotypes. n=7-8. (15J) Bioluminescence imaging of lung metastasis by 4×104 parental MeWo cells over-expressing ApoE or DNAJA4 or expressing a control vector in the setting of miR-1908 over-expression. Representative bioluminescence images and H&E-stained lungs correspond to day 56 post-injection n=4-8. (15K). Expression levels of ApoE and DNAJA4, determined by qRT-PCR, in highly metastatic A375-LM3 derivatives transduced with lentivirus expressing shRNA constructs targeting ApoE and DNAJA4 or a control sequence. All data are represented as mean±SEM. Scale bar, 100 μm.
Figures 15H, 15I, 15J, 15K:
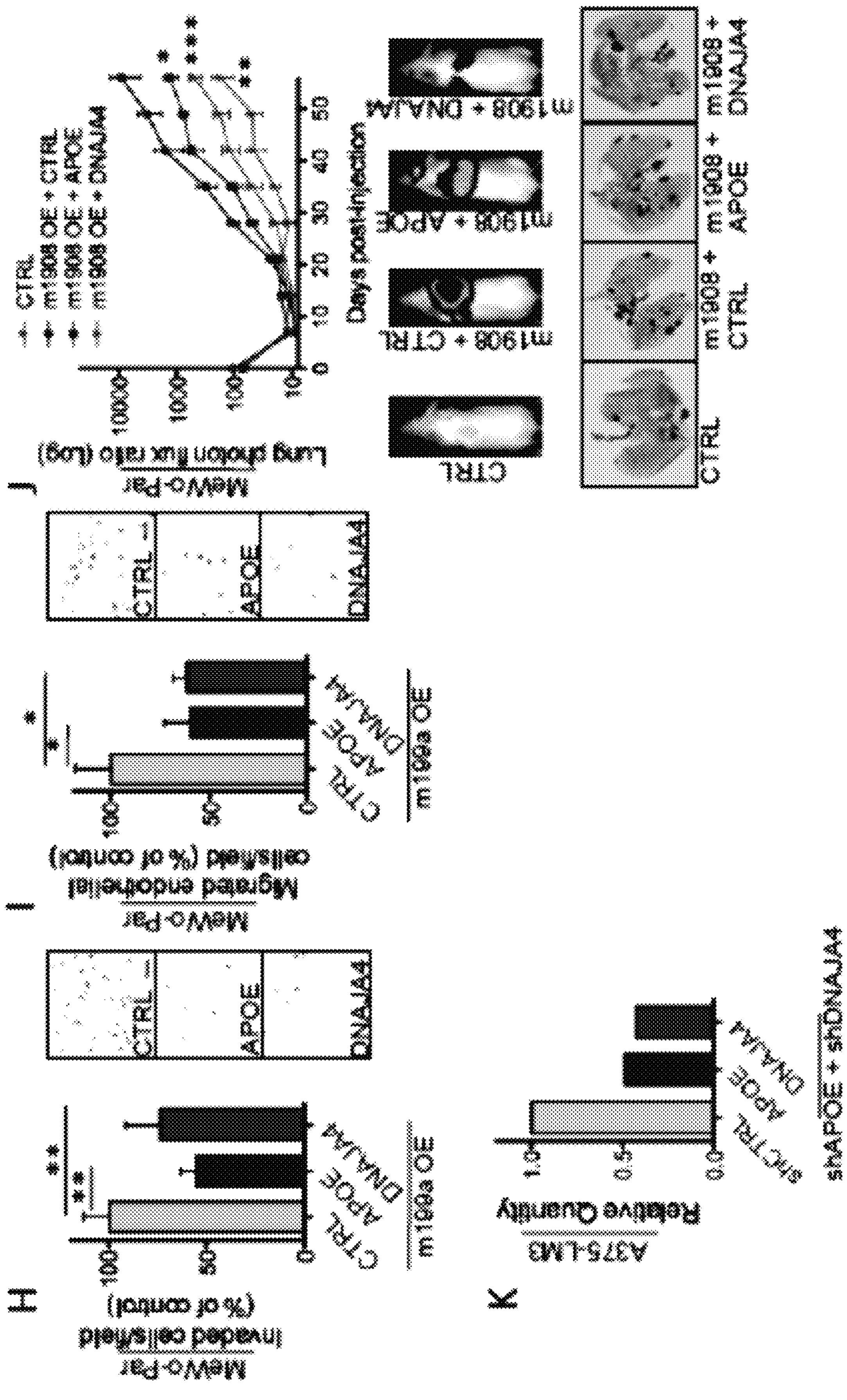

Example 5 ApoE and DNAJA4 Mediate miR-199a- and miR-1908-Dependent Metastatic Invasion, Endothelial Recruitment, and Colonization To determine whether ApoE and DNAJA4 are the direct biological effectors downstream of miR-199a and miR-1908, assays were carried out to examine whether these two target genes epistatically interact with each miRNA. As expected, miRNA silencing reduced the invasion and endothelial recruitment capacity of highly metastatic melanoma cells. Importantly, knock-down of ApoE or DNAJA4 in the setting of miRNA inhibition significantly occluded the suppression of invasion (FIGS. 4A and 4C) and endothelial recruitment (FIGS. 4B and 4D) upon silencing of each miRNA. Strikingly, knock-down of either of these genes in cells depleted for miR-1908 or miR-199a-5p fully rescued the dramatic suppression of metastatic colonization resulting from miRNA inhibition (FIG. 4E-F, 15E). Conversely, over-expression of ApoE or DNAJA4 in cells over-expressing miR-1908 (FIG. 4G-H, 15F) or miR-199a (FIG. 15G-I) was sufficient to suppress cell invasion and endothelial recruitment. Additionally, ApoE or DNAJA4 over-expression was sufficient to inhibit miRNA-mediated metastatic colonization (FIG. 15J). Importantly, ApoE and DNAJA4 were also required for miRNA-dependent enhanced cell invasion and endothelial recruitment by the highly metastatic A375-LM3 cells (FIGS. 4I-J, 15K).

To determine whether ApoE and DNAJA4 also regulate miRNA-dependent metastatic endothelial recruitment in vivo, co-immunostaining of melanoma metastases (human vimentin) and endothelial cells (MECA-32) was performed in lung metastatic nodules formed by cells knocked-down for each of these genes in the context of miRNA inhibition. Notably, knock-down of ApoE or DNAJA4 resulted in a significant (>3.5-fold) increase in metastatic blood vessel density in metastases arising from cells with miRNA silencing (FIG. 4K, P<0.01 for both ApoE and DNAJA4 knock-down cells). These findings reveal ApoE and DNAJA4 as direct downstream effectors of miRNA-dependent metastatic invasion, colonization, and endothelial recruitment phenotypes induced by these pro-metastatic miRNAs in melanoma.

Figures 5A, 5B, 5C, 5D, 5E, 5F, 5G:
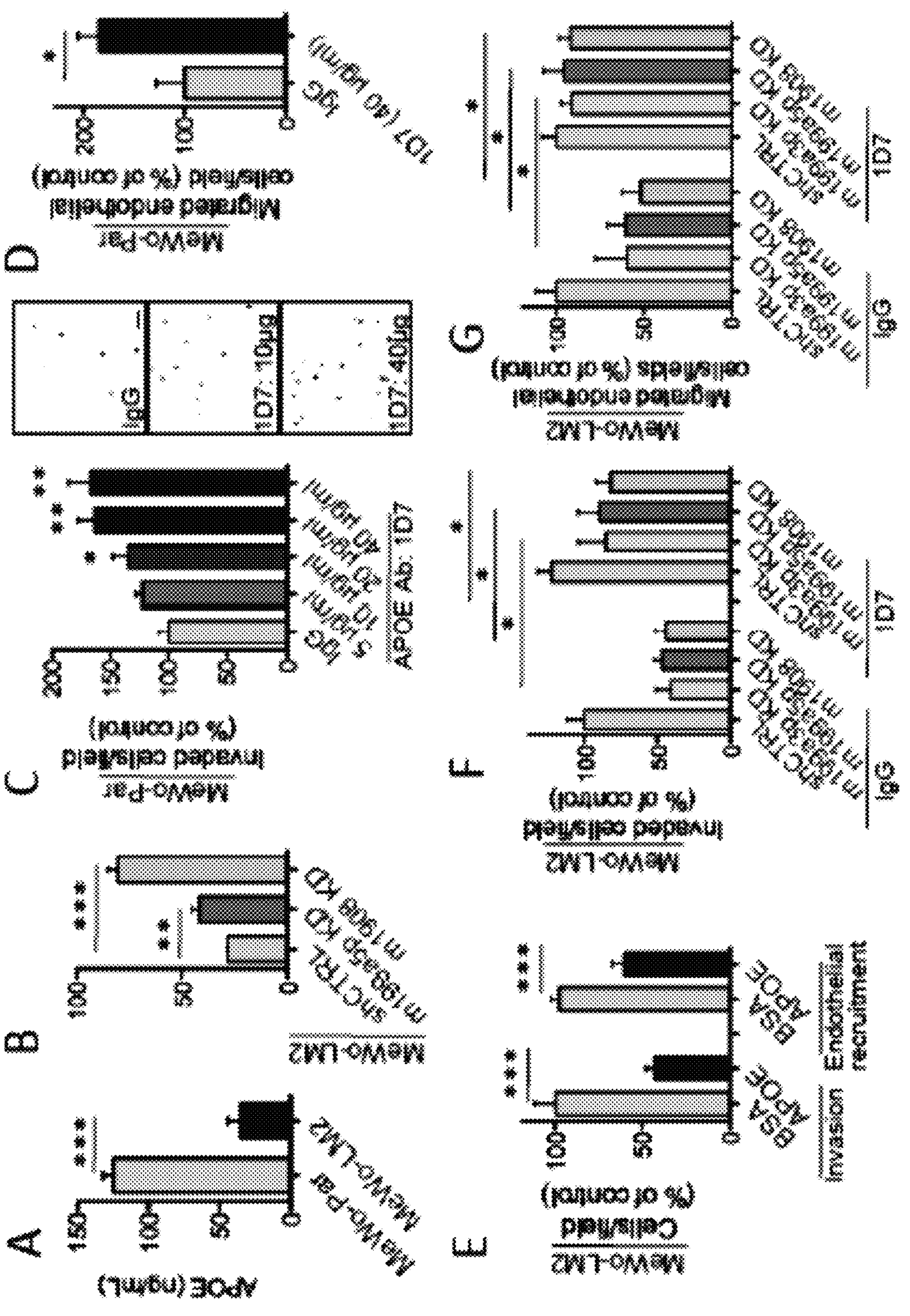
FIGS. 5A, 5B, 5C, 5D, 5E, 5F, 5G, 5H, 5I, 5J, 5K, 5L and 5M. Melanoma-Cell Secreted ApoE Inhibits Melanoma Invasion and Endothelial Recruitment, while Genetic Deletion of ApoE Accelerates Metastasis (5A-5B) Extracellular ApoE levels quantified by ELISA in conditioned media from MeWo-LM2 metastatic derivatives and their parental cells (5A) and LM2 cells silenced for miR-199a-5p, miR-1908, or a control sequence (5B). n=3. (5C) ApoE-neutralizing antibody 1D7 (10-40 μg/mL) or IgG (40 μg/mL) was added to the cell media, and matrigel invasion by parental MeWo cells was assessed. n=4-6. (5D) Endothelial recruitment by parental MeWo cells in the presence of 1D7 (40 μg/mL) or a control IgG antibody (40 μg/mL). n=4. (5E) The matrigel invasion and endothelial recruitment phenotypes were assessed in LM2 cells in the presence of bovine serum albumin (BSA) (100 μM) or recombinant ApoE3 (100 μM) added to the cell media. n=7-10. (5F-5G) LM2 cells with silenced expression of miR-199a-3p, miR-199a-5p, miR-1908, or a control sequence were examined for matrigel invasion capacity (5F) and endothelial recruitment ability (5G) in the presence of IgG or ApoE-neutralizing 1D7 antibodies (40 μg/mL). n=5-6. (5H) ApoE levels quantified by ELISA in conditioned media from parental MeWo cells transduced with shRNAs targeting DNAJA4 or a control sequence. n=3. (5I-5J) Parental MeWo cells with shRNA-induced silencing of DNAJA4 were analyzed for the matrigel invasion (5I) and endothelial recruitment (5J) phenotypes in the presence of either BSA (100 μM) or recombinant ApoE3 (100 μM). n=4. (5K) Array-based ApoE expression levels in nevi (n=9), primary melanomas (n=6), and distant melanoma metastases samples (n=19). (5L) Highly metastatic MeWo-LM2 cells were incubated in the presence of recombinant ApoE3 or BSA at 100 μg/mL. After 24 hours, 4×104 cells were intravenously injected into NOD-SCID mice, and lung colonization was monitored by bioluminescence imaging. n=6. (5M) Lung metastasis by 5×104 B16F10 mouse melanoma cells intravenously injected into ApoE genetically null C57BL/6 mice or their wild-type control littermates. Lung bioluminescence quantification and representative H&E-stained lungs correspond to 19 days post-injection. n=8-18. All data are represented as mean±SEM. Scale bar, 100 μm.
Figures 16A, 16B, 16C, 16D, 16E, 16F:
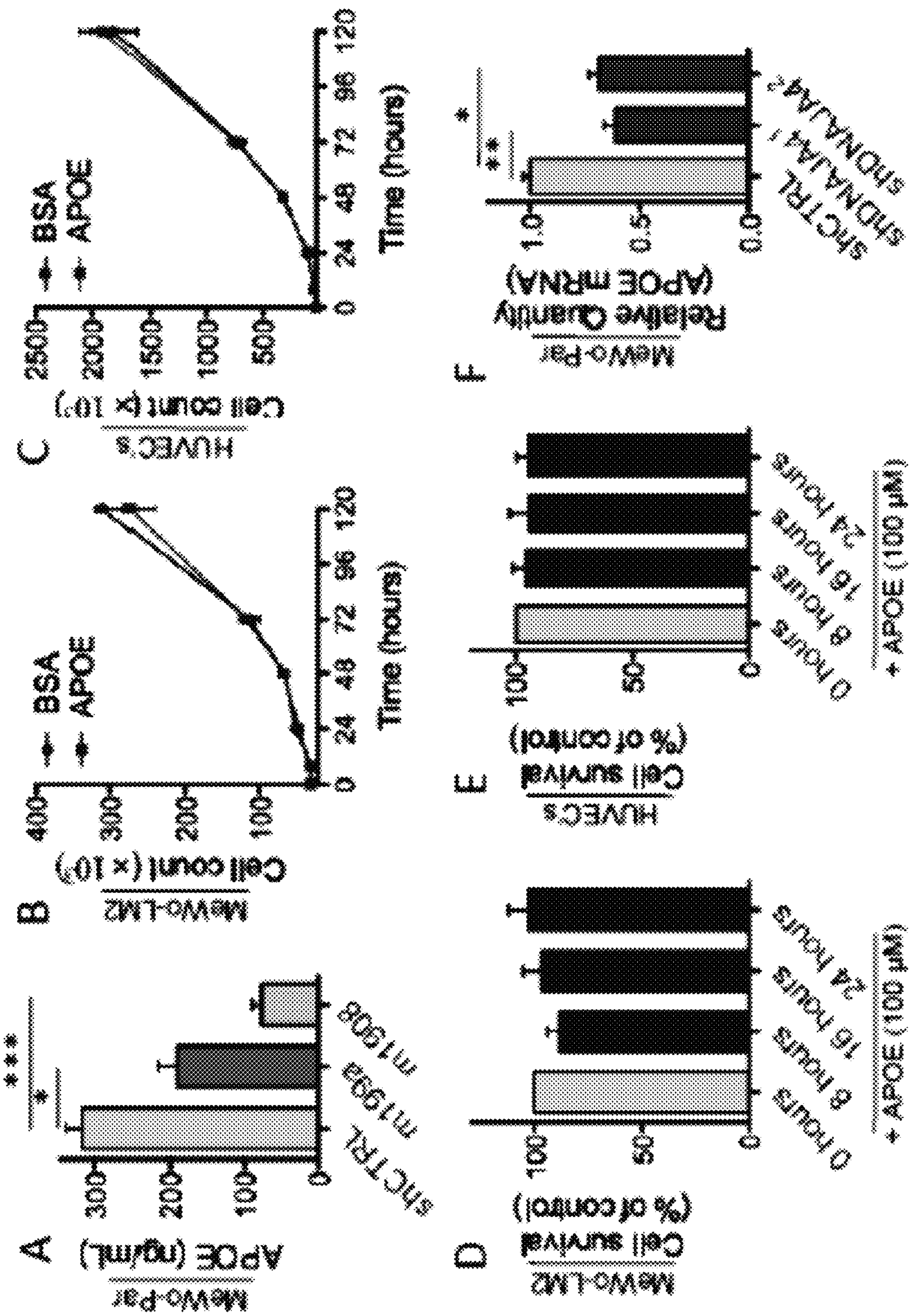
FIGS. 16A, 16B, 16C, 16C, 16D, 16E, 16F, 16G, 16H and 16I. Extracellular ApoE Inhibits Melanoma Invasion and Endothelial Recruitment Phenotypes Independent of Any Effects on Cancer or Endothelial Cell Proliferation and Survival (16A) Extracellular ApoE levels were measured by ELISA in conditioned media from MeWo cells over-expressing miR-199a, miR-1908, or a control hairpin. n=3. (16B-16C) 3× 104 MeWo-LM2 cells (16B) or endothelial cells (16C) were cultured in the presence of BSA (100 μM) or APOE (100 μM), and cell proliferation was monitored over time by counting the number of viable cells at each indicated time-point. n=3. (16D-16E) Survival of MeWo-LM2 cells (16D) or endothelial cells (16E) in the context of serum starvation in the presence of BSA (100 μM) or APOE (100 μM). n=3. (16F-16G) The mRNA expression levels of ApoE were assessed in parental MeWo cells transduced with lentivirus expressing a control hairpin or short hairpin constructs targeting DNAJA4 (16F) and in LM2 cells transduced with retrovirus expressing a control vector or an over-expression vector for DNAJA4 (16G). n=3. (H-I) LM2 cells transduced with retrovirus expressing a control vector or an over-expression vector for DNAJA4 were assessed for their ability to invade through matrigel (16H; n=6-8) and recruit endothelial cells in a trans-well assay (16I; n=4) in the presence of IgG (40 μg/mL) or 1D7 (40 μg/mL) ApoE neutralization antibodies. All data are represented as mean±SEM.

Example 6 Melanoma Cell-Secreted Apoe is Both a Necessary and Sufficient Mediator of Invasion and Endothelial Recruitment, while Genetic Deletion of Apoe Promotes Metastasis ApoE is a secreted factor. As such, it was examined whether melanoma-cell secreted ApoE could suppress invasion and endothelial recruitment. Accordingly, extracellular ApoE levels, detected by ELISA, were 3.5-fold lower in metastatic LM2 cells—which express higher levels of miR-199a and miR-1908—than their less metastatic parental cells (FIG. 5A). Secreted ApoE levels were also significantly suppressed by endogenous miR-199a and miR-1908 (FIGS. 5B and 16A).

Next, inhibiting ApoE through use of a neutralizing antibody (1D7) that recognizes the receptor-binding domain of ApoE enhanced both cell invasion (FIG. 5C; 1.68-fold increase) and endothelial recruitment (FIG. 5D; 1.84-fold increase) by parental MeWo cells, which express high endogenous levels of ApoE (FIG. 14C). Conversely, addition of recombinant human ApoE significantly suppressed invasion and endothelial recruitment by metastatic LM2 cells (FIG. 5E), which exhibit low endogenous ApoE levels (FIG. 14C). Importantly, recombinant ApoE addition did not affect melanoma cell or endothelial cell in vitro proliferation (FIG. 16B-C) or survival in serum starvation conditions (FIG. 16D-E), indicating that suppression of these phenotypes by recombinant ApoE is not secondary to a decrease in proliferation or impaired survival. Consistent with ApoE being epistatically downstream of miR-199a and miR-1908, neutralization of ApoE with the ApoE neutralizing antibody 1D7 significantly abrogated the suppressed invasion and endothelial recruitment phenotypes seen with inhibition of each miRNA (FIGS. 5F-G). The above findings reveal melanoma cell-secreted ApoE as a necessary and sufficient suppressor of miRNA-dependent invasion and endothelial recruitment phenotypes in melanoma.

Figures 5H, 5I, 5J, 5K, 5L, 5M:
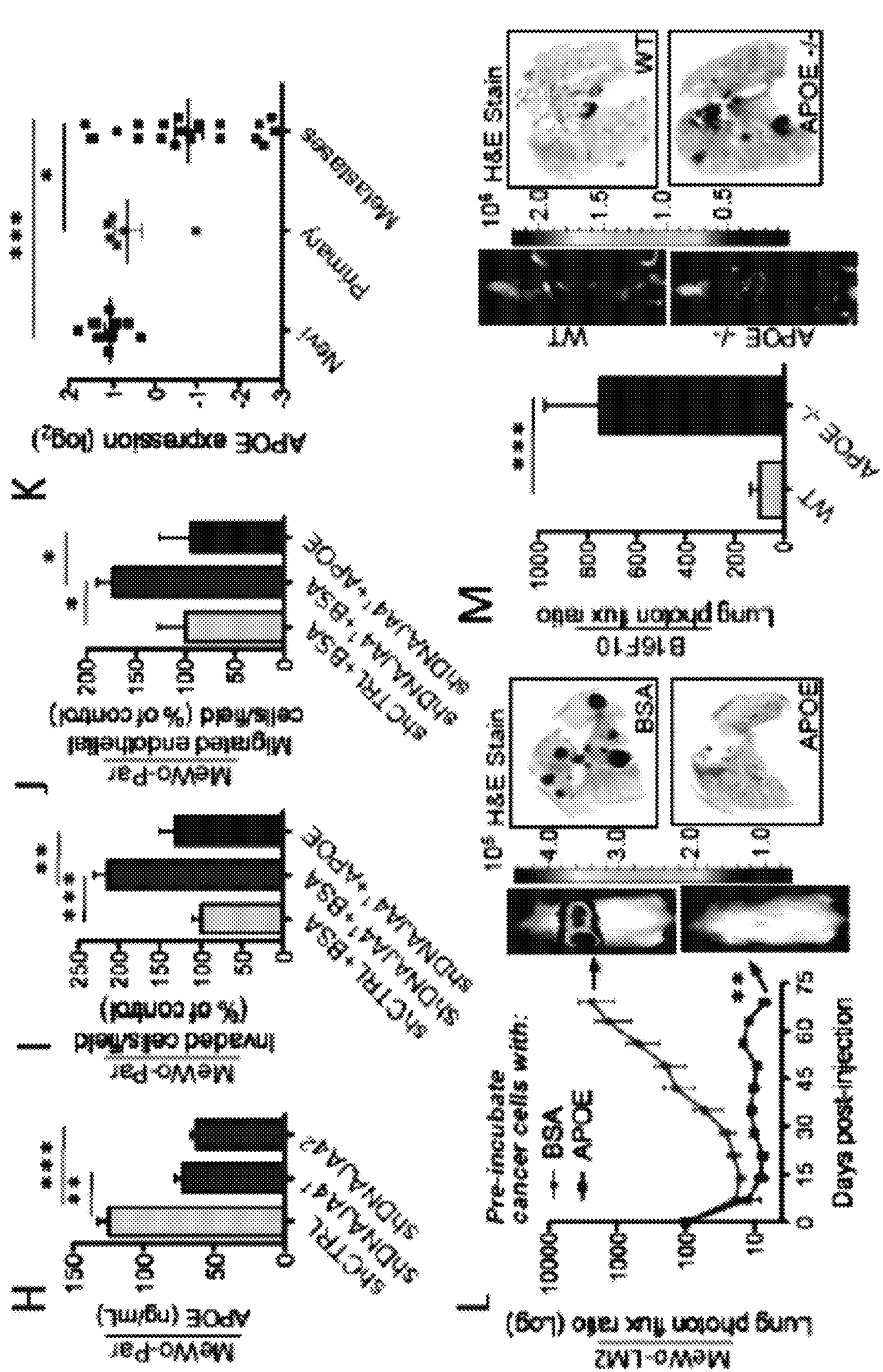
Figures 16G, 16H, 16I:
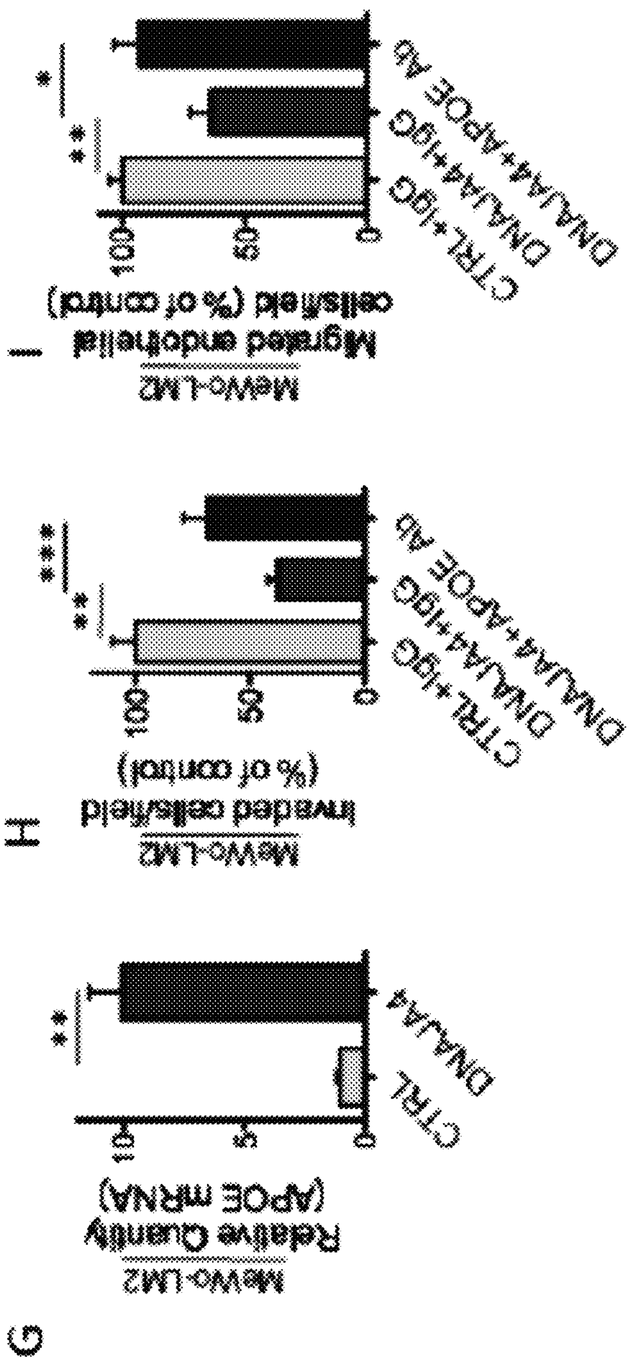

Further assays were carried out to investigate the mechanism by which DNAJA4, a poorly characterized heat-shock protein, mediates endothelial recruitment and invasion. Given the phenotypic commonalities displayed by ApoE and DNAJA4, it was hypothesized that DNAJA4 may play a regulatory role and enhance ApoE levels. Indeed, knock-down of DNAJA4 reduced both ApoE transcript levels (FIG. 16F) as well as secreted ApoE levels (FIG. 5H), while DNAJA4 over-expression substantially elevated ApoE expression (FIG. 16G). Consistent with DNAJA4 acting upstream of ApoE, addition of recombinant ApoE abrogated the enhanced cell invasion and endothelial recruitment phenotypes seen with DNAJA4 knock-down (FIG. 5I-J). Conversely, the suppression of invasion and endothelial recruitment seen with DNAJA4 over-expression phenotypes were significantly occluded by antibody neutralization of ApoE (FIGS. 16H-I). These findings reveal DNAJA4 to suppress melanoma invasion and endothelial recruitment through positive regulation of ApoE expression and resulting secretion.

In view of the regulatory convergence of three metastasis-promoting miRNAs and the DNAJA4 gene on ApoE, assays were carried out to determine whether ApoE expression correlates with human melanoma progression. To this end, published array-based expression data for ApoE (Haqq et al., 2005 Proc. Natl. Acad. Sci. USA 102, 6092-6097) was analyzed in nevi, primary, and metastatic lesions. Consistent with a metastasis-suppressive role, ApoE levels were significantly lower in distal organ metastases relative to primary (P<0.025) and nevi lesions (P<0.0003) (FIG. 5K).

Given its significant correlation with human melanoma progression, it was next examined whether increasing ApoE signaling in melanoma cells could have therapeutic efficacy in suppressing melanoma metastasis. More specifically, metastatic MeWo-LM2 cells were pre-incubated with recombinant ApoE or BSA for 24 hours prior to injection into mice. Strikingly, pre-treatment of cancer cells with ApoE robustly suppressed metastatic colonization by over 300-fold (FIG. 5L). This dramatic suppression of metastasis by ApoE pre-incubation of melanoma cells reflects that the effects of ApoE on melanoma cells are pivotal for metastatic initiation, as cells pre-treated with ApoE exhibit reduced invasive ability, which is needed to initiate metastatic events leading to lung colonization.

Given the robust influence exerted by ApoE on metastasis and metastatic phenotypes, as well as its strong association with human melanoma progression, further assays were carried out to investigate the impact of genetic deletion of systemic ApoE on melanoma progression in an immunocompetent mouse model of melanoma metastasis. Consistent with a major suppressive role for extracellular ApoE in metastasis, B16F10 mouse melanoma cells injected into the circulation exhibited a greater than 7-fold increase in metastatic colonization in ApoE genetically null mice compared to their wild-type littermates (FIG. 5M). These findings establish systemic and cancer-secreted ApoE as a robust suppressor of human and mouse melanoma metastasis.

Example 7 Extracellular ApoE Divergently Targets Melanoma Cell LRP1 and Endothelial Cell LRP8 Receptors In this example, assays were carried out to investigate the molecular mechanisms by which ApoE suppresses metastasis.

Figures 6A, 6B, 6C, 6D, 6E, 6F:
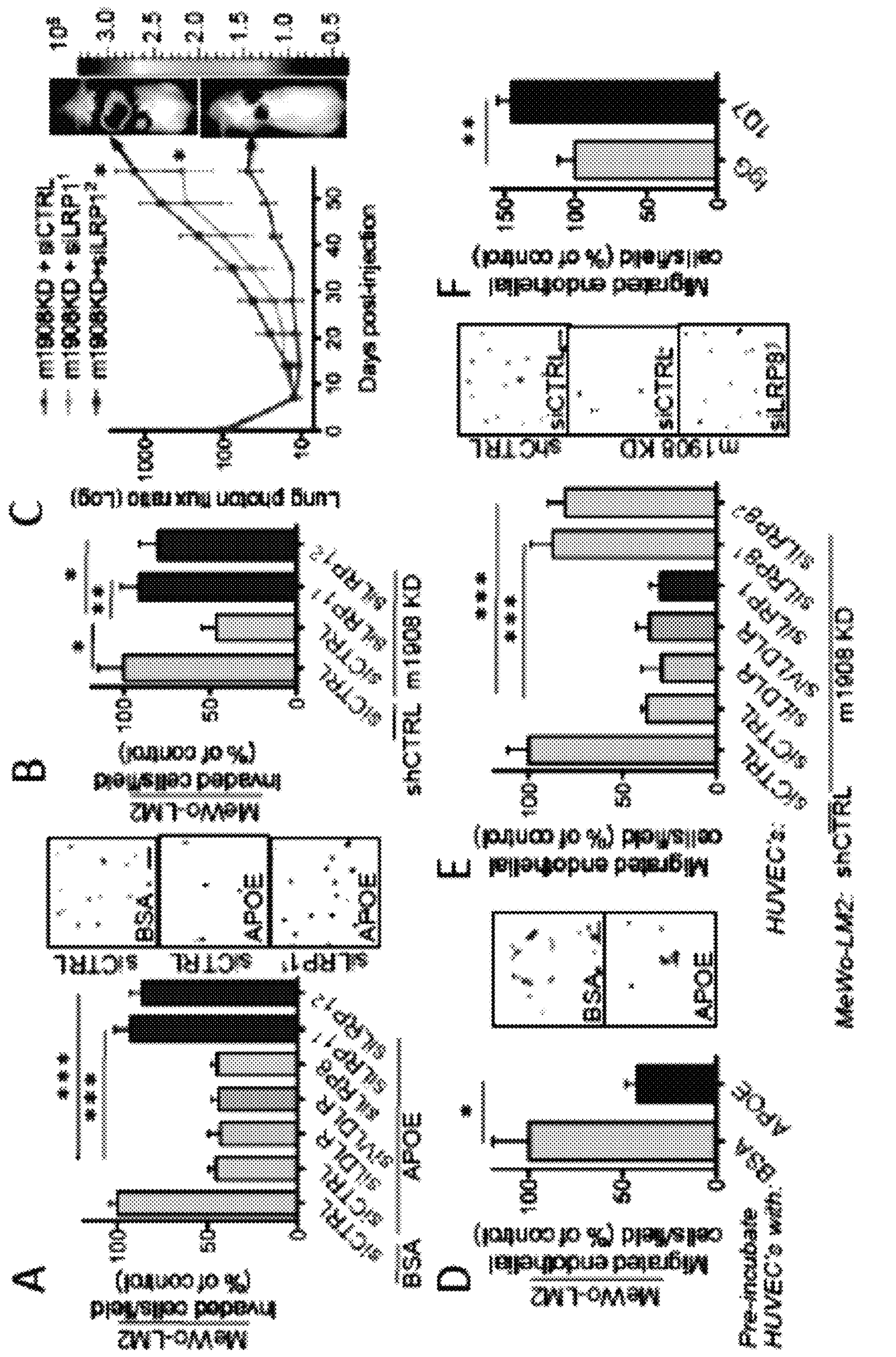
FIGS. 6A, 6B, 6C, 6D, 6E, 6F, 6G, 6H, 6I and 6J. Identification of Distinct Melanoma and Endothelial Cell Receptors that Mediate the Effects of ApoE on Melanoma Invasion and Endothelial Recruitment (6A) Matrigel invasion capacity was examined in 1× 105 LM2 cells transduced with siRNAs targeting LDLR, VLDLR, LRP8, LRP1, or a control sequence in the presence of either BSA (100 μM) or recombinant ApoE3 (100 μM). n=4-7. (6B) 1×105 MeWo-LM2 cells transduced with short hairpins targeting miR-1908 or a control sequence were transfected with siRNAs targeting LRP1 or a control siRNA and subjected to the matrigel invasion assay. n=4. (6C) Bioluminescence imaging of lung colonization by 1× 105 LM2 cells transduced with siRNAs targeting LRP1 or a control sequence in the setting of miR-1908 inhibition. n=5. (6D) 1× 105 endothelial cells pre-incubated with BSA (100 μM) or recombinant ApoE3 (100 μM) for 24 hours were analyzed for the endothelial recruitment phenotype by 5×105 LM2 cells. n=3-4. (6E) 1×105 endothelial cells were transduced with siRNAs targeting LDLR, VLDLR, LRP1, LRP8, or a control sequence and allowed to migrate in a trans-well system towards LM2 cells inhibited for miR-1908 or a control sequence. n=4-12. (6F) Trans-well migration by 1×105 endothelial cells in the presence of IgG (40 μg/mL) or 1D7 antibodies (40 g/mL) added to the cell media. n=6-8. (6G) Trans-well migration by 1×105 endothelial cells transduced with siRNAs targeting LRP8 or a control sequence in the presence of BSA (100 μM) or recombinant ApoE3 (100 μM). n=6-7. (6H) 1×105 endothelial cells were transduced with siRNAs targeting LRP8 or a control sequence, and trans-well chemotactic migration was assessed along an ApoE gradient. n=6-8. (6I) Endothelial recruitment into matrigel plugs, implanted subcutaneously above the ventral flank of mice, containing BSA (10 μg/mL), VEGF (400 ng/mL)+ BSA (10 μg/mL), or VEGF (400 ng/mL)+recombinant ApoE3 (10 μg/mL). n=3-6. (6J) Blood vessel density within lung metastatic nodules formed following intravenous injection of 5×104 B16F10 mouse melanoma cells into wild-type or ApoE genetically null mice. Lung sections from FIG. 5M were immunohistochemically stained for MECA-32, and the percentage MECA-32 positive area within each metastatic nodule, outlined based on cell pigmentation, was quantified. n=17-20. All data are represented as mean±SEM. Scale bar, 100 μm.

In order to identify the ApoE receptor(s) that mediate(s) invasion, down all four known ApoE receptors, VLDLR, LRP1, LRP8, and LDLR (Hatters et al., 2006 Trends Biochem. Sci. 31, 445-454; Hauser et al., 2011 Prog. Lipid Res. 50, 62-74) were knocked in melanoma cells. Interestingly, knock-down of LRP1, but not the other ApoE receptors, abolished the cell invasion suppression effect induced by recombinant ApoE (FIG. 6A). Importantly, knock-down of LRP1 in metastatic LM2 cells, which display low levels of ApoE, only modestly increased cell invasion (FIG. 17A), suggesting the effects of LRP1 to be mediated by endogenous ApoE.

Figures 17A, 17B, 17C, 17D, 17E:
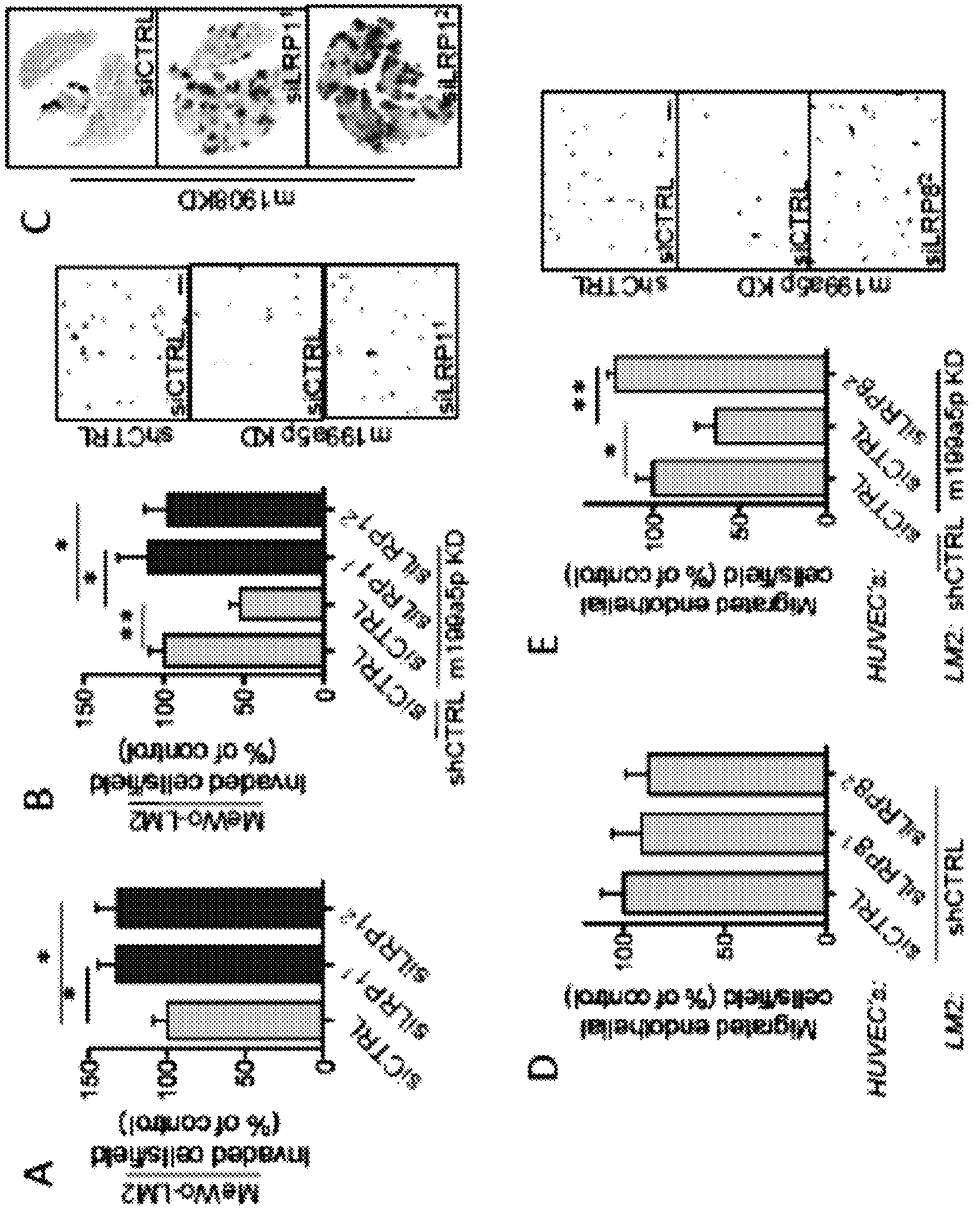
FIGS. 17A, 17B, 17C, 17D and 17E. ApoE Inhibits Cell Invasion and Endothelial Recruitment by Targeting Melanoma Cell LRP1 and Endothelial Cell LRP8 Receptors (17A) 1×105 LM2 cells transduced with siRNAs against LRP1 or a control sequence were analyzed for the ability to invade through matrigel. n=9-12. (17B) 1×105 MeWo-LM2 cells inhibited for miR-199a-5p or a control sequence were transfected with siRNAs targeting LRP1 or a control siRNA and examined for their matrigel invasion capacity. n=4. (17C) Representative H&E-stained lungs extracted at day 56 from NOD-SCID mice injected with MeWo-LM2 miR-1908 KD cells transduced with a control siRNA or siRNAs targeting LRP1 (See FIG. 6C). (17D-17E) 1× 105 endothelial cells were transfected with siRNAs targeting LRP8 or a control sequence and allowed to trans-well migrate towards 5×104 MeWo-LM2 cells expressing a short control hairpin (17D; n=8) or 5×104 MeWo-LM2 cells inhibited for miR-199a-5p or a control sequence (17E; n=4). All data are represented as mean±SEM. Scale bar, 100 μm.

To determine if LRP1 also mediates the miRNA-dependent effects on invasion and metastatic colonization, LRP1 was knocked down in the context of miRNA inhibition. LRP1 knock-down in the setting of miRNA silencing rescued the suppressed invasion phenotype arising from miRNA inhibition (FIGS. 6B, 17B). Consistent with these in vitro results, LRP1 knock-down significantly enhanced in vivo metastatic colonization by LM2 cells silenced for miR-1908 (FIG. 6C, 17C). These findings reveal LRP1 to be epistatically downstream of miRNA/ApoE-dependent melanoma invasion and metastatic colonization.

While the invasion phenotype reflects the cell-autonomous effects of ApoE on melanoma cells, the endothelial recruitment phenotype suggests a non-cell-autonomous role of cancer-expressed ApoE directly on endothelial cells. Consistent with this, pre-treatment of endothelial cells with ApoE significantly reduced their ability to migrate towards highly metastatic cancer cells (FIG. 6D). In order to identify the ApoE receptor(s) on endothelial cells that mediate(s) the endothelial recruitment phenotype, all four known ApoE receptors were knocked down on endothelial cells. Interestingly, unlike for cancer cell invasion, knock-down of endothelial LRP8, but not any of the other receptors, selectively and significantly abrogated the inhibition of endothelial recruitment caused by miRNA silencing (FIGS. 6E, 17D-E). These findings are consistent with the LRP8 receptor being the downstream endothelial mediator of miRNA/ApoE-dependent effects on endothelial recruitment.

Figures 6G, 6H, 6I, 6J:
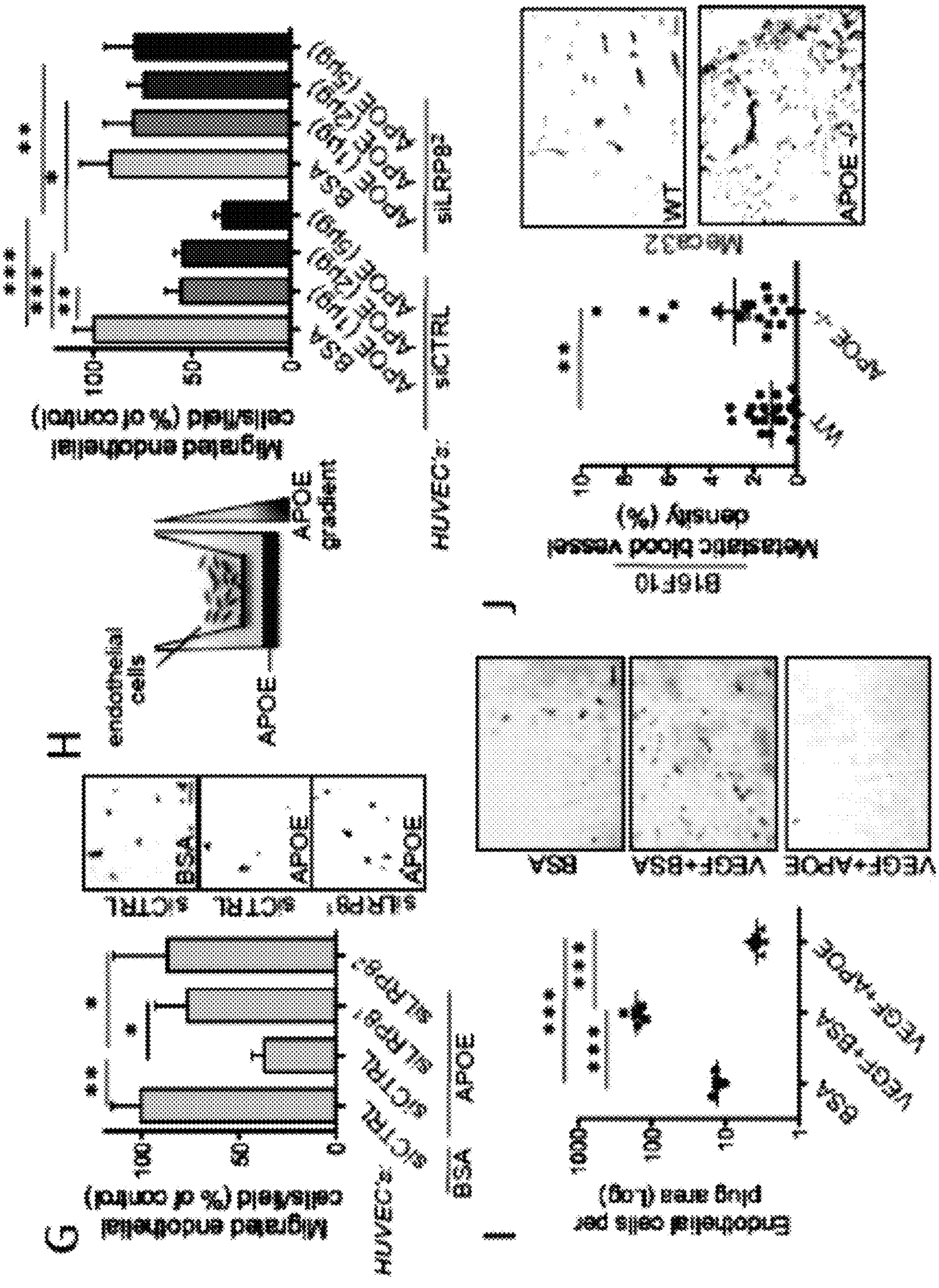

Next, assays were carried out to examine whether ApoE/LRP8 signaling might also regulate general endothelial migration in a cancer cell-free system. Accordingly, antibody neutralization of ApoE, which is present in endothelial cell media, significantly enhanced endothelial migration (FIG. 6F), while recombinant ApoE was sufficient to inhibit endothelial migration in a trans-well assay (FIG. 6G) and a gradient-based chemotactic assay (FIG. 6H) in an endothelial cell LRP8 receptor-dependent manner. Importantly, addition of ApoE lead to a dramatic (greater than 40-fold) suppression of VEGF-induced endothelial recruitment in vivo into subcutaneous matrigel plugs (FIG. 6I).

Given the requirement and sufficiency of ApoE in mediating endothelial recruitment, further assays were carried out to examine whether systemic ApoE might regulate metastatic angiogenesis. Consistent with the robust suppression of metastatic endothelial content by melanoma cell-secreted ApoE (FIG. 4K), genetically null ApoE mice displayed higher blood vessel densities within their lung metastatic nodules formed by B16F10 mouse melanoma cells compared to their wild-type littermates (FIG. 6J; 2.41-fold increase, P=0.0055). Taken together, the above findings reveal dual cell-autonomous/non-cell-autonomous roles for ApoE in metastasis suppression through divergent signaling mediated by melanoma cell LRP1 and endothelial cell LRP8 receptors.

Example 8 MiR-199a-3p, miR-199a-5p, and miR-1908 as Robust Prognostic and Therapeutic Targets in Melanoma Metastasis To examine whether the metastasis promoter miRNAs described herein could serve as clinical predictors of metastatic outcomes, the expression levels of miR-199a-3p, miR-199a-5p, and miR-1908 were quantified in a blinded fashion by qRT-PCR in a cohort of human melanoma samples obtained from patients at MSKCC. The relationships between the levels of these miRNAs in primary melanoma lesions and metastatic relapse outcomes were then determined.

Figures 7A, 7B, 7C, 7D, 7E:
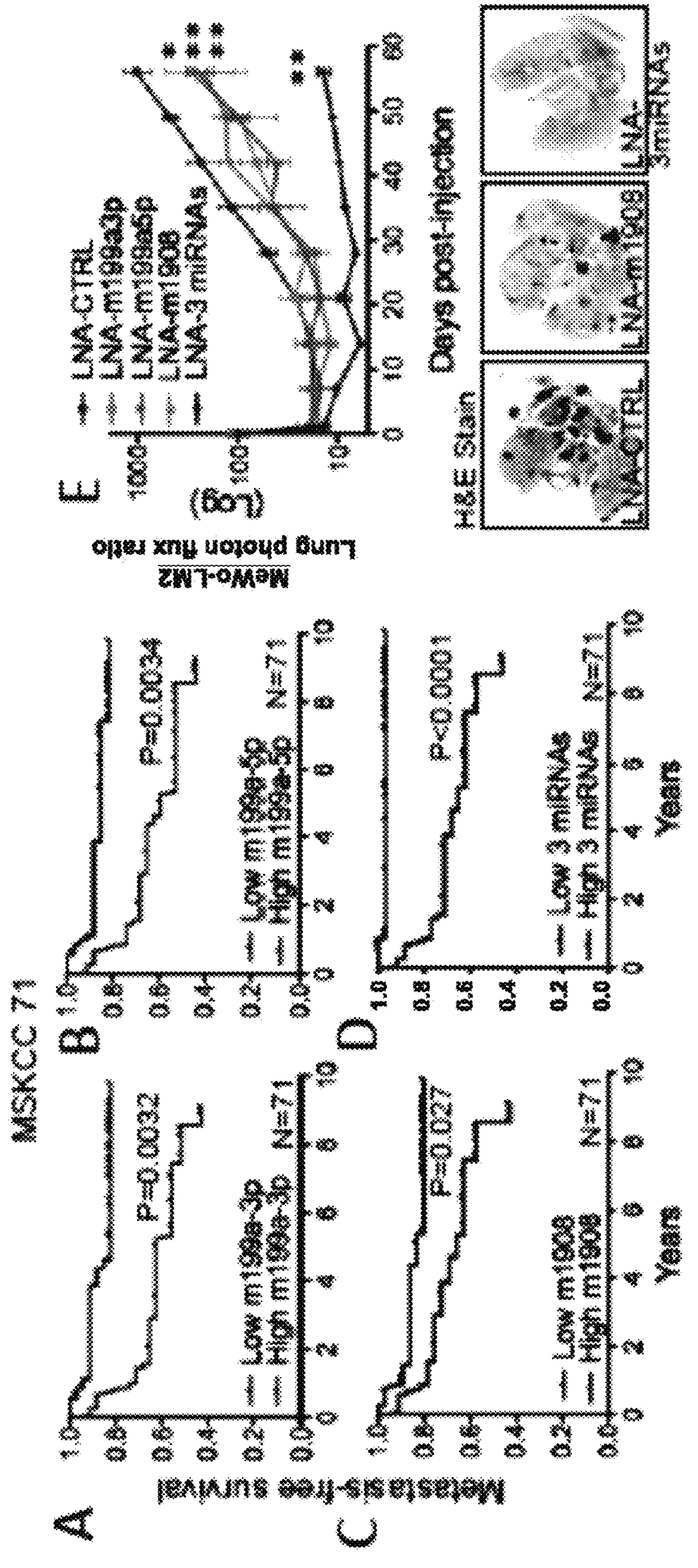
FIGS. 7A, 7B, 7C, 7D, 7E, 7F, 7G, 7H, 7I, 7J and 7K. Clinical and Therapeutic Cooperativity among miR-199a-3p, miR-199a-5p, and miR-1908 in Melanoma Metastasis (7A-7D). Kaplan-Meier curves for the MSKCC cohort (N=71) representing metastasis-free survival of patients as a function of their primary melanoma lesion's miR-199a-3p (7A), miR-199a-5p (7B), miR-1908 (7C), or aggregate three miRNA expression levels (7D). Patients whose primary tumors' miRNA expression or aggregate miRNA expression levels (sum of the expression values of miR-199a-3p, miR-199a-5p, and miR-1908) were greater than the median for the population were classified as miRNA expression positive (red), while those whose primary tumors expressed the given miRNAs at a level below the median were classified as miRNA expression negative (blue). (7E) Lung metastasis by highly metastatic LM2 cells transfected with LNAs individually targeting each miR-1908, miR-199a-3p, or miR-199a-5p, a combination of LNAs targeting all three miRNAs, or a control LNA. 48 hours post-transfection, 1×105 cells were intravenously injected into immuno-deficient mice. n=5-6. (7F) Systemic metastasis by 1× 105 MeWo-LM2 cells transfected with a control LNA (LNA-CTRL) or a cocktail of LNAs targeting miR-1908, miR-199a-3p, miR-199a-5p (LNA-3 miRNAs) 48 hours prior to intracardiac injection into athymic nude mice. n=5. (7G) Number of systemic metastatic foci arising from LNA-CTRL and LNA-3 miRNAs LM2 cells at day 28 post-intracardiac injection. n=5. (7H-7I) Bioluminescence signal quantification of bone metastasis (7H) and brain metastasis (7I) at day 28 post-intracardiac injection of LNA-CTRL and LNA-3 miRNAs LM2 cells. n=5. (7J) 4×104 highly metastatic MeWo-LM2 cells were tail-vein injected into immuno-compromised mice, and the mice were intravenously treated with a cocktail of in vivo-optimized LNAs targeting miR-1908, miR-199a-3p, and miR-199a-5p at a total dose of 12.5 mg/kg or a mock PBS control on a bi-weekly basis for four weeks. Lung colonization was assessed by bioluminescence imaging, and representative H&E-stained lungs extracted at day 56 are shown. n=5-6. (7K) Model of miRNA-dependent regulation of metastatic invasion, endothelial recruitment, and colonization in melanoma through targeting of ApoE-mediated melanoma cell LRP1 and endothelial cell LRP8 receptor signaling.

Importantly, patients whose primary melanoma lesions expressed higher (greater than the median for the population) levels of miR-199a-3p, miR-199a-5p, or miR-1908 were more likely to develop distal metastases and exhibited significantly shorter metastasis-free survival times than patients whose primary melanomas expressed lower levels of each of these miRNAs (FIGS. 7A-C, P=0.0032 for miR-199a-3p, P=0.0034 for miR-199a-5p, and P=0.027 for miR-1908). Strikingly, the aggregate expression levels of the three miRNAs displayed the strongest prognostic capacity in stratifying patients at high risk from those with very low risk for metastatic relapse (FIG. 7D, P<0.0001). These clinical findings are consistent with functional cooperativity between these miRNAs in the regulation of cancer progression and suggest utility for these molecules as clinical prognostic biomarkers of melanoma metastasis.

Figures 18A, 18B, 18C:
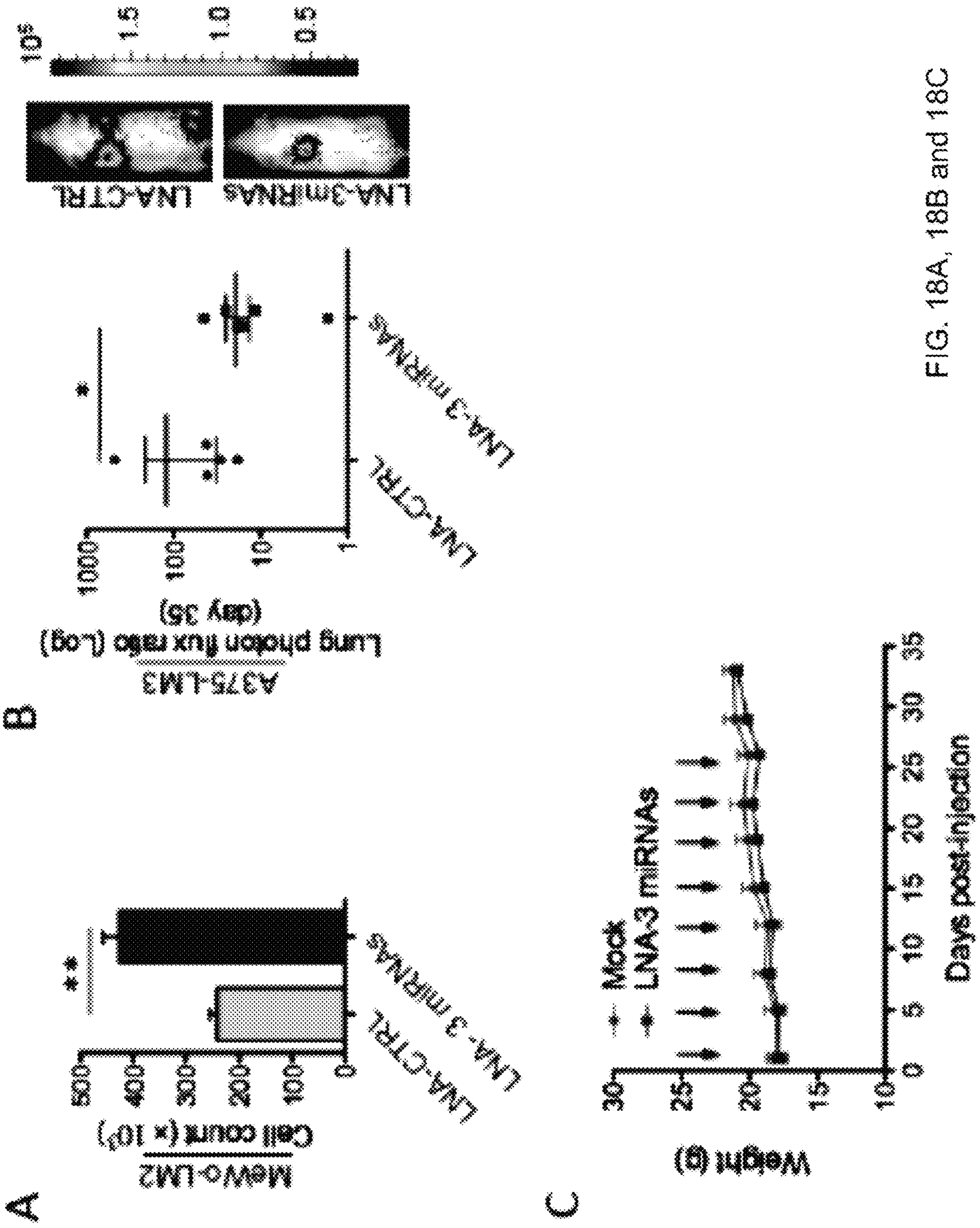
FIGS. 18A, 18B, and 18C. LNA-Based Inhibition of miR-199a and miR-1908 Suppresses Melanoma Metastasis (18A) In vitro cell proliferation by 2.5×104 MeWo-LM2 cells transduced with a control LNA or a cocktail of LNAs targeting miR-199a-3p, miR199a-5p and miR-1908. The number of viable cells was quantified after five days. n=3. (18B) Lung colonization by highly metastatic A375-LM3 derivatives transfected with a control LNA or a cocktail of LNAs targeting miR-199a-3p, miR 199a-5p, and miR-1908. 48 hours post-transfection, 5×105 cells were injected intravenously into NOD-SCID mice, and lung colonization was determined by measuring bioluminescence 35 days later. n=5-6. (18C) The weight of mice treated with a cocktail of LNAs targeting the three miRNAs or a mock PBS control treatment (FIG. 7J) was monitored bi-weekly. n=5-6. All data are represented as mean±SEM.

In light of the current lack of effective treatment options for the prevention of melanoma metastasis and the strong prognostic value of the three regulatory miRNAs in melanoma metastasis, these miRNAs therapeutically targeted using antisense LNA therapy (Elmer et al., 2008(a); Elmer et al., 2008(b)). Highly metastatic MeWo-LM2 cells pre-treated with LNA oligonucleotides antisense to mature miR-199a-3p, miR-199a-5p, or miR-1908 exhibited roughly a four-fold decrease in metastatic activity. Given clinical evidence for cooperativity among these miRNAs, the impact of silencing all three miRNAs on metastatic progression was examined. Remarkably, co-transfection of LNAs against all three miRNAs suppressed metastatic colonization by over seventy-fold, revealing dramatic synergy and cooperativity between endogenous miR-199a-3p, miR-199a-5p, and miR-1908 (FIG. 7E, P=0.004). Importantly, inhibition of these miRNAs with triple LNA pre-treatment did not result in decreased in vitro proliferation (FIG. 18A), indicating that the dramatic metastasis suppression phenotype is not secondary to impaired proliferation. Combinatorial LNA-mediated miRNA targeting in the independent A375 metastatic derivative line also significantly inhibited lung colonization (FIG. 18B).

Figures 7F, 7G, 7H, 7I, 7J:
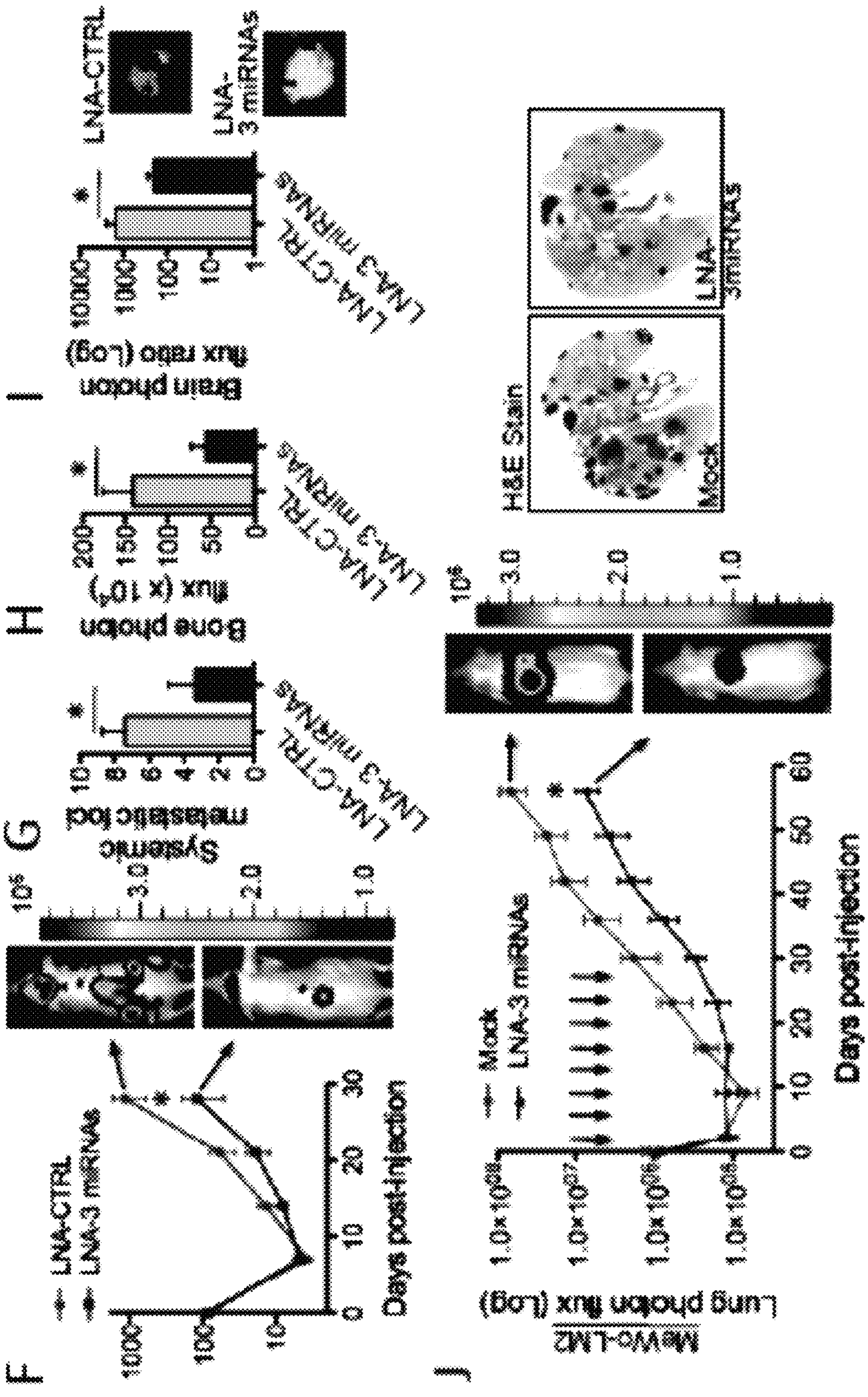

Next, it was examined whether combinatorial LNA-induced miRNA inhibition could suppress systemic melanoma metastasis to multiple distant organs. Indeed, intracardiac injection of highly metastatic melanoma cells pre-treated with a cocktail of LNAs targeting the three regulatory miRNAs revealed endogenous miR-199a-3p, miR-199a-5p, and miR-1908 to promote systemic melanoma metastasis (FIG. 7F). Combinatorial LNA-mediated inhibition of the three miRNAs lead to a reduction in the number of systemic metastatic foci (FIG. 7G) in distal sites such as the brain and bone (FIGS. 7H-I).

Figure 7K:
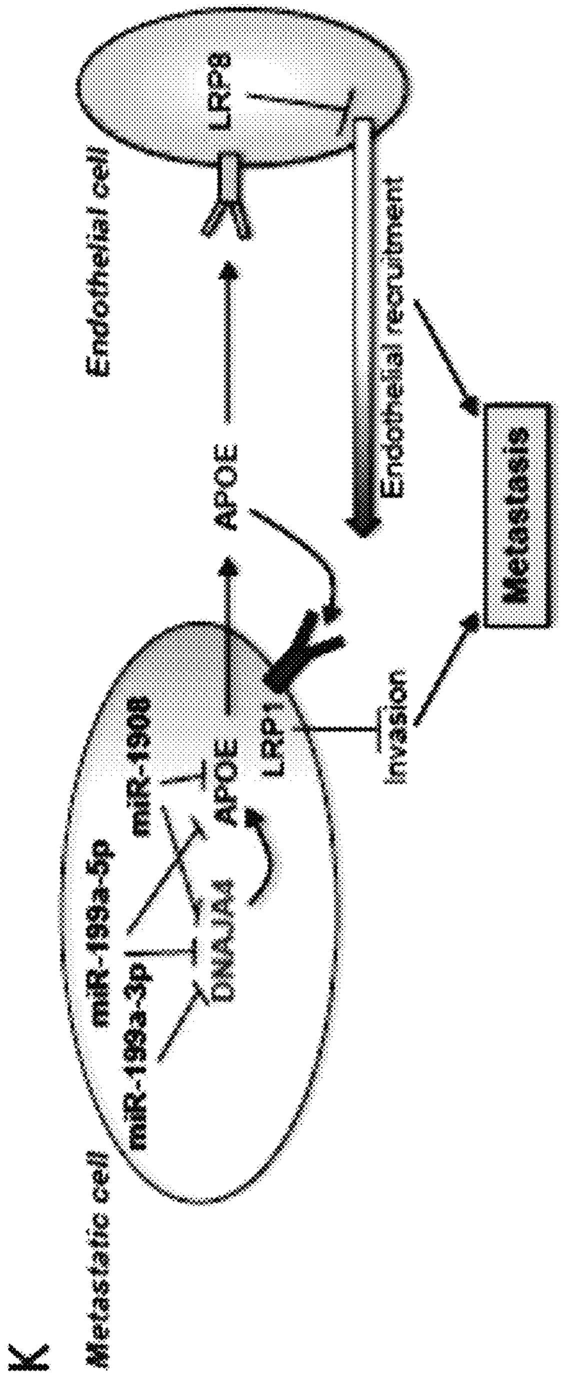

Further assays were carried out to examine the therapeutic efficacy of systemically administered in vivo-optimized LNAs in melanoma metastasis prevention. To this end, highly metastatic MeWo-LM2 cells were injected into mice. The following day, mice were intravenously treated with LNAs targeting miR-199a-3p, miR-199a-5p, and miR-1908 at a low total dose (12.5 mg/kg) on a bi-weekly basis for four weeks. Notably, combinatorial LNA treatment reduced lung colonization by 9-fold (FIG. 7J, P=0.031) without any apparent signs of toxicity (FIG. 18C). Taken together, the above findings reveal a novel miRNA-dependent regulatory network that converges on ApoE signaling to control cell-autonomous and non-cell-autonomous features of melanoma metastatic progression (FIG. 7K). The above basic studies have identified a set of miRNAs with powerful prognostic and therapeutic potential in the clinical management of melanoma.

Figures 8A, 8B, 8C, 8D, 8E:
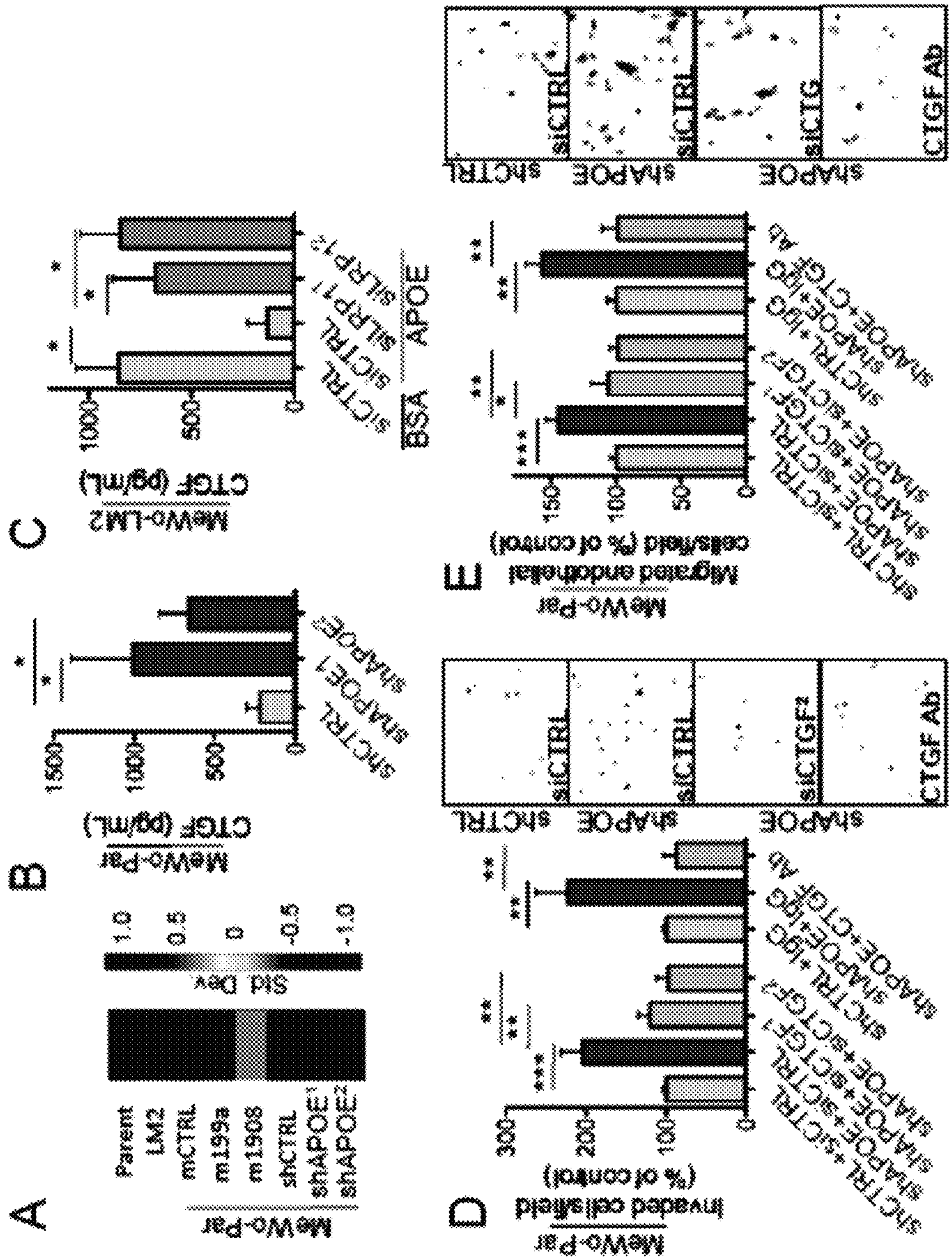
FIGS. 8A, 8B, 8C, 8D and 8E. MiRNA-dependent targeting of ApoE/LRP1 signaling promotes cancer cell invasion and endothelial recruitment through CTGF induction. (8A) A heat-map of variance-normalized CTGF expression levels, determined by qRT-PCR analysis, in (1) MeWo parental and MeWo-LM2 cells, (2) MeWo parental cells over-expressing miR-199a, miR-1908, or a control hairpin, and (3) MeWo parental cells transduced with short hairpins targeting ApoE or a control sequence. Color-map indicates the standard deviations change from the mean. (8B) CTGF levels in conditioned media from MeWo parental cells with ApoE knock-down determined by ELISA. n=6; p-values based on a one-sided student's t-test. (8C) CTGF levels, quantified by ELISA, in conditioned media from highly metastatic MeWo-LM2 cells treated with recombinant ApoE in the setting of LRP1 knock-down or a control knock-down. n=3-4; p-values based on a one-sided student's t-test. (8D-8E) Parental MeWo cells with shRNA-induced ApoE knock-down were (1) transfected with independent siRNAs targeting CTGF or a control sequence or (2) incubated in the presence of a CTGF neutralizing antibody (20 μg/mL) or an IgG control antibody (20 μg/mL), and the cells were subjected to cell invasion (8D) and endothelial recruitment (8E) assays. n=6-8; p-values based on a one-sided student's t-test; scale bar indicates 100 μM. All data are represented as mean±SEM.

Example 9 miRNA-Dependent Targeting of Apoe LRP1 Signaling Promotes Cancer Cell Invasion and Endothelial Recruitment Through CTGF Induction In this example, Connective Tissue Growth Factor (CTGF) was identified as a downstream mediator of ApoE/LRP1 signaling in cancer cell invasion and endothelial recruitment. CTGF expression level, as determined by qRT-PCR analysis and ELISA, is mediated by ApoE/LRP1 signaling (FIGS. 8A, 8B, and 8C). Additionally, ApoE/LRP1 regulated cancer cell invasion and endothelial recruitment are mediated by CTGF (FIG. 8D, 8E).

Figures 9A, 9B, 9C:
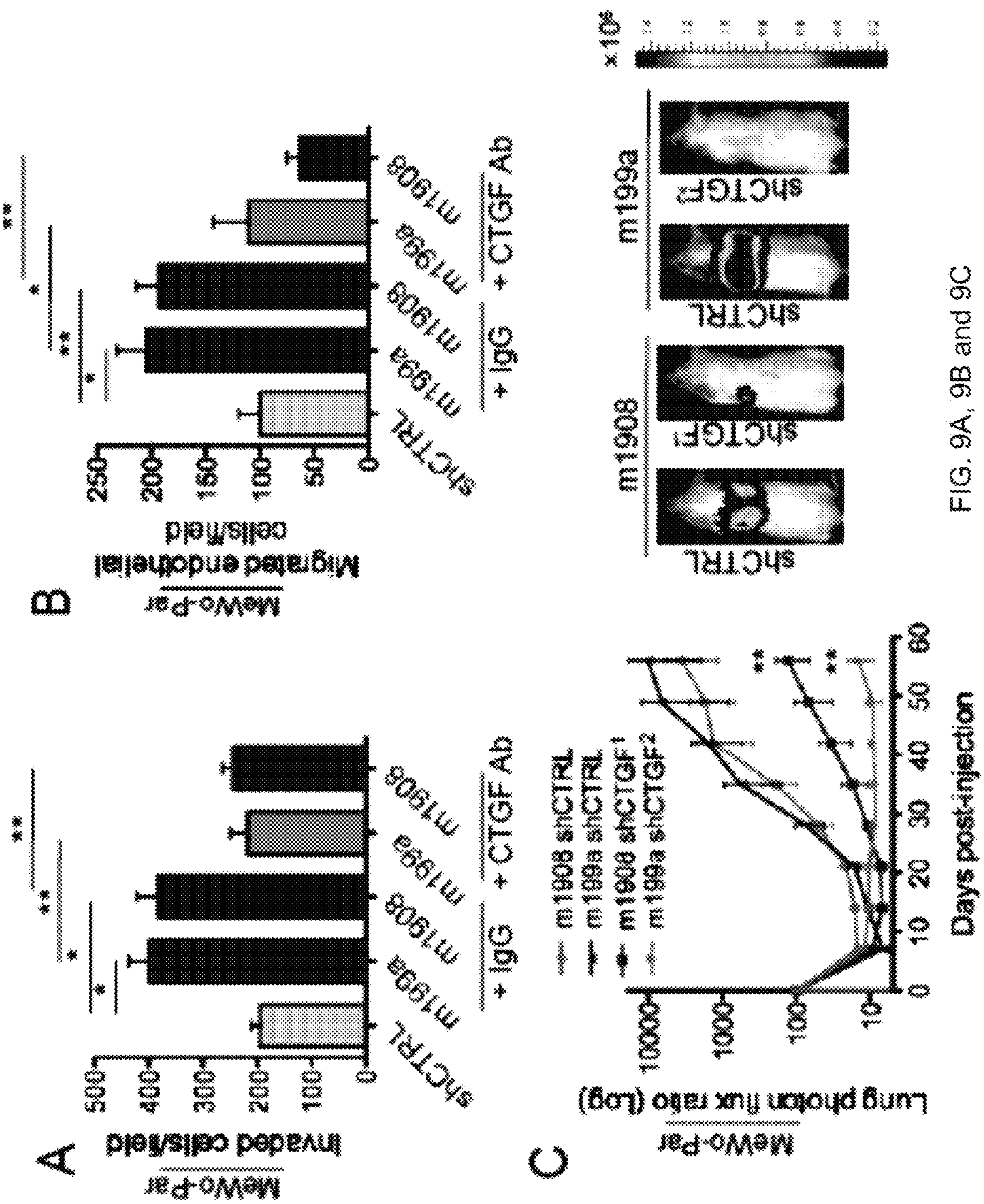
FIGS. 9A, 9B and 9C. CTGF mediates miRNA-dependent metastatic invasion, endothelial recruitment, and colonization. (9A) 1×105 parental MeWo cells expressing a control hairpin or over-expressing miR-199a or miR-1908 were subjected to a trans-well cell invasion assay in the presence of a blocking antibody targeting CTGF (20 μg/mL) or a control IgG antibody (20 μg/mL) as indicated in the figure. n=4-10; p-values based on a one-sided student's t-test. All data are represented as mean±SEM. (9B) Endothelial recruitment by parental MeWo cells expressing a control hairpin or over-expressing miR-199a or miR-1908. At the beginning of the assay, a neutralizing antibody targeting CTGF (20 μg/mL) or a control IgG antibody (20 μg/mL) were added to endothelial cells as indicated, and 1× 105 endothelial cells were allowed to migrate towards 5×104 cancer cells in a trans-well migration assay. n=3-8; p-values based on a one-sided student's t-test. (9C) Bioluminescence imaging of lung metastasis by 5×104 parental MeWo cells knocked down for CTGF in the setting of miR-199a or miR-1908 over-expression. n=5-6; p-values obtained using a one-way Mann-Whitney t-test. All data are represented as mean±SEM.

Example 10 CTGF Mediates miRNA-Dependent Metastatic Invasion, Endothelial Recruitment, and Colonization In this Examiner, assays were carried out to investigate whether CTGF mediates miRNA-dependent invasion and endothelial recruitment. Briefly, trans-well cell invasion and endothelial recruitment assays were performed on parental MeWo cells over-expressing miR-199a or miR-1908 in the presence of a blocking antibody targeting CTGF. Indeed, it was found that mir-199a and mir-1908 dependent metastatic invasion and endothelial recruitment are mediated by CTGF (FIGS. 9A and 9B). In order to investigate whether in vivo melanoma metastasis (metastatic colonization) is mediated by CTGF, bioluminescence imaging was performed on lung metastasis by 5×104 parental MeWo cells knocked down for CTGF in the setting of miR-199a or miR-1908 over-expression. Knock-down of CTGF in this setting resulted in significant reduction of in vivo melanoma metastasis (FIG. 9C).

Figures 10A, 10B, 10C, 10D, 10E:
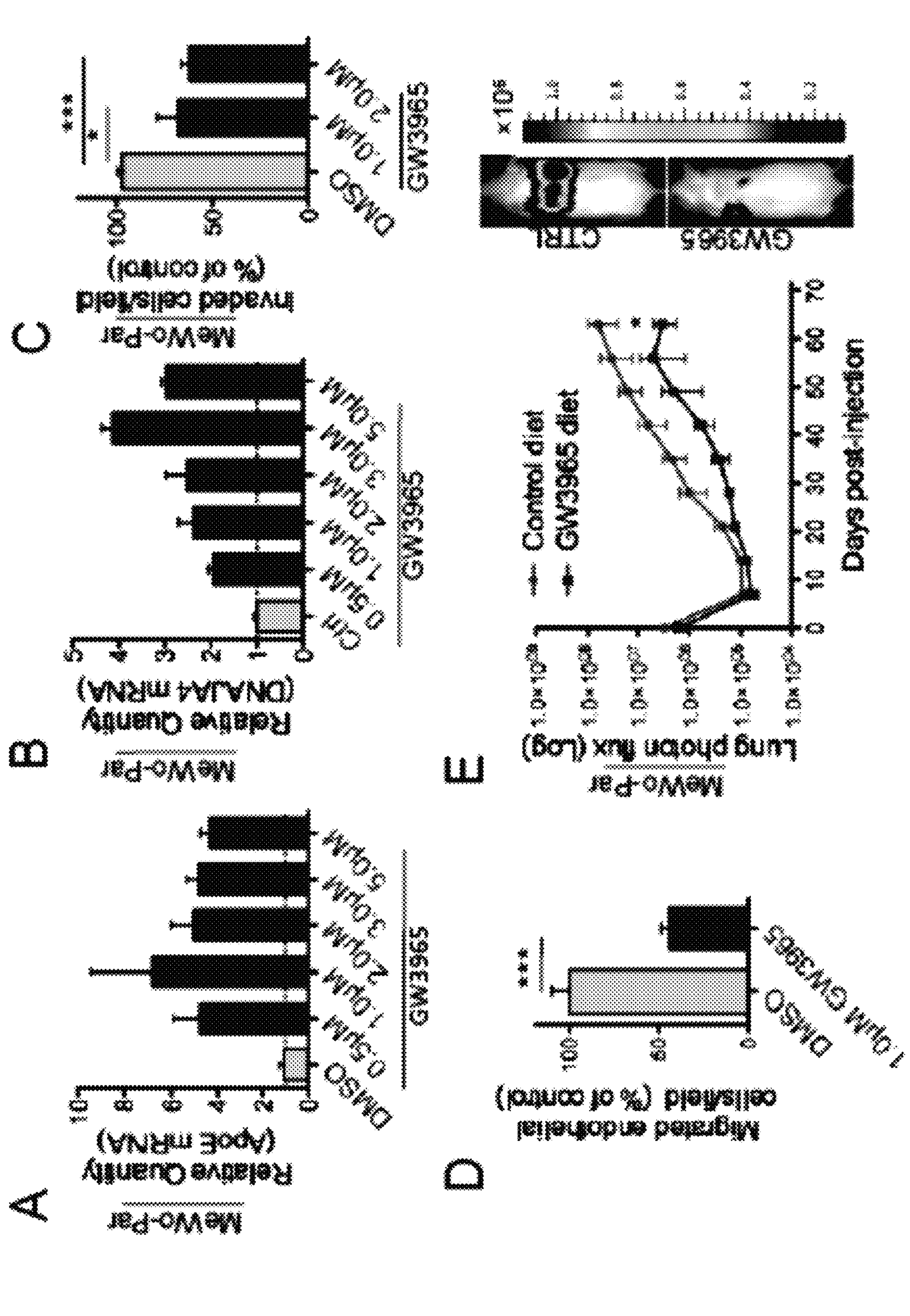
FIGS. 10A, 10B, 10C, 10D and 10E. Treatment with the LXR agonist GW3965 elevates melanoma cell ApoE levels and suppresses cancer cell invasion, endothelial recruitment, and metastatic colonization. (10A-10B) Parental MeWo cells were incubated in the presence of DMSO or GW3965 at the indicated concentrations. After 48 hours, total RNA was extracted, and the levels of ApoE (10A) and DNAJA4 (10B) were determined by qRT-PCR. n=3. (10C) Cell invasion by 1× 105 parental MeWo cells pre-treated with GW3965 or DMSO for 48 hours. n=6-7. p-values based on a one-sided student's t-test. All data are represented as mean±SEM. (10D) Endothelial recruitment by 5×104 parental MeWo cells pre-treated with GW3965 or DMSO for 48 hours. n=6-7. p-values based on a one-sided student's t-test. (10E) Mice were fed with grain-based chow diet containing GW3965 (20 mg/kg) or a control diet. After 10 days, 4×104 parental MeWo cells were tail-vein injected into mice, and the mice were continuously fed with GW3965-containing chow or a control diet throughout the experiment. Lung colonization was assessed by bioluminescence imaging. n=5-6; p-values obtained using a one-way Mann-Whitney t-test All data are represented as mean±SEM.

Example 11 Treatment with LXR Agonist GW3965 Elevates Melanoma Cell ApoE and DNAJA4 Levels and Suppresses Cancer Cell Invasion, Endothelial Recruitment, and Metastatic Colonization Small molecule agonists of the Liver X Receptor (LXR) have previously been shown to increase Apo E levels. To investigate whether increasing Apo-E levels via LXR activation resulted in therapeutic benefit, assays were carried out to assess the effect of the LXR agonist GW3965 [chemical name: 3-[3-[N-(2-Chloro-3-trifluoromethylbenzyl)-(2,2-diphenylethyl)amino]propyloxy] phenylacetic acid hydrochloride) on Apo-E levels, tumor cell invasion, endothelial recruitment, and in vivo melanoma metastasis (FIG. 10). Incubation of parental MeWo cells in the presence of therapeutic concentrations of GW3965 increased expression of ApoE and DNAJA4 (FIGS. 10A and 10B). Pre-treatment of MeWO cells with GW3965 decreased tumor cell invasion (FIG. 10C) and endothelial recruitment (FIG. 10D). To test whether GW3965 could inhibit metastasis in vivo, mice were administered a grain-based chow diet containing GW3965 (20 mg/kg) or a control diet, and lung metastasis was assayed using bioluminescence after tail-vein injection of $4\times10^4$ parental MeWo cells into the mice (FIG. 10E). Oral administration of GW3965 to the mice in this fashion resulted in a significant reduction in in vivo melanoma metastasis (FIG. 10E).

Figures 11A, 11B:
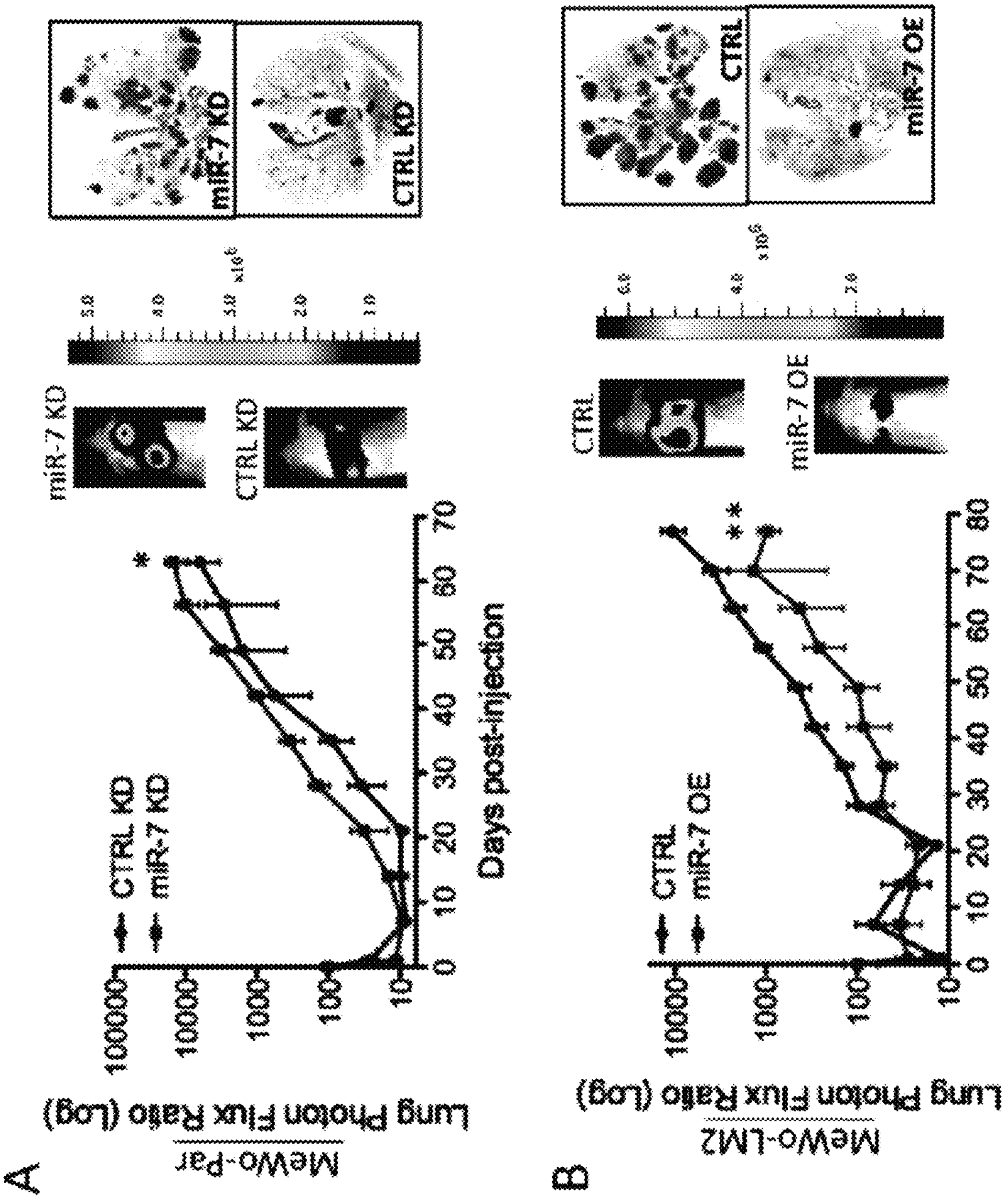
FIGS. 11A and 11B. Identification of miR-7 as an endogenous suppressor of melanoma metastasis. (11A) Bioluminescence imaging plot of lung metastatic colonization following intravenous injection of 4× 104 parental MeWo cells expressing a short hairpin (miR-Zip) inhibiting miR-7 (miR-7 KD). Lungs were extracted 63 days post-injection and H&E-stained. n=5. (11B). Lung metastasis by 4×104 LM2 cells over-expressing the precursor for miR-7 or a control hairpin. Lung colonization was monitored weekly by bioluminescence imaging, and lungs were extracted at day 77 post-injection. n=5. All data are represented as mean±SEM; p-values were determined using a one-way Mann-Whitney t-test. *p<0.05, **p<0.01.

Example 12 Identification of Mir-7 as an Endogenous Suppressor of Melanoma Metastasis In this example, miR-7 was identified as an endogenous suppressor of melanoma metastasis (FIG. 11). To test whether miR-7 suppresses melanoma metastasis in vivo, its expression was knocked down in parental MeWo cells using miR-Zip technology (FIG. 11A). Bioluminescence imaging plot of lung metastatic colonization following intravenous injection of 4×104 parental MeWo cells expressing a short hairpin (miR-Zip) inhibitor of miR-7 (miR-7 KD) significantly increased lung metastasis in vivo (FIG. 11A). Conversely, overexpression of miR-7 in LM2 cells significantly reduced lung metastasis in vivo (FIG. 11B).

The complexity of cancer requires the application of systematic analyses (Pe'er and Hacohen, 2011). Via a systematic global approach, a cooperative network of miRNAs was uncovered. The miRNAs are i) upregulated in highly metastatic human melanoma cells, ii) required and sufficient for metastatic colonization and angiogenesis in melanoma, and iii) robust pathologic predictors of human melanoma metastatic relapse. Through a transcriptomic-based and biologically guided target identification approach, miR-1908, miR-199a-3p, and miR-199a-5p were found to convergently target the heat shock factor DNAJA4 and the metabolic gene ApoE. The requirement of each individual miRNA for metastasis indicates that these three convergent miRNAs are non-redundant in promoting melanoma metastasis, while the robust synergistic metastasis suppression achieved by combinatorial miRNA inhibition reveals functional cooperativity between these miRNAs, presumably achieved through maximal silencing of ApoE and DNAJA4. The identification of ApoE as a gene negatively regulated by three metastasis promoter miRNAs, positively regulated by a metastasis suppressor gene (DNAJA4), and silenced in clinical metastasis samples highlights the significance of this gene as a suppressor of melanoma progression.

Figures 19A, 19B, 19C:
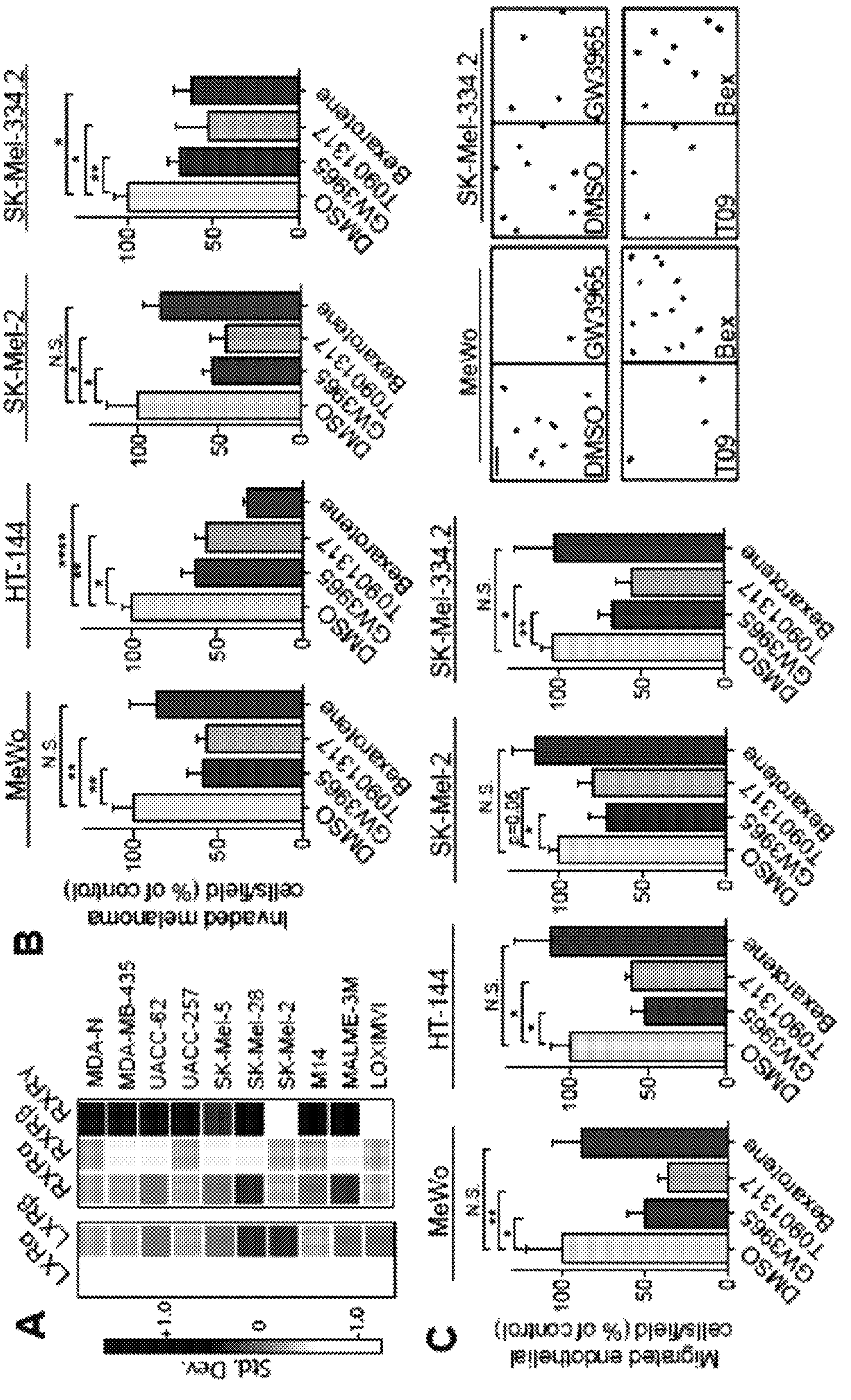
FIGS. 19A, 19B, 19C, 19D, 19E, 19F and 19G. Activation of LXRβ Signaling Suppresses Melanoma Cell Invasion and Endothelial Recruitment. (19A) Heat-map depicting microarray-based expression levels of LXR and RXR isoforms in the NCI-60 melanoma cell line collection. The heat map for these genes is extracted from the larger nuclear hormone receptor family heat map (FIG. 20). Color-map key indicates the change in standard deviations for the expression value of each receptor relative to the average expression value of all microarray-profiled genes (>39,000 transcript variants) in each cell line. (19B) Cell invasion by 1× 105 MeWo, 5×104 HT-144, 5×105 SK-Mel-2, and 5×104 SK-Mel-334.2 human melanoma cells. Cells were treated with DMSO, GW3965, T0901317, or Bexarotene at 1 μM for 72 hours and subjected to a trans-well matrigel invasion assay. n=4-8. (19C) 5×104 MeWo, HT-144, SK-Mel-2, and SK-Mel-334.2 human melanoma cells were tested for their ability to recruit 1×105 endothelial cells in a trans-well migration assay, following treatment of the melanoma cells with DMSO, GW3965, T0901317, or Bexarotene at 1 μM for 72 hours. n=4-8. (19D-19E) 1×105 MeWo (19D) and 1×105 HT-144 (19E) melanoma cells expressing a control shRNA or shRNAs targeting LXRα or LXRβ were subjected to the cell invasion assay following treatment of the cells with DMSO, GW3965, or T0901317 at 1 μM for 72 hours. n=4-12. (19F-19G) 5×104 MeWo (19F) and 5×104 HT-144 (19G) cells, transduced with lentiviral shRNAs targeting LXRα or LXRβ or a control shRNA, were treated with DMSO, GW3965, or T0901317 at 1 μM for 72 hours and tested for their ability to recruit 1×105 endothelial cells in a trans-well migration assay. n=7-8. All data are represented as mean±SEM. Scale bar, 50 μm. *p<0.05, p<0.01, *p<0.001, ****p<0.0001.
Figures 19D, 19E, 19F, 19G:
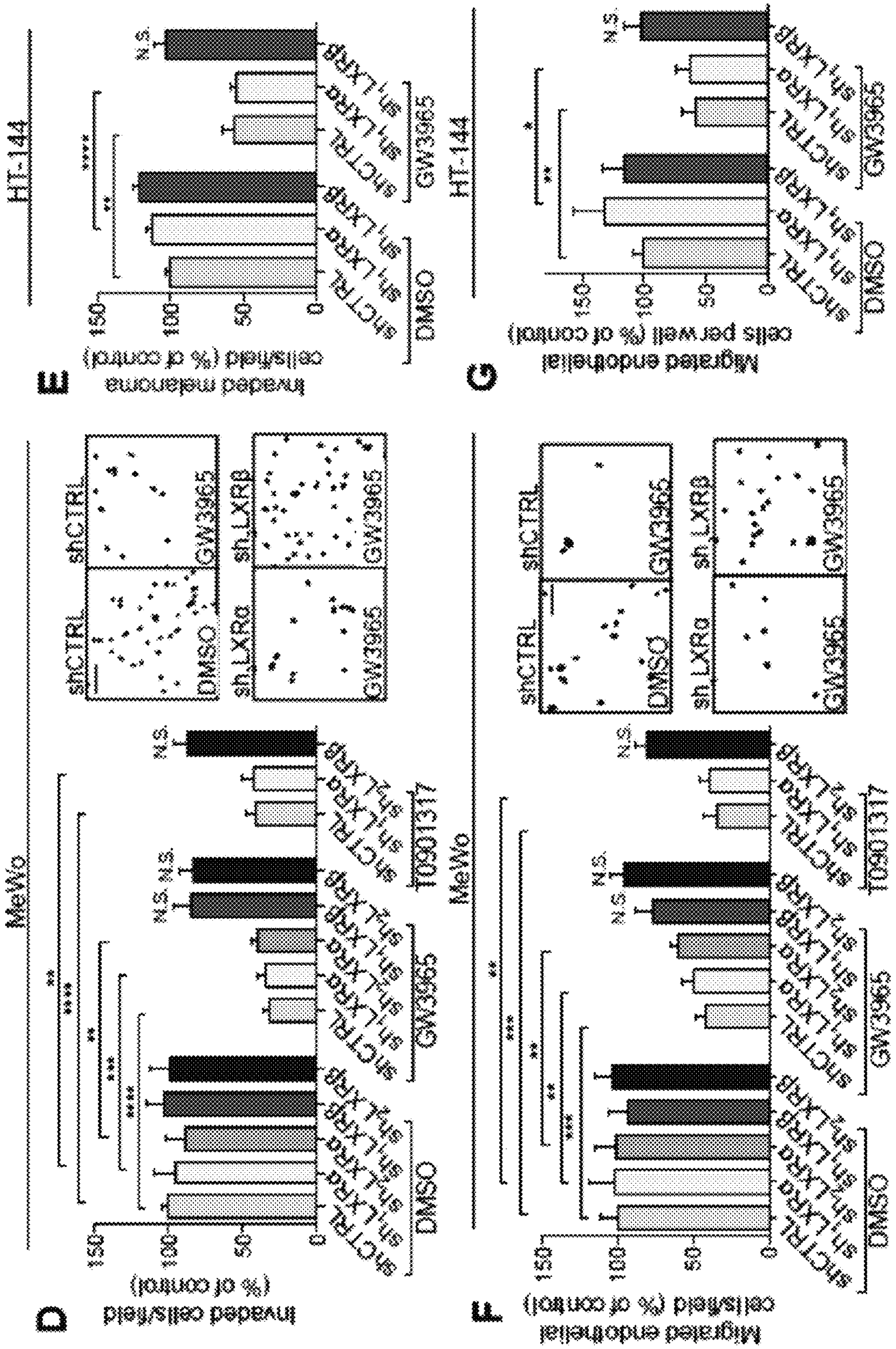
Figure 20A:
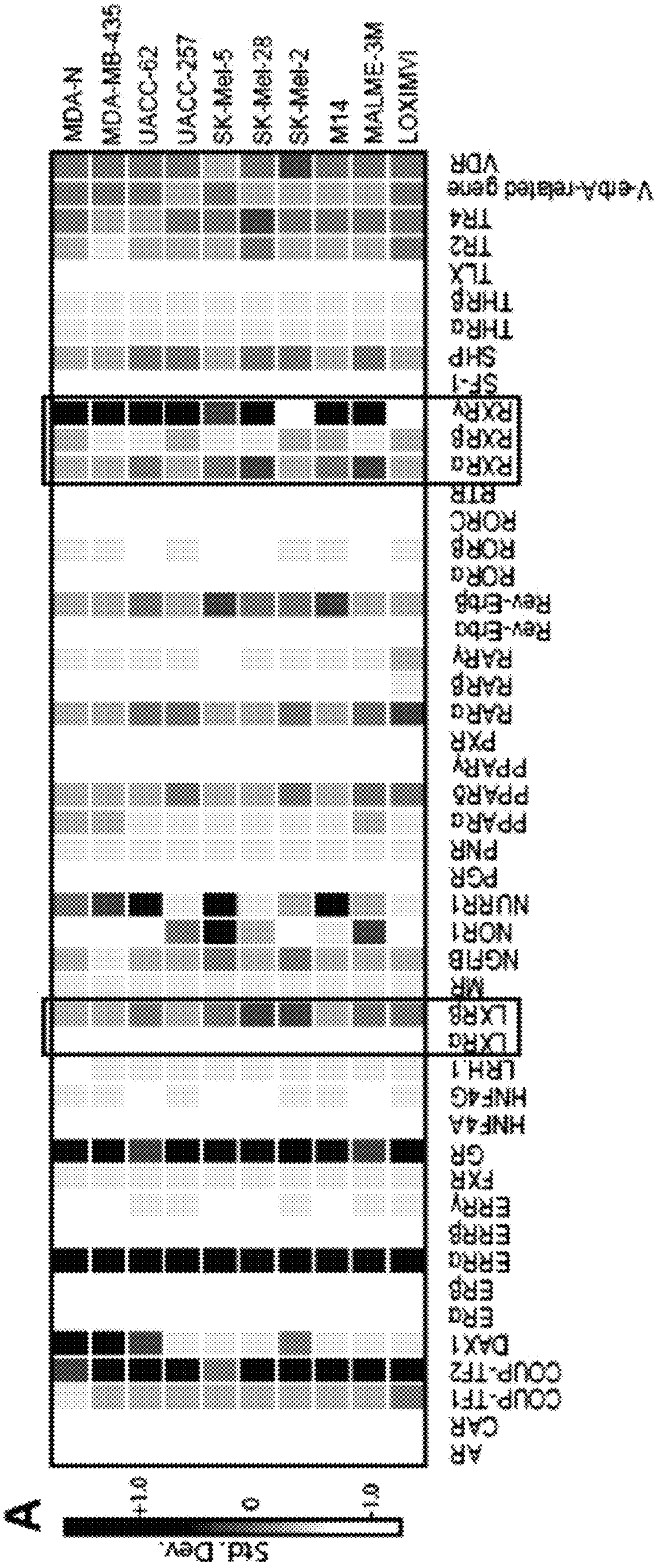
FIGS. 20A, 20B, 20C, 20D, 20E, 20F and 20G. Analysis of Nuclear Hormone Receptor Expression in Melanoma and Effects of LXR and RXR Agonists on In Vitro Cell Growth, Related to FIG. 19(A-G). (20A) Heat-map showing microarray-based expression levels of all nuclear hormone receptor family members across the NCI-60 collection of melanoma lines. The expression levels of each receptor is presented as the number of standard deviations below or above the average expression levels of all genes (>39,000 transcript variants) detected by the microarray in each respective cell line. (20B) 2.5×104 MeWo, HT-144, or SK-Mel-334.2 human melanoma cells were seeded in 6-well plates and cultured in the presence of DMSO, GW3965, T0901317, or Bexarotene at 1 μM. Viable cells were counted on day 5 post-seeding. n=3-6. (20C) 2.5×104 MeWo, HT-144, or SK-Mel-334.2 cells were plated in triplicates and incubated in media containing DMSO, GW3965, T0901317, or Bexarotene at 1 μM for 5 days, after which the number of dead cells was quantified using trypan blue dead cell stain. n=3. (20D-20G) Relative expression of LXRα and LXRβ, determined by qRT-PCR, in MeWo (20D, 20E) and HT-144 (20F, 20G) human melanoma cells expressing a control shRNA or shRNAs targeting LXRα or LXRβ. All data are represented as mean±SEM.

Example 13 Identification of LXRβ Signaling as a Novel Therapeutic Target in Melanoma To identify nuclear hormone receptors that show broad expression in melanoma, we examined the expression levels of all nuclear hormone receptor family members across the NCI-60 collection of human melanoma cell lines. Several receptors exhibited stable expression across multiple melanoma lines, suggesting that they could represent novel potential targets in melanoma (FIGS. 19A and 20A). Notably, out of these, liver-X receptors (LXRs) were previously shown to enhance ApoE transcription in adipocytes and macrophages (Laffitte et al., 2001), while pharmacologic activation of RXRs was found to drive ApoE expression in pre-clinical Alzheimer's models (Cramer et al., 2012).

Given the recently uncovered metastasis-suppressive role of ApoE in melanoma (Pencheva et al., 2012), the ubiquitous basal expression of LXRβ and RXRα in melanoma, and the availability of pharmacologic agents to therapeutically activate LXRs and RXRs, we investigated whether activation of LXRs or RXRs in melanoma cells might inhibit melanoma progression phenotypes. In light of the established roles of nuclear hormone receptors such as ER and AR in regulating breast and prostate cancer cell proliferation, we first examined whether pharmacologic agonism of LXRs or RXRs in melanoma cells affects in vitro cell growth.

Figures 20B, 20C, 20D, 20E, 20F, 20G:
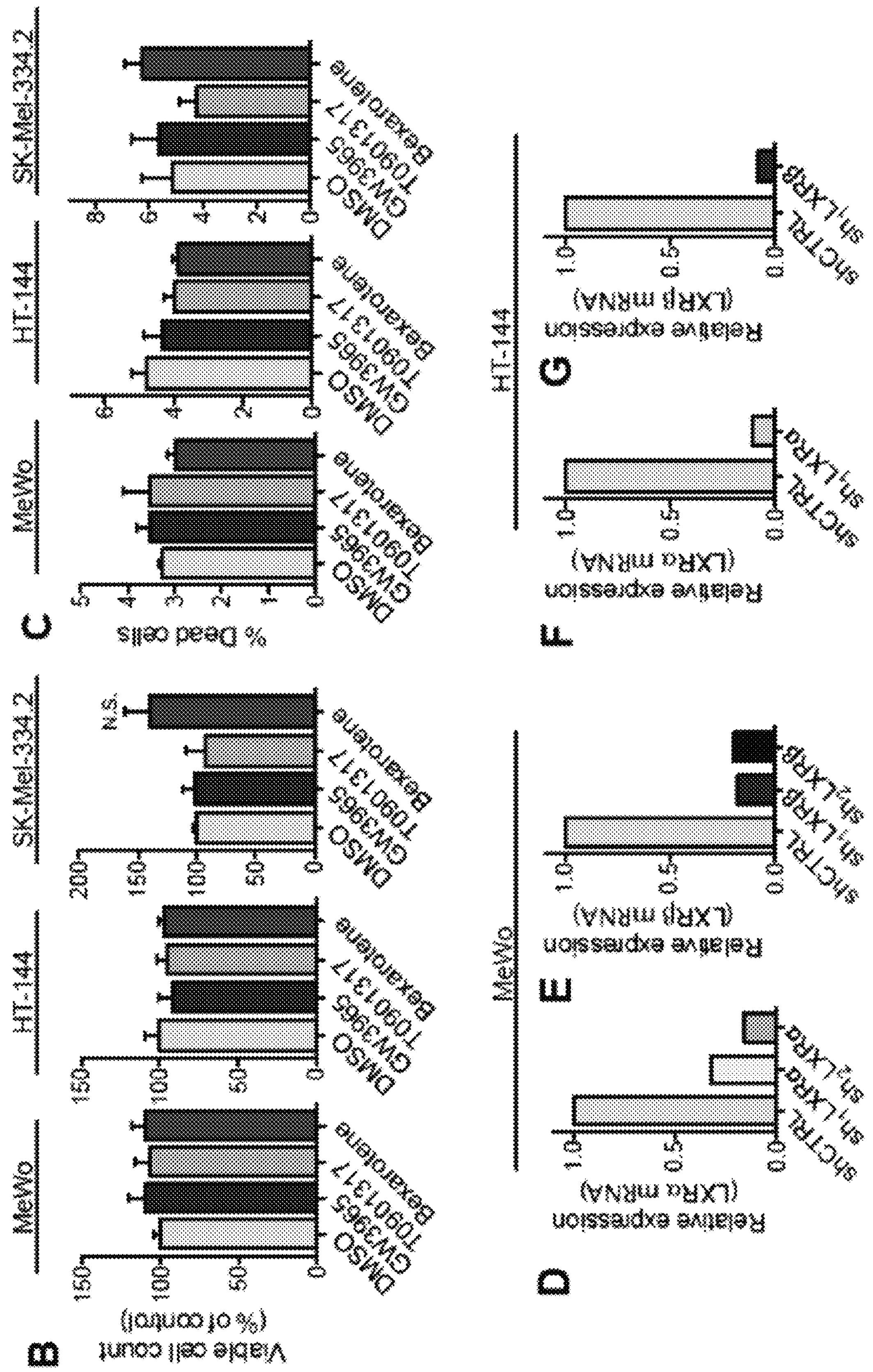

Treatment of melanoma cells with two structurally-distinct LXR agonists, GW3965 2 or T0901317 1, or the RXR agonist bexarotene did not affect cell proliferation or cell viability rates (FIG. 20B-C). We next assessed the effects of LXR or RXR activation on cell invasion and endothelial recruitment-phenotypes displayed by metastatic melanoma and metastatic breast cancer populations (Pencheva et al., 2012; Png et al., 2012). Treatment of the mutationally diverse MeWo (B-Raf/N-Ras wild-type), HT-144 (B-Raf mutant), and SK-Mel-2 (N-Ras mutant) human melanoma lines as well as the SK-Mel-334.2 (B-Raf mutant) primary human melanoma line with GW3965 2 or T0901317 1 consistently suppressed the ability of melanoma cells to invade through matrigel and to recruit endothelial cells in trans-well assays (FIG. 19B-C). In comparison, treatment with bexarotene suppressed invasion only in half of the melanoma lines tested and it did not significantly affect the endothelial recruitment phenotype (FIGS. 19B-C).

Given the superiority of LXR over RXR agonism in broadly inhibiting both cell invasion and endothelial recruitment across multiple melanoma lines, we investigated the requirement for LXR signaling in mediating the suppressive effects of LXR agonists. Knockdown of melanoma LXRβ, but not LXRα, abrogated the ability of GW3965 2 and T0901317 1 to suppress invasion and endothelial recruitment (FIG. 19D-G and FIGS. 20D-G), revealing melanoma-cell LXRβ to be the functional target of LXR agonists in eliciting the suppression of these in vitro phenotypes. Our molecular findings are consistent with LXRβ being the predominant LXR isoform expressed by melanoma cells (FIG. 19A, $P<0.0001$).

The ubiquitous basal expression of LXRβ in melanoma is likely reflective of the general role that LXRs play in controlling lipid transport, synthesis, and catabolism (Calkin and Tontonoz, 2013). While such stable LXRβ expression would be key to maintaining melanoma cell metabolism and growth, it also makes LXR signaling an attractive candidate for broad-spectrum therapeutic targeting in melanoma.

Example 14 Therapeutic Delivery of LXR Agonists Suppresses Melanoma Tumor Growth LXR agonists were originally developed as oral drug candidates for the purpose of cholesterol lowering in patients with dyslipidemia and atherosclerosis (Collins et al., 2002; Joseph and Tontonoz, 2003). These compounds were abandoned clinically secondary to their inability to reduce lipid levels in large-animal pre-clinical models (Groot et al., 2005).

Given the robust ability of GW3965 2 and T0901317 1 to suppress in vitro melanoma progression phenotypes (FIG. 19B-C), we investigated whether therapeutic LXR activation could be utilized for the treatment of melanoma. Indeed, oral administration of GW3965 2 or T0901317 1 at low doses (20 mg/kg), subsequent to formation of subcutaneous tumors measuring 5-10 $mm^3$ in volume, suppressed tumor growth by the aggressive B16F10 mouse melanoma cells in an immunocompetent model by 67% and 61%, respectively (FIG. 21A-B). Administration of a higher LXR agonist dose (100 mg/kg) led to an 80% reduction in tumor growth (FIG. 21A), consistent with dose-dependent suppressive effects.

Oral administration of GW3965 2 also robustly suppressed tumor growth by the MeWo (70% inhibition) and SK-Mel-2 (49% inhibition) human melanoma cell lines, as well as the SK-Mel-334.2 primary human melanoma line (73% inhibition) (FIG. 21C-E and FIG. 22A).

Encouraged by the robust tumor-suppressive impact of LXR agonists on small tumors (5-10 mm3) (FIG. 21A-E), we next investigated whether LXR activation therapy could inhibit the growth of large (~150 mm3) tumors.

We found that treatment with GW3965 2 led to a roughly 50% reduction in the growth of established large B16F10 tumors (FIG. 21F). Importantly, therapeutic delivery of GW3965 2 subsequent to tumor establishment substantially prolonged the overall survival time of immunocompetent mice injected with mouse B16F10 cells, immunocompromised mice bearing tumor xeongrafts derived from the human MeWo established melanoma line, as well as the SK-Mel.334-2 primary human melanoma line (FIG. 21G-I). These findings are consistent with broad-spectrum responsiveness to LXR activation therapy across melanotic and amelanotic established melanoma tumors of diverse mutational subtypes: B-Raf and N-Ras wild-type (B16F10 and MeWo; FIG. 21A-C), B-Raf mutant (SK-Mel-334.2; FIG. 21D), and N-Ras mutant (SK-Mel-2; FIG. 21E).

We next sought to determine the cell biological phenotypes regulated by LXR agonists in suppressing tumor growth. Consistent with the inhibitory effects of GW3965 2 on endothelial recruitment by melanoma cells in vitro, GW3965 2 administration led to a roughly 2-fold reduction in the endothelial cell content of tumors (FIG. 21J). This effect was accompanied by a modest decrease (23%) in the number of actively proliferating tumor cells in vivo (FIG. 21K) without a change in the number of apoptotic cells (FIG. 21L). These results suggest that, in addition to reducing local tumor invasion, LXR activation suppresses melanoma tumor growth primarily through inhibition of tumor angiogenesis with a resulting reduction in in vivo proliferation.

Figures 23A, 23B, 23C, 23D, 23E, 23F:
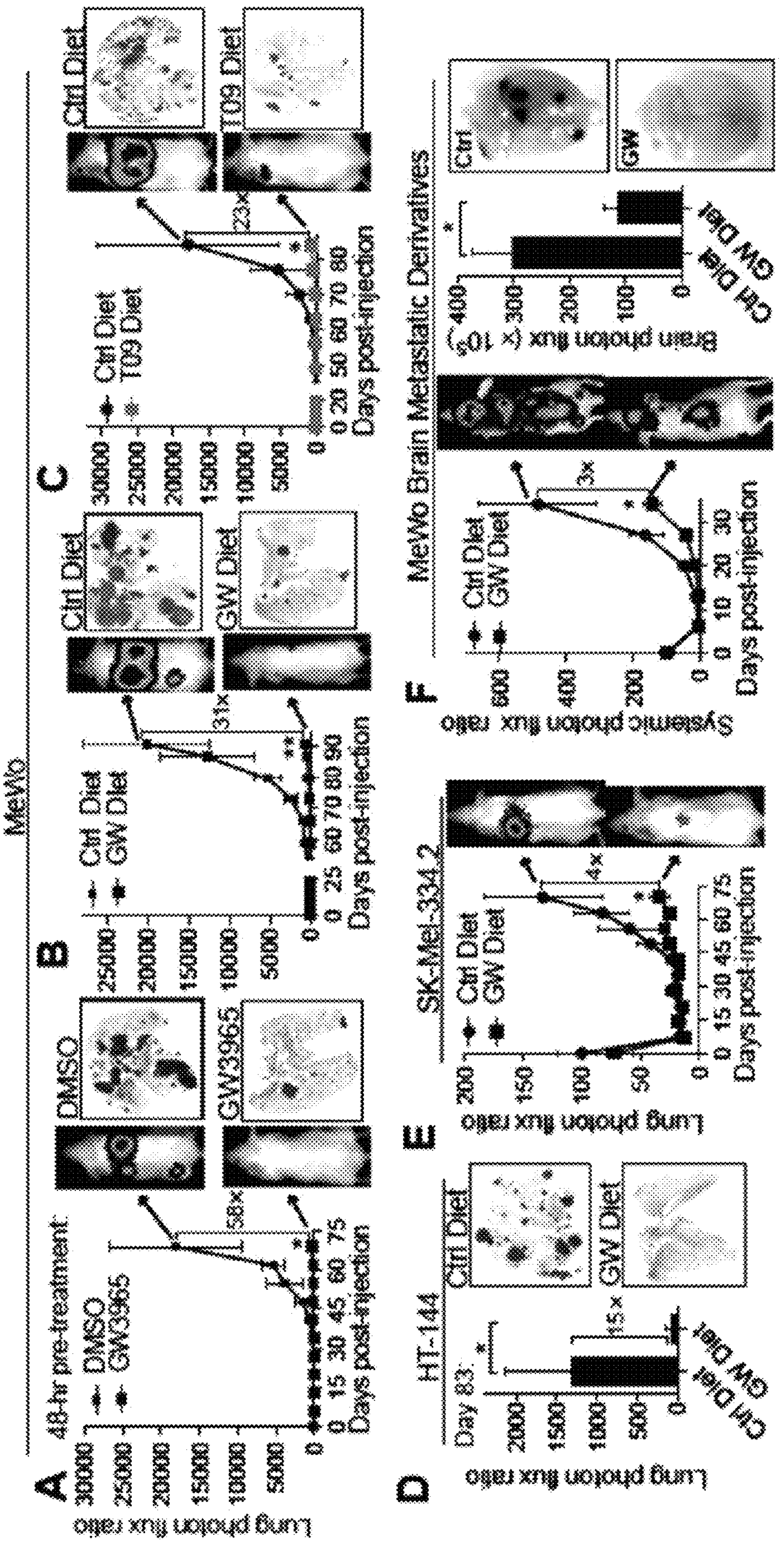

Example 15 LXR Agonism Suppresses Melanoma Metastasis to the Lung and Brain and Inhibits the Progression of Incipient Metastases The strong suppressive effects of LXR agonists on melanoma tumor growth motivated us to examine whether LXR activation could also suppress metastatic colonization by melanoma cells. To this end, pre-treatment of human MeWo melanoma cells with GW3965 2 led to a more than 50-fold reduction in their metastatic colonization capacity (FIG. 23A). In light of this dramatic inhibitory effect, we next assessed the ability of orally administered LXR agonists to suppress metastasis. Immunocompromised mice that were orally administered GW3965 2 or T0901317 1 experienced 31-fold and 23-fold respective reductions in lung metastatic colonization by human MeWo cells (FIG. 23B-C). Treatment with GW3965 2 also suppressed metastatic colonization by the HT-144 melanoma line (FIG. 23D) as well as the SK-Mel-334.2 primary melanoma line (FIG. 23E).

GW3965 2 is a lipophilic molecule that can efficiently cross the blood brain barrier and potently activate LXR signaling in the brain. Consistent with this, oral delivery of GW3965 2 was previously shown to improve amyloid plaque pathology and memory deficits in pre-clinical models of Alzheimer's disease (Jiang et al., 2008). We thus wondered whether LXR agonism could exhibit therapeutic activity in the suppression of melanoma brain metastasis—a dreaded melanoma outcome in dire need of effective therapies (Fonkem et al., 2012). Notably, oral administration of GW3965 2 inhibited both systemic dissemination and brain colonization following intracardiac injection of brain-metastatic melanoma cells derived from the MeWo parental line (FIG. 23F). These results reveal robust metastasis suppression by LXR activation therapy across multiple melanoma lines and in multiple distal organ metastatic sites.

Figures 23G, 23H, 23I, 23J, 23K:
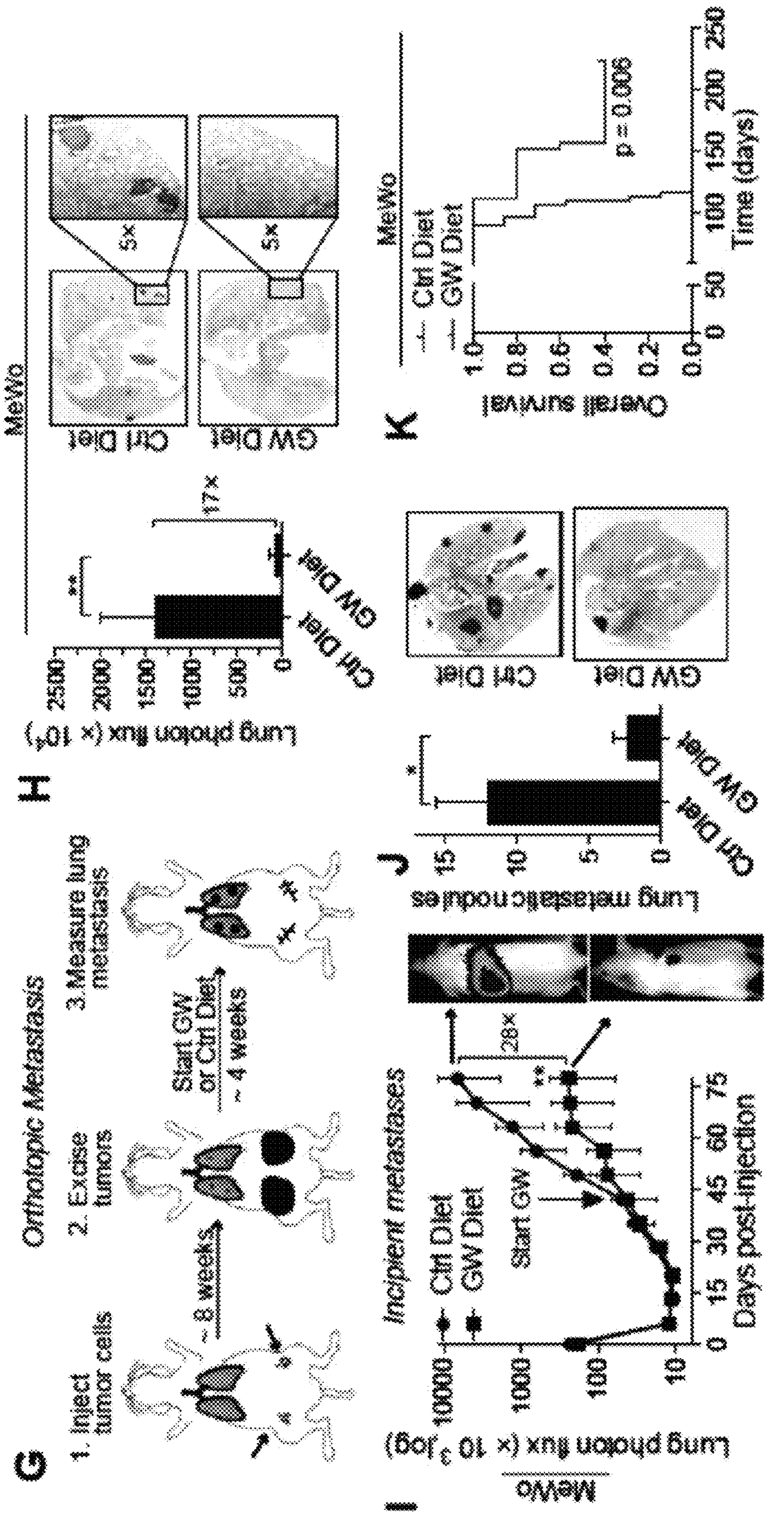

Encouraged by the robust effects observed in suppressing metastasis formation (FIG. 23A-F), we next sought to determine whether LXR activation therapy could halt the progression of melanoma cells that had already metastatically disseminated. We first tested the ability of GW3965 2 to reduce lung colonization by melanoma cells disseminating from an orthotopic site following removal of the primary tumor (FIG. 23G). Importantly, oral administration of GW3965 2 post-tumor excision inhibited lung colonization by disseminated melanoma cells by 17-fold (FIG. 23H). Remarkably, treatment of mice with GW3965 2 also dramatically suppressed (28-fold) colonization by incipient lung metastases that had progressed 8-fold from the baseline at seeding (FIG. 23I). Consistent with LXR activation inhibiting metastatic initiation, GW3965 2 treatment decreased the number of macroscopic metastatic nodules formed (FIG. 23J). Finally, treatment of mice with GW3965 2 in this 'adjuvant' pre-clinical context significantly prolonged their survival times following metastatic colonization (FIG. 23K).

Example 16 LXR Activation Reduces Melanoma Progression and Metastasis in a Genetically-Driven Mouse Model of Melanoma Roughly 60% of human melanoma tumors are marked by activating mutations in the Braf oncogene, with one single amino acid variant, B-RafV600E, being the predominant mutation found (Davies et al., 2002). Nearly 20% of melanomas exhibit activating mutations in B-Raf with concurrent silencing of the Pten tumor-suppressor, which drives progression to a malignant melanoma state (Tsao et al., 2004; Chin et al., 2006). Recently, Tyrosinase (Tyr)-driven conditional B-Raf activation and Pten loss were shown to genetically cooperate in driving mouse melanoma progression (Dankort et al., 2009).

To determine whether LXR activation could suppress melanoma progression in this genetically-initiated model, we induced melanomas in Tyr::CreER; B-RafV600E/+; Ptenlox/+ and Tyr::CreER; B-RafV600E/+; Ptenlox/lox mice by intraperitoneal administration of 4-hydroxytamoxifen (4-HT). Notably, oral administration of GW3965 2 following melanoma initiation attenuated tumor progression and significantly extended the overall survival times of both PTEN heterozygous Tyr::CreER; B-RafV600E/+; Ptenlox/+ and PTEN homozygous Tyr::CreER; B-RafV600E/+; Ptenlox/lox mice (FIG. 24A-B and FIG. 25A-B). Next, we examined the ability of GW3965 2 to suppress melanoma metastasis in this genetic context. While we did not detect macroscopic metastases in the lungs or brains of 4-HT-treated Tyr::CreER; B-Raf$^{V600E/+}$; Pten$^{lox/lox}$ control mice, we consistently observed melanoma metastases to the salivary gland lymph nodes. Importantly, Tyr::CreER; B-Raf$^{V600E/+}$; Pten$^{lox/lox}$ mice treated with GW3965 2 exhibited a decrease in the number of lymphatic metastases detected post-mortem (FIG. 24C). These findings indicate that LXR activation inhibits orthotopic metastasis in a genetically-driven melanoma model, in addition to its suppressive effects on primary melanoma tumor progression.

The cooperativity between B-Raf activation and Pten loss in driving melanoma progression can be further enhanced by inactivation of CDKN2A, a cell cycle regulator frequently mutated in familial melanomas (Hussussian et al., 1994; Kamb et al., 1994). We thus examined the effect of LXR activation on B-Raf$^{V600E/+}$; Pten$^{-/-}$; CDKN2A$^{-/-}$ melanomas, allowing us to test the therapeutic efficacy of LXR agonism in a more aggressive genetically-driven melanoma progression model. Importantly, therapeutic delivery of GW3965 2 robustly inhibited tumor growth and lung metastasis by B-Raf$^{V600E/+}$; Pten$^{-/-}$; CDKN2A$^{-/-}$ primary mouse melanoma cells injected into syngeneic immunocompetent mice and extended the overall survival of mice bearing B-Raf$^{V600E/+}$; Pten$^{-/-}$; CDKN2A$^{-/-}$ melanoma burden (FIG. 24D-F). Taken together, the robust suppression of melanoma progression across independent xenograft and genetically-induced immunocompetent melanoma mouse models that exhibit the diverse mutational profiles of human melanomas motivates the clinical testing of LXR activation therapy.

Example 17 Pharmacologic Activation of LXRβ Suppresses Melanoma Phenotypes by Transcriptionally Inducing Melanoma-Cell ApoE Expression We next sought to determine the downstream molecular target of LXRβ that mediates suppression of melanoma progression. To this end, we transcriptomically profiled human MeWo melanoma cells treated with the LXR agonist GW3965 2.

Figures 27A, 27B, 27C, 27D, 27E, 27F:
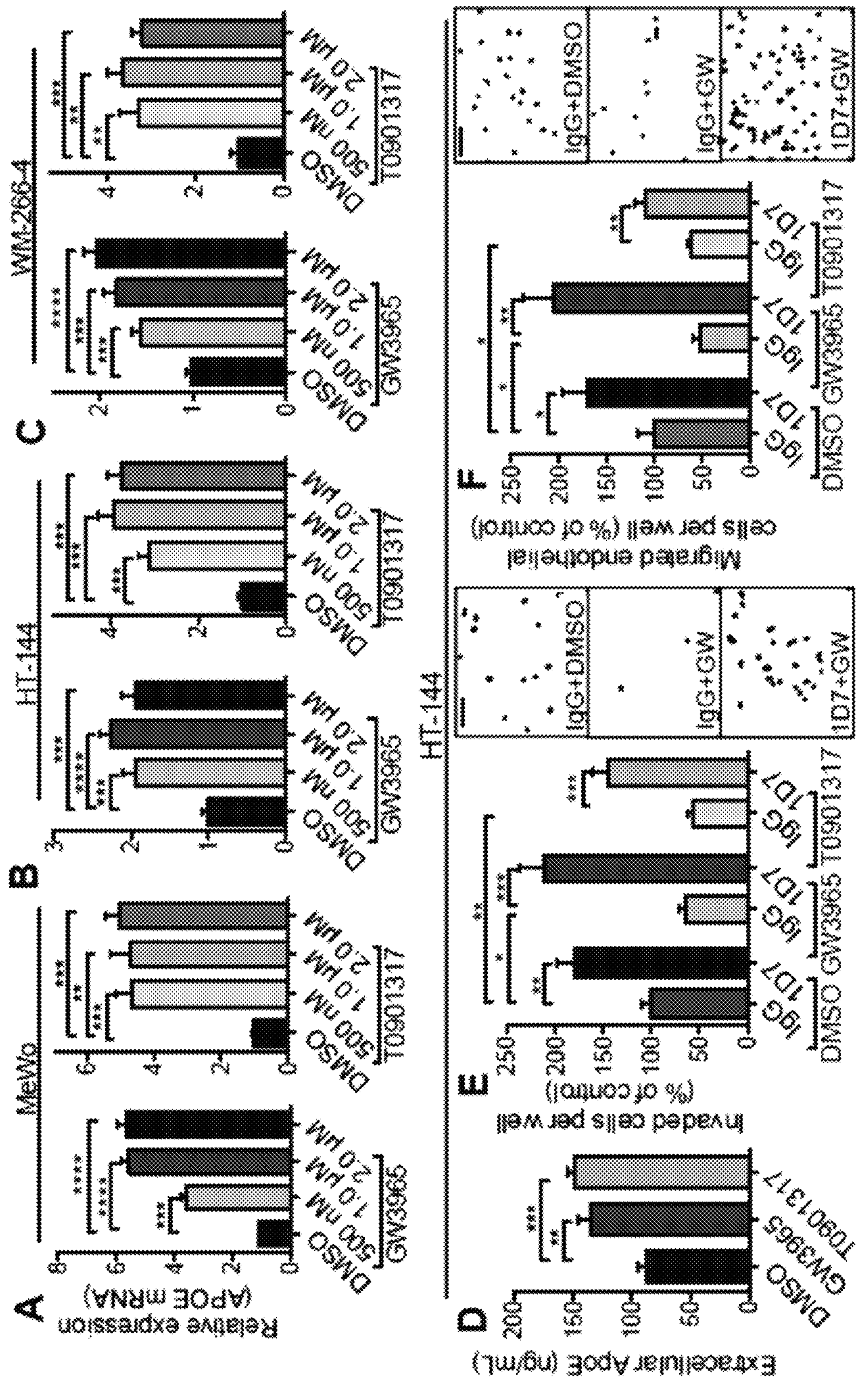

Out of the 365 genes that were significantly induced in response to LXR activation, we identified ApoE, a previously validated transcriptional target of LXRs in macrophages and adipocytes (Laffitte et al., 2001), as the top upregulated secreted factor in melanoma cells (FIG. 26). Quantitative real-time PCR (qRT-PCR) validation revealed robust upregulation of ApoE transcript expression following treatment with independent LXR agonists across multiple human melanoma lines (FIG. 27A-C).

Figures 28A, 28B, 28C, 28D, 28E, 28F, 28G:
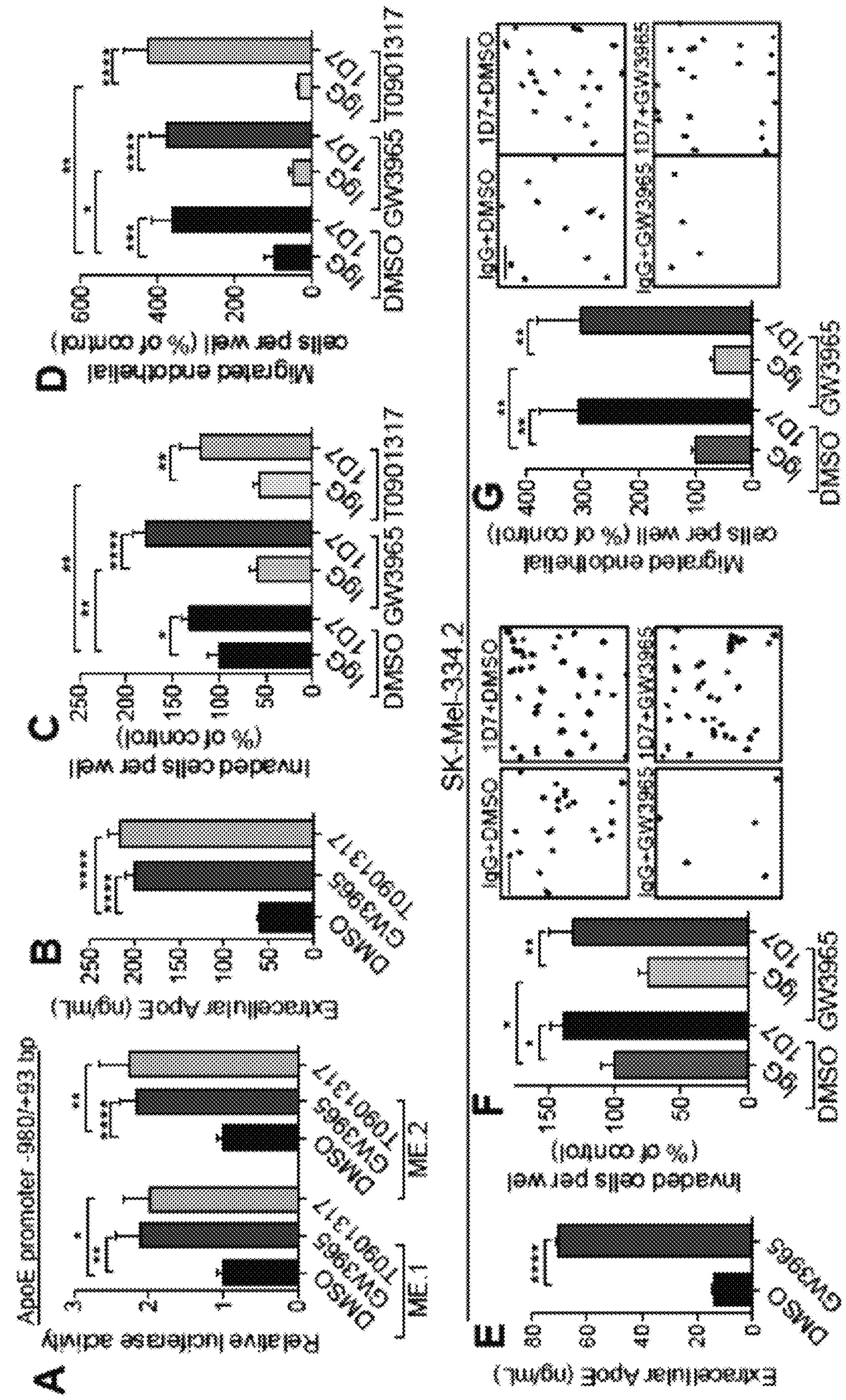
Figures 28H, 28I:
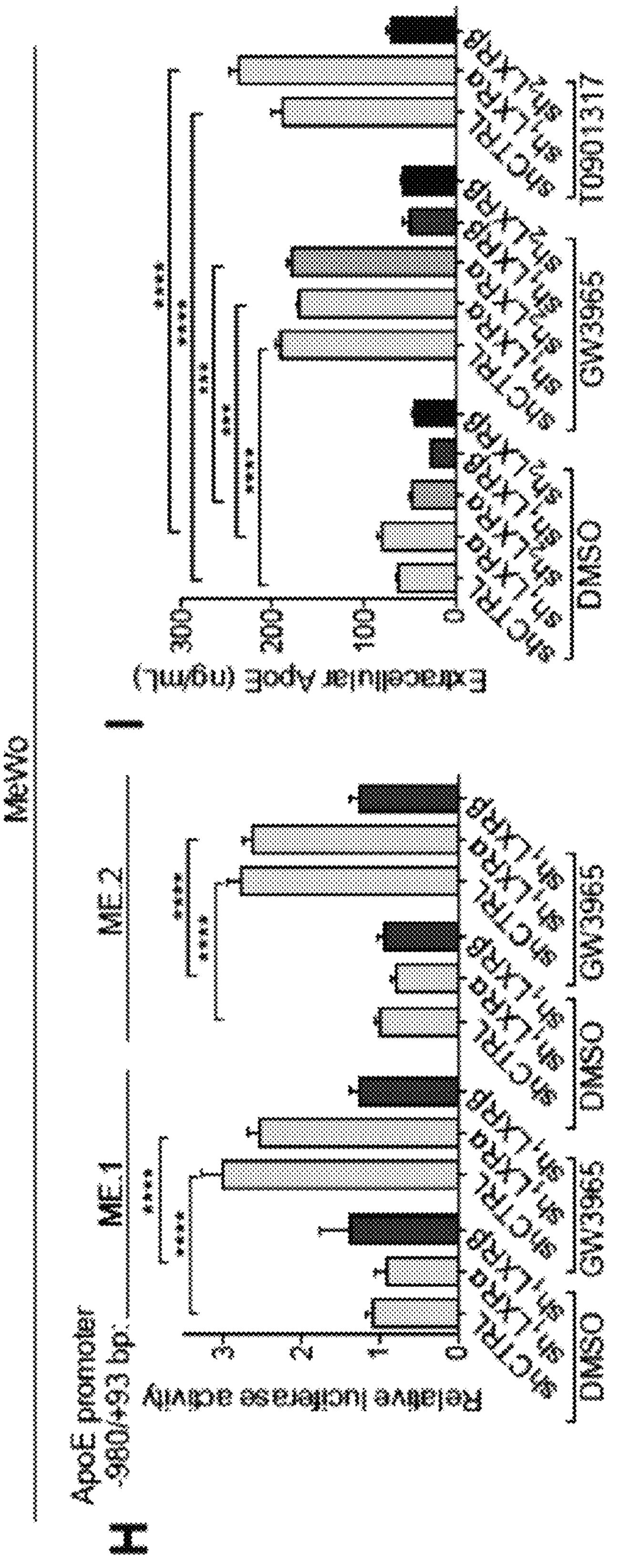

In light of the previously reported metastasis-suppressive function of ApoE in melanoma (Pencheva et al., 2012), we investigated whether LXRβ activation suppresses melanoma progression through transcriptional induction of ApoE. Indeed, GW3965 2 and T0901317 1 were found to enhance the melanoma cell-driven activity of a luciferase reporter construct containing the ApoE promoter fused to either of two previously characterized LXR-binding multi-enhancer elements (ME.1 or ME.2) (Laffitte et al., 2001) (FIG. 28A). Importantly, this transcriptional induction resulted in elevated levels of secreted ApoE protein (FIG. 28B). Consistent with direct LXRβ targeting of ApoE in melanoma cells, neutralization of extracellular ApoE with an antibody fully blocked the LXRβ-mediated suppression of cell invasion and endothelial recruitment and further enhanced these phenotypes relative to the control IgG treatment (FIG. 28C-G and FIG. 27D-F), revealing the effects of LXR agonism to be modulated by extracellular ApoE.

Figures 27G, 27H, 27I, 27J, 27K:
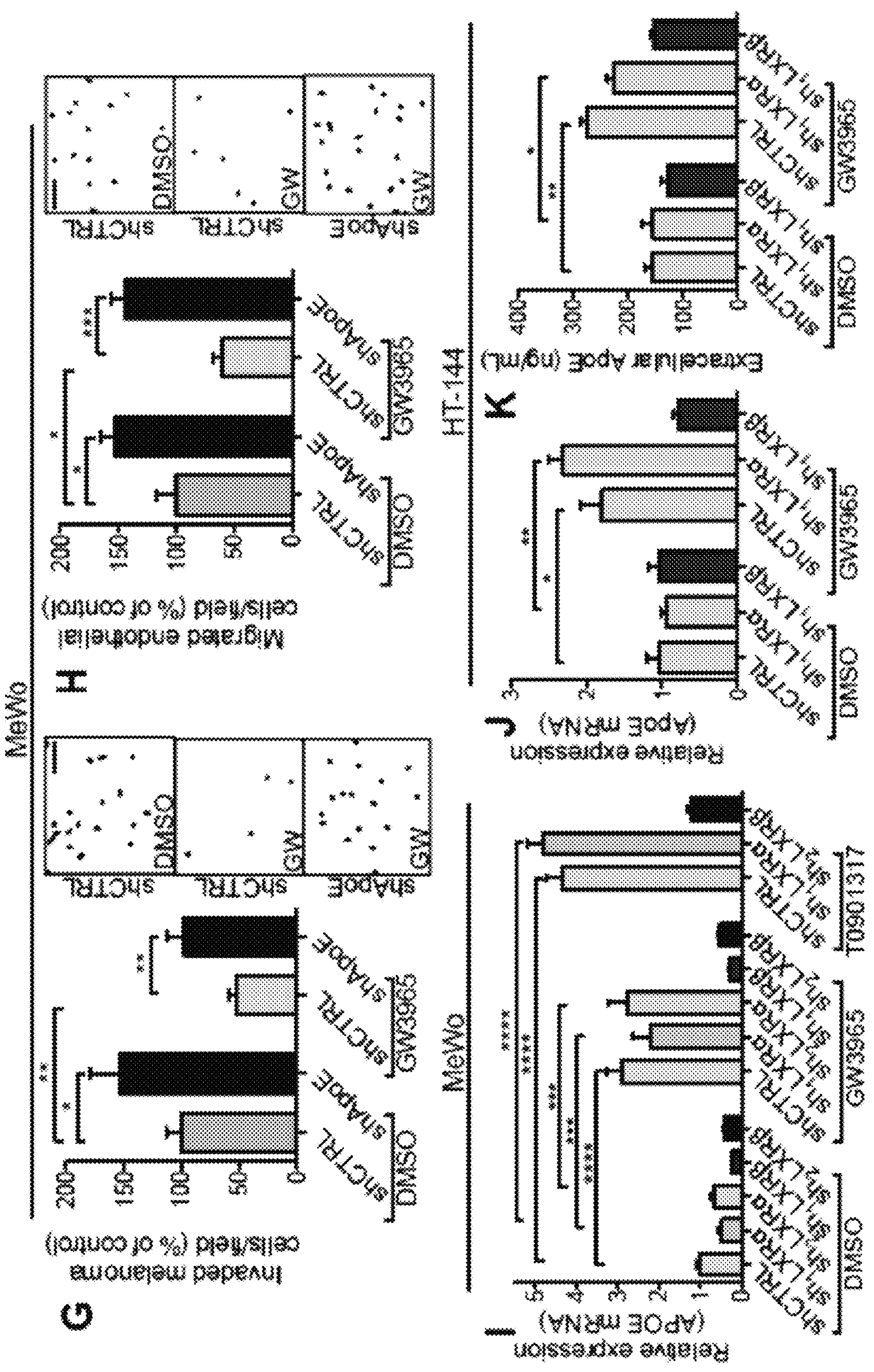

Additionally, molecular knockdown of ApoE in melanoma cells also blocked the GW3965 2-mediated suppression of cell invasion and endothelial recruitment phenotypes (FIG. 27G-H). In agreement with this, melanoma cell depletion of LXRβ, but not LXRα, abrogated the ability of GW3965 2 and T0901317 1 to upregulate ApoE transcription and ultimately protein expression (FIG. 28H-I and FIG. 27I-K). Collectively, these findings indicate that pharmacologic activation of LXRβ, the predominant LXR isoform expressed by melanoma cells, suppresses cell-intrinsic invasion and endothelial recruitment by melanoma cells through transcriptionally activating ApoE expression in melanoma cells.

Example 18 Engagement of Melanoma-Derived and Systemic ApoE by LXRβ Activation Therapy The LXRβ-induced suppression of key melanoma phenotypes by extracellular ApoE in vitro suggested that the suppressive effects of LXR agonists in vivo might be further augmented by the activation of LXRs in peripheral tissues, which could serve as robust sources of extracellular ApoE.

Importantly, such non-transformed tissues would be less vulnerable to developing resistance to LXR activation therapy, allowing for chronic ApoE induction in patients. We thus investigated whether therapeutic LXR agonism suppresses melanoma progression by inducing ApoE derived from melanoma cells or systemic tissues. Consistent with LXRβ agonism increasing ApoE expression in melanoma cells in vivo, ApoE transcript levels were upregulated in melanoma primary tumors as well as in melanoma lung and brain metastases dissociated from mice that were fed an LXR agonist-supplemented diet (FIGS. 29A-E). Importantly, treatment of mice with either GW3965 2 or T0901317 1 significantly elevated ApoE protein expression in systemic adipose, lung, and brain tissues of mice (FIGS. 30A-B) and also upregulated ApoE transcript levels in circulating white blood cells (FIG. 30C). These results indicate that LXR activation therapy induces both melanoma-cell and systemic tissue ApoE expression in vivo.

To determine the in vivo requirement of melanoma-derived and systemic LXR activation for the tumor-suppressive effects of orally administered LXR agonists, we first tested the ability of GW3965 2 to suppress tumor growth by B16F10 mouse melanoma cells depleted of LXRβ.

Figures 29A, 29B, 29C, 29D, 29E, 29F, 29G, 29H:
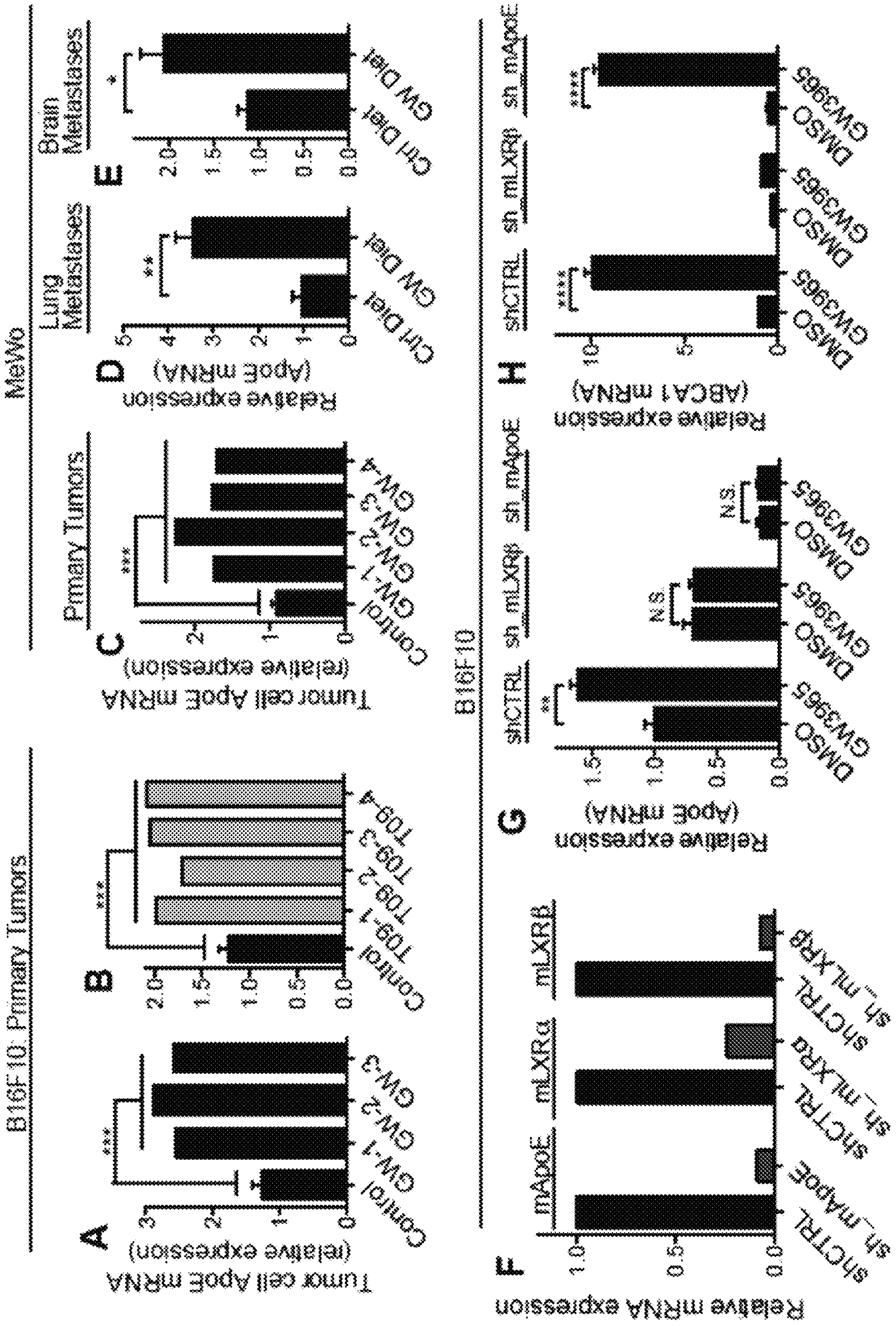
Figures 29I, 29J, 29K:
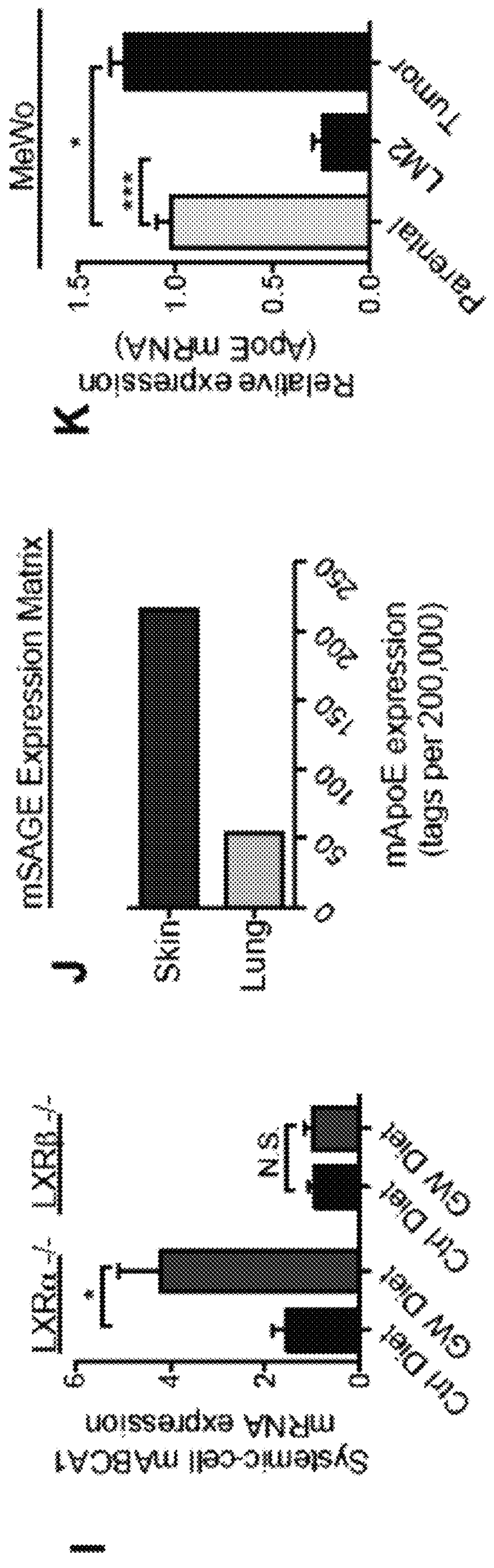
Figures 30A, 30B, 30C, 30D, 30E, 30F:
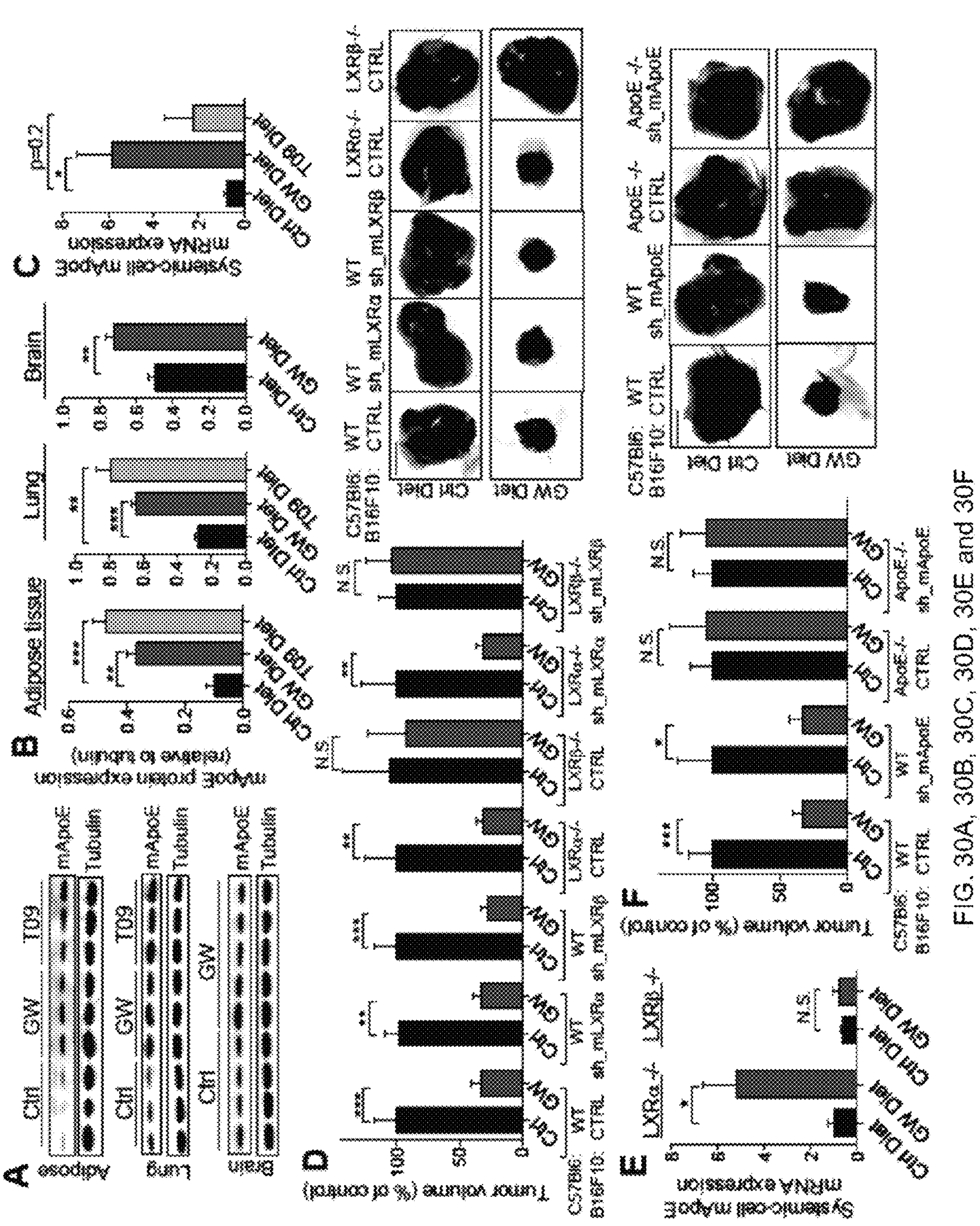

Consistent with our findings in human melanoma cells, knockdown of mouse melanoma-cell LXRβ abrogated the GW3965-mediated induction of ApoE expression (FIGS. 29F-H). Despite this, melanoma-cell LXRβ knockdown was unable to prevent the suppression of tumor growth by GW3965 2 (FIG. 29D), implicating a role for systemic LXR activation in tumor growth inhibition by GW3965 2. To identify the LXR isoform that mediates this non-tumor autonomous suppression of melanoma growth by LXR agonists, we examined the effects of GW3965 2 on tumors implanted onto LXRα or LXRβ genetically null mice. Interestingly, genetic ablation of systemic LXRβ blocked the ability of GW3965 to suppress melanoma tumor growth, while LXRα inactivation had no effect on tumor growth inhibition by GW3965 (FIG. 6D). Importantly, the upregulation of systemic ApoE expression by GW3965 2, an agonist with 6-fold greater activity towards LXRβ than LXRα, was abrogated in LXRβ−/−, but not in LXRα−/− mice (FIG. 30E and FIG. 29I). These results indicate that ApoE induction by GW3965 2 in peripheral tissues is predominantly driven by systemic LXRβ activation. In agreement with this, we find systemic LXRβ to be the primary molecular target and effector of GW3965 2 in mediating melanoma tumor growth suppression.

We next examined whether ApoE is required for the in vivo melanoma-suppressive effects of LXR agonists. Consistent with the lack of an impact for melanoma-cell LXRβ knockdown on the tumor-suppressive activity of GW3965 2, depletion of melanoma-cell ApoE did not prevent tumor growth inhibition by GW3965 2 neither (FIG. 29F-H and FIG. 30F). These findings suggest that the tumor suppressive effects of GW3965 2 might be primarily mediated through ApoE induction in systemic tissues.

Figures 30G, 30H, 30I:
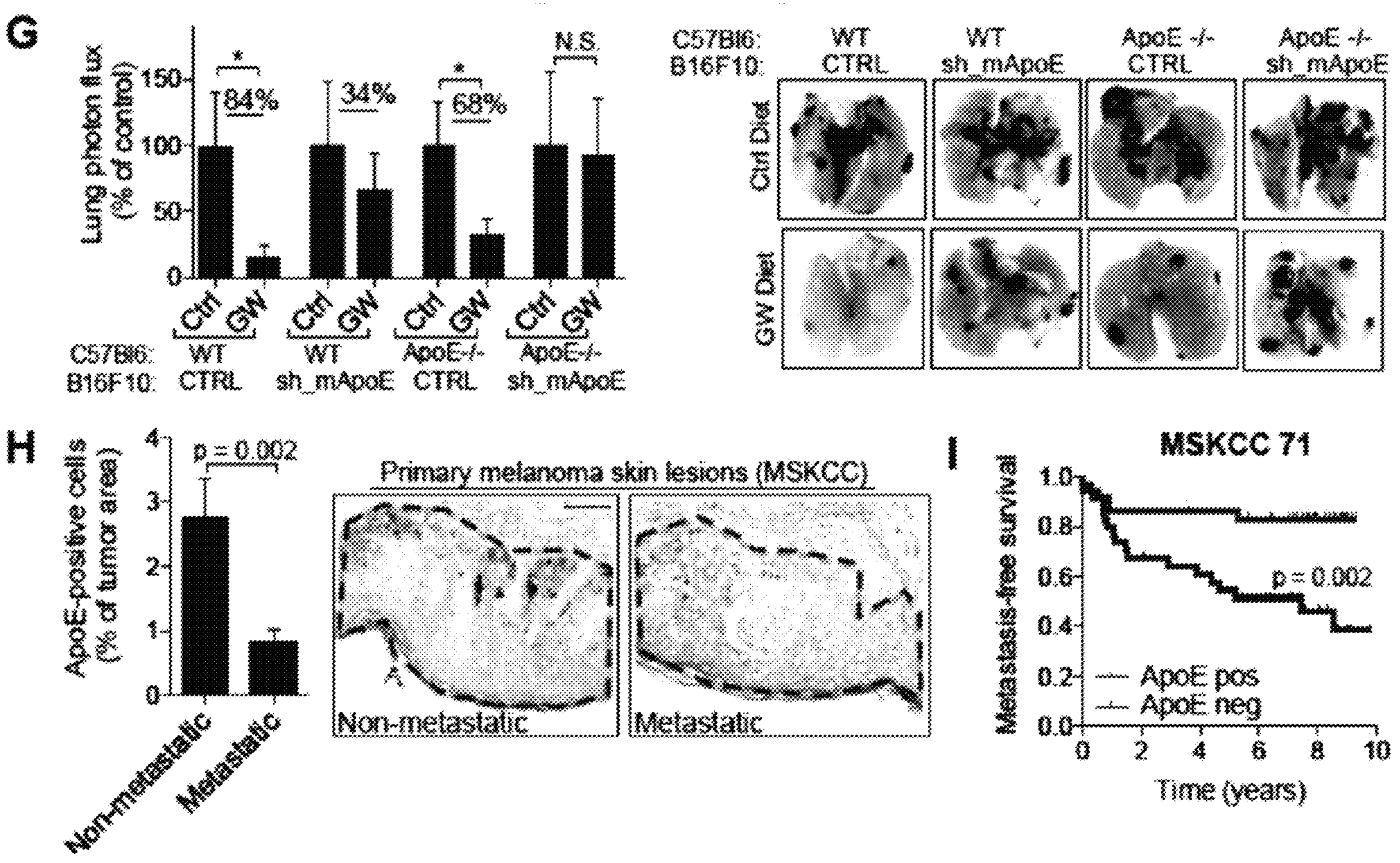

Indeed, GW3965 2 was completely ineffective in suppressing tumor growth in mice genetically inactivated for ApoE (FIG. 30F), revealing systemic ApoE as the downstream effector of systemic LXRβ in driving melanoma tumor growth suppression. Interestingly, in contrast to primary tumor growth regulation, knockdown of melanoma-cell ApoE partially prevented the metastasis-suppressive effect of GW3965 2 (FIG. 30G). Similarly, genetic inactivation of ApoE only partially prevented the metastasis suppression elicited by GW3965 2 as well (FIG. 30G). The GW3965-driven inhibition of metastasis was completely blocked only in the context of both melanoma-cell ApoE knockdown and genetic inactivation of systemic ApoE (FIG. 30G), indicative of a requirement for both melanoma-derived and systemic ApoE engagement by LXRβ in suppressing metastasis. We thus conclude that the effects of LXRβ activation on primary tumor growth are elicited primarily through systemic ApoE induction, while the effects of LXRβ agonism on metastasis are mediated through ApoE transcriptional induction in both melanoma cells and systemic tissues.

The identification of ApoE as the sole downstream mediator of the LXRβ-induced suppression of melanoma phenotypes further highlights the importance of this gene as a suppressor of melanoma progression. To determine whether ApoE expression is clinically prognostic of melanoma metastatic outcomes, we assessed ApoE protein levels by performing blinded immunohistochemical analysis on 71 surgically resected human primary melanoma lesions.

We found that patients whose melanomas had metastasized exhibited roughly 3-fold lower ApoE expression in their primary tumors relative to patients whose melanomas did not metastasize (FIG. 30H, P=0.002). Remarkably, ApoE expression levels in patients' primary melanoma lesions robustly stratified patients at high risk from those at low risk for metastatic relapse (FIG. 30I, P=0.002). These observations are consistent with previous findings that revealed significantly lower levels of ApoE in distant melanoma metastases relative to primary lesions (Pencheva et al., 2012). Collectively, this work indicates that ApoE, as a single gene, could likely act as a prognostic and predictive biomarker in primary melanomas to identify patients that i.) are at risk for melanoma metastatic relapse and as such ii.) could obtain clinical benefit from LXRβ agonist-mediated ApoE induction.

Example 19 LXRβ Activation Therapy Suppresses the Growth of Melanomas Resistant to Dacarbazine and Vemurafenib Encouraged by the robust ability of LXRβ activation therapy to suppress melanoma tumor growth and metastasis across a wide range of melanoma lines of diverse mutational backgrounds, we next sought to determine whether melanomas that are resistant to two of the mainstay clinical agents used in the management of metastatic melanoma-dacarbazine and vemurafenib—could respond to LXRβ-activation therapy.

Figures 31A, 31B, 31C, 31D, 31E, 31F:
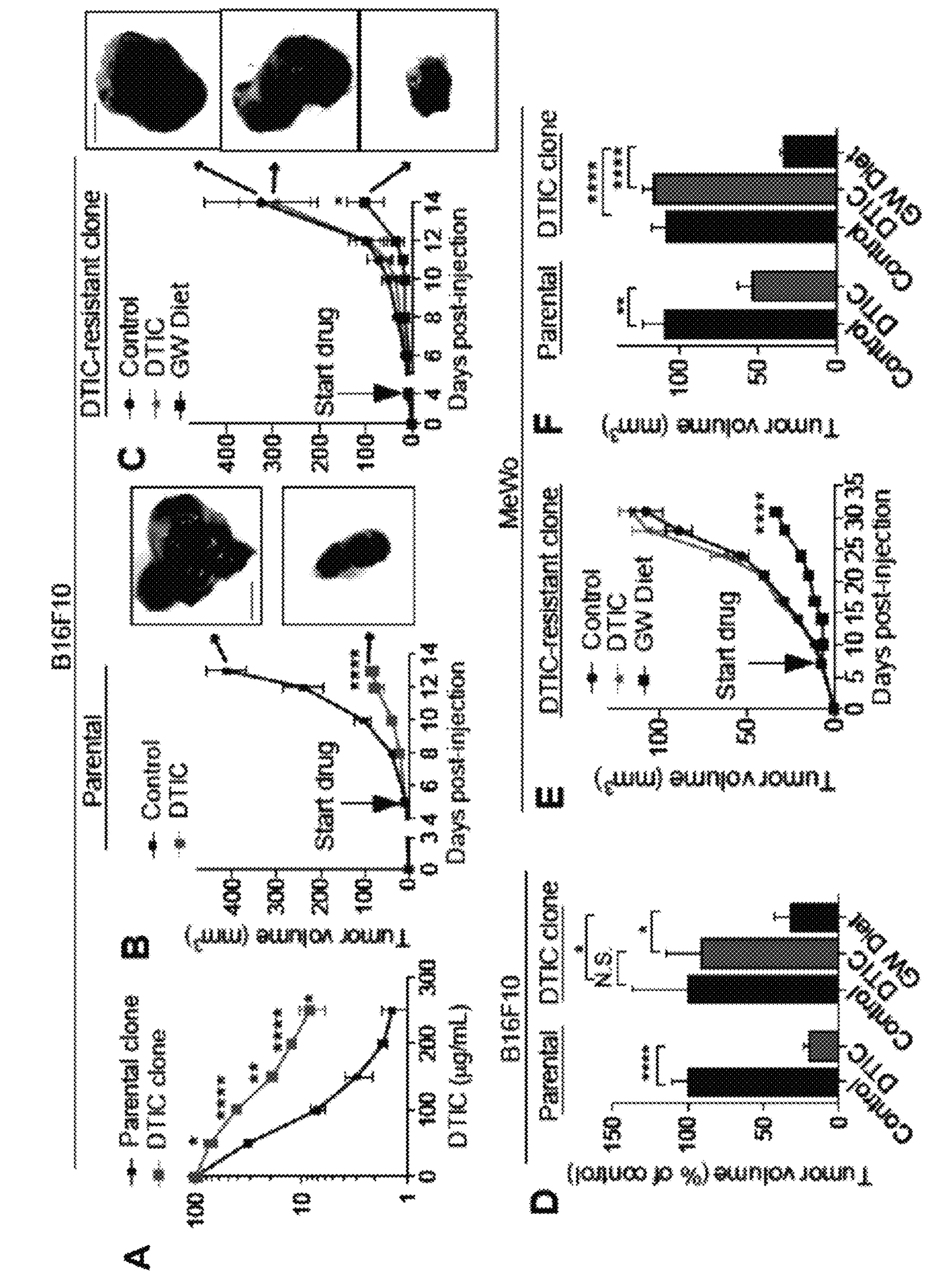

To this end, we generated B16F10 clones resistant to dacarbazine (DTIC) by continuously culturing melanoma cells in the presence of DTIC for two months. This yielded a population of cells that exhibited a 7-fold increase in viability in response to high-dose DTIC treatment compared to the parental B16F10 cell line (FIG. 31A). To confirm that this in vitro-derived DTIC clone was also resistant to DTIC in vivo, we assessed the effects of dacarbazine treatment on tumor growth.

While dacarbazine significantly suppressed the growth of the DTIC-sensitive parental line (FIG. 31B), it did not affect tumor growth by B16F10 DTIC-resistant cells (FIG. 31C). GW3965 2 robustly suppressed tumor growth by the DTIC-resistant B16F10 melanoma clone by more than 70% (FIGS. 31C-D). Importantly, oral delivery of GW3965 2 also strongly inhibited the growth of in vivo-derived DTIC-resistant human melanoma tumors formed by the independent MeWo cell line (FIG. 31E-F and FIG. 32A).

These results reveal that LXRβ agonism is effective in suppressing multiple melanoma cell populations that are resistant to dacarbazine—the only FDA-approved cytotoxic chemotherapeutic in metastatic melanoma. Our findings have important clinical implications for melanoma treatment since all stage IV patients who are treated with dacarbazine ultimately progress by developing tumors that are resistant to this agent.

Figures 31G, 31H, 31I:
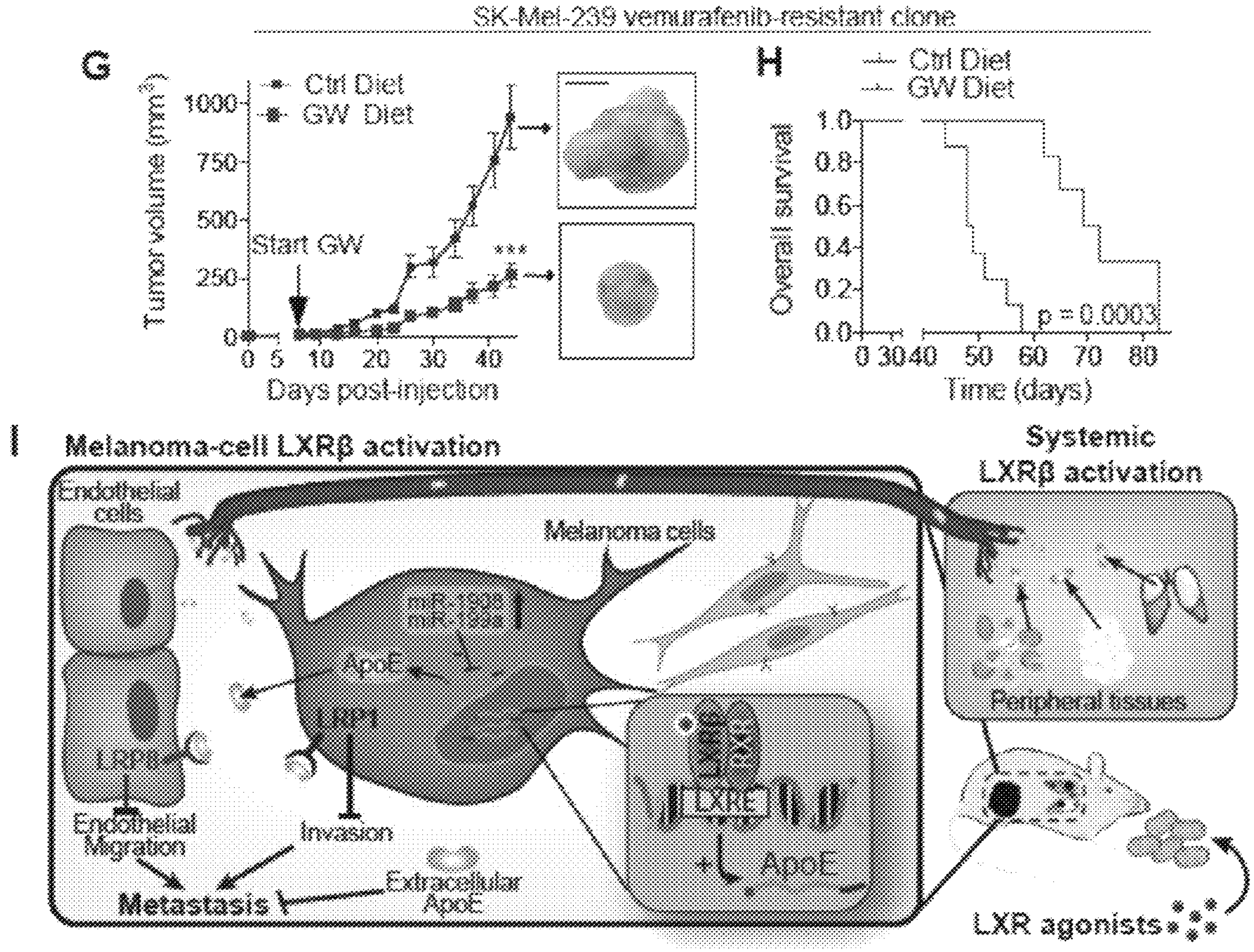

We tested the impact of LXRβ activation therapy on melanoma cells resistant to the recently approved B-Raf kinase inhibitor, vemurafenib—a regimen that shows activity against B-Raf-mutant melanomas (Bollag et al., 2010; Sosman et al., 2012). Numerous investigators have derived melanoma lines resistant to vemurafenib (Poulikakos et al., 2011; Shi et al., 2012, Das Thakur et al., 2013). GW3965 2 treatment suppressed the growth of the previously derived SK-Mel-239 vemurafenib-resistant line by 72% (FIG. 31G) and significantly prolonged the survival of mice bearing vemurafenib-resistant melanoma burden (FIG. 31H). Our findings from combined pharmacologic, molecular and genetic studies in diverse pre-clinical models of melanoma establish LXRβ targeting as a novel therapeutic approach that robustly suppresses melanoma tumor growth and metastasis through the transcriptional induction of ApoE—a key suppressor of melanoma invasion and metastatic angiogenesis (Pencheva et al., 2012; FIG. 31I).

Example 20 Treatment with ApoE Inhibits Tumor Cell Invasion and Endothelial Recruitment Across Multiple Cancer Types, Including Breast Cancer, Renal Cell Cancer and Pancreatic Cancer In order to determine if ApoE treatment could be effective for treating cancer types in addition to melanoma, in vitro assays were performed to assess the effect of ApoE treatment on several different cancer cell lines, including breast cancer, renal cell cancer, and pancreatic cancer cell lines (FIG. 33).

The ability of cancer cells to invade through matrigel in vitro was tested by using a trans-well matrigel invasion chamber system (354480, BD Biosciences). Various cancer cell lines were serum-starved overnight in media containing 0.2% FBS. The following day, invasion chambers were pre-equilibrated prior to the assay by adding 0.5 mL of starvation media to the top and bottom wells. Meanwhile, cancer cells were trypsinized and viable cells were counted using the trypan blue dead cell exclusion dye. Cancer cells were then resuspended at a concentration of 1× 105 cells/1 mL starvation media, and 0.5 mL of cell suspension, containing 5×104 cells, was seeded into each trans-well. To determine the effect of recombinant ApoE on cancer cell invasion, human recombinant ApoE3 (4696, Biovision) or BSA were added to each trans-well at 100 μg/mL at the start of the assay. The invasion assay was allowed to proceed for 24 hours at 37° C. Upon completion of the assay, the inserts were washed in PBS, the cells that did not invade were gently scraped off from the top side of each insert using q-tips, and the cells that invaded into the basal insert side were fixed in 4% PFA for 15 minutes at room temperature. Following fixation, the inserts were washed in PBS and then cut out and mounted onto slides using VectaShield mounting medium containing DAPI nuclear stain (H-1000, Vector Laboratories). The basal side of each insert was imaged using an inverted fluorescence microscope (Zeiss Axiovert 40 CFL) at 5× magnification, and the number of DAPI-positive cells was quantified using ImageJ.

Indeed, treatment with ApoE inhibited both tumor cell invasion and endothelial recruitment across all three of these cancer types (FIG. 33A-I).

Example 21 LXR Agonists LXR-623, WO-2007-002563 Ex. 19, WO-2010-0138598 Ex. 9, and SB742881, Induce ApoE Expression in Human Melanoma Cells Given that ApoE activation by treatment with LXR agonists GW3965 2 and T0901317 1 resulted in therapeutic benefit for inhibiting tumor growth and metastasis, we next examined the ability of other LXR agonists to induce ApoE expression in human melanoma cell lines (FIG. 34).

To determine the effect of the various LXR agonists (LXR-623, WO-2007-002563 Ex. 19, WO-2010-0138598 Ex. 9, and SB742881 on ApoE expression in melanoma cells, 1×105 human MeWo melanoma cells were seeded in a 6-well plate. The following day, DMSO or the respective LXR agonist was added to the cell media at a concentration of 500 nM, 1 μM, or 2 μM, as indicated, and the cells were incubated in the presence of DMSO or the drug for 48 hours at 37° C. The total amount of DMSO added to the cell media was kept below 0.2%. RNA was extracted from whole cell lysates using the Total RNA Purification Kit (17200, Norgen). For every sample, 600 ng of RNA was reverse transcribed into cDNA using the cDNA First-Strand Synthesis kit (Invitrogen). Approximately 200 ng of cDNA was mixed with SYBR® green PCR Master Mix and the corresponding forward and reverse primers specific for detection of human ApoE. Each reaction was carried out in quadruplicates, and ApoE mRNA expression levels were measured by quantitative real-time PCR amplification using an ABI Prism 7900HT Real-Time PCR System (Applied Biosystems). The relative ApoE expression was determined using the ΔΔCt method. GAPDH was used as an endogenous control for normalization purposes.

Figures 34A, 34B, 34C, 34D:
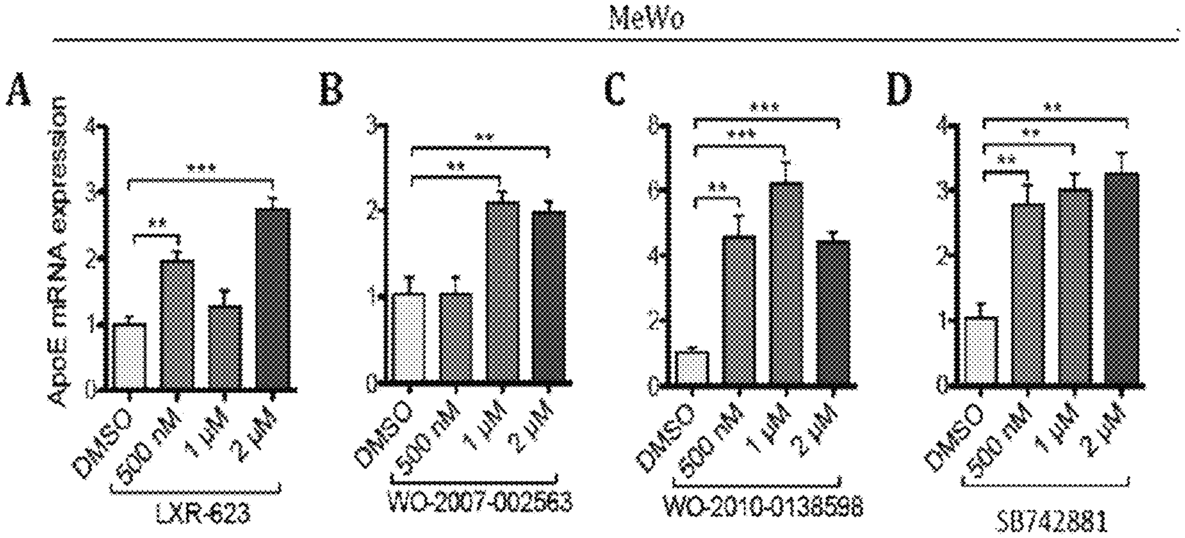

Indeed, treatment with the LXR agonists LXR-623, WO-2007-002563 Ex. 19, WO-2010-0138598 Ex. 9, and SB742881 all led to varied degrees of ApoE expression induction. (FIG. 34A-C).

Example 22 Treatment with the LXR Agonist GW3965 Inhibits In Vitro Tumor Cell Invasion of Renal Cancer, Pancreatic Cancer, and Lung Cancer We have demonstrated that treatment with LXR agonists resulted in inhibition of melanoma tumor cell invasion. Given that this effect is mediated by activation of ApoE expression, we hypothesized that treatment with LXR agonists would result in inhibition of in vitro tumor cell invasion in breast cancer, pancreatic cancer, and renal cancer, since these cancer types were responsive to ApoE treatment. In order to test this hypothesis, we performed in vitro tumor cell invasion assays by treating breast cancer, pancreatic cancer, and renal cell cancer cell lines with the LXR agonist GW3965 2 (FIG. 35).

Various cell lines ($5\times10^4$ RCC human renal cancer cells, $5\times10^4$ PANC1 human pancreatic cancer cells, and $5\times10^4$ H460 human lung cancer cells) were treated with DMSO or GW3965 at 1 μM for 56 hours. The cells were serum starved for 16 hours in 0.2% FBS media in the presence of DMSO or GW3965. Following serum starvation, the cells were subjected to the trans-well invasion assay using a matrigel invasion chamber system (354480, BD Biosciences). Invasion chambers were pre-equilibrated prior to the assay by adding 0.5 mL of starvation media to the top and bottom wells. Meanwhile, cancer cells were trypsinized and viable cells were counted using trypan blue. Cancer cells were then resuspended at a concentration of $1\times10^5$ cells/1 mL starvation media, and 0.5 mL of cell suspension, containing $5\times10^4$ cells, was seeded into each trans-well. The invasion assay was allowed to proceed for 24 hours at 37° C. Upon completion of the assay, the inserts were washed in PBS, the cells that did not invade were gently scraped off from the top side of each insert using q-tips, and the cells that invaded into the basal insert side were fixed in 4% PFA for 15 minutes at room temperature. Following fixation, the inserts were washed in PBS and then cut out and mounted onto slides using VectaShield mounting medium containing DAPI nuclear stain (H-1000, Vector Laboratories). The basal side of each insert was imaged using an inverted fluorescence microscope (Zeiss Axiovert 40 CFL) at 5× magnification, and the number of DAPI-positive cells was quantified using ImageJ.

Indeed, treatment with GW3965 2 resulted in inhibition of tumor cell invasion in all three cancer types tested (FIG. 35A-C). This further demonstrated the broad therapeutic potential of LXR agonists for treating various cancer types.

Example 23 Treatment with the LXR Agonist GW3965 Inhibits Breast Cancer Tumor Growth in Vivo We have demonstrated that LXR agonists inhibit in vitro cancer progression phenotypes in breast cancer, pancreatic cancer, and renal cancer. To investigate if LXR agonist treatment inhibits breast cancer primary tumor growth in vivo, mice injected with MDA-468 human breast cancer cells were treated with either a control diet or a diet supplemented with LXR agonist GW3965 2 (FIG. 36).

To determine the effect of orally delivered GW3965 2 on breast cancer tumor growth, $2\times10^6$ MDA-468 human breast cancer cells were resuspended in 50 μL PBS and 50 μL matrigel and the cell suspension was injected into both lower memory fat pads of 7-week-old Nod Scid gamma female mice. The mice were assigned to a control diet treatment or a GW3965-supplemented diet treatment (75 mg/kg/day) two days prior to injection of the cancer cells. The GW3965 2 drug compound was formulated in the mouse chow by Research Diets, Inc. Tumor dimensions were measured using digital calipers, and tumor volume was calculated as (small diameter)$^2$×(large diameter)/2.

Treatment with GW3965 resulted in significant reduction in breast cancer tumor size in vivo (FIG. 36).

Example 24 Effects of Treatment with LXR Agonists LXR-623, WO-2007-002563 Ex. 19, WO-2010-0138598 Ex. 9, and SB742881 on In Vitro Melanoma Progression Phenotypes We have demonstrated the ability of various LXR agonists to induce ApoE expression with varying potency in melanoma cells (FIG. 34). Since the therapeutic effect of LXR agonists on cancer is via activation of ApoE expression, we hypothesized that the therapeutic potency of any given LXR agonist is directly correlated with its ability to induce ApoE expression. To confirm this, we quantified the effect of treatment with various LXR agonists on in vitro endothelial recruitment and tumor cell invasion of melanoma cells. As shown in FIG. 37, the degree to which LXR agonists inhibit in vitro cancer progression phenotypes is related to the LXR agonist's ApoE induction potency.

Cell Invasion: MeWo human melanoma cells were treated with DMSO, LXR-623, WO-2007-002563 Ex. 19, WO-2010-0138598 Ex. 9, or SB742881 at 1 μM each for 56 hours. The cells were then serum starved for 16 hours in 0.2% FBS media in the presence of each corresponding drug or DMSO. Following serum starvation, the cells were subjected to the trans-well invasion assay using a matrigel invasion chamber system (354480, BD Biosciences). Invasion chambers were pre-equilibrated prior to the assay by adding 0.5 mL of starvation media to the top and bottom wells. Meanwhile, cancer cells were trypsinized and viable cells were counted using trypan blue. Cancer cells were then resuspended at a concentration of $2\times10^5$ cells/1 mL starvation media, and 0.5 mL of cell suspension, containing $1\times10^5$ cells, was seeded into each trans-well. The invasion assay was allowed to proceed for 24 hours at 37° C. Upon completion of the assay, the inserts were washed in PBS, the cells that did not invade were gently scraped off from the top side of each insert using q-tips, and the cells that invaded into the basal insert side were fixed in 4% PFA for 15 minutes at room temperature. Following fixation, the inserts were washed in PBS, cut out, and mounted onto slides using VectaShield mounting medium containing DAPI nuclear stain (H-1000, Vector Laboratories). The basal side of each insert was imaged using an inverted fluorescence microscope (Zeiss Axiovert 40 CFL) at 5× magnification, and the number of DAPI-positive cells was quantified using ImageJ.

Endothelial Recruitment: MeWo human melanoma cells were treated with DMSO, LXR-623, WO-2007-002563 Ex. 19, WO-2010-0138598 Ex. 9, or SB742881 at 1 μM each for 56 hours. Subsequently, $5\times10^4$ cancer cells were seeded into 24-well plates in the presence of each drug or DMSO and allowed to attach for 16 hours prior to starting the assay. Human umbilical vein endothelial cells (HUVEC cells) were serum-starved in 0.2% FBS-containing media overnight. The following day, $1\times10^5$ HUVEC cells were seeded into a 3.0 μm HTS Fluoroblock insert (351151, BD Falcon) fitted into each well containing the cancer cells at the bottom. The HUVEC cells were allowed to migrate towards the cancer cells for 20 hours, after which the inserts were washed in PBS, fixed in 4% PFA, labeled with DAPI, and mounted on slides. The basal side of each insert was imaged using an inverted fluorescence microscope (Zeiss Axiovert 40 CFL) at 5× magnification, and the number of DAPI-positive cells was quantified using ImageJ.

LXR agonists that potently induce ApoE expression (e.g. WO-2010-0138598 Ex. 9 and SB742881) are more effective at inhibiting cancer progression phenotypes (FIG. 37) than lower potency LXR agonists. This further demonstrates that the therapeutic benefit of LXR agonist treatment for cancer is a result of ApoE induction.

Example 25 Treatment with LXR Agonists Inhibit Melanoma Tumor Growth In Vivo

We have demonstrated that LXR agonists that induce ApoE expression inhibit in vitro tumor activity. To confirm if these agonists inhibit melanoma tumor growth in vivo, mice that were injected with B16F10 melanoma cells were treated with either LXR-623, WO-2007-002563 Ex. 19, WO-2010-0138598 Ex. 9, or SB742881.

To assess the effect of orally administered LXR-623, WO-2007-002563 Ex. 19, WO-2010-0138598 Ex. 9, or SB742881 on melanoma tumor growth, $5\times10^4$ B16F10 mouse melanoma cells were resuspended in 50 μL PBS and 50 μL matrigel and the cell suspension was subcutaneously injected into both lower dorsal flanks of 7-week-old C57BL/6 mice. The mice were palpated daily for tumor formation and after detection of tumors measuring 5-10 m3 in volume, the mice were assigned to a control chow or a chow containing each respective LXR agonist: LXR-623 (20 mg/kg/day), WO-2007-002563 Ex. 19 (100 mg/kg/day), WO-2010-0138598 Ex. 9 (10 mg/kg/day or 100 mg/kg/day), or SB742881 (100 mg/kg/day). The LXR drug compounds were formulated in the mouse chow by Research Diets, Inc. Tumor dimensions were measured using digital calipers, and tumor volume was calculated as (small diameter)$^2$×(large diameter)/2.

Consistent with our in vitro data, LXR agonists that potently induce ApoE expression in vitro (WO-2010-0138598 Ex. 9, and SB742881) significantly inhibited melanoma primary tumor growth in vivo (FIG. 38). This is also consistent with our results demonstrating that other LXR agonists which potently induce ApoE expression (GW3965 2, T0901317 1) also inhibit primary tumor growth in vivo (FIG. 21).

Accordingly, the above examples focused on characterizing the molecular and cellular mechanisms by which it exerts its effects. To this end, it was found that ApoE targets two distinct, yet homologous, receptors on two diverse cell types. ApoE acting on melanoma cell LRP1 receptors inhibits melanoma invasion, while its action on endothelial cell LRP8 receptors suppresses endothelial migration. The results from loss-of-function, gain-of-function, epistasis, clinical correlation, and in vivo selection derivative expression analyses give rise to a model wherein three miRNAs convergently target a metastasis suppressor network to limit ApoE secretion, thus suppressing ApoE/LRP1 signaling on melanoma cells and ApoE/LRP8 signaling on endothelial cells (FIG. 7K). Although the above systematic analysis has identified ApoE and DNAJA4 as key targets and direct mediators of the metastatic phenotypes regulated by these miRNAs, it cannot be excluded that the three miRNAs may individually retain additional target genes whose silencing may contribute to metastatic progression. The ability of ApoE or DNAJA4 knock-down to fully rescue the metastasis suppression phenotypes seen with individual miRNA silencing, however, strongly suggests that these genes are the key mediators of the miRNA-dependent effects on metastasis.

The above results reveal combined molecular, genetic, and in vivo evidence for a required and sufficient role for ApoE in the suppression of melanoma metastatic progression. ApoE can distribute in the circulatory system both in a lipoprotein-bound and a lipid-free state (Hatters et al., 2006). While it has been shown that lipid-free recombinant ApoE is sufficient to suppress melanoma invasion and endothelial migration, it is possible that ApoE contained in lipoprotein particles could also suppress melanoma invasion and endothelial recruitment. The ability of recombinant ApoE to inhibit these pro-metastatic phenotypes, as well as the increased melanoma invasion and endothelial recruitment phenotypes seen with antibody-mediated ApoE neutralization suggests that the ApoE molecule itself is the key mediator of these phenotypes. Consistent with the findings disclosed herein, a synthetic peptide fragment of ApoE was previously found to inhibit endothelial migration through unknown mechanisms (Bhattacharjee et al., 2011). The findings disclosed herein are consistent with a role for melanoma cell-secreted and systemic endogenous ApoE in inhibiting endothelial recruitment, which is not secondary to impaired endothelial cell growth.

The above-described molecular, genetic, and in vivo studies reveal a role for endogenous cancer-derived ApoE in the modulation of endothelial migration and cancer angiogenesis through endothelial LRP8 receptor signaling. This robust non-cell-autonomous endothelial recruitment phenotype mediated by ApoE/LRP8 signaling suggests that ApoE may also modulate metastatic angiogenesis in other cancer types, and such a general role for ApoE in cancer angiogenesis biology remains to be explored. ApoE is a polymorphic molecule with well-established roles in lipid, cardiovascular, and neurodegenerative disorders. Its three major variants, ApoE2, ApoE3, and ApoE4, display varying representations in the human population, with ApoE3 being the most common variant (Hatters et al., 2006). The three isoforms differ at residues 112 and 158 in the N-terminal domain, which contains the ApoE receptor-binding domain. These structural variations are thought to give rise to distinct functional attributes among the variants. Consistent with this, the three ApoE isoforms differ in their binding affinity for members of the LDL receptor family, lipoprotein-binding preferences, and N-terminus stability. Namely, ApoE2 has 50- to 100-fold attenuated LDL receptor binding ability compared to ApoE3 and ApoE4 (Weisgraber et al., 1982), while ApoE4, unlike the other two variants, preferentially binds to large lower-density lipoproteins (Weisgraber et al., 1990) and exhibits the lowest N-terminus stability (Morrow et al., 2000). These functional differences confer pathophysiological properties to select ApoE isoforms. While ApoE3, found in 78% of the population, is considered a neutral allele, ApoE2 is associated with type III hyperlipoproteinemia (Hatters et al., 2006) and ApoE4 represents the major known genetic risk factor for Alzheimer's disease (Corder et al., 1993) and also correlates with a modest increase in the risk of developing cardiovascular disease (Luc et al., 1994). Given that the multiple human melanoma cell lines analyzed in the above study are homozygous for the ApoE3 allele, as well as the ability of recombinant ApoE3 to inhibit melanoma invasion and endothelial recruitment, the above findings are consistent with ApoE3 being sufficient and required for the suppression of melanoma metastatic progression. However, it will be of interest in the future to determine whether ApoE2 and ApoE4 can modulate these pro-metastatic phenotypes to a similar extent as ApoE3 and whether specific ApoE genotypes confer enhanced risk of melanoma metastatic progression.

Besides surgical resection of primary melanoma lesions, there are currently no effective therapies for the prevention of melanoma metastasis with interferon therapy increasing overall survival rates at 5 years by a meager 3% based on meta-analyses, while phase III trial data demonstration of significant survival benefits is still outstanding (Garbe et al., 2011). The dramatic enhancement of melanoma metastatic progression in the context of genetic ablation of systemic ApoE suggests that modulating ApoE levels may have significant therapeutic implications for melanoma—a disease that claims approximately 48,000 lives a year globally (Lucas et al., 2006). Given the robust ability of ApoE to suppress melanoma invasion, endothelial migration, metastatic angiogenesis, and metastatic colonization, therapeutic approaches aimed at pharmacological induction of endogenous ApoE levels may significantly reduce melanoma mortality rates by decreasing metastatic incidence.

The above-described unbiased in vivo selection based approach led to discovery of deregulated miRNAs that synergistically and dramatically promote metastasis by cancer cells from independent patients' melanoma cell lines representing both melanotic and amelanotic melanomas. While miR-1908 has not been previously characterized, miR-199a has been implicated in hepatocellular carcinoma (Hou et al., 2011; Shen et al., 2010) and osteosarcoma (Duan et al., 2011) that, contrary to melanoma, display down-regulation of miR-199a expression levels. These differences are consistent with the established tissue-specific expression profiles of miRNAs in various cancer types. The identification of miR-199a as a promoter of melanoma metastasis is supported by a previous clinical association study revealing that increased miR-199a levels correlate with uveal melanoma progression (Worley et al., 2008), suggesting that induced miR-199a expression may be a defining feature of metastatic melanoma regardless of site of origin. Previous studies have implicated additional miRNAs in promoting melanoma metastatic progression such as miR-182 (Segura et al., 2009), miR-214 (which was upregulated in metastatic melanoma cells, but it did not functionally perform in the above studies; Penna et al., 2011), and miR-30b/miR-30d (Gaziel-Sovran et al., 2011). Each of these miRNAs have been reported to only modestly modulate melanoma metastasis, leading to 1.5- to 2-fold increased or decreased metastasis modulation upon miRNA over-expression or knock-down, respectively. In contrast, over-expression of either miR-199a or miR-1908 enhanced metastasis by 9-fold (FIG. 1C), while combinatorial miRNA knock-down synergistically suppressed melanoma metastasis by over 70-fold (FIG. 7E). Therefore, the study disclosed herein represents the first systematic discovery of multiple miRNAs that convergently and robustly promote human melanoma metastasis, as well as the first to assign dual cell-autonomous/non-cell-autonomous roles to endogenous metastasis-regulatory miRNAs in cancer.

Previous systematic analysis of miRNAs in breast cancer revealed primarily a decrease in the expression levels of multiple microRNAs in in vivo selected metastatic breast cancer cells (Tavazoie et al., 2008). Those findings were consistent with the subsequent discovery of many additional metastasis suppressor miRNAs in breast cancer (Shi et al., 2010; Wang and Wang, 2011), the identification of a number of miRNAs as direct transcriptional targets of the p53 tumour suppressor (He et al., 2007), the downregulation of miRNAs in breast cancer relative to normal tissues (Calin and Groce, 2006; Iorio et al., 2005), the downregulation of drosha and dicer in breast cancer (Yan et al., 2011) and metastatic breast cancer (Grelier et al., 2011), as well as the pro-tumorigenic and pro-metastatic effects of global miRNA silencing through dicer knock-down (Kumar et al., 2007; Kumar et al., 2009; Martello et al., 2010; Noh et al., 2011). In contrast to breast cancer, the above findings in melanoma reveal a set of miRNAs upregulated in metastatic human melanoma, raising the intriguing possibility that miRNA processing may actually act in a pro-tumorigenic or pro-metastatic manner in melanoma. Consistent with this, dicer is required for melanocytic development (Levy et al., 2010), and dicer expression was recently found to positively correlate with human melanoma progression in a clinico-pathological study (Ma et al., 2011). These findings, when integrated with the findings disclosed here, motivate future studies to investigate the functional requirement for dicer (Bernstein et al., 2001) in melanoma metastasis.

The establishment of in vivo selection models of melanotic and amelanotic melanoma metastasis has allowed one to identify the cellular phenotypes displayed by highly metastatic melanoma cells. The work reveals that, in addition to enhanced invasiveness, the capacity of melanoma cells to recruit endothelial cells is significantly enhanced in highly metastatic melanoma cells relative to poorly metastatic melanoma cells. Additionally, it was found that three major post-transcriptional regulators of metastasis strongly mediate endothelial recruitment. It was further found that the downstream signaling pathway modulated by these miRNAs also regulates endothelial recruitment. These findings reveal endothelial recruitment to be a defining feature of metastatic melanoma cells. Enhanced endothelial recruitment capacity was also recently found to be a defining feature of metastatic breast cancer, wherein suppression of metastasis by miR-126 was mediated through miRNA targeting of two distinct signaling pathways that promote endothelial recruitment (Png et al., 2012). In breast cancer, endothelial recruitment increased the likelihood of metastatic initiation rather than tumor growth. Similarly, the melanoma metastasis promoter miRNAs studied here dramatically enhanced metastatic colonization, without enhancing primary tumor growth, and increased the number of metastatic nodules-consistent with a role for these miRNAs and their regulatory network in metastatic initiation rather than tumor growth promotion. Taken together, these findings are consistent with endothelial recruitment into the metastatic niche acting as a promoter of metastatic initiation and colonization in these distinct epithelial cancer types. Such a non-canonical role for endothelial cells in cancer progression would contrast with the established role of endothelial cells in angiogenic enhancement of blood flow spurring enhanced tumor growth. Endothelial cells are known to play such non-canonical roles in development by supplying cues to neighboring cells during organogenesis (Lammert et al., 2001). Such cues have also been recently shown to promote organ regeneration (Ding et al., 2011; Ding et al., 2010; Kobayashi et al., 2010). Future work is needed to determine the metastasis stimulatory factors provided by endothelial cells that catalyze metastatic initiation.

The ability of miR-199a-3p, miR-199a-5p, and miR-1908 to individually predict metastasis-free survival in a cohort of melanoma patients indicates the significance of each miRNA as a clinical predictor of melanoma cancer progression. Importantly, the dramatic and highly significant capacity of the three miRNA aggregate signature (FIG. 7D) to stratify patients at high risk from those at essentially no risk for metastatic relapse reveals both the cooperativity of these miRNAs, as well as their clinical potential as melanoma biomarkers (Sawyers, 2008) for identifying the subset of patients that might benefit from miRNA inhibition therapy. Therapeutic miRNA targeting has gained momentum through the use of in vivo LNAs that have been shown to antagonize miRNAs in mice (Elmer et al., 2008(b); Krützfeldt et al., 2005; Obad et al., 2011) and primates (Elmer et al., 2008(a)) and are currently being tested in human clinical trials. The powerful prognostic capacity of the three miRNAs, proof-of-principle demonstration of robust synergistic metastasis prevention achieved by treating highly metastatic melanoma cells with a cocktail of LNAs targeting miR-199a-3p, miR-199a-5p, and miR-1908 (FIG. 7E), as well as the metastasis suppression effect of therapeutically delivered in vivo-optimized LNAs targeting these miRNAs (FIG. 7J) motivate future clinical studies aimed at determining the therapeutic potential of combinatorially targeting these pro-metastatic and pro-angiogenic miRNAs in patients at high risk for melanoma metastasis—an outcome currently lacking effective chemotherapeutic options.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated in their entireties.

The invention claimed is:

1. A method of treating a cancer in a subject in need thereof, comprising administering to the subject an effective amount of an LXRβ agonist selected from the group consisting of:

compound 1

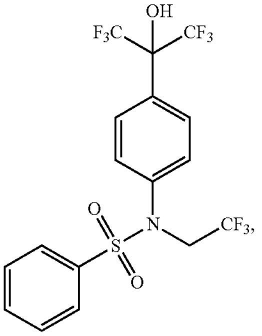

-continued compound 2

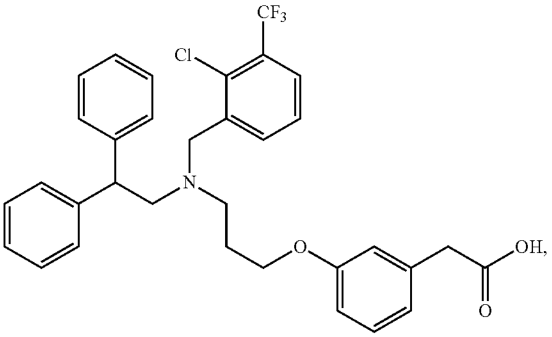

-continued compound 12

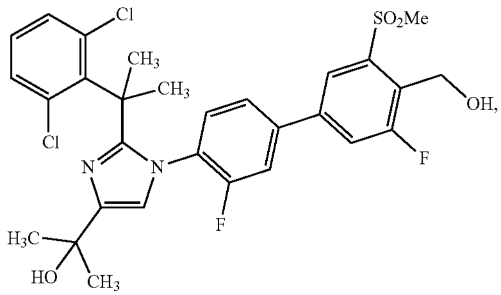

and compound 25

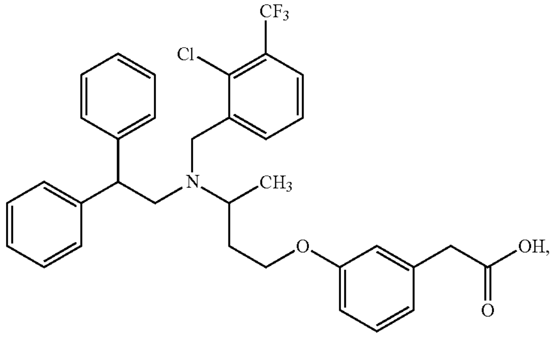

or a pharmaceutically acceptable salt thereof, and a PD-1 inhibitor or a PD-L1 inhibitor.

2. The method of claim 1, further comprising administering to the subject one or more chemotherapeutic agents or cytotoxic agents.

3. The method of claim 2, wherein the one or more chemotherapeutic agents comprise a platinum agent and a cytotoxic agent.

4. The method of claim 2, wherein the one or more chemotherapeutic agents are selected from the group consisting of platinum agent, pemetrexed, paclitaxel, taxol, docetaxel, and taxotere.

5. The method of claim 3, wherein the platinum agent is selected from the group consisting of spiroplatin, tetraplatin, ormaplatin, iproplatin, oxaliplatin, carboplatin, lobaplatin, satraplatin, and cisplatin.

6. The method of claim 3, wherein the one or more chemotherapeutic agents are platinum agent and paclitaxel.

7. The method of claim 3, wherein the one or more chemotherapeutic agents are platinum agent and pemetrexed.

8. The method of claim 1, wherein the PD-1 inhibitor is nivolumab.

9. The method of claim 1, wherein the PD-L1 inhibitor is MPDL3280A.

10. The method of claim 1, wherein the LXRβ agonist is compound 25.

11. The method of claim 1, which is prior to other anti-cancer therapy.

12. The method of claim 1, which is subsequent to a prior anti-cancer therapy.

13. The method of claim 1, wherein the cancer is non-small cell lung cancer.

14. The method of claim 1, wherein the cancer is endometrial cancer or lung cancer.

15. The method of claim 1, wherein the cancer is resistant to a PD-1 inhibitor or a PD-L1 inhibitor.

16. The method of claim 1, wherein the cancer is metastatic cancer.

17. The method of claim 1, wherein the cancer is cell migration cancer.

18. The method of claim 1, wherein the cancer is non-metastatic cell migration cancer.

19. The method of claim 1, wherein the cancer spreads via seeding the surface of peritoneal, pleural, pericardial, or subarachnoid spaces of the subject.

20. The method of claim 1, wherein the migrating cancer spreads via lymphatic system, or spread hematogenously.

21. The method of claim 1, wherein the LXRβ agonist or the pharmaceutically acceptable salt thereof is in an amount sufficient to reduce tumor seeding.

* * * * *